United States Patent

Marsters, Jr. et al.

[11] Patent Number: 5,843,941
[45] Date of Patent: Dec. 1, 1998

[54] RAS FARNESYL TRANSFERASE INHIBITORS

[75] Inventors: James C. Marsters, Jr., Oakland, Calif.; Michael S. Brown, Dallas, Tex.; Craig W. Crowley, Portola Valley, Calif.; Joseph L. Goldstein; Guy L. James, both of Dallas, Tex.; Robert S. McDowell, San Francisco, Calif.; David Oare, Belmont, Calif.; Thomas E. Rawson, Mountain View, Calif.; Mark Reynolds, South San Francisco, Calif.; Todd C. Somers, Foster City, Calif.

[73] Assignees: Genentech, Inc., South San Francisco, Calif.; Board of Regents University of Texas, Austin, Tex.

[21] Appl. No.: 313,068

[22] PCT Filed: May 10, 1994

[86] PCT No.: PCT/US94/05157

§ 371 Date: Sep. 26, 1994

§ 102(e) Date: Sep. 26, 1994

[87] PCT Pub. No.: WO94/26723

PCT Pub. Date: Nov. 24, 1994

Related U.S. Application Data

[63] Continuation-in-part of Ser. No. 82,202, Jun. 24, 1993, abandoned, which is a continuation-in-part of Ser. No. 61,961, May 14, 1993, abandoned.

[51] Int. Cl.⁶ .................... A61K 31/55; C07D 243/14; C07D 243/24
[52] U.S. Cl. ................ 514/221; 540/509; 540/514
[58] Field of Search ................ 540/509, 514; 514/221

[56] References Cited

U.S. PATENT DOCUMENTS

| | | | |
|---|---|---|---|
| 3,296,252 | 1/1967 | Frey et al. | 260/239.3 |
| 3,329,676 | 7/1967 | Bell et al. | 260/239.3 |
| 3,335,134 | 8/1967 | Frey et al. | 260/239.3 |
| 3,927,016 | 12/1975 | Hester, Jr. et al. | 260/300 |
| 4,280,957 | 7/1981 | Walser et al. | 260/244.4 |
| 4,647,560 | 3/1987 | Boltze et al. | 514/220 |
| 4,692,522 | 9/1987 | Parsons et al. | |
| 5,055,464 | 10/1991 | Murakami et al. | |
| 5,141,851 | 8/1992 | Brown et al. | |
| 5,206,234 | 4/1993 | Bock et al. | |
| 5,206,237 | 4/1993 | Freidinger et al. | 514/219 |
| 5,220,018 | 6/1993 | Bock et al. | 540/509 |
| 5,238,922 | 8/1993 | Graham et al. | |
| 5,245,061 | 9/1993 | Singh. | |

FOREIGN PATENT DOCUMENTS

| | | | |
|---|---|---|---|
| 166357 | 1/1986 | European Pat. Off. | C07K 5/00 |
| 167919 | 1/1986 | European Pat. Off. | C07D 243/18 |
| 284256 | 9/1988 | European Pat. Off. | C07D 403/12 |
| 322779 | 7/1989 | European Pat. Off. | C07K 5/06 |
| 461869 | 12/1991 | European Pat. Off. | A61K 37/02 |
| 496162 | 7/1992 | European Pat. Off. | C12N 15/12 |
| 519678 | 12/1992 | European Pat. Off. | A61K 31/55 |
| 520823 | 12/1992 | European Pat. Off. | C07K 5/10 |
| 523873 | 1/1993 | European Pat. Off. | C07K 5/10 |
| 2237592 | 2/1973 | Germany | C07D 487/04 |
| 2321705 | 11/1973 | Germany | C07D 57/02 |
| 2540522 | 4/1976 | Germany | C07D 57/02 |
| WO 91/16340 | 10/1991 | WIPO | C07K 7/06 |
| WO 92/01683 | 2/1992 | WIPO | C07D 403/06 |
| WO 92/13878 | 8/1992 | WIPO | C07K 5/02 |
| WO 92/20336 | 11/1992 | WIPO | A61K 31/335 |
| WO 93/00095 | 1/1993 | WIPO | A61K 31/55 |
| WO 94/04561 | 3/1994 | WIPO | C07K 5/10 |

OTHER PUBLICATIONS

James et al, *Science*, vol. 260 (Jun. 25 1993), pp. 1937–1942.

Barbacid et al., "ras GENES" *Ann. Rev. Biochem.* 56:779–827 (1987).

Casey et al., "P21ras is modified by a farnesyl isoprenoid" *Proc. Natl. Acad. Sci. USA* 86:8323–8327 (1989).

Freidinger, Roger M., "Cholecystokinin and Gastrin Antagonists" *Medical Research Reviews* 9(3):271–290 (1989).

Hancock et al., "All ras Proteins are Polyisoprenylated But Only Some are Palmitoylated" *Cell* 57:1167–1177 (1989).

Hara et al., "Identification of ras Farnesyltransferase Inhibitors by Microbial Screening" *Proc. Natl. Acad. Sci. USA* 90:2281–2285 (1993).

(List continued on next page.)

*Primary Examiner*—Robert T. Bond
*Attorney, Agent, or Firm*—Daryl B. Winter

[57] ABSTRACT

Benzodiazepine derivatives represented by the structure below are disclosed that act as potent inhibitors of ras farnesyl:protein transferase. Pharmaceutical compositions containing these benzodiazepines are provided for treatment of diseases foe which inhibition of the ras farnesyl:protein transferase as indicated.

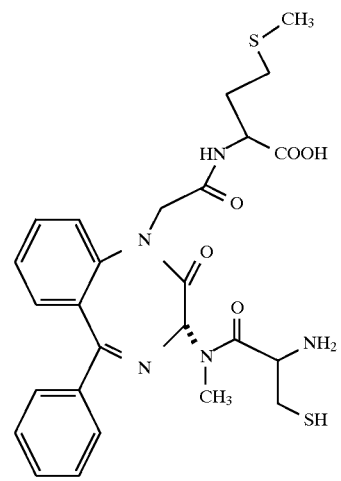

17 Claims, 8 Drawing Sheets

OTHER PUBLICATIONS

James et al., "Benzodiazepine Peptidomimetics: Potent Inhibitors of ras Farnesylation in Animal Cells" *Science* 260:1937–1941 (1993).

Kukla et al., "Synthesis and Anti–HIV–1 Activity of 4, 5, 6, 7–Tetrahydro–5–methylimidazo [4, 5, 1–jk][1, 4]benzodiazepin –2 (IH)–one(TIBO) Derivatives. 2" *J. Med. Chem.* 34:3187–3197 (1991).

Kuzumaki, N., "Suppression of ras–Transformants (Review)" *Anticancer Res.* 11:313–320 (1991).

McCormick, F., "How Receptors Turn ras On" *Nature* 363:15–16 (1993).

Powers, S., "Protein Prenylation: A Modification that Sticks" *Current Biology* 1(2):114–116 (1991).

Reiss et al., "Inhibition of Purified p21$^{ras}$ Farnesyl: Protein Transferase by Cys–AAX Tetrapeptides" *Cell* 62:81–88 (1990).

Reiss et al., "Sequence Requirements for Peptide Recognition by Rat Brain p21$^{ras}$ Protein Farnesyltransferase" *Proc. Natl. Acad. Sci. USA* 88:732–736 (1991).

Schafer et al., "Genetic and Pharmacological Suppression of Oncogenic Mutations in RAS Genes of Yeast and Humans" *Science* 245:379–385 (1989).

Sigal et al., "Molecular Approaches Towards an Anti–ras Drug" *Anti–Cancer Drug Design* 2:107–115 (1987).

Venuti, M., "Isatoic Anhydride/4–Dimethylaminopyridine as a Reagent for Ortho–Aminobenzoylation" *Synthesis* 4:266–268 (Apr. 1982).

Watjen et al., "Novel Benzodiazepine Receptor Partial Agonists: Oxadiazolylimidazobenzodiazepines" *J. Med. Chem.* 32:2282–2291 (1989).

Cheeseman et al., "Synthesis of 5, 6–Dihydro–4H–Pyrrolo [1,2–a] [1,4] benzodiazepines" *Journal of Heterocyclic Chemistry* 16:241–244 (1979).

Gall et al., "Mannich Reactions of Heterocycles with Dimethyl(methylene) Ammonium Chloride: A High Yield, One–step Conversion of Estazolam to Adinazolam" *Journal of Heterocyclic Chemistry* 25:1649–1661 (1988).

RAS FARNESYL TRANSFERASE INHIBITORS

This application is a 371 of PCT/US94/05157, filed May 10, 1994, which is a continuation in part of Ser. No. 08/082,202, filed Jun. 24, 1993; now abandoned, which is a continuation in part of Ser. No. 08/061,961, filed May 15, 1993, now abandoned.

FIELD OF THE INVENTION

This invention relates generally to non-peptidyl inhibitors of farnesyl:protein transferase, an enzyme capable of catalizing farnesylation of p21$^{ras}$ and related low molecular weight G-proteins. More specifically, the instant inhibitors are analogs of benzodiazepine and structurally related 6–7 fused ring systems. The invention further relates to use of these inhibitors in pharmaceutical compositions where inhibition of posttranslational farnesylation of p21$^{ras}$ and related proteins is indicated.

BACKGROUND OF THE INVENTION

Proteins encoded by the ras proto-oncogene act as molecular switches responding to growth stimuli and signaling to the intracellular machinery the occurrence of an extracellular event such as binding of a growth hormone to a growth hormone receptor molecule. Binding of the hormone to its receptor (the external signal) switches the ras protein to the "on" position characterized by exchange of ras bound GDP for GTP. The tightly bound GTP in turn stimulates downstream target proteins, ultimately triggering a cascade of reactions leading to specific gene transcription and ultimately cell division [Barbacid, *Ann. Rev. Biochem.* 56:779 (1987), McCormick, *Nature* 363:15–16 (1993)]. The normal (i.e., non-transformed) ras protein eventually switches to the off position by hydrolyzing bound GTP to GDP and the cell is poised to receive the next external signal.

Mutations to the ras proto-oncogene translate into amino acid substitutions in the GTP binding domain, activating the ras protein (p21$^{ras}$) and biasing this molecular switch in the "on" position. Thus, the ras transformed cell behaves like a cell with a faulty switch, signaling extracellular hormone binding when none is present. Cells transformed in this way grow and differentiate in an abnormal way.

Transforming ras genes are the oncogenes most frequently identified in human cancers. Clinical investigations have identified activated ras genes in a wide variety of human neoplasms, including carcinomas, sarcomas, leukemias, and lymphomas. It is estimated that 40% of all human colon cancers and 95% of human pancreatic cancers contain activated ras oncogenes [Kuzumaki, *Anticancer Res.* 11:313–320 (1991)].

Recently, it has been discovered that the ras protein must be properly posttranslationally modified before it can function as a molecular switch. Stable modification of the carboxy terminus of ras proteins appears to be essential for correct localization within the cell membrane so that extracellular signals for cell growth and differentiation can be correctly passed along to the intracellular messengers (see e.g., Gibbs et al., *Microbiol. Rev.* 53:171–286 [1989]). The ras proteins are posttranslationally modified by farnesylation of a cysteine residue located four residues from the carboxy terminus, followed by proteolytic cleavage of the three following amino acid residues and methylation of the free cysteine carboxyl. The farnesylation reaction is catalyzed by a 94 Kda heterodimeric Zn$^{2+}$ metalloenzyme, farnesyl:protein transferase, which transfers the farnesyl group, a 15 carbon isoprenoid lipid derived from mevalonate (a cholesterol precursor), from farnesyl pyrophosphate to the carboxy terminus cysteine sulfur of rasforming a stable thioether linkage. The farnesyl:protein transferase recognizes the ras carboxy terminus consensus sequence, CAAX, where the cysteine (C) is followed by two aliphatic (A) amino acids (usually valine, leucine, or isoleucine) and any amino acid X (including methionine) [Willumsen et al., *Nature* 310:583–586 (1984)]. This consensus sequence or motif is frequently referred to as the "CAAX box" and is found in other ras related GTP-binding proteins such as fungal mating factors, nuclear lamins, the gamma subunit of transducin, rhodopsin kinase, and the alpha subunit of cGMP-phosphodiesterase.

Surprisingly, this enzyme does not require intact ras protein for transferase activity and can utilize tetrapeptides with the CAAX motif as substrates [Reiss et al., *Cell* 62:81–88 (1990)]. This observation suggested that small tetrapeptides like CAAX or nonpeptide analogs thereof could compete with p21$^{ras}$ for the active site of the transferase and therefore might be of therapeutic utility.

Previously, it had been observed that mutation of the cysteine in the CAAX carboxy sequence of p21$^{ras}$ to serine prevented farnesylation, proteolysis, and methylation [Hancock et al., *Cell* 57:1167–1177 (1989); Reiss et al., *PNAS* 88:732–736 (1991)]. Additionally, cells incubated with an inhibitor of mevalonate synthesis prevented ras farnesylation and the cells were no longer capable of cell division [Schafer et al., *Science*, 245:379–385 (1989)].

These results, taken together, suggest that inhibition of farnesyl:protein transferase with peptides containing the CAAX motif would prevent farnesylation of p21$^{ras}$ and block the ability of ras to transform normal cells to cancer cells. (see e.g., WO 94/04561, EP 0 461 869 A2, EP 0 496 162 A2, EP 0 523 873, and EP 0 520 823). Thus it is believed that intracellular delivery of peptides having the CAAX motif to transformed cells would be an effective antineoplastic therapy.

Generally, however, small linear peptides do not make good therapeutics because of their susceptability to proteolysis, oxidation, and lack of transportability across cell membranes. Accordingly, a need exists for a stable and potent non-peptidyl farnesyl:protein transferase inhibitor that is permeable to cell membranes.

Recently, several non-peptidyl ras farnesyl transferase inhibitors were identified through microbial screening. Several antibiotics (UCF1-A through UCF1-C) structurally related to manumycin inhibited growth of Ki-ras-transformed fibrosarcoma [Hara et al, *Proc. Natl, Sci. USA* 90:2281–2285 (1993)].

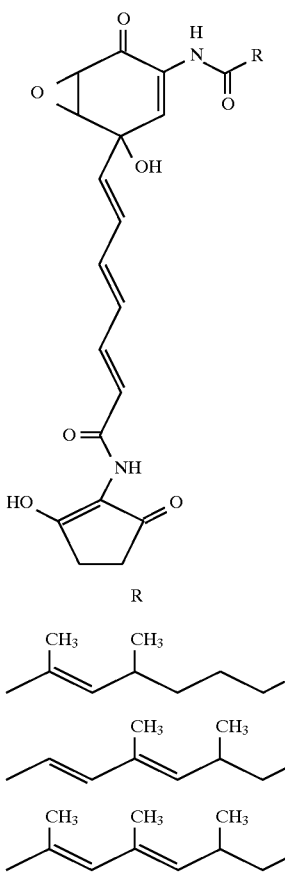

UCF1

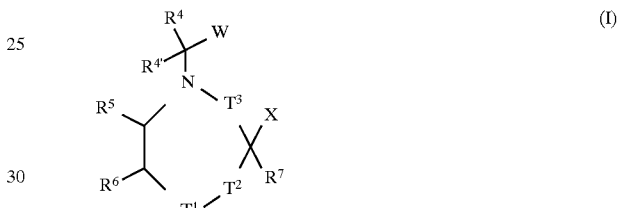

R UCF1-A

UCF1-B

UCF1-C

These inhibitors are reported to have potential application in cancer therapy. See also farnesyl transferase inhibitor OH-4652 (WO 93/24643), and ras-GAP (GTPase activating protein) interaction inhibitors (EP 0 496 162 A2).

Burk et al. WO 92/20336(Merck) also describe nonpeptidyl farnesyltransferase inhibitors prepared by modification of natural products having structures similar to the following compound:

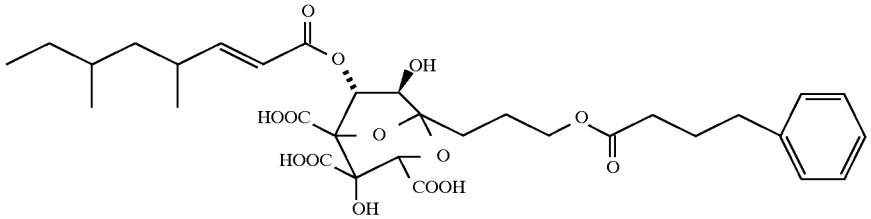

These compounds are reported to be useful in treating cancer, especially colorectal carcinoma, exocrine pancreatic carcinoma, and myloid leukemia.

Benzodiazepines and analogs thereof have been widely exploited as therapeutics, but have not been reported to be inhibitors of farnesylation of G-proteins such as p21$^{ras}$. For example, benzodiazepines are well known as central nervous system (CNS) drugs effecting the neuro-inhibitory postsynaptic GABA receptor and chloride ionophore channel [see e.g., Watjen et al., *J. Med. Chem.* 32:2282–2291 (1989)]. Benzodiazepine analogs have also been employed as intermediates in the synthesis of various anti-HIV-1 compounds [see e.g., Kukla et al., *J. Med. Chem.* 34:3187–3197 (1991)] and as antagonists of gastrin and cholecystokinin (CCK) [see e.g. EP 0 284 256, WO 94/03447, U.S. Pat. No. 5,206,237 and U.S. Pat. No. 5,206,234 assigned to Merck, and Friedinger, *Med. Res, Rev.* 9:271 (1989)]. More recently, benzodiazepine analogs have been reported to be fibrinogen antagonists, inhibiting platelet aggregation [see e.g., WO 93/00095 assigned to Smit Kline Beecham.]

It was therefore an object of this invention to identify nonpeptidyl compounds that more effectively antagonize farnesylation of low molecular weight G-proteins such as p21$^{ras}$ in disease states in animals, preferably mammals, and especially humans. It was a further object of this invention to identify compounds that inhibit isoprenylation of proteins in microorganisms, such as yeast and fungi, that produce disease states in plants or animals, preferably mammals, and especially humans. These and other objects of this invention will be apparent from consideration of the specification and claims as a whole.

SUMMARY OF THE INVENTION

The objects of this invention are accomplished by providing a nonpeptidyl compound represented by structural formula (I):

where $T^1$ is selected from $CR^1R^{1'}$, $CR^1$, $NR^1$, N, O, and $S(O)_u$, where u is 0, 1, or 2;

$T^2$ is selected from $CR^2R^{2'}$, $CR^2$, $NR^2$ and N;

$T^3$ is selected from $CR^3R^{3'}$, $CR^3$, N, and $NR^3$;

$R^1$, $R^{1'}$, $R^2$, $R^{2'}$, $R^3$ and $R^{3'}$ are independently selected from hydrogen, $C_1$–$C_6$alkyl, halo(F, Cl, Br, I)$C_1$–$C_6$alkyl, halo(F, Cl, Br, I), cyclohexyl, cyclohexenyl, phenyl, benzyl, and diphenylmethyl where any phenyl moiety may be substituted with R or R', provided no halo is bonded to any nitrogen;

$R^1/R^{1'}$, $R^2/R^{2'}$, and $R^3/R^{3'}$ each pair taken together may independently form oxo (=O), provided $R^1/R^{1'}$, and $R^2/R^2$ are not simultaneously =O;

$R^4$ and $R^{4'}$ are independently selected from hydrogen, hydroxy, $C_1$–$C_6$alkyl, halo(F, Cl, Br, I), halo(F, Cl, Br, I)$C_1$–$C_6$alkyl, phenyl, and substituted phenyl where the substituents are selected from halo(F, Cl, Br, I), halo(F, Cl, Br, I)$C_1$–$C_6$alkyl, $C_1$–$C_6$alkoxy, and nitro;

$R^5$ and $R^6$ are independently selected from hydrogen, $C_1$–$C_6$alkyl, halo(F, Cl, Br, I)$C_1$–$C_6$alkyl, phenyl, diphenylmethyl and substituted phenyl where the substituents are selected from halo(F, Cl, Br, I) and nitro, optionally, $R^5$ and $R^6$ together with the carbons to which they are bonded may form a fused ring represented by

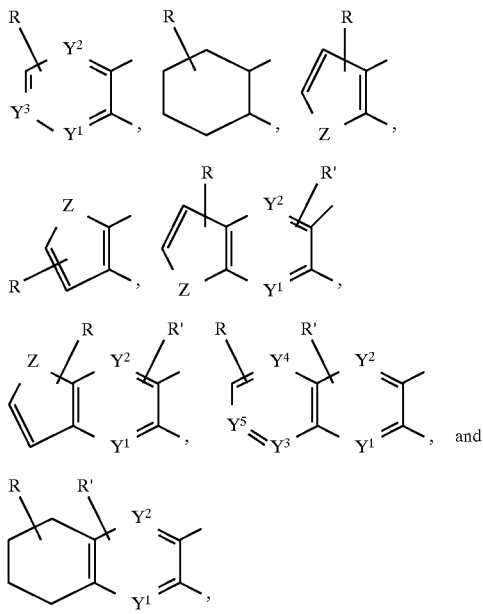

$R^5$, $R^6$, and $R^1$ together with the carbons to which they are bonded may form a fused ring system represented by

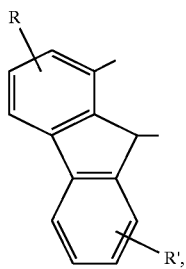

R and R' are one to three optional groups independently selected from hydrogen, halo(F, Cl, Br, I), cyano, carboxamido, carbamoyloxy, carboxy$C_1$–$C_{12}$alkyl, formyloxy, formyl, azido, nitro, ureido, thioureido, hydroxy, mercapto, sulfonamido, and an optionally substituted radical selected from $C_1$–$C_{12}$alkyl, $C_2$–$C_{12}$alkenyl, $C_3$–$C_{12}$alkynyl, $C_3$–$C_{12}$cycloalkyl, $C_6$–$C_{14}$aryl, $C_6$–$C_{10}$aryl-$C_1$–$C_8$alkyl, $C_1$–$C_{12}$alkyloxy, $C_6$–$C_{14}$aryloxy, and $C_1$–$C_{12}$alkanoylamino, where the substituents are selected from halo(F, Cl, Br, I), cyano, azido, nitro, hydroxy, mercapto, sulfonamido, ureido, thioureido, carboxamido, carbamoyloxy, formyloxy, formyl, $C_1$–$C_4$alkyl, $C_1$–C4alkoxy, phenyl, and phenoxy;

X is an amino or lower alkyl substituted amino group bonded to the α-carboxy moiety of any α-amino acid preferably an L-α-amino acid where the free α-amino group and any side chain group may optionally be protected, preferably selected from the group —$NR^{24}$—$C(=O)$—$R^{25}$, —$NR^{24}$—$C(=O)$—$R^8$, —$NR^{24}$—$C(=O)NR^{7'}R^8$, —$NR^{24}$—$C(=O)O$—$R^8$, —$NR^{24}$—$C(=O)S$—$R^8$, —$(CH_2)_{1-4}$—$NR^{24}$—$C(=O)$—$R^{25}$, —$(CH_2)_{1-4}$—$C(=O)$—$R^{25}$, —$(CH_2)_{1-4}$—$C(=O)NH$—$R^{25}$, —$(CH_2)_{0-4}$—$NR^{24}$—$CH(OH)$—$R^{25}$, —$CHR^{24}$phenyl—$R^{25}$, —$CHR^{24}$phenoxy—$R^{25}$, —$CHR^{24}$—O—$R^{25}$, —$(CH_2)_{0-4}$—$NR^{24}$—$CH_2$—$R^{25}$, —$(CH_2)_{0-4}$—$NR^{24}$—$S(O)_u$—$R^{25}$ where u is 0, 1, or 2, —$CHR^{24}$—$CH_2R^{25}$, —$CHR^{24}$—$R^{25}$, —$CR^{24}$=$CHR^{25}$ (E or Z), —$(CH_2)_{0-4}$—$C_6$–$C_{10}$aryl—$R^{25}$, —$(CH_2)_{0-4}$-heterocycle—$R^{25}$, —$C_1$–$C_2$haloalkyl—$C_6$–$C_{10}$aryl—$R^{25}$, and —$C_1$–$C_2$haloalkyl-heterocycle—$R^{25}$, where any heterocyde is a 5- or 6-member saturated or unsaturated ring containing 1 to 3 heteroatoms selected from O, N, and S;

X together with the carbon to which it is bound and $T^2$ may form a heterocycle, where the heterocyde is a 5 or 6-member saturated or unsaturated fused ring having from 1–3 hetero atoms selected from O, N, and S, where any carbon atom of the heterocycle is optionally substituted with oxo (=O) or R;

$Y^1$, $Y^2$, $Y^3$, $Y^4$ and $Y^5$ are independently selected from CH, CR, CR', and N;

Z is S or O;

W is selected from the group C('O)—$NR^{7'}R^8$, $CH_2$—C(=O)—$NR^{7'}R^8$, C(=O)—O—$R^8$, $CR^{8'}$(OH)—$CHR^7R^8$, $CHR^{8'}$—$CHR^7R^8$, $CR^{8'}$=$CR^7R^8$ (E or Z), C(=O)—$CHR^7R^8$, $CHR^{8'}$—$NR^{7'}R^8$, $CHR^{8'}$—O—$R^8$, $CHR^{8'}$—$S(O)_u$—$R^8$ where u is 0, 1, or 2, $CR^{8'}$=N—$R^8$, $CHR^{8'}$—$R^8$, W', $C_1$–$C_4$alkyl—Z—$C_1$–$C_4$alkyl—W', where Z is S or O, $C_1$–$C_4$alkyl—Z—$C_6$–$C_{12}$aryl—W', where Z is S or O, $C_1$–$C_3$alkyl—W', $C_6$–$C_{12}$aryl—W', $C_6$–$C_{12}$aryl—$C_1$–$C_3$alkyl-W', heterocyle—W', heterocycle—$C_1$–$C_3$alkyl-W', $C_1$–$C_2$alkyl—$C_6$–$C_{10}$aryl—W', and $C_1$–$C_2$alkyl-heterocycle-W', where any heterocycle is a 5- or 6-member saturated or unsaturated ring containing 1 to 3 heteroatoms selected from O, N, and S;

W/$R^{4'}$ together with W/$R^{3'}$ and the carbon atoms to which they are bound may form heterocycle—W' or heterocycle—$C_1$–$C_6$alkyl —W', where the heterocycle is a 5- or 6-member saturated or unsaturated ring containing 1 to 3 heteroatoms selected from O, N, and S and where the heterocycle is unsubstituted or substituted with one or two substituents selected from the group (i) —OH, (ii) —SH, (iii) —($C_1$–$C_4$alkyl), (iv) —$C_1$–$C_4$alkoxyl, (v) $CF_3$, (vi) halo(F, Cl, Br, I), (vii) $NO_2$, (viii) —COOH, (ix) —COO—($C_1$–$C_4$alkyl), (x) —$NH_2$, (xi) —NH($C_1$–$C_4$alkyl), and (xii) —N($C_1$–$C_4$allyl)$_2$;

W' is selected from one to three substituents selected from the group hydrogen, —$SR^9$, —$SSR^9$, SC(=O)—$R^9$, —$OR^9$, —C(=NH)—$NH_2$, —N=CH—$NH_2$, —NH—CH=NH, $R^8$, and V;

$R^7$ is independently selected from the group hydrogen, $C_1$–$C_4$alkyl, halo(F, Cl, Br, I), and halo(F, Cl, Br, I)$C_1$–$C_4$alkyl;

$R^7$ and X together may form

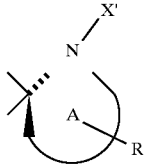

where

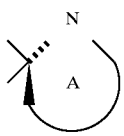

represents a heterocycle bonded to the benzodiazepine moiety through a spiro linkage, where the heterocycle is a 5- or 6-member saturated or unsaturated nitrogen containing ring having from 0 to 2 additional heteroatoms selected from O, N, and S, the ring optionally containing a keto [—C(=O)—] group; and where X' is selected from the group C(=O)—R²⁵, CH(OH)—R²⁵, CHR²⁴—R²⁵, S(O)ᵤ—R²⁵ where u is 0, 1, or 2, CHR²⁴—R²⁵, R²⁵, C₆-C₁₀aryl—R²⁵, heterocycle—R²⁵, C₁-C₂alkyl—C₆-C₁₀aryl—R²⁵, and C₁-C₂alkyl-heterocycle—R²⁵, where any heterocycle is a 5- or 6-member saturated or unsaturated ring containing 1 to 3 heteroatoms selected from O, N, and S;

R⁷' and R⁸' are selected from the group hydrogen, C₁-C₈alkyl, C₂-C₈alkenyl, C₂-C₈alkynyl, C₃-C₁₂cycloalkyl—C₁-C₃alkyl, C₃-C₁₂cycloalkyl, C₁-C₄alkyl—Z—C₁-C₄alkyl, where Z is S or O, C₂-C₄alkyl—NR—C₂-C₄alkyl, C₂-C₄alkyl—C₆-C₁₂aryl, C₂-C₄alkyl—C₆-C₁₂cycloalkyl, C₂-C₈alkenyl, C₆-C₁₂aryl—C₁-C₃alkyl, C₆-C₁₂aryl—C₂-C₄alkynyl, indol—3—yl—C₁-C₃alkyl, and imidazol-4-yl—C₁-C₃alkyl, where any aryl, alkyl, cycloalkyl or alkenyl moiety is optionally substituted with halo(F, Cl, Br, I), or —OR⁹;

R⁷' and R⁸ together with the nitrogen to which they are bonded may form a heterocyclic 5-, 6-, or 7-member ring containing 0, 1, or 2 additional heteroatoms selected from N, S, and O, optionally substituted with one or two groups selected from oxo(=O), —SR⁹, —SSR⁹, SC(=O)—R⁹, —OR⁹, —C(=O)NHOH, —NHR⁹, —C(=O)NR²⁷R²⁸, and —V;

R⁸' together with R³ and R⁸' together with R³' may independently form a divalent radical selected from =CH—, —CH=, —CH₂—, —CH₂—CH₂—, =CH₂—CH₂—, —CH=CH—, and —CH₂—CH=;

R⁸ is selected from the group C₁-C₈alkyl, C₂-C₈alkenyl, C₂-C₈alkynyl, C₃-C₁₂cycloalkyl—C₁-C₄alkyl, C₃-C₁₂cycloalkyl, C₁-C₄alkyl—Z—C₁-C₄alkyl, where Z is S or O, C₂-C₄alkyl—NR⁹—C₂-C₄alkyl, C₂-C₄alkyl—C₆-C₁₂aryl, C₂-C₄alkyl—C₆-C₁₂cycloalkyl, C₂-C₈alkenyl, C₆-C₁₂aryl—C₁-C₄alkyl, C₆-C₁₂aryl—C₂-C₄alkynyl, indol—3—yl—C₁-C₃alkyl, and imidazol-4-yl—C₁-C₃alkyl, where any aryl moiety is optionally substituted with —OR⁹ and V, and where any alkyl or alkenyl group is optionally substituted with one to three groups selected from —SR⁹, —SSR⁹, SC(=O)—R⁹, —OR⁹, —C(=NH)—NH₂, —N=CH—NH₂, —NH—CH=NH, —NH—C(=NH)—NH₂, —C(=O)NHOH, —NHR⁹, —(=O)NR²⁷R²⁸, —C(=O)OR⁹ and V;

V is selected from halo(F, Cl, Br, I), NO₂, CN, CF₃, or a substituted or unsubstituted group selected from (a) —COR¹⁰, (b) —SO₃R¹³, (c) —NHSO₂CF₃, (d) —PO(OR¹³)₂, (e) —SO₂NHR¹⁰, (f) —CONHOR¹³, (g) —C(OH)R¹⁰PO(OR¹³)₂, (h) —CHNR¹⁰, (i) —SO₂NH-heteroaryl where the heteroaryl is a 5- or 6-member aromatic ring containing 1 to 3 heteroatoms selected from O, N, and S and where the heteroaryl is unsubstituted or substituted with one or two substituents selected from the group (i) —OH, (ii) CN, (iii) —(C₁-C₄alkyl), (iv) —C₁-C₄alkoxyl, (v) CF₃, (vi) halo(F, Cl, Br, I), (vii) NO₂, (viii) —COOH, (ix) —COO—(C₁-C₄alkyl), (x) —NH₂, (xi) —NH(C₁-C₄alkyl), and (xii) —N(C₁-C₄alkyl)₂, (j) —CH₂SO₂-heterocycle, (k) —SO₂NHCOR¹⁰, (l) —CH₂SO₂NHCOR¹⁰, (m) —CONHSO₂R¹⁵, (n) —CH₂CONHSO₂R¹⁵, (o) —NHCONHSO₂R¹⁵, (p) —NHSO₂NHCOR¹⁵, (q) —CONHNHSO₂CF₃, (r) CON(OH)R¹³, (s) —CONHCOCF₃, (t) —CONHSO₂R¹⁰, (u) —CONHSO₂R¹¹, (v) —CONHSO₂R¹³,

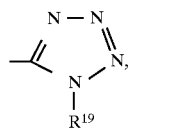 (w)

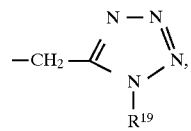 (x)

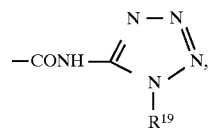 (y)

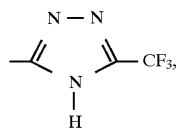 (z)

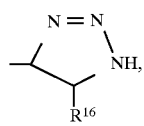 (aa)

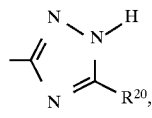 (ab)

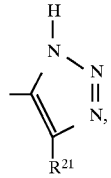 (ac)

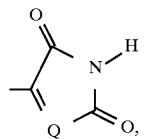 (ad)

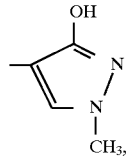 (ae)

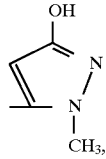 (af)

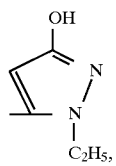 (ag)

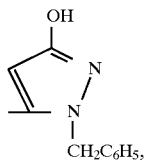

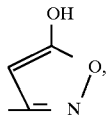

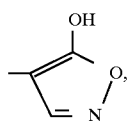

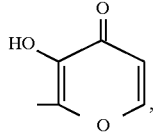

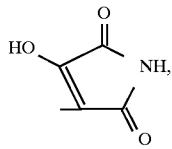

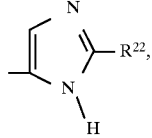

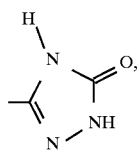

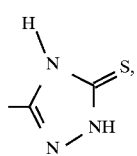

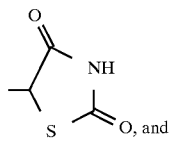

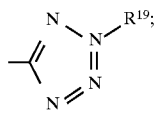

$R^9$ is selected from hydrogen, $C_1$–$C_6$alkyl, cycloalkyl, phenyl, and benzyl;

$R^{10}$ is selected from the group consisting of (a) hydroxy, (b) $C_1$–$C_8$-alkoxy, (c) $C_3$–$C_{12}$-alkenoxy, (d) $C_6$–$C_{12}$-aryloxy, (e) $C_1$–$C_6$-alkyl-$C_6$–$C_{12}$-aryloxy, (f) di-$C_1$–$C_8$-alkylamino-$C_1$–$C_8$-alkoxy, (g) alkanoylamino-$C_1$–$C_8$-alkoxy selected from the group (i) acetylaminoethoxy, (ii) nicotinoylaminoethoxy, and (iii) succinamidoethoxy, (h) $C_1$–$C_8$-alkanoyloxy-$C_1$–$C_8$-alkoxy, (i) $C_6$–$C_{12}$-aryl-$C_1$–$C_8$-alkoxy where the aryl group is unsubstituted or substituted with one to three of the groups (i) nitro, (ii) halo (F, Cl, Br, I), (iii) $C_1$–$C_4$-alkoxy, and (iv) amino, (j) hydroxy-$C_2$–$C_8$-alkoxy, (k) dihydroxy-$C_3$–$C_8$-alkoxy, and (l) $NR^{11}R^{12}$;

$R^{11}$ and $R^{12}$ are independently selected from the group consisting of (a) hydrogen, (b) $C_1$–$C_6$ alkyl, (c) $C_2$–$C_6$ alkanoyl, (d) $C_1$–$C_6$ alkanoyl unsubstituted or substituted with one to three of the groups (i) nitro, (ii) halo (F, Cl, Br, I), (iii) $C_1$–$C_4$-alkoxy, and (iv) amino, and (e) $C_6$–$C_{12}$-aryl-$C_1$–$C_8$-alkyl where the aryl group is unsubstituted or substituted with one to three of the groups (i) nitro, (ii) halo (F, Cl, Br, I), and (iii) $C_1$–$C_4$-alkoxy;

$R^{13}$ is selected from the group consisting of (a) H, (b) $C_1$–$C_6$ alkyl, (c) halo(F, Cl, Br, I)-$C_1$–$C_6$ alkyl, (d) phenyl, (e) benzyl, and (f) $-CH_2-O-COCH_3$;

$R^{14}$ is selected from the group consisting of (a) H, (b) benzyl and (c) $-CH(R^{17})-O-C(O)R^{17}$;

$R^{15}$ is selected from the group consisting of (a) $C_6$–$C_{14}$-aryl, (b) heteroaryl, (c) $(C_3$–$C_7)$-cycloalkyl, (d) $(C_1$–$C_4)$-alkyl, unsubstituted or substituted with a substituent selected from the group consisting of (i) aryl, (ii) heteroaryl, (iii) $-OH$, (iv) $-SH$, (v) $(C_1$–$C_4)$-alkyl, (vi) $(C_1$–$C_4)$-alkoxy, (vii) $(C_1$–$C_4)$-alkylthio, (viii) $-CF_3$, (ix) halo (F, Cl, Br, I), (x) $-NO_2$, (xi) $-CO_2H$, (xii) $CO_2-(C_1$–$C_4)$-alkyl, (xiii) $-NH_2$, (xiv) $-N[(C_1$–$C_4)$-alkyl$]_2$, (xv) $-NH[(C_1$–$C_4)$-alkyl], (xvi) $PO_3H$ and (xvii) $PO(OH)(C_1$–$C_4)$-alkoxy, and (e) $(C_1$–$C_4)$-perfluoroalkyl;

$R^{16}$ is selected from the group consisting of (a) $-CN$, (b) $-NO_2$, (c) $-COOR^{13}$, (d) $C_1$–$C_6$-perfluoroalkyl, and (e) $CF_3$;

$R^{17}$ is independently selected from the group consisting of (a) H, (b) $(C_1$–$C_6)$-alkyl, $(C_2$–$C_6)$-alkenyl, $(C_2$–$C_6)$-alkynyl or $(C_3$–$C_8)$-cycloalkyl, each of which is unsubstituted or substituted with (i) OH, (ii) $(C_1$–$C_4)$-alkoxy, (iii) $CO_2R^{15}$, (iv) $OCOR^{15}$, (v) $CONHR^{15}$, (vi) $CON(R^{15})_2$, (vii) $N(R^{15})C(O)R^{15}$, (viii) $NH_2$, (ix) $(C_1$–$C_4)$-alkylamino, (x) di[$(C_1$–$C_4)$-alkyl]amino, (xi) aryl, and (xii) heteroaryl, (c) $-C(O)-$aryl, (d) $-NO_2$, (e) halo(Cl, Br, I, F), (f) $-OH$, (g) $-OR^{18}$, (h) $(C_1$–$C_4)$-perfluoroalkyl, (i) $-SH$, (j) $-S(O)_{1-2}$ $(C_1$–$C_4)$-alkyl, (k) $CO_2R^{15}$, (l) $-SO_3H$, (m) $-NR^{15}R^{18}$, (n) $-NR^{15}C(O)R^{18}$, (o) $-NR^{15}COOR^{14}$, (p) $-SO_2NHR^{14}$, (q) $-SO_2NR^{15}R^{15}$, (r) $-NHSO_2R^{14}$, (s) $-C(O)NHSO_2R^{14}$, (t) aryl, (u) heteroaryl, (v) morpholin-4-yl, (w) $CONH_2$, and (y) 1H-tetrazol-5-yl;

$R^{18}$ is selected from the group consisting of (a) H and (b) $(C_1$–$C_4)$-alkyl unsubstituted or substituted with (i) $NH_2$, (ii) $NH[(C_1$–$C_4)$-alkyl], (iii) $N[(C_1$–$C_4)$-alkyl$]_2$, (iv) $CO_2H$, (v) $CO_2(C_1$–$C_4)$-alkyl, (vi) OH, (vii) $SO_3H$, and (viii) $SO_2NH_2$;

$R^{19}$ is selected from the group consisting of (a) H, (b) $(C_1$–$C_6)$-alkyl, (c) $(C_2$–$C_6)$-alkenyl, (d) $(C_1$–$C_6)$-alkoxy, (e) $(C_2$–$C_6)$-alkoxyalkyl, (f) $-CH_2-O-COCH_3$, or (g) benzyl, where the phenyl moiety is unsubstituted or substituted with a group selected from $-NO_2$, $-NH_2$, $-OH$, or $-OCH_3$;

$R^{20}$, $R^{21}$, and $R^{22}$ are each independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CH_3$ and $SO_2C_6F_5$, where Q is selected from O, S, $NR^{23}$ and $CH_2$;

$R^{23}$ is selected from hydrogen, $CH_3$, and $CH_2C_6H_5$;

$R^{24}$ is selected from hydrogen, $C_1$–$C_6$alkyl, benzyl, halo (F, Cl, Br, I)benzyl, and halo(F, Cl, Br, I)$C_1$–$C_6$alkyl;

$R^{24}$ and $R^7$ together may form an ethylene, ethenylene, propylene, propenylene, butylene, or butenylene bridge;

$R^{25}$ is selected from $R^{25'}$,

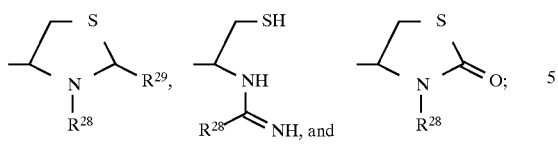

$R^{25'}$ is selected from —SR$^{26}$, —SSR$^{26}$, —OR$^{26}$, —NOR$^{26}$, $C_1$–$C_6$alkyl, $C_2$–$C_6$alkenyl, $C_1$–$C_6$alkylamine, $C_2$–$C_6$alkenylamine, and halo(F, Cl, Br, I)$C_1$–$C_6$alkyl where any allyl or alkenyl moiety is optionally substituted with one to three groups selected from —SR$^{26}$, —SSR$^{26}$, —OR$^{26}$, (C=O)OR$^{26}$, —NOR$^{26}$ C(=NR$^{27}$)—NR$^{27}$R$^{28}$, N=CR$^{27}$—NR$^{27}$R$^{28}$, NR$^{27}$—CR$^{28}$=NR$^{27}$, NR27—C (=NR$^{28}$)—NHR$^{27}$ and —NR$^{27}$R$^{28}$;

$R^{26}$ is selected from hydrogen, $C_1$–$C_6$alkyl, halo(F, Cl, Br, I)$C_1$–$C_6$alkyl, and $C_1$–$C_6$alkanoyl;

$R^{27}$ and $R^{28}$ are independently selected from hydrogen, $C_1$–$C_6$alkyl, (C=O)—NHR$^{29}$, phenyl, napthyl, benzyl, —CH$_2$-napthyl, $C_1$–$C_6$alkanoyl, $C_2$–$C_6$alkanoyl optionally substituted with —COOH and —NH$_2$, $C_1$–$C_6$cycloalkanoyl. $C_6$–$C_{10}$aroyl, $C_6$–$C_{10}$aryol, $C_1$–$C_6$alkanoyl, $C_1$–$C_6$alkylsulfonyl, $C_6$–$C_{10}$arylsulfonyl, $C_6$–$C_{10}$aryl$C_1$–$C_6$alkylcarbamoyl, cinnamoyl, heterocyclecarbonyl, $C_1$–$C_6$alkoxycarbonyl, $C_6$–$C_{10}$aryloxycarbonyl, $C_6$–$C_{10}$aryl$C_1$–$C_6$alkoxycarbonyl, and pyroglutamyl;

$R^{27}$ and $R^{24}$ together may form a diradical selected from —CH$_2$—, —C(=O)—, —CH$_2$—CH$_2$—, and —CH$_2$—C(=O)—;

$R^{27}$ and $R^{28}$ together with the nitrogen atom to which they are bonded may form

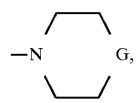

or a cyclic imide represented by

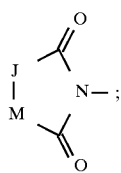

G is selected from —CH$_2$—, O, S(O)$_u$ where u is 0, 1, or 2, and NR$^{28}$;

J—M is selected from $C_2$–$C_4$alkylene and $C_2$–$C_4$alkenylene;

$R^{29}$ is selected from hydrogen, $C_1$–$C_6$alkyl, halo(F, Cl, Br, I)$C_1$–$C_6$alkyl, phenyl, benzyl, and pyridyl where any phenyl moiety may be substituted with halo(F and Cl), —CF$_3$, —NO$_2$, —NH$_2$, —OH, and —OCH$_3$; and pharmaceutically acceptable salts thereof.

Preferably the compounds of this invention are selected from those represented by structural formulae II-X:

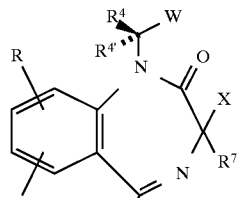
(II)

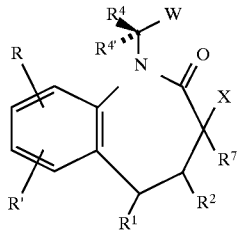
(III)

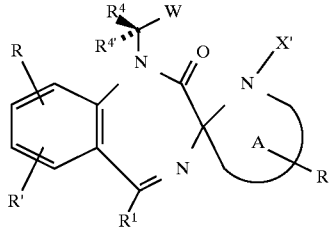
(IV)

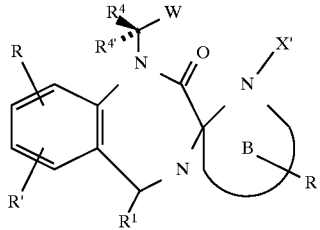
(V)

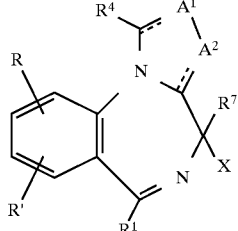
(VI)

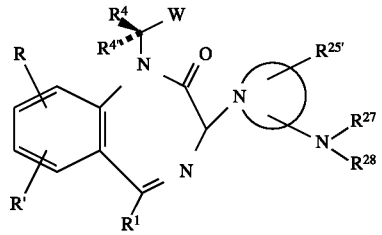
(VII)

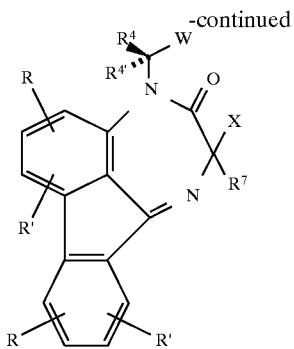 (VIII)

represents a heterocycle bonded to the benzodiazepine moiety through a ring nitrogen, where the heterocycle is a 5- or 6-member saturated or unsaturated nitrogen containing ring having from 0 to 2 additional heteroatoms selected from O, N, and S, the ring optionally containing a keto [—C(=O)—] group;

(IX)

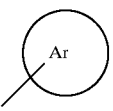

represents $C_6$–$C_{10}$ aryl or a heteroaryl where the heteroaryl is a 5- or 6-member aromatic ring containing 1 to 3 heteroatoms selected from O, N, and S, the $C_6$–$C_{10}$ aryl or heteroaryl is optionally substituted with V and $R^8$;

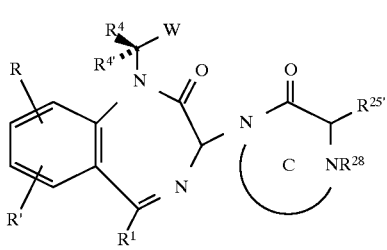 (X)

$A^1$ and $A^2$ are independently selected from CRR', CR', $CRR^8$, $CR^8$, N, O, and S provided one of $A^1$ and $A^2$ is $CRR^8$ or $CR^8$; and ===represents a single of double bond.

Other preferred compounds of the instant invention are represented by formulae (IIa)–(IIIa):

where R, R', $R^1$, $R^4$, $R^{4'}$, $R^7$, $R^{7'}$, $R^8$, $R^{8'}$, $R^9$, $R^{10}$, $R^{11}$, $R^{12}$, $R^{13}$, $R^{15}$, $R^{16}$, $R^{19}$, $R^{24}$, $R^{25}$, $R^{25'}$, $R^{26}$, $R^{27}$, $R^{28}$, $R^{29}$, W, W', V, X, X', G, and J–M are defined above;.

Optionally, $R^1$ and $R^2$ taken together may form a covalent bond or fused benzene substituted with R and R';

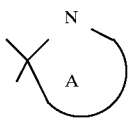

represents a heterocycle bonded to the benzodiazepine moiety through a spiro linkage, where the heterocycle is a 5- or 6-member saturated or unsaturated nitrogen containing ring having from 0 to 2 additional heteroatoms selected from O, N, and S, the ring optionally containing a keto [—C(=O)—] group;

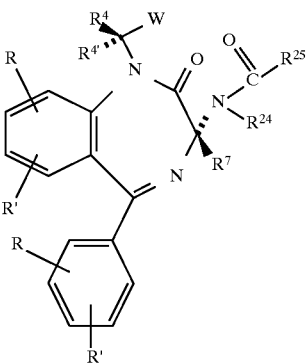 (IIa)

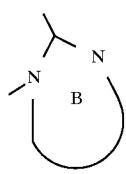

represents a heterocycle fused to the benzodiazepine moiety, where the heterocycle is a 5- or 6-member saturated or unsaturated di-nitrogen containing ring having from 0 to 1 additional heteroatom selected from O, N, and S, the ring optionally containing a keto [—C(=O)—] group;

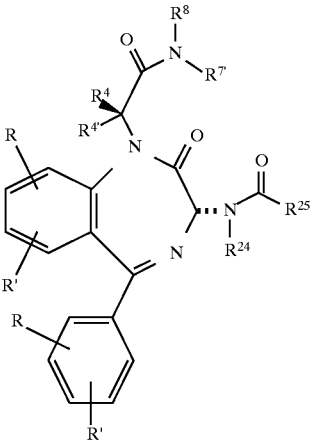 (IIb)

-continued

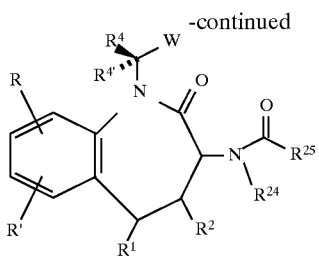

(IIIa)

Where R and R' are independently selected from the group hydrogen, halo(F, Cl, Br, I), halo(F, Cl, Br, I)$C_1$–$C_6$ alkyl, and $C_1$–$C_6$ alkoxy;

$R^4$ and $R^{4'}$ are independently selected from hydrogen, halo(F, Cl, Br, I), $C_1$–$C_6$ alkyl, and halo(F, Cl, Br, I)$C_1$–$C_6$ alkyl, $R^7$ is hydrogen;

$R^{7'}$ is selected from the group hydrogen, $C_1$–$C_6$alkyl, $C_6$–$C_{10}$aryl-$C_1$–$C_4$alkyl, and halo(F, Cl, Br, I)$C_1$–$C_4$alkyl, where any alkyl or aryl moiety is optionally substituted with V;

$R^8$ is selected from the group unsubstituted and substituted $C_1$–$C_8$alkyl, phenyl-$C_1$–$C_3$alkyl, indol-3-yl-$C_1$–$C_3$alkyl, and imidazol-4-yl-$C_1$–$C_3$alkyl, where any phenyl moiety is optionally substituted with —$OR^9$ and where any alkyl group is optionally substituted with one or two groups selected from —$SR^9$, —$SSR^9$, —$SC(=O)$—$R^9$, —$OR^9$, —$C(=O)NHOH$, —$NHR^9$, —$C(=O)NR^{27}R^{28}$, and —V;

$R^9$ is selected from hydrogen, $C_1$–$C_6$alkyl, cycloalkyl, phenyl, and benzyl, preferably t-butyl and cyclohexyl;

V is selected from the group —$COR^{10}$, halo(F, Cl, Br, I), CN, $NO_2$, and

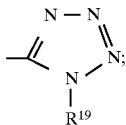

$R^{10}$ is selected from the group hydroxy, $C_1$–$C_8$-alkoxy and $C_3$–$C_6$ cycloalkyl;

$R^{19}$ is selected from hydrogen, $C_1$–$C_6$-alkyl, and halo(F, Cl, Br, I)$C_1$–$C_6$-alkyl;

W is selected from the group $C(=O)$—$NR^{7'}R^8$, $CH_2$—$C(=O)$—$NR^{7'}R^8$, $C(=O)$—$O$—$R^8$, $CR^{8'}(OH)$—$CHR^7R^8$, $CHR^{8'}$—$CHR^7R^8$, $CR^{8'}=CR^7R^8$ (E or Z), $C(=O)$—$CHR^7R^8$, $CHR^{8'}$—$NR^{7'}R^8$, $CHR^{8'}$—$O$—$R^8$, $CHR^{8'}$—$S(O)_u$—$R^8$ where u is 0, 1, or 2, $CR^{8'}=N$—$R^8$, $CHR^{8'}$—$R^8$, W', $C_1$–$C_4$alkyl—Z—$C_1$–$C_4$alkyl-W', where Z is S or O, $C_1$–$C_4$alkyl—Z—$C_6$–$C_{12}$aryl-W', where Z is S or O, $C_1$–$C_3$alkyl—W', $C_6$–$C_{12}$aryl-W', $C_6$–$C_{12}$aryl-$C_1$–$C_3$alkyl-W', heterocycle-W', heterocycle-$C_1$–$C_3$alkyl-W', $C_1$–$C_2$alkyl-$C_6$–$C_{10}$aryl-W', and $C_1$–$C_2$alkyl-heterocycle-W', where any heterocycle is a 5- or 6-member saturated or unsaturated ring containing 1 to 3 heteroatoms selected from O, N, and S;

W' is selected from one to three substituents selected from the group hydrogen, —$SR^9$, —$SSR^9$, $SC(=O)$—$R^9$, —$OR^9$, —$C(=NH)$—$NH_2$, —$N=CH$—$NH_2$, —$NH$—$CH=NH$, $R^8$, and V;

X is selected from the group —$NR^{24}$—$C(=O)$—$R^{25}$, —$NR^{24}$—$C(=O)$—$R^8$, —$NR^{24}$—$C(=O)NR^{7'}R^8$, —$NR^{24}$—$CH(OH)$—$R^{25}$, —$NR^{24}$—$CH_2$—$R^{25}$, —$NR^{24}$—$S(O)_u$—$R^{25}$ where u is 0, 1, or 2, —$CHR^{24}$—$CH_2R^{25}$, —$CHR^{24}$—$R^{25}$, —$CR^{24}=CHR^{25}$ (E or Z), —$C_6$–$C_{10}$aryl-$R^{25}$, -heterocycle-$R^{25}$, —$C_1$–$C_2$alkyl-$C_6$–$C_{10}$aryl-$R^{25}$, and —$C_1$–$C_2$alkyl-heterocycle-$R^{25}$, where any heterocycle is a 5- or 6-member saturated or unsaturated ring containing 1 to 3 heteroatoms selected from O, N, and S;

$R^{24}$ is selected from $C_1$–$C_6$alkyl, benzyl, and halo(F, Cl, Br, I)$C_1$–$C_6$alkyl, preferably methyl;

$R^{25}$ is selected from $R^{25'}$,

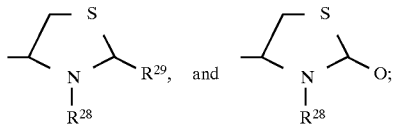

$R^{25'}$ is selected from —$SR^{26}$, —$SSR^{26}$, —$OR^{26}$, —(C=O)$NOR^{26}$, $C_1$–$C_6$alkyl, $C_6$–$C_{12}$aryl$C_1$–$C_6$alkyl, $C_2$–$C_6$alkenyl, $C_1$–$C_6$alkylamine, $C_2$–$C_6$alkenylamine, and halo(F, Cl, Br, I)$C_1$–$C_6$alkyl where any alkyl or alkenyl moiety is optionally substituted with —$SR^{26}$, —$SSR^{26}$, —$OR^{26}$, —(C=O)$NOR^{26}$ and —$NR^{27}R^{28}$, and where any amine moiety is optionally substituted with $R^{27}$ or $R^{28}$;

$R^{25''}$ is selected from hydrogen, $C_1$–$C_6$alkyl, halo(F, Cl, Br, I)$C_1$–$C_6$alkyl, $C_6$–$C_{12}$aryl, $C_6$–$C_{12}$aryl$C_1$–$C_6$alkyl, where any alkyl or aryl moiety may optionally be substituted with a group selected from —$SR^{26}$, —$SSR^{26}$, —$OR^{26}$, $COR^{10}$, and $NOR^{26}$;

$R^{26}$ is selected from hydrogen, $C_1$–$C_6$alkyl, halo(F, Cl, Br, I)$C_1$–$C_6$alkyl, and $C_1$–$C_6$alkanoyl;

$R^{27}$ and $R^{28}$ are independently selected from hydrogen, $C_1$–$C_6$alkyl, phenyl, napthyl, benzyl, —$CH_2$-napthyl, $C_1$–$C_6$alkanoyl, $C_1$–$C_6$cycloalkanoyl, $C_6$–$C_{10}$aroyl, $C_6$–$C_{10}$aryl$C_1$–$C_6$alkanoyl, $C_1$–$C_6$alkylsulfonyl, $C_6$–$C_{10}$arylsulfonyl, $C6$–$C_{10}$aryl$C_1$–$C_6$alkykarbamoyl, cinnamoyl, heterocyclecarbonyl, $C_1$–$C_6$alkoxycarbonyl, $C_6$–$C_{10}$aryloxycarbonyl, $C_6$–$C_{10}$aryl$C_1$–$C_6$alkoxycarbonyl, and pyroglutamyl;

$R^{27}$ and $R^{28}$ together with the nitrogen atom to which they are bonded may form a cyclic amine represented by

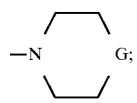

G is selected from —$CH_2$—, O, $S(O)_u$ where u is 0, 1, or 2, and $NR^{28}$, and pharmaceutically acceptable salts thereof.

Highly preferred compounds of this invention include;

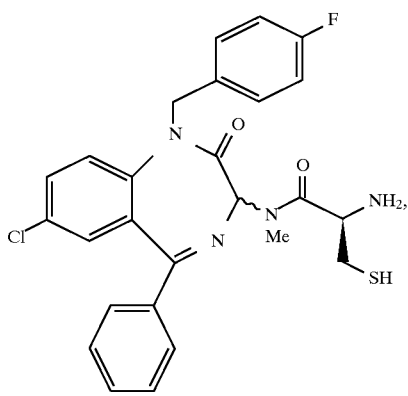

-continued
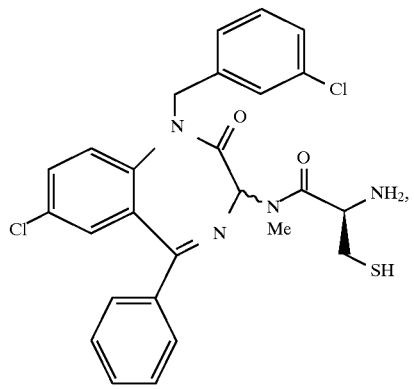
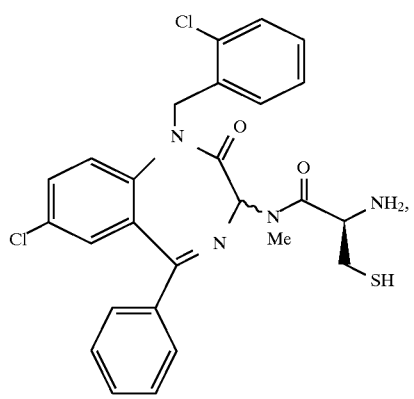
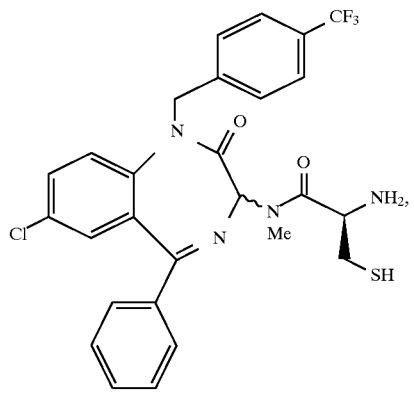
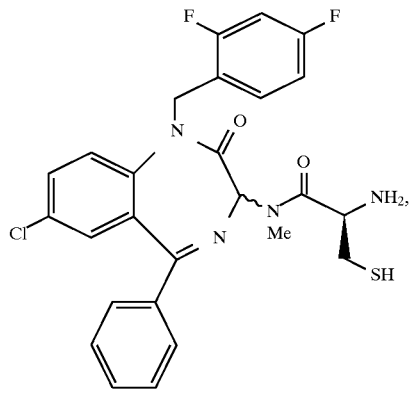
-continued
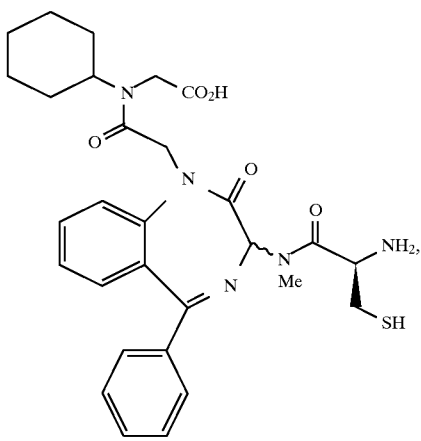
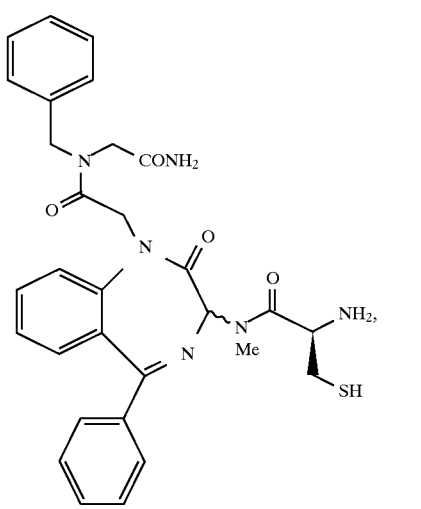
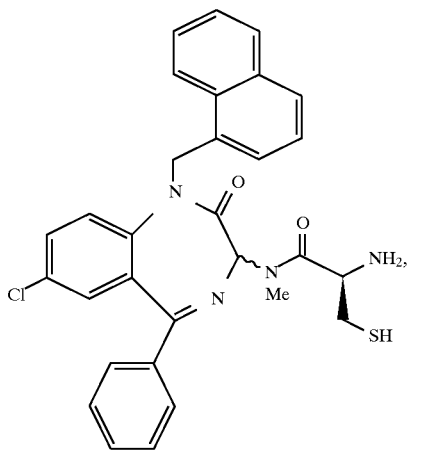

-continued
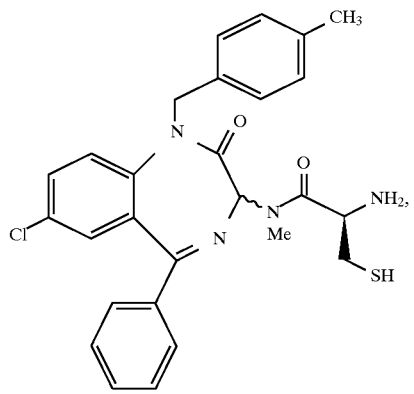
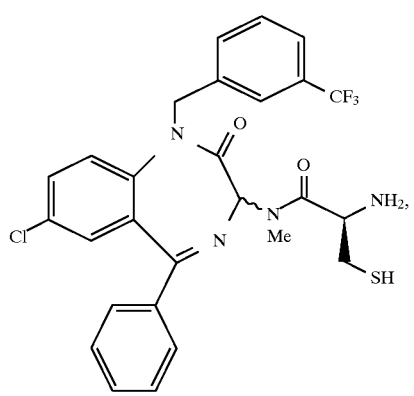
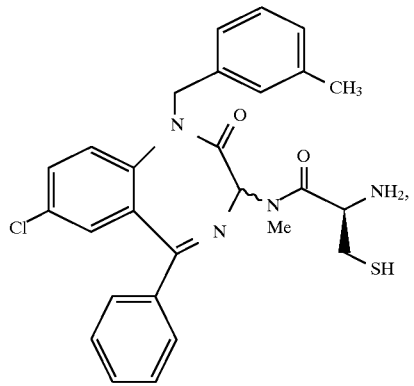
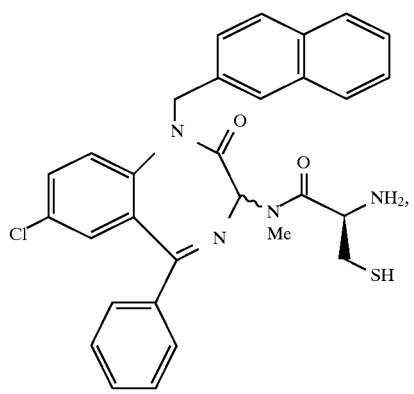
-continued
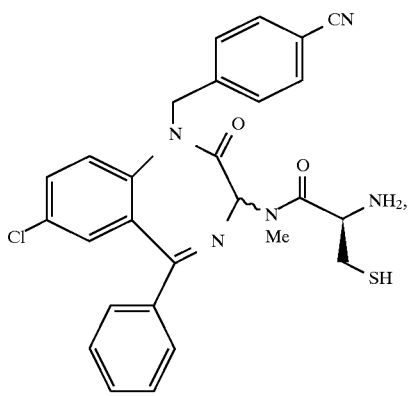
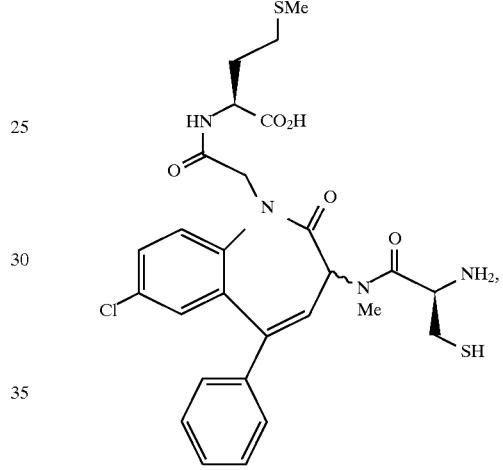
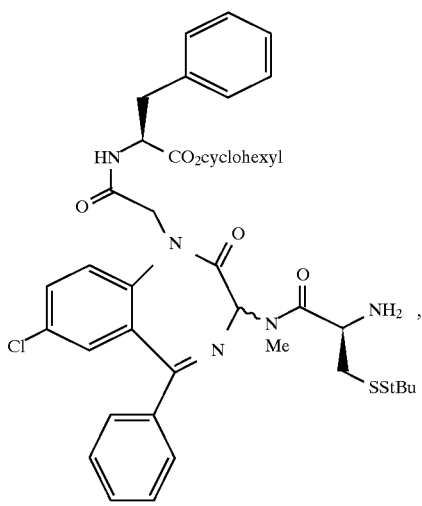

21
-continued
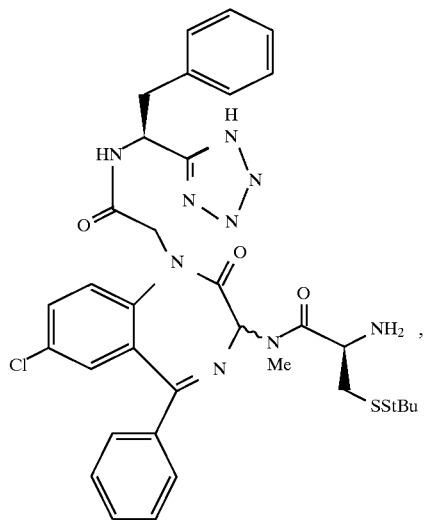
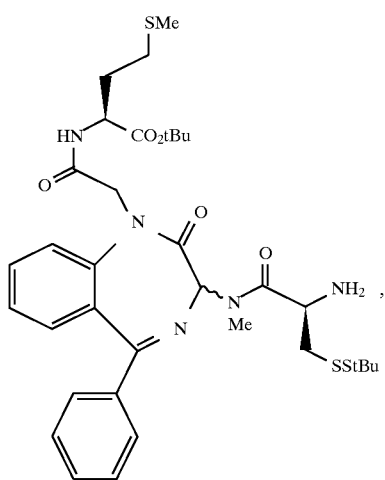
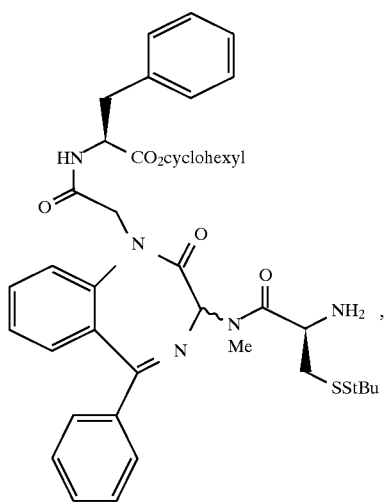
22
-continued
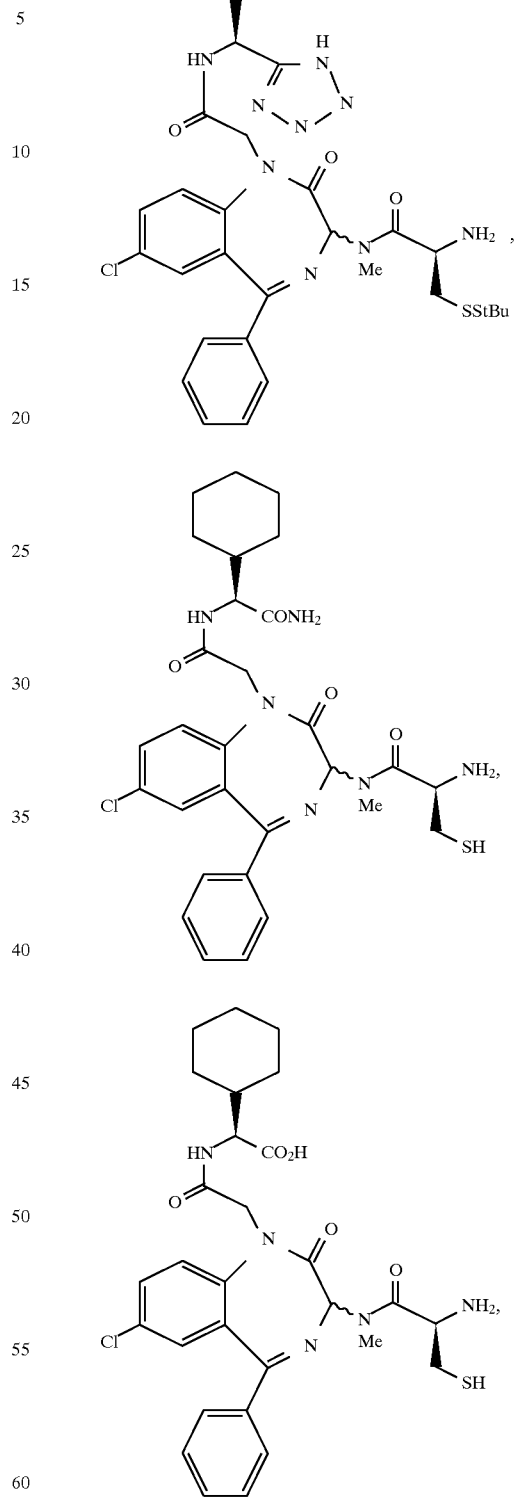

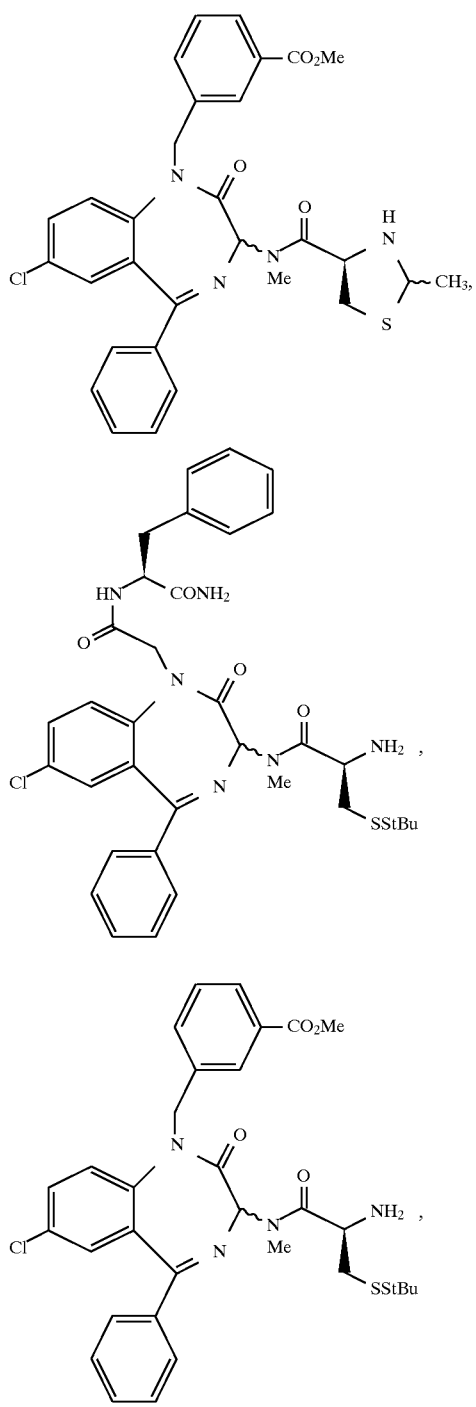
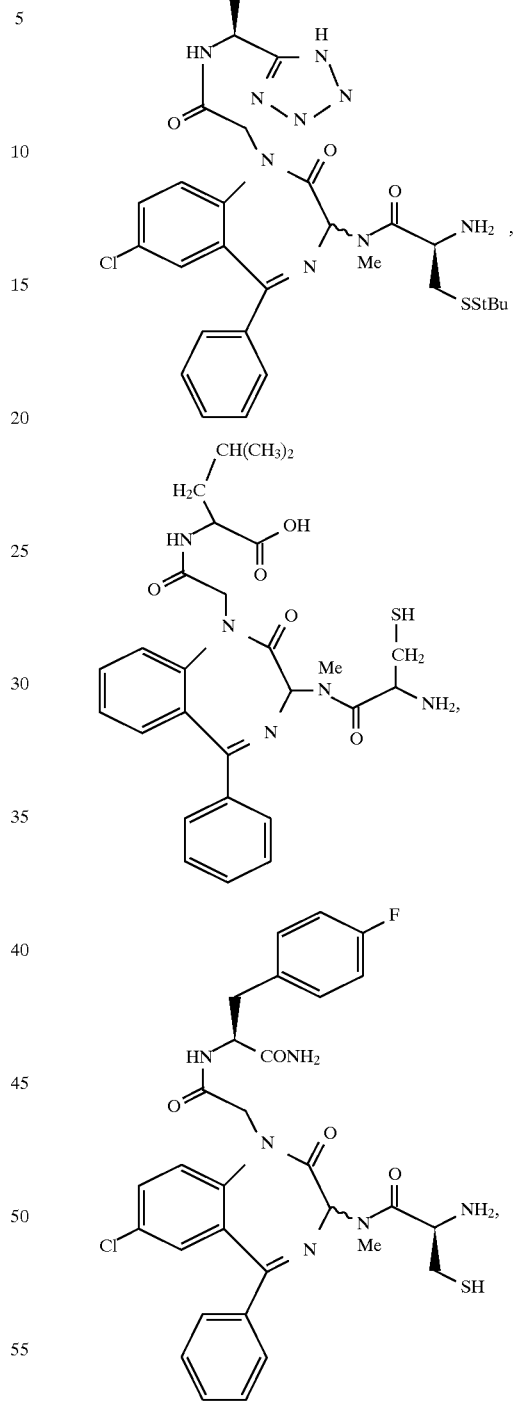

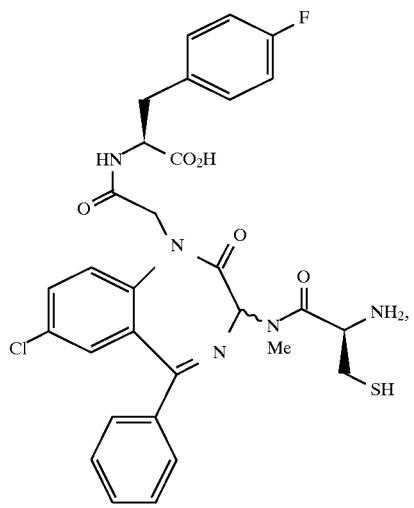
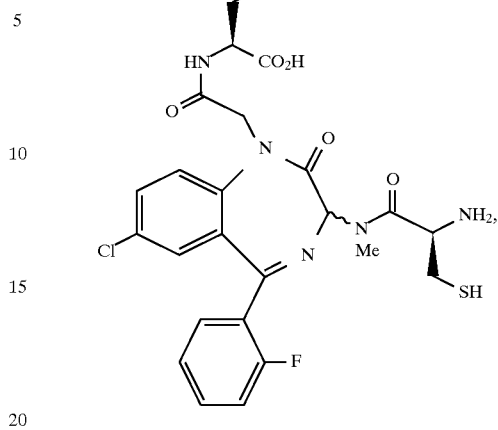
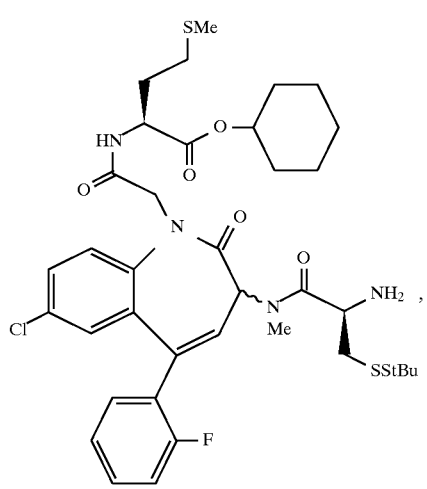
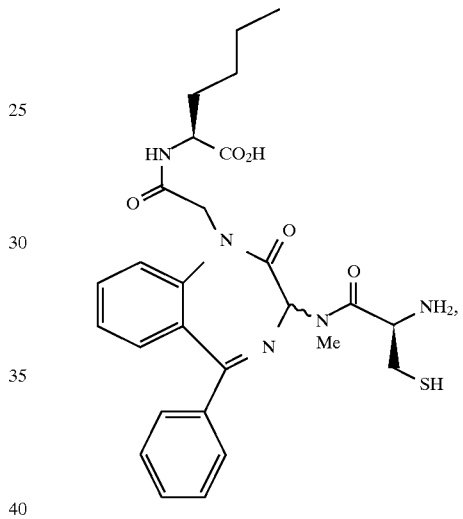
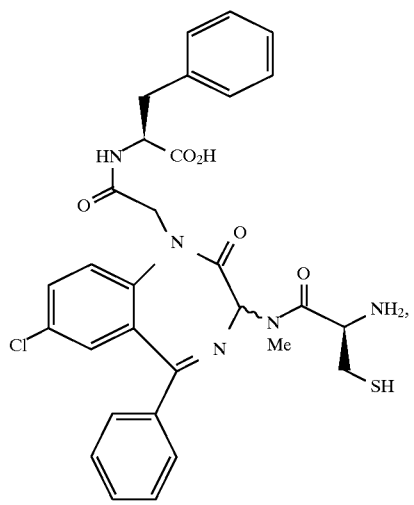
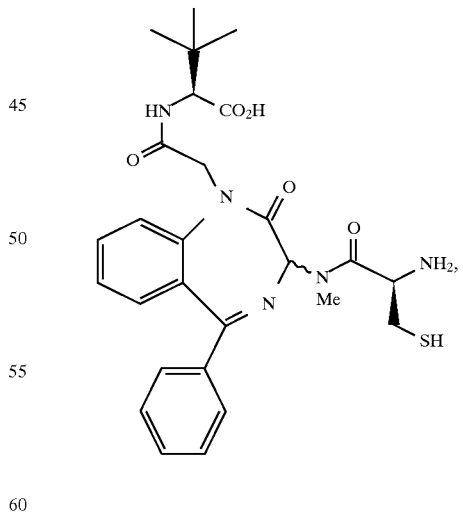

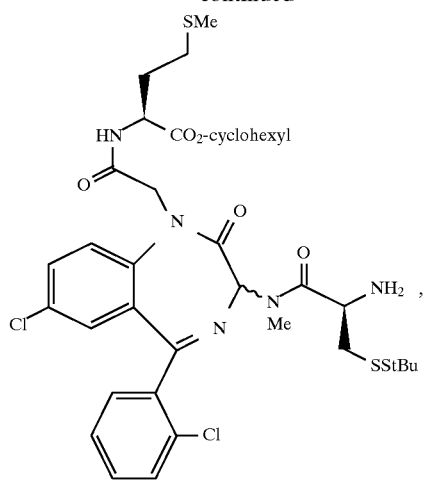
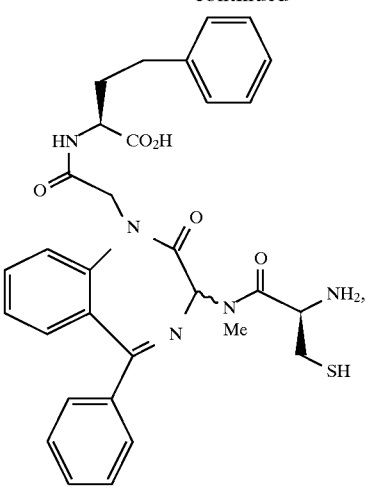
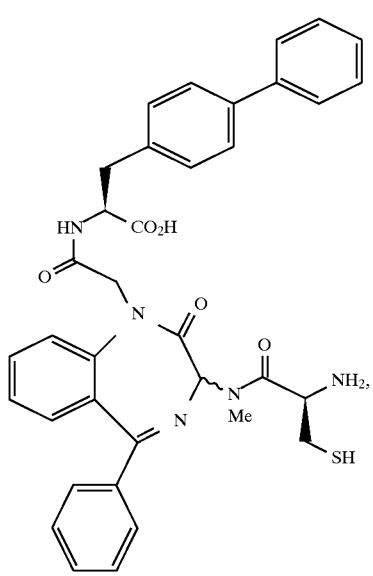
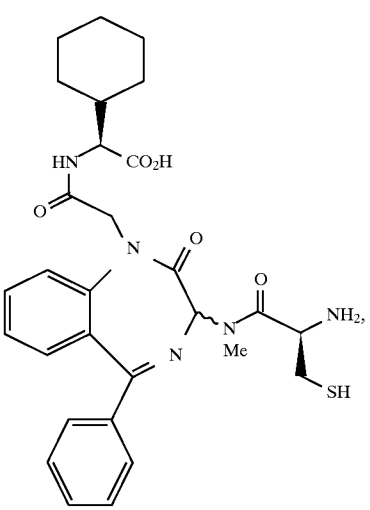
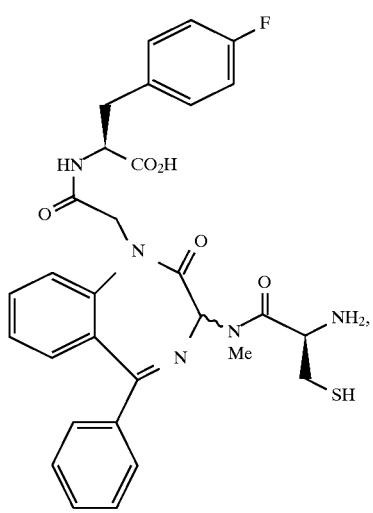
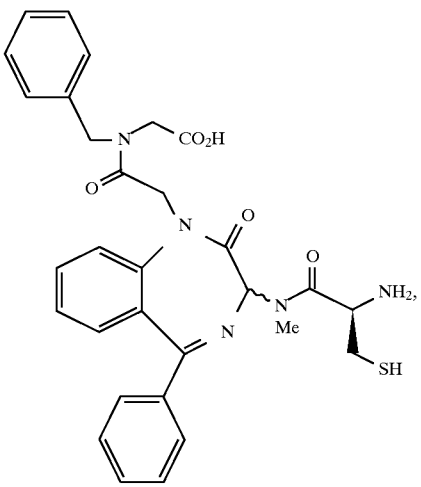

29
-continued
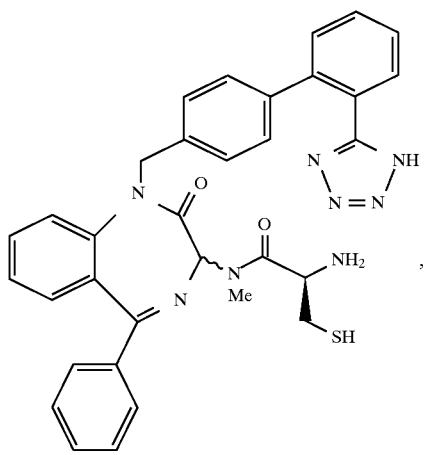
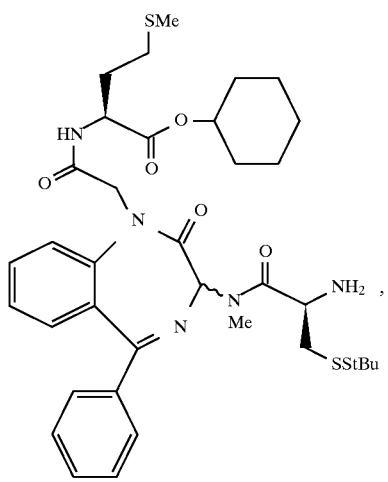
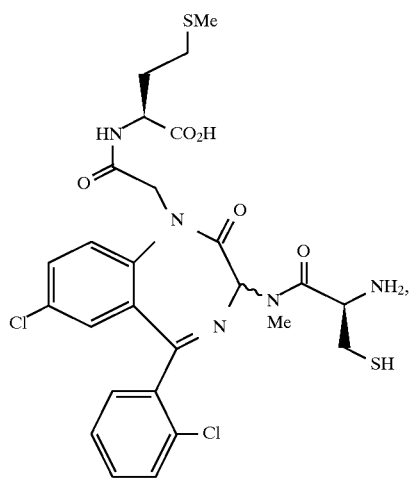
30
-continued
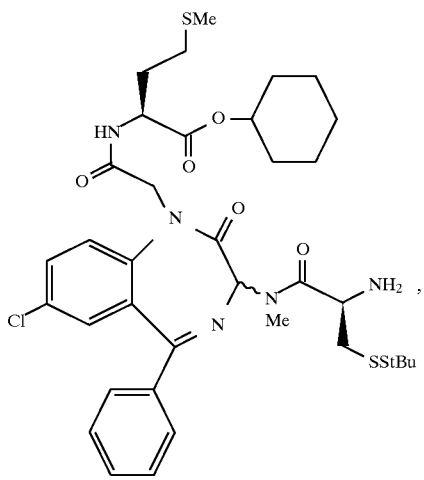
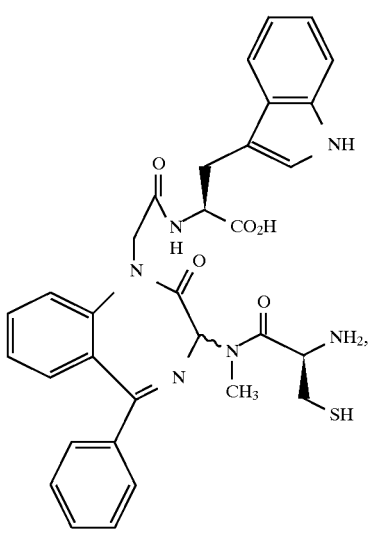
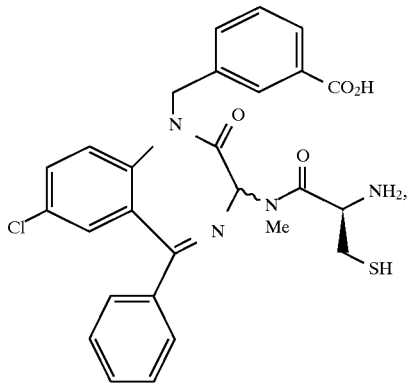

31
-continued
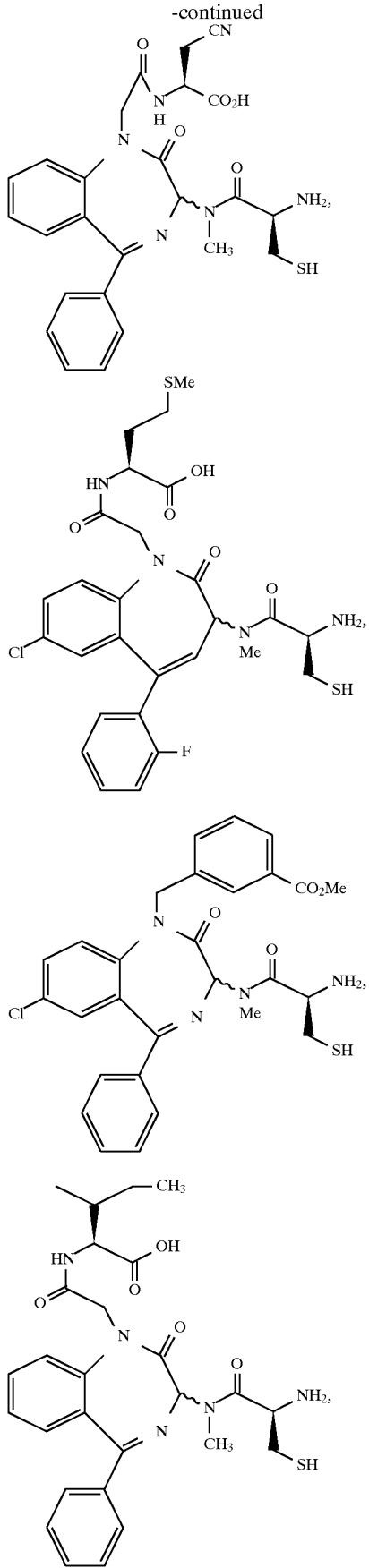
32
-continued
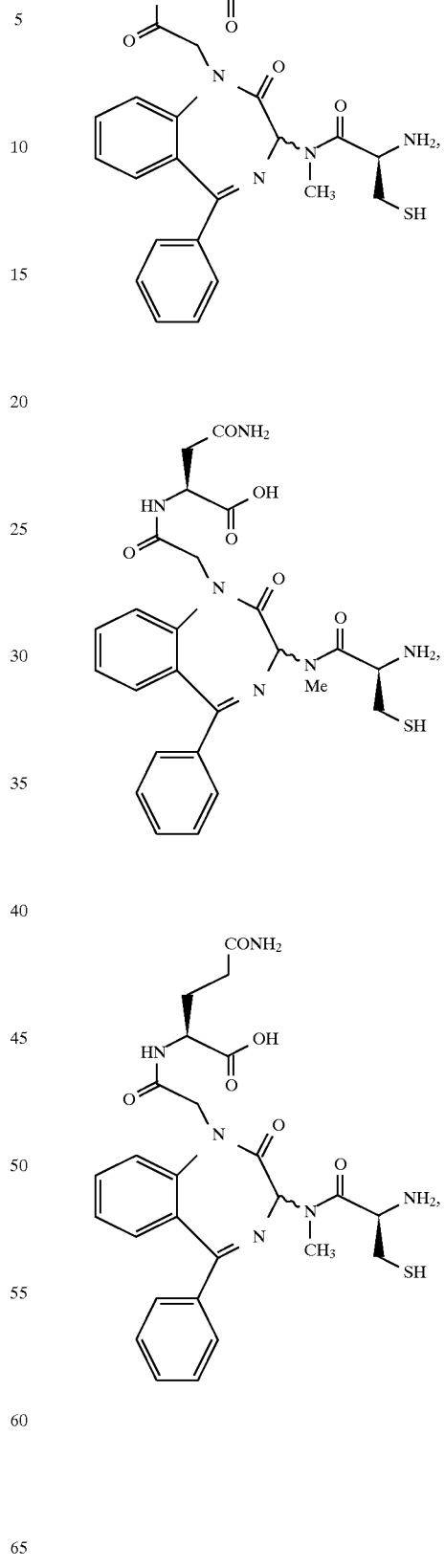

33
-continued
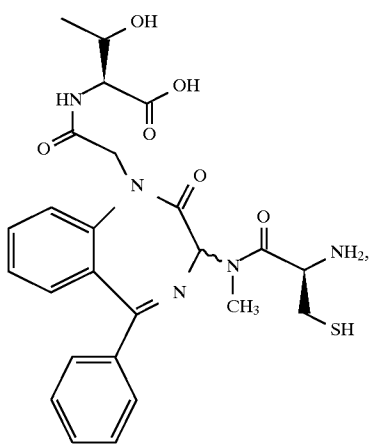
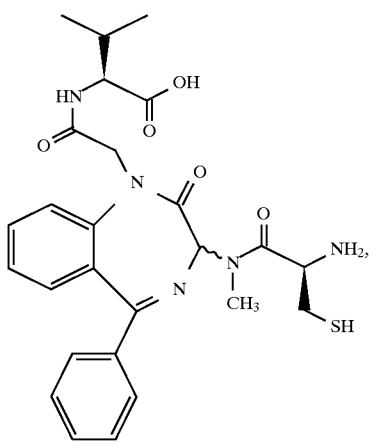
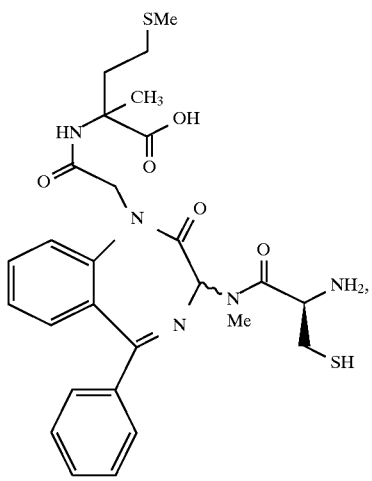
34
-continued
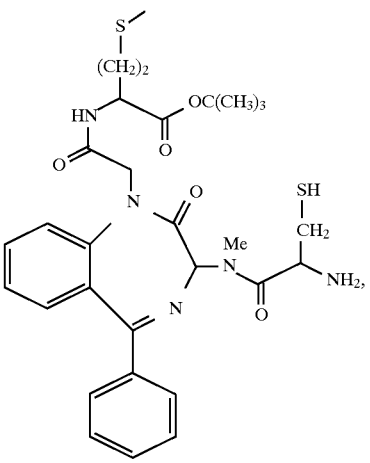
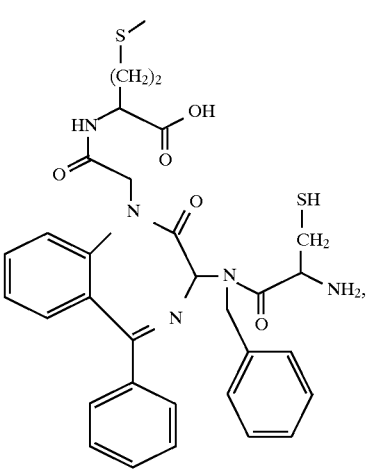
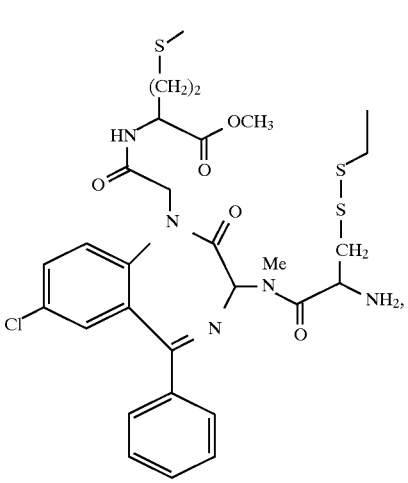

35
-continued
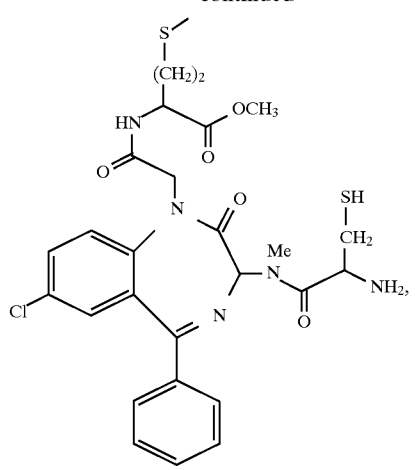
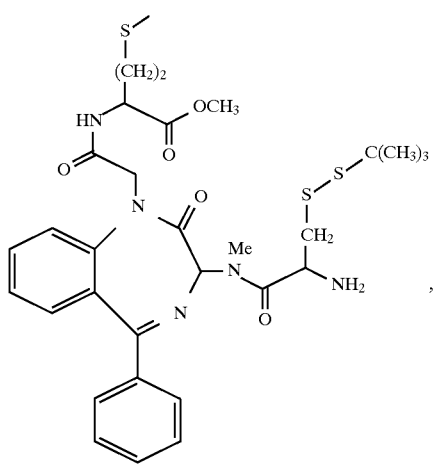
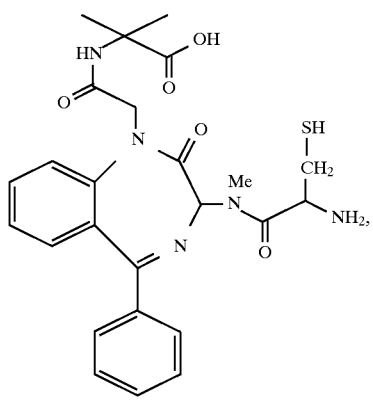
36
-continued
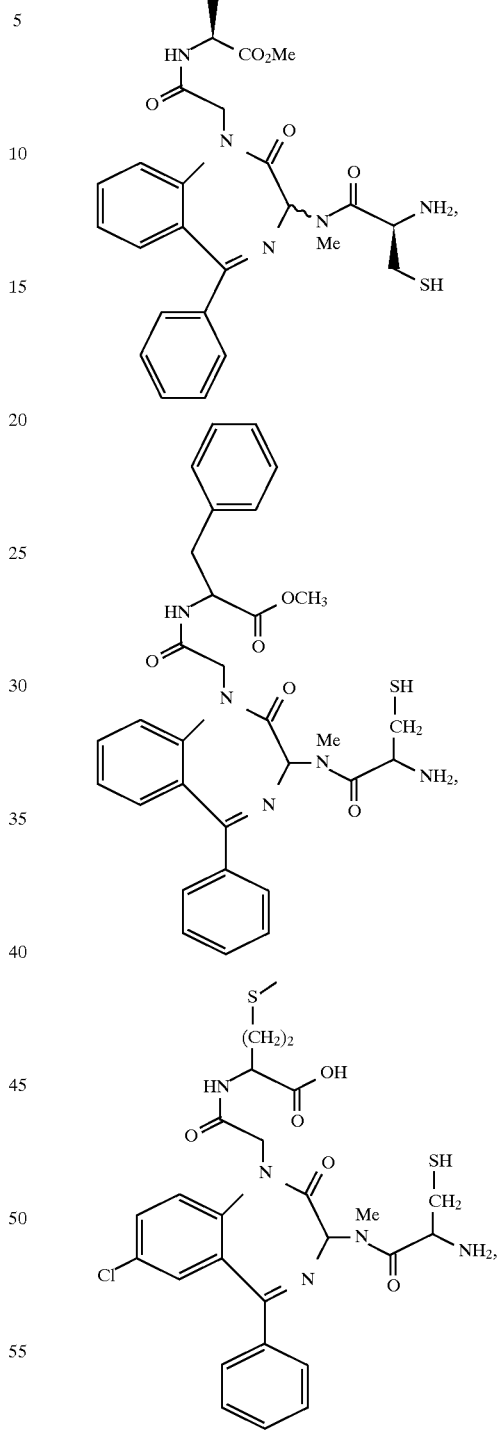

37
-continued
38
-continued
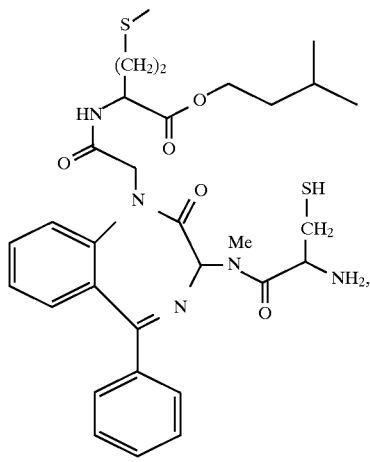
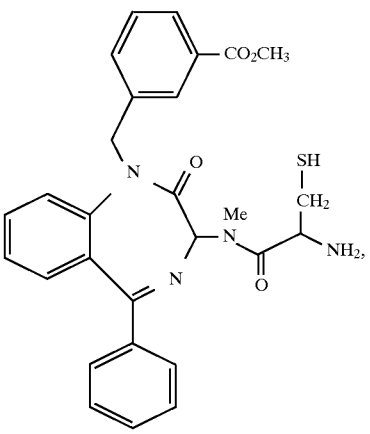
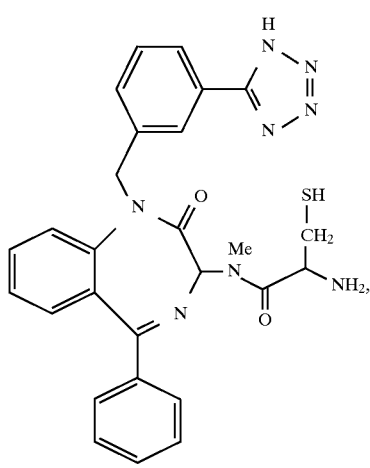
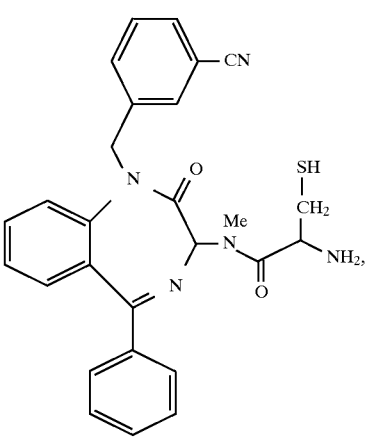
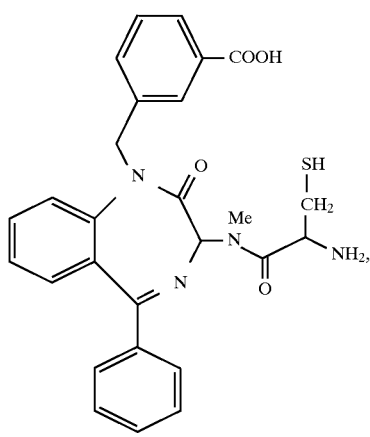
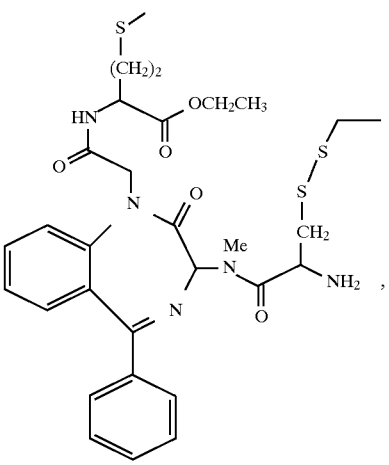

39
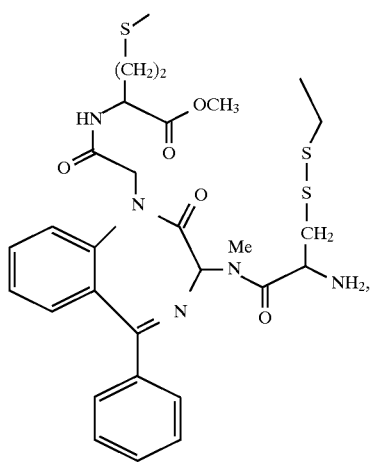
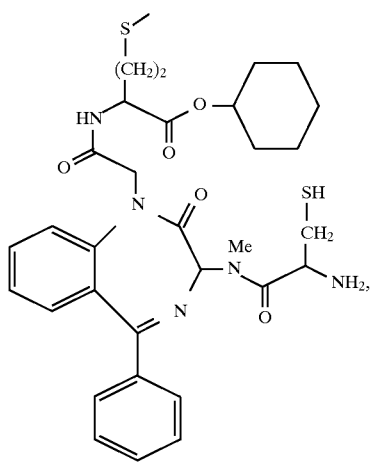
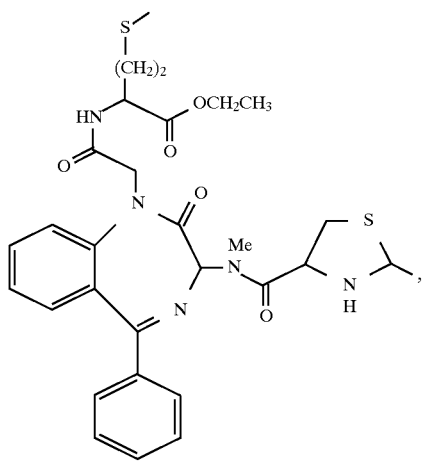
40
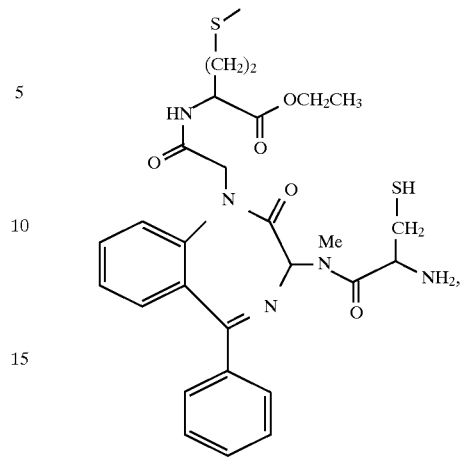
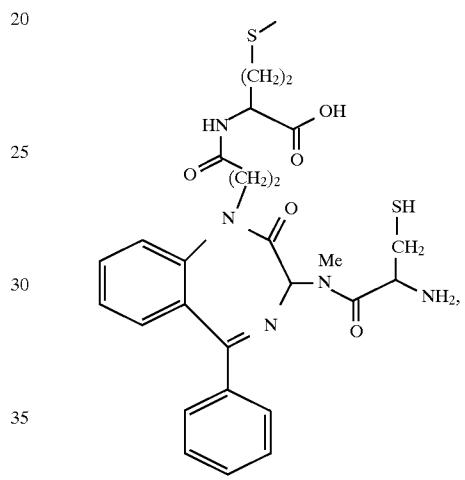
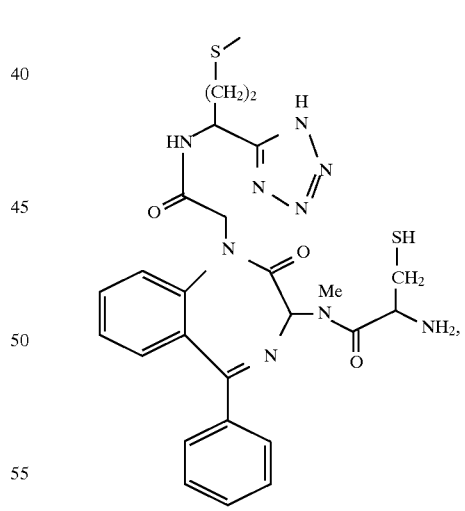

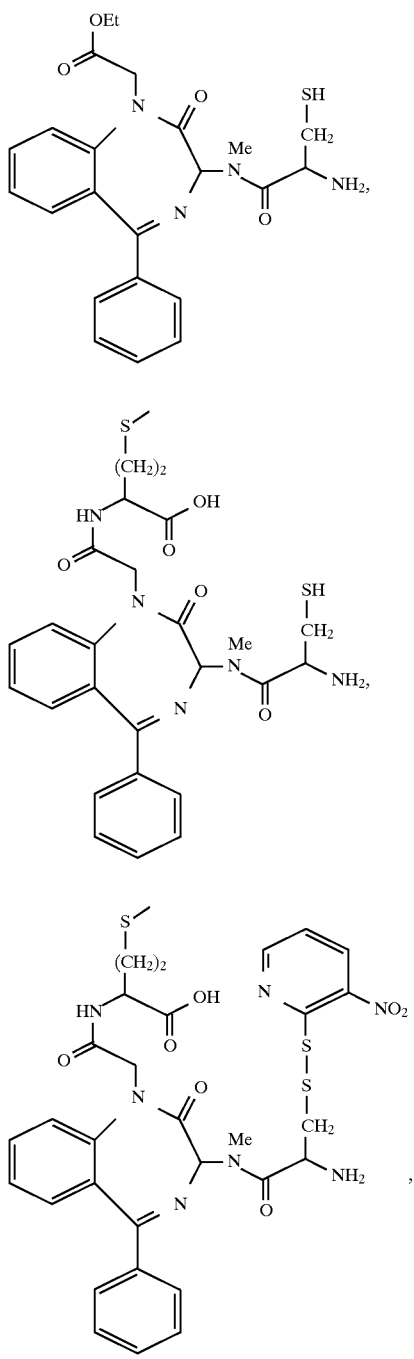
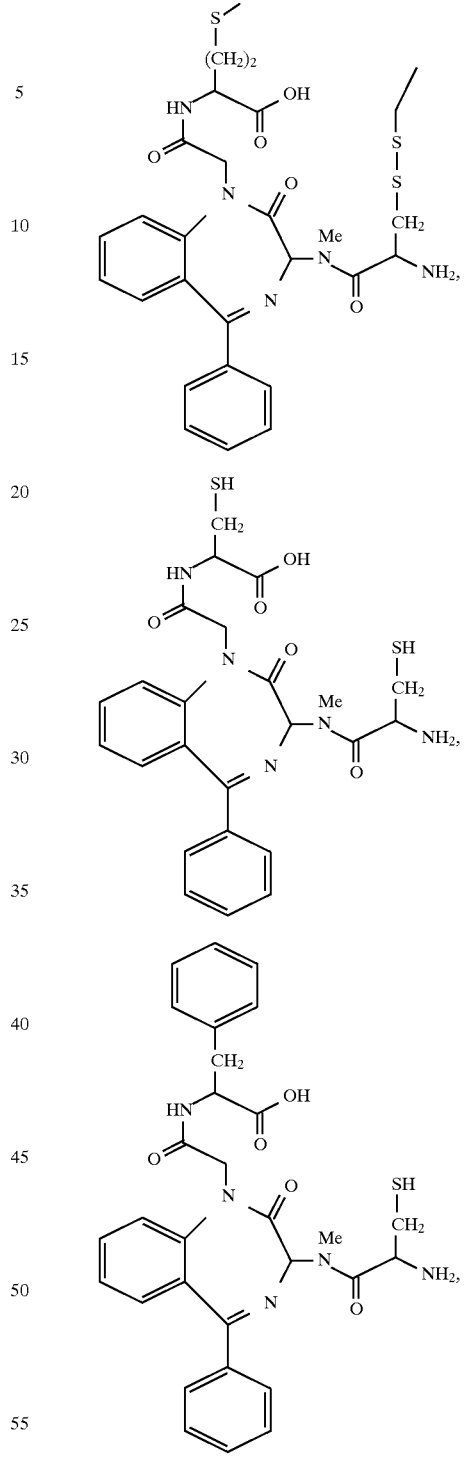

-continued

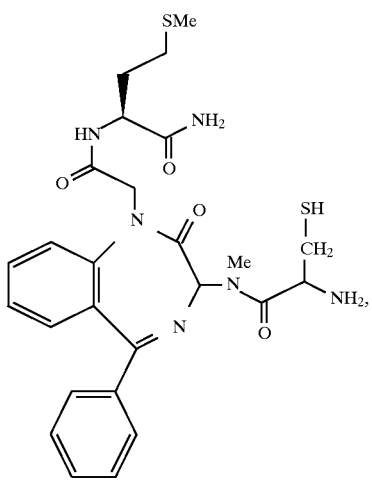

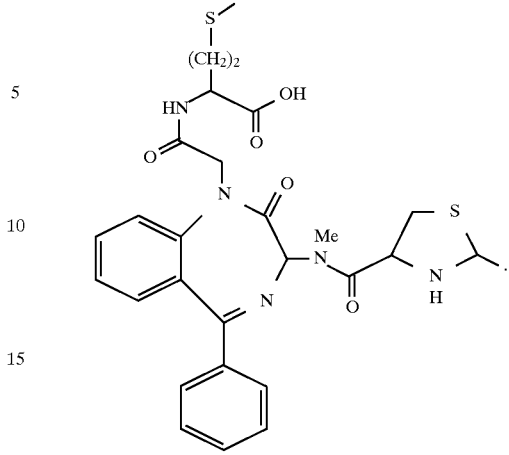

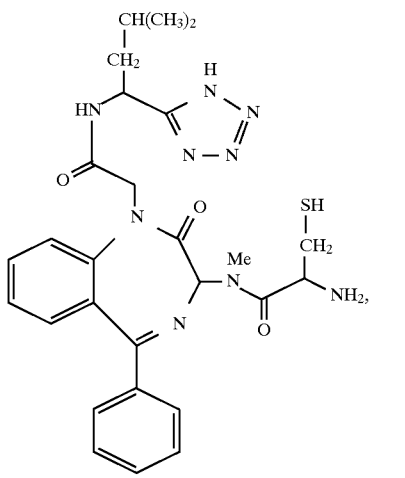

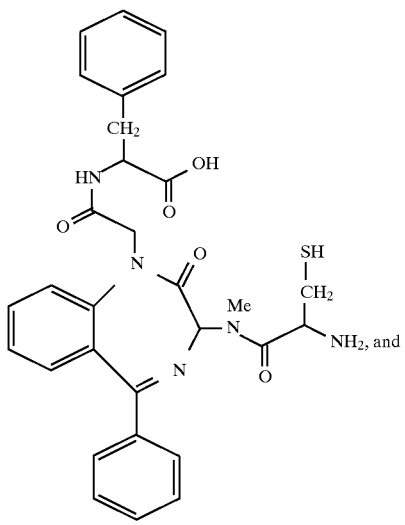

The invention further provides a pharmaceutical composition comprising a pharmaceutically acceptable excipient and a compound of formulae I-X and a method of inhibiting farnesyl:protein transferase comprising administering to a subject in need of such treatment a therapeutically effective amount of the pharmaceutical composition. The invention also provides a method of inhibiting farnesylation of the oncogene protein ras in a subject and a method of amelioration of a neoplastic or proliferative condition in a subject having such a condition comprising administering to the subject in need of such treatment a therapeutically effective amount of the pharmaceutical composition.

The invention further provides a method of inhibiting fungal growth or reproduction in a living organism (or an area where growth or reproduction is to be controlled) in need of such treatment comprising administering an antifungally effective amount of the compound of formulae I-X.

DETAILED DESCRIPTION OF THE INVENTION

A. Definitions

Figure 1A:
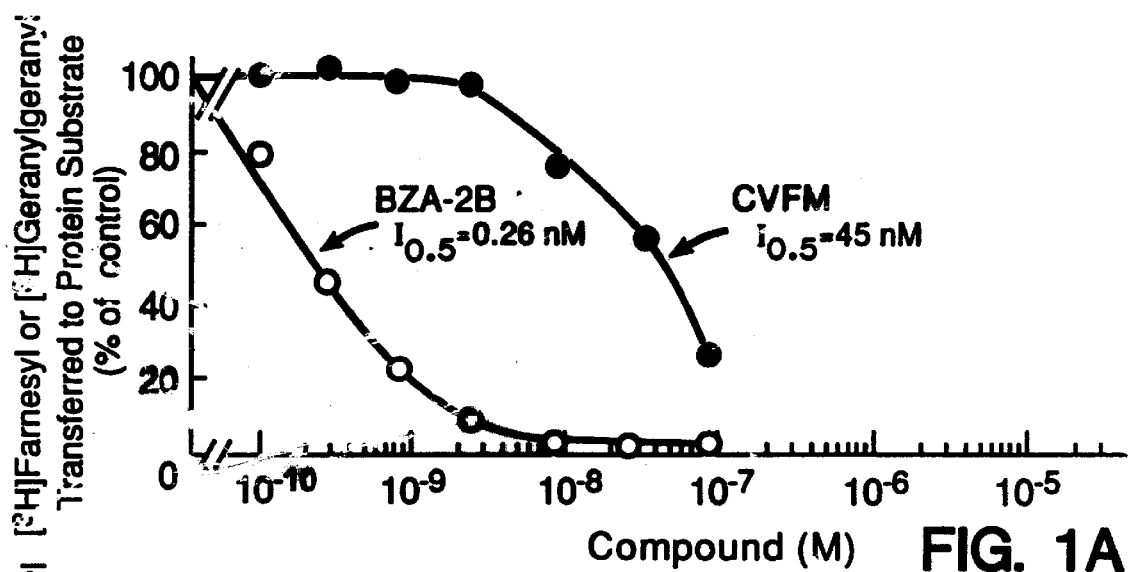
FIG. 1. Differential inhibition of CAAX farnesyltransferase (A), CAAX GG transferase (B) and Rab GG transferase (C) by compound 27 B (denoted as BZA-2B in the figure, open circles) and the tetrapeptide Cys-Val-Phe-Met (CVFM) (solid circles).

Terms used in the claims and specification are defined as set forth below unless otherwise specified.

The term "alkyl" means a cyclic or linear, branched or unbranched, saturated aliphatic hydrocarbon radical, having the number of carbon atoms specified, or if no number is specified, having up to 12 carbon atoms. Examples of alkyl radicals include methyl, ethyl, n-propyl, isopropyl(iPr), n-butyl, iso-butyl, sec-butyl, tert-butyl(tBu), n-pentyl, 2-methylbutyl, 2,2-dimethylpropyl, n-hexyl, 2-methylpentyl, 2,2-dimethylbutyl, n-heptyl, 2-methylhexyl, cyclohexyl, and the like. The terms "lower alkyl" and "$C_1$–$C_6$alkyl" are synonymous and used interchangeably.

The term "substituted $C_n$-$C_m$alkyl" where m and n are integers identifying the range of carbon atoms contained in the alkyl group, denotes the above alkyl groups that are substituted by one, two or three; halogen(F, Cl, Br, I), hydroxy, protected hydroxy, amino, protected amino, $C_1$–$C_6$acyloxy, nitro, carboxy, protected carboxy, carbamoyl, carbamoyloxy, cyano, methylsulfonylamino or $C_1$–$C_6$alkoxy groups. The substituted alkyl groups may be substituted once, twice or three times with the same or with different substituents.

Examples of the above substituted alkyl groups include but are not limited to; cyanomethyl, nitromethyl, hydroxymethyl, trityloxymethyl, propionyloxymethyl, aminomethyl, carboxymethyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluromethyl, 6-hydroxyhexyl, 2,4dichloro(n-butyl), 2-amino(iso-propyl), 2-carbamoyloxyethyl and the like. A preferred group of examples within the above "$C_1$–$C_{12}$ substituted alkyl" group includes the substituted methyl group, e.g. a methyl group substituted by the same substituents as the "substituted $C_n$-$C_m$alkyl" group. Examples of the substituted methyl group include groups such as hydroxymethyl, protected hydroxymethyl (e.g. tetrahydropyranyloxymethyl), acetoxymethyl, carbamoyloxymethyl, trifluromethyl, chloromethyl, bromomethyl and iodomethyl.

The terms "$C_1$–$C_6$alkyloxy" or "$C_1$–$C_6$alkoxy" are used interchangeably herein and denote groups such as methoxy, ethoxy, n-propoxy, isopropoxy, n-butoxy, t-butoxy, cyclohexyloxy and like groups.

The terms "$C_1$–$C_{12}$acyloxy" or "$C_1$–$C_{12}$alkanoyloxy" are used interchangeably and denote herein groups such as formyloxy, acetoxy, propionyloxy, butyryloxy, pentanoyloxy, hexanoyloxy, heptanoyloxy, and the like.

The terms "$C_1$–$C_{12}$alkylcarbonyl", "$C_1$–$C_{12}$alkanoyl" and "$C_1$–$C_{12}$acyl" are used interchangeably herein encompass groups such as formyl, acetyl, propionyl, butyryl, pentanoyl, hexanoyl, heptanoyl, benzoyl and the like.

The term "cycloalkyl" as used herein refers to a mono-, bi-, or tricyclic aliphatic ring having 3 to 14 carbon atoms and preferably 3 to 7 carbon atoms. An exemplary cycloalkyl is cyclohexyl.

The term "alkenyl" means a branched or unbranched hydrocarbon radical having the number of carbon atoms designated, containing one or more carbon-carbon double bonds, each double bond being independently cis, trans, or a non-geometric isomer.

The terms "$C_1$–$C_{12}$alkylthio" and "$C_1$–$C_{12}$ substituted alkylthio" denote $C_1$–$C_{12}$alkyl and $C_1$–$C_{12}$ substituted alkyl groups, respectively, attached to a sulfur which is in turn the point of attachment for the alkylthio or substituted alkylthio group to the group or substituent designated.

The term "aryl" when used alone means a homocyclic hydrocarbon aromatic radical, whether or not fused, having the number of carbon atoms designated. Preferred aryl groups include phenyl, napthyl, biphenyl, phenanthrenyl, naphthacenyl, and the like (see e.g. *Lang's Handbook of Chemistry* (Dean, J. A., ed) 13$^{th}$ ed. Table 7-2 [1985]).

The term "substituted phenyl" or "substituted aryl" denotes a phenyl group or aryl group substituted with one, two or three substituents chosen from halogen(F, CI, Br, I), hydroxy, protected hydroxy, cyano, nitro, $C_1$–$C_6$alkyl, $C_1$–$C_6$alkoxy, carboxy, protected carboxy, carboxymethyl, protected carboxymethyl, hydroxymethyl, protected hydroxymethyl, aminomethyl, protected aminomethyl, trifluoromethyl N-(methylsulfonylamino) or other groups specified.

Examples of the term "substituted phenyl" includes but is not limited to a mono- or di(halo)phenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 2,6-dimethoxyphenyl, 4-methoxyphenyl, 3-ethoxyphenyl, 4-(isopropoxy)phenyl, 4-(t-butoxy)phenyl, 3-ethoxy-4-methoxyphenyl and the like; 3- or 4- trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl)phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))-phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like. Preferred substituted phenyl groups include the 2- and 3-trifluoromethylphenyl, the 4-hydroxyphenyl, the 2-aminomethylphenyl and the 3-(N-methylsulfonylamino)) phenyl groups.

The term "arylalkyl" means one, two, or three aryl groups having the number of carbon atoms designated, appended to an alkyl radical having the number of carbon atoms designated including but not limited to; benzyl, napthylmethyl, phenethyl, benzyhydryl (diphenylmethyl), trityl, and the like. A preferred arylalkyl group is the benzyl group.

The term "substituted $C_6$–$C_{12}$aryl-$C_1$–$C_6$alkyl" denotes a $C_1$–$C_6$alkyl group substituted at any carbon with a $C_6$–$C_{12}$aryl group bonded to the alkyl group through any aryl ring position and substituted on the $C_1$–$C_6$alkyl portion with one, two or three groups chosen from halogen(F, Cl, Br, I), hydroxy, protected hydroxy, amino, protected amino, $C_1$–$C_6$acyloxy, nitro, carboxy, protected carboxy, carbamoyl, carbamoyloxy, cyano, $C_1$–$C_6$alkylthio, N-(methylsulfonylamino) $C_1$–$C_6$alkoxy, or other groups specified. Optionally, the aryl group may be substituted with one, two, or three groups chosen from halogen(especially F), cyano, hydroxy, protected hydroxy, nitro, $C_1$–$C_6$alkyl, $C_1$–$C_4$alkoxy, carboxy, protected carboxy, carboxymethyl, protected carboxymethyl, hydroxymethyl, protected hydroxymethyl, aminomethyl, protected aminomethyl, or an N-(methylsulfonylamino) group. As before, when either the $C_1$–$C_6$alkyl portion or the aryl portion or both are disubstituted, the substituents can be the same or different.

Examples of the term "substituted $C_6$–$C_{10}$aryl-$C_1C_6$alkyl" include groups such as 2-phenyl-1-chloroethyl, 2-(4-methoxyphenyl)ethyl, 2,6-dihydroxy-4-phenyl(n-hexyl), 5-cyano-3-methoxy-2-phenyl(n-pentyl), 3-(2,6-dimethylphenyl)n-propyl, 4 chloro-3-aminobenzyl, 6-(4-methoxyphenyl)-3-carboxy(n-hexyl), 5-(4-aminomethyl phenyl)-3-(aminomethyl)(n-pentyl), and the like.

The term "carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl,4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β-(trimethylsilyl)ethyl, β-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the benzodiazepine molecule and can be removed at the appropriate point without disrupting the remainder of the molecule. In particular, it is important not to subject the carboxy-protected benzodiazepine molecule to strong nucleophilic bases or reductive conditions employing highly activated metal catalysts such as Raney nickel. (Such harsh removal conditions are also to be avoided when removing amino-protecting groups and hydroxy-protecting groups, discussed below.) Preferred carboxylic acid protecting groups are the allyl and p-nitrobenzyl, groups. Similar carboxy-protecting groups used in the cephalosporin, penicillin and peptide arts can also be used to protect carboxy group substituents of the benzodiazepine. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups.

As used herein the term "amide-protecting group" refers to any group typically used in the peptide art for protecting the peptide nitrogens from undesirable side reactions. Such groups include p-methoxyphenyl, 3,4-dimethoxybenzyl, benzyl, o-nitrobenzyl, di-(p-methoxyphenyl)methyl, triphenylmethyl, (p-methoxyphenyl)diphenylmethyl, diphenyl-4-pyridylmethyl, m-2-(picolyl)-N'-oxide, 5-dibenzosuberyl, trimethylsilyl, t-butyl dimethylsilyl, and the like. Further descriptions of these protecting groups can be found in "Protective Groups in Organic Synthesis", by Theodora W. Greene, 1981, John Wiley and Sons, New York.

Unless otherwise specified, the terms "heterocycle", "heterocyclic group", "heterocyclic" or "heterocyclyl" are used interchangeably herein and refer to any mono-, bi-, or tricyclic saturated, unsaturated, or aromatic ring having the number of ring atoms designated where at least one ring is a 5-, 6- or 7-membered hydrocarbon ring containing from one to four heteroatoms selected from nitrogen, oxygen, and sulfur, preferably at least one heteroatom is nitrogen (*Lang's Handbook of Chemistry*, supra). Preferably, the heterocycle is a 5- or 6-member saturated, unsaturated, or aromatic hydrocarbon ring containing 1, 2, or 3 heteroatoms selected from O, N, and S. Typically, the 5-membered ring has 0 to 2 double bonds and the 6- or 7-membraned ring has 0 to 3 double bonds and the nitrogen or sulfur heteroatoms may optionally be oxidized, and any nitrogen heteroatom may optionally be quarternized. Included in the definition are any bicyclic groups where any of the above heterocyclic rings are fused to a benzene ring. Heterocyclics in which nitrogen is the heteroatom are preferred.

The following ring systems are examples of the heterocyclic (whether substituted or unsubstituted) radicals denoted by the term "heterocyclic": thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b] pyridazinyl and purinyl, as well as benzo-fused derivatives, for example benzoxazolyl, benzthiazolyl, benzimidazolyl and indolyl.

Heterocyclic 5-membered ring systems containing a sulfur or oxygen atom and one to three nitrogen atoms are also suitable for use in the instant invention. Examples of such preferred groups include thiazolyl, in particular thiazol-2-yl and thiazol-2-yl N-oxide, thiadiazolyl, in particular 1,3,4- thiadiazol-5-yl and 1,2,4-thiadiazol-5-yl, oxazolyl, preferably oxazol-2-yl, and oxadiazolyl, such as 1,3,4-oxadiazol-5-yl, and 1,2,4-oxadiazol-5-yl. A group of further preferred examples of 5-membered ring systems with 2 to 4 nitrogen atoms include inidazolyl, preferably imidazol-2-yl; triazolyl, preferably 1,3,4-triazol-5-yl; 1,2,3-triazol-5-yl, 1,2,4-triazol-5-yl, and tetrazolyl, preferably 1H-tetrazol-5-yl. A preferred group of examples of benzo-fused derivatives are benzoxazol-2-yl, benzthiazol-2-yl and benzimidazol-2-yl.

Further suitable specific examples of the above heterocylic ring systems are 6-membered ring systems containing one to three nitrogen atoms. Such examples include pyridyl, such as pyrid-2-yl, pyrid-3-yl, and pyrid-4-yl; pyrimidyl, preferably pyrimid-2-yl and pyrimid-4-yl; triazinyl, preferably 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid4-yl, pyridazinyl and the 1,3,4-triazin-2-yl radicals, are a preferred group. Optionally preferred 6-membered ring heterocycles are; piperazinyl, piperazin-2-yl, piperidyl, piperid-2-yl, piperid-3-yl, piperid-4-yl, morpholino, morpholin-2-yl, and morpholin-3-yl.

An optionally preferred group of "heterocyclics" include; 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carboxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5 -dihydro-5-oxo-2,6-dimethyl-as-triazin-3-yl, tetrazolo[1,5-b]pyridazin-6-yl and 8-aminotetrazolo[1,5-b]-pyridazin-6-yl.

An alternative group of "heterocyclics" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5,6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl.

The terms "heteroaryl group" or "heteroaryrl" are used interchangeably herein and refer to any mono-, bi-, or tricyclic aromatic rings having the number of ring atoms designated where at least one ring is a 5-, 6- or 7-membered hydrocarbon ring containing from one to four heteroatoms selected from nitrogen, oxygen, and sulfur, preferably at least one heteroatom is nitrogen. The aryl portion of the term "heteroaryrl" refers to aromaticity, a term known to those skilled in the art and defined in greater detail in *Advanced Organic Chemistry* J. March, $3^{rd}$ ed., pages 37–69, John Wiley & Sons, New York (1985).

Each substituent or term used in any formula or expression herein, e.g., $T^1$, $T^2$, W, $R^n$, $R^m$, Z, $Y^n$, Ar, $A^n$, X, V, $C_1$–$C_6$alkyl, etc. when it appears more than once, is independent of its definition elsewhere in that or any other formula or structure.

"Pharmaceutically acceptable salts" include both acid and base addition salts.

"Pharmaceutically acceptable acid addition salt" refers to those salts which retain the biological effectiveness and properties of the free bases and which are not biologically or otherwise undesirable, formed with inorganic acids including but not limited to hydrochloric acid, hydrobromic add, sulfuric add, sulfamic nitric acid, phosphoric acid and the like, and organic acids such as acetic acid, propionic acid, glycolic acid, pyruvic acid, lactic acid, oxalic acid, maleic acid, malic acid, maloneic acid, succinic acid, fumaric acid, tartaric acid, citric acid, stearic acid, ascorbic acid, benzoic acid, cinnamic acid, mandelic acid, methanesulfonic acid, ethanesulfonic acid, isethionic acid, p-toluenesulfonic acid, salicyclic acid, naturally occurring amino acids and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediarnine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

The term "prodrug" as used herein means a pharmacologically inactive derivative of a parent drug molecule that requires biotransformation, either spontaneous or enzymatic, within the organism to release the active drug.

B. Utility

The present invention is the result of the unexpected discovery that substituted benzodizepines and analogs thereof defined by formulae I-X inhibit farnesyl:protein transferase and the farnsylation of $p21^{ras}$. Accordingly, pharmaceutical compositions containing the compounds of structural formula I are useful as pharmaceutical agents for mammals, especially humans, in the treatment of diseases where inhibition of farnesylation of $p21^{ras}$ and related low molecular weight Gproteins is indicated. In a preferred embodiment of the invention inhibition of farnesylation is indicated for neoplastic and proliferative diseases including but not limited to, colorectal carcinoma, exocrine pancreatic carcinoma, and myeloid leukemias. In an alternative embodiment, inhibition of farnesylation is contemplated to be useful for proliferating skin diseases where ras positive cells are found in the differentiated layer, including but not limited to, psoriasis vulgaris, lichen planus, verruca vulgaris, verruca plana juvenlls, and seborrheic keratosis. Other ras positive diseases where inhibition of ras signaling by the inhibitors of this invention is indicated include; neurofibromatosis, rheumatoid arthritis, human papiroma viral infection, Kapoli's sarcoma and scleroderma.

The present invention is also useful in a method directed to treating fungal infections in an organism in need of such treatment, which method comprises administering a non toxic (to the organism) therapeutically effective amount of compounds represented by structural formulae I-X. In one embodiment, the fungally infected organisms are animal, preferably mammal, most preferably human, especially immunologically compromised individuals. In an alternative embodiment the organisms are plants infected with or succeptable to blight, rust, and mildew (especially *fusarium wilt*). Optionally, nonliving material such as soil may be usefully treated with the instant compounds to prevent fungal infection of an organism.

Finally, the instant compounds may be usefully employed as metal ion and metalloprotein chelators.

C. Preferred Embodiments

One preferred embodiment of the invention comprises a compound capable of inhibiting famesyl:protein transferase at a concentration equal to or lower than that of the tetrapeptide CVFM represented by Formula II(a)

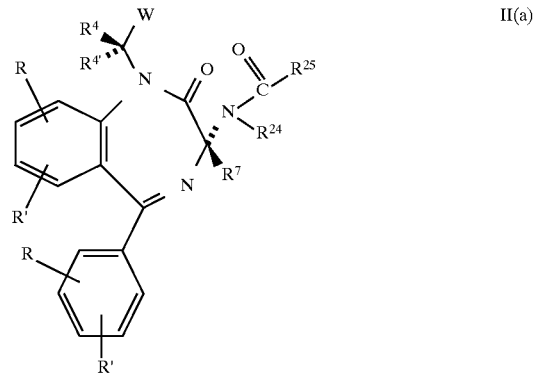

II(a)

where the substituents R, and R' are hydrogen, halogen or perfluro-lower alkyl. Most preferably, R and R' are generally hydrogen with one R being a chloro bonded to the 7 benzo position. $R^4$ and $R^{4'}$ are hydrogen or lower alkyl, and $R^7$, W, $R^{24}$, and $R^{25}$ are selected according to Table II(a).

TABLE II(a)

| $R^7$ | W | $R^{24}$ | $R^{25}$ |
|---|---|---|---|
| H | 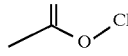 | $CH_3$ | 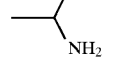 |
| H | 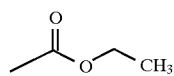 | $CH_3$ | 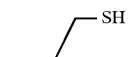 |
| H | 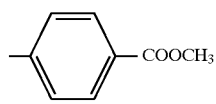 | $CH_3$ | 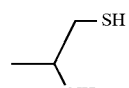 |
| H | 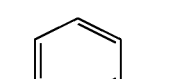 | $CH_3$ | 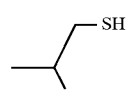 |
| H | 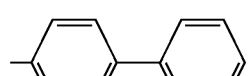 | $CH_3$ | 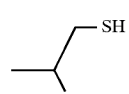 |
| H | 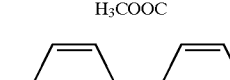 | $CH_3$ | 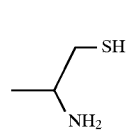 |
| H | 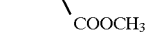 | $CH_3$ |  |

TABLE II(a)-continued

| R⁷ | W | R²⁴ | R²⁵ |
|---|---|---|---|
| H | 4-(1H-tetrazol-5-yl)phenyl | CH₃ | 1-mercapto-2-aminopropyl |
| H | 3-(1H-tetrazol-5-yl)phenyl | CH₃ | 1-mercapto-2-aminopropyl |
| H | 4'-[2-(1H-tetrazol-5-yl)]biphenyl | CH₃ | 1-mercapto-2-aminopropyl |
| H | 4-[2-(1H-tetrazol-5-yl)phenyl]phenyl | CH₃ | 1-mercapto-2-aminopropyl |
| H | 4-[1-(5-(1H-tetrazol-5-yl)pyrrol-2-yl)]phenyl | CH₃ | 1-mercapto-2-aminopropyl |
| H | 6-methyl-2-(2-methylthioethyl)-3-(1H-tetrazol-5-yl)pyridinyl | CH₃ | 1-mercapto-2-aminopropyl |
| H | 6-methyl-2-(methyldithiomethyl)-3-(1H-tetrazol-5-yl)pyridinyl | CH₃ | 1-mercapto-2-aminopropyl |
| H | 5-methyl-2-[1-(methylthiomethyl)-1-(1H-tetrazol-5-yl)methyl]pyrrolyl | CH₃ | 1-mercapto-2-aminopropyl |

TABLE II(a)-continued
| R⁷ | W | R²⁴ | R²⁵ |
|---|---|---|---|
| H | 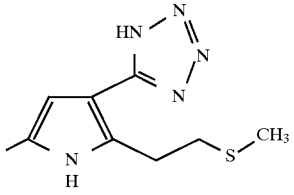 | $CH_3$ | 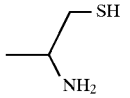 |
| H | 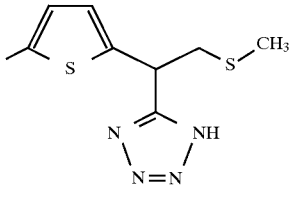 | $CH_3$ | 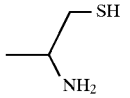 |
| H | 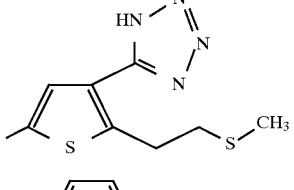 | $CH_3$ | 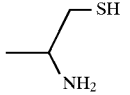 |
| H | 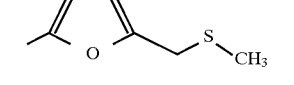 | $CH_3$ | 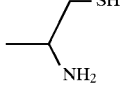 |
| H | 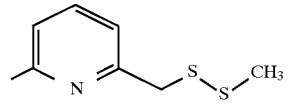 | $CH_3$ | 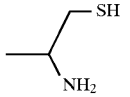 |
| H | 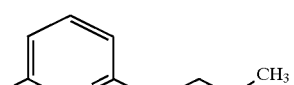 | $CH_3$ | 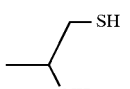 |
| H | 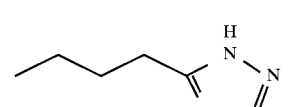 | $CH_3$ | 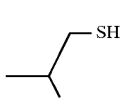 |
| H | 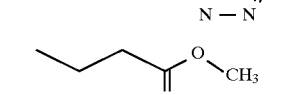 | $CH_3$ | 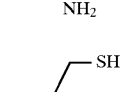 |
| H | 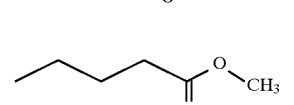 | $CH_3$ | 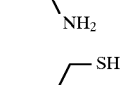 |
| H | 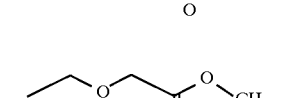 | $CH_3$ | 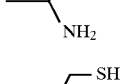 |
| H | 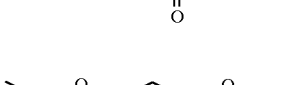 | $CH_3$ | 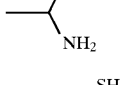 |
| H |  | $CH_3$ | 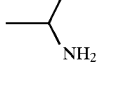 |

TABLE II(a)-continued

| R[7] | W | R[24] | R[25] |
|---|---|---|---|
| H | 4-methyl-3-fluorophenyl-O-CH2CH2-COOCH3 | CH3 | -CH(CH2SH)(NH2)CH3 |
| H | 3-chlorophenyl | CH3 | -CH(CH2SH)(NH2)CH3 |
| H | 2,4-difluorophenyl | CH3 | -CH(CH2SH)(NH2)CH3 |
| H | 3-methylphenyl | CH3 | -CH(CH2SH)(NH2)CH3 |
| H | 3-cyanophenyl | CH3 | -CH(CH2SH)(NH2)CH3 |
| H | 4-cyanophenyl | CH3 | -CH(CH2SH)(NH2)CH3 |
| H | 3-(COOCH3)phenyl | CH3 | -CH(CH2SH)(NH2)CH3 |
| H | 4-CF3-3-fluorophenyl | CH3 | -CH(CH2SH)(NH2)CH3 |
| H | 4-methylphenyl | CH3 | -CH(CH2SH)(NH2)CH3 |
| H | 4-fluorophenyl | CH3 | -CH(CH2SH)(NH2)CH3 |
| H | 4-fluoro-2-methylphenyl | CH3 | -CH(CH2SH)(NH2)CH3 |
| H | 4-methyl-3-fluorophenyl | CH3 | -CH(CH2SH)(NH2)CH3 |

TABLE II(a)-continued

| R[7] | W | R[24] | R[25] |
|---|---|---|---|
| H | 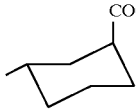 COOCH₃ (cyclohexyl) | CH₃ | 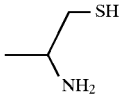 —SH, NH₂ |
| H | 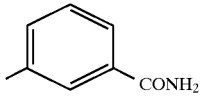 CONH₂ (phenyl) | CH₃ | 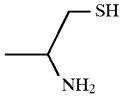 —SH, NH₂ |
| H | 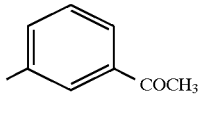 COCH₃ (phenyl) | CH₃ | 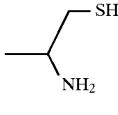 —SH, NH₂ |
| H | 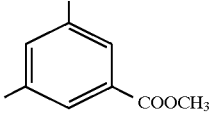 F, COOCH₃ (phenyl) | CH₃ | 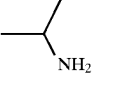 —SH, NH₂ |
| H | 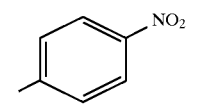 NO₂ (phenyl) | CH₃ | 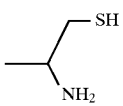 —SH, NH₂ |
| H | 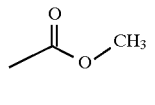 O, OCH₃ | CH₃ | 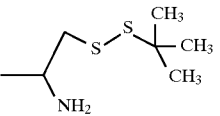 S-S-C(CH₃)₃, NH₂ |
| H | 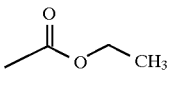 O, OCH₂CH₃ | CH₃ | 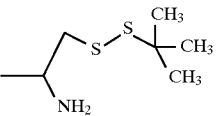 S-S-C(CH₃)₃, NH₂ |
| H | 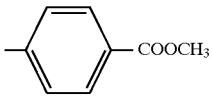 COOCH₃ (phenyl) | CH₃ | 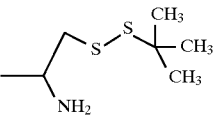 S-S-C(CH₃)₃, NH₂ |
| H | 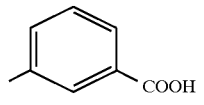 COOH (phenyl) | CH₃ | 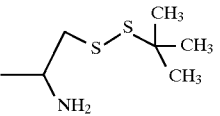 S-S-C(CH₃)₃, NH₂ |
| H | 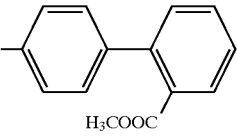 biphenyl, H₃COOC | CH₃ | 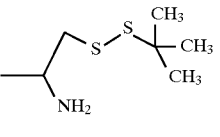 S-S-C(CH₃)₃, NH₂ |
| H | 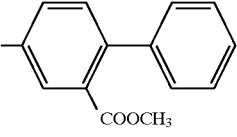 biphenyl, COOCH₃ | CH₃ | 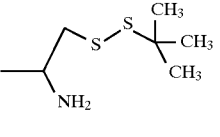 S-S-C(CH₃)₃, NH₂ |
| H | 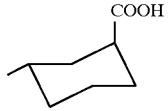 COOH (cyclohexyl) | CH₃ | 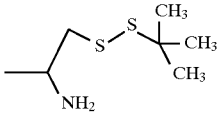 S-S-C(CH₃)₃, NH₂ |

TABLE II(a)-continued
| R[7] | W | R[24] | R[25] |
|---|---|---|---|
| H | 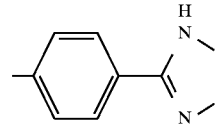 | CH$_3$ | 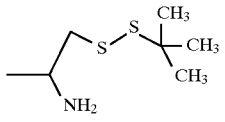 |
| H |  | CH$_3$ | 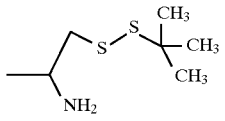 |
| H | 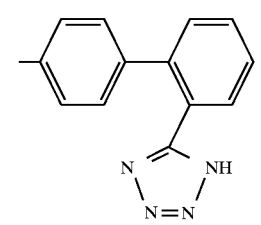 | CH$_3$ | 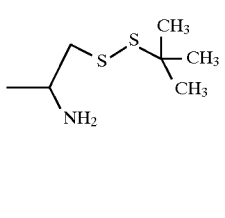 |
| H | 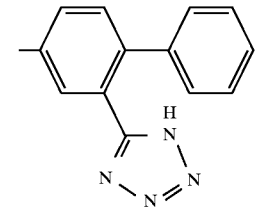 | CH$_3$ | 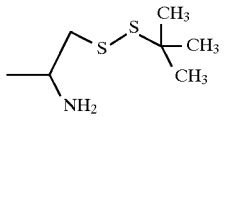 |
| H | 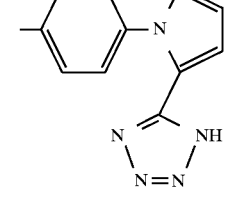 | CH$_3$ | 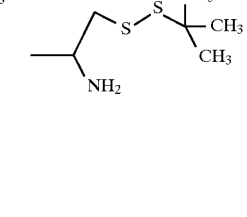 |
| H | 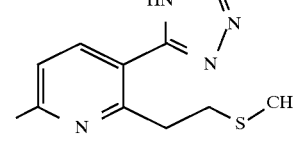 | CH$_3$ | 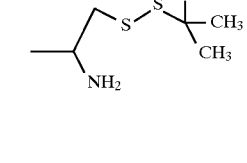 |
| H | 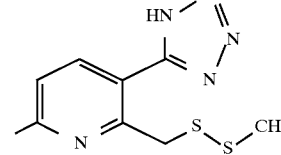 | CH$_3$ | 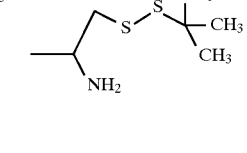 |
| H | 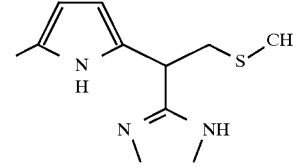 | CH$_3$ | 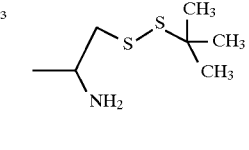 |

TABLE II(a)-continued
| R⁷ | W | R²⁴ | R²⁵ |
|---|---|---|---|
| H |  | CH₃ | 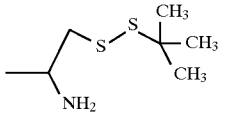 |
| H | 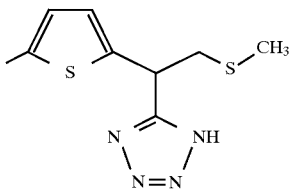 | CH₃ |  |
| H |  | CH₃ | 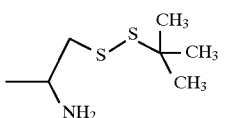 |
| H |  | CH₃ | 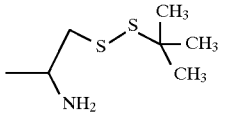 |
| H | 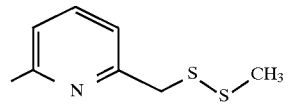 | CH₃ |  |
| H | 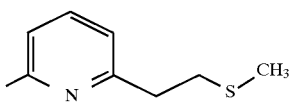 | CH₃ | 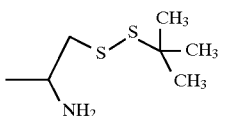 |
| H |  | CH₃ | 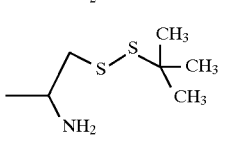 |
| H |  | CH₃ | 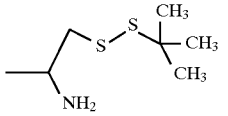 |
| H | 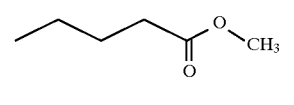 | CH₃ | 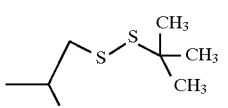 |
| H | 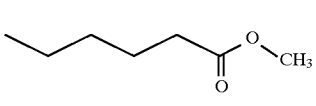 | CH₃ | 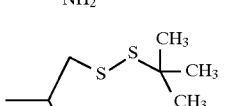 |
| H | 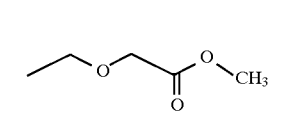 | CH₃ | 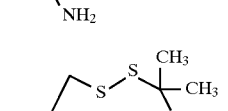 |

TABLE II(a)-continued

| R[7] | W | R[24] | R[25] |
|---|---|---|---|
| H | 2-ethoxy-2-methylpropanoic acid methyl ester | CH$_3$ | 1-amino-2-propyl tert-butyl disulfide |
| H | methyl 3-(3-fluoro-4-methylphenoxy)propanoate | CH$_3$ | 1-amino-2-propyl tert-butyl disulfide |
| H | 3-chloro-4-methylphenyl | CH$_3$ | 1-amino-2-propyl tert-butyl disulfide |
| H | 2,4-difluoro-toluene | CH$_3$ | 1-amino-2-propyl tert-butyl disulfide |
| H | 3,4-dimethylphenyl | CH$_3$ | 1-amino-2-propyl tert-butyl disulfide |
| H | 3-cyano-4-methylphenyl | CH$_3$ | 1-amino-2-propyl tert-butyl disulfide |
| H | 4-cyano-toluene | CH$_3$ | 1-amino-2-propyl tert-butyl disulfide |
| H | methyl 4-methyl-3-benzoate | CH$_3$ | 1-amino-2-propyl tert-butyl disulfide |
| H | 3-fluoro-4-methyl-(trifluoromethyl)benzene | CH$_3$ | 1-amino-2-propyl tert-butyl disulfide |
| H | 4-methyl-toluene | CH$_3$ | 1-amino-2-propyl tert-butyl disulfide |
| H | 4-fluoro-toluene | CH$_3$ | 1-amino-2-propyl tert-butyl disulfide |

TABLE II(a)-continued
| R⁷ | W | R²⁴ | R²⁵ |
|---|---|---|---|
| H | 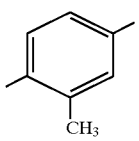 | $CH_3$ | 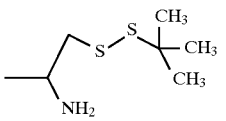 |
| H |  | $CH_3$ | 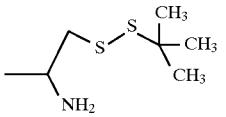 |
| H | 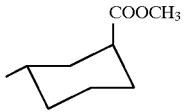 | $CH_3$ |  |
| H | 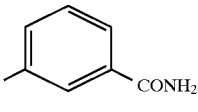 | $CH_3$ | 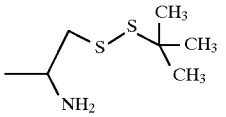 |
| H |  | $CH_3$ | 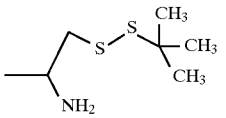 |
| H | 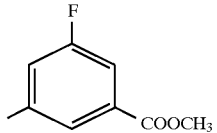 | $CH_3$ |  |
| H | 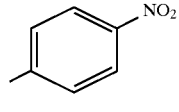 | $CH_3$ | 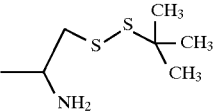 |
| H |  | $CH_3$ | 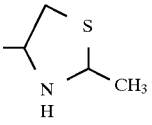 |
| H | 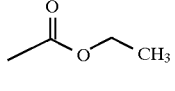 | $CH_3$ |  |
| H | 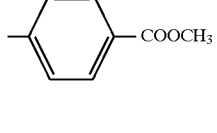 | $CH_3$ | 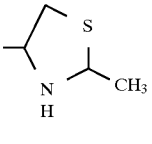 |
| H |  | $CH_3$ | 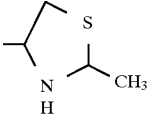 |

TABLE II(a)-continued
| R[7] | W | R[24] | R[25] |
|---|---|---|---|
| H | 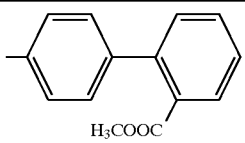 | CH$_3$ | 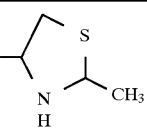 |
| H |  | CH$_3$ | 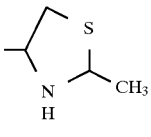 |
| H | 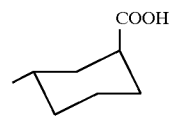 | CH$_3$ |  |
| H | 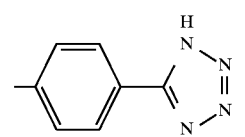 | CH$_3$ | 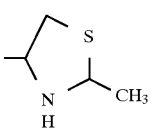 |
| H |  | CH$_3$ | 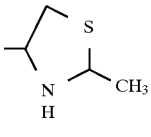 |
| H | 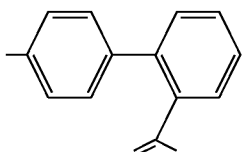 | CH$_3$ |  |
| H | 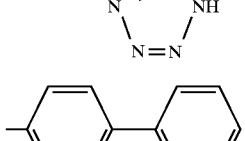 | CH$_3$ | 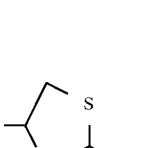 |
| H |  | CH$_3$ | 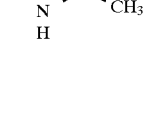 |
| H | 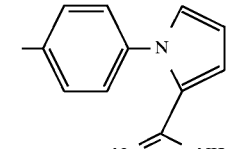 | CH$_3$ |  |

TABLE II(a)-continued

| R[7] | W | R[24] | R[25] |
|---|---|---|---|
| H | 6-methyl-3-(1H-tetrazol-5-yl)-2-(methyldithiomethyl)pyridine | CH$_3$ | 2-methyl-thiazolidin-4-yl (NH) |
| H | 5-methyl-2-[1-(methylthiomethyl)-1-(1H-tetrazol-5-yl)methyl]pyrrole | CH$_3$ | 2-methyl-thiazolidin-4-yl (NH) |
| H | 5-methyl-2-[2-(methylthio)ethyl]-3-(1H-tetrazol-5-yl)pyrrole | CH$_3$ | 2-methyl-thiazolidin-4-yl (NH) |
| H | 5-methyl-2-[1-(methylthiomethyl)-1-(1H-tetrazol-5-yl)methyl]thiophene | CH$_3$ | 2-methyl-thiazolidin-4-yl (NH) |
| H | 5-methyl-2-[2-(methylthio)ethyl]-3-(1H-tetrazol-5-yl)thiophene | CH$_3$ | 2-methyl-thiazolidin-4-yl (NH) |
| H | 5-methyl-2-(methylthiomethyl)furan | CH$_3$ | 2-methyl-thiazolidin-4-yl (NH) |
| H | 6-methyl-2-(methyldithiomethyl)pyridine | CH$_3$ | 2-methyl-thiazolidin-4-yl (NH) |
| H | 6-methyl-2-[2-(methylthio)ethyl]pyridine | CH$_3$ | 2-methyl-thiazolidin-4-yl (NH) |
| H | 5-butyl-1H-tetrazole | CH$_3$ | 2-methyl-thiazolidin-4-yl (NH) |

TABLE II(a)-continued
| R⁷ | W | R²⁴ | R²⁵ |
|---|---|---|---|
| H | 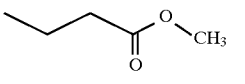 | CH₃ | 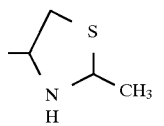 |
| H | 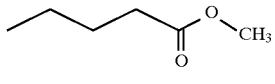 | CH₃ | 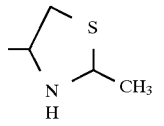 |
| H | 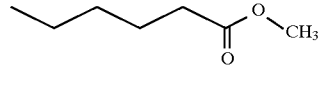 | CH₃ | 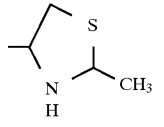 |
| H | 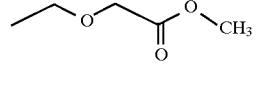 | CH₃ | 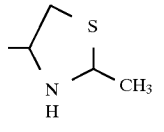 |
| H | 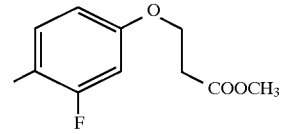 | CH₃ | 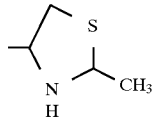 |
| H | 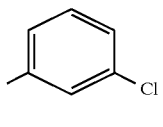 | CH₃ | 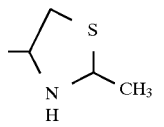 |
| H | 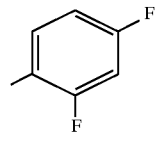 | CH₃ | 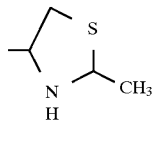 |
| H | 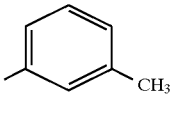 | CH₃ | 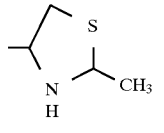 |
| H | 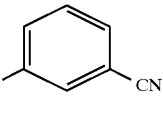 | CH₃ | 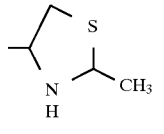 |
| H | 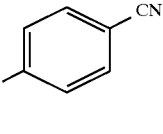 | CH₃ | 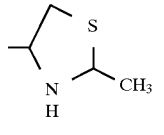 |

TABLE II(a)-continued
| R⁷ | W | R²⁴ | R²⁵ |
|---|---|---|---|
| H | 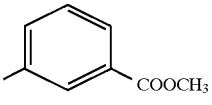 3-COOCH₃-phenyl | CH₃ | 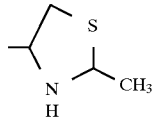 |
| H | 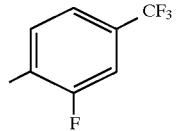 3-F, 4-CF₃-phenyl | CH₃ | 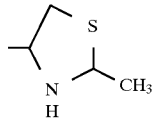 |
| H | 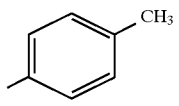 4-CH₃-phenyl | CH₃ | 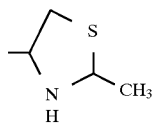 |
| H | 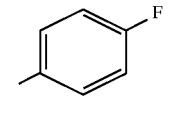 4-F-phenyl | CH₃ | 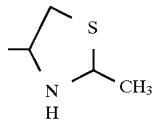 |
| H | 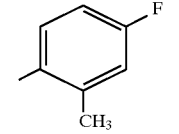 2-CH₃, 5-F-phenyl | CH₃ | 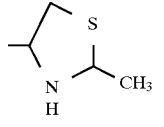 |
| H | 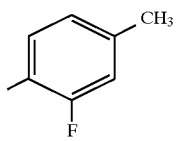 3-F, 4-CH₃-phenyl | CH₃ | 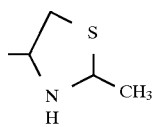 |
| H | 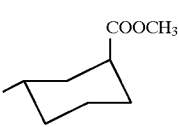 cyclohexyl-COOCH₃ | CH₃ | 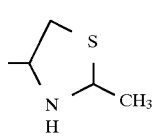 |
| H | 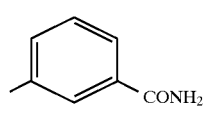 3-CONH₂-phenyl | CH₃ | 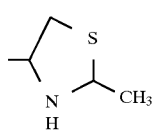 |
| H | 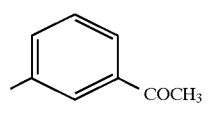 3-COCH₃-phenyl | CH₃ | 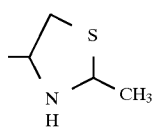 |
| H | 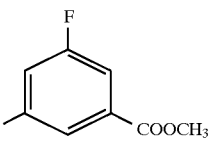 3-F, 5-COOCH₃-phenyl | CH₃ | 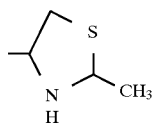 |
| H |  4-NO₂-phenyl | CH₃ | 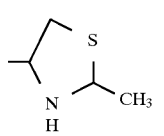 |

TABLE II(a)-continued
| R[7] | W | R[24] | R[25] |
|---|---|---|---|
| H |  | CH$_3$ |  |
| H |  | CH$_3$ |  |
| H |  | CH$_3$ |  |
| H |  | CH$_3$ |  |
| H |  | CH$_3$ |  |
| H |  | CH$_3$ |  |
| H |  | CH$_3$ |  |
| H |  | CH$_3$ |  |
| H |  | CH$_3$ |  |
| H |  | CH$_3$ |  |
| H |  | CH$_3$ |  |

TABLE II(a)-continued

| R⁷ | W | R²⁴ | R²⁵ |
|---|---|---|---|
| H | (4-methylphenyl-pyrrole linked to tetrazole) | $CH_3$ | $-NH-CH_2CH_2-SH$ |
| H | (6-methylpyridine with tetrazole and -CH₂CH₂-S-CH₃) | $CH_3$ | $-NH-CH_2CH_2-SH$ |
| H | (6-methylpyridine with tetrazole and -S-S-CH₃) | $CH_3$ | $-NH-CH_2CH_2-SH$ |
| H | (5-methylpyrrole with -CH(CH₂SCH₃)- tetrazole) | $CH_3$ | $-NH-CH_2CH_2-SH$ |
| H | (5-methylpyrrole with tetrazole and -CH₂CH₂-S-CH₃) | $CH_3$ | $-NH-CH_2CH_2-SH$ |
| H | (5-methylthiophene with -CH(CH₂SCH₃)- tetrazole) | $CH_3$ | $-NH-CH_2CH_2-SH$ |
| H | (5-methylthiophene with tetrazole and -CH₂CH₂-S-CH₃) | $CH_3$ | $-NH-CH_2CH_2-SH$ |
| H | (5-methylfuran with -CH₂-S-CH₃) | $CH_3$ | $-NH-CH_2CH_2-SH$ |
| H | (6-methylpyridine with -CH₂-S-S-CH₃) | $CH_3$ | $-NH-CH_2CH_2-SH$ |

TABLE II(a)-continued
| R⁷ | W | R²⁴ | R²⁵ |
|---|---|---|---|
| H | 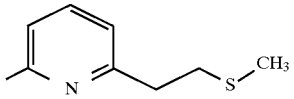 | CH₃ | 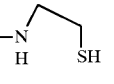 |
| H | 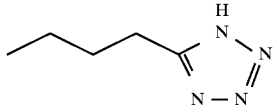 | CH₃ | 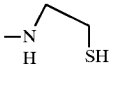 |
| H | 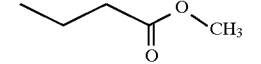 | CH₃ | 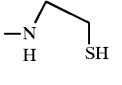 |
| H | 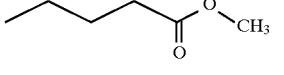 | CH₃ | 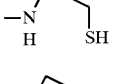 |
| H |  | CH₃ | 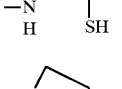 |
| H | 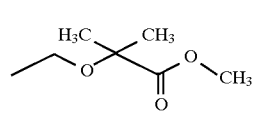 | CH₃ | 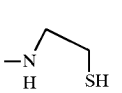 |
| H |  | CH₃ | 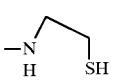 |
| H | 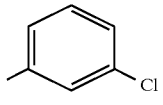 | CH₃ | 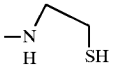 |
| H | 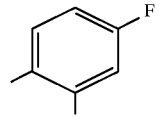 | CH₃ | 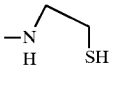 |
| H | 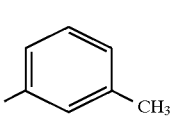 | CH₃ | 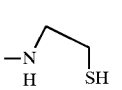 |
| H | 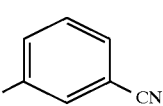 | CH₃ | 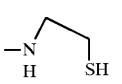 |
| H | 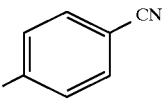 | CH₃ | 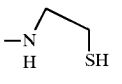 |
| H | 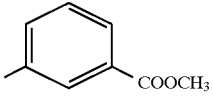 | CH₃ |  |

TABLE II(a)-continued

| R[7] | W | R[24] | R[25] |
|---|---|---|---|
| H | 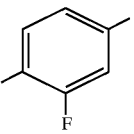 (3-F, 4-CF$_3$ phenyl) | CH$_3$ |  —NH—CH$_2$CH$_2$—SH |
| H | 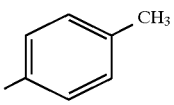 (4-CH$_3$ phenyl) | CH$_3$ |  —NH—CH$_2$CH$_2$—SH |
| H | 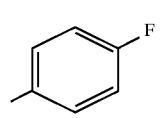 (4-F phenyl) | CH$_3$ |  —NH—CH$_2$CH$_2$—SH |
| H | 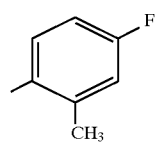 (3-CH$_3$, 5-F phenyl) | CH$_3$ |  —NH—CH$_2$CH$_2$—SH |
| H |  (3-F, 4-CH$_3$ phenyl) | CH$_3$ | 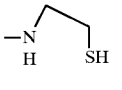 —NH—CH$_2$CH$_2$—SH |
| H |  (4-COOCH$_3$ cyclohexyl) | CH$_3$ | 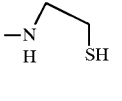 —NH—CH$_2$CH$_2$—SH |
| H | 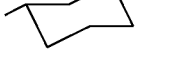 (3-CONH$_2$ phenyl) | CH$_3$ |  —NH—CH$_2$CH$_2$—SH |
| H | 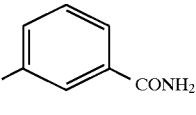 (3-F, 5-COOCH$_3$ phenyl) | CH$_3$ | 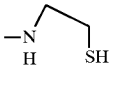 —NH—CH$_2$CH$_2$—SH |
| H | 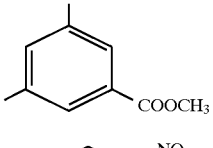 (4-NO$_2$ phenyl) | CH$_3$ | 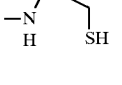 —NH—CH$_2$CH$_2$—SH |
| H | 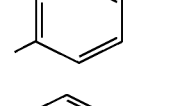 (3-COCH$_3$ phenyl) | CH$_3$ | 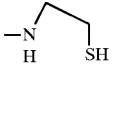 —NH—CH$_2$CH$_2$—SH |
| H | 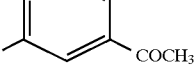 (—CH$_2$COOCH$_3$) | CH$_3$ | 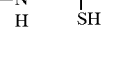 (thiazolidinone) |
| H | 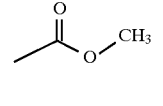 (—CH$_2$COOC$_2$H$_5$) | CH$_3$ | 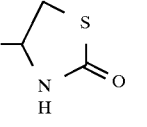 (thiazolidinone) |

TABLE II(a)-continued

| R[7] | W | R[24] | R[25] |
|---|---|---|---|
| H | 4-(COOCH$_3$)phenyl | CH$_3$ | thiazolidinone |
| H | 3-(COOH)phenyl | CH$_3$ | thiazolidinone |
| H | 4'-methyl-2-(COOCH$_3$)biphenyl | CH$_3$ | thiazolidinone |
| H | 4-methyl-2-(COOCH$_3$)biphenyl | CH$_3$ | thiazolidinone |
| H | 4-(COOH)cyclohexyl | CH$_3$ | thiazolidinone |
| H | 4-(tetrazol-5-yl)phenyl | CH$_3$ | thiazolidinone |
| H | 3-(tetrazol-5-yl)phenyl | CH$_3$ | thiazolidinone |
| H | 4'-methyl-2-(tetrazol-5-yl)biphenyl | CH$_3$ | thiazolidinone |
| H | 4-methyl-2-(tetrazol-5-yl)biphenyl | CH$_3$ | thiazolidinone |

TABLE II(a)-continued

| R[7] | W | R[24] | R[25] |
|---|---|---|---|
| H | (4-methylphenyl-pyrrolyl-tetrazole) | CH$_3$ | (thiazolidinone) |
| H | (6-methyl-pyridine with tetrazole and CH$_2$CH$_2$SCH$_3$) | CH$_3$ | (thiazolidinone) |
| H | (6-methyl-pyridine with tetrazole and CH$_2$SSCH$_3$) | CH$_3$ | (thiazolidinone) |
| H | (5-methyl-pyrrole with CH(CH$_2$SCH$_3$)-tetrazole) | CH$_3$ | (thiazolidinone) |
| H | (5-methyl-pyrrole with tetrazole and CH$_2$CH$_2$SCH$_3$) | CH$_3$ | (thiazolidinone) |
| H | (5-methyl-thiophene with CH(CH$_2$SCH$_3$)-tetrazole) | CH$_3$ | (thiazolidinone) |
| H | (5-methyl-thiophene with tetrazole and CH$_2$CH$_2$SCH$_3$) | CH$_3$ | (thiazolidinone) |
| H | (5-methyl-furan with CH$_2$SCH$_3$) | CH$_3$ | (thiazolidinone) |

TABLE II(a)-continued
| $R^7$ | W | $R^{24}$ | $R^{25}$ |
|---|---|---|---|
| H | 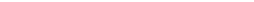 | $CH_3$ |  |
| H |  | $CH_3$ |  |
| H | 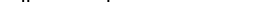 | $CH_3$ |  |
| H |  | $CH_3$ |  |
| H |  | $CH_3$ |  |
| H |  | $CH_3$ |  |
| H |  | $CH_3$ |  |
| H | 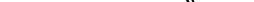 | $CH_3$ |  |
| H | 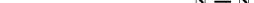 | $CH_3$ |  |
| H | 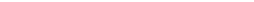 | $CH_3$ |  |
| H |  | $CH_3$ |  |

TABLE II(a)-continued
| R[7] | W | R[24] | R[25] |
|---|---|---|---|
| H | 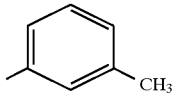 3-CH₃-phenyl | CH₃ | 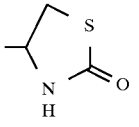 |
| H | 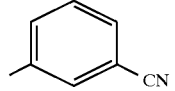 3-CN-phenyl | CH₃ | 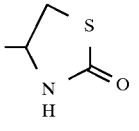 |
| H | 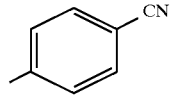 4-CN-phenyl | CH₃ | 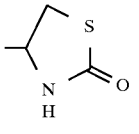 |
| H | 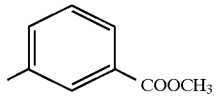 3-COOCH₃-phenyl | CH₃ | 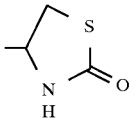 |
| H | 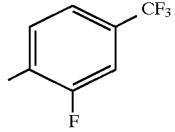 3-CF₃-4-F-phenyl | CH₃ | 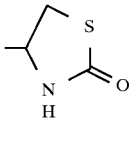 |
| H | 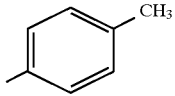 4-CH₃-phenyl | CH₃ | 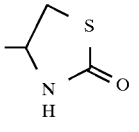 |
| H | 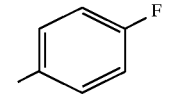 4-F-phenyl | CH₃ | 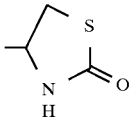 |
| H | 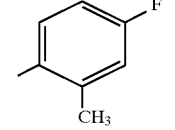 4-F-2-CH₃-phenyl | CH₃ | 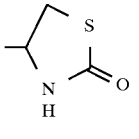 |
| H | 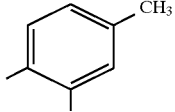 4-CH₃-2-F-phenyl | CH₃ | 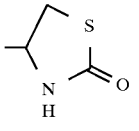 |
| H | 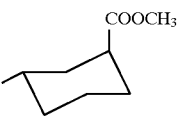 4-COOCH₃-cyclohexyl | CH₃ | 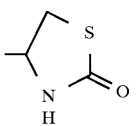 |
| H | 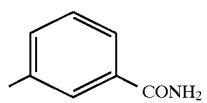 3-CONH₂-phenyl | CH₃ | 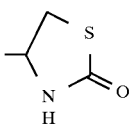 |

TABLE II(a)-continued

| R[7] | W | R[24] | R[25] |
|---|---|---|---|
| H | 3-methylphenyl-COCH₃ | CH₃ | thiazolidinone (S,NH,C=O) |
| H | 3-fluoro-5-methylphenyl-COOCH₃ | CH₃ | thiazolidinone (S,NH,C=O) |
| H | 4-nitrophenyl-methyl | CH₃ | thiazolidinone (S,NH,C=O) |
| H | CH₃-C(=O)-O-CH₃ (methyl acetate) | CH₃ | -CH₂-CH(SH)-SH |
| H | CH₃-C(=O)-O-CH₂CH₃ (ethyl acetate) | CH₃ | -CH₂-CH(SH)-SH |
| H | 4-(COOCH₃)phenyl-methyl | CH₃ | -CH₂-CH(SH)-SH |
| H | 3-(COOH)phenyl-methyl | CH₃ | -CH₂-CH(SH)-SH |
| H | biphenyl-2-COOCH₃, 4'-methyl | CH₃ | -CH₂-CH(SH)-SH |
| H | biphenyl-2-COOCH₃, 4-methyl | CH₃ | -CH₂-CH(SH)-SH |
| H | cyclohexyl-COOH | CH₃ | -CH₂-CH(SH)-SH |
| H | 4-(tetrazol-5-yl)phenyl-methyl | CH₃ | -CH₂-CH(SH)-SH |
| H | 3-(tetrazol-5-yl)phenyl-methyl | CH₃ | -CH₂-CH(SH)-SH |

TABLE II(a)-continued
| R[7] | W | R[24] | R[25] |
|---|---|---|---|
| H | 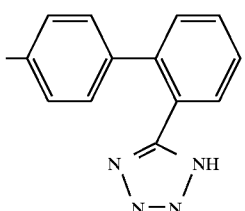 | CH$_3$ | 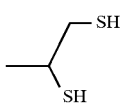 |
| H | 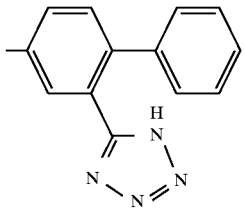 | CH$_3$ | 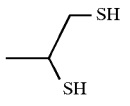 |
| H | 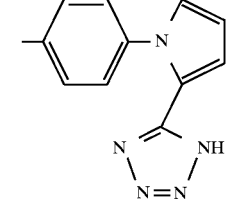 | CH$_3$ | 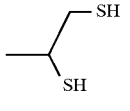 |
| H | 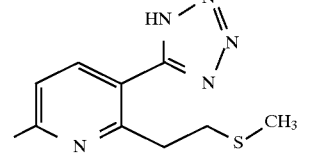 | CH$_3$ | 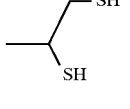 |
| H | 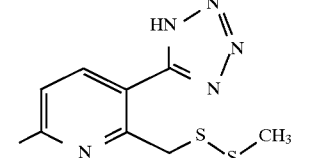 | CH$_3$ | 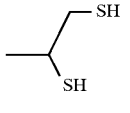 |
| H | 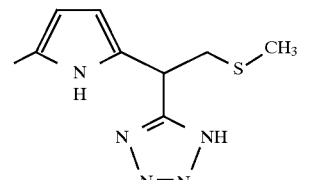 | CH$_3$ | 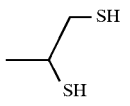 |
| H |  | CH$_3$ | 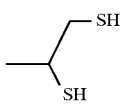 |

TABLE II(a)-continued
| R⁷ | W | R²⁴ | R²⁵ |
|---|---|---|---|
| H | 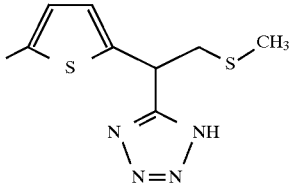 | $CH_3$ | 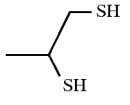 |
| H | 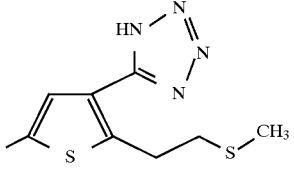 | $CH_3$ |  |
| H | 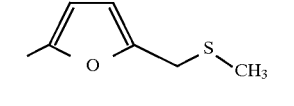 | $CH_3$ | 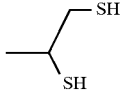 |
| H | 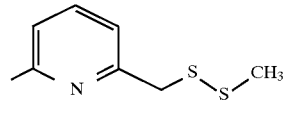 | $CH_3$ |  |
| H | 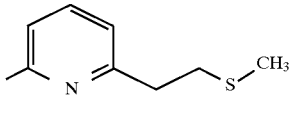 | $CH_3$ | 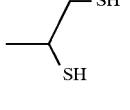 |
| H | 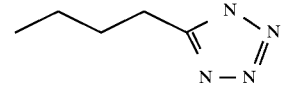 | $CH_3$ |  |
| H | 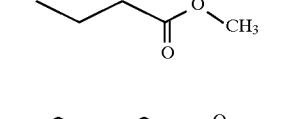 | $CH_3$ | 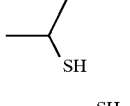 |
| H | 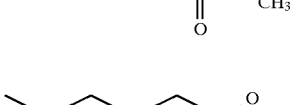 | $CH_3$ |  |
| H | 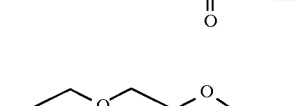 | $CH_3$ | 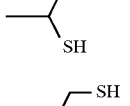 |
| H | 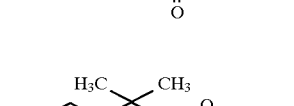 | $CH_3$ |  |
| H |  | $CH_3$ | 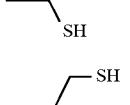 |
| H | 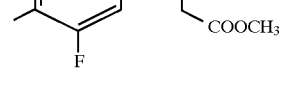 | $CH_3$ |  |

TABLE II(a)-continued

| R⁷ | W | R²⁴ | R²⁵ |
|---|---|---|---|
| H | 3-chlorophenyl | CH₃ | CH₂(SH)CH(SH)- |
| H | 2,5-difluorophenyl | CH₃ | CH₂(SH)CH(SH)- |
| H | 2,5-dimethylphenyl | CH₃ | CH₂(SH)CH(SH)- |
| H | 3-cyanophenyl | CH₃ | CH₂(SH)CH(SH)- |
| H | 4-cyanophenyl | CH₃ | CH₂(SH)CH(SH)- |
| H | 3-(COOCH₃)phenyl | CH₃ | CH₂(SH)CH(SH)- |
| H | 3-fluoro-4-CF₃-phenyl | CH₃ | CH₂(SH)CH(SH)- |
| H | 4-methylphenyl | CH₃ | CH₂(SH)CH(SH)- |
| H | 4-fluorophenyl | CH₃ | CH₂(SH)CH(SH)- |
| H | 2-methyl-4-fluorophenyl | CH₃ | CH₂(SH)CH(SH)- |
| H | 3-fluoro-4-methylphenyl | CH₃ | CH₂(SH)CH(SH)- |
| H | 4-(COOCH₃)cyclohexyl | CH₃ | CH₂(SH)CH(SH)- |
| H | 3-(CONH₂)phenyl | CH₃ | CH₂(SH)CH(SH)- |

TABLE II(a)-continued

| R⁷ | W | R²⁴ | R²⁵ |
|---|---|---|---|
| H | 3-(COCH₃)-phenyl | CH₃ | CH₂(SH)-CH(SH)-CH₃ |
| H | 3-F-5-(COOCH₃)-phenyl | CH₃ | CH₂(SH)-CH(SH)-CH₃ |
| H | 4-NO₂-phenyl | CH₃ | CH(SH)-CH₂-SH |
| H | CH₂-C(O)-O-CH₃ | CH₃ | CH₂-CH(SH)-CH₂-SH |
| H | CH₂-C(O)-O-CH₂CH₃ | CH₃ | CH₂-CH(SH)-CH₂-SH |
| H | 4-(COOCH₃)-phenyl | CH₃ | CH₂-CH(SH)-CH₂-SH |
| H | 3-(COOH)-phenyl | CH₃ | CH₂-CH(SH)-CH₂-SH |
| H | 4'-(COOCH₃)-biphenyl-2-yl | CH₃ | CH₂-CH(SH)-CH₂-SH |
| H | 4-(2-COOCH₃-phenyl)-phenyl | CH₃ | CH₂-CH(SH)-CH₂-SH |
| H | 4-COOH-cyclohexyl | CH₃ | CH₂-CH(SH)-CH₂-SH |
| H | 4-(tetrazol-5-yl)-phenyl | CH₃ | CH₂-CH(SH)-CH₂-SH |
| H | 3-(tetrazol-5-yl)-phenyl | CH₃ | CH₂-CH(SH)-CH₂-SH |

TABLE II(a)-continued
| R⁷ | W | R²⁴ | R²⁵ |
|---|---|---|---|
| H | 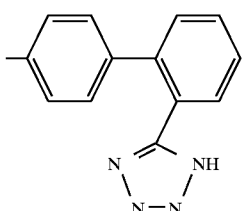 | CH₃ | 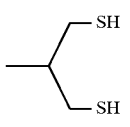 |
| H | 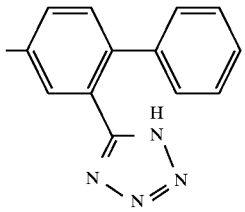 | CH₃ | 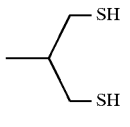 |
| H | 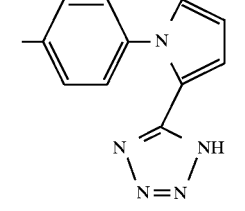 | CH₃ | 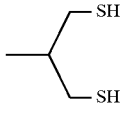 |
| H | 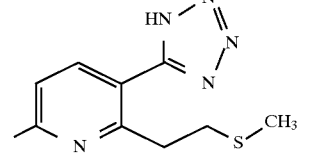 | CH₃ | 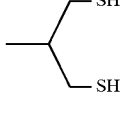 |
| H |  | CH₃ | 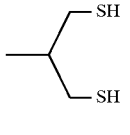 |
| H | 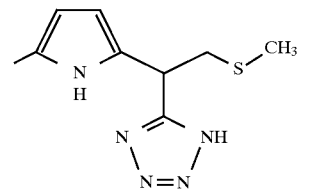 | CH₃ | 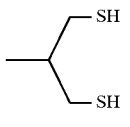 |
| H | 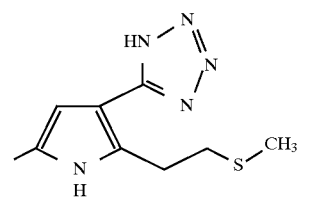 | CH₃ | 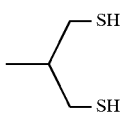 |

TABLE II(a)-continued

| R⁷ | W | R²⁴ | R²⁵ |
|---|---|---|---|
| H | 5-methyl-2-thienyl substituted with CH(CH₂SCH₃)- group attached to 1H-tetrazol-5-yl | CH₃ | CH₂(SH)CH(CH₃)– with second SH (2,3-dimercaptobutyl) |
| H | 5-methyl-thiophene with 2-(methylthio)ethyl and (1H-tetrazol-5-yl) substituents | CH₃ | 2,3-dimercapto-1-methylpropyl |
| H | 5-methyl-2-(methylthiomethyl)furan | CH₃ | 2,3-dimercapto-1-methylpropyl |
| H | 6-methyl-2-(methyldithiomethyl)pyridine | CH₃ | 2,3-dimercapto-1-methylpropyl |
| H | 6-methyl-2-[2-(methylthio)ethyl]pyridine | CH₃ | 2,3-dimercapto-1-methylpropyl |
| H | 5-butyl-1H-tetrazole | CH₃ | 2,3-dimercapto-1-methylpropyl |
| H | methyl butanoate | CH₃ | 2,3-dimercapto-1-methylpropyl |
| H | methyl pentanoate | CH₃ | 2,3-dimercapto-1-methylpropyl |
| H | methyl hexanoate | CH₃ | 2,3-dimercapto-1-methylpropyl |
| H | methyl 2-ethoxyacetate | CH₃ | 2,3-dimercapto-1-methylpropyl |
| H | methyl 2-ethoxy-2-methylpropanoate | CH₃ | 2,3-dimercapto-1-methylpropyl |

TABLE II(a)-continued
| R⁷ | W | R²⁴ | R²⁵ |
|---|---|---|---|
| H | 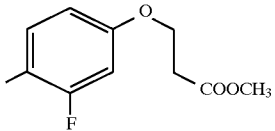 | CH₃ | 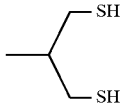 |
| H | 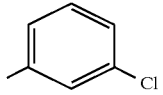 | CH₃ |  |
| H | 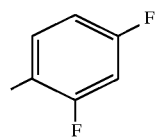 | CH₃ | 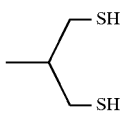 |
| H | 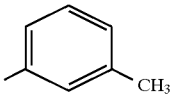 | CH₃ |  |
| H | 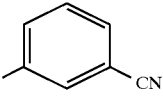 | CH₃ | 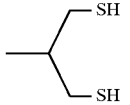 |
| H | 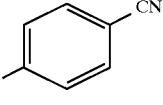 | CH₃ |  |
| H | 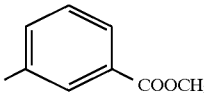 | CH₃ | 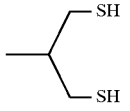 |
| H | 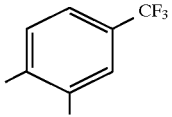 | CH₃ |  |
| H | 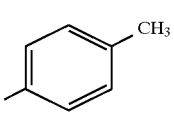 | CH₃ | 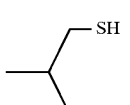 |
| H | 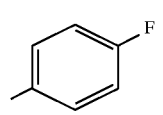 | CH₃ |  |
| H | 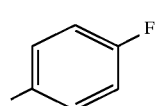 | CH₃ | 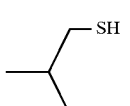 |
| H | 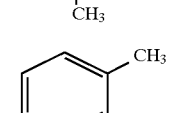 | CH₃ |  |

TABLE II(a)-continued

| R⁷ | W | R²⁴ | R²⁵ |
|---|---|---|---|
| H | cyclohexyl-COOCH₃ | CH₃ | -CH₂-CH(SH)-CH₂-SH |
| H | 3-(CONH₂)-phenyl | CH₃ | -CH₂-CH(SH)-CH₂-SH |
| H | 3-(COCH₃)-phenyl | CH₃ | -CH₂-CH(SH)-CH₂-SH |
| H | 3-F-5-(COOCH₃)-phenyl | CH₃ | -CH₂-CH(SH)-CH₂-SH |
| H | 4-NO₂-phenyl | CH₃ | -CH₂-CH(SH)-CH₂-SH |
| H | -CH₂-C(=O)-O-CH₃ | CH₃ | -CH₂-CH(SH)-CH₂-NH₂ |
| H | -CH₂-C(=O)-O-CH₂CH₃ | CH₃ | -CH₂-CH(SH)-CH₂-NH₂ |
| H | 4-(COOCH₃)-phenyl | CH₃ | -CH₂-CH(SH)-CH₂-NH₂ |
| H | 3-(COOH)-phenyl | CH₃ | -CH₂-CH(SH)-CH₂-NH₂ |
| H | 4'-(2-COOCH₃)-biphenyl | CH₃ | -CH₂-CH(SH)-CH₂-NH₂ |
| H | 4-(2-COOCH₃)-biphenyl | CH₃ | -CH₂-CH(SH)-CH₂-NH₂ |
| H | cyclohexyl-COOH | CH₃ | -CH₂-CH(SH)-CH₂-NH₂ |

TABLE II(a)-continued
| R⁷ | W | R²⁴ | R²⁵ |
|---|---|---|---|
| H | 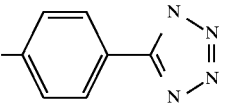 | CH₃ | 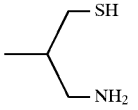 |
| H | 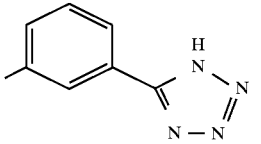 | CH₃ | 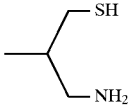 |
| H | 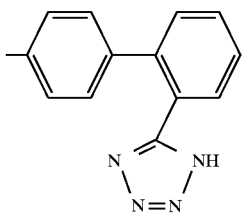 | CH₃ | 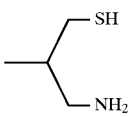 |
| H | 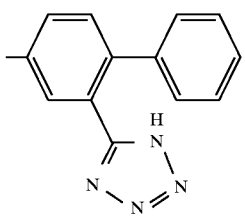 | CH₃ | 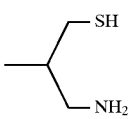 |
| H | 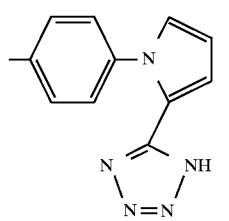 | CH₃ | 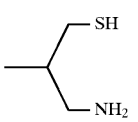 |
| H | 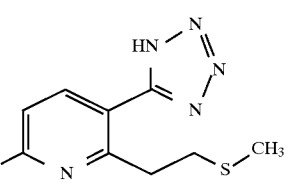 | CH₃ | 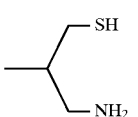 |
| H | 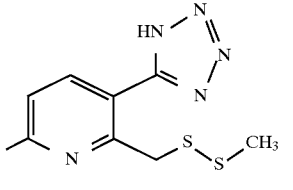 | CH₃ | 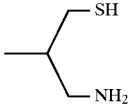 |
| H | 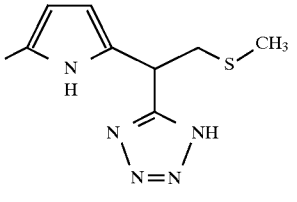 | CH₃ | 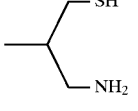 |

TABLE II(a)-continued
| R⁷ | W | R²⁴ | R²⁵ |
|---|---|---|---|
| H | 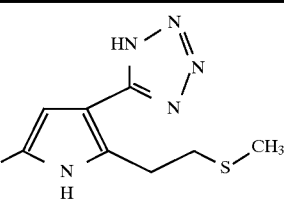 | CH₃ | 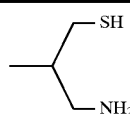 |
| H | 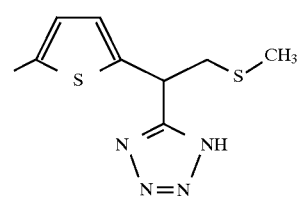 | CH₃ | 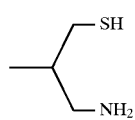 |
| H | 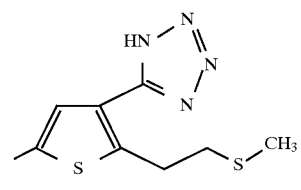 | CH₃ | 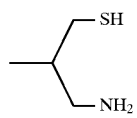 |
| H | 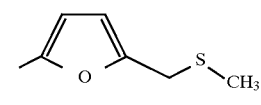 | CH₃ | 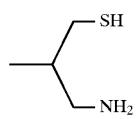 |
| H | 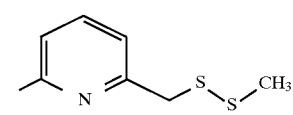 | CH₃ | 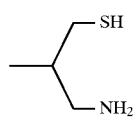 |
| H | 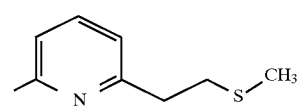 | CH₃ | 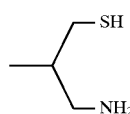 |
| H | 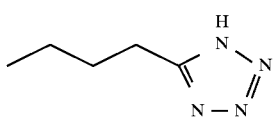 | CH₃ | 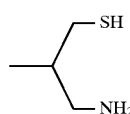 |
| H | 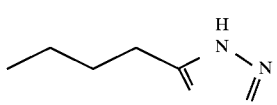 | CH₃ | 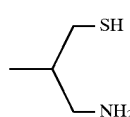 |
| H | 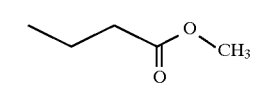 | CH₃ | 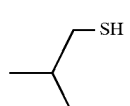 |
| H | 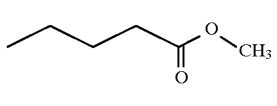 | CH₃ | 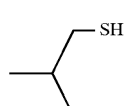 |
| H | 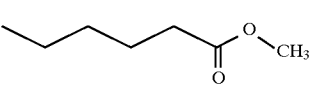 | CH₃ | 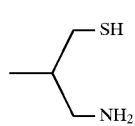 |

TABLE II(a)-continued
| R⁷ | W | R²⁴ | R²⁵ |
|---|---|---|---|
| H | 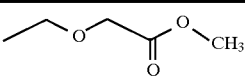 | CH₃ | 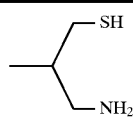 |
| H | 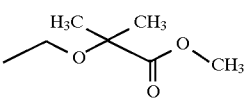 | CH₃ | 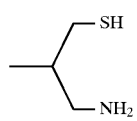 |
| H | 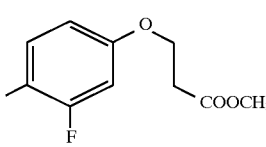 | CH₃ | 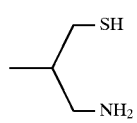 |
| H | 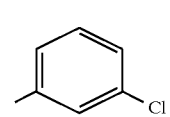 | CH₃ | 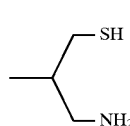 |
| H | 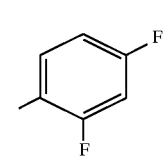 | CH₃ | 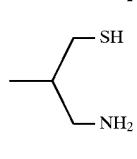 |
| H | 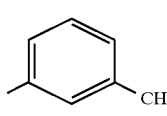 | CH₃ | 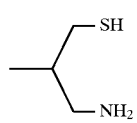 |
| H | 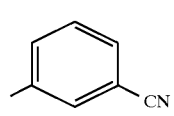 | CH₃ | 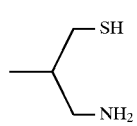 |
| H | 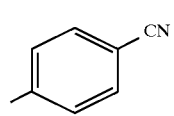 | CH₃ | 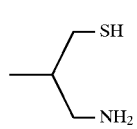 |
| H | 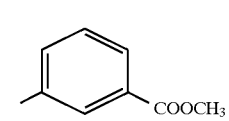 | CH₃ | 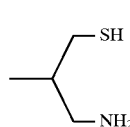 |
| H | 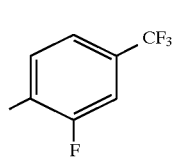 | CH₃ | 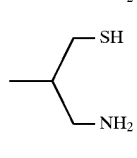 |
| H | 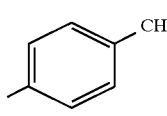 | CH₃ | 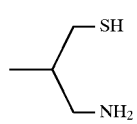 |
| H | 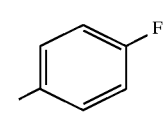 | CH₃ | 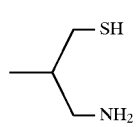 |

TABLE II(a)-continued
| $R^7$ | W | $R^{24}$ | $R^{25}$ |
|---|---|---|---|
| H | 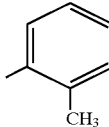 | $CH_3$ | 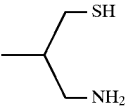 |
| H |  | $CH_3$ | 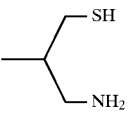 |
| H | 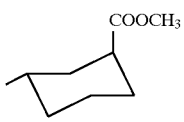 | $CH_3$ | 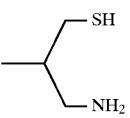 |
| H | 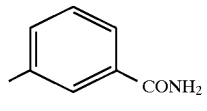 | $CH_3$ | 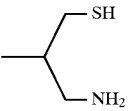 |
| H | 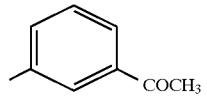 | $CH_3$ | 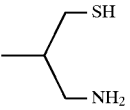 |
| H | 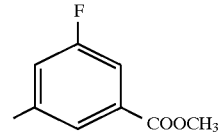 | $CH_3$ | 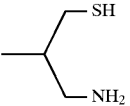 |
| H | 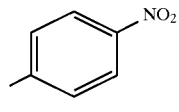 | $CH_3$ | 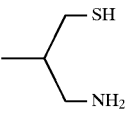 |
| H | 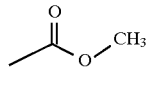 | $CH_3$ | 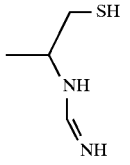 |
| H | 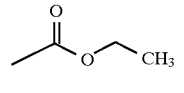 | $CH_3$ | 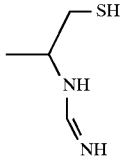 |
| H | 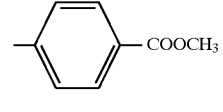 | $CH_3$ | 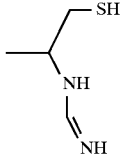 |

TABLE II(a)-continued

| R[7] | W | R[24] | R[25] |
|---|---|---|---|
| H | 3-carboxyphenyl (m-COOH-C6H4-) | CH3 | -CH(CH3)-CH2-SH with NH-CH=NH |
| H | 4'-methyl-biphenyl-2-yl with H3COOC at 2-position | CH3 | -CH(CH3)-CH2-SH with NH-CH=NH |
| H | biphenyl-2-yl with COOCH3 | CH3 | -CH(CH3)-CH2-SH with NH-CH=NH |
| H | cyclohexyl-COOH | CH3 | -CH(CH3)-CH2-SH with NH-CH=NH |
| H | 4-(1H-tetrazol-5-yl)phenyl | CH3 | -CH(CH3)-CH2-SH with NH-CH=NH |
| H | 3-(1H-tetrazol-5-yl)phenyl | CH3 | -CH(CH3)-CH2-SH with NH-CH=NH |
| H | 4'-methyl-2-(1H-tetrazol-5-yl)biphenyl-2-yl | CH3 | -CH(CH3)-CH2-SH with NH-CH=NH |
| H | 2'-(1H-tetrazol-5-yl)biphenyl-2-yl | CH3 | -CH(CH3)-CH2-SH with NH-CH=NH |

TABLE II(a)-continued
| R[7] | W | R[24] | R[25] |
|---|---|---|---|
| H | 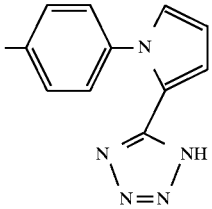 | CH$_3$ | 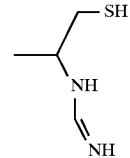 |
| H | 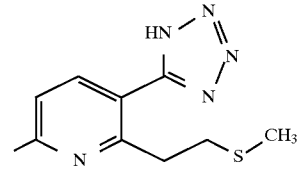 | CH$_3$ | 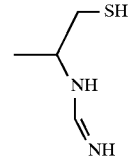 |
| H | 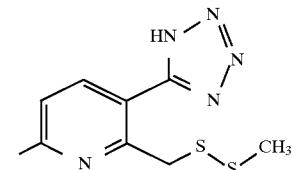 | CH$_3$ | 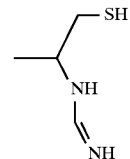 |
| H | 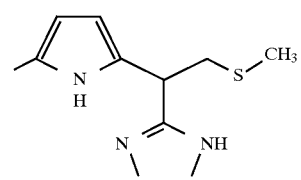 | CH$_3$ | 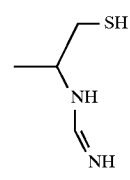 |
| H | 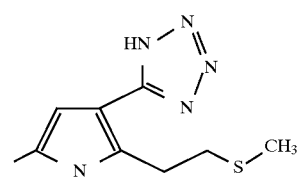 | CH$_3$ | 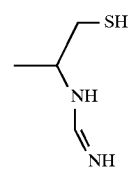 |
| H | 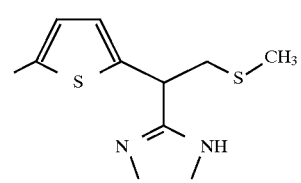 | CH$_3$ | 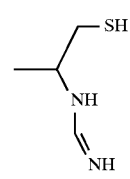 |
| H | 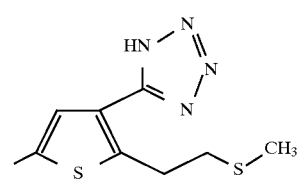 | CH$_3$ | 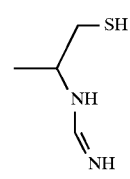 |
| H | 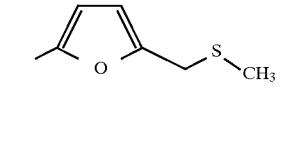 | CH$_3$ | 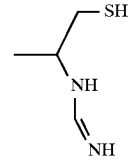 |

TABLE II(a)-continued

| R[7] | W | R[24] | R[25] |
|---|---|---|---|
| H | 6-methyl-2-(methyldithiomethyl)pyridine | CH$_3$ | -CH$_2$-SH, -CH(NH-C(=NH)NH$_2$)-CH$_3$ |
| H | 6-methyl-2-(2-(methylthio)ethyl)pyridine | CH$_3$ | -CH$_2$-SH, -CH(NH-C(=NH)NH$_2$)-CH$_3$ |
| H | 5-butyl-1H-tetrazole | CH$_3$ | -CH$_2$-SH, -CH(NH-C(=NH)NH$_2$)-CH$_3$ |
| H | 5-pentyl-1H-tetrazole | CH$_3$ | -CH$_2$-SH, -CH(NH-C(=NH)NH$_2$)-CH$_3$ |
| H | methyl butanoate | CH$_3$ | -CH$_2$-SH, -CH(NH-C(=NH)NH$_2$)-CH$_3$ |
| H | methyl pentanoate | CH$_3$ | -CH$_2$-SH, -CH(NH-C(=NH)NH$_2$)-CH$_3$ |
| H | methyl hexanoate | CH$_3$ | -CH$_2$-SH, -CH(NH-C(=NH)NH$_2$)-CH$_3$ |
| H | methyl 2-ethoxyacetate | CH$_3$ | -CH$_2$-SH, -CH(NH-C(=NH)NH$_2$)-CH$_3$ |
| H | methyl 2-ethoxy-2-methylpropanoate | CH$_3$ | -CH$_2$-SH, -CH(NH-C(=NH)NH$_2$)-CH$_3$ |

TABLE II(a)-continued

| R⁷ | W | R²⁴ | R²⁵ |
|---|---|---|---|
| H | 3-fluoro-4-methyl-phenoxy-CH₂CH₂-COOCH₃ | CH₃ | CH₂SH-CH(CH₃)-NH-CH=NH |
| H | 3-chlorophenyl | CH₃ | CH₂SH-CH(CH₃)-NH-CH=NH |
| H | 2,5-difluorophenyl | CH₃ | CH₂SH-CH(CH₃)-NH-CH=NH |
| H | 3-methylphenyl | CH₃ | CH₂SH-CH(CH₃)-NH-CH=NH |
| H | 3-cyanophenyl | CH₃ | CH₂SH-CH(CH₃)-NH-CH=NH |
| H | 4-cyanophenyl | CH₃ | CH₂SH-CH(CH₃)-NH-CH=NH |
| H | 3-(COOCH₃)-phenyl | CH₃ | CH₂SH-CH(CH₃)-NH-CH=NH |
| H | 3-fluoro-4-trifluoromethyl-phenyl | CH₃ | CH₂SH-CH(CH₃)-NH-CH=NH |
| H | 4-methylphenyl | CH₃ | CH₂SH-CH(CH₃)-NH-CH=NH |

TABLE II(a)-continued

| R⁷ | W | R²⁴ | R²⁵ |
|---|---|---|---|
| H | 4-fluorophenyl | CH₃ | -CH(CH₃)CH₂SH with NH-C(=NH)NH₂ group |
| H | 5-fluoro-2-methylphenyl | CH₃ | -CH(CH₃)CH₂SH with NH-C(=NH)NH₂ group |
| H | 3-fluoro-4-methylphenyl | CH₃ | -CH(CH₃)CH₂SH with NH-C(=NH)NH₂ group |
| H | 4-(methoxycarbonyl)cyclohexyl | CH₃ | -CH(CH₃)CH₂SH with NH-C(=NH)NH₂ group |
| H | 3-carbamoylphenyl | CH₃ | -CH(CH₃)CH₂SH with NH-C(=NH)NH₂ group |
| H | 3-acetylphenyl | CH₃ | -CH(CH₃)CH₂SH with NH-C(=NH)NH₂ group |
| H | 3-fluoro-5-(methoxycarbonyl)phenyl | CH₃ | -CH(CH₃)CH₂SH with NH-C(=NH)NH₂ group |
| H | 4-nitrophenyl | CH₃ | -CH(CH₃)CH₂SH with NH-C(=NH)NH₂ group |
| H | -CH₂-C(=O)-O-CH₃ | CH₃ | -CH(CH₃)CH₂SH with C(=NH)NH₂ group |

TABLE II(a)-continued

| R⁷ | W | R²⁴ | R²⁵ |
|---|---|---|---|
| H | -C(=O)-O-CH₂CH₃ (ethyl acetate group) | CH₃ | -CH₂-CH(CH₃)-C(=NH)-NH₂ with SH |
| H | -C₆H₄-COOCH₃ (para) | CH₃ | -CH₂-CH(CH₃)-C(=NH)-NH₂ with SH |
| H | -C₆H₄-COOH (meta) | CH₃ | -CH₂-CH(CH₃)-C(=NH)-NH₂ with SH |
| H | biphenyl with H₃COOC | CH₃ | -CH₂-CH(CH₃)-C(=NH)-NH₂ with SH |
| H | biphenyl with COOCH₃ | CH₃ | -CH₂-CH(CH₃)-C(=NH)-NH₂ with SH |
| H | cyclohexyl-COOH | CH₃ | -CH₂-CH(CH₃)-C(=NH)-NH₂ with SH |
| H | phenyl-tetrazole (para) | CH₃ | -CH₂-CH(CH₃)-C(=NH)-NH₂ with SH |
| H | phenyl-tetrazole (meta) | CH₃ | -CH₂-CH(CH₃)-C(=NH)-NH₂ with SH |
| H | biphenyl-tetrazole | CH₃ | -CH₂-CH(CH₃)-C(=NH)-NH₂ with SH |

TABLE II(a)-continued
| R⁷ | W | R²⁴ | R²⁵ |
|---|---|---|---|
| H | 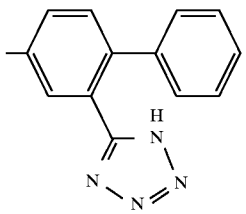 | CH₃ | 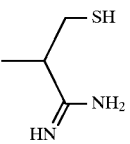 |
| H | 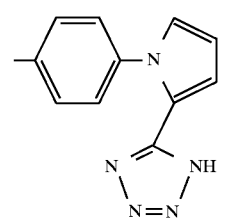 | CH₃ | 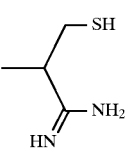 |
| H | 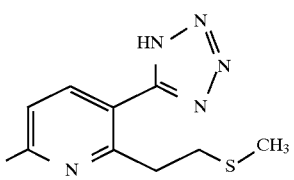 | CH₃ | 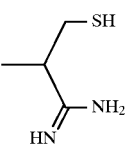 |
| H | 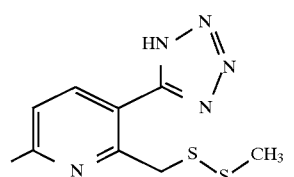 | CH₃ | 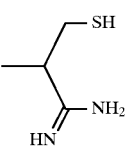 |
| H | 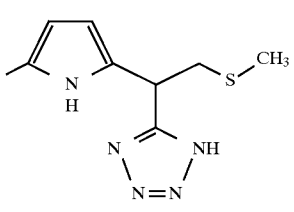 | CH₃ | 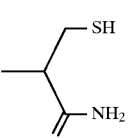 |
| H | 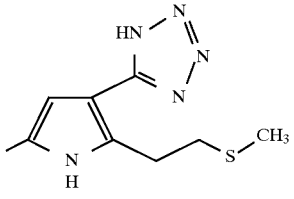 | CH₃ | 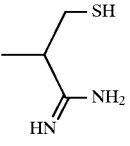 |
| H | 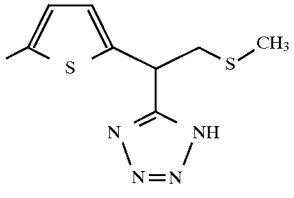 | CH₃ | 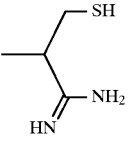 |
| H | 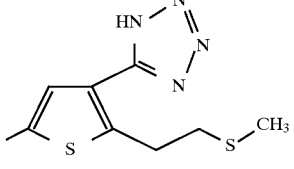 | CH₃ | 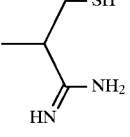 |

TABLE II(a)-continued

| R[7] | W | R[24] | R[25] |
|---|---|---|---|
| H | 5-methyl-2-(methylthiomethyl)furan | CH$_3$ | CH$_2$SH, CH(CH$_3$)C(=NH)NH$_2$ |
| H | 6-methyl-2-(methyldithiomethyl)pyridine | CH$_3$ | CH$_2$SH, CH(CH$_3$)C(=NH)NH$_2$ |
| H | 6-methyl-2-(2-(methylthio)ethyl)pyridine | CH$_3$ | CH$_2$SH, CH(CH$_3$)C(=NH)NH$_2$ |
| H | 5-butyl-1H-tetrazole | CH$_3$ | CH$_2$SH, CH(CH$_3$)C(=NH)NH$_2$ |
| H | 5-butyl-1H-tetrazole | CH$_3$ | CH$_2$SH, CH(CH$_3$)C(=NH)NH$_2$ |
| H | methyl butanoate | CH$_3$ | CH$_2$SH, CH(CH$_3$)C(=NH)NH$_2$ |
| H | methyl pentanoate | CH$_3$ | CH$_2$SH, CH(CH$_3$)C(=NH)NH$_2$ |
| H | methyl hexanoate | CH$_3$ | CH$_2$SH, CH(CH$_3$)C(=NH)NH$_2$ |
| H | methyl 2-ethoxyacetate | CH$_3$ | CH$_2$SH, CH(CH$_3$)C(=NH)NH$_2$ |
| H | methyl 2-ethoxy-2-methylpropanoate | CH$_3$ | CH$_2$SH, CH(CH$_3$)C(=NH)NH$_2$ |

TABLE II(a)-continued

| R⁷ | W | R²⁴ | R²⁵ |
|---|---|---|---|
| H | 3-fluoro-4-methyl-phenoxy-CH₂-COOCH₃ | CH₃ | -CH₂-C(CH₃)(SH)-C(=NH)-NH₂ |
| H | 3-chloro-4-methyl-phenyl | CH₃ | -CH₂-C(CH₃)(SH)-C(=NH)-NH₂ |
| H | 2,5-difluoro-4-methyl-phenyl | CH₃ | -CH₂-C(CH₃)(SH)-C(=NH)-NH₂ |
| H | 3,4-dimethyl-phenyl | CH₃ | -CH₂-C(CH₃)(SH)-C(=NH)-NH₂ |
| H | 3-cyano-4-methyl-phenyl | CH₃ | -CH₂-C(CH₃)(SH)-C(=NH)-NH₂ |
| H | 4-cyano-3-methyl-phenyl | CH₃ | -CH₂-C(CH₃)(SH)-C(=NH)-NH₂ |
| H | 4-methyl-3-(COOCH₃)-phenyl | CH₃ | -CH₂-C(CH₃)(SH)-C(=NH)-NH₂ |
| H | 3-fluoro-4-methyl-5-CF₃-phenyl | CH₃ | -CH₂-C(CH₃)(SH)-C(=NH)-NH₂ |
| H | 3,4-dimethyl-phenyl (4-CH₃) | CH₃ | -CH₂-C(CH₃)(SH)-C(=NH)-NH₂ |
| H | 4-fluoro-phenyl | CH₃ | -CH₂-C(CH₃)(SH)-C(=NH)-NH₂ |

TABLE II(a)-continued
| R⁷ | W | R²⁴ | R²⁵ |
|---|---|---|---|
| H | 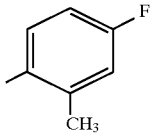 | CH₃ | 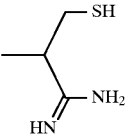 |
| H |  | CH₃ | 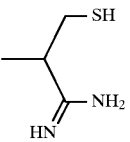 |
| H | 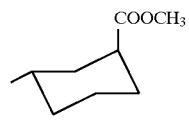 | CH₃ | 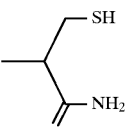 |
| H | 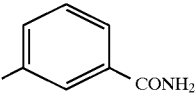 | CH₃ | 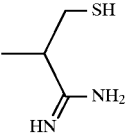 |
| H | 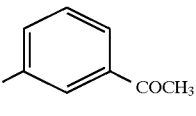 | CH₃ | 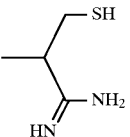 |
| H | 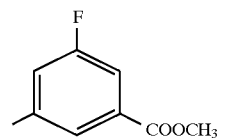 | CH₃ | 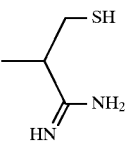 |
| H | 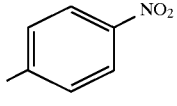 | CH₃ | 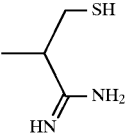 |
| H | 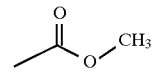 | CH₃ | 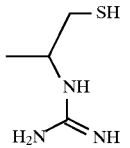 |
| H | 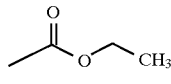 | CH₃ | 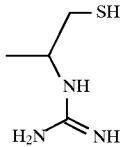 |
| H | 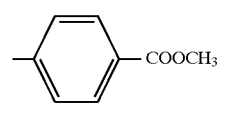 | CH₃ | 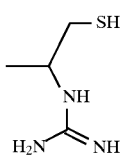 |

TABLE II(a)-continued

| R[7] | W | R[24] | R[25] |
|---|---|---|---|
| H | 3-carboxyphenyl (COOH meta) | CH$_3$ | CH$_2$SH, CH(CH$_3$)NH-C(=NH)NH$_2$ |
| H | 4'-substituted-2-(methoxycarbonyl)biphenyl (H$_3$COOC) | CH$_3$ | CH$_2$SH, CH(CH$_3$)NH-C(=NH)NH$_2$ |
| H | 4-substituted-2-(methoxycarbonyl)biphenyl (COOCH$_3$) | CH$_3$ | CH$_2$SH, CH(CH$_3$)NH-C(=NH)NH$_2$ |
| H | cyclohexyl-COOH | CH$_3$ | CH$_2$SH, CH(CH$_3$)NH-C(=NH)NH$_2$ |
| H | 4-(1H-tetrazol-5-yl)phenyl | CH$_3$ | CH$_2$SH, CH(CH$_3$)NH-C(=NH)NH$_2$ |
| H | 3-(1H-tetrazol-5-yl)phenyl | CH$_3$ | CH$_2$SH, CH(CH$_3$)NH-C(=NH)NH$_2$ |
| H | 4'-substituted-2-(1H-tetrazol-5-yl)biphenyl | CH$_3$ | CH$_2$SH, CH(CH$_3$)NH-C(=NH)NH$_2$ |
| H | 4-substituted-2'-(1H-tetrazol-5-yl)biphenyl | CH$_3$ | CH$_2$SH, CH(CH$_3$)NH-C(=NH)NH$_2$ |
| H | 4-[2-(1H-tetrazol-5-yl)pyrrol-1-yl]phenyl | CH$_3$ | CH$_2$SH, CH(CH$_3$)NH-C(=NH)NH$_2$ |

TABLE II(a)-continued
| R⁷ | W | R²⁴ | R²⁵ |
|---|---|---|---|
| H | 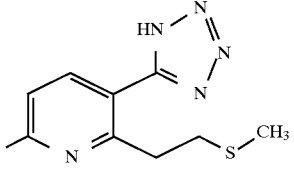 | CH₃ | 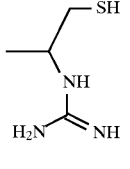 |
| H | 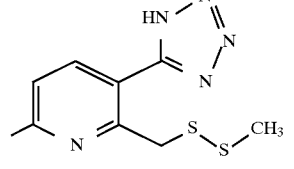 | CH₃ | 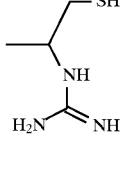 |
| H | 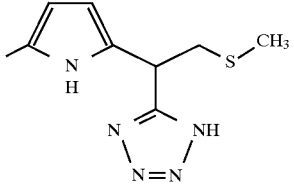 | CH₃ | 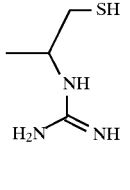 |
| H | 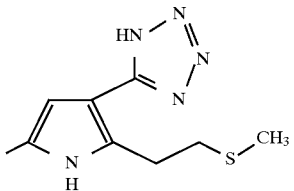 | CH₃ | 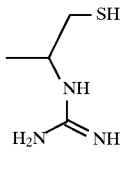 |
| H | 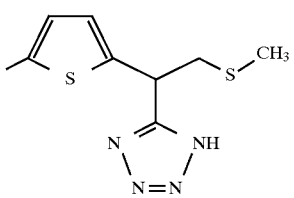 | CH₃ | 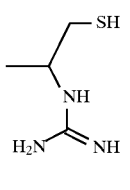 |
| H | 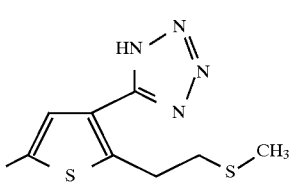 | CH₃ | 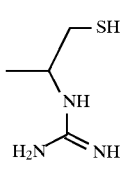 |
| H | 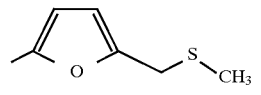 | CH₃ | 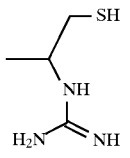 |
| H | 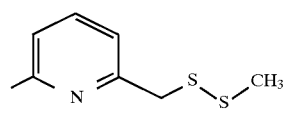 | CH₃ | 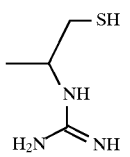 |

TABLE II(a)-continued

| R⁷ | W | R²⁴ | R²⁵ |
|---|---|---|---|
| H | 6-methyl-2-(2-methylthioethyl)pyridine | CH₃ | 1-mercapto-2-guanidinopropyl |
| H | 5-butyl-1H-tetrazole | CH₃ | 1-mercapto-2-guanidinopropyl |
| H | 5-butyl-2H-tetrazole | CH₃ | 1-mercapto-2-guanidinopropyl |
| H | methyl butanoate | CH₃ | 1-mercapto-2-guanidinopropyl |
| H | methyl pentanoate | CH₃ | 1-mercapto-2-guanidinopropyl |
| H | methyl hexanoate | CH₃ | 1-mercapto-2-guanidinopropyl |
| H | methyl ethoxyacetate | CH₃ | 1-mercapto-2-guanidinopropyl |
| H | methyl 2-ethoxy-2-methylpropanoate | CH₃ | 1-mercapto-2-guanidinopropyl |
| H | methyl 3-(3-fluoro-4-methylphenoxy)propanoate | CH₃ | 1-mercapto-2-guanidinopropyl |
| H | 3-chlorotoluene | CH₃ | 1-mercapto-2-guanidinopropyl |

TABLE II(a)-continued
| R[7] | W | R[24] | R[25] |
|---|---|---|---|
| H | 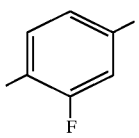 2,5-difluorophenyl | CH$_3$ | 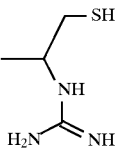 |
| H | 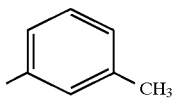 3-methylphenyl | CH$_3$ | 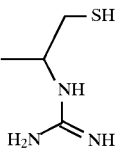 |
| H | 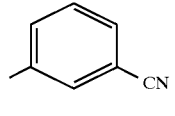 3-cyanophenyl | CH$_3$ | 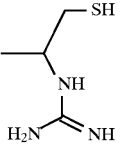 |
| H | 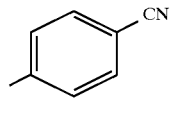 4-cyanophenyl | CH$_3$ | 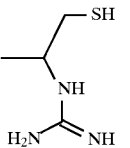 |
| H | 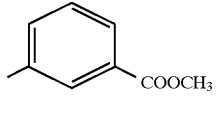 3-(COOCH$_3$)phenyl | CH$_3$ | 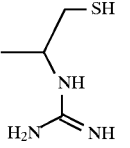 |
| H |  3-fluoro-4-CF$_3$-phenyl | CH$_3$ | 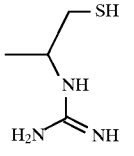 |
| H | 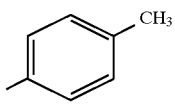 4-methylphenyl | CH$_3$ | 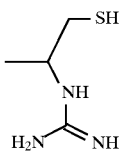 |
| H | 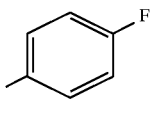 4-fluorophenyl | CH$_3$ | 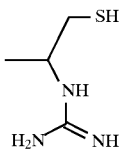 |
| H | 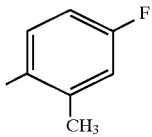 2-methyl-4-fluorophenyl | CH$_3$ | 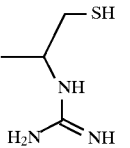 |
| H | 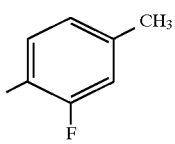 3-fluoro-4-methylphenyl | CH$_3$ | 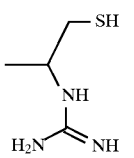 |

TABLE II(a)-continued

| R⁷ | W | R²⁴ | R²⁵ |
|---|---|---|---|
| H | cyclohexyl-COOCH₃ | CH₃ | -SH, -NH-C(=NH)NH₂ (on propyl) |
| H | 3-CONH₂-phenyl | CH₃ | -SH, -NH-C(=NH)NH₂ (on propyl) |
| H | 3-COCH₃-phenyl | CH₃ | -SH, -NH-C(=NH)NH₂ (on propyl) |
| H | 3-F-5-COOCH₃-phenyl | CH₃ | -SH, -NH-C(=NH)NH₂ (on propyl) |
| H | 4-NO₂-phenyl | CH₃ | -SH, -NH-C(=NH)NH₂ (on propyl) |

An alternate preferred embodiment of the invention comprises a compound capable of inhibiting farnesyl:protein transferase at a concentration equal to or lower than that of the tetrapeptide CVFM represented by Formula II(b).

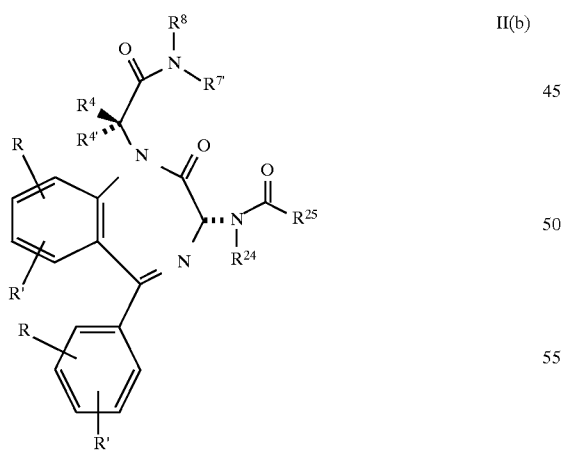

II(b)

Substituents R and R' are hydrogen or halogen (Cl and F). Preferably, halogen substituents R and R' are located at ring positions 7 and 2' of the compound of Formula II(b). Substituents $R^4$ and $R^{4'}$ are hydrogen or lower alkyl, and $R^{7'}$, $R^8$, $R^{24}$, and R25 are selected according to Table II(b)(1) and Table II(b)(2).

TABLE II(b)(1)

| R⁷ | R⁸ | R²⁴ | R²⁵ |
|---|---|---|---|
| H | 2-methyl-4-(methylthio)butanoic acid | CH₃ | 2-amino-1-mercaptoethyl |
| H | methyl 2-methyl-4-(methylthio)butanoate | CH₃ | 2-amino-1-mercaptoethyl |
| H | cyclohexyl 2-methyl-4-(methylthio)butanoate | CH₃ | 2-amino-1-mercaptoethyl |
| H | 2,4-dimethylpentanoic acid | CH₃ | 2-amino-1-mercaptoethyl |
| H | 2,3-dimethylpentanoic acid | CH₃ | 2-amino-1-mercaptoethyl |
| H | 2-methyl-3-phenylpropanoic acid | CH₃ | 2-amino-1-mercaptoethyl |
| H | 3-(4-fluorophenyl)-2-methylpropanoic acid | CH₃ | 2-amino-1-mercaptoethyl |
| H | 2-methyl-3-(1-naphthyl)propanoic acid | CH₃ | 2-amino-1-mercaptoethyl |
| H | 3-(4-methoxyphenyl)-2-methylpropanoic acid | CH₃ | 2-amino-1-mercaptoethyl |
| H | 2-methyl-4-(methylthio)butanamide | CH₃ | 2-amino-1-mercaptoethyl |
| H | 3-methoxy-2-methylpropanoic acid | CH₃ | 2-amino-1-mercaptoethyl |
| H | 3-cyclohexyl-2-methylpropanoic acid | CH₃ | 2-amino-1-mercaptoethyl |
| H | 5-(1-methyl-2-phenylethyl)-1H-tetrazole | CH₃ | 2-amino-1-mercaptoethyl |

TABLE II(b)(1)-continued

| R⁷ | R⁸ | R²⁴ | R²⁵ |
|---|---|---|---|
| H | 5-(1-methyl-3-(methylthio)propyl)-1H-tetrazole | CH₃ | 2-aminoethanethiol |
| H | 5-(1,3-dimethylbutyl)-1H-tetrazole | CH₃ | 2-aminoethanethiol |
| H | 5-(1,2-dimethylbutyl)-1H-tetrazole | CH₃ | 2-aminoethanethiol |
| H | cyclohexyl 2-methylhexanoate | CH₃ | 2-aminoethanethiol |
| H | tert-butyl 2-methyloctanoate | CH₃ | 2-aminoethanethiol |
| H | 2-methylheptanoic acid | CH₃ | 2-aminoethanethiol |
| H | 5-(2-cyclohexyl-1-methylethyl)-1H-tetrazole | CH₃ | 2-aminoethanethiol |
| H | cyclohexyl 3-cyclohexyl-2-methylpropanoate | CH₃ | 2-aminoethanethiol |
| H | 3-cyclohexyl-2-methylpropanoic acid | CH₃ | 2-aminoethanethiol |
| H | cyclohexyl 2-methyl-4-phenylbutanoate | CH₃ | 2-aminoethanethiol |

TABLE II(b)(1)-continued
| R⁷ | R⁸ | R²⁴ | R²⁵ |
|---|---|---|---|
| H | 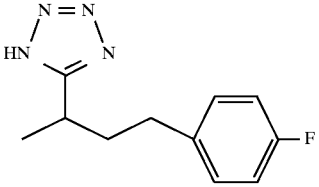 | CH₃ | 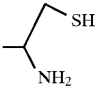 |
| H | 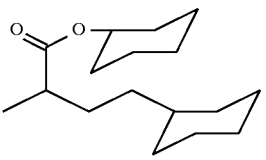 | CH₃ | 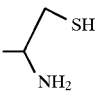 |
| H | 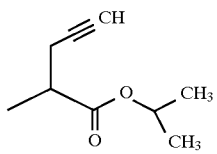 | CH₃ | 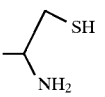 |
| H | 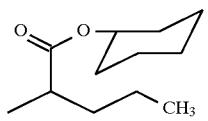 | CH₃ | 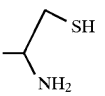 |
| H | 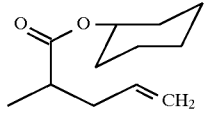 | CH₃ | 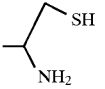 |
| H | 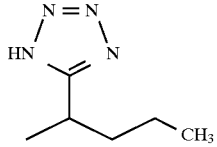 | CH₃ | 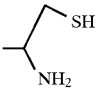 |
| H | 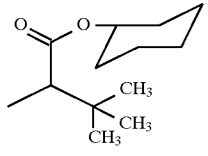 | CH₃ | 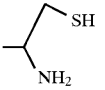 |
| H | 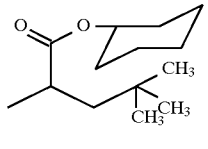 | CH₃ | 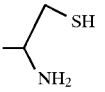 |
| H | 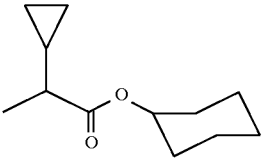 | CH₃ | 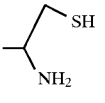 |
| H | 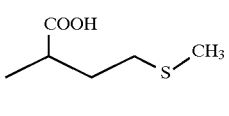 | CH₃ | 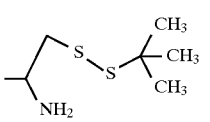 |

TABLE II(b)(1)-continued

| R⁷ | R⁸ | R²⁴ | R²⁵ |
|---|---|---|---|
| H | COOCH₃, CH(CH₃)CH₂CH₂SCH₃ | CH₃ | CH₂CH(NH₂)S-S-C(CH₃)₃ |
| H | cyclohexyl ester of 2-methyl-4-(methylthio)butanoate | CH₃ | CH₂CH(NH₂)S-S-C(CH₃)₃ |
| H | COOH, CH(CH₃)CH(CH₃)₂ (2,4-dimethyl) | CH₃ | CH₂CH(NH₂)S-S-C(CH₃)₃ |
| H | COOH, CH(CH₃)CH(CH₃)CH₂CH₃ | CH₃ | CH₂CH(NH₂)S-S-C(CH₃)₃ |
| H | COOH, CH(CH₃)CH₂-phenyl | CH₃ | CH₂CH(NH₂)S-S-C(CH₃)₃ |
| H | COOH, CH(CH₃)CH₂-(4-F-phenyl) | CH₃ | CH₂CH(NH₂)S-S-C(CH₃)₃ |
| H | COOH, CH(CH₃)CH₂-(1-naphthyl) | CH₃ | CH₂CH(NH₂)S-S-C(CH₃)₃ |
| H | COOH, CH(CH₃)CH₂-(4-OCH₃-phenyl) | CH₃ | CH₂CH(NH₂)S-S-C(CH₃)₃ |
| H | CONH₂, CH(CH₃)CH₂CH₂SCH₃ | CH₃ | CH₂CH(NH₂)S-S-C(CH₃)₃ |
| H | COOH, CH(CH₃)CH₂OCH₃ | CH₃ | CH₂CH(NH₂)S-S-C(CH₃)₃ |
| H | COOH, CH(CH₃)CH₂-cyclohexyl | CH₃ | CH₂CH(NH₂)S-S-C(CH₃)₃ |
| H | tetrazolyl-C(CH₃)CH₂-phenyl | CH₃ | CH₂CH(NH₂)S-S-C(CH₃)₃ |

TABLE II(b)(1)-continued

| R⁷ | R⁸ | R²⁴ | R²⁵ |
|---|---|---|---|
| H | 1-methyl-3-(methylthio)propyl-tetrazole | $CH_3$ | 2-amino-1-(tert-butyldisulfanyl)propyl |
| H | 1,3-dimethylbutyl-tetrazole | $CH_3$ | 2-amino-1-(tert-butyldisulfanyl)propyl |
| H | 1,2-dimethylbutyl-tetrazole | $CH_3$ | 2-amino-1-(tert-butyldisulfanyl)propyl |
| H | cyclohexyl 2-methylhexanoate | $CH_3$ | 2-amino-1-(tert-butyldisulfanyl)propyl |
| H | isopropyl 2-methyloctanoate | $CH_3$ | 2-amino-1-(tert-butyldisulfanyl)propyl |
| H | 2-methylheptanoic acid | $CH_3$ | 2-amino-1-(tert-butyldisulfanyl)propyl |
| H | 1-cyclohexyl-2-methyl-tetrazole | $CH_3$ | 2-amino-1-(tert-butyldisulfanyl)propyl |
| H | cyclohexyl 2-methyl-3-cyclohexylpropanoate | $CH_3$ | 2-amino-1-(tert-butyldisulfanyl)propyl |
| H | 2-methyl-3-cyclohexylpropanoic acid | $CH_3$ | 2-amino-1-(tert-butyldisulfanyl)propyl |
| H | cyclohexyl 2-methyl-4-phenylbutanoate | $CH_3$ | 2-amino-1-(tert-butyldisulfanyl)propyl |

TABLE II(b)(1)-continued
| $R^{7'}$ | $R^8$ | $R^{24}$ | $R^{25}$ |
|---|---|---|---|
| H | 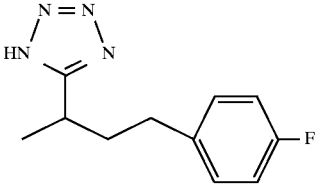 | $CH_3$ | 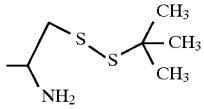 |
| H | 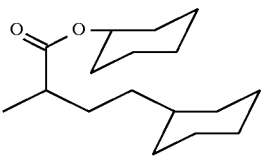 | $CH_3$ | 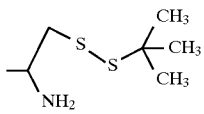 |
| H | 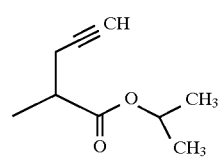 | $CH_3$ | 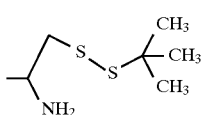 |
| H | 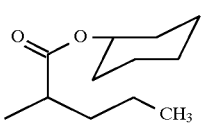 | $CH_3$ | 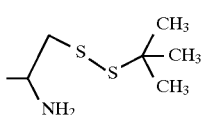 |
| H | 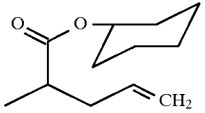 | $CH_3$ | 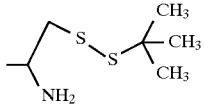 |
| H | 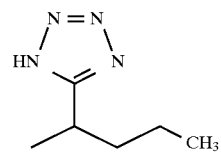 | $CH_3$ | 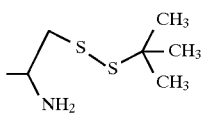 |
| H | 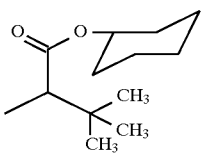 | $CH_3$ | 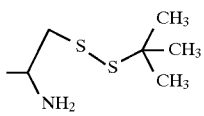 |
| H | 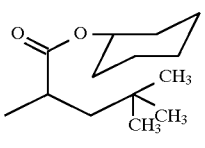 | $CH_3$ | 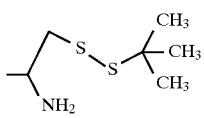 |
| H | 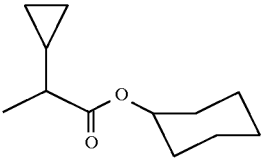 | $CH_3$ | 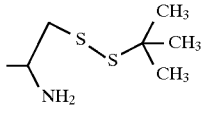 |
| H | 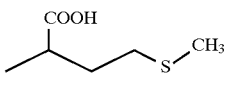 | $CH_3CF_3$ | 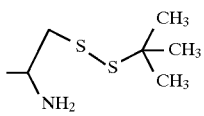 |

TABLE II(b)(1)-continued

| R⁷ | R⁸ | R²⁴ | R²⁵ |
|---|---|---|---|
| H | CH₃OOC-CH(CH₃)-CH₂-CH₂-S-CH₃ | CH₃CF₃ | (CH₃)₃C-S-S-CH₂-CH(NH₂)- |
| H | HOOC-CH(CH₃)-CH₂-CH₂-S-S-CH₂CH₃ | CH₃CF₃ | (CH₃)₃C-S-S-CH₂-CH(NH₂)- |
| H | HOOC-CH(CH₃)-CH₂-CH(CH₃)₂ | CH₃CF₃ | (CH₃)₃C-S-S-CH₂-CH(NH₂)- |
| H | HOOC-CH(CH₃)-CH(CH₃)-CH₂CH₃ | CH₃CF₃ | (CH₃)₃C-S-S-CH₂-CH(NH₂)- |
| H | HOOC-CH(CH₃)-CH₂-C₆H₅ | CH₃CF₃ | (CH₃)₃C-S-S-CH₂-CH(NH₂)- |
| H | HOOC-CH(CH₃)-CH₂-(2-naphthyl) | CH₃CF₃ | (CH₃)₃C-S-S-CH₂-CH(NH₂)- |
| H | HOOC-CH(CH₃)-CH₂-(1-naphthyl) | CH₃CF₃ | (CH₃)₃C-S-S-CH₂-CH(NH₂)- |
| H | HOOC-CH(CH₃)-CH₂-(4-OCH₃-C₆H₄) | CH₃CF₃ | (CH₃)₃C-S-S-CH₂-CH(NH₂)- |
| H | H₂NOC-CH(CH₃)-CH₂-CH₂-S-CH₃ | CH₃CF₃ | (CH₃)₃C-S-S-CH₂-CH(NH₂)- |
| H | HOOC-CH(CH₃)-CH₂-OCH₃ | CH₃CF₃ | (CH₃)₃C-S-S-CH₂-CH(NH₂)- |
| H | HOOC-CH(CH₃)-CH₂-cyclohexyl | CH₃CF₃ | (CH₃)₃C-S-S-CH₂-CH(NH₂)- |
| H | (1H-tetrazol-5-yl)-CH(CH₃)-CH₂-C₆H₅ | CH₃CF₃ | (CH₃)₃C-S-S-CH₂-CH(NH₂)- |

TABLE II(b)(1)-continued

| R⁷ | R⁸ | R²⁴ | R²⁵ |
|---|---|---|---|
| H | tetrazole-CH(CH₃)CH₂CH₂SCH₃ | CH₃CF₃ | CH(CH₃)(CH₂-S-S-C(CH₃)₃)NH₂ |
| H | tetrazole-CH(CH₃)CH₂CH(CH₃)₂ | CH₃CF₃ | CH(CH₃)(CH₂-S-S-C(CH₃)₃)NH₂ |
| H | tetrazole-CH(CH₃)CH(CH₃)CH₂CH₃ | CH₃CF₃ | CH(CH₃)(CH₂-S-S-C(CH₃)₃)NH₂ |
| H | cyclohexyl-O-C(O)-CH(CH₃)CH₂CH₂CH₂CH₃ | CH₃CF₃ | CH(CH₃)(CH₂-S-S-C(CH₃)₃)NH₂ |
| H | (CH₃)₂CH-O-C(O)-CH(CH₃)CH₂CH₂CH₂CH₂CH₂CH₃ | CH₃CF₃ | CH(CH₃)(CH₂-S-S-C(CH₃)₃)NH₂ |
| H | HO-C(O)-CH(CH₃)CH₂CH₂CH₂CH₂CH₃ | CH₃CF₃ | CH(CH₃)(CH₂-S-S-C(CH₃)₃)NH₂ |
| H | tetrazole-CH(CH₃)CH₂-cyclohexyl | CH₃CF₃ | CH(CH₃)(CH₂-S-S-C(CH₃)₃)NH₂ |
| H | cyclohexyl-O-C(O)-CH(CH₃)CH₂-cyclohexyl | CH₃CF₃ | CH(CH₃)(CH₂-S-S-C(CH₃)₃)NH₂ |
| H | HO-C(O)-CH(CH₃)CH₂-cyclohexyl | CH₃CF₃ | CH(CH₃)(CH₂-S-S-C(CH₃)₃)NH₂ |
| H | cyclohexyl-O-C(O)-CH(CH₃)CH₂CH₂-phenyl | CH₃CF₃ | CH(CH₃)(CH₂-S-S-C(CH₃)₃)NH₂ |

TABLE II(b)(1)-continued

| R[7] | R[8] | R[24] | R[25] |
|---|---|---|---|
| H | 5-(4-(4-fluorophenyl)butan-2-yl)-1H-tetrazole | CH$_3$CF$_3$ | 1-amino-3-(tert-butyldisulfanyl)propan-2-yl |
| H | cyclohexyl 2-methyl-4-cyclohexylbutanoate | CH$_3$CF$_3$ | 1-amino-3-(tert-butyldisulfanyl)propan-2-yl |
| H | isopropyl 2-methylpent-4-ynoate | CH$_3$CF$_3$ | 1-amino-3-(tert-butyldisulfanyl)propan-2-yl |
| H | cyclohexyl 2-methylpentanoate | CH$_3$CF$_3$ | 1-amino-3-(tert-butyldisulfanyl)propan-2-yl |
| H | cyclohexyl 2-methylpent-4-enoate | CH$_3$CF$_3$ | 1-amino-3-(tert-butyldisulfanyl)propan-2-yl |
| H | 5-(pentan-2-yl)-1H-tetrazole | CH$_3$CF$_3$ | 1-amino-3-(tert-butyldisulfanyl)propan-2-yl |
| H | cyclohexyl 2,4,4-trimethylpentanoate | CH$_3$CF$_3$ | 1-amino-3-(tert-butyldisulfanyl)propan-2-yl |
| H | cyclohexyl 2,4-dimethyl-4-methylpentanoate | CH$_3$CF$_3$ | 1-amino-3-(tert-butyldisulfanyl)propan-2-yl |
| H | cyclohexyl 2-cyclopropylpropanoate | CH$_3$CF$_3$ | 1-amino-3-(tert-butyldisulfanyl)propan-2-yl |
| CH$_3$ | 2-methyl-4-(methylthio)butanoic acid | CH$_3$ | 2-(isopropylamino)-ethanethiol cyclic |

TABLE II(b)(1)-continued

| R⁷ | R⁸ | R²⁴ | R²⁵ |
|---|---|---|---|
| $CH_3$ | 2-methyl-4-(methylthio)butanoic acid methyl ester group | $CH_3$ | 2-methyl-thiazolidine group (NH, CH₃) |
| $CH_3$ | cyclohexyl 2-methyl-4-(methylthio)butanoate group | $CH_3$ | 2-methyl-thiazolidine group |
| $CH_3$ | 2,4-dimethylpentanoic acid group | $CH_3$ | 2-methyl-thiazolidine group |
| $CH_3$ | 2,3-dimethylpentanoic acid group | $CH_3$ | 2-methyl-thiazolidine group |
| $CH_3$ | 2-methyl-3-phenylpropanoic acid group | $CH_3$ | 2-methyl-thiazolidine group |
| $CH_3$ | 2-methyl-3-(4-fluorophenyl)propanoic acid group | $CH_3$ | 2-methyl-thiazolidine group |
| $CH_3$ | 2-methyl-3-(1-naphthyl)propanoic acid group | $CH_3$ | 2-methyl-thiazolidine group |
| $CH_3$ | 2-methyl-3-(4-methoxyphenyl)propanoic acid group | $CH_3$ | 2-methyl-thiazolidine group |
| $CH_3$ | 2-methyl-4-(methylthio)butanamide group | $CH_3$ | 2-methyl-thiazolidine group |
| $CH_3$ | 2-methyl-3-methoxypropanoic acid group | $CH_3$ | 2-methyl-thiazolidine group |
| $CH_3$ | 2-methyl-3-cyclohexylpropanoic acid group | $CH_3$ | 2-methyl-thiazolidine group |

TABLE II(b)(1)-continued

| R⁷ | R⁸ | R²⁴ | R²⁵ |
|---|---|---|---|
| CH₃ | 5-(1-methyl-2-phenylethyl)-1H-tetrazole | CH₃ | 2-methylthiazolidine |
| CH₃ | 5-[1-methyl-3-(methylthio)propyl]-1H-tetrazole | CH₃ | 2-methylthiazolidine |
| CH₃ | 5-(1,3-dimethylbutyl)-1H-tetrazole | CH₃ | 2-methylthiazolidine |
| CH₃ | 5-(1,2-dimethylbutyl)-1H-tetrazole | CH₃ | 2-methylthiazolidine |
| H | cyclohexyl 2-methylhexanoate | CH₃ | 2-methylthiazolidine |
| H | isopropyl 2-methyloctanoate | CH₃ | 2-methylthiazolidine |
| H | 2-methylheptanoic acid | CH₃ | 2-methylthiazolidine |
| H | 5-(1-methyl-2-cyclohexylethyl)-1H-tetrazole | CH₃ | 2-methylthiazolidine |
| H | cyclohexyl 2-methyl-3-cyclohexylpropanoate | CH₃ | 2-methylthiazolidine |
| H | 2-methyl-3-cyclohexylpropanoic acid | CH₃ | 2-methylthiazolidine |

TABLE II(b)(1)-continued

| R⁷ | R⁸ | R²⁴ | R²⁵ |
|---|---|---|---|
| H | (cyclohexyl ester of 2-methyl-4-phenylbutanoate) | CH₃ | (thiazolidine with CH₃) |
| H | (tetrazole-CH(CH₃)-CH₂CH₂-(4-fluorophenyl)) | CH₃ | (thiazolidine with CH₃) |
| H | (cyclohexyl ester of 2-methyl-4-cyclohexylbutanoate) | CH₃ | (thiazolidine with CH₃) |
| H | (isopropyl ester of 2-methyl-4-pentynoate) | CH₃ | (thiazolidine with CH₃) |
| H | (cyclohexyl ester of 2-methylpentanoate) | CH₃ | (thiazolidine with CH₃) |
| H | (cyclohexyl ester of 2-methyl-4-pentenoate) | CH₃ | (thiazolidine with CH₃) |
| H | (tetrazole-CH(CH₃)-CH₂CH₂CH₃) | CH₃ | (thiazolidine with CH₃) |
| H | (cyclohexyl ester of 2,4,4-trimethylpentanoate) | CH₃ | (thiazolidine with CH₃) |
| H | (cyclohexyl ester of 2-methyl-4,4-dimethylpentanoate) | CH₃ | (thiazolidine with CH₃) |
| H | (cyclohexyl propanoate) | CH₃ | (thiazolidine with CH₃) |

TABLE II(b)(1)-continued

| R⁷ | R⁸ | R²⁴ | R²⁵ |
|---|---|---|---|
| H | CH(CH₃)CH₂CH₂SCH₃ with COOH | CH₃ | thiazolidinone |
| H | CH(CH₃)CH₂CH₂SCH₃ with COOCH₃ | CH₃ | thiazolidinone |
| H | CH(CH₃)CH₂CH₂SCH₃ with COO-cyclohexyl | CH₃ | thiazolidinone |
| H | CH(CH₃)CH₂CH(CH₃)₂ with COOH | CH₃ | thiazolidinone |
| H | CH(CH₃)CH(CH₃)CH₂CH₃ with COOH | CH₃ | thiazolidinone |
| H | CH(CH₃)CH₂Ph with COOH | CH₃ | thiazolidinone |
| H | CH(CH₃)CH₂(4-F-Ph) with COOH | CH₃ | thiazolidinone |
| H | CH(CH₃)CH₂(1-naphthyl) with COOH | CH₃ | thiazolidinone |
| H | CH(CH₃)CH₂(4-OCH₃-Ph) with COOH | CH₃ | thiazolidinone |
| H | CH(CH₃)CH₂CH₂SCH₃ with CONH₂ | CH₃ | thiazolidinone |
| H | CH(CH₃)CH₂OCH₃ with COOH | CH₃ | thiazolidinone |

TABLE II(b)(1)-continued

| R⁷ | R⁸ | R²⁴ | R²⁵ |
|---|---|---|---|
| H | 2-methyl-2-cyclohexyl-acetic acid (COOH, CH₃, cyclohexyl) | CH₃ | thiazolidinone |
| H | 5-(1-methyl-2-phenylethyl)-tetrazole | CH₃ | thiazolidinone |
| H | 5-(1-methyl-3-methylthio-propyl)-tetrazole | CH₃ | thiazolidinone |
| H | 5-(1,3-dimethylbutyl)-tetrazole | CH₃ | thiazolidinone |
| H | 5-(1-methyl-2-methylbutyl)-tetrazole | CH₃ | thiazolidinone |
| H | cyclohexyl 2-methylhexanoate | CH₃ | thiazolidinone |
| H | isopropyl 2-methyloctanoate | CH₃ | thiazolidinone |
| H | 2-methylheptanoic acid | CH₃ | thiazolidinone |
| H | 5-(1-methyl-2-cyclohexylethyl)-tetrazole | CH₃ | thiazolidinone |
| H | cyclohexyl 2-methyl-3-cyclohexylpropanoate | CH₃ | thiazolidinone |

TABLE II(b)(1)-continued

| R⁷ | R⁸ | R²⁴ | R²⁵ |
|---|---|---|---|
| H | 2-methyl-2-cyclohexyl-acetic acid (structure) | CH₃ | thiazolidinone (structure) |
| H | cyclohexyl 2-methyl-4-phenylbutanoate (structure) | CH₃ | thiazolidinone (structure) |
| H | 5-[4-(4-fluorophenyl)butan-2-yl]-1H-tetrazole (structure) | CH₃ | thiazolidinone (structure) |
| H | cyclohexyl 4-cyclohexyl-2-methylbutanoate (structure) | CH₃ | thiazolidinone (structure) |
| H | 5-ethyl-1H-tetrazole (structure) | CH₃ | thiazolidinone (structure) |
| H | cyclohexyl 2-methylpentanoate (structure) | CH₃ | thiazolidinone (structure) |
| H | cyclohexyl 2-methylpent-4-enoate (structure) | CH₃ | thiazolidinone (structure) |
| H | 5-(pentan-2-yl)-1H-tetrazole (structure) | CH₃ | thiazolidinone (structure) |
| H | cyclohexyl 2,4,4-trimethylpentanoate (structure) | CH₃ | thiazolidinone (structure) |
| H | cyclohexyl 2,5-dimethylhexanoate (structure) | CH₃ | thiazolidinone (structure) |

TABLE II(b)(1)-continued

| R⁷' | R⁸ | R²⁴ | R²⁵ |
|---|---|---|---|
| H | cyclopropyl-CH(CH₃)-C(=O)-O-cyclohexyl | CH₃ | thiazolidinone ring (4-methyl-2-oxo-thiazolidin-3-yl, NH) |
| H | CH₃-S-CH₂-CH₂-CH(COOH)-CH₃ | CH₃ | CH(SH)-CH₂-SH |
| H | CH₃-S-CH₂-CH₂-CH(COOCH₃)-CH₃ | CH₃ | CH(SH)-CH₂-SH |
| H | cyclohexyl-O-C(=O)-CH(CH₃)-CH₂-CH₂-S-CH₃ | CH₃ | CH(SH)-CH₂-SH |
| H | (CH₃)₂CH-CH₂-CH(COOH)-CH₃ | CH₃ | CH(SH)-CH₂-SH |
| H | CH₃-CH₂-CH(CH₃)-CH(COOH)-CH₃ | CH₃ | CH(SH)-CH₂-SH |
| H | Ph-CH₂-CH(COOH)-CH₃ | CH₃ | CH(SH)-CH₂-SH |
| H | 4-F-C₆H₄-CH₂-CH(COOH)-CH₃ | CH₃ | CH(SH)-CH₂-SH |
| H | 1-naphthyl-CH₂-CH(COOH)-CH₃ | CH₃ | CH(SH)-CH₂-SH |
| H | 4-CH₃O-C₆H₄-CH₂-CH(COOH)-CH₃ | CH₃ | CH(SH)-CH₂-SH |
| H | CH₃-S-CH₂-CH₂-CH(CONH₂)-CH₃ | CH₃ | CH(SH)-CH₂-SH |
| H | CH₃O-CH₂-CH(COOH)-CH₃ | CH₃ | CH(SH)-CH₂-SH |
| H | cyclohexyl-CH₂-CH(COOH)-CH₃ | CH₃ | CH(SH)-CH₂-SH |

TABLE II(b)(1)-continued
| R⁷ | R⁸ | R²⁴ | R²⁵ |
|---|---|---|---|
| H | 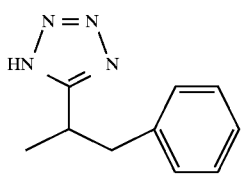 | CH₃ | 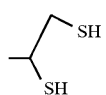 |
| H | 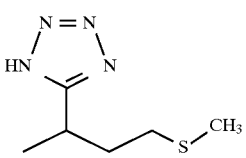 | CH₃ | 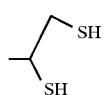 |
| H | 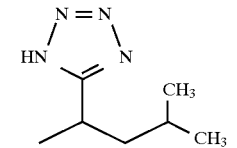 | CH₃ | 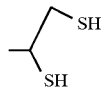 |
| H | 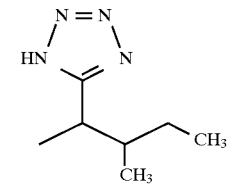 | CH₃ | 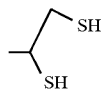 |
| H | 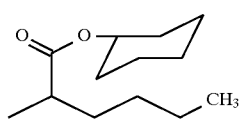 | CH₃ | 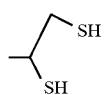 |
| H | 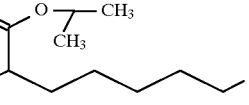 | CH₃ | 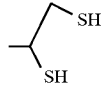 |
| H | 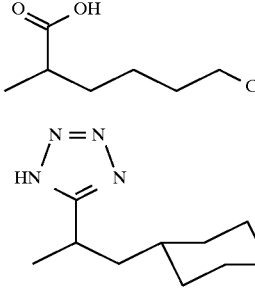 | CH₃ | 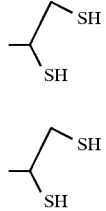 |
| H | 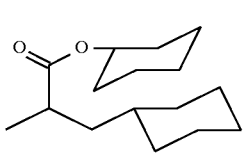 | CH₃ | 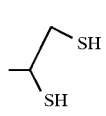 |
| H | 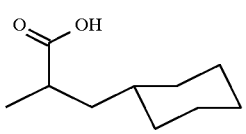 | CH₃ | 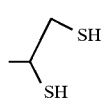 |

TABLE II(b)(1)-continued
| R⁷ | R⁸ | R²⁴ | R²⁵ |
|---|---|---|---|
| H | 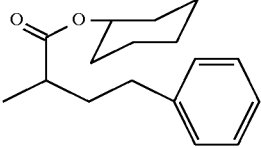 | CH₃ |  |
| H | 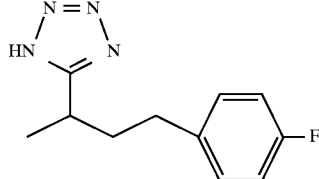 | CH₃ |  |
| H | 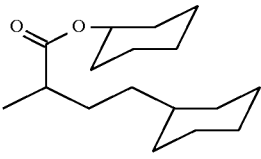 | CH₃ |  |
| H | 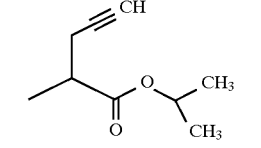 | CH₃ |  |
| H | 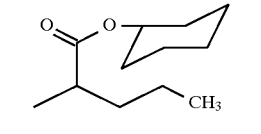 | CH₃ |  |
| H | 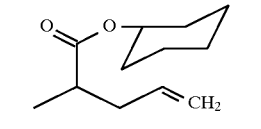 | CH₃ |  |
| H | 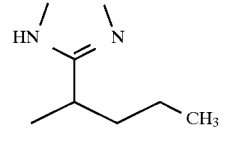 | CH₃ |  |
| H | 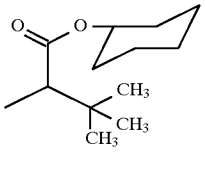 | CH₃ |  |
| H | 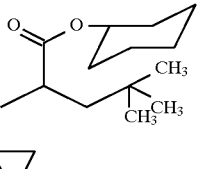 | CH₃ |  |
| H | 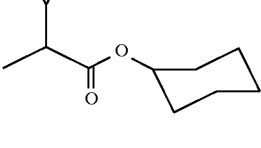 | CH₃ |  |

TABLE II(b)(1)-continued

| R[7] | R[8] | R[24] | R[25] |
|---|---|---|---|
| H | CH(CH₃)CH₂CH₂SCH₃ with COOH | CH₃ | CH(CH₂SH)₂ |
| H | CH(CH₃)CH₂CH₂SCH₃ with COOCH₃ | CH₃ | CH(CH₂SH)₂ |
| H | CH(CH₃)CH₂CH₂SCH₃ with C(=O)O-cyclohexyl | CH₃ | CH(CH₂SH)₂ |
| H | CH(CH₃)CH(CH₃)₂ with COOH | CH₃ | CH(CH₂SH)₂ |
| H | CH(CH₃)CH(CH₃)CH₂CH₃ with COOH | CH₃ | CH(CH₂SH)₂ |
| H | CH(CH₃)CH₂Ph with COOH | CH₃ | CH(CH₂SH)₂ |
| H | CH(CH₃)CH₂(4-F-C₆H₄) with COOH | CH₃ | CH(CH₂SH)₂ |
| H | CH(CH₃)CH₂(1-naphthyl) with COOH | CH₃ | CH(CH₂SH)₂ |
| H | CH(CH₃)CH₂(4-OCH₃-C₆H₄) with COOH | CH₃ | CH(CH₂SH)₂ |
| H | CH(CH₃)CH₂CH₂SCH₃ with CONH₂ | CH₃ | CH(CH₂SH)₂ |
| H | CH(CH₃)CH₂OCH₃ with COOH | CH₃ | CH(CH₂SH)₂ |
| H | CH(CH₃)CH₂-cyclohexyl with COOH | CH₃ | CH(CH₂SH)₂ |

TABLE II(b)(1)-continued
| R[7'] | R[8] | R[24] | R[25] |
|---|---|---|---|
| H | 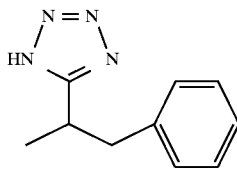 | CH$_3$ | 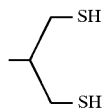 |
| H | 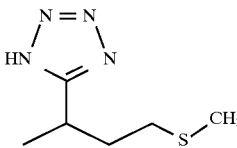 | CH$_3$ | 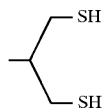 |
| H | 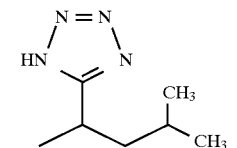 | CH$_3$ | 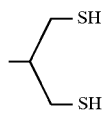 |
| H | 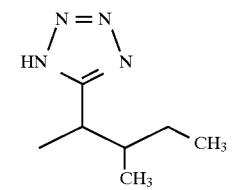 | CH$_3$ | 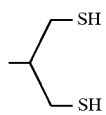 |
| H | 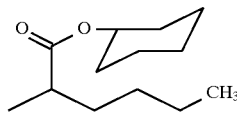 | CH$_3$ | 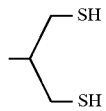 |
| H | 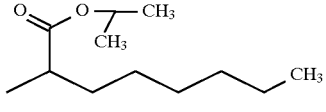 | CH$_3$ | 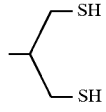 |
| H | 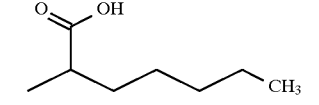 | CH$_3$ | 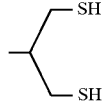 |
| H | 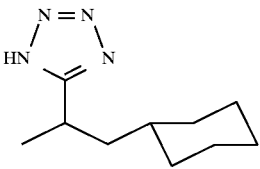 | CH$_3$ | 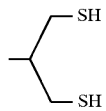 |
| H | 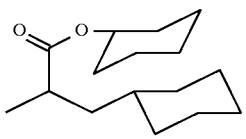 | CH$_3$ | 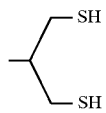 |
| H | 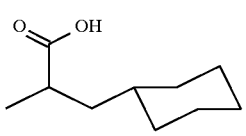 | CH$_3$ | 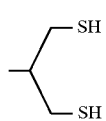 |

TABLE II(b)(1)-continued
| R[7] | R[8] | R[24] | R[25] |
|---|---|---|---|
| H | 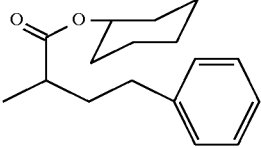 | CH₃ | 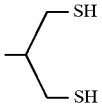 |
| H | 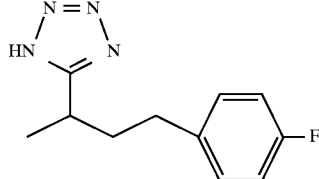 | CH₃ | 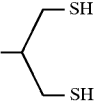 |
| H | 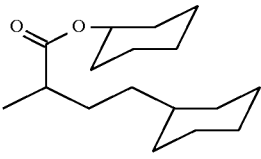 | CH₃ | 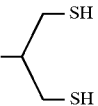 |
| H | 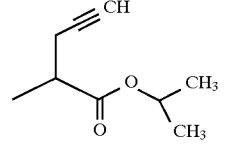 | CH₃ | 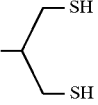 |
| H | 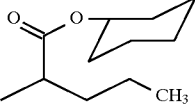 | CH₃ | 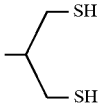 |
| H | 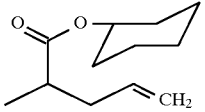 | CH₃ | 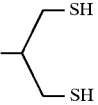 |
| H | 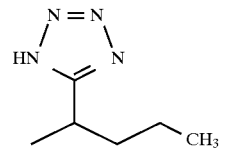 | CH₃ | 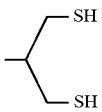 |
| H | 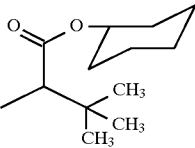 | CH₃ | 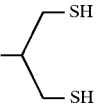 |
| H | 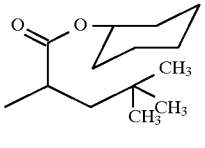 | CH₃ | 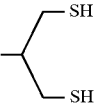 |
| H | 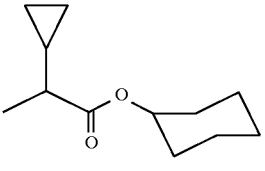 | CH₃ | 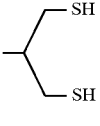 |

TABLE II(b)(1)-continued

| R⁷ | R⁸ | R²⁴ | R²⁵ |
|---|---|---|---|
| H | CH(CH₃)CH₂CH₂SCH₃ with COOH | CH₃ | CH₂SH / CH / CH₂NH₂ |
| H | CH(CH₃)CH₂CH₂SCH₃ with COOCH₃ | CH₃ | CH₂SH / CH / CH₂NH₂ |
| H | CH(CH₃)CH₂CH₂SSC₂H₅ with COOH | CH₃ | CH₂SH / CH / CH₂NH₂ |
| H | CH(CH₃)CH₂CH(CH₃)₂ with COOH | CH₃ | CH₂SH / CH / CH₂NH₂ |
| H | CH(CH₃)CH(CH₃)C₂H₅ with COOH | CH₃ | CH₂SH / CH / CH₂NH₂ |
| H | CH(CH₃)CH₂Ph with COOH | CH₃ | CH₂SH / CH / CH₂NH₂ |
| H | CH(CH₃)CH₂-(2-naphthyl) with COOH | CH₃ | CH₂SH / CH / CH₂NH₂ |
| H | CH(CH₃)CH₂-(1-naphthyl) with COOH | CH₃ | CH₂SH / CH / CH₂NH₂ |
| H | CH(CH₃)CH₂-(4-OCH₃-C₆H₄) with COOH | CH₃ | CH₂SH / CH / CH₂NH₂ |
| H | CH(CH₃)CH₂CH₂SCH₃ with CONH₂ | CH₃ | CH₂SH / CH / CH₂NH₂ |
| H | CH(CH₃)CH₂OCH₃ with COOH | CH₃ | CH₂SH / CH / CH₂NH₂ |
| H | CH(CH₃)CH₂-cyclohexyl with COOH | CH₃ | CH₂SH / CH / CH₂NH₂ |

TABLE II(b)(1)-continued
| R⁷ | R⁸ | R²⁴ | R²⁵ |
|---|---|---|---|
| H | 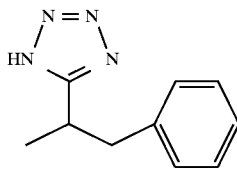 | CH₃ | 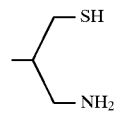 |
| H | 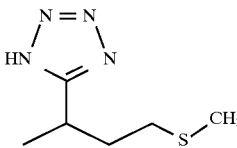 | CH₃ | 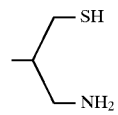 |
| H | 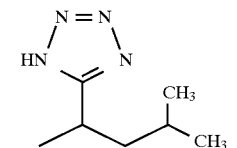 | CH₃ | 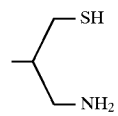 |
| H | 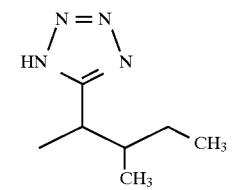 | CH₃ | 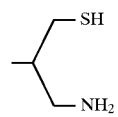 |
| H | 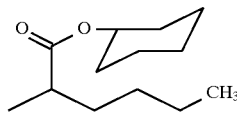 | CH₃ | 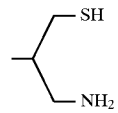 |
| H | 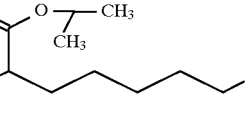 | CH₃ | 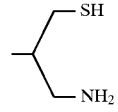 |
| H | 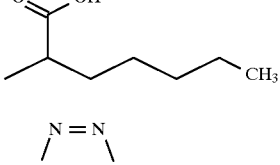 | CH₃ | 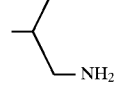 |
| H | 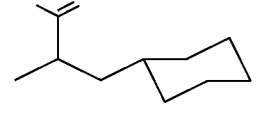 | CH₃ | 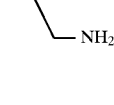 |
| H | 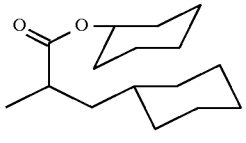 | CH₃ | 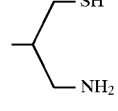 |
| H | 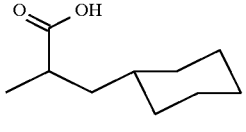 | CH₃ | 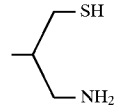 |

TABLE II(b)(1)-continued
| R⁷ | R⁸ | R²⁴ | R²⁵ |
|---|---|---|---|
| H | 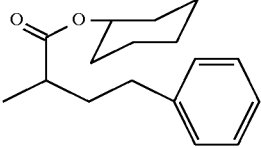 | CH₃ | 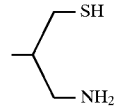 |
| H | 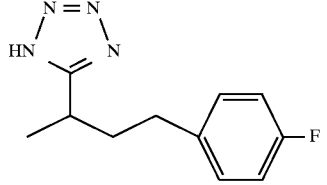 | CH₃ | 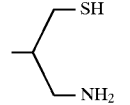 |
| H | 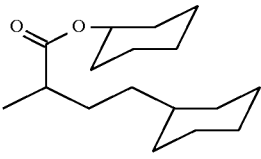 | CH₃ | 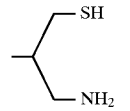 |
| H | 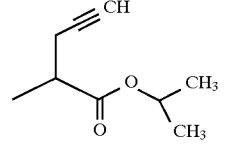 | CH₃ | 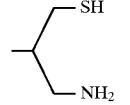 |
| H | 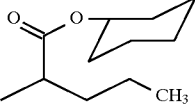 | CH₃ | 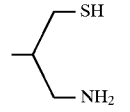 |
| H | 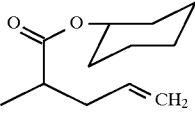 | CH₃ | 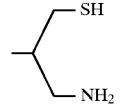 |
| H | 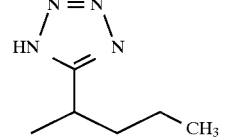 | CH₃ | 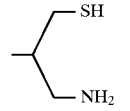 |
| H | 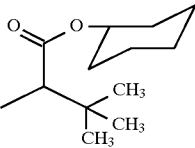 | CH₃ | 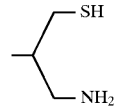 |
| H | 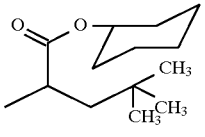 | CH₃ | 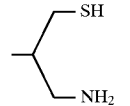 |
| H | 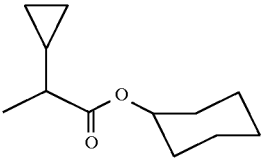 | CH₃ | 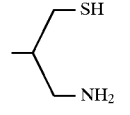 |

TABLE II(b)(1)-continued
| R⁷ | R⁸ | R²⁴ | R²⁵ |
|---|---|---|---|
| H | 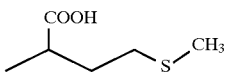 | CH₃ | 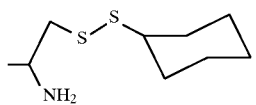 |
| H | 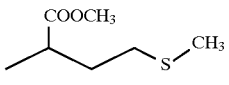 | CH₃ | 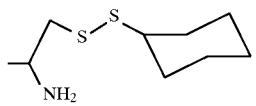 |
| H | 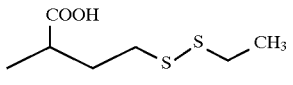 | CH₃ | 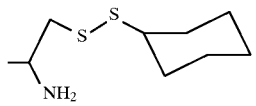 |
| H | 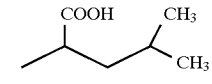 | CH₃ | 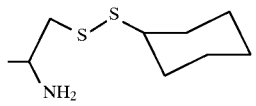 |
| H | 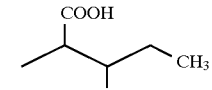 | CH₃ | 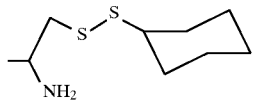 |
| H | 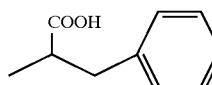 | CH₃ | 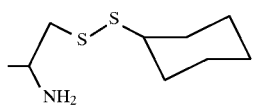 |
| H | 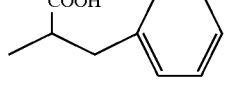 | CH₃ | 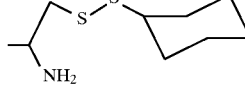 |
| H | 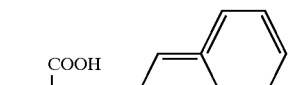 | CH₃ | 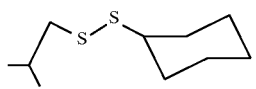 |
| H | 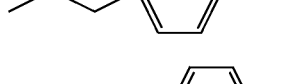 | CH₃ | 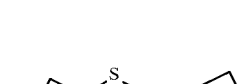 |
| H |  | CH₃ |  |
| H | 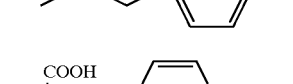 | CH₃ | 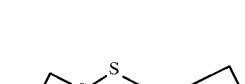 |
| H | 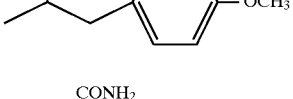 | CH₃ |  |

TABLE II(b)(1)-continued
| R[7] | R[8] | R[24] | R[25] |
|---|---|---|---|
| H | 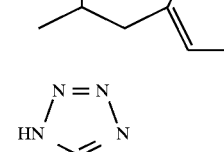 | CH₃ | 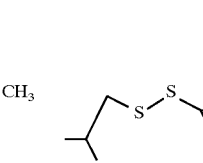 |
| H | 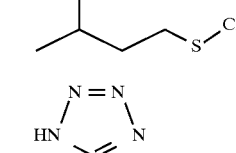 | CH₃ | 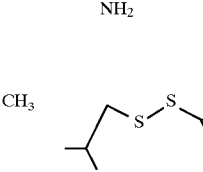 |
| H | 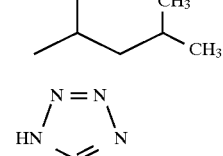 | CH₃ | 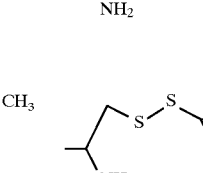 |
| H | 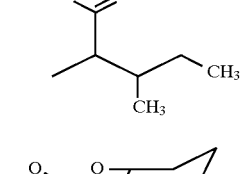 | CH₃ | 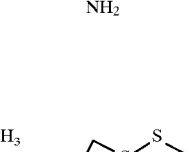 |
| H | 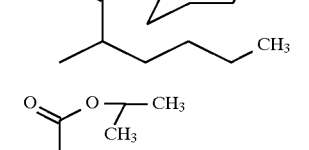 | CH₃ | 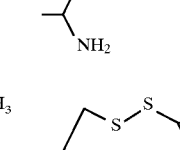 |
| H | 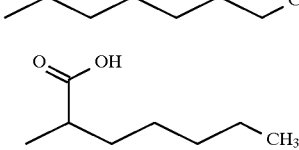 | CH₃ | 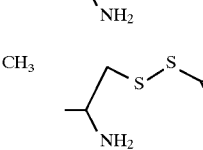 |
| H | 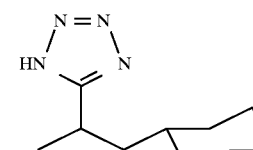 | CH₃ | 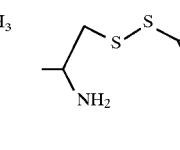 |
| H | 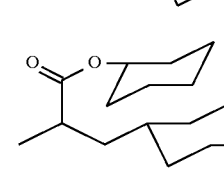 | CH₃ | 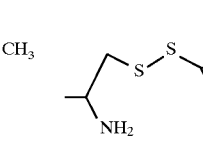 |
| H | 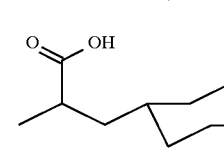 | CH₃ | 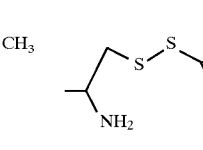 |

TABLE II(b)(1)-continued
| R⁷ | R⁸ | R²⁴ | R²⁵ |
|---|---|---|---|
| H | 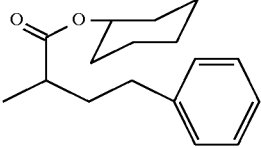 | CH₃ | 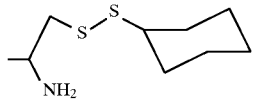 |
| H | 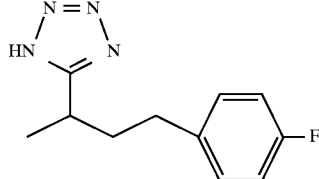 | CH₃ | 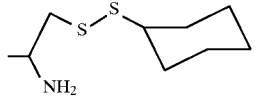 |
| H | 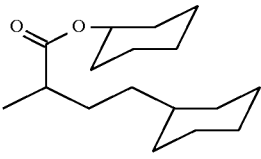 | CH₃ | 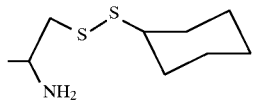 |
| H | 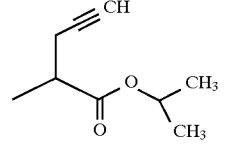 | CH₃ | 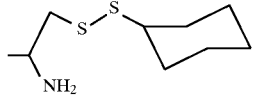 |
| H | 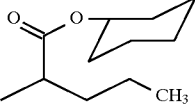 | CH₃ | 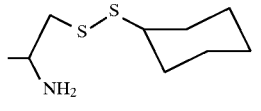 |
| H | 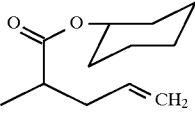 | CH₃ | 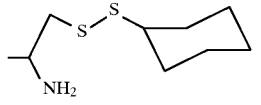 |
| H | 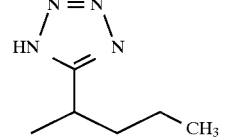 | CH₃ | 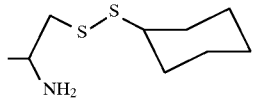 |
| H | 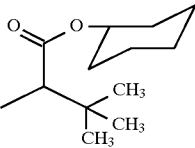 | CH₃ | 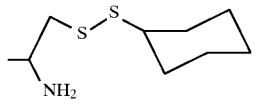 |
| H | 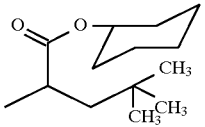 | CH₃ | 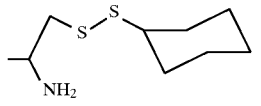 |
| H | 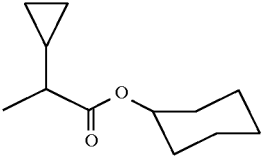 | CH₃ | 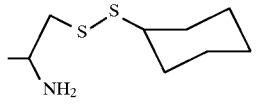 |

TABLE II(b)(1)-continued

| R⁷ | R⁸ | R²⁴ | R²⁵ |
|---|---|---|---|
| H | 2-methyl-4-(methylthio)butanoic acid | CH₃ | -NH-CH₂CH₂-SH |
| H | methyl 2-methyl-4-(methylthio)butanoate | CH₃ | -NH-CH₂CH₂-SH |
| H | cyclohexyl 2-methyl-4-(methylthio)butanoate | CH₃ | -NH-CH₂CH₂-SH |
| H | 2,4-dimethylpentanoic acid | CH₃ | -NH-CH₂CH₂-SH |
| H | 2,3-dimethylpentanoic acid | CH₃ | -NH-CH₂CH₂-SH |
| H | 2-methyl-3-phenylpropanoic acid | CH₃ | -NH-CH₂CH₂-SH |
| H | 2-methyl-3-(4-fluorophenyl)propanoic acid | CH₃ | -NH-CH₂CH₂-SH |
| H | 2-methyl-3-(1-naphthyl)propanoic acid | CH₃ | -NH-CH₂CH₂-SH |
| H | 2-methyl-3-(4-methoxyphenyl)propanoic acid | CH₃ | -NH-CH₂CH₂-SH |
| H | 2-methyl-4-(methylthio)butanamide | CH₃ | -NH-CH₂CH₂-SH |
| H | 2-methyl-3-methoxypropanoic acid | CH₃ | -NH-CH₂CH₂-SH |
| H | 2-methyl-3-cyclohexylpropanoic acid | CH₃ | -NH-CH₂CH₂-SH |
| H | 5-(1-methyl-2-phenylethyl)-1H-tetrazole | CH₃ | -NH-CH₂CH₂-SH |

TABLE II(b)(1)-continued
| R⁷ | R⁸ | R²⁴ | R²⁵ |
|---|---|---|---|
| H | 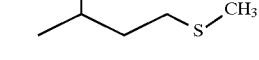 | CH₃ |  |
| H | 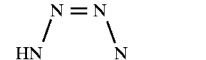 | CH₃ | 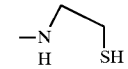 |
| H | 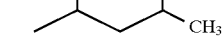 | CH₃ |  |
| H | 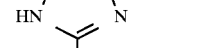 | CH₃ | 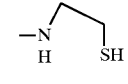 |
| H | 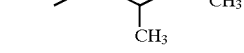 | CH₃ |  |
| H |  | CH₃ | 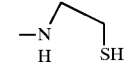 |
| H | 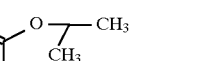 | CH₃ | 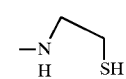 |
| H |  | CH₃ |  |
| H | 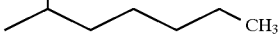 | CH₃ |  |
| H | 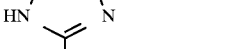 | CH₃ | 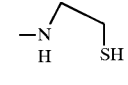 |

TABLE II(b)(1)-continued
| R⁷ | R⁸ | R²⁴ | R²⁵ |
|---|---|---|---|
| H | 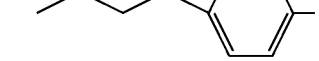 | CH₃ |  |
| H |  | CH₃ | 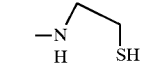 |
| H |  | CH₃ | 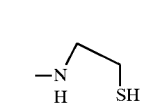 |
| H | 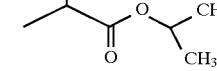 | CH₃ |  |
| H | 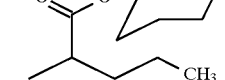 | CH₃ | 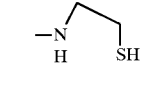 |
| H | 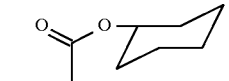 | CH₃ | 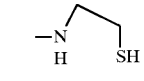 |
| H | 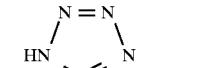 | CH₃ | 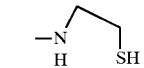 |
| H | 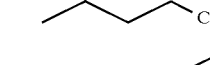 | CH₃ |  |
| H | 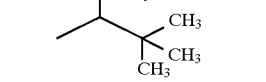 | CH₃ |  |
| H | 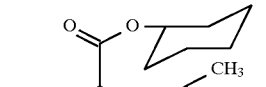 | CH₃ | 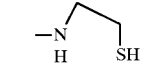 |

TABLE II(b)(1)-continued

| R[7] | R[8] | R[24] | R[25] |
|---|---|---|---|
| H | ![COOCH3, CH2CH2SCH3 branched] | CH3 | HOHN-C(=O)-CH(NH-)-CH2-SH |
| H | ![cyclohexyl ester with CH2CH2SCH3] | CH3 | HOHN-C(=O)-CH(NH-)-CH2-SH |
| H | ![COOH, CH2CH(CH3)2 branched] | CH3 | HOHN-C(=O)-CH(NH-)-CH2-SH |
| H | ![COOH, CH(CH3)CH2CH3] | CH3 | HOHN-C(=O)-CH(NH-)-CH2-SH |
| H | ![COOH, CH2-phenyl] | CH3 | HOHN-C(=O)-CH(NH-)-CH2-SH |
| H | ![COOH, CH2-(4-F-phenyl)] | CH3 | HOHN-C(=O)-CH(NH-)-CH2-SH |
| H | ![COOH, CH2-naphthyl] | CH3 | HOHN-C(=O)-CH(NH-)-CH2-SH |
| H | ![COOH, CH2-(4-OCH3-phenyl)] | CH3 | HOHN-C(=O)-CH(NH-)-CH2-SH |
| H | ![CONH2, CH2CH2SCH3] | CH3 | HOHN-C(=O)-CH(NH-)-CH2-SH |

TABLE II(b)(1)-continued

| R⁷ | R⁸ | R²⁴ | R²⁵ |
|---|---|---|---|
| H | 2-methyl-3-methoxypropanoic acid | $CH_3$ | N-hydroxy cysteinamide |
| H | 2-methyl-3-cyclohexylpropanoic acid | $CH_3$ | N-hydroxy cysteinamide |
| H | 5-phenyl-4-(tetrazol-5-yl)pentane | $CH_3$ | N-hydroxy cysteinamide |
| H | 4-(methylthio)-2-(tetrazol-5-yl)butane | $CH_3$ | N-hydroxy cysteinamide |
| H | 4-methyl-2-(tetrazol-5-yl)pentane | $CH_3$ | N-hydroxy cysteinamide |
| H | 3-methyl-2-(tetrazol-5-yl)pentane | $CH_3$ | N-hydroxy cysteinamide |
| H | cyclohexyl 2-methylhexanoate | $CH_3$ | N-hydroxy cysteinamide |
| H | isopropyl 2-methyloctanoate | $CH_3$ | N-hydroxy cysteinamide |
| H | 2-methyloctanoic acid | $CH_3$ | N-hydroxy cysteinamide |

TABLE II(b)(1)-continued
| R[7'] | R[8] | R[24] | R[25] |
|---|---|---|---|
| H | 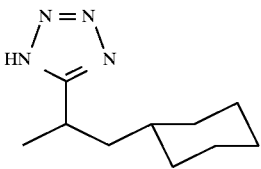 | CH₃ | 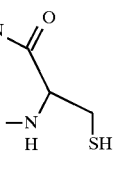 |
| H | 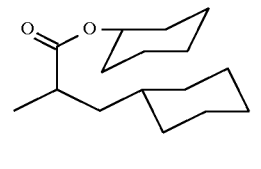 | CH₃ | 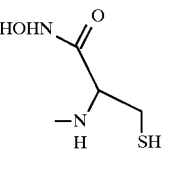 |
| H | 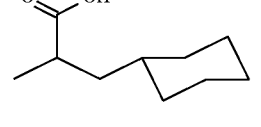 | CH₃ | 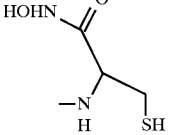 |
| H | 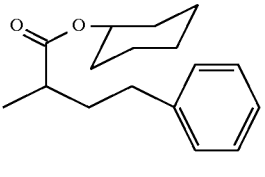 | CH₃ | 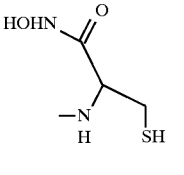 |
| H | 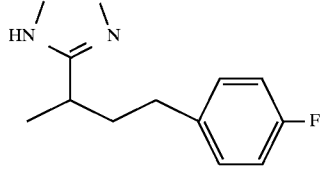 | CH₃ | 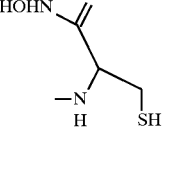 |
| H | 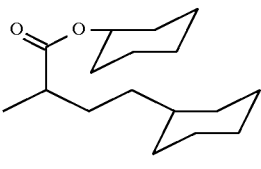 | CH₃ | 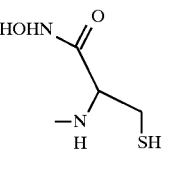 |
| H | 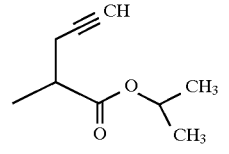 | CH₃ | 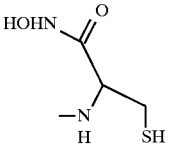 |
| H | 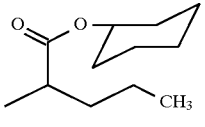 | CH₃ | 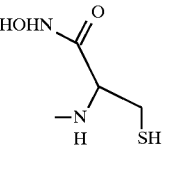 |
| H | 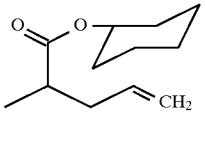 | CH₃ | 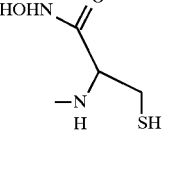 |

TABLE II(b)(1)-continued
| R⁷' | R⁸ | R²⁴ | R²⁵ |
|---|---|---|---|
| H | 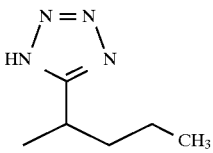 | CH₃ | 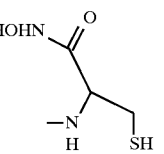 |
| H | 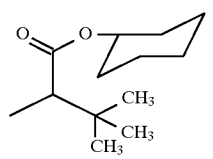 | CH₃ | 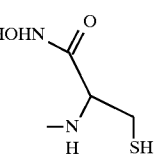 |
| H | 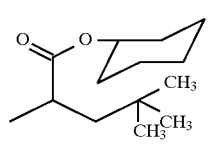 | CH₃ | 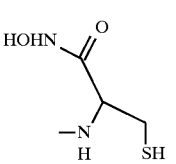 |
| H | 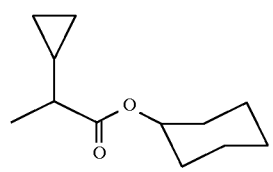 | CH₃ | 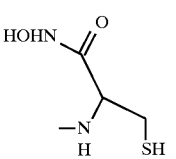 |
| 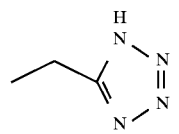 | 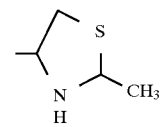 | CH₃ | 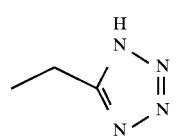 |
| 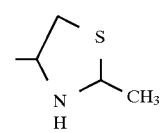 | 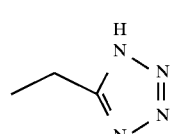 | CH₃ | 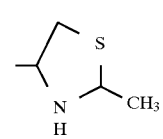 |
| 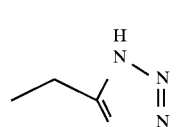 | 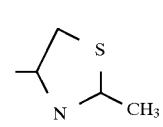 | CH₃ | 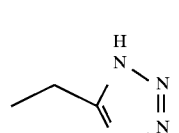 |
| 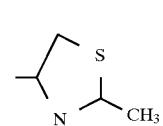 | 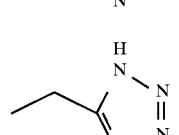 | CH₃ | 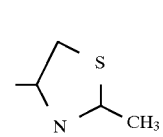 |
| 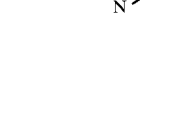 |  | CH₃ | |

TABLE II(b)(1)-continued

| R⁷ | R⁸ | R²⁴ | R²⁵ |
|---|---|---|---|
| tert-butyl (C(CH₃)₃) | 5-ethyl-1H-tetrazole | CH₃ | 2-(propan-2-ylamino)-thietane/thiazolidine-like group with CH₃ |
| 2-methylbutan-2-yl (C(CH₃)₂CH₂CH₃) | 5-ethyl-1H-tetrazole | CH₃ | same R²⁵ as above |
| but-2-enyl (CH₃CH=CHCH₂–) | 5-ethyl-1H-tetrazole | CH₃ | same R²⁵ |
| but-2-ynyl (CH₃C≡C-CH₂–) | 5-ethyl-1H-tetrazole | CH₃ | same R²⁵ |
| 3-phenylpropyl | 5-ethyl-1H-tetrazole | CH₃ | same R²⁵ |
| 2-phenylethyl | 5-ethyl-1H-tetrazole | CH₃ | same R²⁵ |
| 2-(4-fluorophenyl)ethyl | 5-ethyl-1H-tetrazole | CH₃ | same R²⁵ |
| 2-(naphthalen-1-yl)ethyl | 5-ethyl-1H-tetrazole | CH₃ | same R²⁵ |
| cyclohexyl | 5-ethyl-1H-tetrazole | CH₃ | same R²⁵ |
| cyclohexylmethyl | 5-ethyl-1H-tetrazole | CH₃ | same R²⁵ |
| cyclopropyl | 5-ethyl-1H-tetrazole | CH₃ | same R²⁵ |

TABLE II(b)(1)-continued
| $R^7$ | $R^8$ | $R^{24}$ | $R^{25}$ |
|---|---|---|---|
|  | 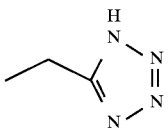 | $CH_3$ |  |
| 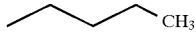 | 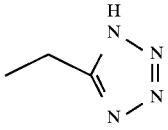 | $CH_3$ |  |
| 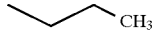 | 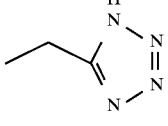 | $CH_3$ |  |
|  | 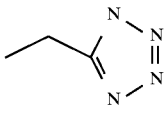 | $CH_3$ |  |
| 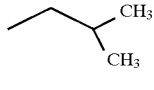 | 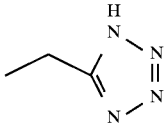 | $CH_3$ |  |
| 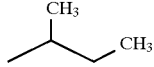 | 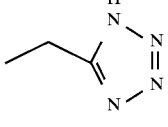 | $CH_3$ |  |
| 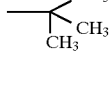 | 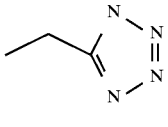 | $CH_3$ |  |
| 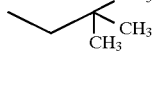 | 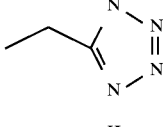 | $CH_3$ |  |
| 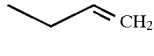 | 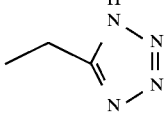 | $CH_3$ |  |
|  | 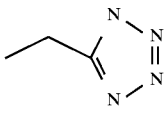 | $CH_3$ |  |
| 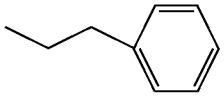 | 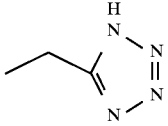 | $CH_3$ |  |

TABLE II(b)(1)-continued

| R⁷ | R⁸ | R²⁴ | R²⁵ |
|---|---|---|---|
| ethylphenyl | ethyl-tetrazole (NH) | CH₃ | CH(CH₃)(CH₂SH)(NH₂) |
| ethyl-(4-fluorophenyl) | ethyl-tetrazole (NH) | CH₃ | CH(CH₃)(CH₂SH)(NH₂) |
| ethyl-naphthyl | ethyl-tetrazole (NH) | CH₃ | CH(CH₃)(CH₂SH)(NH₂) |
| ethyl-cyclohexyl | ethyl-tetrazole (NH) | CH₃ | CH(CH₃)(CH₂SH)(NH₂) |
| ethyl-cyclohexyl | ethyl-tetrazole (NH) | CH₃ | CH(CH₃)(CH₂SH)(NH₂) |
| cyclopropyl | ethyl-tetrazole (NH) | CH₃ | CH(CH₃)(CH₂SH)(NH₂) |
| n-hexyl-CH₃ | ethyl-tetrazole (NH) | CH₃ | CH(CH₃)(CH₂-S-S-C(CH₃)₃)(NH₂) |
| n-pentyl-CH₃ | ethyl-tetrazole (NH) | CH₃ | CH(CH₃)(CH₂-S-S-C(CH₃)₃)(NH₂) |
| n-butyl-CH₃ | ethyl-tetrazole (NH) | CH₃ | CH(CH₃)(CH₂-S-S-C(CH₃)₃)(NH₂) |
| propyl-CH₃ | ethyl-tetrazole (NH) | CH₃ | CH(CH₃)(CH₂-S-S-C(CH₃)₃)(NH₂) |
| sec-butyl | ethyl-tetrazole (NH) | CH₃ | CH(CH₃)(CH₂-S-S-C(CH₃)₃)(NH₂) |

TABLE II(b)(1)-continued

| R⁷ | R⁸ | R²⁴ | R²⁵ |
|---|---|---|---|
| isobutyl | ethyl-tetrazole (NH) | CH₃ | CH₂-S-S-C(CH₃)₃ with CH(NH₂) |
| neopentyl (tert-butyl-CH₂) | ethyl-tetrazole (NH) | CH₃ | CH₂-S-S-C(CH₃)₃ with CH(NH₂) |
| 2,2-dimethylbutyl | ethyl-tetrazole (NH) | CH₃ | CH₂-S-S-C(CH₃)₃ with CH(NH₂) |
| but-3-enyl (=CH₂) | ethyl-tetrazole (NH) | CH₃ | CH₂-S-S-C(CH₃)₃ with CH(NH₂) |
| but-3-ynyl (≡CH) | ethyl-tetrazole (NH) | CH₃ | CH₂-S-S-C(CH₃)₃ with CH(NH₂) |
| 3-phenylpropyl | ethyl-tetrazole (NH) | CH₃ | CH₂-S-S-C(CH₃)₃ with CH(NH₂) |
| 2-phenylethyl | ethyl-tetrazole (NH) | CH₃ | CH₂-S-S-C(CH₃)₃ with CH(NH₂) |
| 2-(4-fluorophenyl)ethyl | ethyl-tetrazole (NH) | CH₃ | CH₂-S-S-C(CH₃)₃ with CH(NH₂) |
| 2-(1-naphthyl)ethyl | ethyl-tetrazole (NH) | CH₃ | CH₂-S-S-C(CH₃)₃ with CH(NH₂) |
| cyclohexylmethyl | ethyl-tetrazole (NH) | CH₃ | CH₂-S-S-C(CH₃)₃ with CH(NH₂) |

TABLE II(b)(1)-continued

| R[7'] | R[8] | R[24] | R[25] |
|---|---|---|---|
| ethylcyclohexyl | ethyl-tetrazole (NH) | CH$_3$ | CH$_2$-S-S-C(CH$_3$)$_3$, CH(NH$_2$) |
| cyclopropyl | ethyl-tetrazole (NH) | CH$_3$ | CH$_2$-S-S-C(CH$_3$)$_3$, CH(NH$_2$) |
| n-hexyl | cyclohexyl propanoate | CH$_3$ | thiazolidine-CH$_3$ |
| n-pentyl | cyclohexyl propanoate | CH$_3$ | thiazolidine-CH$_3$ |
| n-butyl | cyclohexyl propanoate | CH$_3$ | thiazolidine-CH$_3$ |
| ethyl | cyclohexyl propanoate | CH$_3$ | thiazolidine-CH$_3$ |
| sec-butyl | cyclohexyl propanoate | CH$_3$ | thiazolidine-CH$_3$ |
| isobutyl | cyclohexyl propanoate | CH$_3$ | thiazolidine-CH$_3$ |
| tert-butyl | cyclohexyl propanoate | CH$_3$ | thiazolidine-CH$_3$ |
| 2,2-dimethylbutyl | cyclohexyl propanoate | CH$_3$ | thiazolidine-CH$_3$ |
| allyl (=CH$_2$) | cyclohexyl propanoate | CH$_3$ | thiazolidine-CH$_3$ |

TABLE II(b)(1)-continued
| R⁷' | R⁸ | R²⁴ | R²⁵ |
|---|---|---|---|
|  | 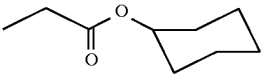 | CH₃ | 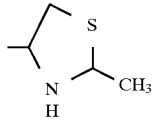 |
| 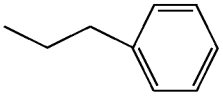 | 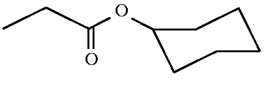 | CH₃ | 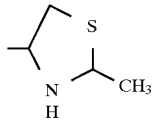 |
| 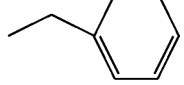 | 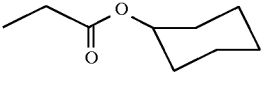 | CH₃ | 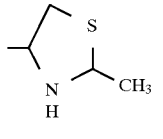 |
| 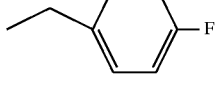 | 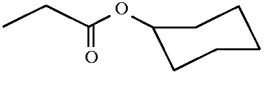 | CH₃ | 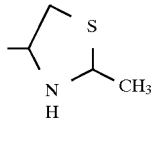 |
| 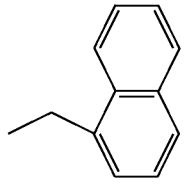 | 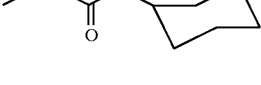 | CH₃ | 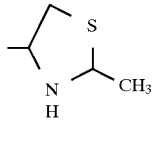 |
|  | 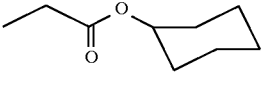 | CH₃ | 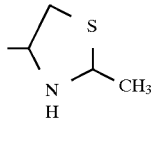 |
|  | 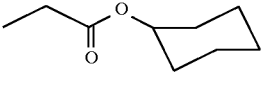 | CH₃ | 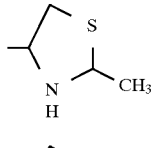 |
|  |  | CH₃ | 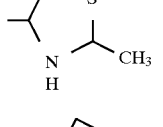 |
|  |  | CH₃ | 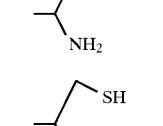 |
|  | 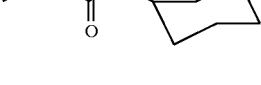 | CH₃ | 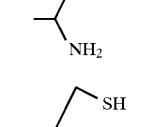 |
|  | 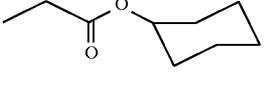 | CH₃ | 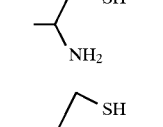 |
|  | 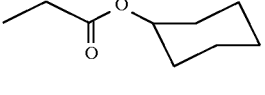 | CH₃ | 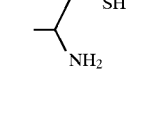 |

5,843,941
TABLE II(b)(1)-continued
| R⁷ | R⁸ | R²⁴ | R²⁵ |
|---|---|---|---|
| 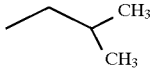 | 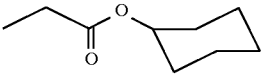 | CH₃ | 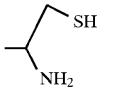 |
| 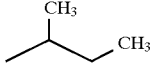 | 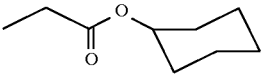 | CH₃ | 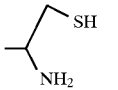 |
| 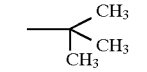 | 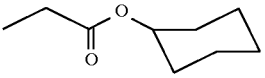 | CH₃ | 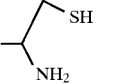 |
|  | 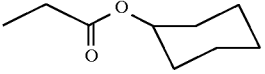 | CH₃ | 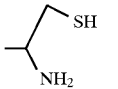 |
| 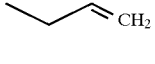 | 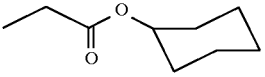 | CH₃ | 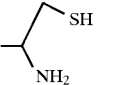 |
| 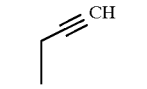 | 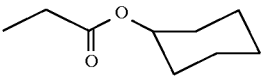 | CH₃ | 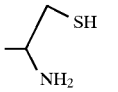 |
| 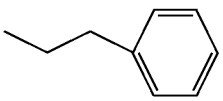 | 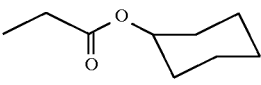 | CH₃ | 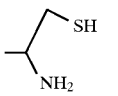 |
| 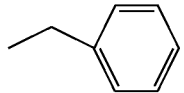 | 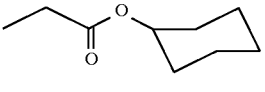 | CH₃ | 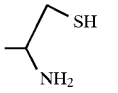 |
| 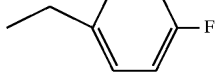 | 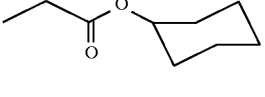 | CH₃ | 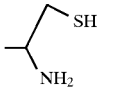 |
| 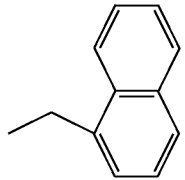 | 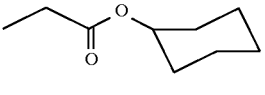 | CH₃ | 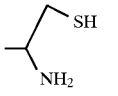 |
| 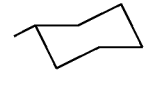 | 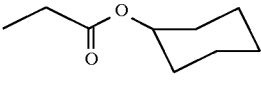 | CH₃ | 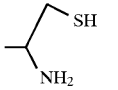 |
|  | 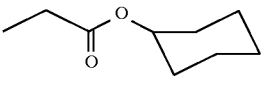 | CH₃ | 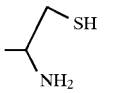 |
|  | 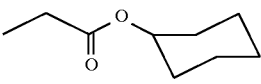 | CH₃ | 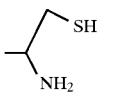 |
| 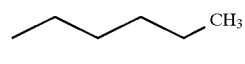 | 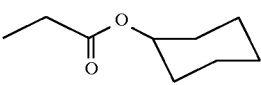 | CH₃ | 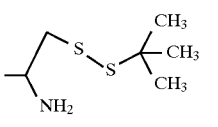 |

TABLE II(b)(1)-continued

| R⁷ | R⁸ | R²⁴ | R²⁵ |
|---|---|---|---|
| CH₃(CH₂)₃CH₂– | cyclohexyl propanoate ester | CH₃ | CH₃-C(CH₃)₂-S-S-CH₂-CH(NH₂)- |
| CH₃(CH₂)₂CH₂– | cyclohexyl propanoate ester | CH₃ | CH₃-C(CH₃)₂-S-S-CH₂-CH(NH₂)- |
| CH₃CH₂CH₂– | cyclohexyl propanoate ester | CH₃ | CH₃-C(CH₃)₂-S-S-CH₂-CH(NH₂)- |
| sec-butyl (CH₃CH₂CH(CH₃)–) | cyclohexyl propanoate ester | CH₃ | CH₃-C(CH₃)₂-S-S-CH₂-CH(NH₂)- |
| isobutyl ((CH₃)₂CHCH₂–) | cyclohexyl propanoate ester | CH₃ | CH₃-C(CH₃)₂-S-S-CH₂-CH(NH₂)- |
| neopentyl ((CH₃)₃CCH₂–) | cyclohexyl propanoate ester | CH₃ | CH₃-C(CH₃)₂-S-S-CH₂-CH(NH₂)- |
| CH₃CH₂C(CH₃)₂CH₂– | cyclohexyl propanoate ester | CH₃ | CH₃-C(CH₃)₂-S-S-CH₂-CH(NH₂)- |
| CH₂=CHCH₂CH₂– | cyclohexyl propanoate ester | CH₃ | CH₃-C(CH₃)₂-S-S-CH₂-CH(NH₂)- |
| HC≡CCH₂CH₂– | cyclohexyl propanoate ester | CH₃ | CH₃-C(CH₃)₂-S-S-CH₂-CH(NH₂)- |
| PhCH₂CH₂CH₂– | cyclohexyl propanoate ester | CH₃ | CH₃-C(CH₃)₂-S-S-CH₂-CH(NH₂)- |
| PhCH₂CH₂– | cyclohexyl propanoate ester | CH₃ | CH₃-C(CH₃)₂-S-S-CH₂-CH(NH₂)- |
| 4-F-C₆H₄-CH₂CH₂– | cyclohexyl propanoate ester | CH₃ | CH₃-C(CH₃)₂-S-S-CH₂-CH(NH₂)- |

TABLE II(b)(1)-continued

TABLE II(b)(1)-continued
| R⁷ | R⁸ | R²⁴ | R²⁵ |
|---|---|---|---|
| 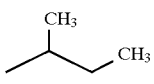 | 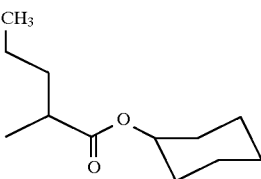 | CH₃ | 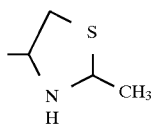 |
| 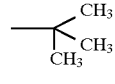 | 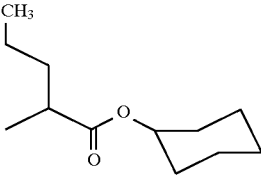 | CH₃ | 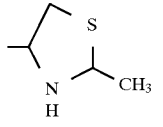 |
| 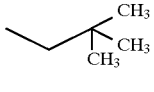 | 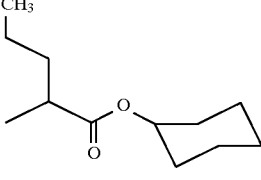 | CH₃ | 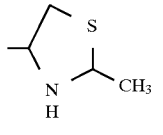 |
| 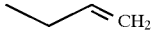 | 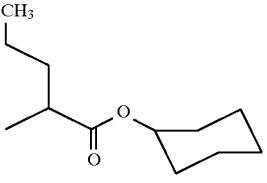 | CH₃ | 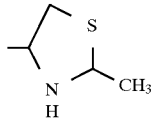 |
|  | 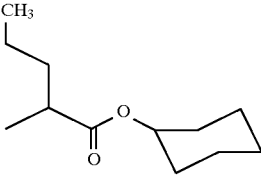 | CH₃ | 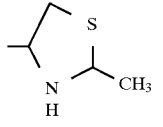 |
| 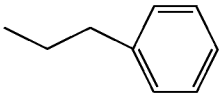 | 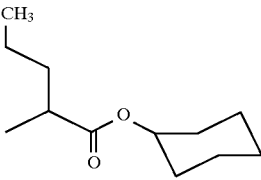 | CH₃ | 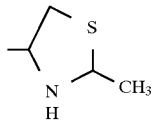 |
| 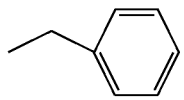 | 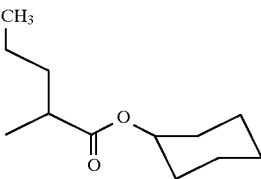 | CH₃ | 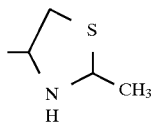 |
| 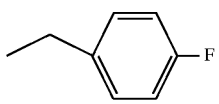 | 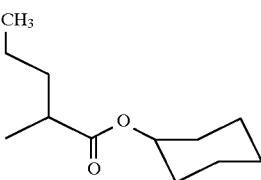 | CH₃ | 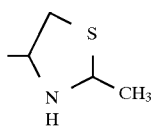 |

TABLE II(b)(1)-continued

| R⁷ | R⁸ | R²⁴ | R²⁵ |
|---|---|---|---|
| 1-ethylnaphthalene | cyclohexyl 2-methylpentanoate | CH₃ | 2-methylthiazolidine |
| cyclohexyl | cyclohexyl 2-methylpentanoate | CH₃ | 2-methylthiazolidine |
| ethylcyclohexyl | cyclohexyl 2-methylpentanoate | CH₃ | 2-methylthiazolidine |
| cyclopropyl | cyclohexyl 2-methylpentanoate | CH₃ | 2-methylthiazolidine |
| n-hexyl | cyclohexyl 2-methylpentanoate | CH₃ | 1-amino-2-mercaptopropane |
| n-pentyl | cyclohexyl 2-methylpentanoate | CH₃ | 1-amino-2-mercaptopropane |
| n-butyl | cyclohexyl 2-methylpentanoate | CH₃ | 1-amino-2-mercaptopropane |
| n-propyl | cyclohexyl 2-methylpentanoate | CH₃ | 1-amino-2-mercaptopropane |

TABLE II(b)(1)-continued
| R[7'] | R[8] | R[24] | R[25] |
|---|---|---|---|
| 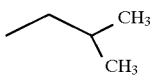 | 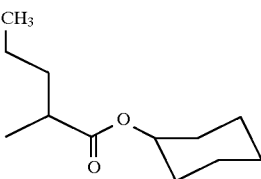 | CH₃ |  |
| 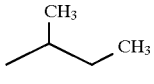 | 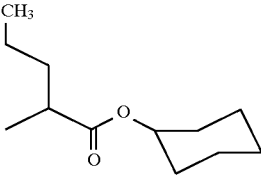 | CH₃ |  |
| 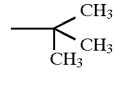 | 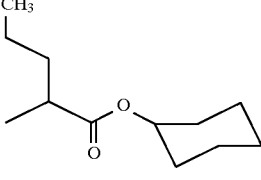 | CH₃ |  |
|  | 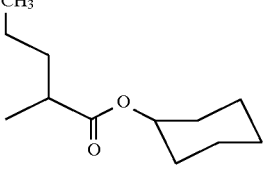 | CH₃ |  |
|  | 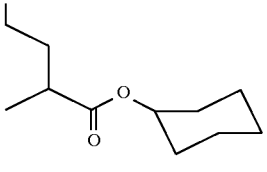 | CH₃ |  |
|  | 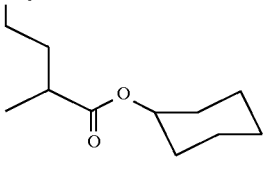 | CH₃ |  |
| 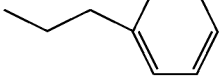 | 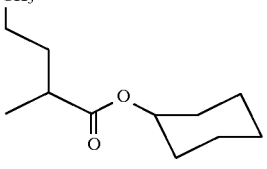 | CH₃ |  |
| 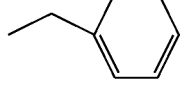 | 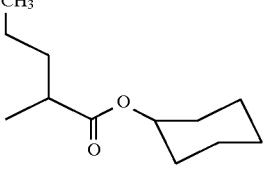 | CH₃ |  |

TABLE II(b)(1)-continued
| R[7'] | R[8] | R[24] | R[25] |
|---|---|---|---|
| 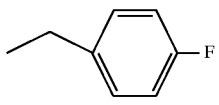 | 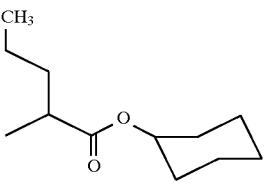 | CH₃ | 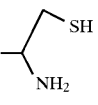 |
| 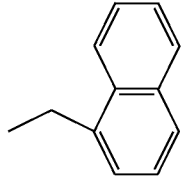 | 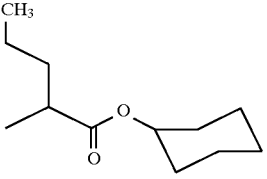 | CH₃ |  |
|  | 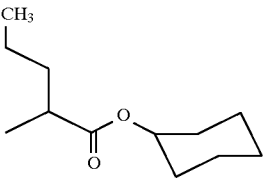 | CH₃ |  |
|  | 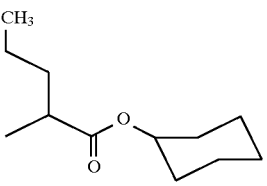 | CH₃ |  |
|  | 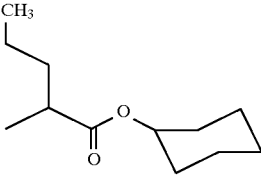 | CH₃ |  |
| 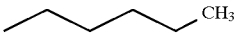 | 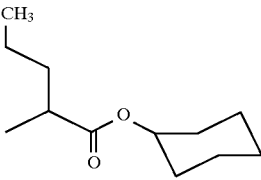 | CH₃ | 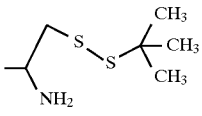 |
| 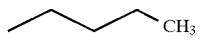 | 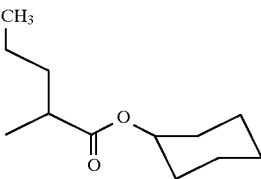 | CH₃ | 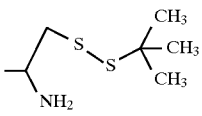 |
| 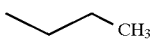 | 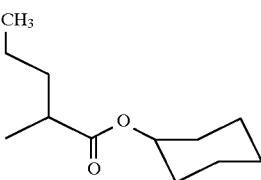 | CH₃ | 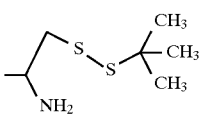 |

TABLE II(b)(1)-continued

| R[7'] | R[8] | R[24] | R[25] |
|---|---|---|---|
| CH₃CH₂CH(CH₃)– | 2-methylpentanoic acid cyclohexyl ester | CH₃ | aminopropyl tert-butyl disulfide |
| (CH₃)₂CHCH₂– (sec-butyl) | 2-methylpentanoic acid cyclohexyl ester | CH₃ | aminopropyl tert-butyl disulfide |
| (CH₃)₂CHCH(CH₃)– | 2-methylpentanoic acid cyclohexyl ester | CH₃ | aminopropyl tert-butyl disulfide |
| (CH₃)₃C–CH₂– | 2-methylpentanoic acid cyclohexyl ester | CH₃ | aminopropyl tert-butyl disulfide |
| CH₃CH₂C(CH₃)₂–CH₂– | 2-methylpentanoic acid cyclohexyl ester | CH₃ | aminopropyl tert-butyl disulfide |
| CH₃CH₂CH=CH– | 2-methylpentanoic acid cyclohexyl ester | CH₃ | aminopropyl tert-butyl disulfide |
| CH₃CH₂C≡CH | 2-methylpentanoic acid cyclohexyl ester | CH₃ | aminopropyl tert-butyl disulfide |
| PhCH₂CH₂CH₂– | 2-methylpentanoic acid cyclohexyl ester | CH₃ | aminopropyl tert-butyl disulfide |

An alternative preferred embodiment of the invention comprises a compound capable of inhibiting farnesyl:protein transferase at a concentration equal to or lower than that of the tetrapeptide CVFM represented by Formula III(a)

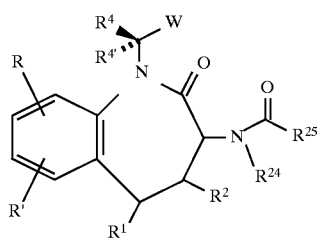

III(a)

where the substituents R and R' are as defined above, $R^4$ and $R^{4'}$ are hydrogen or lower alkyl, and where W, $R^1$ and $R^2$, $R^{24}$ and $R^{25}$, are selected according to Table III(a).

TABLE III(a)

| R¹ and R² | W | R²⁴ | R²⁵ |
|---|---|---|---|
| CF₃, H | methyl acetate | CH₃ | CH₂SH-CH(NH₂)-CH₃ |
| CF₃, H | ethyl acetate | CH₃ | CH₂SH-CH(NH₂)-CH₃ |
| CF₃, H | 4-(methoxycarbonyl)phenyl | CH₃ | CH₂SH-CH(NH₂)-CH₃ |
| CF₃, H | 3-carboxyphenyl | CH₃ | CH₂SH-CH(NH₂)-CH₃ |
| CF₃, H | 2'-(methoxycarbonyl)biphenyl-4-yl | CH₃ | CH₂SH-CH(NH₂)-CH₃ |
| CF₃, H | 2-(methoxycarbonyl)biphenyl-4-yl | CH₃ | CH₂SH-CH(NH₂)-CH₃ |
| CF₃, H | 4-carboxycyclohexyl | CH₃ | CH₂SH-CH(NH₂)-CH₃ |
| CF₃, H | 4-(tetrazol-5-yl)phenyl | CH₃ | CH₂SH-CH(NH₂)-CH₃ |
| CF₃, H | 3-(tetrazol-5-yl)phenyl | CH₃ | CH₂SH-CH(NH₂)-CH₃ |
| CF₃, H | 2'-(tetrazol-5-yl)biphenyl-4-yl | CH₃ | CH₂SH-CH(NH₂)-CH₃ |
| CF₃, H | 2-(tetrazol-5-yl)biphenyl-4-yl | CH₃ | CH₂SH-CH(NH₂)-CH₃ |

TABLE III(a)-continued

| R¹ and R² | W | R²⁴ | R²⁵ |
|---|---|---|---|
| CF₃, H | methyl butanoate (CH₂CH₂CH₂C(O)OCH₃) | CH₃ | -CH₂-CH(NH₂)-SH |
| CF₃, H | methyl 2-ethoxyacetate (-CH₂-O-CH₂-C(O)OCH₃) | CH₃ | -CH₂-CH(NH₂)-SH |
| CF₃, H | methyl 2-ethoxy-2-methylpropanoate (C(CH₃)₂(OCH₂CH₃)C(O)OCH₃) | CH₃ | -CH₂-CH(NH₂)-SH |
| CF₃, H | 4-(SO₂NH₂)-phenyl | CH₃ | -CH₂-CH(NH₂)-SH |
| CF₃, H | 4-(SO₂NHCF₃)-phenyl | CH₃ | -CH₂-CH(NH₂)-SH |
| CF₃, H | 2,5-difluorophenyl | CH₃ | -CH₂-CH(NH₂)-SH |
| CF₃, H | 3-cyanophenyl | CH₃ | -CH₂-CH(NH₂)-SH |
| CF₃, H | 4-cyanophenyl | CH₃ | -CH₂-CH(NH₂)-SH |
| CF₃, H | 3-(COOCH₃)-phenyl | CH₃ | -CH₂-CH(NH₂)-SH |
| CF₃, H | 3-fluoro-4-(CF₃)-phenyl | CH₃ | -CH₂-CH(NH₂)-SH |
| CF₃, H | 4-(SO₃CH₃)-phenyl | CH₃ | -CH₂-CH(NH₂)-SH |
| covalent bond | methyl acetate (CH₃C(O)OCH₃) | CH₃ | -CH₂-CH(NH₂)-SH |
| covalent bond | ethyl acetate (CH₃C(O)OCH₂CH₃) | CH₃ | -CH₂-CH(NH₂)-SH |
| covalent bond | 4-(COOCH₃)-phenyl | CH₃ | -CH₂-CH(NH₂)-SH |

TABLE III(a)-continued

| R¹ and R² | W | R²⁴ | R²⁵ |
|---|---|---|---|
| covalent bond | 3-carboxyphenyl (COOH) | CH₃ | -CH₂-SH, -CH(NH₂)- |
| covalent bond | 4'-(2-methoxycarbonyl)biphenyl (H₃COOC) | CH₃ | -CH₂-SH, -CH(NH₂)- |
| covalent bond | 4'-(2-methoxycarbonyl)biphenyl (COOCH₃) | CH₃ | -CH₂-SH, -CH(NH₂)- |
| covalent bond | cyclohexyl-COOH | CH₃ | -CH₂-SH, -CH(NH₂)- |
| covalent bond | 4-(tetrazol-5-yl)phenyl | CH₃ | -CH₂-SH, -CH(NH₂)- |
| covalent bond | 3-(tetrazol-5-yl)phenyl | CH₃ | -CH₂-SH, -CH(NH₂)- |
| covalent bond | 4'-(2-tetrazol-5-yl)biphenyl | CH₃ | -CH₂-SH, -CH(NH₂)- |
| covalent bond | 4'-(2-tetrazol-5-yl)biphenyl (isomer) | CH₃ | -CH₂-SH, -CH(NH₂)- |
| covalent bond | CH₃CH₂CH₂C(=O)OCH₃ | CH₃ | -CH₂-SH, -CH(NH₂)- |
| covalent bond | CH₃CH₂OCH₂C(=O)OCH₃ | CH₃ | -CH₂-SH, -CH(NH₂)- |
| covalent bond | CH₃CH₂OC(CH₃)₂C(=O)OCH₃ | CH₃ | -CH₂-SH, -CH(NH₂)- |

TABLE III(a)-continued

| R¹ and R² | W | R²⁴ | R²⁵ |
|---|---|---|---|
| covalent bond | 4-(SO₂NH₂)-phenyl | CH₃ | CH₂(SH)CH(NH₂)- |
| covalent bond | 4-(SO₂NHCF₃)-phenyl | CH₃ | CH₂(SH)CH(NH₂)- |
| covalent bond | 3-CN-phenyl | CH₃ | CH₂(SH)CH(NH₂)- |
| covalent bond | 4-CN-phenyl | CH₃ | CH₂(SH)CH(NH₂)- |
| covalent bond | 3-(COOCH₃)-phenyl | CH₃ | CH₂(SH)CH(NH₂)- |
| covalent bond | 2,4-difluoro-phenyl | CH₃ | CH₂(SH)CH(NH₂)- |
| covalent bond | 4-fluoro-phenyl | CH₃ | CH₂(SH)CH(NH₂)- |
| covalent bond | 3-fluoro-5-(COOCH₃)-phenyl | CH₃ | CH₂(SH)CH(NH₂)- |
| 1-phenyl-propyl | CH₃C(O)OCH₃ | CH₃ | CH₂(SH)CH(NH₂)- |
| 1-phenyl-propyl | CH₃C(O)OCH₂CH₃ | CH₃ | CH₂(SH)CH(NH₂)- |
| 1-phenyl-propyl | 4-(COOCH₃)-phenyl | CH₃ | CH₂(SH)CH(NH₂)- |

TABLE III(a)-continued

| R¹ and R² | W | R²⁴ | R²⁵ |
|---|---|---|---|
| sec-butylphenyl | 3-carboxyphenyl | CH₃ | CH(CH₃)(CH₂SH)(NH₂) |
| sec-butylphenyl | 4'-(2-methoxycarbonyl)biphenyl | CH₃ | CH(CH₃)(CH₂SH)(NH₂) |
| sec-butylphenyl | 2-(methoxycarbonyl)biphenyl | CH₃ | CH(CH₃)(CH₂SH)(NH₂) |
| sec-butylphenyl | 4-carboxycyclohexyl | CH₃ | CH(CH₃)(CH₂SH)(NH₂) |
| sec-butylphenyl | 4-(tetrazol-5-yl)phenyl | CH₃ | CH(CH₃)(CH₂SH)(NH₂) |
| sec-butylphenyl | 3-(tetrazol-5-yl)phenyl | CH₃ | CH(CH₃)(CH₂SH)(NH₂) |
| sec-butylphenyl | 4'-[2-(tetrazol-5-yl)]biphenyl | CH₃ | CH(CH₃)(CH₂SH)(NH₂) |
| sec-butylphenyl | 2-(tetrazol-5-yl)biphenyl | CH₃ | CH(CH₃)(CH₂SH)(NH₂) |

TABLE III(a)-continued
| R¹ and R² | W | R²⁴ | R²⁵ |
|---|---|---|---|
| 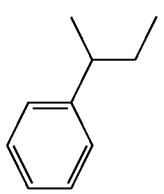 | 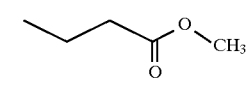 | CH₃ | 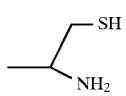 |
| 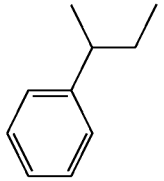 | 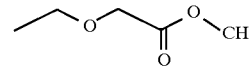 | CH₃ | 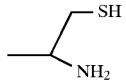 |
| 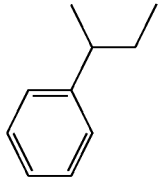 | 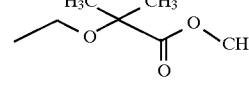 | CH₃ | 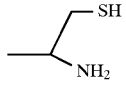 |
| 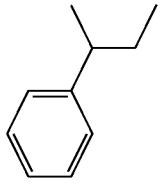 | 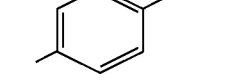 | CH₃ | 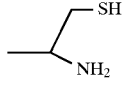 |
| 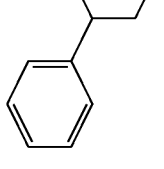 | 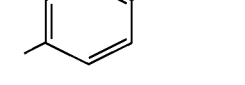 | CH₃ | 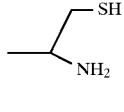 |
| 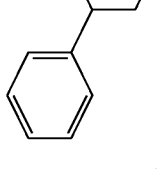 | 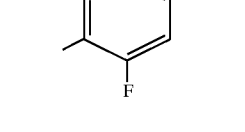 | CH₃ | 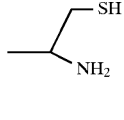 |
| 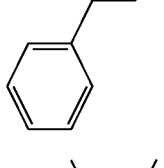 | 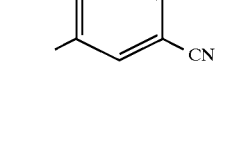 | CH₃ | 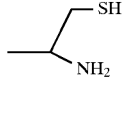 |
| 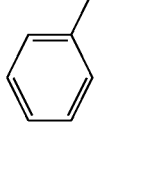 | 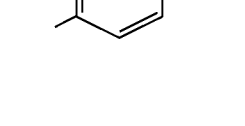 | CH₃ | 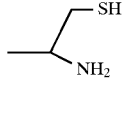 |

TABLE III(a)-continued
| R¹ and R² | W | R²⁴ | R²⁵ |
|---|---|---|---|
| 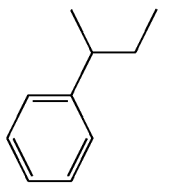 | 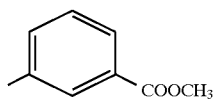 | CH₃ | 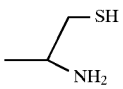 |
| 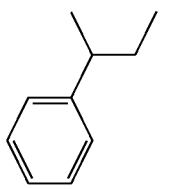 | 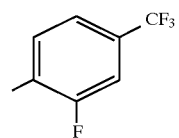 | CH₃ | 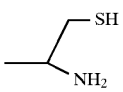 |
| 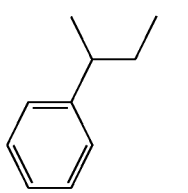 | 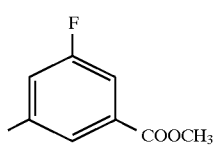 | CH₃ | 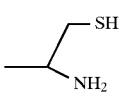 |
| 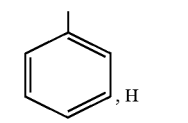 | 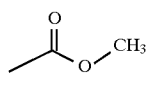 | CH₃ | 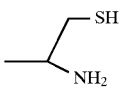 |
| 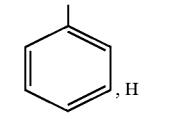 | 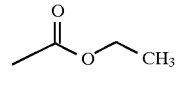 | CH₃ | 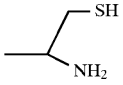 |
| 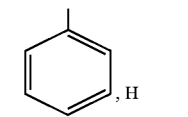 | 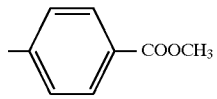 | CH₃ | 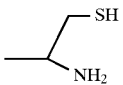 |
| 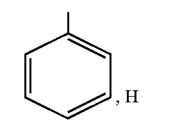 | 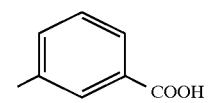 | CH₃ | 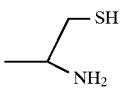 |
| 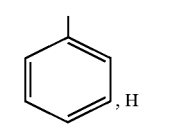 | 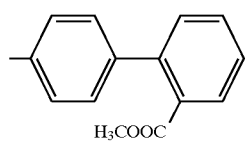 | CH₃ | 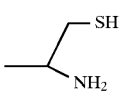 |
| 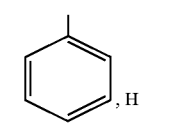 | 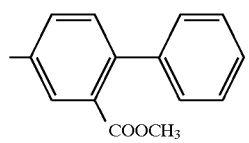 | CH₃ | 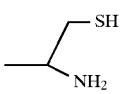 |
| 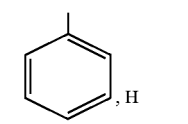 | 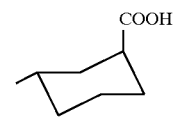 | CH₃ | 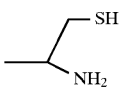 |

TABLE III(a)-continued
| R¹ and R² | W | R²⁴ | R²⁵ |
|---|---|---|---|
| 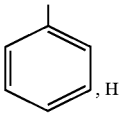, H | 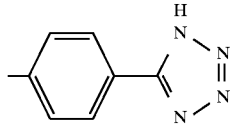 | CH₃ | 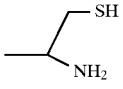 |
| 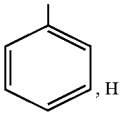, H | 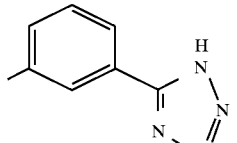 | CH₃ | 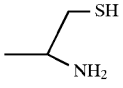 |
| 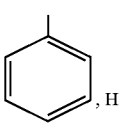, H | 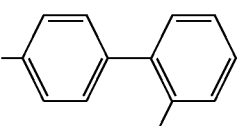 | CH₃ | 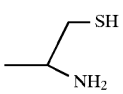 |
| 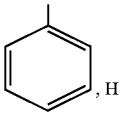, H | 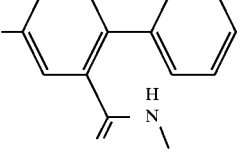 | CH₃ | 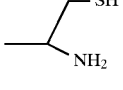 |
| 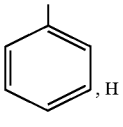, H | 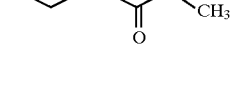 | CH₃ | 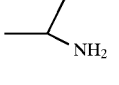 |
| 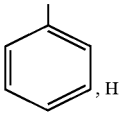, H | 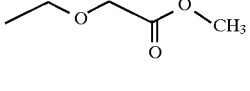 | CH₃ | 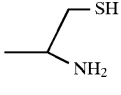 |
| 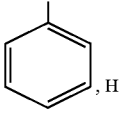, H | 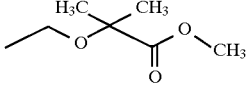 | CH₃ | 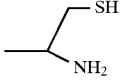 |
| 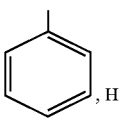, H | 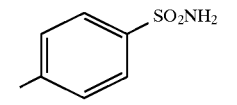 | CH₃ | 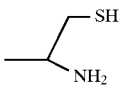 |
| 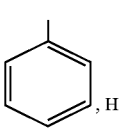, H | 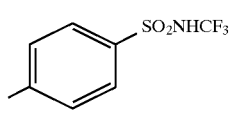 | CH₃ | 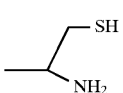 |
| 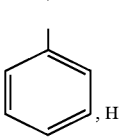, H | 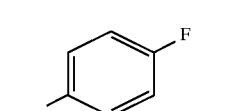 | CH₃ | 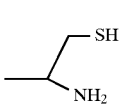 |

TABLE III(a)-continued

| R¹ and R² | W | R²⁴ | R²⁵ |
|---|---|---|---|
| phenyl, H | 3-CN-phenyl | CH₃ | CH(CH₃)(SH)(NH₂) |
| phenyl, H | 4-CN-phenyl | CH₃ | CH(CH₃)(SH)(NH₂) |
| phenyl, H | 3-COOCH₃-phenyl | CH₃ | CH(CH₃)(SH)(NH₂) |
| phenyl, H | 4-F-phenyl | CH₃ | CH(CH₃)(SH)(NH₂) |
| phenyl, H | 3-F-5-COOCH₃-phenyl | CH₃ | CH(CH₃)(SH)(NH₂) |

An alternative preferred embodiment of the invention comprises a compound capable of inhibiting farnesyl:protein transferase at a concentration equal to or lower than that of the tetrapeptide CVFM represented by Formula IV

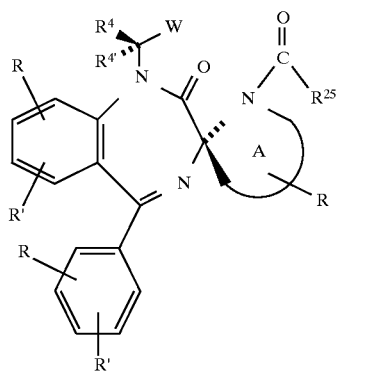

where the substituents R and R' are as defined above, R⁴ and R⁴' are hydrogen or lower alkyl, and W, R²⁵ and

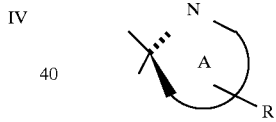   IV are selected according to Table IV.

TABLE IV

| W | (ring with N, A, R) | R²⁵ |
|---|---|---|
| CH₃-O-C(=O)-CH< | pyrrolidine-N | CH(CH₃)(SH)(NH₂) |

TABLE IV-continued
| W | (structure with N, A, R) | R²⁵ |
|---|---|---|
| 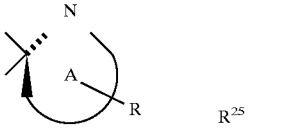 | 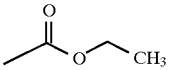 |  |
| 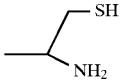 | 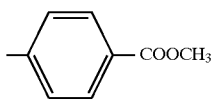 |  |
| 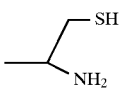 | 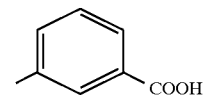 |  |
| 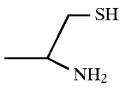 | 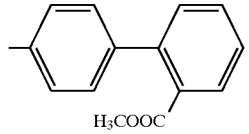 |  |
| 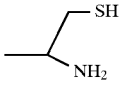 | 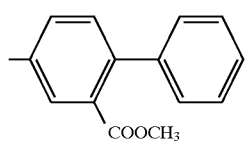 |  |
| 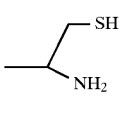 | 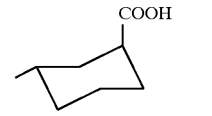 | 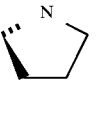 |
| 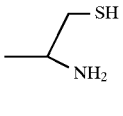 | 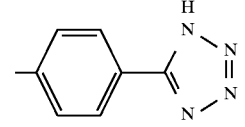 |  |
| 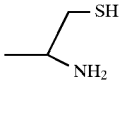 | 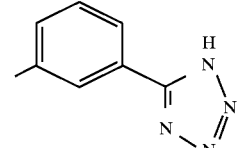 |  |
| 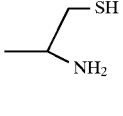 | 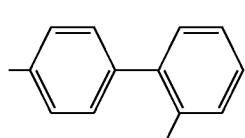 |  |
| 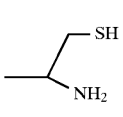 | 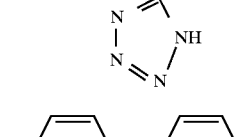 |  |

TABLE IV-continued
| W | 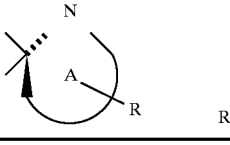 | R[25] |
|---|---|---|
| 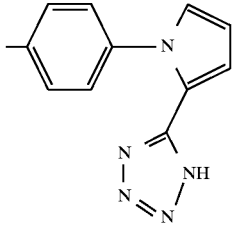 |  | 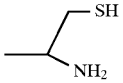 |
| 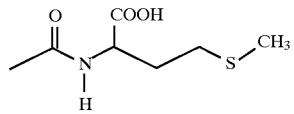 |  | 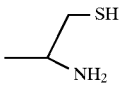 |
| 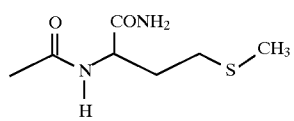 |  | 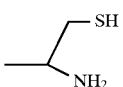 |
| 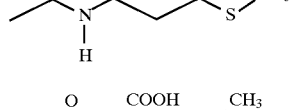 |  | 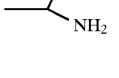 |
| 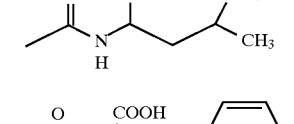 |  | 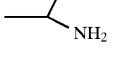 |
| 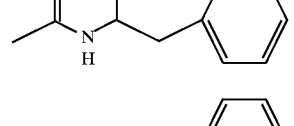 |  | 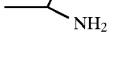 |
| 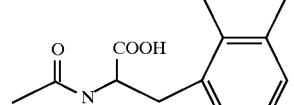 |  | 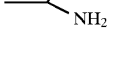 |
| 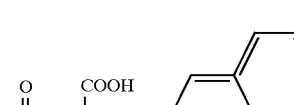 |  | 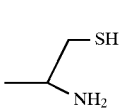 |
| 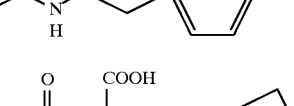 |  |  |
| 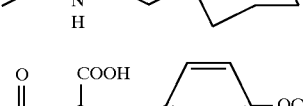 |  | 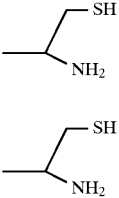 |

TABLE IV-continued
| W | 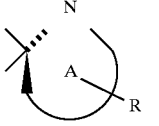 | $R^{25}$ |
|---|---|---|

TABLE IV-continued
| W | [structure with N, A, R] | $R^{25}$ |
|---|---|---|
| 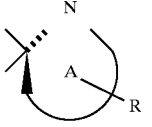 | 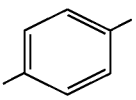 | 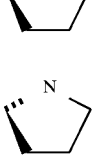 |
| 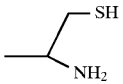 | 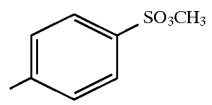 |  |
| 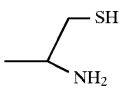 | 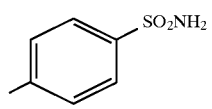 |  |
| 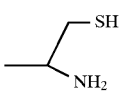 | 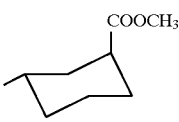 |  |
| 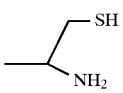 | 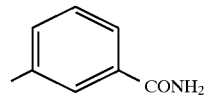 |  |
| 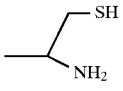 | 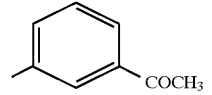 |  |
| 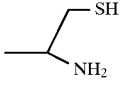 | 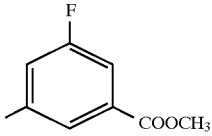 |  |
| 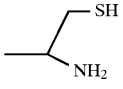 | 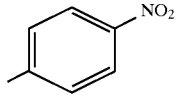 |  |
| 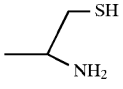 | 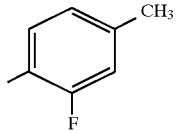 |  |
| 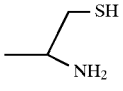 | 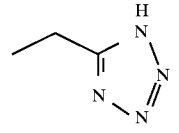 |  |
| 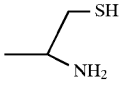 | 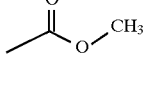 | 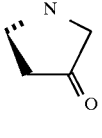 |

TABLE IV-continued

TABLE IV-continued
| W | 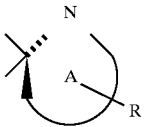 | R²⁵ |
|---|---|---|
| 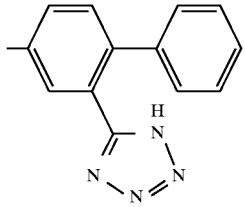 | 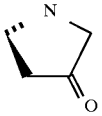 | 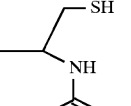 |
| 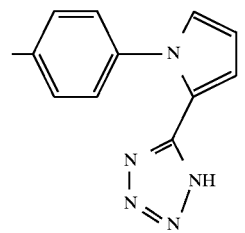 | 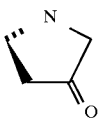 | 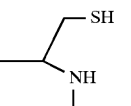 |
| 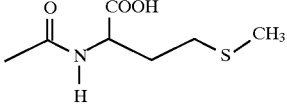 | 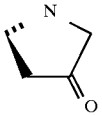 | 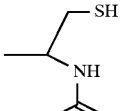 |
| 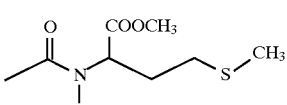 | 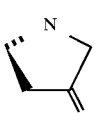 | 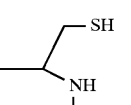 |
| 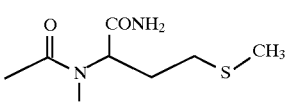 | 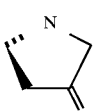 | 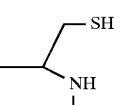 |
| 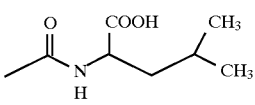 | 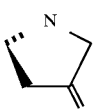 | 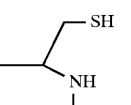 |
| 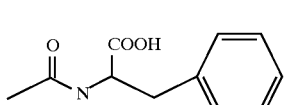 |  | 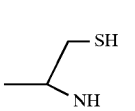 |
| 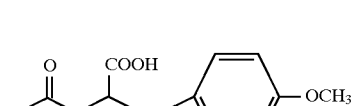 |  | 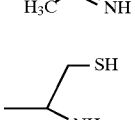 |

TABLE IV-continued

| W | (structure with N, A, R) | R²⁵ |
|---|---|---|

TABLE IV-continued
| W | | R²⁵ |
|---|---|---|
| 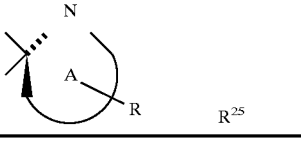 | 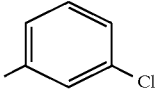 | 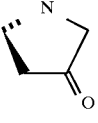 |
| 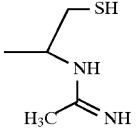 | 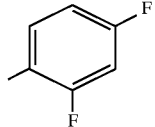 | 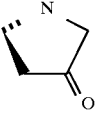 |
| 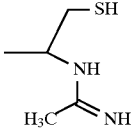 | 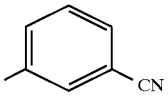 | 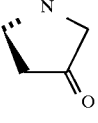 |
| 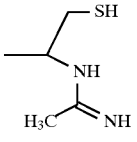 | 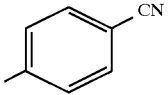 | 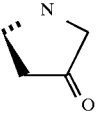 |
| 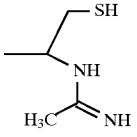 | 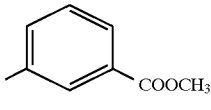 | 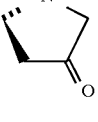 |
| 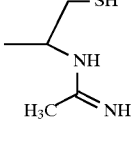 | 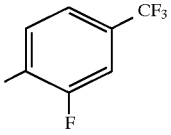 | 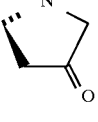 |
| 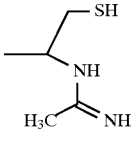 | 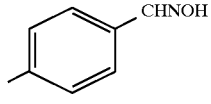 | 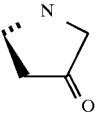 |
| 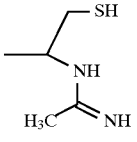 | 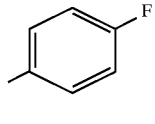 | 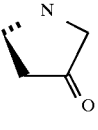 |
| 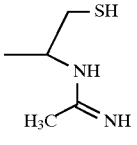 | 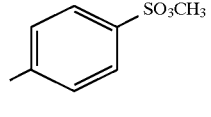 | 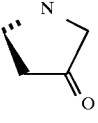 |
| 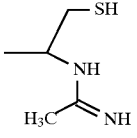 | 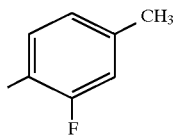 | 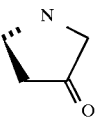 |

TABLE IV-continued

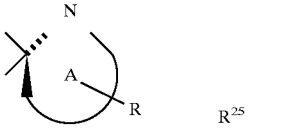

An alternative preferred embodiment of the invention comprises a compound capable of inhibiting farnesyl:protein transferase at a concentration equal to or lower than that of the tetrapeptide CVFM represented by Formula V

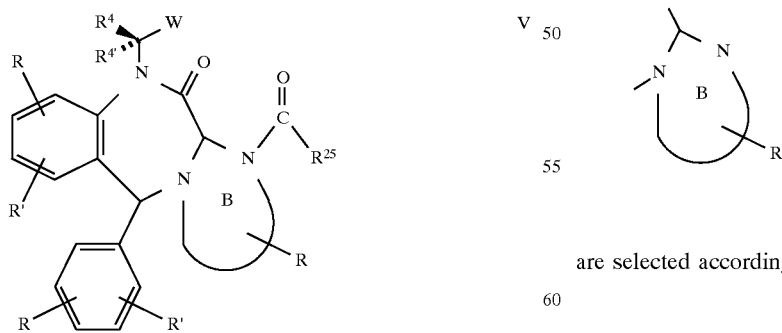

where the substituents R and R' are as defined above, $R^4$ and $R^{4'}$ are hydrogen or lower alkyl, and W, $R^{25}$ and are selected according to Table V.

TABLE V
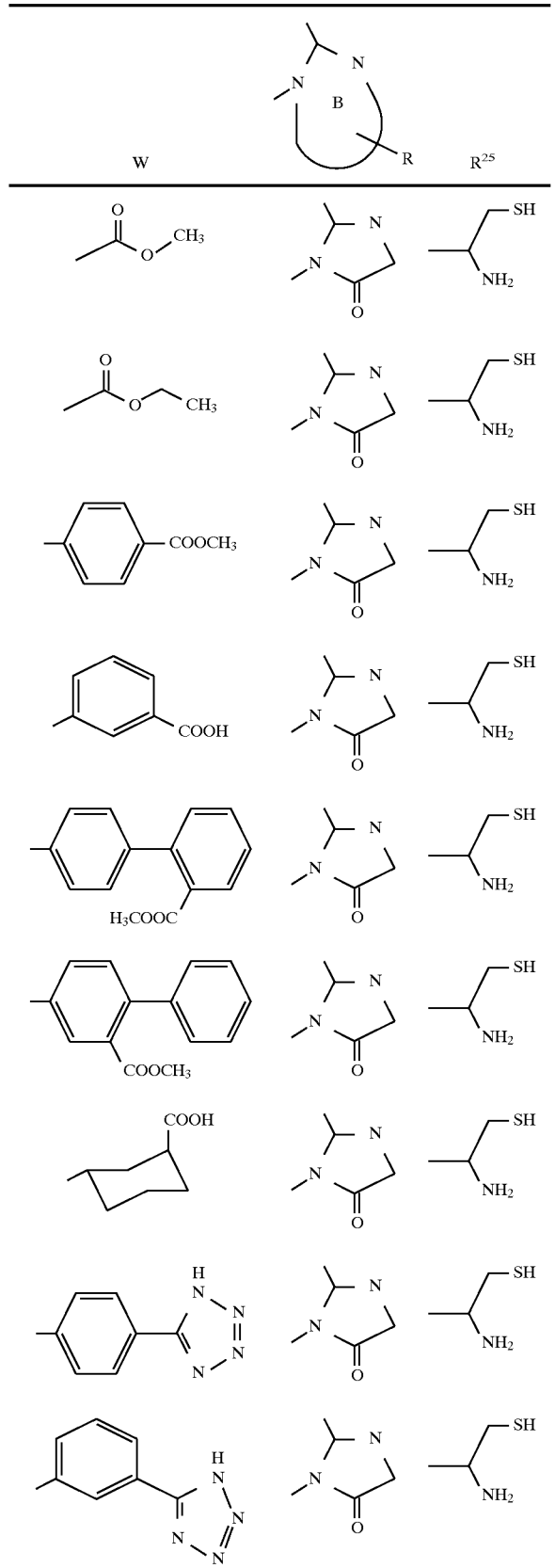
TABLE V-continued
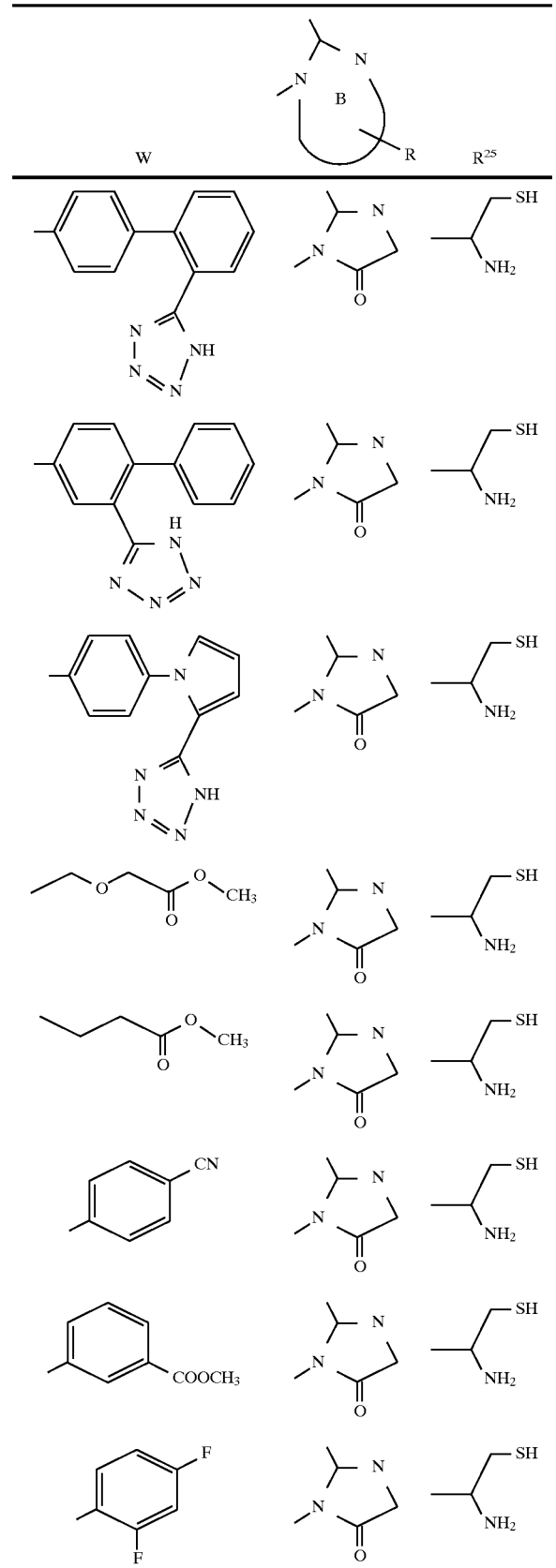

TABLE V-continued

//

TABLE V-continued

TABLE V-continued

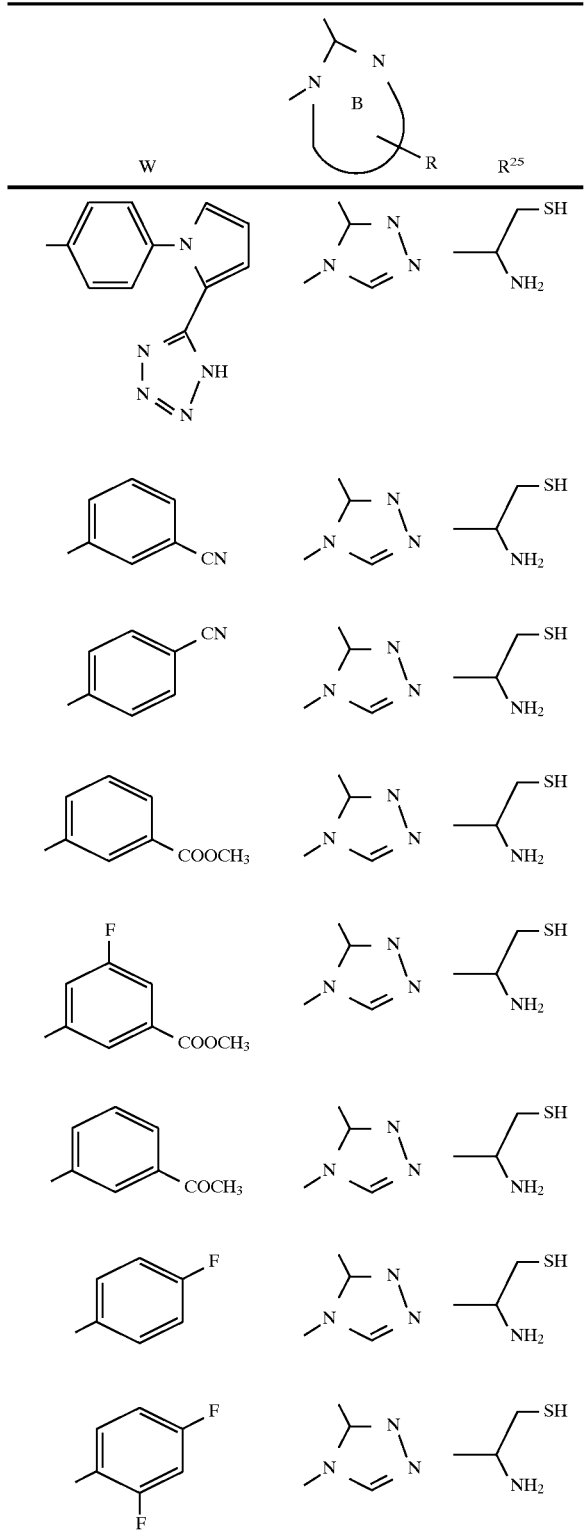

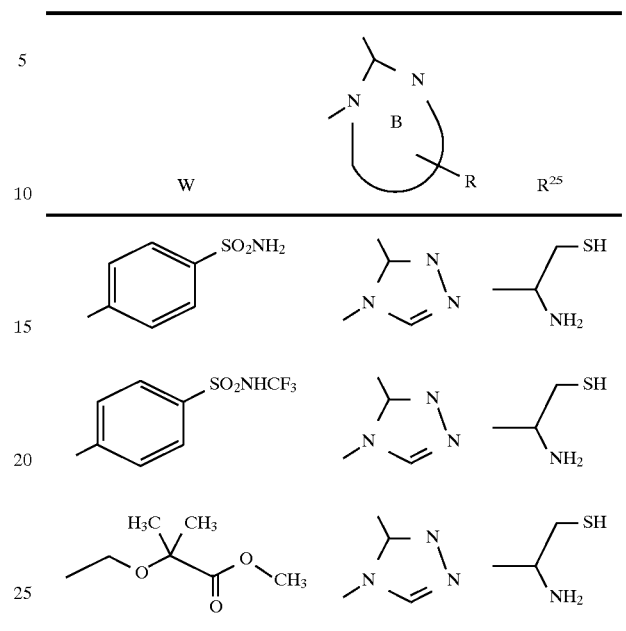

An alternative preferred embodiment of the invention comprises a compound capable of inhibiting farnesyl:protein transferase at a concentration equal to or lower then that of the tetrapeptide CVFM represented by Formula VI

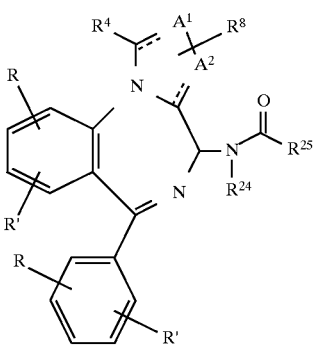

VI where the substitutes R and R' are halo or perfluroloweralkyl, $R^4$ is hydrogen or lower alkyl, and $R^{24}$, $R^{25}$ and

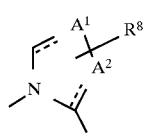

are selected according to Table VI.

TABLE VI
| | $R^8$ | $R^{24}$ | $R^{25}$ |
|---|---|---|---|
| 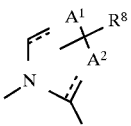 | 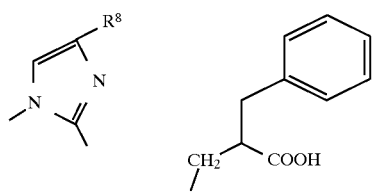 | CH₃ | 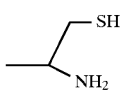 |
| 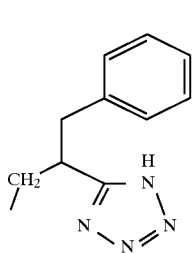 | 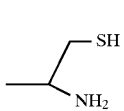 | CH₃ | 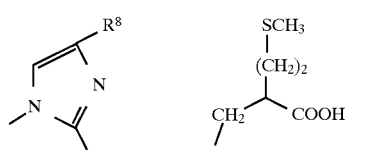 |
| 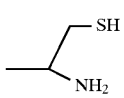 | 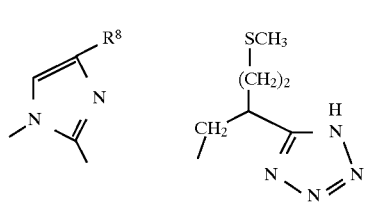 | CH₃ | 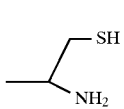 |
| 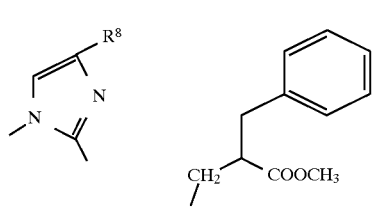 | 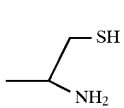 | CH₃ | 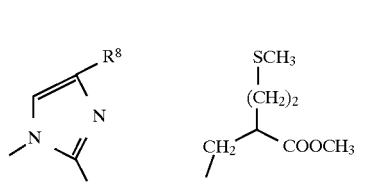 |
| 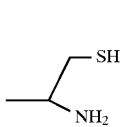 | 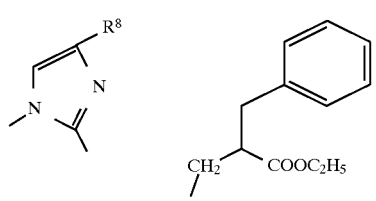 | CH₃ | 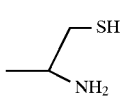 |

TABLE VI-continued
| | R⁸ | R²⁴ | R²⁵ |
|---|---|---|---|
| 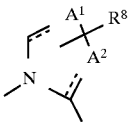 | 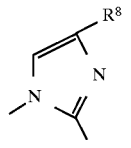 | CH₃ | 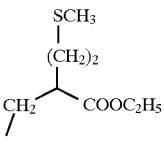 |
| 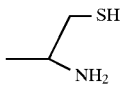 | 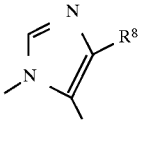 | CH₃ | 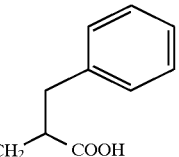 |
| 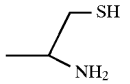 | 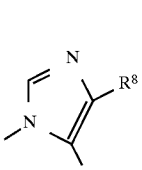 | CH₃ | 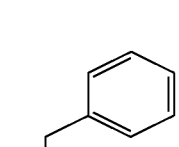 |
| 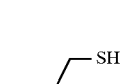 | 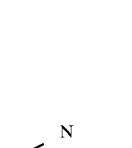 | CH₃ | 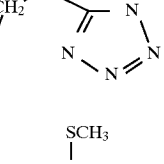 |
|  | 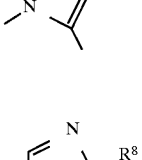 | CH₃ | 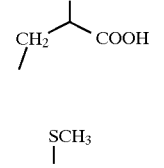 |
| 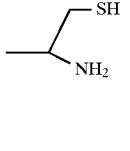 | 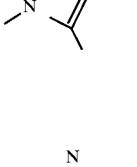 | CH₃ | 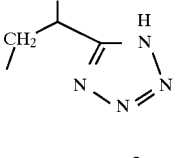 |
| 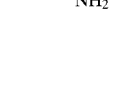 | 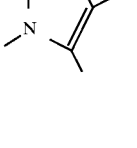 | CH₃ | 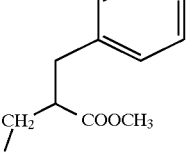 |

TABLE VI-continued
| | R⁸ | R²⁴ | R²⁵ |
|---|---|---|---|
| 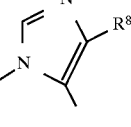 | 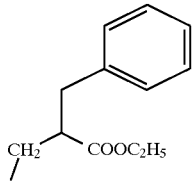 | CH₃ |  |
| 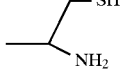 | 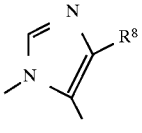 | CH₃ | 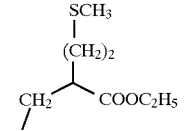 |
|  | 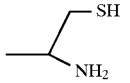 | CH₃ | 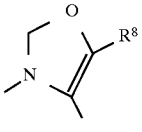 |
| 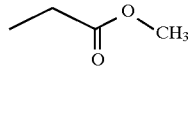 |  | CH₃ | 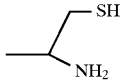 |
| 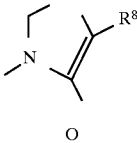 | 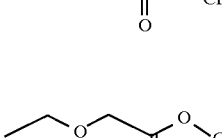 | CH₃ |  |
| 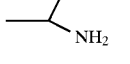 | 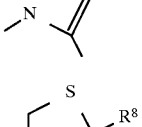 | CH₃ | 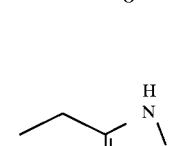 |
|  |  | CH₃ | 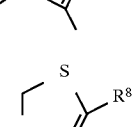 |
| 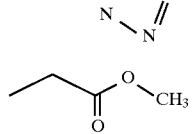 |  | CH₃ |  |
| 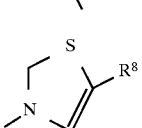 | COOH | CH₃ | 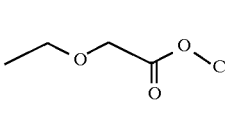 |
|  | 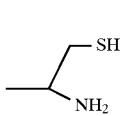 | CH₃ | 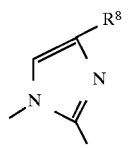 |

TABLE VI-continued
| | R⁸ | R²⁴ | R²⁵ |
|---|---|---|---|
| 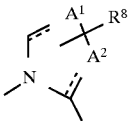 | 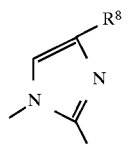 4-CN-C₆H₄ | CH₃ | 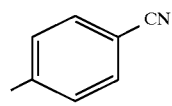 |
| 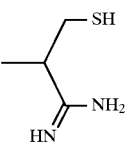 | 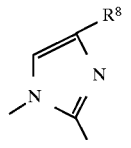 3-COOCH₃-C₆H₄ | CH₃ | 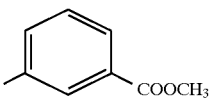 |
| 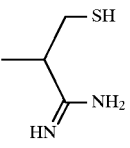 | 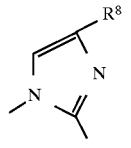 3-CF₃-4-F-C₆H₃ | CH₃ | 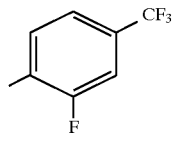 |
| 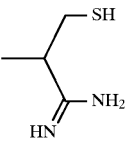 | 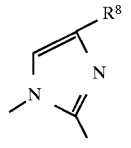 3-CONH₂-C₆H₄ | CH₃ | 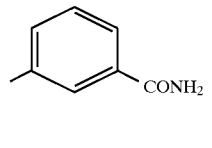 |
| 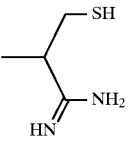 | 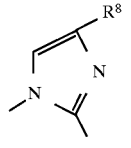 3-F-5-COOCH₃-C₆H₃ | CH₃ | 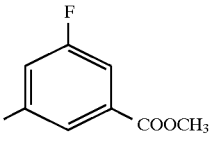 |
| 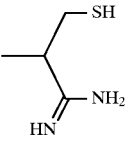 | 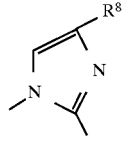 4-SO₃CH₃-C₆H₄ | CH₃ | 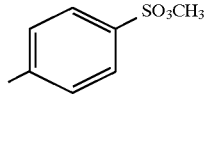 |
| 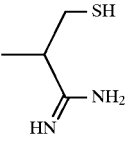 | 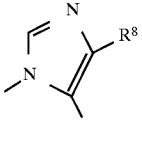 CH₃CH₂COOCH₃ | CH₃ | 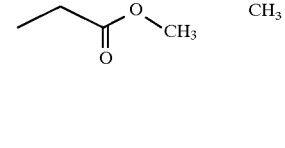 |
| 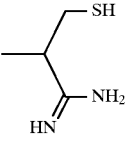 | 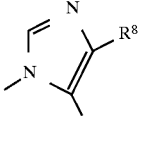 CH₃CH₂CH₂COOCH₃ | CH₃ | 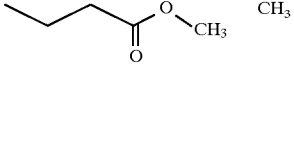 |
| 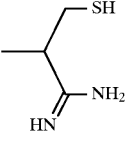 | 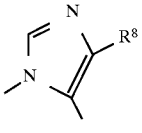 CH₃CH₂OCH₂COOCH₃ | CH₃ | 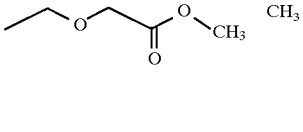 |

TABLE VI-continued
| | R⁸ | R²⁴ | R²⁵ |
|---|---|---|---|
| 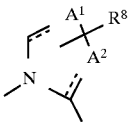 | 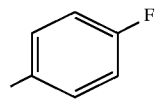 | CH₃ |  |
| 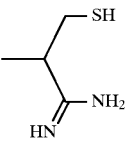 | 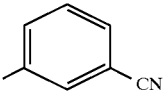 | CH₃ |  |
| 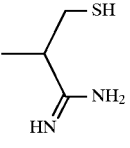 | 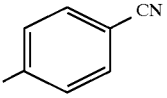 | CH₃ |  |
| 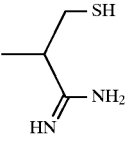 | 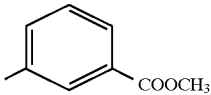 | CH₃ |  |
| 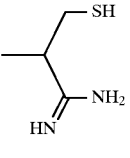 | 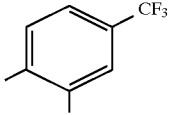 | CH₃ |  |
| 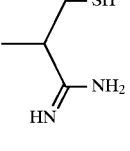 | 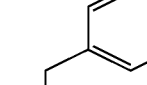 | CH₃ |  |
| 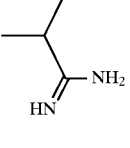 | 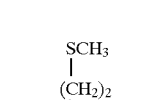 | CH₃ |  |
| 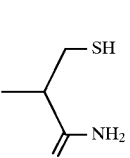 | 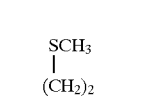 | CH₃ |  |

TABLE VI-continued
| | R[8] | R[24] | R[25] |
|---|---|---|---|
| 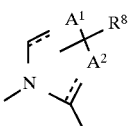 | 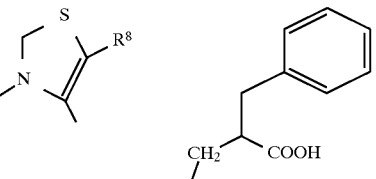 | CH_3 | 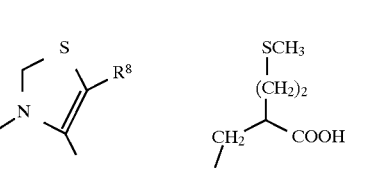 |
| 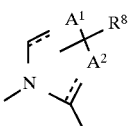 | 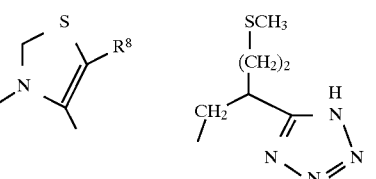 | CH_3 | 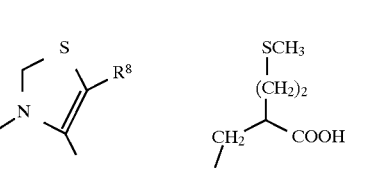 |
| 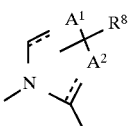 | 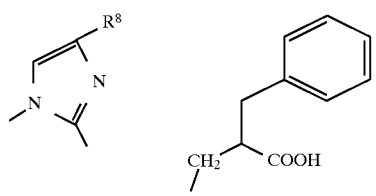 | CH_3 | 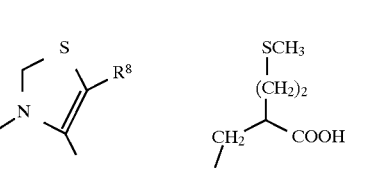 |
| 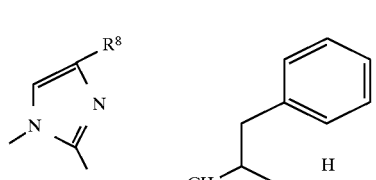 | 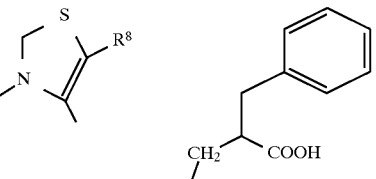 | CH_3 | 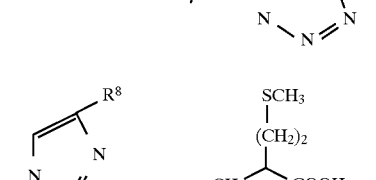 |
| 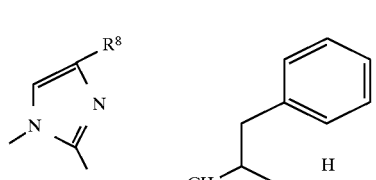 | 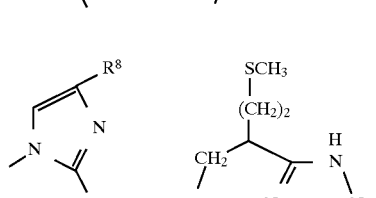 | CH_3 | 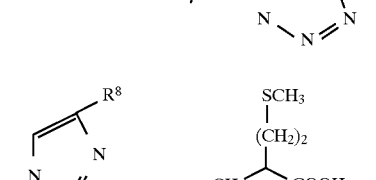 |
| 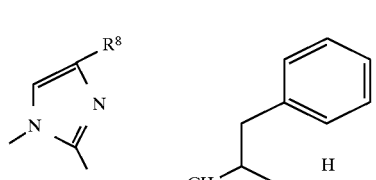 | 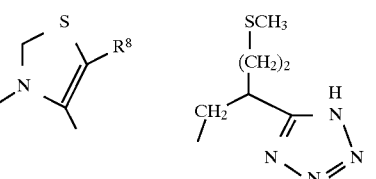 | CH_3 | 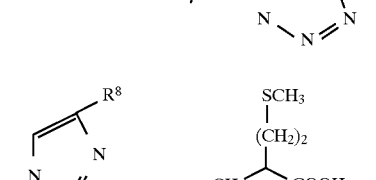 |
| 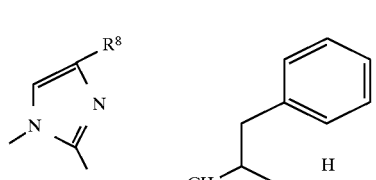 |  | CH_3 | 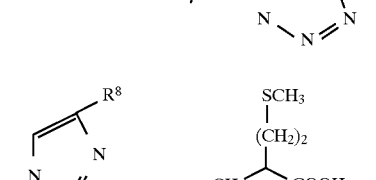 |

TABLE VI-continued

| R⁸ | R⁸ | R²⁴ | R²⁵ |
|---|---|---|---|
| N-methylimidazole (R⁸ at 4-position) | benzyl-CH(COOCH₃)- | CH₃ | -CH₂SH, -CH(CH₃)-NH-CH=NH |
| N-methylimidazole (R⁸ at 4-position) | CH₃S-(CH₂)₂-CH(COOCH₃)- | CH₃ | -CH₂SH, -CH(CH₃)-NH-CH=NH |
| N-methylimidazole (R⁸ at 4-position) | benzyl-CH(COOC₂H₅)- | CH₃ | -CH₂SH, -CH(CH₃)-NH-CH=NH |
| N-methylimidazole (R⁸ at 4-position) | CH₃S-(CH₂)₂-CH(COOC₂H₅)- | CH₃ | -CH₂SH, -CH(CH₃)-NH-CH=NH |
| N-methylimidazole (R⁸ at 5-position) | benzyl-CH(COOH)- | CH₃ | -CH₂SH, -CH(CH₃)-NH-CH=NH |
| N-methylimidazole (R⁸ at 5-position) | benzyl-CH(tetrazolyl)- | CH₃ | -CH₂SH, -CH(CH₃)-NH-CH=NH |
| N-methylimidazole (R⁸ at 5-position) | CH₃S-(CH₂)₂-CH(COOH)- | CH₃ | -CH₂SH, -CH(CH₃)-NH-CH=NH |

TABLE VI-continued

| | R⁸ | R²⁴ | R²⁵ |
|---|---|---|---|

TABLE VI-continued
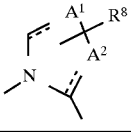
| | $R^8$ | $R^{24}$ | $R^{25}$ |
|---|---|---|---|
| 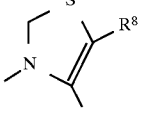 | 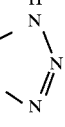 | CH$_3$ |  |
|  | 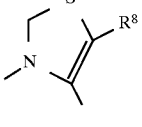 | CH$_3$ | 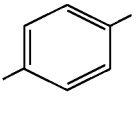 |
|  | 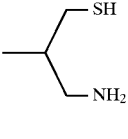 | CH$_3$ | 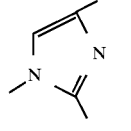 |
| 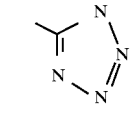 |  | CH$_3$ | 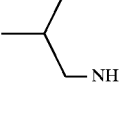 |
| 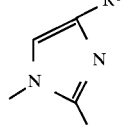 | 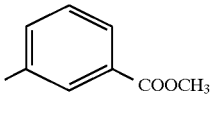 | CH$_3$ |  |
| 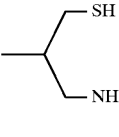 | 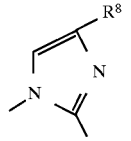 | CH$_3$ | 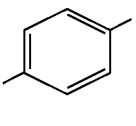 |
|  | 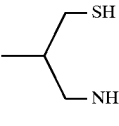 | CH$_3$ | 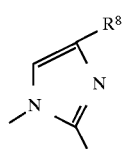 |
| 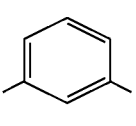 |  | CH$_3$ | 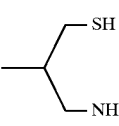 |
| 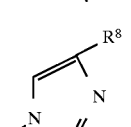 | 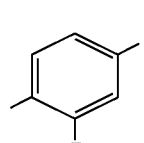 | CH$_3$ | 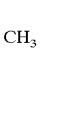 |
| 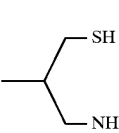 | 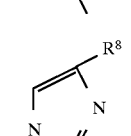 | CH$_3$ | 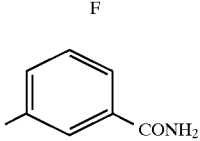 |

TABLE VI-continued
| | R⁸ | R²⁴ | R²⁵ |
|---|---|---|---|
| 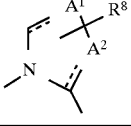 | 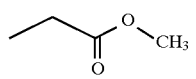 | CH₃ | 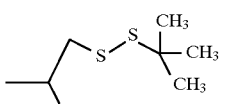 |
| 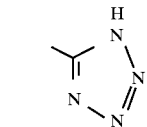 | 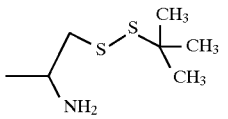 | CH₃ | 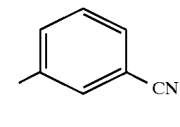 |
| 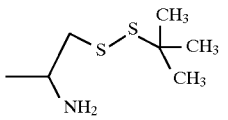 | 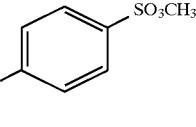 | CH₃ | 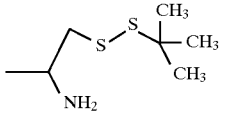 |
| 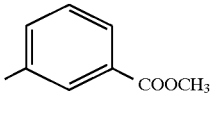 | 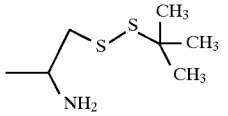 | CH₃ | 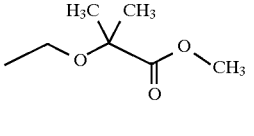 |
| 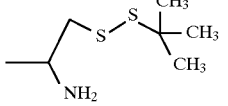 | 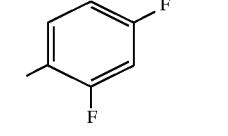 | CH₃ | 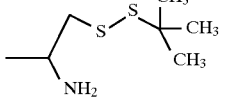 |
| 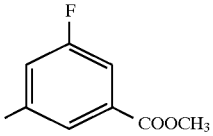 | 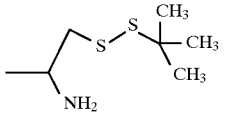 | CH₃ | 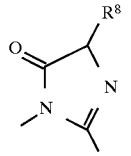 |
| 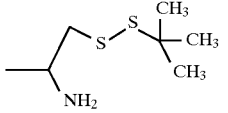 | 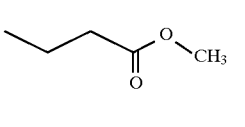 | CH₃ | 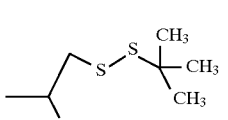 |

TABLE VI-continued

| R[8] | R[24] | R[25] |
|---|---|---|

An alternative preferred embodiment of the invention comprises a compound capable of inhibiting farnesyl:protein transferase at a concentration equal to or lower than that of the tetrapeptide CVFM represented by Formula VIII(a)

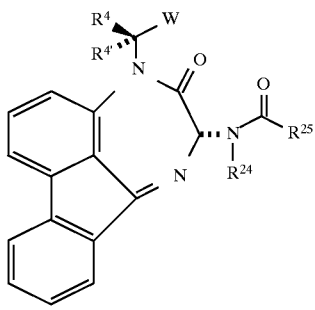

VIII(a)

where the substituent R[4] and R[4'] are hydrogen or lower alkyl, and R[24], R[25] and W are selected according to Table VIII(a).

TABLE VIII(a)

| W | R[24] | R[25] |
|---|---|---|

TABLE VIII(a)-continued

| W | R[24] | R[25] |
|---|---|---|

TABLE VIII(a)-continued

| W | R²⁴ | R²⁵ |
|---|---|---|
| (cyclohexane-COOH) | CH₃ | CH₂CH(NH₂)CH₂SH |
| (4-methylphenyl-tetrazole) | CH₃ | CH₂CH(NH₂)CH₂SH |
| (3-methylphenyl-tetrazole) | CH₃ | CH₂CH(NH₂)CH₂SH |
| (4'-methylbiphenyl-2-tetrazole) | CH₃ | CH₂CH(NH₂)CH₂SH |
| (5'-methylbiphenyl-2-tetrazole isomer) | CH₃ | CH₂CH(NH₂)CH₂SH |
| (4-methylphenyl-pyrrole-tetrazole) | CH₃ | CH₂CH(NH₂)CH₂SH |
| (6-methylpyridine, 2-(methylthio)ethyl, 3-tetrazole) | CH₃ | CH₂CH(NH₂)CH₂SH |
| (6-methylpyridine, 2-(methyldithio)methyl, 3-tetrazole) | CH₃ | CH₂CH(NH₂)CH₂SH |
| (5-methylpyrrole, 1-(methylthio)-2-yl, tetrazole) | CH₃ | CH₂CH(NH₂)CH₂SH |
| (5-methylpyrrole, 2-(methylthio)ethyl, 3-tetrazole) | CH₃ | CH₂CH(NH₂)CH₂SH |
| (5-methylthiophene, 1-(methylthio)-2-yl, tetrazole) | CH₃ | CH₂CH(NH₂)CH₂SH |
| (5-methylthiophene, 2-(methylthio)ethyl, 3-tetrazole) | CH₃ | CH₂CH(NH₂)CH₂SH |
| (5-methylfuran, 2-(methylthio)methyl) | CH₃ | CH₂CH(NH₂)CH₂SH |
| (6-methylpyridine-2-CH₂-S-S-CH₃) | CH₃ | CH₂CH(NH₂)CH₂SH |
| (6-methylpyridine-2-CH₂CH₂-S-CH₃) | CH₃ | CH₂CH(NH₂)CH₂SH |
| (pentyl-tetrazole) | CH₃ | CH₂CH(NH₂)CH₂SH |
| (methyl butanoate) | CH₃ | CH₂CH(NH₂)CH₂SH |
| (methyl pentanoate) | CH₃ | CH₂CH(NH₂)CH₂SH |
| (methyl hexanoate) | CH₃ | CH₂CH(NH₂)CH₂SH |

TABLE VIII(a)-continued

| W | R²⁴ | R²⁵ |
|---|-----|-----|
| ethoxyacetic acid methyl ester | CH₃ | 2-amino-propanethiol |
| 2-ethoxy-2-methylpropanoic acid methyl ester | CH₃ | 2-amino-propanethiol |
| 4-methyl-2-nitrophenol | CH₃ | 2-amino-propanethiol |
| 3-chlorotoluene | CH₃ | 2-amino-propanethiol |
| 2,4-difluorotoluene | CH₃ | 2-amino-propanethiol |
| 3-methylbenzaldehyde | CH₃ | 2-amino-propanethiol |
| 3-methylbenzonitrile | CH₃ | 2-amino-propanethiol |
| 4-methylbenzonitrile | CH₃ | 2-amino-propanethiol |
| methyl 3-methylbenzoate | CH₃ | 2-amino-propanethiol |
| 3-fluoro-4-methylbenzotrifluoride | CH₃ | 2-amino-propanethiol |
| 4-methylbenzaldoxime | CH₃ | 2-amino-propanethiol |
| 4-fluorotoluene | CH₃ | 2-amino-propanethiol |
| 4-methylphenyl methyl sulfone | CH₃ | 2-amino-propanethiol |
| 3-fluoro-4-methyltoluene | CH₃ | 2-amino-propanethiol |
| methyl 4-methylcyclohexanecarboxylate | CH₃ | 2-amino-propanethiol |
| 3-methylbenzamide | CH₃ | 2-amino-propanethiol |
| 3'-methylacetophenone | CH₃ | 2-amino-propanethiol |
| methyl 3-fluoro-5-methylbenzoate | CH₃ | 2-amino-propanethiol |
| 4-methyl-1-nitrobenzene | CH₃ | 2-amino-propanethiol |
| methyl acetate | CH₃ | 2-amino-3-mercapto-propanimidamide |
| ethyl acetate | CH₃ | 2-amino-3-mercapto-propanimidamide |
| methyl 4-methylbenzoate | CH₃ | 2-amino-3-mercapto-propanimidamide |
| 3-methylbenzoic acid | CH₃ | 2-amino-3-mercapto-propanimidamide |
| methyl 4'-methylbiphenyl-2-carboxylate | CH₃ | 2-amino-3-mercapto-propanimidamide |

TABLE VIII(a)-continued
| W | R²⁴ | R²⁵ |
|---|---|---|
|  | CH₃ | 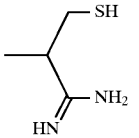 |
|  | CH₃ | 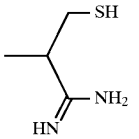 |
| 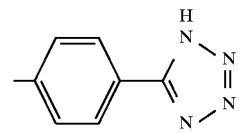 | CH₃ | 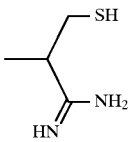 |
| 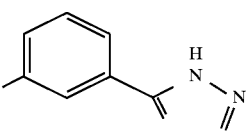 | CH₃ | 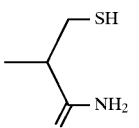 |
| 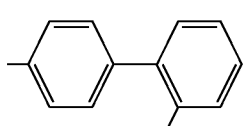 | CH₃ | 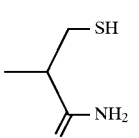 |
| 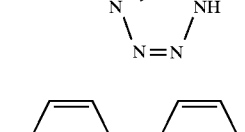 | CH₃ | 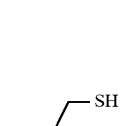 |
| 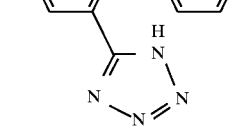 | CH₃ | 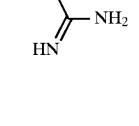 |
| 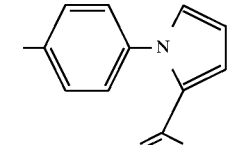 | CH₃ | 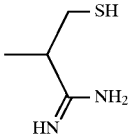 |
TABLE VIII(a)-continued
| W | R²⁴ | R²⁵ |
|---|---|---|
| 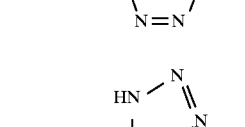 | CH₃ | 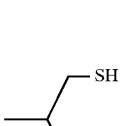 |
| 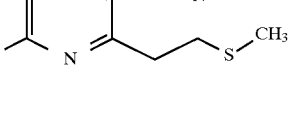 | CH₃ | 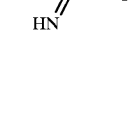 |
| 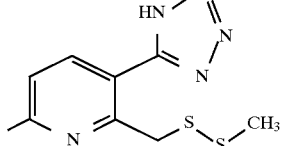 | CH₃ | 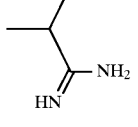 |
| 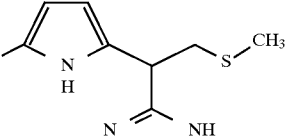 | CH₃ | 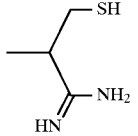 |
| 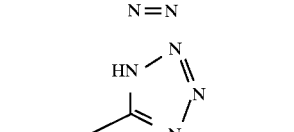 | CH₃ | 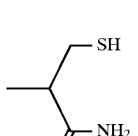 |
| 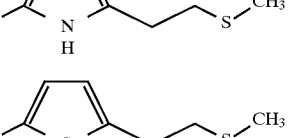 | CH₃ | 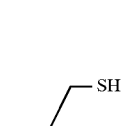 |
| 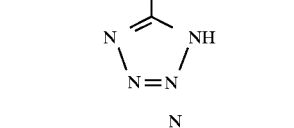 | CH₃ | 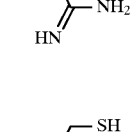 |
| 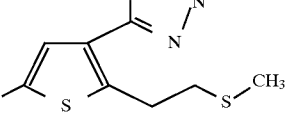 | CH₃ | 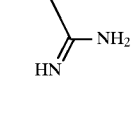 |
| 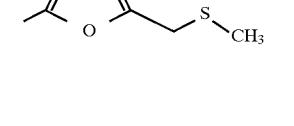 | CH₃ | 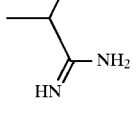 |
| 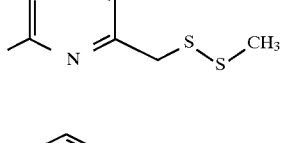 | CH₃ | 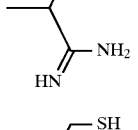 |
| 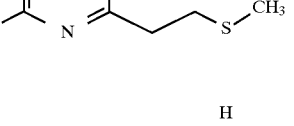 | CH₃ | 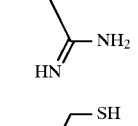 |
| 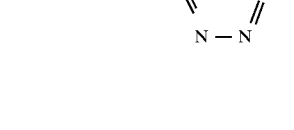 | CH₃ | 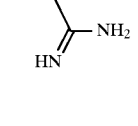 |

TABLE VIII(a)-continued

| W | $R^{24}$ | $R^{25}$ |
|---|---|---|
| methyl butanoate | $CH_3$ | 2-methyl-3-mercapto-propanimidamide |
| methyl pentanoate | $CH_3$ | 2-methyl-3-mercapto-propanimidamide |
| methyl hexanoate | $CH_3$ | 2-methyl-3-mercapto-propanimidamide |
| methyl ethoxyacetate | $CH_3$ | 2-methyl-3-mercapto-propanimidamide |
| methyl 2-ethoxy-2-methylpropanoate | $CH_3$ | 2-methyl-3-mercapto-propanimidamide |
| 4-methyl-2-nitrophenol | $CH_3$ | 2-methyl-3-mercapto-propanimidamide |
| 3-chlorotoluene | $CH_3$ | 2-methyl-3-mercapto-propanimidamide |
| 2,4-difluorotoluene | $CH_3$ | 2-methyl-3-mercapto-propanimidamide |
| 3-methylbenzaldehyde | $CH_3$ | 2-methyl-3-mercapto-propanimidamide |
| 3-methylbenzonitrile | $CH_3$ | 2-methyl-3-mercapto-propanimidamide |

TABLE VIII(a)-continued

| W | $R^{24}$ | $R^{25}$ |
|---|---|---|
| 4-methylbenzonitrile | $CH_3$ | 2-methyl-3-mercapto-propanimidamide |
| methyl 3-methylbenzoate | $CH_3$ | 2-methyl-3-mercapto-propanimidamide |
| 2-fluoro-4-(trifluoromethyl)toluene | $CH_3$ | 2-methyl-3-mercapto-propanimidamide |
| 4-methylbenzaldehyde oxime | $CH_3$ | 2-methyl-3-mercapto-propanimidamide |
| 4-fluorotoluene | $CH_3$ | 2-methyl-3-mercapto-propanimidamide |
| 4-(methylsulfonyl)toluene | $CH_3$ | 2-methyl-3-mercapto-propanimidamide |
| 3-fluoro-4-methyltoluene | $CH_3$ | 2-methyl-3-mercapto-propanimidamide |
| methyl cyclohexanecarboxylate | $CH_3$ | 2-methyl-3-mercapto-propanimidamide |
| 3-methylbenzamide | $CH_3$ | 2-methyl-3-mercapto-propanimidamide |
| 3-methylacetophenone | $CH_3$ | 2-methyl-3-mercapto-propanimidamide |

TABLE VIII(a)-continued

| W | R24 | R25 |
|---|---|---|
| 3-fluoro-5-methyl-benzoic acid methyl ester | CH3 | CH(CH3)CH2SH with C(=NH)NH2 |
| 4-methyl-nitrobenzene | CH3 | CH(CH3)CH2SH with C(=NH)NH2 |

An alternative preferred embodiment of the invention comprises a compound capable of inhibiting farnesyl:protein transferase at a concentration equal to or lower than that of the tetrapeptide CVFM represented by Formula IX(a)

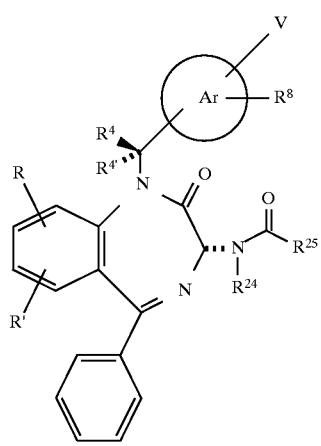

IX(a)

where the substituents R and R' are hydrogen, halo or perfluro-loweralkyl, $R^4$ is hydrogen or lower alkyl, and $R^{24}$, $R^{25}$, V, and

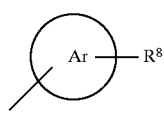

are selected according to Table IX(a).

TABLE IX(a)

| V | Ar—R8 | R24 | R25 |
|---|---|---|---|
| F | 3-V-methylphenyl | CH3 | CH(CH3)CH2SH, NH2 |
| COH | 4-V-methylphenyl | CH3 | CH(CH3)CH2SH, NH2 |

TABLE IX(a)-continued

| V | Ar—R8 | R24 | R25 |
|---|---|---|---|
| SO3CH3 | 3-V-methylphenyl | CH3 | CH(CH3)CH2SH, NH2 |
| NO2 | 4-V-methylphenyl | CH3 | CH(CH3)CH2SH, NH2 |
| COOC2H5 | 3-V-methylphenyl | CH3 | CH(CH3)CH2SH, NH2 |
| C(=O)CH3 | 3-V-methylphenyl | CH3 | CH(CH3)CH2SH, NH2 |
| N(CH3)3+ | 3-V-methylphenyl | CH3 | CH(CH3)CH2SH, NH2 |
| CN | 2-SCH3-4-methyl-V-phenyl | CH3 | CH(CH3)CH2SH, NH2 |
| tetrazolyl | 2-SCH3-4-methyl-V-phenyl | CH3 | CH(CH3)CH2SH, NH2 |
| COOCH3 | 2-SCH3-4-methyl-V-phenyl | CH3 | CH(CH3)CH2SH, NH2 |
| COOCH3 | imidazole-CH2SH methyl | CH3 | CH(CH3)CH2SH, NH2 |
| COOCH3 | 2,5-dimethyl-furan (V) | CH3 | CH(CH3)CH2SH, NH2 |
| COOCH3 | 2,5-dimethyl-thiophene (V) | CH3 | CH(CH3)CH2SH, NH2 |
| CN | 2,6-dimethyl-pyridine (V) | CH3 | CH(CH3)CH2SH, NH2 |

TABLE IX(a)-continued

| V | Ar–R⁸ | R²⁴ | R²⁵ |
|---|---|---|---|
| COOCH₃ | methylpyridine with SCH₃ | CH₃ | CH(CH₃)CH(SH)NH₂ |
| tetrazole (HN–N=N–N) | methylpyridine with SCH₃ | CH₃ | CH(CH₃)CH(SH)NH₂ |
| CH(=NOH) | phenyl-V | CH₃ | CH(CH₃)CH(SH)NH₂ |
| OH | phenyl-V | CH₃ | CH(CH₃)CH(SH)NH₂ |
| SH | phenyl-V | CH₃ | CH(CH₃)CH(SH)NH₂ |
| C(=O)CF₃ | phenyl-V | CH₃ | CH(CH₃)CH(SH)NH₂ |
| SO₃H | phenyl-V | CH₃ | CH(CH₃)CH(SH)NH₂ |
| NHCOCH₃ | phenyl-V | CH₃ | CH(CH₃)CH(SH)NH₂ |
| CONH₂ | phenyl-V | CH₃ | CH(CH₃)CH(SH)NH₂ |
| NO₂ | methylphenyl-V with SCH₃ | CH₃ | CH(CH₃)CH(SH)NH₂ |
| F | methylphenyl-V with SCH₃ | CH₃ | CH(CH₃)CH(SH)NH₂ |
| SO₃CH₃ | methylphenyl-V with SCH₃ | CH₃ | CH(CH₃)CH(SH)NH₂ |
| | imidazole with SCH₃ | CH₃ | CH(CH₃)CH(SH)NH₂ |
| F | methylfuran | CH₃ | CH(CH₃)CH(SH)NH₂ |
| CN | methylthiophene-V | CH₃ | CH(CH₃)CH(SH)NH₂ |
| COH | methylpyridine-V | CH₃ | CH(CH₃)CH(SH)NH₂ |
| CN | methylpyridine-V with SCH₃ | CH₃ | CH(CH₃)CH(SH)NH₂ |
| SO₃CH₃ | methylpyridine-V with SCH₃ | CH₃ | CH(CH₃)CH(SH)NH₂ |

An alternative preferred embodiment of the invention comprises a compound capable of inhibiting farnesyl:protein transferase at a concentration equal to or lower than that of the tetrapeptide CVFM represented by Formula X

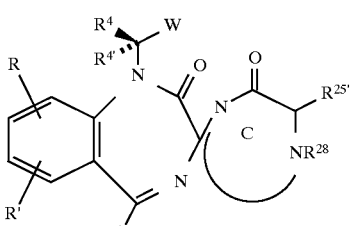

X where the substituents R and R' are halo or perfluroloweralkyl, $R^1$ is $CF_3$ or phenyl optionally substituted with halo or haloloweralkyl, $R^4$, $R^{4'}$, and $R^{28}$ are hydrogen or lower alkyl, W is aryl-V, heteroaryl-V, or —(C=O)—$NR^{7'}R^8$, $R^{25'}$ is $C_1$–$C_4$alkyl—SH or $C_1$–$C_4$alkyl—SS—$C_1$–$C_6$alkyl, and represents methylene, ethylene, or ethenylene, optionally substituted with oxo (=O), loweralkyl, or haloloweralkyl. Subgeneric prefered examples of X include;

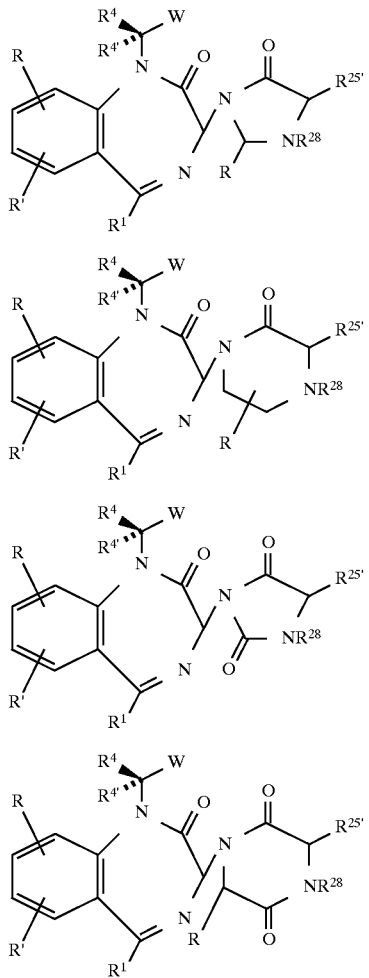

where the substituents are as described above.

Most prefered compounds of the invention indude;

N-[[3-[(2-amino-3-mercapto-1-oxopropyl)methylamino]-2,3-dihydro-2-oxo-5-phenyl-1H-1,4-benzodiazepin-1-yl]acetyl]-(α-methyl)-methionine, N-[[3-[(2-amino-3-mercapto-1-oxopropyl)methylamino]-2,3-dihydro-2-oxo-5-phenyl-1H-1,4-benzodiazepin-1-yl]acetyl]-L-valine, N-[[3-[(2-amino-3-mercapto-1-oxopropyl)methylamino]-2,3-dihydro-2-oxo-5-phenyl-1H-1,4-benzodiazepin-1-yl]acetyl]-L-threonine, N-[[3-[(2-amino-3-mercapto-1-oxopropyl)methylamino]-2,3-dihydro-2-oxo-5-phenyl-1H-1,4-benzodiazepin-1-yl]acetyl]-L-glutamine, N-[[3-[(2-amino-3-mercapto-1-oxopropyl)methylamino]-2,3-dihydro-2-oxo-5-phenyl-1H-1,4-benzodiazepin-1-yl]acetyl]-glycine, N-[[3-[(2-amino-3-mercapto-1-oxopropyl)methylamino]-2,3-dihydro-2-oxo-5-phenyl-1H-1,4-benzodiazepin-1-yl]acetyl]-L-tyrosine, N-[[3-[(2-amino-3-mercapto-1-oxopropyl)methylamino]-2,3-dihydro-2-oxo-5-phenyl-1H-1,4-benzodiazepin-1-yl]acetyl]-L-isoleucine, N-[[3-[(2-amino-3-mercapto-1-oxopropyl)methylamino]-2,3-dihydro-2-oxo-5-phenyl-1H-1,4-benzodiazepin-1-yl]acetyl]-L-tryptophan, N-[[3-[(2-amino-3-mercapto-1-oxopropyl)methylamino]-2,3-dihydro-2-oxo-5-phenyl-1H-1,4-benzodiazepin-1-yl]acetyl]-(β-cyclohexyl)-L-alanine, N-[[3-[(2-amino-3-mercapto-1-oxopropyl)methylamino]-2,3-dihydro-2-oxo-5-phenyl-1H-1,4-benzodiazepin-1-yl]acetyl]-(α-cyclohexyl)-glycine, N-[[3-[(2-amino-3-mercapto-1-oxopropyl)methylamino]-2,3-dihydro-2-oxo-5phenyl-1H-1,4-benzodiazepin-1-yl]acetyl]-L-homo-phenylalanine, N-[[3-[(2-amino-3-mercapto-1-oxopropyl)methylamino]-2,3-dihydro-2-oxo-5-phenyl-1H-1,4-benzodiazepin-1-yl]acetyl]-L-4-fluorophenylalanine, N-[[3-[(2-amino-3-mercapto-1-oxopropyl)methylamino]-2,3-dihydro-2-oxo-5-phenyl-1H-1,4-benzodiazepin-1-yl]acetyl]-(β-biphenyl)-L-alanine, N-[[3-[(2-amino-3-mercapto-1-oxopropyl)methylamino]-2,3-dihydro-2-oxo-5-phenyl-1H-1,4-benzodiazepin-1-yl]acetyl]-L-norleucine, N-[[3-[(2-amino-3-mercapto-1-oxopropyl)amino]-2,3-dihydro-2-oxo-5-phenyl-1H-1,4-benzodiazepin-1-yl]acetyl]-(N-methyl)-L-methionine, N-[[3-[(2-amino-3-mercapto-1-oxopropyl)methylamino]-2,3-dihydro-2-oxo-5-phenyl-1H-1,4-benzodiazepin-1-yl]acetyl]-(N-methyl)-L-methionine, N-[[3-[(2-amino-3-mercapto-1-oxopropyl)methylamino]-2,3-dihydro-2-oxo-5-phenyl-1H-1,4-benzodiazepin-1-yl]acetyl]-(N-methyl)-glycine, N-[[3-[(2-amino-3-mercapto-1-oxopropyl)methylamino]-2,3-dihydro-2-oxo-5-phenyl-1H-1,4-benzodiazepin-1-yl]acetyl]-(N-benzyl)-glycine, N-[[3-[($^2$-amino-3-mercapto-1-oxopropyl)methylamino]-2,3-dihydro-2-oxo-5-phenyl-7-chloro-1H-1,4-benzodiazepin-1-yl]acetyl]-L-methionine, N-[[3-[($^2$-amino-3-mercapto-1-oxopropyl)methylamino]-2,3-dihydro-2-oxo-5-phenyl-7-chloro-1H-1,4-benzodiazepin-1-yl]acetyl]-L-phenylalanine, N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-phenylalanine amide, N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-4-fluoro-phenylalanine, N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-(α-cyclohexyl)-alanine, N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-(α-cyclohexyl)-alanine amide, N-[[3-[(2-amino-3-mercapto-1-oxopropyl)methylamino]-2,3-dihydro-2-oxo-5-(2'-fluorophenyl)-7-chloro-1H-1,4-benzazepin-1-yl]acetyl]-L-methionine, N-[[3-[(2-amino-3-mercapto-1-oxopropyl)methylamino]-2,3-dihydro-2-oxo-5-(2'-chlorophenyl)-7-chloro-1H-1,4-benzodiazepin-1-yl]acetyl]-L-methionine, N-[[3-[(2-amino-3-mercapto-1-oxopropyl)methylamino]-2,3-dihydro-2-oxo-5-(2'-fluorophenyl)-7-chloro-1H-1,4-benzodiazepin-1-yl]acetyl]-L-methionine, N-[[3-[(2-amino-3-mercapto-1-oxopropyl)methylamino]-2,3-dihydro-2-oxo-5-phenyl-7-chloro-1H-1,4-benzazepin-1-yl]acetyl]-L-methionine, N-[[3-[(2-amino-3-mercapto-1-oxopropyl)methylamino]2,3-dihydro-2-oxo-5-(2'-chlorophenyl)-7-chloro-1H-1,4-benzazepin-1-yl]acetyl]-L-methionine, N-[[3-[(2-amino-3-mercapto-1-oxopropyl)methylamino]-2,3-dihydro-2-oxo-5-phenyl-1H-1,4-benzodiazepin-1-yl]methyl]-3-cyanobenzene, N-[[3-[(2-amino-3-mercapto-1-oxopropyl)methylamino]-2,3-dihydro-2-oxo-5-phenyl-1H-1,4-benzodiazepin-1-yl]methyl]-3-carboxymethylbenzene, N-[[3-[(2-amino-3-mercapto-1-oxopropyl)methylamino]-2,3-dihydro-2-oxo-5-phenyl-1H-1,4-benzodiazepin-1-yl]methyl]-3-carboxybenzene, N-[[3-[(2-amino-3-mercapto-1-oxopropyl)methylamino]-2,3-dihydro-2-oxo-5-phenyl-1H-1,4-benzodiazepin-1-yl]methyl]-3-tetrazolylbenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-benzene, N-[[³-[(2-amino-3-mercapto-1-oxopropyl)methylamino]-2,3-dihydro-2-oxo-5-phenyl-7-chloro-1H-1,4-benzodiazepin-1-yl]methyl]-4-fluorobenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-trifluoromethylbenzene, N-[[3-[(2-amino-3-mercapto-1-oxopropyl)methylamino]-2,3-dihydro-2-oxo-5-phenyl-7-chloro-1H-1,4-benzodiazepin- 1 -yl]methyl]-4-nitrobenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-benzonitrile, N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-chlorobenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-bromobenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-2,4-difluorobenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-3-carboxymethylbenzene, N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-(2-tetrazolylphenyl)benzene, N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]methyl]-3-carboxymethylbenzene, N-[[3-[(2-methylthiazolidine-4-carboxyl)methylamino]-2,3-dihydro-2-oxo-5-phenyl-7-chloro-1H-1,4-benzodiazepin-1-yl]methyl]-3-carboxymethylbenzene, N-[[3-[(2-methylthiazolidine-4-carboxyl)methylamino]-2,3-dihydro-2-oxo-5-phenyl-1H-1,4-benzodiazepin-1-yl]acetyl]-L-methionine ethyl ester, N-[[3-[(2-amino-3-tert-butylthiomercapto-1-oxopropyl)methylamino]-2,3-dihydro-2-oxo-5-phenyl-1H-1,4-benzodiazepin-1-yl]acetyl]-L-methionine methyl ester, N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-methionine cyclohexyl ester, N-[[3-[(2-amino-3-tert-butylthiomercapto-1-oxopropyl)methylamino]-2,3-dihydro-2-oxo-5-phenyl-1H,4benzodiazepin-1-yl]acetyl]-L-methionine cyclohexyl ester, N-[[3-[(2-amino-3-tert-butylthiomercapto-1-oxopropyl)methylamino]-2,3-dihydro-2-oxo-5-(2'-fluorophenyl)-7-chloro-1H-1,4-benzazepin-1-yl]acetyl]-L-methionine cyclohexyl ester, N-[[3-[(2-amino-3-tert-butylthiomercapto-1-oxopropyl)methylamino]-2,3-dihydro-2-oxo-5-phenyl-7-chloro-1H-1,4-benzazepin-1-yl]acetyl]-L-leucine tetrazole, N-[[3-[(2-amino-3-tert-butylthiomercapto-1-oxopropyl)methylamino]-2,3-dihydro-2-oxo-5-phenyl-7-chloro-1H-1,4-benzazepin-1-yl]acetyl]-L-phenylalanine amide, N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-methionine tetrazole, N-[[3-[(2-amino-3-tert-butylthiomercapto-1-oxopropyl)methylamino]-2,3-dihydro-2-oxo-5-phenyl-1H-1,4-benzodiazepin-1-yl]acetyl]-L-phenylalanine cyclohexyl ester, N-[[3-[(2-amino-3-tert-butylthiomercapto-1-oxopropyl)methylamino]-2,3-dihydro-2-oxo-5-phenyl-1H-1,4-benzodiazepin-1-yl]acetyl]-L-methionine tert-butyl ester, N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-phenylalanine tetrazole, N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-phenylalanine cyclohexyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-methionine cyclohexyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-methionine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-methionine morpholino-N-ethyl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-methionine ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-methionine methyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-methionine cholesteryl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-methionine isobutyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-leucine cyclohexyl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-leucine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-leucine morpholino-N-ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-leucine ethyl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-leucine methyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-leucine cholesteryl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-leucine isobutyl ester, N-[[3-(2-Amino-3-mercapto-1-oxopropyl) methylarnino]-2,3-dihydro-2-oxo-5-phenyl-1H-1, 4benzodiazepin-1-yl] acetyl]-(D or L)-phenylalanine cyclohexyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-phenylalanine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-phenylalanine morpholino-N-ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-phenylalanine ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-phenylalanine methyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-phenylalanine cholesteryl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-phenylalanine isobutyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-isoleucine cyclohexyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-isoleucine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-isoleucine morpholino-N-ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-isoleucine ethyl ester, N-[[3-(2-Amio-3-mercapto-1-oxopropyl) methylamino]-2,3-dihydro-2-oxo-5-phenyl-1H-1, 4-benzodiazepin-1-yl] acetyl]-(D or L)-isoleucine methyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-isoleucine cholesteryl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-isoleucine isobutyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-norleucine cyclohexyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-norleucine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-norleucine morpholino-N-ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-norleucine ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-norleucine methyl ester, N-[[3-(2-Amino-3-mercapto-1-oxopropyl) methylamino]-2,3dihydro-2-oxo-5-phenyl-1H-1, 4-benzodiazepin-1-yl] acetyl]-(D or L)-norleucine cholesteryl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-norleucine isobutyl ester, N-[[3-(2-Amino-3-mercapto-1-oxopropyl) methylamino]-2,3dihydro-2-oxo-5-phenyl-1H-1, 4-benzodiazepin-1-yl] acetyl]-(D or L)-valine cyclohexyl ester, N-[[$^3$-(2-Amino-3-mercapto-1-oxopropyl) methylamino]-2,3-dihydro-2-oxo-5-phenyl-1H-1, 4-benzodiazepin-1-yl] acetyl]-(D or L)-valine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-valine morpholino-N-ethyl ester, N-[[$^3$-($^2$-Amino-3-mercapto-1-oxopropyl) methylamino]-2,3-dihydro-2-oxo-5-phenyl-1H-1, 4-benzodiazepin-1-yl] acetyl]-(D or L)-valine ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-valine methyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-valine cholesteryl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-valine isobutyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tyrosine cyclohexyl ester, N-[[3-($^2$-Amino-3-mercapto-1-oxopropyl) methylamino]-2,3-dihydro-2-oxo-5-phenyl-1H-1, 4-benzodiazepin-1-yl] acetyl]-(D or L)-tyrosine isopentyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tyrosine morpholino-N-ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tyrosine ethyl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-tyrosine methyl ester, N-[[3-(2-Amino-3-mercapto-1-oxopropyl) methylamino]-2,3-dihydro-2-oxo-5-phenyl-1H-1, 4benzodiazepin-1-yl] acetyl]-(D or L)-tyrosine cholesteryl ester, N-[[3-(2-Amino-3mercapto-1-oxopropyl) methylamino]-2,3-dihydro-2-oxo-5-phenyl-1H-1, 4benzodiazepin-1-yl] acetyl]-(D or L)-tyrosine isobutyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tryptophan cyclohexyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tryptophan isopentyl ester, N-[[$^3$-($^2$-Amino-3-mercapto-1-oxopropyl) methylamino]-2,3-dihydro-2-oxo-5-phenyl-1H-1, 4-benzodiazepin-1-yl] acetyl]-(D or L)-tryptophan morpholino-N-ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tryptophan ethyl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tryptophan methyl ester, N-[3-(2-Amino-3-mercapto-1-oxopropyl) methylamino]-2,3-dihydro-2-oxo-5-phenyl-1H-1, 4benzodiazepin-1-yl] acetyl]-(D or L)-tryptophan cholesteryl ester, N-[[3-(2-Amino-3-mercapto-1-oxopropyl) methylamino]-2,3-dihydro-2-oxo-5-phenyl-1H-1, 4-benzodiazepin-1-yl] acetyl]-(D or L)-tryptophan isobutyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-methionine cyclohexyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-methionine isopentyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-methionine morpholino-N-ethyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-methionine ethyl ester, N-[[3-(2-Amino-3-ethylthiomercapt-1-oxopropyl) methylamino]-2,3-dihydro-2-oxo-5-phenyl-1H-1, 4-benzodiazepin-1-yl] acetyl]-(D or L)-methionine methyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-methionine cholesteryl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-methionine isobutyl ester, N-[[3-(2-Amino-3-ethylthiomercapto-1-oxopropyl) methylamino]-2,3-dihydro-2-oxo-5-phenyl-1H-1,4benzodiazepin-1-yl] acetyl]-(D or L)-leucine cyclohexyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-leucine isopentyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-leucine morpholino-N-ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-leucine ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-leucine methyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-leucine cholesteryl ester, N-[[3-(2-Amino-3-ethylthiomercapto-1-oxopropyl) methylamino]-2,3-dihydro-2-oxo-5-phenyl-1H-1,4-benzodiazepin-1-yl]acetyl]-(D or L)-leucine isobutyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine cyclohexyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine isopentyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine morpholino-N-ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine methyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine cholesteryl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-phenylalanine isobutyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine cyclohexyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine isopentyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine morpholino-N-ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine methyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine cholesteryl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-isoleucine isobutyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine cyclohexyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine isopentyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine morpholino-N-ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine methyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine cholesteryl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-norleucine isobutyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-valine cyclohexyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-valine isopentyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-valine morpholino-N-ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-valine ethyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-valine methyl ester, N-[[3-(2-Amino-3-ethylthiomercapto-1-oxopropyl) methylamino]-2,3-dihydro-2-oxo-5-phenyl-1H-1,4-benzodiazepin-1-yl] acetyl]-(D or L)-valine cholesteryl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-valine isobutyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tyrosine cyclohexyl ester, N-[[3-(2-Amino-3-ethylthiomercapto-1-oxopropyl) methylarnino]-2,3-dihydro-2-oxo-5-phenyl-1H-1, 4-benzodiazepin-1-yl] acetyl]-(D or L)-tyrosine isopentyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tyrosine morpholino-N-ethyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tyrosine ethyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tyrosine methyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tyrosine cholesteryl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tyrosine isobutyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tryptophan cyclohexyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tryptophan isopentyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tryptophan morpholino-N-ethyl ester, N-[[3-(2-Amino-3-ethylthiomercapto-1-oxopropyl) methylaminol-2,3-dihydro-2-oxo-5-phenyl-1H-1, 4-benzodiazepin-1-yl] acetyl]-(D or L)-tryptophan ethyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tryptophan methyl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tryptophan cholesteryl ester, N-[[3-(2-Amino-3-ethylthiomercapto-1-oxopropyl) methylamino]-2,3-dihydro-2-oxo-5-phenyl-1H-1, 4-benzodiazepin-1-yl] acetyl]-(D or L)-tryptophan isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-methionine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-methionine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-methionine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-methionine ethyl ester, N-[[3-(2-Amino-3-tert-butylthiomercapto-1-oxopropyl) methylarnino]-2,3-dihydro-2-oxo-5-phenyl-1H-1, 4-benzodiazepin-1-yl] acetyl]-(D or L)-methionine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-methionine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-methionine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-eucine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-leucine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-leucine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-leucine ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-leucine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-leucine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-leucine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-phenylalanine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-isoleucine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-norleucine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-valine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrosine cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrosine isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrosine morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrosine ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrosine methyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrbsine cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tyrosine isobutyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tryptophan cyclohexyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tryptophan isopentyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tryptophan morpholino-N-ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tryptophan ethyl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tryptophan methyl ester, N-[[3-(2-Amino-3-tert-butylthiomercapto-1-oxopropyl) methylaminol-2,3-dihydro-2-oxo-5-phenyl-1H-1, 4-benzodiazepin-1-yl] acetyl]-(D or L)-tryptophan cholesteryl ester, N-[[3-(2-Amino-3-tert-butylthiomercapto-1-oxopropyl) methylamino]-2,3-dihydro-2-oxo-5-phenyl-1H-1, 4-benzodiazepin-1-yl] acetyl]-(D or L)-tryptophan isobutyl ester, N-[[3(S)-3-(2-Amino-3-mercapto-1-oxopropyl) methylamino]-2,3,4,5-tetrahydro-2-oxo-1H-1-benzazepin-1-yl] acetyl]-L-methionine cyclohexyl ester, N-[[3(S)-3-(2-Amino-3-mercapto-1-oxopropyl) methylanino]-2,3,4,5-tetrahydro-2-oxo-1H-1-benzazepin-1-yl] acetyl]-L-methionine isopenyl ester, N-[[3(S)-3-(2-Amino-3-mercapto-1-oxopropyl) methylamino]-2,3,4,5-tetrahydro-2-oxo-1H-1-benzazepin-1-yl] acetyl]-L-methionine morpholinoethyl ester, N-[[3(S)-3-(2-Amino-3-mercapto-1-oxopropyl) methylamino]-2,3,4,5-tetrahydro-2-oxo-1H-1-benzazepin-1-yl] acetyl]-L-methionine ethyl ester, N-[[3(S)-3-(2-Amino-3-mercapto-1-oxopropyl) methylamino]-2,3,4,5-tetrahydro-2-oxo-1H-1-benzazepin-1-yl] acetyl]-L-methionine methyl ester, N-[[3(S)-3-(2-Amino-3-mercapto-1-oxopropyl) methylamino]-2,3,4,5-tetrahydro-2-oxo-1H-1-benzazepin-1-yl] acetyl]-L-methionine cholesteryl ester, and N-[[3(S)-3-(2-Amino-3-mercapto-1-oxopropyl) methylamino]-2,3,4,5-tetrahydro-2-oxo-1H-1-benzazepin-1-yl] acetyl]-L-methionine isobutyl ester.

D. Methods of Making

In the schemes and examples below, the following standard abbreviations are employed.

ABBREVIATIONS

ACN acetonitrile
Boc or BOC tert-butyloxycarbonyl
BOP benzotriazolyloxy-trisdimethylamino-phosphonium hexafluorophosphate
Cbz carbobenzoxy
DCC dicyclohexylcarbodiimide
DCM dichloromethane
DEAD diethylazodicarboxylate
DIPC diisopropylcarbodiimide
DIPEA diisopropylethylamine
DMA dimethylacetamide.
DMAP dimethylaminopyridine
DMEM Dulbecco's modified essential media
DMF dimethylformamide
DMSO dimethylsulfoxide
DTT dithiothreitol
EDC 1-(3-dimethylaminopropyl)-3-ethylcarbodiimide hydrochloride
EtN(iPr)$_2$ diisopropylethylamine
Fmoc or FMOC fluorenylmethyloxycarbonyl
HOBt N-hydroxybenzotriazole
HPLC high pressure liquid chromatography
LDA lithium diisopropylamine
MBHA methylbenzhydryamine
NMM N-methylmorpholine
NMP 1-methyl-2-pyrrolidinone
Ph$_3$P triphenylphosphine
PyBrOP bromo-tri-pyrrolidinophosphoniumhexafluorophosphate
SPPS solid phase peptide synthesis
t-BuO$_2$C tert-butoxycarbonyl
TFA trifluoroacetic acid
THF tetrahydrofuran General methods of synthesis of the compounds of this invention are shown in Schemes I-XIV. Compounds bearing a 3-amino substituent in the benzodiazepine ring are synthesized as shown in Schemes I–III. Typically, a triply convergent route is employed, which joins the key intermediates 9 or 10 (Scheme I) with suitably functionalized amine and carboxyl components (Schemes II and III) using standard amide bond-forming procedures.

As shown in Scheme I, the protected amino acids 9 and 10 may be prepared from a suitably substituted 2-aminobenzophenone (1). Many 2-aminobenzophenones are known in the art or are available from commercial sources such as Aldrich Chemical Co. General methods for the synthesis of new 2-aminobenzophenones may be found in the literature (c.f. Walsh, D. A. *Synthesis,* 1980, 677–688).

SCHEME 1

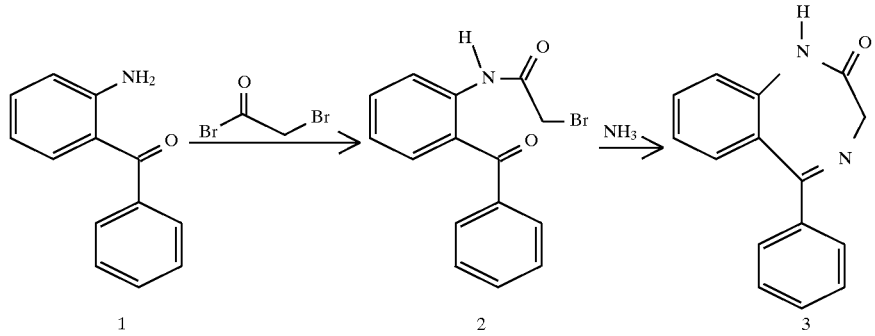

-continued
SCHEME 1

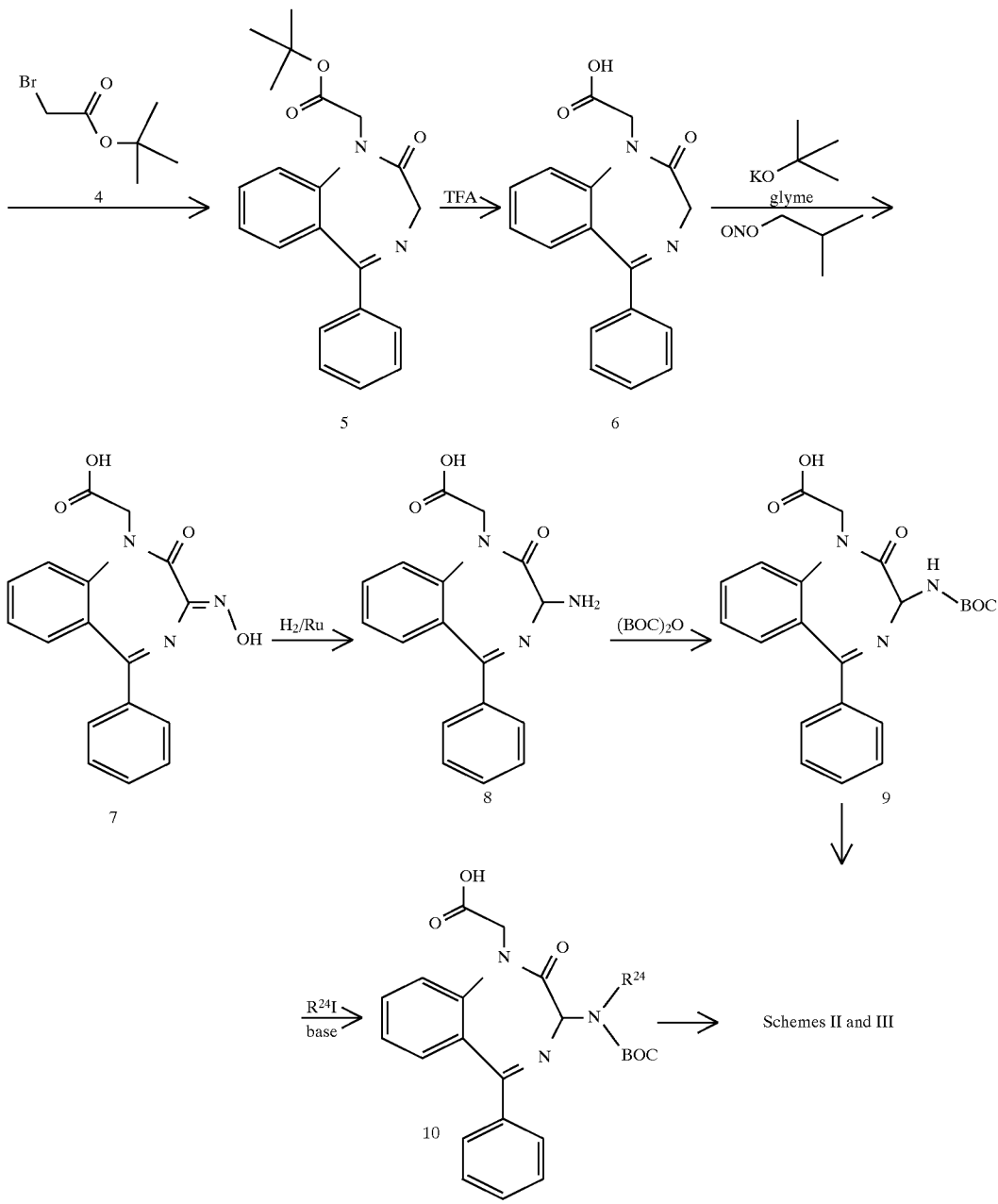

Acylation of 1 with a haloacetyl halide, such as bromoacetyl bromide in a suitable solvent mixture, such as water/$CH_2Cl_2$, typically at temperatures ranging from 0° C. to 25° C., produces amide 2. Reaction of 2 with ammonia in a polar solvent such as methanol at 25° to 75° C. then gives the 1,4-benzodiazepin-2-one 3, after evaporation of the solvent. Alkylation of 3 with a substituted organic ester (4), preferably tert-butyl bromoacetate, in the presence of a base, preferably $Cs_2CO_3$ in 1-methyl-2-pyrrolidinone at ambient temperature, gives 5. Alternatively, 3 may be alkylated at N-1 with a variety of other alkylating agents, for instance, esters of substituted or unsubstituted acrylates, 4-bromobutanoates, etc. Branched compounds (i.e. $R^4$ and/ or $R^{4'}$ ≠ H), may be prepared by generation of the polyanion of 5 with base and alkylation with an appropriate alkyl halide. Subsequent to alkylation, the ester of 5 may be cleaved with an acid such as TFA (for the tert-butyl esters) or under mild aqueous base hydrolysis (for other alkyl esters) at temperatures between 0° and 25 ° C.

The acid 6 is converted to amino add 8 via reaction of the dianion, generated with at least two equivalents of a strong base with an electrophilic aminating agent. Alternatively, 6 may be halogenated and reacted with an amine source such as azide (followed by reduction) or ammonia. Preferably, 6 is reacted with 4 equivalents of potassium tert-butoxide in glyme at −5° C. for 30 min and treated with 1.1 equivalents of isobutyl nitrite. The resulting oxime 7 can then be reduced to the racemic amino acid 8 using a variety of reductants, preferably hydrogenation at 40 psig in the presence of Ruthenium on carbon or Raney nickel in methanol at 50° to 70° C. for 1–4 days.

Amino acid 8 is then suitably protected for selective coupling at the carboxyl terminus. For example, 8 can be converted to the N—BOC derivitive 9 using standard amino acid protection conditions, preferably, reaction with equimolar amounts of di-tert-butyl dicarbonate and triethyl amine in DMF/water at ambient temperature.

For compounds where $R^{24} \neq H$, 9 can be alkylated at nitrogen with a wide variety of alkylating agents including n-alkyl, branched alkyl, and benzyl, according to the standard procedure of Benoiton, et al., Can. J. Chem. 1977, 55, 906. For example, reaction of 9 with at least 2 equivalents of base and an alkylating agent in a polar, aprotic solvent at 0° to 50 ° C. for 0.5 to 48 h gives 10. Preferably, reaction with 3 equivalents of sodium hydride and 4 equivalents of methyl iodide in THF at −5° to 5 ° C. gives 10 ($R^{24}$=Me).

Compounds 9 and 10 can be further elaborated according to Schemes II and III. In general, the carboxylic acid function of 9 and 10 is reacted with a suitably protected amine component using standard solid phase (Scheme II) or solution phase (Scheme III) peptide synthesis procedures. The BOC or other protecting group on N-3 of the benzodiazapinone is removed and the amine function then coupled with a third component, for example, a suitably protected amino acid, and then deprotected, again employing standard procedures. The resulting product is subsequently purified by chromatography or crystallization.

SCHEME II

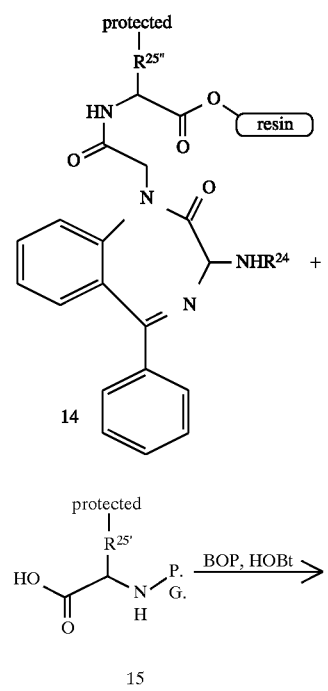

-continued
SCHEME II

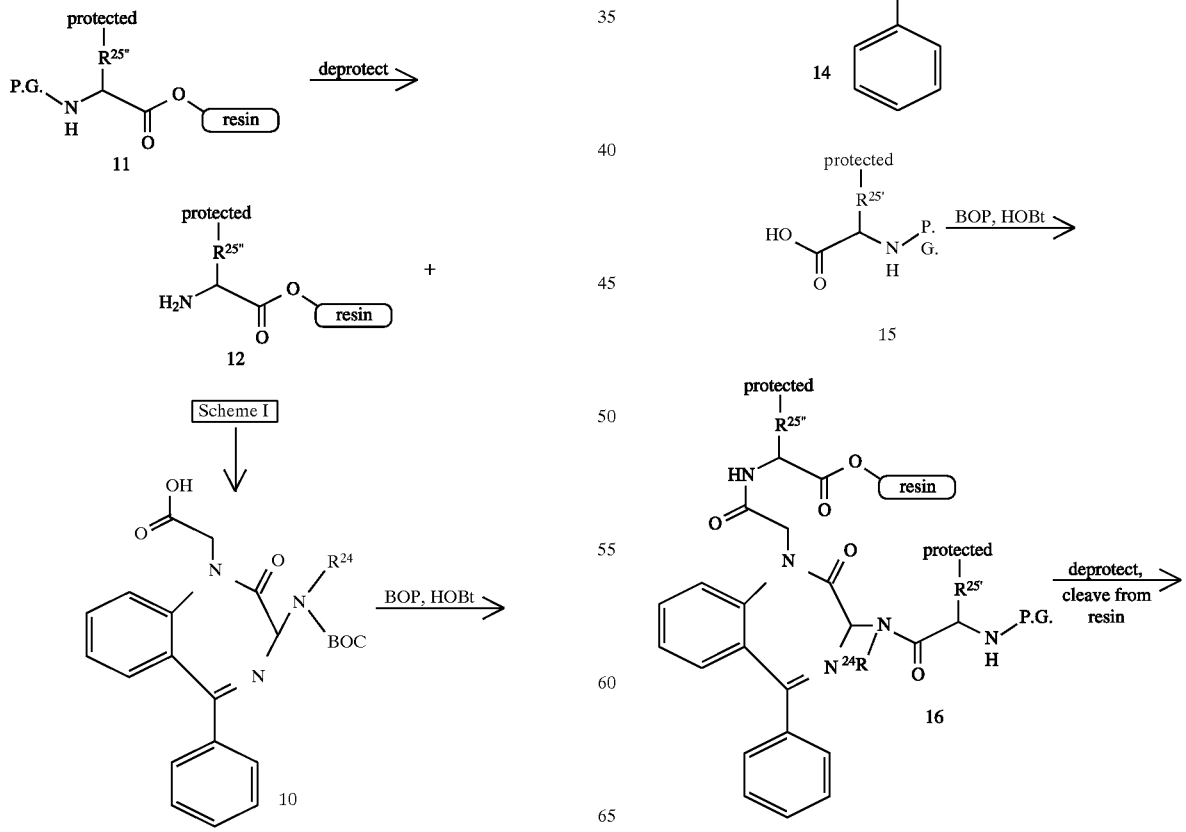

SCHEME II -continued
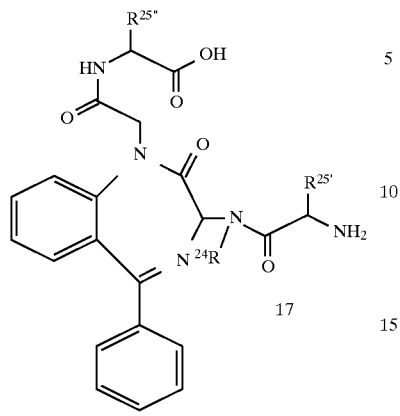
Once fully deprotected, compounds of the type 17 and 23, and salts thereof, may be further modified at the carboxy and/or amino terminus by esterification or acylation, respectively, employing standard procedures.
SCHEME III
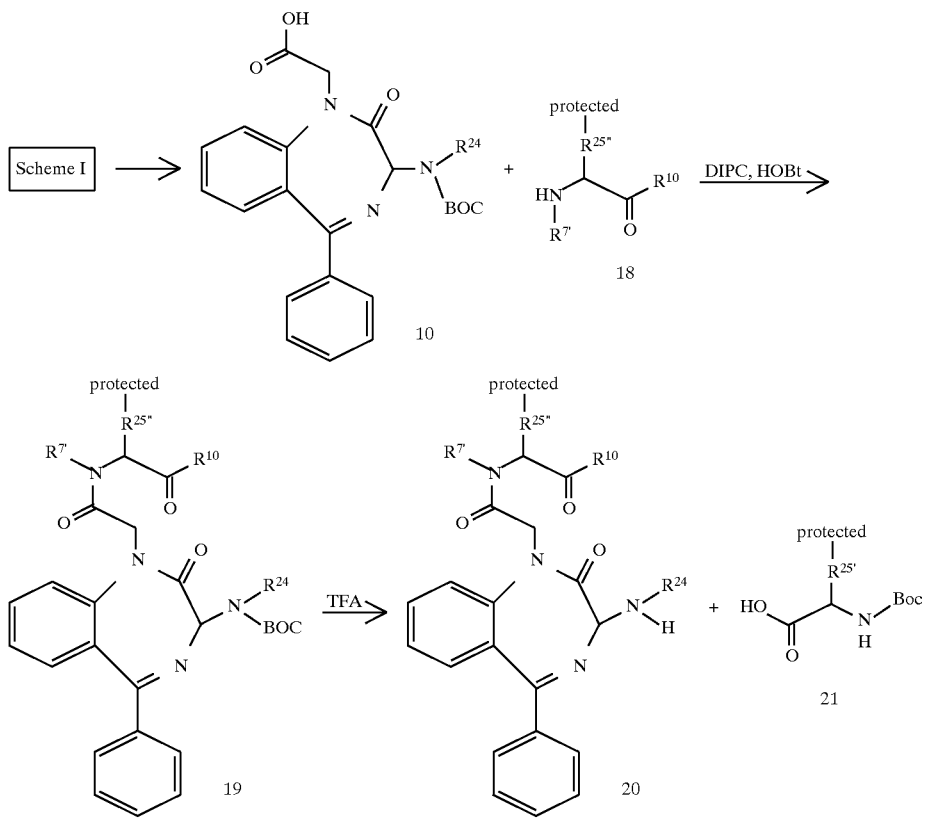

-continued
SCHEME III

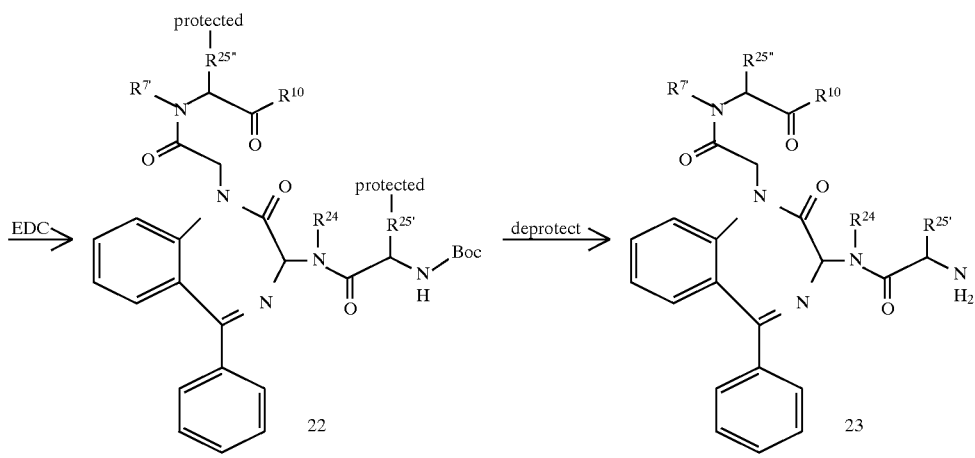

The synthesis of a second class of compounds of this invention is shown in Scheme IV. Acylation of the 2-aminobenzophenones 1 with an N-protected (preferably BOC) amino acid using DCC or the mixed anhydride method gives 25. A wide variety of protected amino acids 24 may be used in this reaction, including side chain protected natural amino acids (both D and L), substituted phenyl glycines, thiolysine, and the variety of synthetic, non-natural amino acids known to one skilled in the art (see e.g. U.S. Pat. No. 5,120,859, WO 93/04081 and 37 CFR 1.822(b)(2) and 1.822(p)(2)). Preferably, the side chain functions of the amino acid are protected orthogonally to the alpha-amine to facilitate selective deprotection. Treatment of the deblocked compound with base, preferably in methanol, gives the 3-substituted benzodiazepin-2-one 26. Alkylation at N-1 with a substituted ester as described for 3 (Scheme I) gives 7 which is deprotected and coupled to a protected amino acid using standard procedures to afford 29. Final deblocking of the side chain protecting groups and purification gives 30.

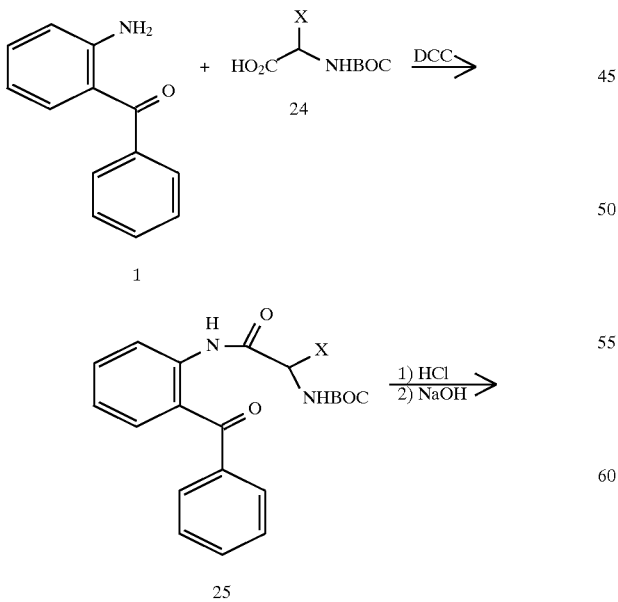

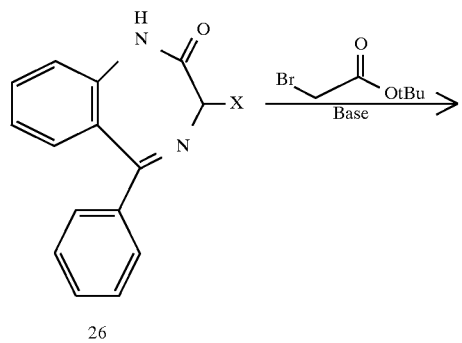

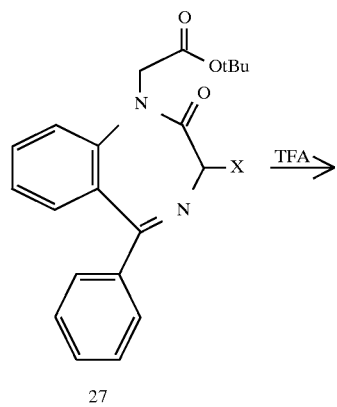

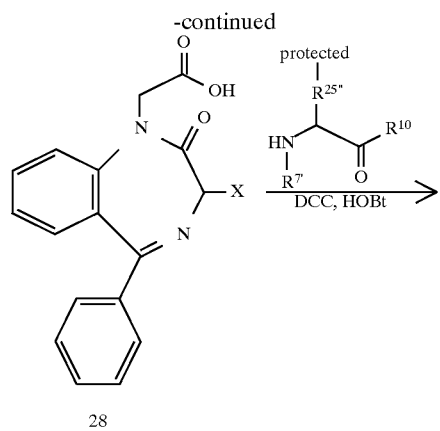

28

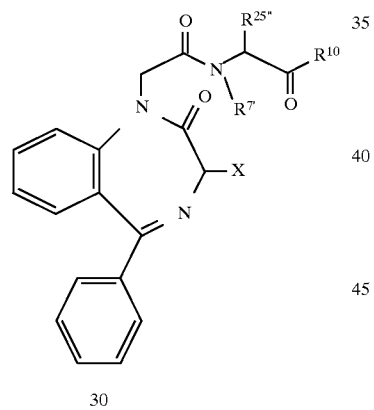

29

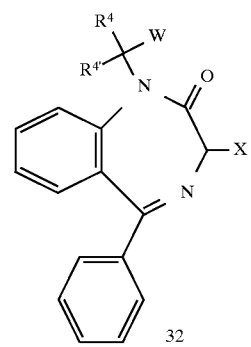

30

Alternatively, 26 may be directly alkylated with the "top" sidechain in one intact piece, as shown in Scheme V. Reaction of 26 with an alkyl halide such as a suitably substituted benzyl bromide, alkyl bromide, in the presence of a base, preferably NaH or $Cs_2CO_3$, gives 31. Deprotection under standard conditions and purification affords 32.

SCHEME V

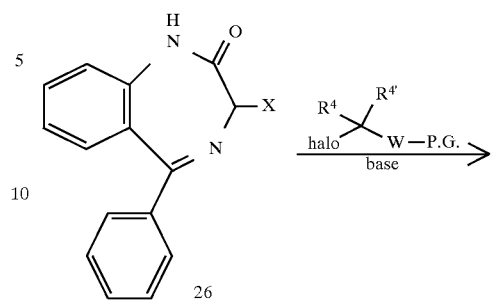

26

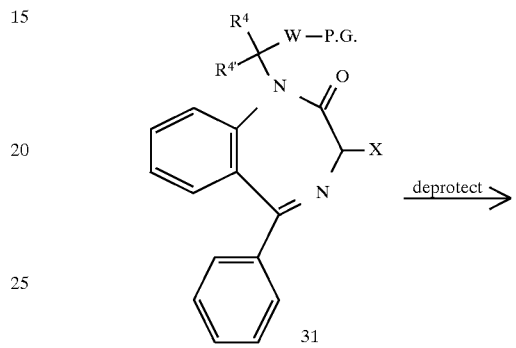

31

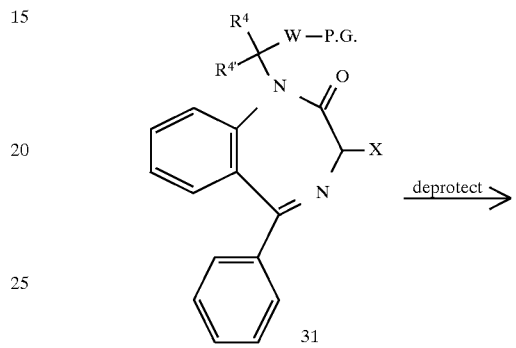

32

When the amino acid side chain of 32 is that of serine, futher manipulation is possible as described in Scheme VI. Deprotection of the hydroxyl function gives free alcohol 34 which can be alkylated or acylated at oxygen to give 35 using standard ether synthesis or acylation procedures. Compounds of the type 32, with the side chain of cysteine are treated in an analogous fashion to 33.

Alternatively, 34 may be converted to amine 36 under Mitsunobu conditions, preferably using $Ph_3P$, diethyl azodicarboxylate (DEAD), and $HN_3$. Reduction of the resulting azide, preferably by hydrogenation over Pd/C, gives amine 36. 36 is then alkylated or acylated to give 37 and 38, respectively, after deprotection and purification.

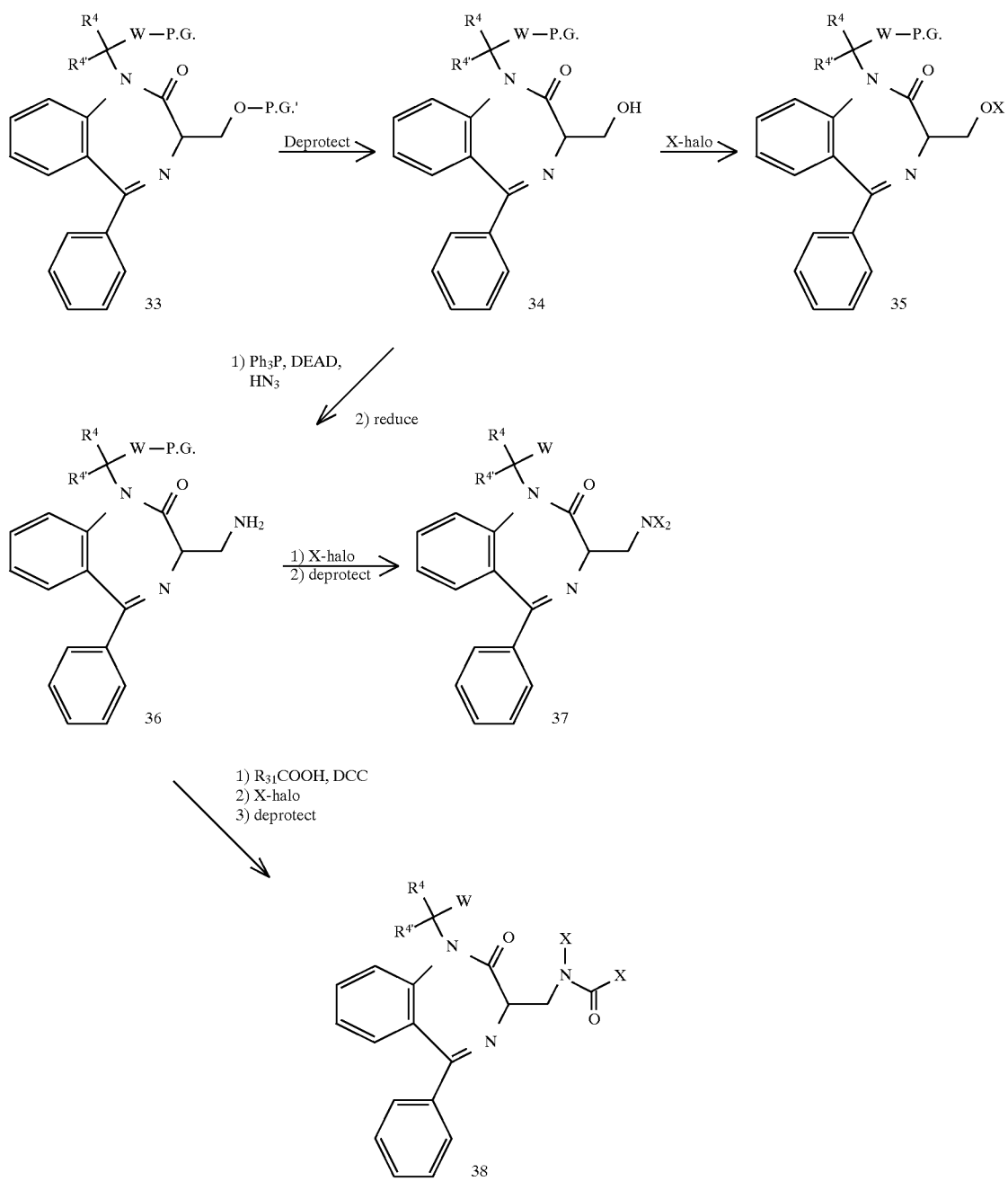

SCHEME VI

For compounds 32, with the side chains derived from aspartic or glutamic acids, further modification is carried out as per Scheme VII. Thus, selective removal of the side chain ester function, preferably benzyl or lower alkyl, using appropriate conditions, preferably aqueous NaOH, gives the free acid. Coupling to a second amine component, such as 2-mercaptoethyl amine, using standard conditions, preferably DCC, gives the protected amide which is fully deprotected and purified to afford 40.

SCHEME VII

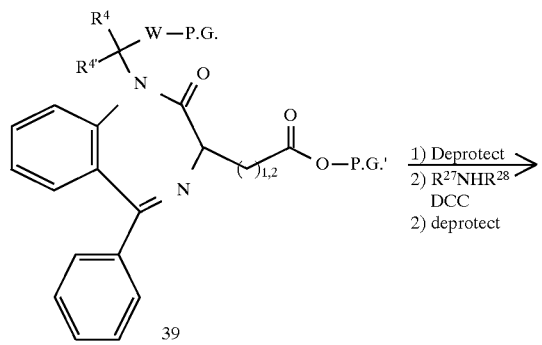

39

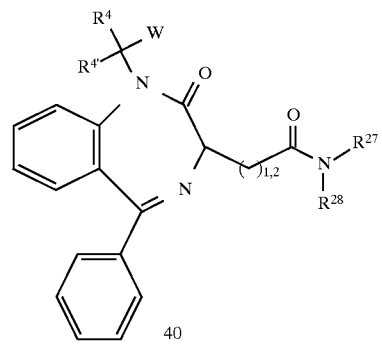

40

Another variety of compounds which are the subject of this invention are synthesized as shown in Scheme VIII. Alkylation at N-1 of benzodiazepinone 3 (as described for 31, Scheme V) gives 41. This alkylation may, for example, be conducted with any halo substituted loweralkyl, loweralkylaryl, or loweralkylheterocycle (—CR$^4$R$^{4'}$—W— in Scheme VIII). The alkyl, aryl, or heterocycle moieties may be substituted with protected (-P.G.) carboxyls, tetrazoles, thiols, etc, or precursors of these groups (e.g. nitriles for tetrazoles, etc.). Deprotonation at C-3 of the heterocycle, preferably with LDA in THF at less than 50° C., gives anion 42 which can be reacted with a variety of electrophiles. For example, reaction with substituted aldehydes, active esters, and alkyl halides gives, after deprotection and purification, products 43, 44, and 45, respectively.

SCHEME VIII

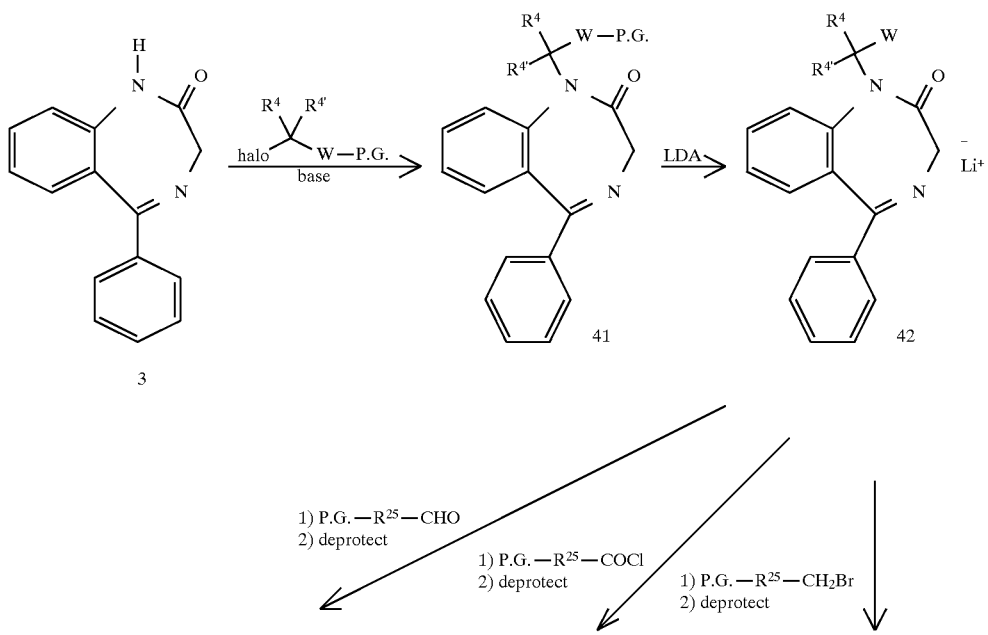

-continued
SCHEME VIII

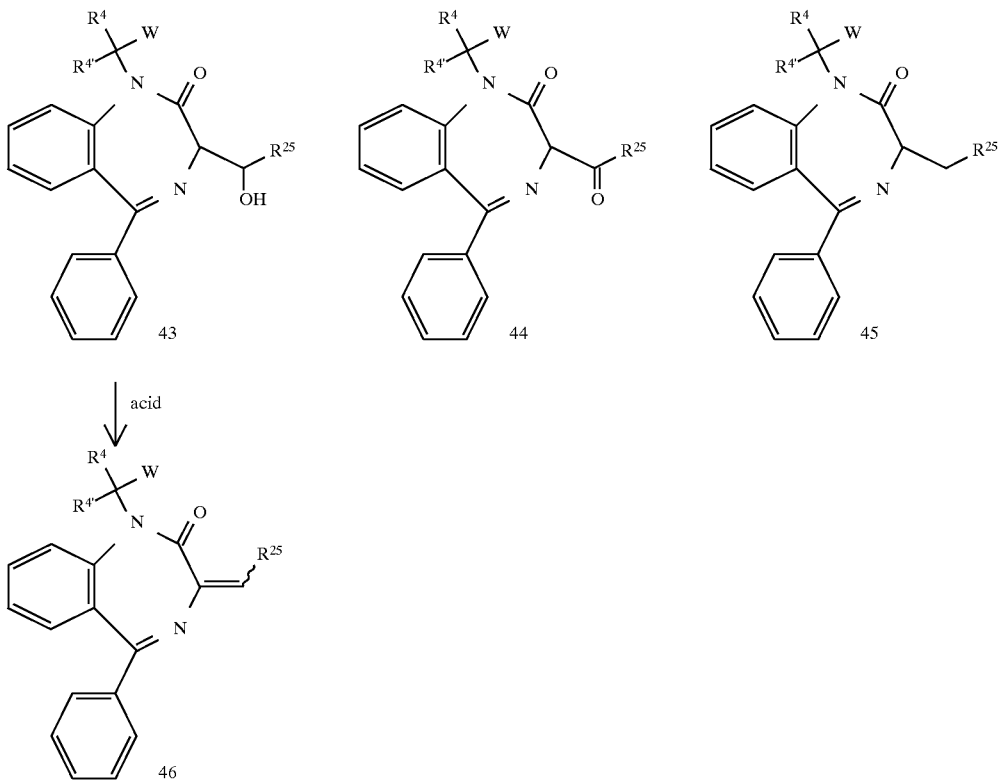

In cases where the starting materials are optically active, the chirality at C-3 of the benzodiazepinone is controlled by the starting materials. When racemic starting materials are employed, diastereomeric products are obtained. The diastereomers may be separated by chromatography.

Benzodiazepines of the instant invention with a spiro linkage at C-3 may be made according to Scheme IX. The C-3 amine is first coupled to a 9-phenylfluorenyl protected amino acid to give 48, followed by reaction with a dihalo substituted alkane in base to give 49. The 9-phenylfluorenyl group is then replaced with BOC and the resulting compound 50 is reacted with an immobilized free amine (e.g. compound 12, Scheme II) in a solid phase synthesis procedure.

SCHEME IX

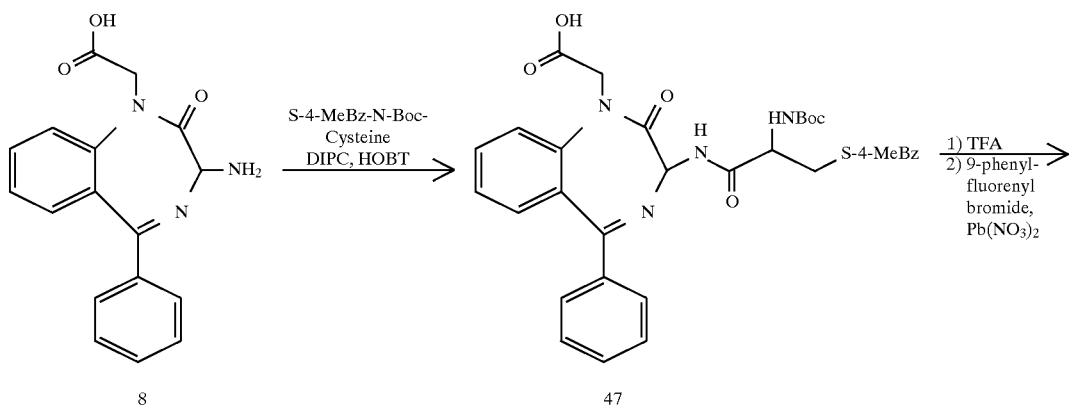

-continued
SCHEME IX
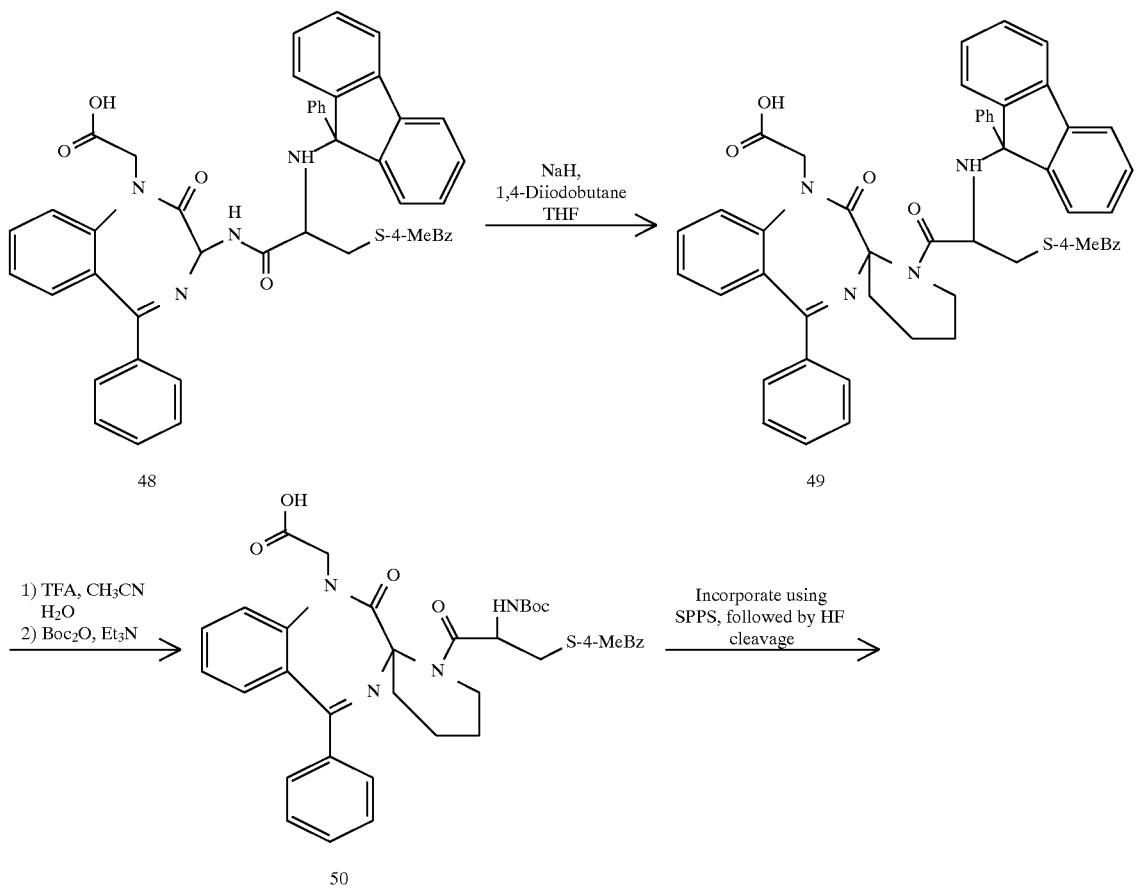
Benzodiazepines of the instant invention with a hydroxamic or carboxylic terminus at C-3 may be made according to Scheme X. Compound 14 from Scheme II may be treated with an acid anhydride in N-methyl-morpholine (NMM) to produce 52 contemplated to be a suitable ras F inhibitor. 52 in turn may be coupled to a hydroxamic acid and cleaved to produce 54.

SCHEME X
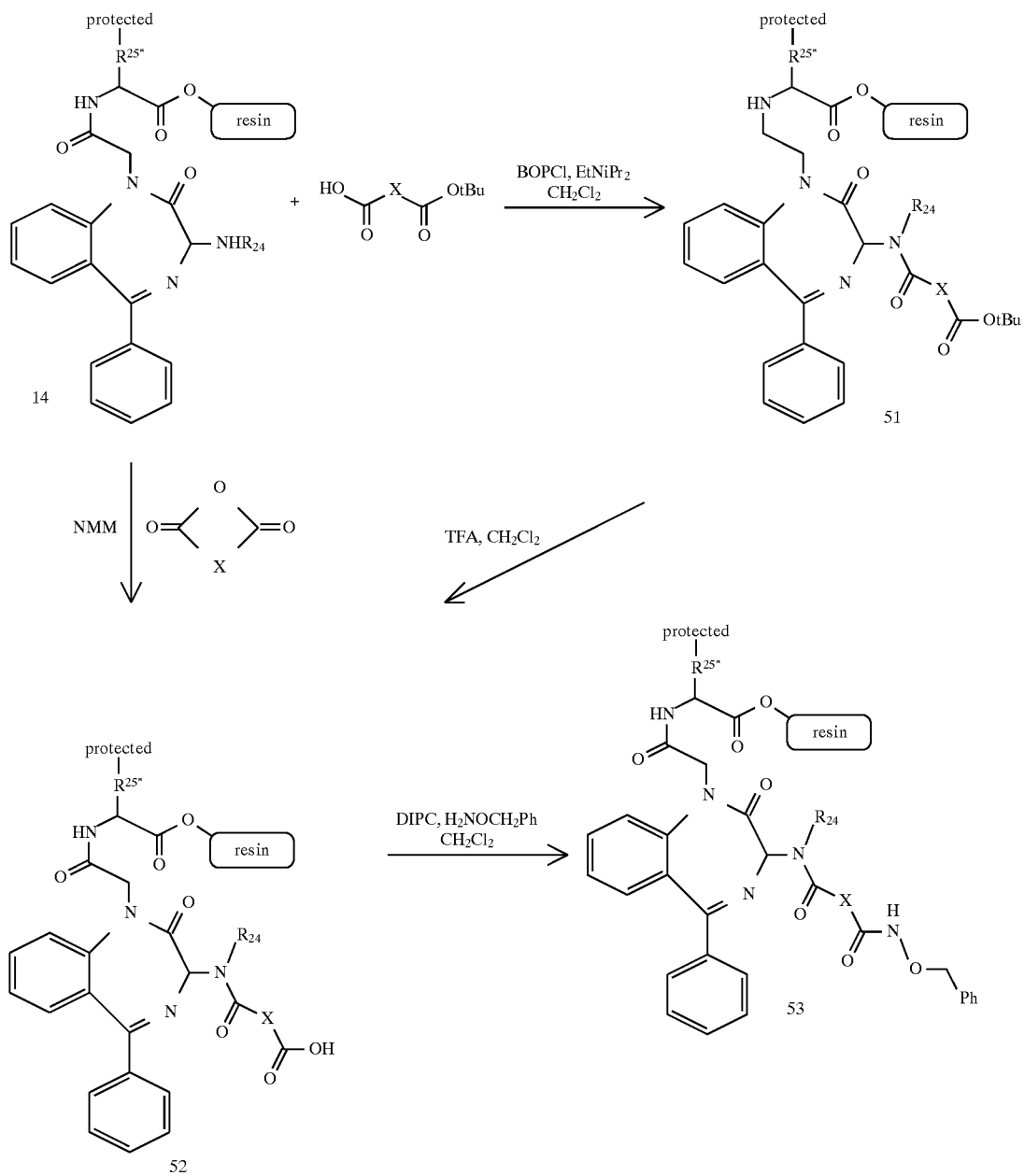

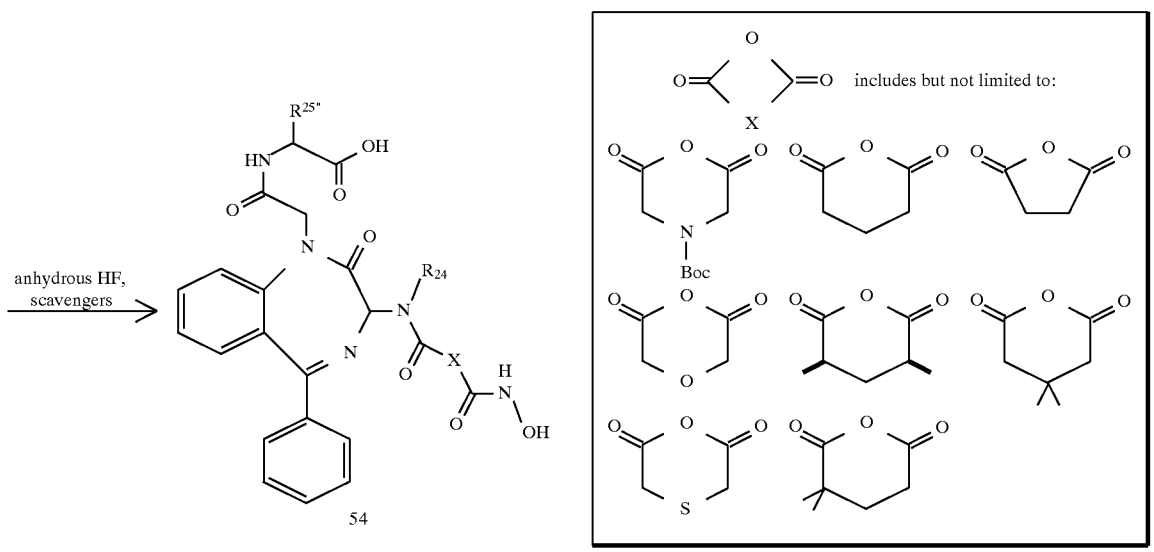
Benzodiazepine compounds 16 and 22 of Schemes II and III, where $R^{24}$ is hydrogen may be convereted to heterocycles of formulae IXa–IXd according to Scheme XI. Here, $R^{25'}$ and W are suitably blocked prior to reacting with the cyclizing agent, followed by deblocking and release from the resin as described in Schemes II and III.
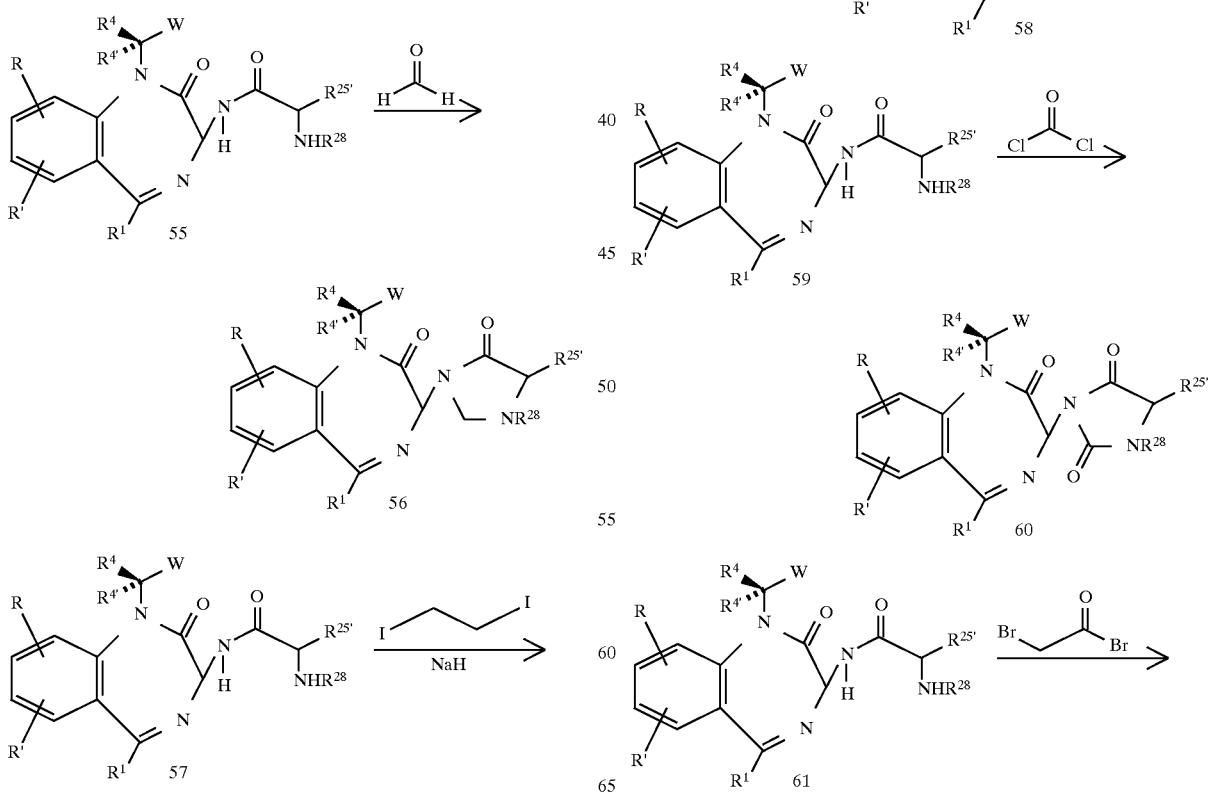

SCHEME XI -continued

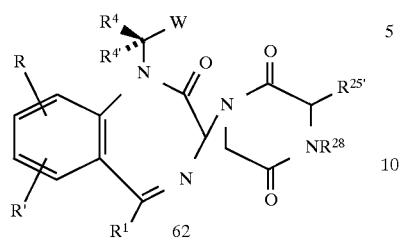

SCHEME XII -continued

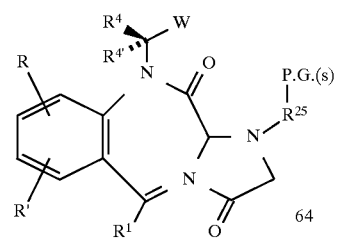

The imine nitrogen of the instant benzodiazepines may be cyclized with an amide nitrogen bonded to C-3 by first reacting 63 with bromoacetyl bromide followed by reduction of the imine and closure to give 64.

SCHEME XII

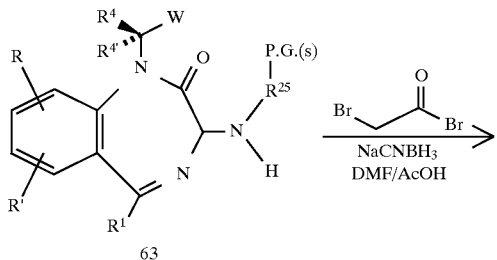

The synthesis of a class of compounds represented by formula (V) is shown in Scheme XIII. Reductive alkylation of the 2-amino-benzophenones 1 with an N-protected (preferably BOC) aldehyde using $NaCNBH_3$ gives 65. A wide variety of aldehydes derived from protected amino acids may be used in this reaction, including side chain protected natural amino acids (both D and L), substituted phenyl glycines, thiolysine, and the variety of synthetic, non-natural amino acids known to one skilled in the art. 65 is then acylated with an N-protected (preferably Fmoc) amino acid in the presence of DCC (see Scheme IV) to afford 66. 66 is then treated with base to form the benzodiazepine 67. This benzodiazepine is treated with Lawessons Reagent (Fluka) followed by MeI and then anhydrous HCl, followed by neutralization and heating to give the tricyclic compound 68. The optionally protected sidechain is deprotected to give 69.

SCHEME XIII

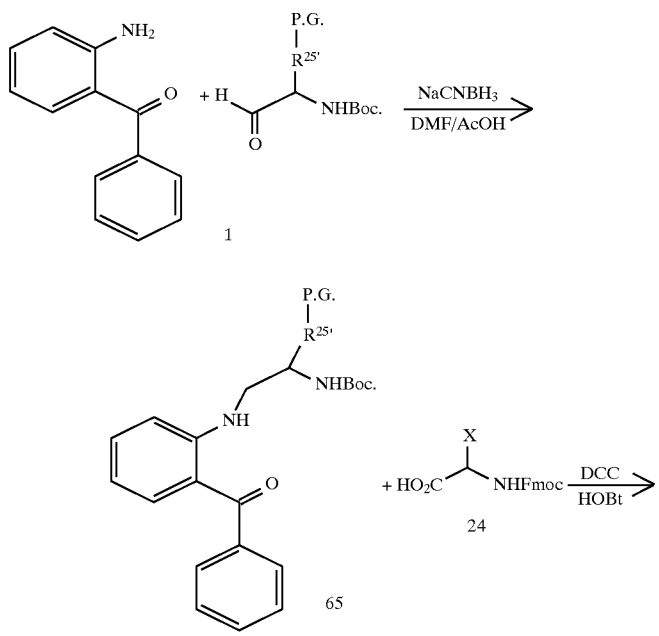

-continued
SCHEME XIII
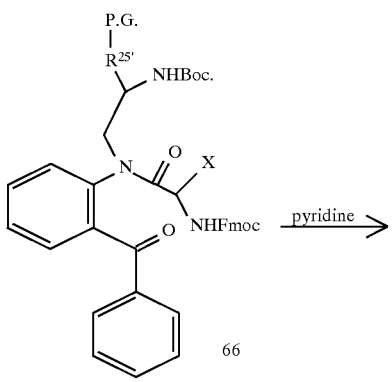
66
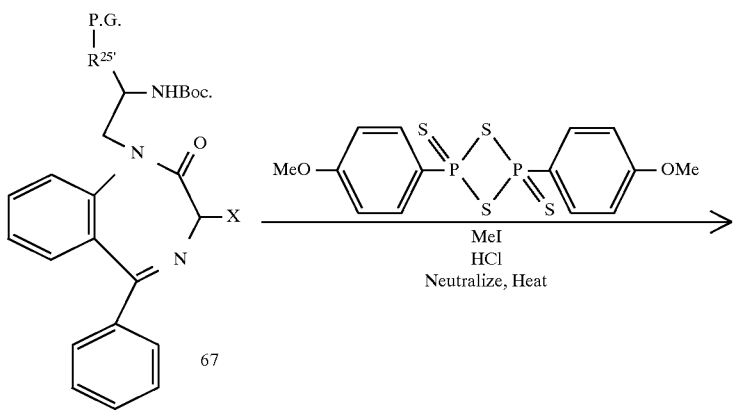
67
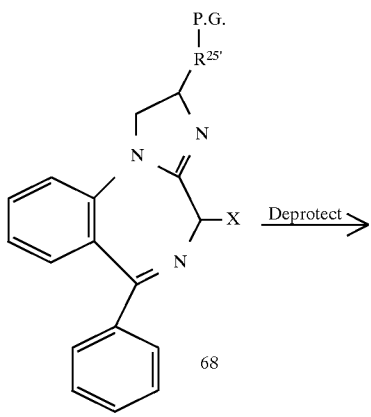
68
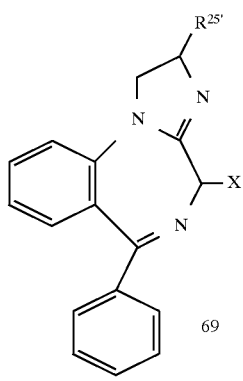
69

Compounds bearing a 3-ureido, 3-carbamoyl, or 3-thiocarbamoyl substituent on the benzodiazepine ring are synthesized as shown in Scheme XIV. Compound 9 from Scheme I may be esterified and reacted with IFA to yield 70. The 3-amino group is then converted to the isocyanate 71 with phosgene or 1,1'-carbonyldiimidazole. 71 may be converted into the corresponding ureido, carbamoyl, or thiocarbamoyl, by reacting it with suitably protected amines, alcohols, or thiols yielding 72, 73, and 74 respectively. A wide variety of protected amino acids having a free amino group are prefered in this reaction, including side chain protected natural amino acids (both D and L), substituted phenyl glycines, thiolysine, and a variety of synthetic, non-natural amino acids (e.g. thioproline, β-alanine, etc.) known to one skilled in the art (see e.g. U.S. Pat. No. 5,120,859, and WO 93/04081). Simple suitably protected alkylaminothiols and hydroxyalkylthiols may similarly be employed to produce 72, 73, or 74.

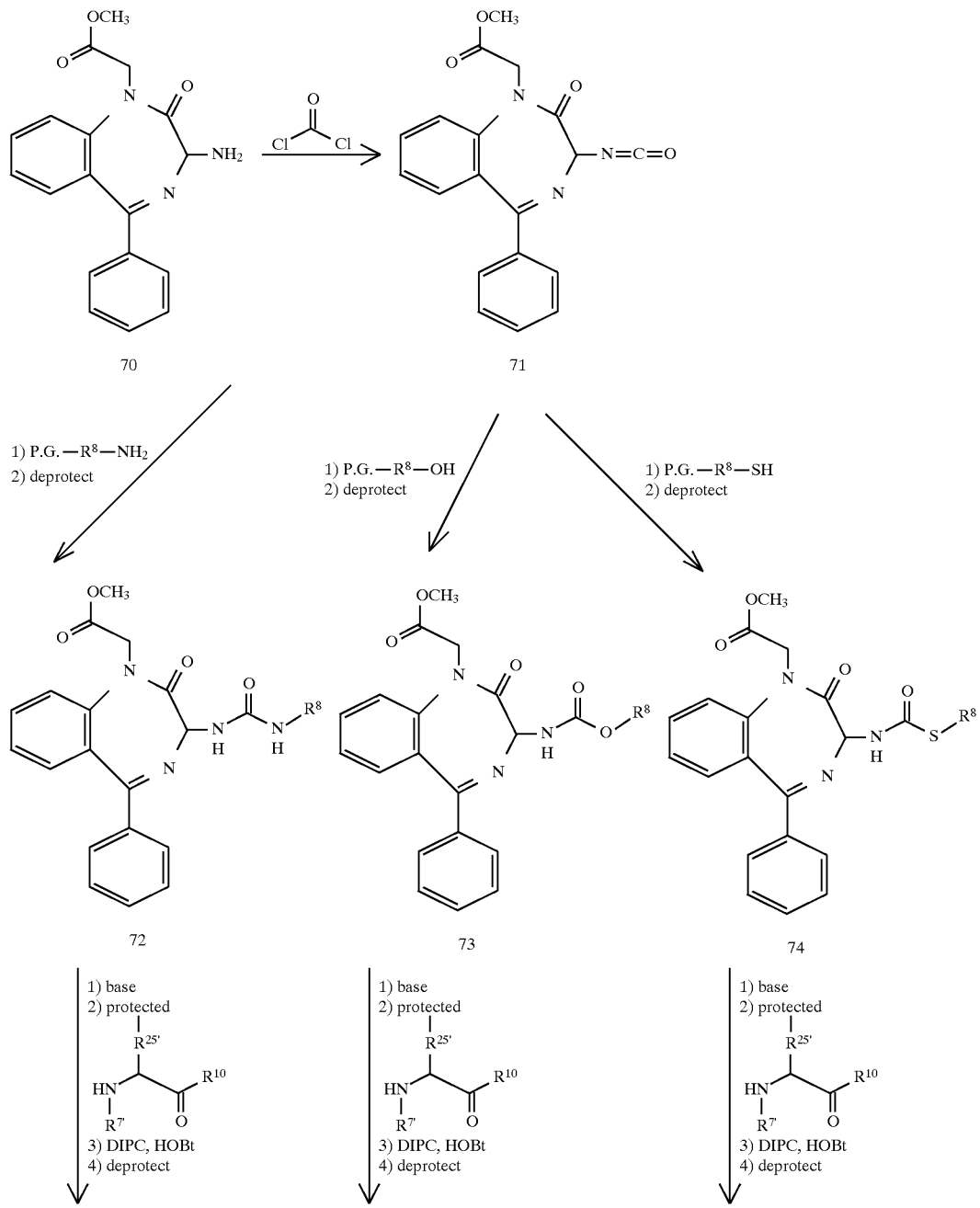

SCHEME XIV

-continued
SCHEME XIV

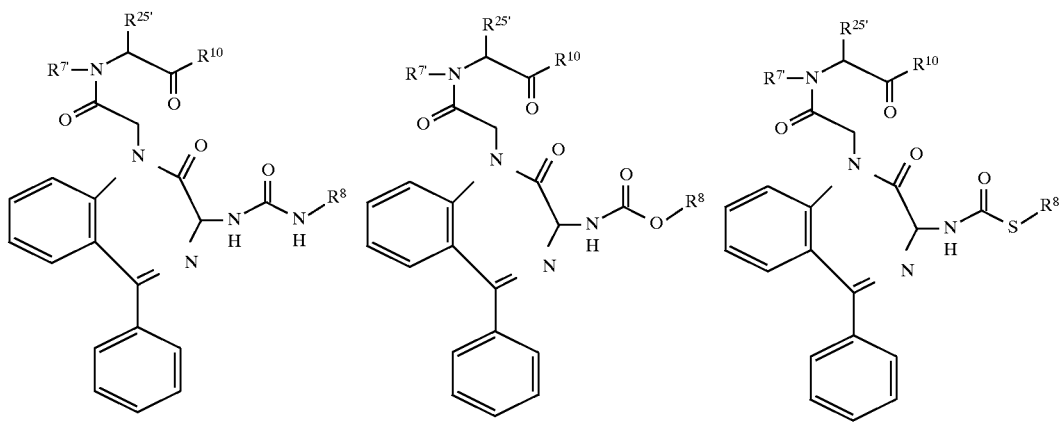

72, 73, or 74 may be used as inhibitors per se or further converted into compounds 75, 76, or 77 by coupling protected amino acids to the free acid forms of 72, 73, or 74 using the standard procedures shown above.

E. Isomeric Products

In products of Formula I-X carbon atoms bonded to four nonidentical substituents are asymmetric. Accordingly, the compounds may exist as diastereoisomers, enantiomers or mixtures thereof. The syntheses described above may employ racemates, enantiomers or diastereomers as starting materials or intermediates. Diastereomeric products resulting from such syntheses may be separated by chromatographic or crystallization methods. Likewise, enantiomeric product mixtures may be separated using the same techniques or by other methods known in the art. Each of the asymmetric carbon atoms, when present in compounds of Formula I-X, may be in one of two configurations (R or S) and both are within the scope of the present invention.

F. Pharmaceutical Compositions

The compounds described in this invention may be isolated as the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric and the like. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of Formula I-X with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

In the management of proliferative disease the compounds of this invention may be utilized in compositions such as tablets, capsules or elixirs for oral administration; suppositories for rectal administration; sterile solutions or suspensions for injectable administration, and the like. Animals in need of treatment using compounds of this invention can be administered dosages that will provide optimal efficacy. The dose and method of administration will vary from animal to animal and be dependent upon such factors as weight, diet, concurrent medication and other factors which those skilled in the medical arts will recognize.

Dosage formulations of the nonpeptidyl Ras FT inhibitors of the present invention are prepared for storage or administration by mixing the inhibitor having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as Tween, Pluronics or polyethyleneglycol.

Dosage formulations of the nonpeptidyl Ras FT inhibitors of the present invention to be used for therapeutic administration must be sterile. Sterility is readily accomplished by filtration through sterile filtration membranes such as 0.2 micron membranes. Nonpeptidyl Ras FT inhibitor formulations ordinarily will be stored in lyophilized form or as an aqueous solution. The pH of the nonpeptidyl Ras FT inhibitor preparations typically will be between 3 and 11, more preferably from 5 to 9 and most preferably from 7 to 8. It will be understood that use of certain of the foregoing excipients, carriers, or stabilizers will result in the formation of inhibitor salts. While the preferred route of administration is by oral dosage formulation or hypodermic injection, other methods of administration are also anticipated such as suppositories, aerosols, and topical formulations such as ointments, drops and dermal patches.

Therapeutic nonpeptidyl Ras FT inhibitor formulations generally are placed into a container having a sterile access port, for example, an intravenous solution bag or vial having a stopper pierceable by hypodermic injection needle.

Therapeutically effective dosages may be determined by either in vitro or in vivo methods. For each particular nonpeptidyl Ras FT inhibitor of the present invention, individual determinations may be made to determine the optimal dosage required. The range of therapeutically effective dosages will naturally be influenced by the route of administration. For injection by hypodermic needle it may be assumed the dosage is delivered into the body's fluids. For other routes of administration, the absorption efficiency must be individually determined for each inhibitor by methods well known in pharmacology The range of therapeutic dosages is from about 0.001 nM to 1.0 mM, more preferably from 0.1 nM to 100 mM, and most preferably from 1.0 nM to 50 mM.

Typical formulation of compounds of Formula I-X as pharmaceutical compositions are discussed below.

About 0.5 to 500 mg of a compound or mixture of compounds of Formula I-X, as the free acid, base or prodrug form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic add; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

EXAMPLES

In Examples 1–8 the parenthetical compound numbers refer to the numbers in Scheme 1 below.

Scheme 1

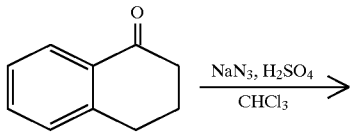

-continued
Scheme 1

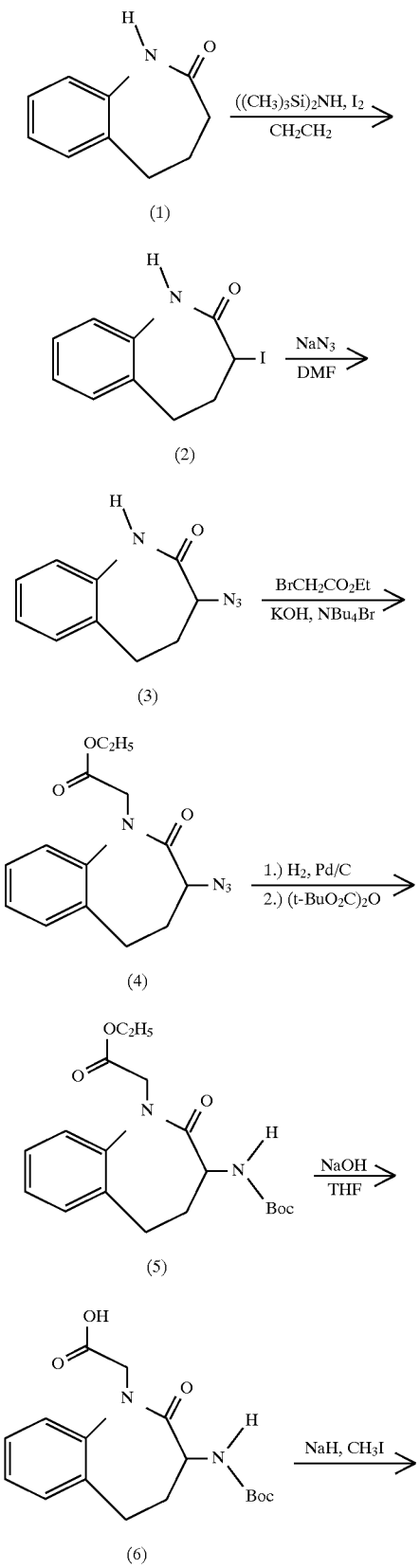

-continued
Scheme 1

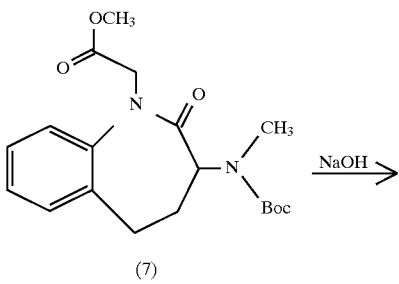

(7)

(8)

EXAMPLE 1

2,3,4,5-Tetrahydro-1H-[1]-benzazapin-2-one (1)

To a stirred suspension of 13.4 g (207 mmol) of sodium azide and 25.0 ml (188 mmol) of α-tetralone in 150 mL of chloroform, was added 50.0 mL of concentrated sulfuric acid, dropwise over 1 h. After 30 min., the chloroform phase was decanted and the acidic phase poured into 1 L of water. The precipitated solid was collected on a filter, washed with water, and recrystallized from 1 L of boiling water. The product was collected and dried under vacuum to yield 14.3 g (47%) of tan needles. $^1$H NMR (300 MHz, CDCl$_3$) d 8.63 (1H, bs), 7.24 (2H, m), 7.13 (1H, m), 7.03 (1H, d, J=8 Hz), 2.82 (2H, t, J=6 Hz), 2.38 (2H, t, J=6 Hz), 2.24 (2H, m).

EXAMPLE 2

3-Iodo-2,3,4,5-tetrahydro-1H-[1]-benzazapin-2-one (2)

A suspension of 34.2 g (212 mmol) of 2,3,4,5tetrahydro-1H-[1]-benzazapin-2-one and 224 mL (171.2 g, 1.06 mol) of hexamethyldisilazane in 400 mL of methylene chloride was heated at reflux for 15 min and cooled to 30° C. Iodine (161.5 g, 636 mmol) was added in one portion, the solution heated at reflux for 2.5 h, cooled, and poured into a 0° C. solution of 88.6 g of sodium sulfite in 800 mL of water, with vigorous stirring. The aqueous phase was separated, extracted with methylene choride and the combined organics were washed with water and concentrated in vacuo to approximately 200 mL. Toluene (800 mL) was added, the solution was concentrated to a slurry, and the product collected on a filter. Drying under vacuum gave 36.7 g (60%) of a tan powder. $^1$H NMR (300 MHz, CDCl$_3$) d 8.47 (1H, bs), 7.3–7.1 (3H, m), 7.06 (1H, d, J=8 Hz), 4.68 (1H, t, J=8.7 Hz), 2.97 (1H, m), 2.80–2.60 (3H, m).

EXAMPLE 3

3-Azido-2,3,4,5-tetrahydro-1H-[1]-benzazapin-2-one (3)

To a solution of 36.7 g (128 mmol) of 3-Iodo-2,3,4,5-tetrahydro-1H-[1]-benzazapin-2-one in 200 mL of dimethylformamide was added 9.97 g (153 mmol) of sodium azide. After 3 h, the mixture was poured into 800 mL of ice water and the precipitate collected on a filter. After washing the solid successively with water, 3% aqueous sodium bisulfite, and water, the product was dried under vacuum to give 21.5 g (83%) of a tan powder. $^1$H NMR (300 MHz, CDCl$_3$) d 8.91 (1H, bs), 7.4–7.0 (4H, m), 3.89 (1H, t, J=9 Hz), 2.97 (1H, m), 2.73 (1H, m), 2.52 (1H, m), 2.32 (1H, m).

EXAMPLE 4

Ethyl 3-azido-2,3,4,5-tetrahydro-lH-[1]-benzazapin-2-one-1-acetate (4)

To a solution of 5.00 g (24.7 mmol) of 3-Azido-2,3,4,5-tetrahydro-1H-[1]-benzazapin-2-one, 1.48 g (26.5 mmol) of powdered potassium hydroxide, and 780 mg (2.47 mmol) of tetrabutylammonium bromide in 25 mL of tetrahydrofuran was added 2.95 mL (4.42 g, 26.5 mmol) of ethyl bromoacetate. The mixture was rapidly stirred at ambient temperature for 4 h and partitioned between ethyl acetate and water. The organic phase was washed with water, dried (magnesium sulfate), and concentrated, to yield 6.43 g of an oil, used without further purification. $^1$H NMR (300 MHz, CDCl$_3$) d 7.38–7.13 (4H, m), 4.72 (1H, d, J=17 Hz), 4.42 (1H, d, J=17 Hz), 4.18 (2H, q, J=7 Hz), 3.75 (1H, m), 3.38 (1H, m), 2.70 (1H, m), 2.40 (2H, m), 1.26 (3H, t, J=7 Hz).

EXAMPLE 5

Ethyl 3-(tert-butoxycarbonylamino)-2,3,4,5-tetrahydro-1H-[1]-benzaza-pin-2-one-1-acetate (5)

A suspension of 6.43 g of crude ethyl 3azido-2,3,4,5-tetrahydro-1H-[1]-benzazapin-2-one-1-acetate and 1 g of 10% palladium on carbon in 40 mL of ethanol was shaken under 50 psig H$_2$ for 12 h. The mixture was filtered through celite, concentrated to a foam, and redissolved in 100 ml of methylene chloride/1N aqueous sodium bicarbonate (1:1). Di-t-butyl-dicarbonate (10.8 g, 49.4 mmol) was added, the mixture was rapidly stirred at ambient temperature for 12 h, and partitioned between water and methylene chloride. The organic phase was separated and washed successively with 1N sodium bicarbonate, 1N sodium bisulfate, water, brine, and dried over magnesium sulfate. Concentration in vacuo gave a solid that was chromatographed (200 g silica gel 60, ethyl acetate/hexane 1:3 to 1:2). Recrystallization from ethyl acetate/hexane gave 5.93 g (69% from 3-azido-2,3,4,5-tetrahydro-1H-[1]-benzazapin-2-one) of a colorless crystalline solid. $^1$H NMR (300 MHz, CDCl$_3$) d 7.3–7.1 (4H, m), 5.42 (1H, bd), 4.75 (1H, d, J=17 Hz), 4.33 (1H, d, J=17 Hz), 4.25 (1H, m), 4.17 (1H, bq, J=7 Hz), 3.32 (1H, m), 2.57 (2H, m), 1.98 (1H, m), 1.38 (9H, s), 1.24 (3H, t, J=7 Hz). Exact mass (FAB, M+H$^+$) calcd for C$_{19}$H$_{27}$N$_2$O$_5$: 363.1920; Found: 363.1929.

EXAMPLE 6

3-(tert-Butoxycarbonylamino)-2,3,4,5-tetrahydro-1H-[1]-benzazapin-2-one-1-acetic acid (6)

A solution of 5.00 g (14.3 mmol) of ethyl 3-(tert-butoxycarbonylamino)-2,3,4,5-tetrahydro-1H-[1]-benzazapin-2-one-1-acetate in 30 mL of methanol was cooled to 0° C. and treated with 28.5 mL of 1N sodium hydroxide. Tetrahydrofuran was added until the mixture was homogeneous (about 10 mL) and the solution warmed to ambient temperature for 3 h. The volatiles were removed in vacuo and the residue was diluted with water and extracted with ether. The aqueous phase was acidified to pH 2 with 1N sodium bisulfate and extracted twice with ethyl acetate. The combined organics were washed with brine, dried over magnesium sulfate, and concentrated to 20 mL. Hexane was added and the resulting suspension was aged overnight at 0° C., filtered, and the solid dried in vacuo to give 4.62 g (100%) of colorless product. $^1$H NMR (300 MHz, CDCl$_3$) d 8.65 (1H, b), 7.3–7.1 (4H, m), 5.52 (1H, bd), 4.71 (1H, d, J=17 Hz), 4.40 (1H, d, J=17 Hz), 4.25 (1H, m), 3.25 (1H, m), 2.56 (2H, m), 1.98 (1H, m), 1.37 (9H, s). Exact mass (FAB, M+H$^+$) calcd for $C_{17}H_{23}N_2O_5$: 335.1607; Found: 335.1609.

EXAMPLE 7

Methyl 3-(tert-butoxycarbonylmethylamino)-2,3,4,5-tetrahydro-1H-[1]-benzazapin-2-one-1-acetate (7)

To a solution of 2.58 g ( 8.00 mmol) of 3-(tert-butoxycarbonylamino)-2,3,4,5-tetrahydro-1H-[1]-benzazapin-2-one-1-acetic acid in 40 mL of tetrahydrofuran/dimethylformamide/glyme (6:1:1) was added 3.98 mL (64.0 mmol) of methyl iodide and 960 mg of sodium hydride (60% dispersion in mineral oil, 24.0 mmol). The suspension was heated at 50° C. (at which point it became homogeneous) for 3 h and cooled. 30 mL of 1N sodium bisulfate was added, the volatiles removed in vacuo, and the aqueous slurry extracted twice with ethyl acetate. The organic phase was washed with brine, dried over magnesium sulfate, filtered, and concentrated. Chromatography (150 g silica gel 60, ethyl acetate/hexane/acetic acid (40:60:1)) gave a solid that was recrystallized from methanol/water to yield 2.01 g (69%) of colorless product. $^1$H NMR (300 MHz, CDCl$_3$, spectrum broad due to carbamate rotomers) d 7.3–7.1 (4H, m), 4.95–4.15 (3H, bm), 3.69 (3H, bs), 3.35 (1H, m), 3.02 (3H, s), 2.68 (1H, m), 2.50 (1H, m), 2.15 (1H, m), 1.39 (4.5H, bs), 1.29 (4.5H, bs). Mass spec. (FAB, M+H$^+$) calcd for $C_{19}H_{27}N_2O_5$: 363.19; Found: 363.1.

EXAMPLE 8

3-(tert-Butoxycarbonylmethylamino)-2,3,4,5-tetrahydro-1H-[1]-benz-azapin-2-one-1-acetic acid (8)

To a 0° C. methanolic solution of 1.59 g (4.39 mmol) of methyl 3-(tert-butoxycarbonylmethylamino)-2,3,4,5-tetrahydro-1H-[1]-benzazapin-2-one-1-acetate was added 8.6 mL of 1N sodium hydroxide and 5 mL of tetrahydrofuran. The mixture was magnetically stirred for 3 h at ambient temperature and concentrated in vacuo to remove the volatiles. The slurry was diluted with water, extracted with ether (discarded), and acidified to pH 2 with 1N sodium hydrogen sulfate. The aqueous phase was extracted twice with ethyl acetate and the combined organics were washed with brine, dried over magnesium sulfate, filtered, and concentrated to a colorless foam. $^1$H NMR (300 MHz, CDCl$_3$) d 8.40 (1H, b), 7.35–7.05 (4H, m), 4.80 (1H, m), 4.50 (1H, m), 4.25 (1H, m), 3.25 (1H, m), 3.00 (3H, s), 2.65 (1H, m), 2.45 (1H, m), 2.13 (1H, m), 1.38 (4.5H, bs), 1.27 (4.5H, bs). Exact mass (FAB, M+H$^+$) calcd for $C_{18}H_{25}N_2O_5$: 349.1763; Found: 349.1761.

EXAMPLE 9

N-[[3-(2-Amino-3-mercapto-1-oxopropyl)methylamino]-2,3,4,5tetrahydro-2-oxo-1H-1-benzazepin-1-yl] acetyl]-L-methionine (9)

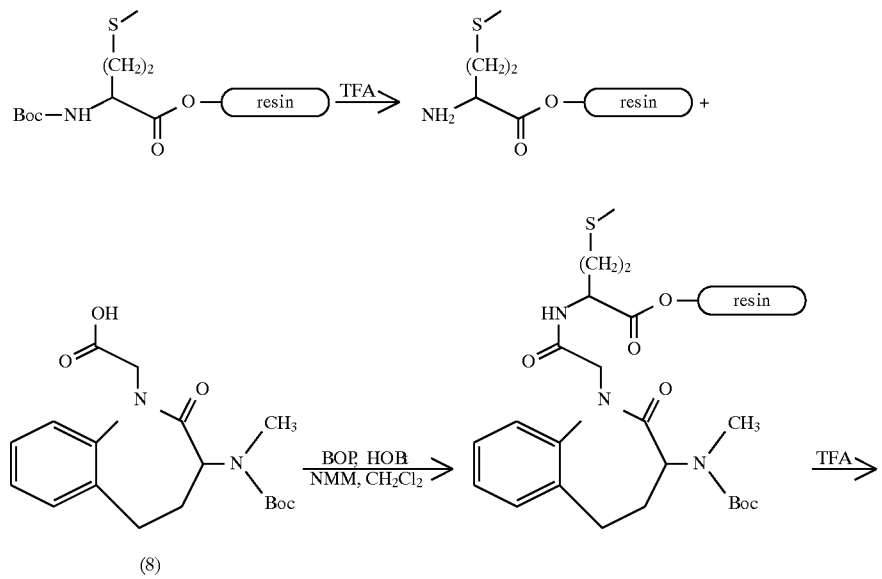

Scheme 2

-continued
Scheme 2

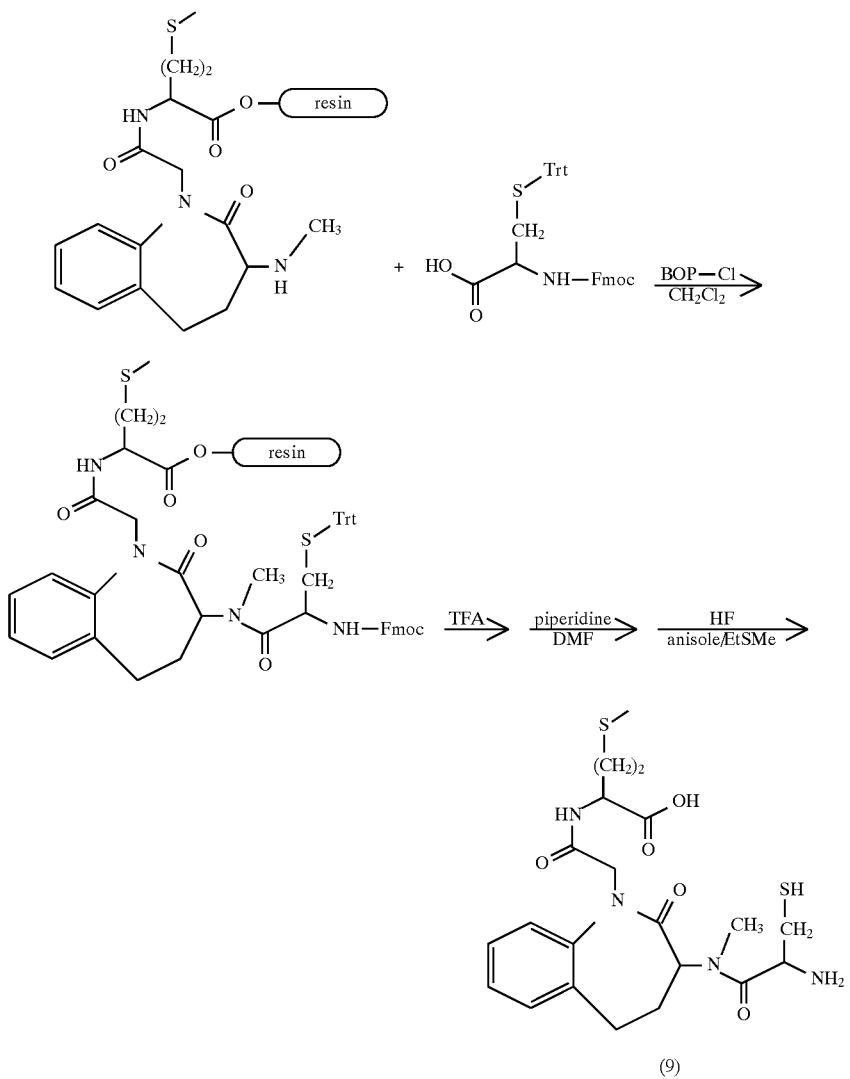

The compounds synthesized via the route shown in Scheme 2 followed standard solid-phase methodologies (Barany, G. and Merrifield, R. B. (1980) in "The Peptides", 2, 1–284. Gross, E. and Meienhofer, J. Eds. Academic Press, New York). 3-(tert-Butoxycarbonylmethylamino)-2,3,4,5-tetrahydro-1H-[1]-benz-azapin-2-one-1-acetic acid (1.6 mmol, 558 mg), benzotriazol-1-yloxy-tris-(dimethylamino)-phosphonium hexafluorophosphate (BOP, 1.6 mmol, 706 mg), N-methylmorpholine (NMM, 1.6 mmol, 217 ul), and N-hydroxbenztriazole (HOBt, 1.6 mmol, 175 mg) in dimethylacetamide (DMA, 30 ml) were added to deprotected L-methionine-linked Merrifield resin (Bachem, 1.5 gm, 0.71 meq/gm, 12hrs.). After wash (DMA, then dichloromethane (DCM)) and deprotection steps (45% TFA/5% anisole/5% EtSMe/DCM), the resin was neutralized (20% Et3N/DCM) and washed (DCM). Next, Fmoc-(S-trityl)-L-cysteine (4.3 mmol, 2.5 gm), bis(2-oxo-3-oxazolidinyl)phosphinic chloride (BOP-Cl, 4.7 mmol, 1.2 gm), and diisopropylethylamine (9.4 mmol, 1.6 ml) were combined and added to the resin (DCM, 30 ml, 10 hrs). After removal of the Fmoc (20% piperidine/DMA) and trityl (45% TFA/5% EtSMe/5% anisole/DCM) protecting groups the resin was washed with MeOH, dried under vacuum, cleaved from the resin (32 ml, HF/10% anisole/5% EtMeS, 0° C., 1 hr.) and purified via HPLC. Purification of 119 mg of crude material (Vydac C18, ACN/water/0.1% TFA) afforded the product, N-[[3-(2-amino-3-mercapto-1-oxopropyl) methylamino]-2,3,4,5-tetrahydro-2-oxo-1H-1-benzazepin-1-yl] acetyl]-L-methionine, as two separable diastereomers (opposite configuration at C-3 of the benzodiazepine) designated 9A (24 mg) and 9B (27 mg) corresponding to the early and late eluting peaks respectively.

Mass (electrospray, M+H$^+$) calc: 483.1 found: 482.8 (9A), 482.8 (9B).

EXAMPLE 10

N-[[3-(2-Amino-3-mercapto-1-oxopropyl) amino]-2,3,4,5-tetrahydro-2-oxo-1H-1-benzazepin-1-yl]acetyl]-L-methionine (10)

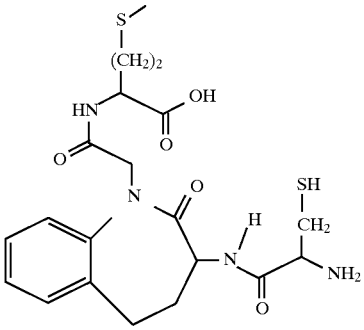

The title compound was prepared using the procedure of Example 9 in which 3-(tert-butoxycarbonylamino)-2,3,4,5-tetrahydro-1H-[1]-benzazapin-2-one-1-acetic acid (428 mg, 1.3 mmol) was coupled to L-methionine resin (1.2 gms, 0.71 mmol/gm) with BOP (565 mg, 1.3 mmol), NMM (170 ul, 1.3 mmol), and HOBt (140 mg, 1.3 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). Purification of 102 mg of the crude material yielded the two diastereomers 10A (18 mg) and 10B (12 mg).

Mass (electrospray, M+H$^+$) calc: 469.1 found: 468.8 (10A), 468.8 (10B).

In Examples 11–17 the parenthetical compound numbers refer to the numbers in Scheme 3 below.

Scheme 3

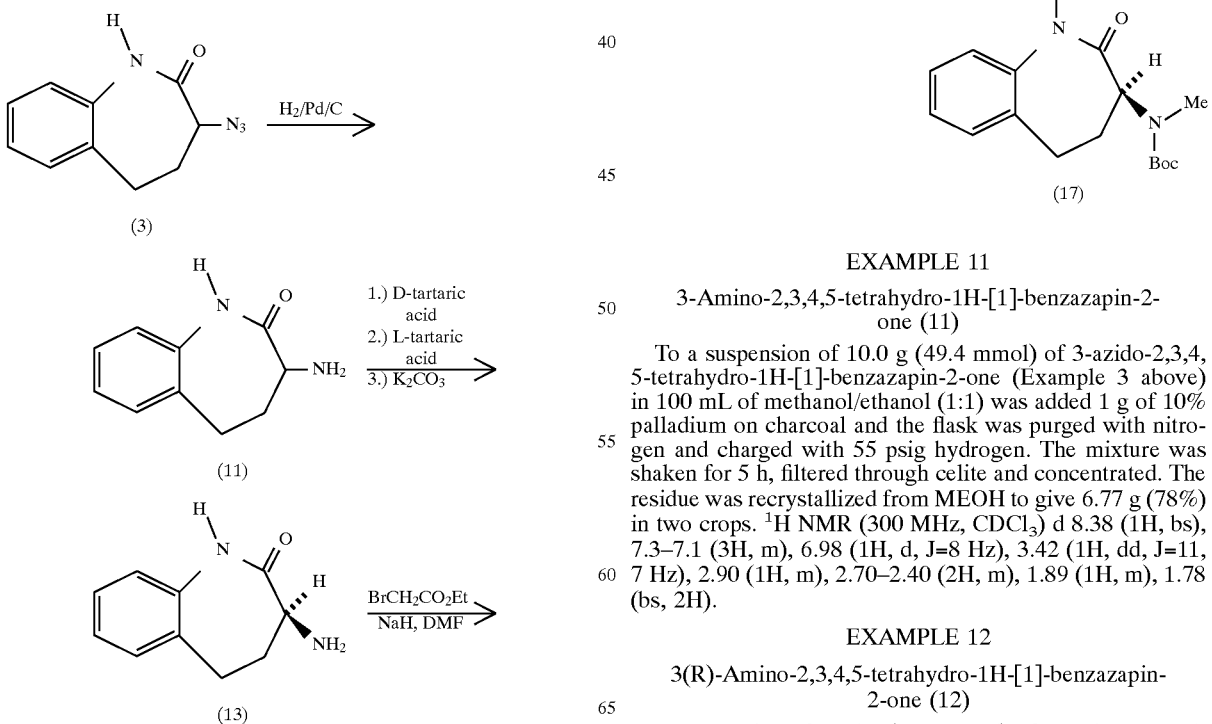

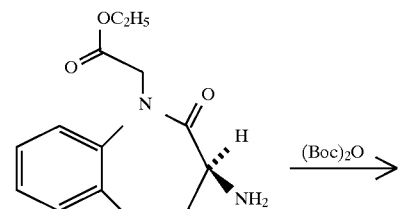

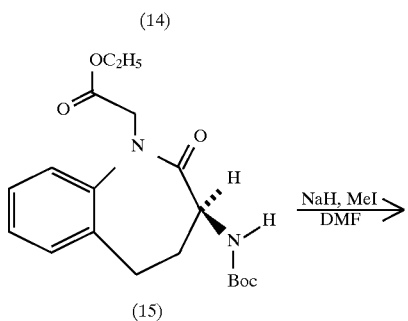

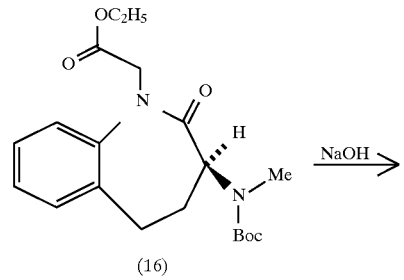

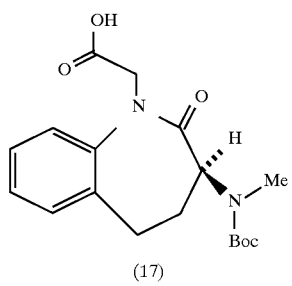

EXAMPLE 11

3-Amino-2,3,4,5-tetrahydro-1H-[1]-benzazapin-2-one (11)

To a suspension of 10.0 g (49.4 mmol) of 3-azido-2,3,4,5-tetrahydro-1H-[1]-benzazapin-2-one (Example 3 above) in 100 mL of methanol/ethanol (1:1) was added 1 g of 10% palladium on charcoal and the flask was purged with nitrogen and charged with 55 psig hydrogen. The mixture was shaken for 5 h, filtered through celite and concentrated. The residue was recrystallized from MEOH to give 6.77 g (78%) in two crops. $^1$H NMR (300 MHz, CDCl$_3$) d 8.38 (1H, bs), 7.3–7.1 (3H, m), 6.98 (1H, d, J=8 Hz), 3.42 (1H, dd, J=11, 7 Hz), 2.90 (1H, m), 2.70–2.40 (2H, m), 1.89 (1H, m), 1.78 (bs, 2H).

EXAMPLE 12

3(R)-Amino-2,3,4,5-tetrahydro-1H-[1]-benzazapin-2-one (12)

A suspension of 6.75 g (38.3 mmol) of 3-amino-2,3,4,5-tetrahydro-1H-[1]-benzazapin-2-one and 5.18 g (34.5 mmol) of D-tararic acid in 80 ml of ethanol/water (4:1) was warmed to effect solution and aged overnight at ambient temperature. The crystals were collected, recrystallized again from ethanol/water, and dried under vacuum to give 4.61 g (37%) of purified D-tartrate salt. The salt was dissolved in water, solid potassium carbonate was added until the pH was 10–11, and the solution extracted four times with methylene chloride. The combined organics were dried over magnesium sulfate, filtered, and concentrated in vacuo to give 2.03 g (30% overall) of the 3(R)-amine. [α]D=+407° (c=1, MEOH); lit. Fisher, M. H.; et al EP 513974-A1, 2/28/92, [α]D=+455° (c=1, MeOH).

EXAMPLE 13

3(S)-Amino-2,3,4,5-tetrahydro-1H-[1]-benzazapin-2-one (13)

The mother liquors from Example 12, enriched in the 3(S)-isomer were free-based as above, treated with L-tartaric acid (1 eq), and recrystallized from ethanol/water. The crystals were collected, free-based with aqueous potassium carbonate and extracted as above. Drying and concentration gave 1.50 g (22% overall) of the 3(S)-amine.

EXAMPLE 14

Ethyl 3(S)-3-amino-2,3,4,5-tetrahydro-1H-[1]-benzazapin-2-one-1-acetate (14)

To a solution of 1.50 g (8.51 mmol) of 3(S)-amino-2,3,4,5-tetrahydro-1H-[1]-benzazapin-2-one in 20 mL of dimethylformamide at 0° C. was added 340 mg (8.51 mmol, 60% disp. in mineral oil) of sodium hydride. The suspension was warmed to ambient temperature for 1.5 h, recooled to 0° C., and treated with 1.42 g (0.948 mL, 8.51 mmol) of ethyl bromoacetate in 5 mL of dimethylformamide. The ice bath was removed, and after 1 h the mixture was concentrated in vacuo. The residue was partitioned between ethyl acetate and 1 N sodium bicarbonate, the organic phase removed, washed with brine, dried over magnesium sulfate, and concentrated. Trituration with ether gave 767 mg (34%) of a colorless solid in the first crop. [α]D=−295° (c=0.95, EtOH); (lit. Watthey, J. W. H.; et al J. Med. Chem. 1985, 28, 1511., [α]D=−285.5° (c=0.99, EtOH)). $^1$H NMR (300 MHz, CDCl$_3$) d 7.30–7.10 (4H, m), 4.62 (1H, d, J=17.8 Hz), 4.45 (1H, d, J=17.8 Hz), 4.19 (2H, q, J=7 Hz), 3.43 (1H, m), 3.23 (1H, m), 2.58 (1H, m), 2.41 (1H, m), 1.78 (2H, bs), 1.26 (3H, t, J=7 Hz).

EXAMPLE 15

Ethyl 3(S)-3-(tert-butoxycarbonylamino)-2,3,4,5-tetrahydro-1H-[1]-benzazepin-2-one-1-acetate (15)

Di-t-butyl-dicarbonate (1.23 g, 5.62 mmol) was added to a slurry of 737 mg (2.81 mmol) of Ethyl 3(S)-3-amino-2,3, 4,5-tetrahydro-1H-[1]-benzazapin-2-one-1-acetate in 20 mL methylene chloride/water (1:1) and the mixture was rapidly stirred at ambient temperature for 30 min. The organic phase was separated and washed with 1N sodium bicarbonate, brine, dried over magnesium sulfate, and filtered. Concentration in vacuo gave a foam that was chromatographed (70 g silica gel 60, ethyl acetate/hexane (1:2)) to give 987 mg (97%) of a colorless foam identical with material prepared above (Example 5).

EXAMPLE 16

Ethyl 3(S)-3-(tert-butoxycarbonylmethylamino)-2,3,4,5-tetrahydro-1H-[1]-benzazapin-2-one-1-acetate (16)

To a 0° C. solution of 488 mg (1.35 mmol) of Ethyl 3(S)-3-(tert-butoxycarbonylamino)-2,3,4,5-tetrahydro-1H-[1]-benzazapin-2-one-1-acetate in 5 mL of dimethylformamide was added 0.170 mL (2.69 mmol) of methyl iodide and 59 mg of sodium hydride (60% dispersion in mineral oil, 1.48 mmol). The suspension was stirred at ambient temperature for 15 h and partitioned between ethyl acetate and 1 N sodium bicarbonate. The organic phase was washed with 3% sodium bisulfite, water, brine, dried over magnesium sulfate, filtered, and concentrated. Chromatography (35 g silica gel 60, ethyl acetate/hexane (1:3)) gave 410 mg (81%) of a colorless foam. $^1$H NMR (300 M, CDCl$_3$, spectrum broad due to carbamate rotomers) d 7.3–7.1 (4H, m), 4.90–4.05 (5H, bm), 3.35 (1H, bm), 3.01 (3H, s), 2.65 (1H, m), 2.48 (1H, m), 2.15 (1H, m), 1.4–1.1 (12H, b).

EXAMPLE 17

3(S)-3-(tert-Butoxycarbonylmethylamino)-2,3,4,5-tetrahydro-1-[1]-benzazepin-2-one-1-acetic acid (17)

To a 0° C. solution of 410 mg (1.09 mmol) of Ethyl 3(S)-3-(tert-butoxycarbonylmethylamio)-2,3,4,5-tetrahydro-1H-[1]-benzazapin-2-one-1-acetate in 6 mL of tetrahydrofuran/water (2:1) was added 2.2 mL of 1N sodium hydroxide. The mixture was magnetically stirred for 3 h at ambient temperature and concentrated in vacuo to remove the volatiles. The slurry was diluted with water, extracted with ether (discarded), and acidified to pH 2 with 1N sodium hydrogen sulfate. The aqueous phase was extracted twice with ethyl acetate and the combined organics were washed with brine, dried over magnesium sulfate, filtered, and concentrated to a colorless foam. This material was identical with racemic material prepared above (Example 8). [α]$_D$= −177° (c=0.90, EtOH).

EXAMPLE 18

N-[[3(S)-3-(2-Amino-3-mercapto-1-oxopropyl) methylamino]-2,3,4,5-tetrahydro-2-oxo-1H-1-benzazepin-1-yl] acetyl]-L-methionine (18)

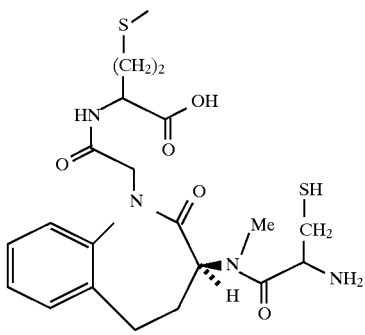

The title compound was prepared using the procedure of Example 9 in which 3(S)-3-acid (338 mg, 0.8 mmol) was coupled to L-methionine resin (0.75 gm, 0.71 mmol/gm) using BOP (353 mg, 0.8 mmol), NMM (108 ul, 0.8 mmol), and HOBt (88 mg, 0.8 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). HPLC analysis of the product showed that it was identical to a single diastereomer of the compound shown in Example 9. Co-injection of the compound prepared in Example 18 with the diastereomeric mixture of compounds prepared in Example 9 showed that the material prepared in Example 18 co-eluted with the first peak (9A) of Example 9. Therefore, for these compounds and all other molecules of similar structure described here we can conclude the configuration at the 3-carbon of the seven-membered ring is such that the 3(S) isomer elutes first (A peak) and the 3(R) isomer follows (B peak). It should be noted that in the benzodiazepine series the assignment of stereochemistry reverses from that of the benzazepine compound discussed in this example due to a shift in priority of the atoms bound to C-3 of the seven-membered ring. Therefore, in the benzodiazepine examples discussed below, we can conclude that the 3(R) isomer elutes first, and the 3(S) isomer follows.

In Examples 19–26 the parenthetical compound numbers refer to the numbers in Scheme 4 below.

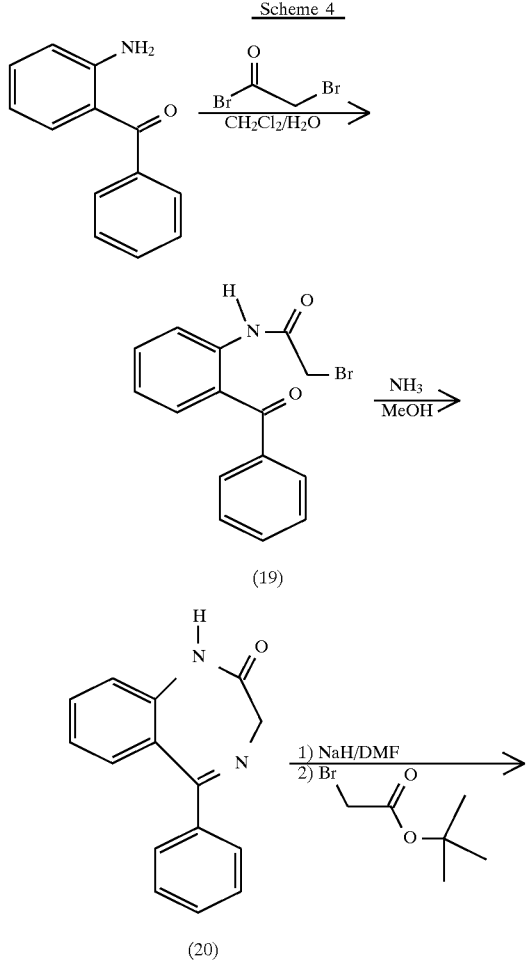

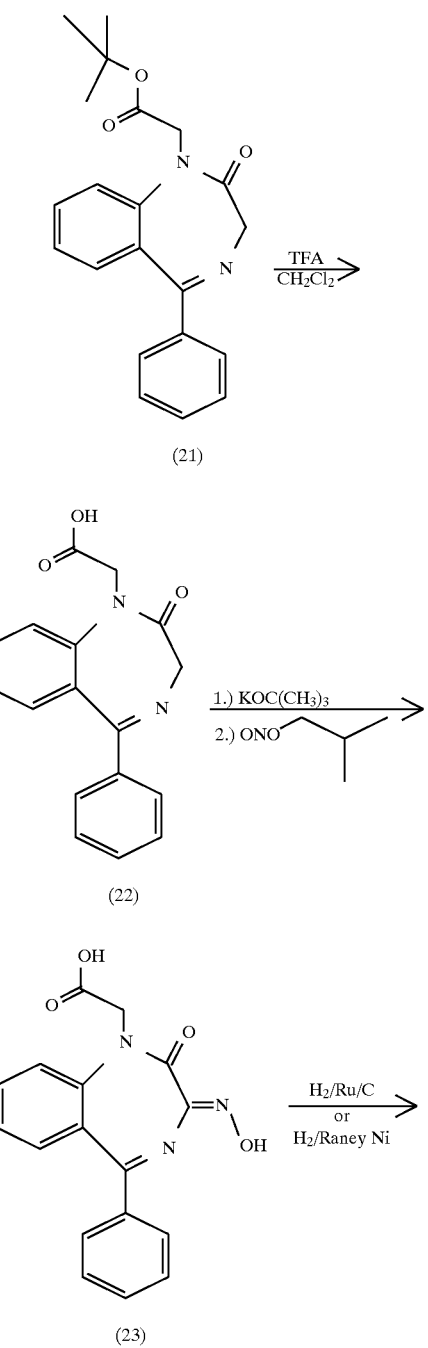

-continued
Scheme 4

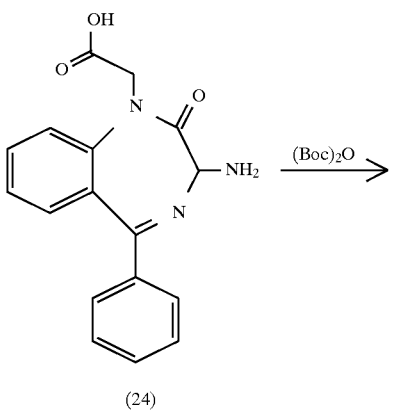

(24)

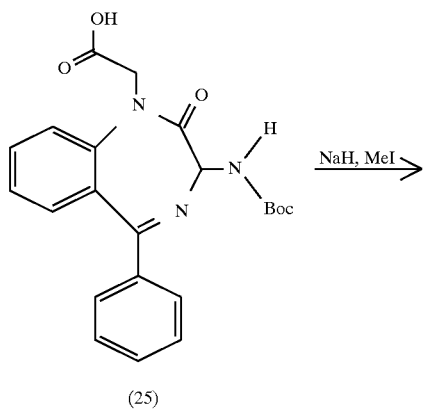

(25)

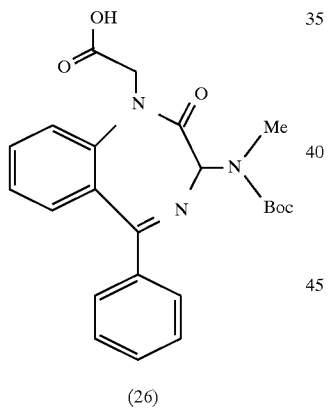

(26)

EXAMPLE 19

2-Bromoacetamido-benzophenone (19)

A solution of bromoacetyl bromide (100 mL, 1.15 mol, Aldrich) dissolved in dichloromethane (300 mL) was added over 30 min to a solution of 2-aminobenzophenone (197 g, 1.0 mol, Fluka) dissolved in dichloromethane (1.3 L) and water (100 mL) cooled to −10° C. under vigorous mechanical stirring. The resulting mixture was stirred for an additional 1 h at —5° C. and then was allowed to warm to ambient temperature. The layers were separated, and the organic extract was washed with dilute sodium bicarbonate, then was dried over sodium sulfate. Evaporation afforded 309.8 g (95%) of 2-bromoacetamidobenzophenone as off-white crystals.

EXAMPLE 20

2,3Dihydro-5-phenyl-1H-1,4-benzodiazepin-2-one (20)

A suspension of 2-bromoacetamidobenzophenone (275 g, 0.86 mol) in methanol (1 L) was treated with a solution of saturated ammonia in methanol (3 L), and the resulting solution was stirred at ambient temperature for 6 h, then was heated at reflux for an additional 4 h. After cooling, water (500 mL) was added, and the solution was concentrated by evaporation to about 1 L in volume, yielding crystalline 2,3-dihydro-5-phenyl-1H-1,4-benzodiazepin-2-one (20) (200.7 g, 98%).

EXAMPLE 21 tert-Butyl-2,3-dihydro-5-phenyl-1H-1,4-benzodiazepin-2-one-1-acetate (21)

A 1 L round-bottomed flask was equipped with a magnetic stirring bar and nitrogen inlet and was sequentially charged with 100 g (0.423 mol) of 2,3-dihydro-5-phenyl-1H-1,4-benzodiazepin-2-one, 600 mL of 1-methyl-2-pyrrolidinone (Aldrich, anhydrous), 97 mL (117 g, 0.601 mol) of tert-butyl bromoacetate (Aldrich), and 194 g (0.595 mol) of cesium carbonate (Aldrich). After stirring overnight at room temperature, the reaction mixture was diluted with 2 L $H_2O$ and extracted with EtOAc (3–600 mL). The combined organic extracts were washed with $H_2O$ (4–300 mL) and brine (200 mL), dried, with anhydrous $Na_2SO_4$, filtered, and concentrated under reduced pressure to provide 202 g of a solid. This material was recrystallized from hexanes/EtOAc to provide 123 g (83 %) of tert-butyl-2,3-dihydro-5-phenyl-1H-1,4-benzodiazepin-2-one-1-acetate (21) as a white crystalline solid.

EXAMPLE 22

2,3-dihydro-5-phenyl-1H-1,4-benzodiazepin-2-one-1-acetic acid (22)

A solution of tert-butyl-2,3-dihydro-5-phenyl-1H-1,4-benzodiazepin-2-one-1-acetate (58 g, 0.172 mol) in neat trifluoroacetic acid (100 mL) was stirred overnight, followed by evaporation and retreatment with an additional amount of TFA (100 mL). The mixture was evaporated, and the residue was dissolved in dichloromethane, and was washed with water and brine. The organic layer was dried over sodium sulfate and evaporated to yield 2,3-dihydro-5-phenyl-1H-1,4-benzodiazepin-2-one-1-acetic acid (22) (48.4 g, 100%) as a yellow foam.

EXAMPLE 23

3-oximino-2,3-dihydro-5-phenyl-1H-1,4-benzodiazepin-2-one-1-acetic acid (23)

A solution of 2,3-dihydro-5-phenyl-1H-1,4-benzodiazepin-2-one-1-acetic acid (22) (30 g, 0.106 mol) in glyme (1 L) was cooled to −5° C. and degassed under nitrogen. Solid potassium tert-butoxide (47.7 g, 0.43 mol) was added portionwise, and the resulting red solution was stirred for 30 min at 0°–5° C. A solution of isobutyl nitrite (13.8 mL, 0.117 mol, Aldrich) in glyme (20 mL) was then added, producing an orange-yellow solid. The mixture was neutralized with acetic acid (200 mL) with slight warming, and then was evaporated. The residue was partitioned between butanol and brine, and the organic layer was dried over sodium sulfate. Additional residual inorganics precipitated on standing, and were removed by filtration. Addition of hexane to the butanol solution afforded a crude precipitate (34.3 g), which was recrystallized from ethyl acetate-ethanol to yield 3-oximino-2,3-dihydro-5-phenyl-1H-1,4-benzodiazepin-2-one-1-acetic acid (23) (21.85 g, 66%).

EXAMPLE 24

3-Amino-2,dihydro-5-phenyl-1H-1,4-benzodiazepin-2-one-1-acetic acid (24)

A solution of 3-oximino-2,3-dihydro-5-phenyl-1H-1,4-benzodiazepin-2-one-1-acetic acid (15.0 g, 48 mmol) in methanol (1 L) was hydrogenated over catalytic ruthenium on carbon (5.0 g, Aldrich) at 40 psi and 70° C. for 4 days. The catalyst was removed by filtration, and the solution was evaporated to yield a crude solid (13.5 g). Flash chromatography (50 ethyl acetate: 49 methanol: 1 water) yielded pure 3-amino-2,3-dihydro-5-phenyl-1H-1,4-benzodiazepin-2-one-1-acetic acid (9.69 g).

Alternatively, a solution of 3-oximino-2,3-dihydro-5-phenyl-1H-1,4-benzodiazepin-2-one-1-acetic acid (33 g, 102 mmol) in methanol (200 ml) containing 2 ml acetic acid, was hydrogenated over Raney Nickel (1:1 by weight to oxime, washed twice with water than once with ethanol) at 65 psi and 70 C. for 1 ½ days. The catalyst was removed by suction filtration through celite, and the solution evaporated to yield crude 3-amino-2,3-dihydro-5-phenyl-1H-1,4-benzodiazepin-2-one-1-acetic acid which was used directly in the next step (see alternative synthesis in Example 25 below).

EXAMPLE 25

3-(tert-Butoxycarbonyl)amino-2,3-dihydro-5-phenyl-1H-1,4-benzodiazepin-2-one-1-acetic acid (25)

A solution of 3-amino-2,3-dihydro-5-phenyl-1H-1,4-benzodiazepin-2-one-1-acetic acid (1.0 g, 3.37 mmol) in DMF (10 mL) and water (5 mL) was treated with triethylamine (0.34 g, 3.37 mmol) and di-tert-butyl dicarbonate (0.73 g, 3.37 mmol) under nitrogen. After stirring at ambient temperature overnight, the mixture was evaporated and the residue was partitioned between ethyl acetate and water (pH=2 w/6 N HCl). The organic extract was dried over sodium sulfate and evaporated. Flash chromatography (80 ethyl acetate: 19 methanol: 1 water) of the residue afforded 3-(tert-butoxycarbonyl)amino-2,3-dihydro-5-phenyl-1H-1,4-benzodiazepin-2-one-1-acetic acid (940 mg) as a yellow solid. 1HNMR: consistent with structure
Mass (electrospray, M+H$^+$) calc: 410.2 found: 410.0.

Alternatively, 3-amino-2,3-dihydro-5-phenyl-1H-1,4-benzodiazepin-2-one-1-acetic acid prepared above (alternative synthesis, Example 24) in THF (100 ml) and water (100 ml) was cooled to 0 C. and di-tert-butyl dicarbonate (28.8 g, 132 mmol) was added under nitrogen followed by 1 N NaOH until the pH of the solution was ~10. The solution was allowed to come to ambient temperature, stirred overnight, and cooled again to 0° C. and acidified (pH ~3) with dropwise addition of concentrated H2SO4. The solution was partitioned (EtOAc) and the organic extract dried over sodium sulfate and evaporated. The residue was recrystallized from 120 ml MeOH yielding 18 g (44 mmol, 37%) of 3-(tert-butoxycarbonyl)amino-2,3-dihydro-5-phenyl-1H-1,4-benzodiazepin-2-one-1-acetic acid as yellow needles.

EXAMPLE 26

3-(tert-Butoxycarbonyl)methylamino-2,3-dihydro-5-phenyl-1H-1,4-benzodiazepin-2-one-1-acetic acid (26)

An oven-dried, 100 mL round-bottomed flask was equipped with a magnetic stirring bar and nitrogen inlet and was sequentially charged with 4.628 g (11.3 mmol) of 3-(tert-butoxycarbonyl)amino-2,3-dihydro-5-phenyl-1H-1,4-benzodiazepin-2-one-1-acetic acid, 50 mL of anhydrous THF (Aldrich), and 2.80 mL (6.38 g, 45.0 mmol) of methyl iodide (Aldrich). The reaction flask was cooled to −5° C. in an ice/acetone bath and 1.18 g (29.5 mmol) of a 60 % oil dispersion of sodium hydride was added in portions over a 5 min period (caution: vigorous gas evolution). After a 50-min period, the reaction mixture was quenched with a 5% (w/v) aqueous solution of citric acid, diluted with H$_2$O and extracted with EtOAc (3×40 mL). The combined organics were washed with H$_2$O (30 mL), brine (30 mL), dried with anhydrous Na$_2$SO$_4$, filtered, and concentrated under reduced pressure to provide 6.27 g of a viscous yellow oil. Flash chromatography of the crude material on 150 g of silica using 43:55:2 EtOAc/hexanes/AcOH as eluent yielded 4.54 g (10.7 mmol, 95%) of 3-(tert-butoxycarbonyl) methylamino-2,3-dihydro-5-phenyl-1H-1,4-benzodiazepin-2-one-1-acetic acid as a clear glass.

1HNMR consistent with structure.

Mass calc for C23H26N3O5: 424.1872 found: 424.1909

EXAMPLE 27

N-[[3-[(2-amino-3-mercapto-1-oxopropyl) methylamnino]-2,3-dihydro-2-oxo-5-phenyl-1H -1, 4-benzodiazepin-1-yl]acetyl]-L-methionine (27)

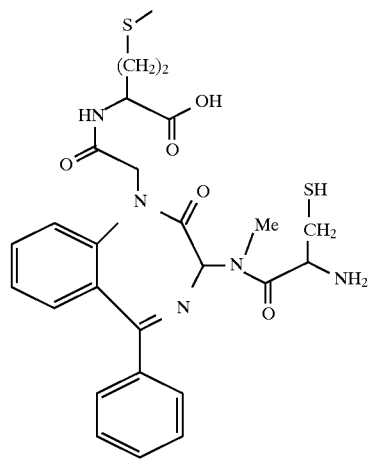

The title compound was prepared using the procedure of Example 9 in which 3-(tert-butoxycarbonyl)methylamino-2,3-dihydro-5-phenyl-1H-1,4-benzodiazepin-2-one-1-acetic acid (675 mg, 1.6 mmol) was coupled to L-methionine resin (1.5 gms, 0.71 mmol/gm) with BOP (710 mg, 1.6 mmol), HOBt (220 mg, 1.6 mmol), and NMM (180 ul, 1.6 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). Purification of 107 mg of the crude material yielded the two diastereomers 27A (27 mg) and 27B (15 mg).

Mass (FAB, M+H$^+$) calc: 558.2 found:558.3 (27A), 558.3 (27B).

EXAMPLE 28

N-[[3-[(2-amino-3-mercapto-1-oxopropyl)amino]-2,3-dihydro-2-oxo-5phenyl-1H-1,4-benzodiazepin-1-yl]acetyl]-L-methionine (28)

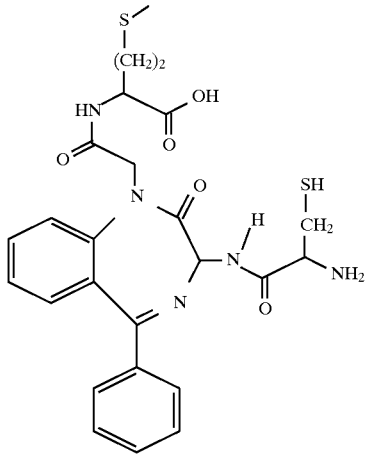

The title compound was prepared using the procedure of Example 9 in which 3-(tert-butoxycarbonyl)amino-2,3-dihydro-5-phenyl-1H-1,4-benzodiazepin-2-one-1-acetic acid (1.3 gm, 3.2 mmol) was coupled to L-methionine resin (1.5 gms, 0.71 mmol/gm) with BOP (1.4 gm, 3.2 mmol), HOBt (430 mg, 1.6 mmol), and NMM (350 ul, 3.2 mmol). Again, after deprotection and washing steps, Fmoc-L-(S-trityl) cysteine (2.5 gm, 4.7 mmol) was coupled using BOP (1.9 gm, 4.3 mmol), HOBt (600 mg, 4.3 mmol), and NMM (500 ul, 4.3 mmol). Purification of 107 mg of the crude material yielded the two diastereomers 28A (38 mg) and 28B (14 mg).
Mass (electrospray, M+H$^+$) calc: 544.2 found:544.8 (28A), 544.8 (28B).

EXAMPLE 29

N-[[3-[(3-mercapto-1-oxopropyl)methylamino]-2,3-dihydro-2-oxo-5-phenyl-1H-1,4-benzodiazepin-1-yl]acetyl]-L-methionine (28)

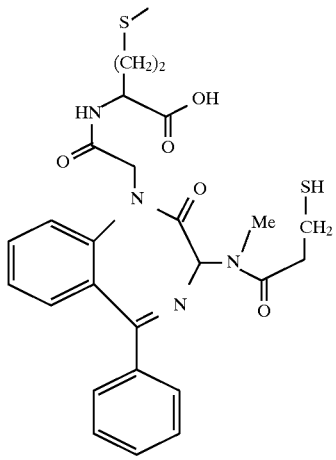

The title compound was prepared using the procedure of Example 9 in which 3-(tert-butoxycarbonyl)methylamino-2,3-dihydro-5-phenyl-1H-1,4-benzodiazepin-2-one-1-acetic acid (0.45 gm, 1.1 mmol) was coupled to L-methionine resin (1.0 gms, 0.71 mmol/gm) with BOP (0.47 gm, 1.1 mmol), HOBt (150 mg, 1.1 mmol), and NMM (120 ul, 1.1 mmol). Again, after deprotection and washing steps, (S-methylbenzyl)propionic acid (0.6 gm, 2.8 mmol) was coupled using BOP-CL (0.8 gm, 3.1 mmol) and DIPEA (1.09 ml, 6.2 mmol). Purification of 150mg of the crude material yielded the two diastereomers as an unseparable mixture 29A+B (9.5 mg).

Mass (electrospray, M+H$^+$) calc: 543.2 found:543.3 (29A+B).

EXAMPLE 30

N-[[3-[(2-amino-3-mercapto-1-oxopropyl)amino]-2,3-dihydro-2-oxo-5-phenyl-1H-1,4-benzodiazepin-1-yl]acetyl]-L-serine (30)

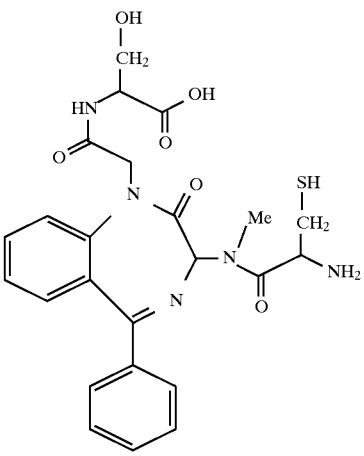

The title compound was prepared using the procedure of Example 9 in which 3-(tert-butoxycarbonyl)methylamino-2,3-dihydro-5-phenyl-1H-1,4-benzodiazepin-2-one-1-acetic acid (0.47 gm, 1.1 mmol) was coupled to L-(O-benzyl) serine resin (0.8 gms, 0.92 mmol/gm) with BOP (0.49 gm, 1.1 mmol), HOBt (150 mg, 1.1 mmol), and NMM (120 ul, 1.1 mmol). Again, after deprotection and washing steps, Fmoc-L-(S-trityl) cysteine (1.65 gm, 2.8 mmol) was coupled using BOP-Cl (0.8 gm, 3.1 mmol) and DIPEA (1.09 ml, 6.2 mmol). Purification of 160 mg of the crude material yielded the two diastereomers 30A (14 mg) and 30B (12 mg).

Mass (electrospray, M+H$^+$) calc: 514.1 found:513.5 (30A), 513.5 (30B).

EXAMPLE 31

N-[[3-[(2-amino-3-mercapto-1-oxopropyl) methylamino]-2,3-dihydro-2-oxo-5-phenyl-1H-1,4-benzodiazepin-1-yl]acetyl]-L-leucine (31)

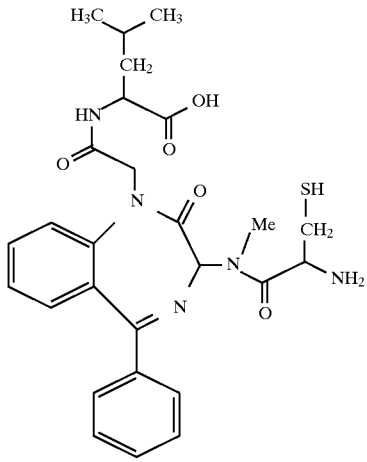

The title compound was prepared using the procedure of Example 9 in which 3-(tert-butoxycarbonyl)methylamino-2,3-dihydro-5-phenyl-1H-1,4-benzodiazepin-2-one-1-acetic acid (0.45 gm, 1.1 mmol) was coupled to L-leucine resin (1.5 gms, 0.47 mmol/gm) with BOP (0.47 gm, 1.1 mmol), HOBt (140 mg, 1.1 mmol), and NMM (120 ul, 1.1 mmol). Again, after deprotection and washing steps, Fmoc-L-(Strityl) cysteine (1.65 gm, 2.8 mmol) was coupled using BOP-Cl (0.8 gm, 3.1 mmol) and DIPEA (1.09 ml, 6.2 mmol). Purification of 86 mg of the crude material yielded the two diastereomers 31A (16 mg) and 31B (15 mg).
Mass (electrospray, M+H$^+$) calc: 540.2 found:540.3 (31A), 540.3 (31B).

EXAMPLE 32

N-[[3-[(2-acetylamino-3-mercapto-1-oxopropyl) methylamino]-2,3-dihydro-2-oxo-5-phenyl-1H-1,4-benzodiazepin-1-yl]acetyl]-L-methionine (32)

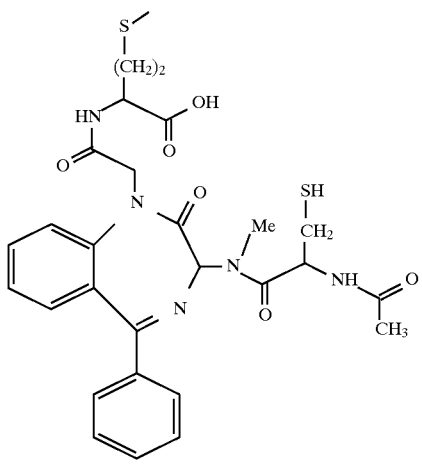

The title compound was prepared using the procedure of Example 9 in which the synthesis of Example 27 was conducted, and the amino-terminus acetylated via treatment with acetic anhydride (5%) in 5% NMM/DCM for 5 min. Purification of 204 mg of the crude material yielded the two diastereomers 32A (30 mg) and 32B (36 mg).

Mass (electrospray, M—H$^+$) calc: 598.2 found:598.1 (32A), 598.1 (32B).

EXAMPLE 33

N-[[3-[(2-amino-3-mercapto-1-oxopropyl) methylamino]-2,3-dihydro-2-oxo-5phenyl-1H-1,4-benzodiazepin-1-yl]acetyl]-L-methionine amide (33)

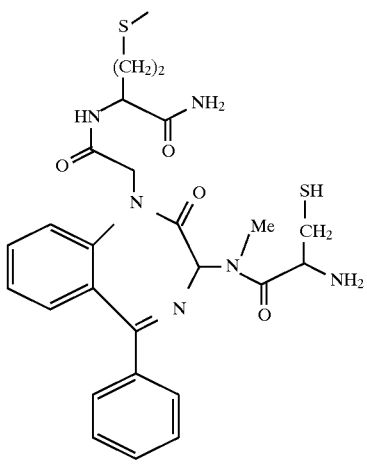

The title compound was prepared using the procedure of Example 9 in which Boc-L-methionine (0.6 gm, 2.4 mmol) was coupled to MBHA-resin (1.5 gm, 0.53 mmol/gm) using BOP (0.33 gm, 2.4 mmol), HOBt (0.26 gm, 2.4 mmol), and NMM (130 µl, 2.4 mmol). Following suitable deprotection and washing steps, 3-(tert-butoxycarbonyl)methylamino-2,3-dihydro-5-phenyl-1H-1,4-benzodiazepin-2-one-1-acetic acid (0.5 mg, 1.2 mmol) was coupled with BOP (0.53 mg, 1.2 mmol), HOBt (160 mg, 1.2 mmol), and NMM (130 µl, 1.2 mmol). Again, after deprotection and washing steps, Fmoc-L-(S-trityl) cysteine (2.5 gm, 4.7 mmol) was coupled using BOP-Cl (1.2 gm, 4.7 mmol) and DIPEA (1.6 ml, 9.4 mmol). Purification of 300 mg of the crude material yielded the two diastereomers 33A (43 mg) and 33B (42 mg).

Mass (electrospray, M—H$^+$) calc: 557.2 found:557.9 (33A), 556.9 (33B).

EXAMPLE 34

N-[[3-[(2-amino-3-mercapto-1-oxopropyl)methylamino]-2,3-dihydro-2-oxo-5-phenyl-1H-1,4-benzodiazepin-1-yl]acetyl]-L-phenylalanine (34)

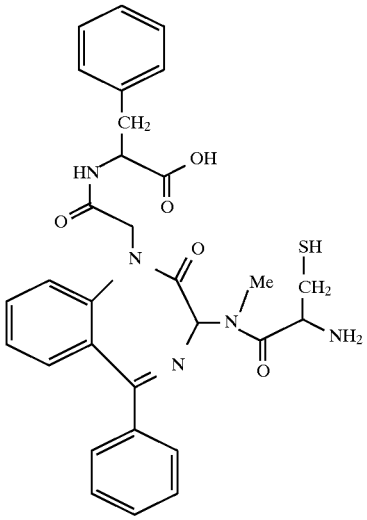

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-phenylalanine resin. Again, after deprotection and washing steps, Fmoc-L-(S-trityl) cysteine was coupled as above. Purification of 106 mg of the crude material yielded the two diastereomers 34A (39 mg) and 34B (32 mg).
Mass (electrospray, M+H$^+$) calc: 574.2 found:574.3 (34A), 574.3 (34B).

EXAMPLE 35

N-[[3-[(2-amino-3-mercapto-1-oxopropyl)methylamino]-2,3dihydro-2-oxo-5-phenyl-1H-1,4-benzodiazepin-1-yl]acetyl]-L-alanine (35)

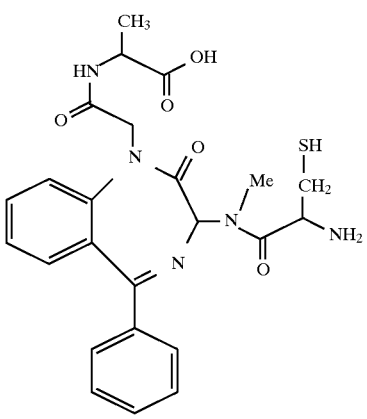

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-alanine resin. Again, after deprotection and washing steps, Fmoc-L-(S-trityl) cysteine was coupled as above. Purification of 116 mg of the crude material yielded the two diastereomers 35A (26 mg) and 35B (28 mg).

Mass (electrospray, M+H$^+$) calc: 498.2 found: 498 (35A), 498 (35B).

EXAMPLE 36

N-[[3-[(2-amino-3-mercapto-1-oxopropyl)methylamino]-2,3-dihydro-2-oxo-5-phenyl-1H-1,4-benzodiazepin-1-yl]acetyl]-L-proline (36)

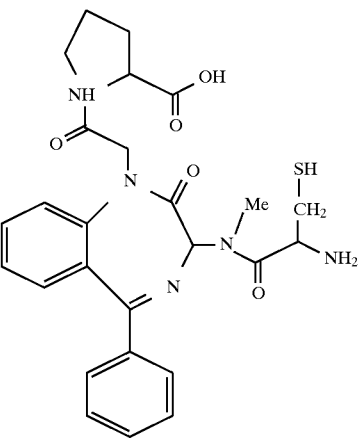

The title compound was prepared using the procedure of Example 9 in which 3-(tert-butoxycarbonyl)methylamino-2,3-dihydro-5phenyl-1H-1,4-benzodiazepin-2-one-1-acetic acid was coupled to L-alanine resin. Again, after deprotection and washing steps, Fmoc-L-(S-trityl) cysteine was coupled as above. Purification of 114 mg of the crude material yielded the two diastereomers 36A (28 mg) and 36B (27 mg).

Mass (electrospray, M+H$^+$) calc: 524.2 found: 524.3 (36A), 524.3 (36B).

EXAMPLE 37

N-[[3-(2-Amino-3-mercapto-1-oxopropyl)methylamino]-2,3-dihydro-2-oxo-5-phenyl-1H-1,4-benzodiazepin-1-yl] acetyl]-L-methionine methyl ester (37)

Scheme 5

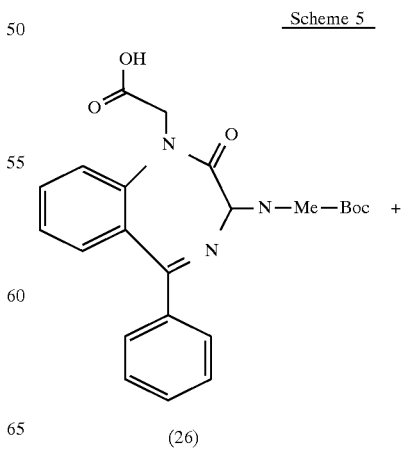

(26)

Scheme 5

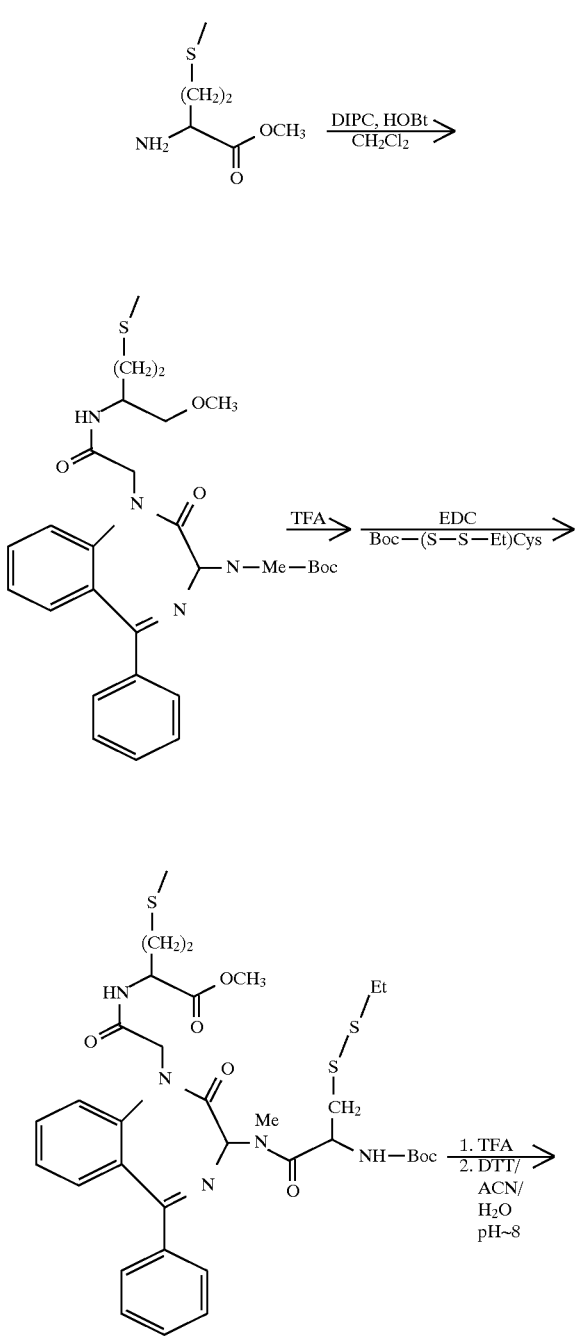

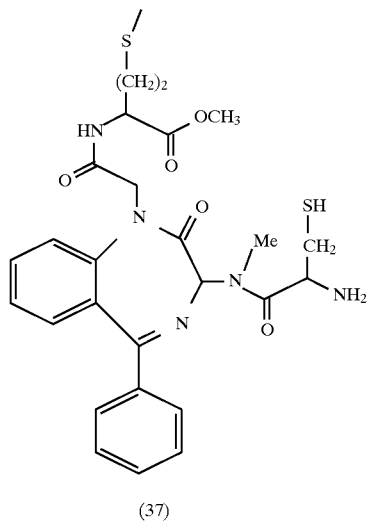

(37)

3-(tert-Butoxycarbonyl)methylamino-2,3-dihydro-5-phenyl-1H-1,4-benzodiazepin-2-one-1-acetic add (5.5 mmol, 2.3 gm), L-methionine methyl ester (16.5 mmol, 2.7 gm, Sigma), diisopropykarbodiimde (DIPC, 6.6 mmol, 1.04 ml), and HOBt (6.6 mmol, 0.9 gm) were combined in DCM (20 ml). After 10 hrs, the reaction was diluted (DCM, 90 ml), extracted (0.1 N $H_2SO_4$ then brine), dried ($MgSO_4$), and concentrated to yield 3.5 gm (113%) of crude N-[[3-(tert-butoxycarbonyl)methylamino-2,3-dihydro-2-oxo-5-phenyl-1H-1, 4-benzodiazepin-1-yl] acetyl]-L-methionine methyl ester.

0.75 gm of this material was deprotected (30% TFA, 30 ml, 3 hrs), concentrated, neutralized via extraction in 100 ml EtOAc (saturated $NaHCO_3$ then brine), and purified. (silica, DCM/MeOH/$Et_3N$ 99:1:0.2%) to yield N-[[3-amino-2,3-dihydro-2-oxo-5-phenyl-1H-1, 4-benzodiazepin-1-yl] acetyl]-L-methionine methyl ester as a clear oil (0.55 gm, 89%).

Reaction of this material with Boc-(Sethylthio)-cysteine (3.6 mmol, 0.99 gm), 1-(3-dimethylaminopropyl)-3-ethylcarbodiimide hydrochloride (EDC, 3.6 mmol, 0.68 gm), and HOBT (1.2 mmol, 0.16 gm) in DMF (10 ml, 12 hrs) was followed by concentration, aqueous workup and chromatography (as above), to yield N-[[3-[(2-(tert-butoxycarbonyl)amino-3-mercapto-1-oxopropyl)methylamino]-2,3-dihydro-2-oxo-5-phenyl-1H-1,4-benzodiazepin-1-yl]acetyl]-L-methionine methyl ester (0.82 gm, 93%). After removal of the Boc- (30% TFA as above) and ethylthio- (60 mg dithiothreitol, 20 ml 50% ACN/$H_2O$, pH 7.5) protecting groups, N-[[3-(2-amino-3-mercapto-1-oxopropyl) methylamo]-2,3-dihydro-2-oxo-5-phenyl-1H-1, 4-benzodiazepin-1-yl] acetyl]-L-methionine methyl ester was purified by HPLC (Vydac C18, ACN/H₂O/TFA) which resolved each of diastereomers possessing opposite configuration at C-3. These isomers were designated A and B as before (see Example 9). Purification of 120 mg of the crude material yielded the two diastereomers 37A (26 mg) and 37B (30 mg).

Mass (electrospray, M+H⁺) calc: 572.2 found: 572.3 (37A), 572.3 (37B).

EXAMPLE 38

N-[[3-(2-Amino-3-ethylthiomercapto-1-oxopropyl) methylamino]-2,3-dihydro-2-oxo-5-phenyl-1H-1, 4-benzodiazepin-1-yl] acetyl]-L-methionine methyl ester (38)

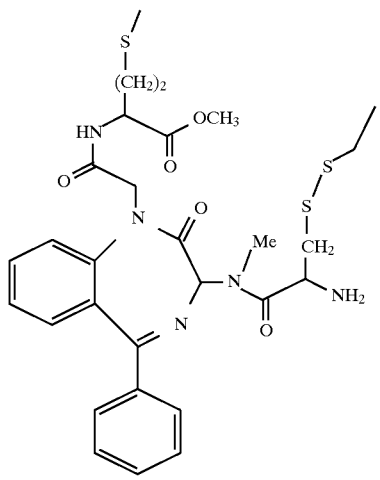

The title compound was prepared using the procedure of Example 37 in which an identical procedure was performed, omitting the step for removal of the ethylthio protecting group. Purification of 140 mg of the crude material yielded the two diastereomers 38A (30 mg) and 38B (30 mg).

Mass (electrospray, M+H⁺) calc: 632.3 found: 631.9 (38A), 631.9 (38B).

EXAMPLE 39

N-[[3-(2-Amino-3-mercapto-1-oxopropyl) methylamino]-2,3-dihydro-2-oxo-5-phenyl-1H-1, 4-benzodiazepin-1-yl] acetyl]-L-methionine ethyl ester (39)

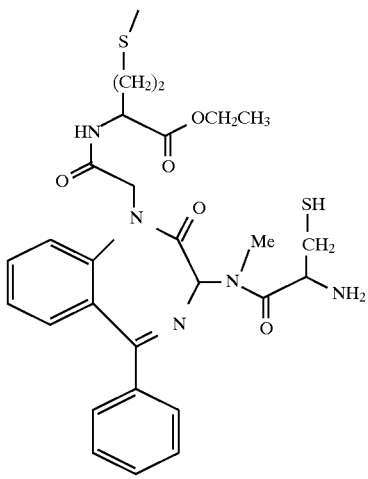

The title compound was prepared using the procedure of Example 37 in which 3-(tert-butoxycarbonyl)methylamino-2,3-dihydro-5-phenyl-1H-1,4-benzodiazepin-2-one-1-acetic acid (0.85 mmol, 0.36 gm), L-methionine ethyl ester (2.55 mmol, 0.45 gm), DIPC (1.02 mmol, 0.16 ml), and HOBt (1.02 mmol, 0.14 gm) were combined in the first step. Subsequent reactions to yield the title compound were completed in a manner similar to that shown in Example 37. Purification of 150 mg of the crude material yielded the two diastereomers 39A (21 mg) and 39B (22 mg).
Mass (electrospray, M+H⁺) calc: 586.3 found: 585.9 (39A), 585.9 (39B).

EXAMPLE 40

N-[[3-(2-Amino-3-ethylthiomercapto-1-oxopropyl) methylamino]-2,3-dihydro-2-oxo-5-phenyl-1H-1, 4-benzodiazepin-1-yl] acetyl]-L-methionine ethyl ester (40)

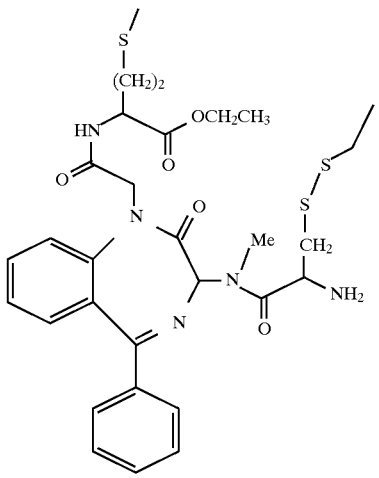

The title compound was prepared using the procedure of Example 37 in which an identical procedure was performed, omitting the step for removal of the ethylthio protecting group. Purification of 150 mg of the crude material yielded the two diastereomers 40A and 40B.

Mass (electrospray, M+H$^+$) calc: 646.3 found: 645.7 (40A), 645.7 (40B).

EXAMPLE 41

N-[[3-(2-Amino-3-mercapto-1-oxopropyl) methylamino]-2,3-dihydro-2-oxo-5phenyl-1H-1, 4-benzodiazepin-1-yl] acetyl]-L-methionine cyclohexyl ester (41)

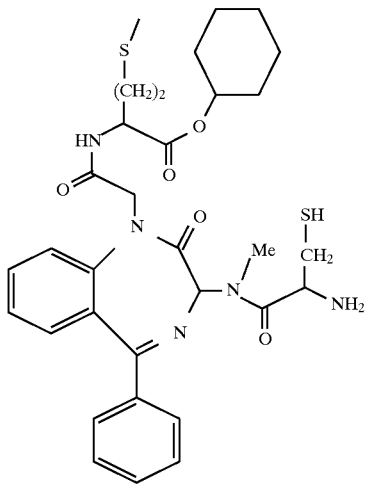

L-methionine cyclohexyl ester was prepared by combining Boc-L-methionine (2.5 g, 10 mmol), cyclohexanol (3.12 ml, 30 mmol), DIPC (1.9 ml, 12 mmol) and 4-dimethylaminopyridine (DMAP, 0.12 g, 1.0 mmol) in DCM, followed by aqueous workup, flash chromatography (silica, hexane/EtOAc (4:1)), removal of the Boc protecting group (4N HCl/dioxane, 2 h), and basic workup (EtOAc/sat. Na$_2$CO$_3$).

The title compound was prepared using the procedure of Example 37 in which 3-(tert-butoxycarbonyl)methylamino-2,3-dihydro-5-phenyl-1H-1,4-benzodiazepin-2-one-1-acetic acid (3.3 mmol, 1.4 gm), L-methionine cyclohexyl ester (6.6 mmol, 1.53 gm), DIPC (3.96 mmol, 0.62 ml), and HOBt (3.96 mmol, 0.54 gm) were combined in the first step. Subsequent reactions to yield the title compound were completed in a manner similar to that shown in Example 37. Purification of 150 mg of the crude material yielded the two diastereomers 41A (35 mg) and 41B (37 mg).

Mass (electrospray, M+H$^+$) calc: 640.3 found: 640.1 (41A), 640.1 (41B).

The following examples were prepared similarly to above syntheses.

EXAMPLE 42

N-[[3-[(2-ethylamino-3-mercapto-1-oxopropyl) methylamino]-2,3-dihydro-2-oxo-5-phenyl-1H-1,4-benzodiazepin-1-yl]acetyl]-L-methionine (42)

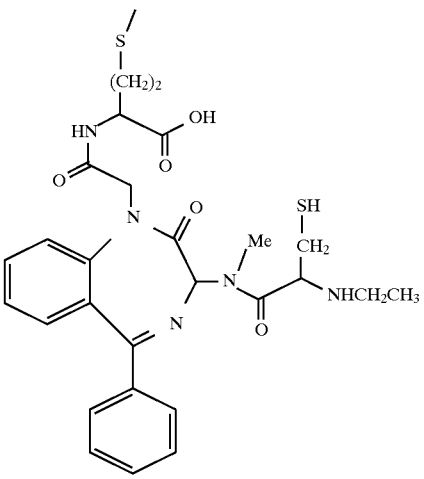

The title compound was prepared as above with the addition of a step following deprotection of the N-terminal Boc-residue on cysteine. This step allowed attachment of an ethyl moiety on nitrogen through reductive amination using acetaldehyde and sodium cyanoborohydride in DMF/1% ACOH. The molecule was then cleaved, purified and analyzed as above.

EXAMPLE 43

N-[[3-[(2-methylthiazolidine-4-carboxyl) methylamino]-2,3-dihydro-2-oxo-5-phenyl-1H-1,4-benzodiazepin-1-yl]acetyl]-L-methionine (43)

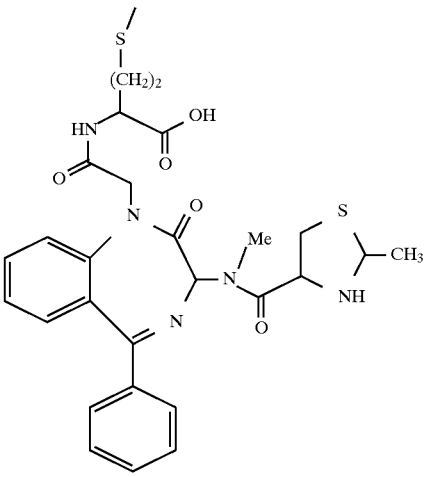

The title compound was prepared by coupling N-Boc-2-methyl thiazolidine-4-carboxylic acid instead of cysteine. Purified and analyzed as above.

EXAMPLE 44

N-[[3-[(2-Amino-3-mercapto-1-oxopropyl)
methylamino]-2,3-dihydro-2-oxo-5phenyl-1H-1,4-
benzodiazepin-1-yl]acetyl]-L-cysteine (44)

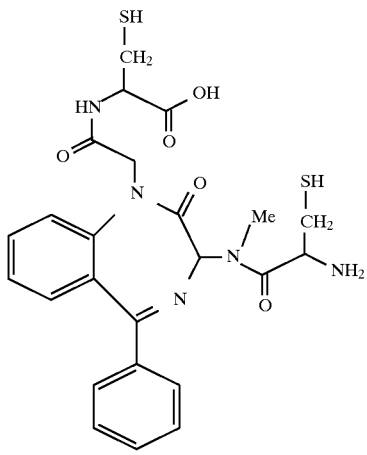

The title compound was prepared following the protocol shown in Example 9, except S(4-methylbenzyl)-N-Boc-L-cysteine-linked Merrifield resin was used.

EXAMPLE 45

N-[[3-[(2-amino-3-hydroxy-1-oxopropyl)
methylamino]-2,3-dihydro-2-oxo-5-phenyl-1H-1,4-
benzodiazepin-1-yl]acetyl]-L-methionine (45)

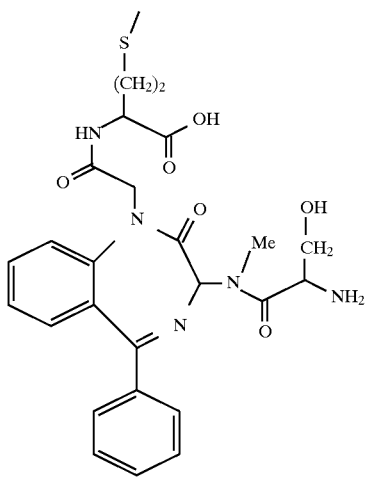

The title compound was prepared following the protocol shown in Example 9, except O—(tert-butyl)—N—Boc—L-serine was used in place of cysteine.

EXAMPLE 46

N-[[3-[(2-amino-3-mercapto-1-oxopropyl)
methylamino]-2,3-dihydro-2-oxo-5-phenyl-1H-1,4-
benzodiazepin-1-yl]acetyl]-L-leucine tetrazole (46)

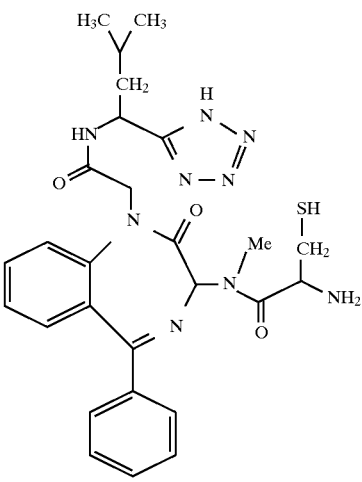

The title compound was prepared using a similar procedure to that shown for Example 37, except that tetrazole derivative of leucine, denoted as L-leucine tetrazole, was used instead of a carboxy-terminal ester. The synthesis of this material is shown below in Scheme 6.

Scheme 6

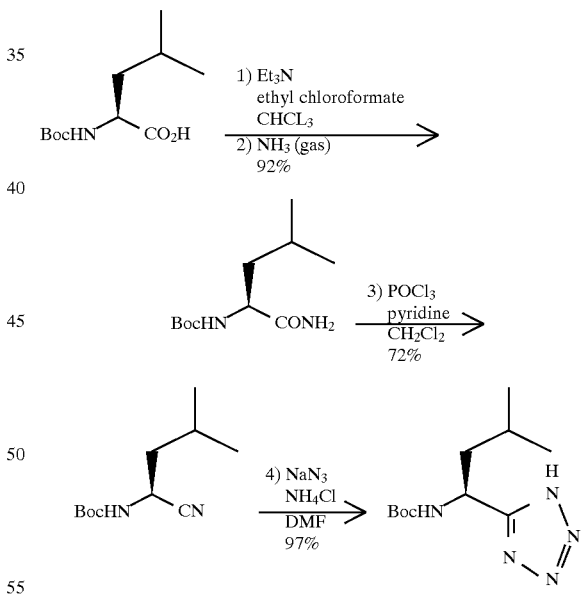

steps 1 and 2)

The N-Boc-L-leucine monohydrate (10 g, 40.2 mmol) and triethylamine (5.6 mL, 40.2 mmol) were dissolved in 50 mL dry chloroform and cooled to 0° C. Ethyl chloroformate (3.84 mL, 40.2 mmol) was add dropwise and stirred for 10 minutes. 40 mL dry chloroform saturated with ammonia was added, stirred for 15 minutes, then warmed to ambient temperature and stirred for 1hr. Evaporation of the solvent gave the crude product which was washed with aqueous NaHCO$_3$ then with water. The product was collected by filtration, washed with water, and dried by vacuum to yield 8.53g (37.1 mmol, 92% yield) of the desired amide as a white solid. $R_f$=0.36 (75%EtOAc/hexanes). $^1$H NMR (300 MHz, CD$_3$OD): 4.05 (1H, br t), 1.70 (1H, m), 1.50 (2H, m), 1.45 (9H, s), 0.95 (6H, dd).

step 3)

The N-Boc-L-leucine amide (6.45g, 28 mmol) was dissolved in 40 mL dry pyridine and cooled to −5 ° C. Phosphorous oxychloride (3.66 mL, 39.3 mmol), in 6 mL dry methylene chloride was added dropwise and the solution was stirred at −5° C. for 1 hr. Ice water was added to the reaction and the nitrile was extracted with EtOAc (3×200 mL). The combined organics were washed successively with 100 mL water, 1N HCl (2×100 mL), aq. NaHCO$_3$ (2×100 mL) and 100 mL water. The organics were dried over MgSO$_4$ and concentrated to yield 4.27g (20.1 mmol, 72% yield) as a light yellow solid. $R_f$=0.79 (75%EtOAc/hexanes). $^1$H NMR (300 MHz, CD$_3$OD): 4.45 (1H, br t), 1.75 (1H, m), 1.65 (2H, dd), 1.45 (9H, s), 0.95 (6H, dd). IR: 2240 cm$^{-1}$.

step 4)

The N-Boc-L-leucine nitrile (1.65g, 7.78 mmol), sodium azide (0.53g, 8.15 mmol) and ammonium chloride (0.46g, 8.6 mmol) were dissolved in 7 mL dry DMF and the flask was placed in a 105 ° C. oil bath. After 7 hr., sodium azide (0.26g, 4.0 mmol) and ammonium chloride (0.27g, 5.0 mmol) were added and the solution was stirred overnight at 105° C. Cooled and concentrated. Flash chromatography (7% MeOH in methylene chloride ramping to 25% MeOH in methylene chloride) provided 1.93g (7.56 mmol, 97% yield) as a white solid. $R_f$=0.33 (10%MeOH/methylene chloride). $^1$H NMR (300 MHz, CD$_3$OD): 5.90 (1H, s), 5.15 (1H, br t), 1.60–1.90 (3H, m), 1.40 (9H, s), 0.95 (6H, dd).

preparation of the title compound:

The N-Boc-L-leucine tetrazole (0.45g, 1.75 mmol) was suspended in 5 mL 4N HCl/dioxane. Dissolves is 10 min. Concentrated after 2 hr. to a tan foam. Dissolved in 5 mL water and taken to pH=9 with 1N NaOH. The resulting free-amine was concentrated to a white solid and used directly in the coupling reaction (below). $R_f$=0.20 (25%MeOH/methylene chloride). $^1$H NMR (300 MHz, CD$_3$OD): 4.40 (1H, br m), 3.65 (1H, m), 1.90 (1H, m), 1.75 (1H, m), 1.25 (1H, m) 0.95 (6H, dd).

Coupling reactions were identical to those describe in Example 37. The leucine tetrazole was suspended in 3 mL CH$_2$Cl$_2$ - does not dissolve. 3-(tert-Butoxycarbonylmethylamino-2,3-dihydro-5-phenyl-1H-1,4-benzodiazepin-2-one-1-acetic acid (0.343g, 0.81 mmol), HOBT (0.17g, 1.26 mmol) and DIPC (1.1 mL, 1.1 mmol) were added and the solution was stirred overnight. Workup and coupling of the cysteine was identical to the procedure for Example 37. Purification of 50 mg of the crude material yielded the two diastereomers 46A (7 mg) and 46B (8 mg).

Mass (electrospray, M+H$^+$) calc: 564.2 found: 564.3 (46A), 564.3 (46B).

EXAMPLE 47

N-[[3-[(2-amino-3-mercapto-1-oxopropyl) methylamino]-2,3-dihydro-2-oxo-5-phenyl-1H-1,4-benzodiazepin-1-yl]acetyl]-L-methionine tetrazole (47)

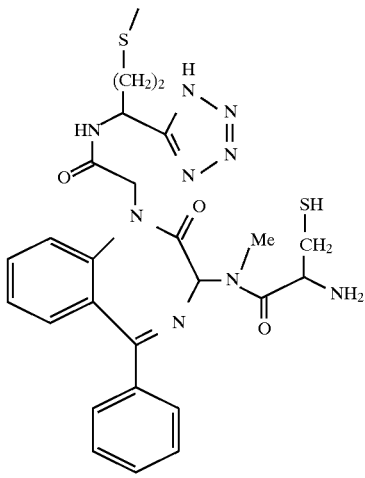

Synthesis of the title material was identical to that describe in Example 46, substituting methionine for leucine. Purification of 50 mg of the crude material yielded the two diastereomers 47A (5 mg) and 47B (5 mg).
Mass (electrospray, M+H$^+$) calc: 582.2 found: 582.4 (47A), 582.4 (47B).

EXAMPLE 48

N-[[3-[(2-amino-3-mercapto-1-oxopropyl) methylaminol-2,3-dihydro-2-oxo-5-phenyl-1H-1,4-benzodiazepin-1-yl]propionyl]-L-methionine (48)

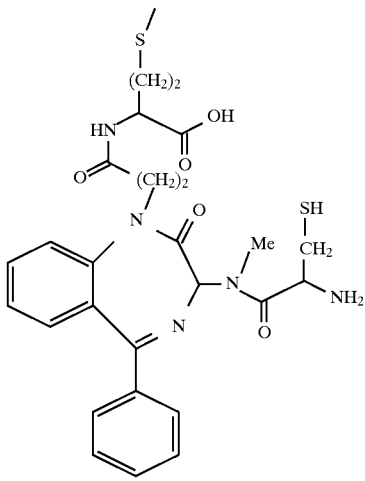

The title compound was prepared using a procedure similar to that described for Example 9, substituting the acetyl modification at the N-1 of the benzodiazepine with a propionyl moiety. This was accomplished using a modification of the protocol used for the preparation of compound 26. Purification of 105 mg of the crude material yielded the two diastereomers 48A (20 mg) and 48B (18 mg).
Mass (electrospray, M+H$^+$) calc: 572.2 found: 573.1 (48A), 573.1 (48B).

EXAMPLE 49

N-[[3-[(2-amino-3-mercapto-1-oxopropyl)
methylamino]-2,3-dihydro-2-oxo-5-phenyl-1H-1,4-
benzodiazepin-1-yl]acetyl]-(α-methyl)-methionine
(49)

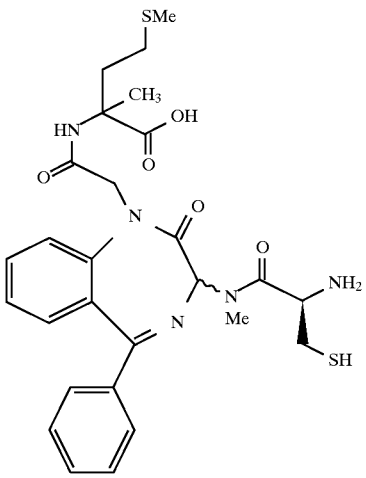

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to (α-methyl)-methionine resin. Again, after deprotection and washing steps, Fmoc-L-(S-trityl) cysteine was coupled as above. Purification of 101 mg of the crude material yielded the product, 49A+B, as an unseparable mixture of diasteriomers (16 mg). Mass (electrospray, $M+H^+$) calc: 572.2 found: 572.2 (49A+B).

EXAMPLE 50

N-[[3-[(2-amino-3-mercapto-1-oxopropyl)
methylamino]-2,3-dihydro-2-oxo-5-phenyl-1H-1,
4benzodiazepin-1-yl]acetyl]-L-valine (50)

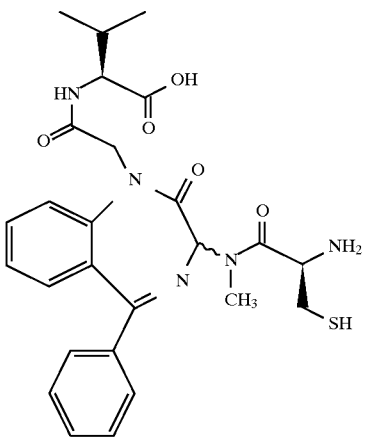

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-valine resin. Again, after deprotection and washing steps, Fmoc-L-(S-trityl) cysteine was coupled as above. Purification of 79 mg of the crude material yielded the two diastereomers 50A (15 mg) and S0B (11 mg).

Mass (electrospray, $M+H^+$) calc: 526.6 found: 526.2 (SOA), 526.2 (50B).

EXAMPLE 51

N-[[3-[(2-amino-3-mercapto-1-oxopropyl)
methylamino]-2,3-dihydro-2-oxo-5-phenyl-1H-1,4-
benzodiazepin-1-yl]acetyl]-L-threonine (51)

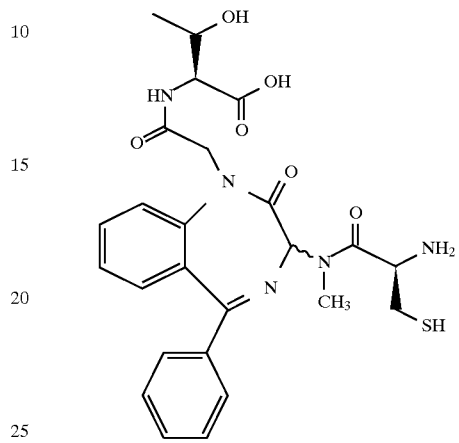

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-threonine resin. Again, after deprotection and washing steps, Fmoc-L- (S-trityl) cysteine was coupled as above. Purification of 116 mg of the crude material yielded the two diastereomers 51A (22 mg) and 51B (23 mg).
Mass (electrospray, $M+H^+$) calc: 528.6 found: 528.2 (51A), 528.2 (51B).

EXAMPLE 52

N-[[3-[(2-amino-3-mercapto-1-oxopropyl)
methylamino]-2,3-dihydro-2-oxo-5-phenyl-1H-1,4-
benzodiazepin-1-yl]acetyl]-L-glutamine (52)

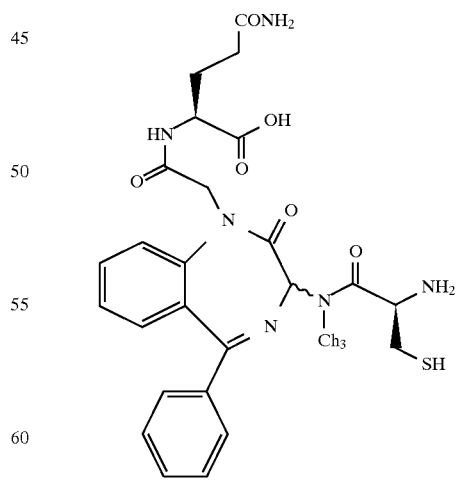

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-glutamine resin. Again, after deprotection and washing steps, Fmoc-L-(Strityl) cysteine was coupled as above. Purification of 72 mg of the crude material yielded the two diastereomers 52A (14 mg) and 52B (13 mg).
Mass (electrospray, M+H$^+$) calc: 555.6 found: 555.2 (52A), 555.2 (52B).

EXAMPLE 53

N-[[3-[(2-amino-3-mercapto-1-oxopropyl) methylamino]-2,3-dihydro-2-oxo-5-phenyl-1H-1,4-benzodiazepin-1-yl]acetyl]-glycine (53)

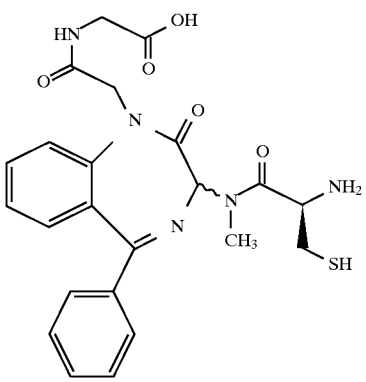

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to glycine resin. Again, after deprotection and washing steps, Fmoc-L-(S-trityl) cysteine was coupled as above. Purification of 96 mg of the crude material yielded the two diastereomers 53A (15 mg) and 53B (20 mg).
Mass (electrospray, M+H$^+$) calc: 484.6 found: 484.1 (53A), 484.3 (53B).

EXAMPLE 54

N-[[3-[(2-amino-3-mercapto-1-oxopropyl) methylamino]-2,3-dihydro-2-oxo-5-phenyl-1H-1,4-benzodiazepin-1-yl]acetyl]-L-tyrosine (54)

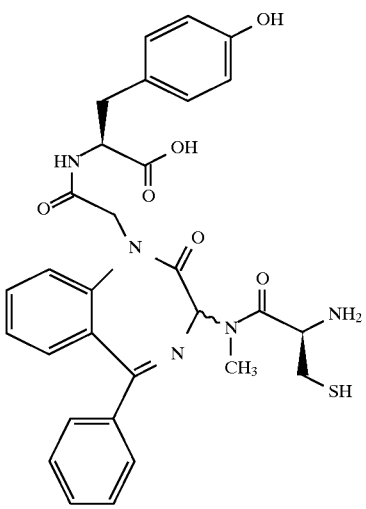

The title compound was prepared using the procedure of Example 9 in which 3-(tert-butoxycarbonyl)methylamino-2,3dihydro-5-phenyl-1H-1,4-benzodiazepin-2-one-1-acetic acid was coupled to L-(bromo-Z)tyrosine resin. Again, after deprotection and washing steps, Fmoc-L-(S-trityl) cysteine was coupled as above. Purification of 90 mg of the crude material yielded the two diastereomers 54A (14 mg) and 54B (22 mg).

Mass (electrospray, M+H$^+$) calc: 590.7 found: 590.2 (5), 590.2 (54B).

EXAMPLE 55

N-[[3-[(2-amino-3-mercapto-1-oxopropyl) methylamino]-2,3-dihydro-2-oxo-5-phenyl-1H-1,4-benzodiazepin-1-yl]acetyl]-L-isoleucine (55)

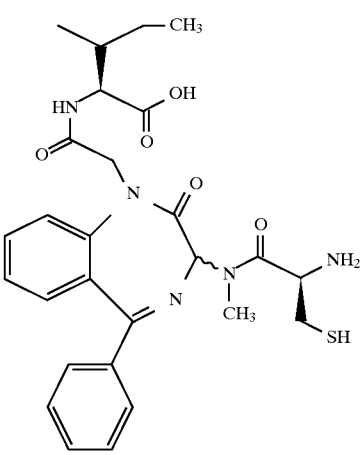

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-isoleucine resin. Again, after deprotection and washing steps, Fmoc-L-(S-trityl) cysteine was coupled as above. Purification of 112 mg of the crude material yielded the two diastereomers 55A (14 mg) and 55B (14 mg).

Mass (electrospray, M+H$^+$) calc: 540.7 found: 540.2 (55A), 540.2 (55B).

EXAMPLE 56

N-[[3-[(2-amino-3-mercapto-1-oxopropyl)
methylamino]-2,3-dihydro-2-oxo-5-phenyl-1H-1,4-
benzodiazepin-1-yl]acetyl]-L-tryptophane (56)

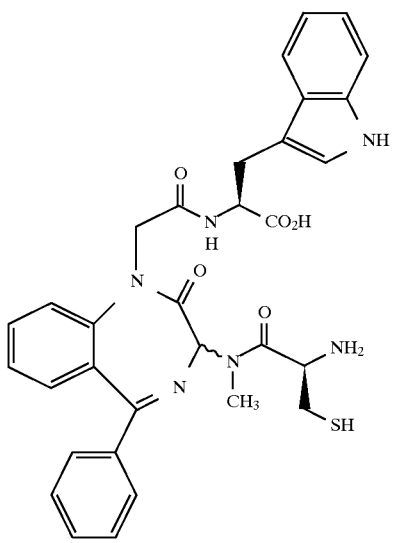

The title compound was prepared using the procedure of Example 9 in which 3-(tert-butoxycarbonyl)methylamino-2,3dihydro-5phenyl-1H-1,4-benzodiazepin-2-one-1-acetic acid was coupled to suitably protected L-tryptophane resin. Again, after deprotection and washing steps, Fmoc-L-(S-trityl) cysteine was coupled as above. Purification of 91 mg of the crude material yielded the two diastereomers 56A (7 mg) and 56B (2 mg).
Mass (electrospray, M+H$^+$) calc: 613.7 found: 613.2 (56A), 613.2 (56B).

EXAMPLE 57

N-[[3-[(2-amino-3-mercapto-1-oxopropyl)
methylamino]-2,3-dihydro-2-oxo-5-phenyl-1H-1,4-
benzodiazepin-1-yl]acetyl]-(β-cyclohexyl)-L-alanine (57)

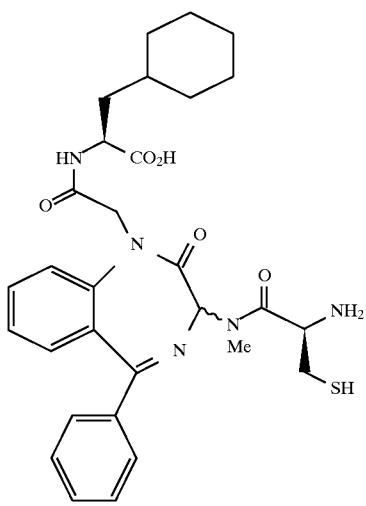

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to (β-cyclohexyl)-L-alanine resin. Again, after deprotection and washing steps, Fmoc-L-(S-trityl) cysteine was coupled as above. Purification of 82 mg of the crude material yielded the two diastereomers 57A (9 mg) and 57B (10 mg).

Mass (electrospray, M+H$^+$) calc: 580.3 found: 580.2 (57A), 580.2 (57B).

EXAMPLE 58

N-[[3-[(2-amino-3-mercapto-1-oxopropyl)
methylamino]-2,3-dihydro-2-oxo-5-phenyl-1H-1,4-
benzodiazepin-1-yl]acetyl]-(α-cyclohexyl)-glycine (58)

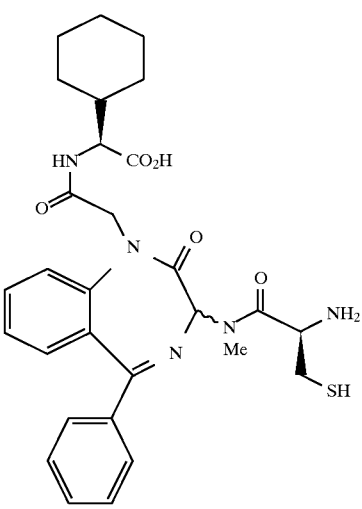

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to (α-cyclohexyl)-glycine resin. Again, after deprotection and washing steps, Fmoc-L-(S-trityl) cysteine was coupled as above. Purification of 107 mg of the crude material yielded the two diastereomers 58A (17 mg) and 58B (14 mg).

Mass (electrospray, M+H$^+$) calc: 567.3 found: 566.2 (58A), 566.2 (58B).

EXAMPLE 59

N-[[3-[-(2-amino-3-mercapto-1-oxopropyl)
methylamino]-2,3-dihydro-2-oxo-5-phenyl-1H-1,4-
benzodiazepin-1-yl]acetyl]-L-homo-phenylalanine
(59)

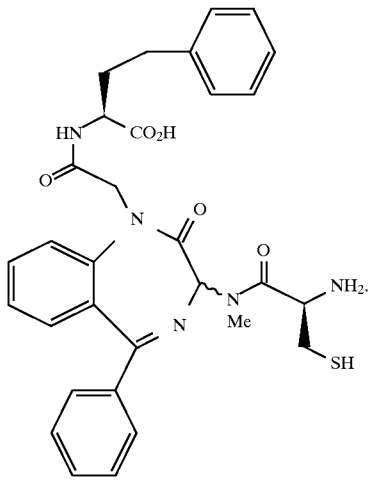

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-homo-phenylalanine resin. Again, after deprotection and washing steps, Fmoc-L-(S-trityl) cysteine was coupled as above. Purification of 84 mg of the crude material yielded the two diastereomers 59A (13 mg) and 59B (11 mg).

Mass (electrospray, M+H$^+$) calc: 588.4 found: 588.4 (59A), 588.4 (59B).

EXAMPLE 60

N-[[3-[(2-amino-3-mercapto-1-oxopropyl)
methylamino]-2,3-dihydro-2-oxo-5-phenyl-1H-1,4-
benzodiazepin-1-yl]acetyl]-L-4-fluorophenylalanine
(60)

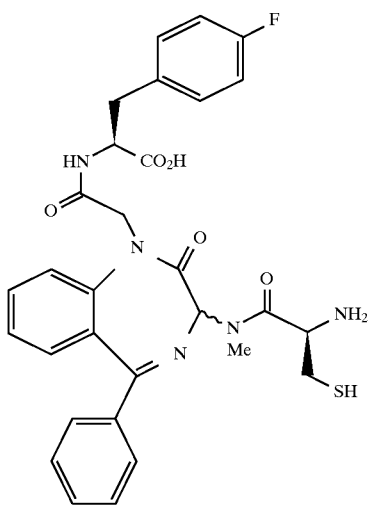

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-4-fluorophenylalanine resin. Again, after deprotection and washing steps, Fmoc-L-(S-trityl) cysteine was coupled as above. Purification of 53 mg of the crude material yielded the two diastereomers 60A (10 mg) and 60B (8 mg).

Mass (electrospray, M+H$^+$) calc: 592.4 found: 592.1 (60A), 592.1 (60B).

EXAMPLE 61

N-[[3-[(2-amino-3-mercapto-1-oxopropyl)
methylamino]-2,3-dihydro-2-oxo-5-phenyl-1H-1,4-
benzodiazepin-1-yl]acetyl]-(β-biphenyl)-L-alanine
(61)

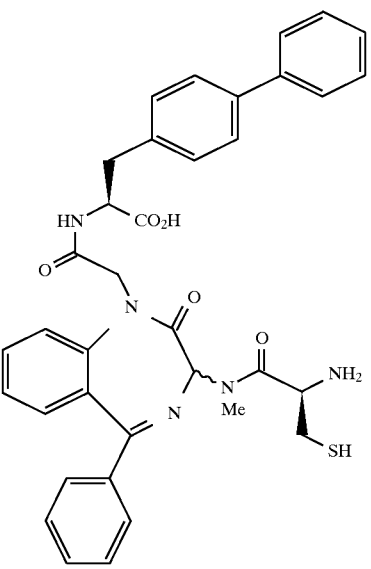

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to (β-biphenyl)-L-alanine resin. Again, after deprotection and washing steps, Fmoc-L-(S-trityl) cysteine was coupled as above. Purification of 59 mg of the crude material yielded the two diastereomers 61A (6 mg) and 61B (8 mg).

Mass (electrospray, M+H$^+$) calc: 650.5 found: 650.1 (61A), 650.1 (61B).

EXAMPLE 62

N-[[3-[(2-amino-3-mercapto-1-oxopropyl)methylamino]-2,3-dihydro-2-oxo-5-phenyl-1H-1,4benzodiazepin-1-yl]acetyl]-L-norleucine (62)

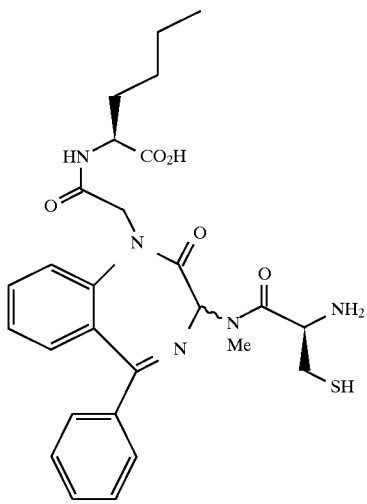

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to L-norleucine resin. Again, after deprotection and washing steps, Fmoc-L-(S-trityl) cysteine was coupled as above. Purification of 102 mg of the crude material yielded the two diastereomers 62A (24 mg) and 62B (22 mg).
Mass (electrospray, M+H$^+$) calc: 540.7 found: 540.1 (62A), 539.9 (62B).

EXAMPLE 63

N-[13-[(2-amino-3-mercapto-1-oxopropyl)amino]-2,3-dihydro-2-oxo-5-phenyl-1H-1,4-benzodiazepin-1-yl]acetyl]-(N-methyl)-L-methionine (63)

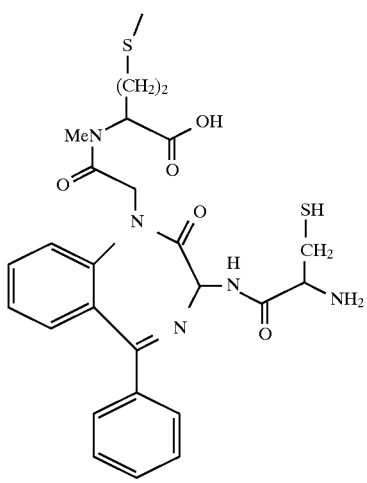

The title compound was prepared using the procedure of Example 9 in which 3-(tert-butoxycarbonyl)amino-2,3-dihydro-5-phenyl-1H-1,4-benzodiazepin-2-one-1-acetic acid was coupled to (N-methyl)-L-methionine resin. Again, after deprotection and washing steps, Fmoc-L-(S-trityl) cysteine was coupled as above. Purification of 100 mg of the crude material yielded the two diastereomers 63A (17 mg) and 63B (12 mg).
Mass (electrospray, M+H$^+$) calc: 558.2 found: 558 (63A), 558 (63B).

EXAMPLE 64

N-[[3-[(2-amino-3-mercapto-1-oxopropyl)methylamino]-2,3-dihydro-2-oxo-5-phenyl-1H-1,4-benzodiazepin-1-yl]acetyl]-(N-methyl)-L-methionine (64)

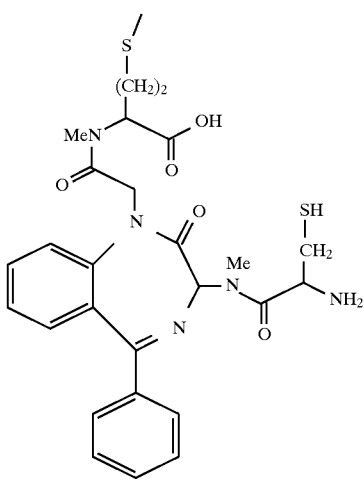

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to (N-methyl)-L-methionine resin. Again, after deprotection and washing steps, Fmoc-L-(S-trityl) cysteine was coupled as above. Purification of 107 mg of the crude material yielded the two diastereomers 64A (18 mg) and 64B (17 mg).
Mass (electrospray, M+H$^+$) calc: 572.2 found: 572 (64A), 572 (64B).

EXAMPLE 65

N-[[3-[(2-amino-3-mercapto-1-oxopropyl)methylamino]-2,3-dihydro-2-oxo-5-phenyl-1H-1,4-benzodiazepin-1-yl]acetyl]-(N-methyl)-glycine (65)

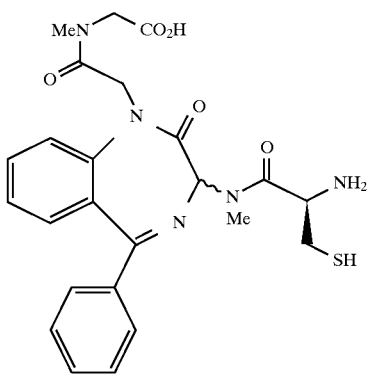

The title compound was prepared using the procedure of Example 9 in which 3-(tert-butoxycarbonyl)methylamino- 2,3-dihydro-5-phenyl-1H-1,4-benzodiazepin-2-one-1-acetic acid was coupled to (N-methyl)-glycine resin. Again, after deprotection and washing steps, Fmoc-L-(S-trityl) cysteine was coupled as above. Purification of 114 mg of the crude material yielded the two diastereomers 65A (13 mg) and 65B (12 mg).
Mass (electrospray, M+H$^+$) calc: 498.3 found: 498 (65A), 498.1 (65B).

EXAMPLE 66

N-[[3-[(2-amino-3-mercapto-1-oxopropyl) methylaminol-2,3-dihydro-2-oxo-5-phenyl-1H-1,4-benzodiazepin-1-yl]acetyl]-(N-benzyl)-glycine (66)

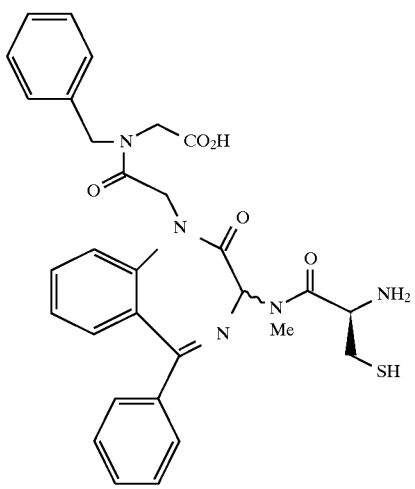

The title compound was prepared using the procedure of Example 9 in which 3-(tert-butoxycarbonyl)methylamino-2,3-dihydro-5-phenyl-1H-1,4-benzodiazepin-2-one-1-acetic acid was coupled to (N-benzyl)-glycine resin. Again, after deprotection and washing steps, Fmoc-L-(Strityl) cysteine was coupled as above. Purification of 55 mg of the crude material yielded the two diastereomers 66A (4 mg) and 66B (4 mg).
Mass (electrospray, M+H$^+$) calc: 574.3 found: 574.3 (66A), 574.3 (66B).

EXAMPLE 67

N-[[3-[(2-amino-3-mercapto-1-oxopropyl) methylamino]-2,3-dihydro-2-oxo-5-phenyl-7-chloro-1H-1,4-benzodiazepin-1-yl]acetyl]-L-methionine (67)

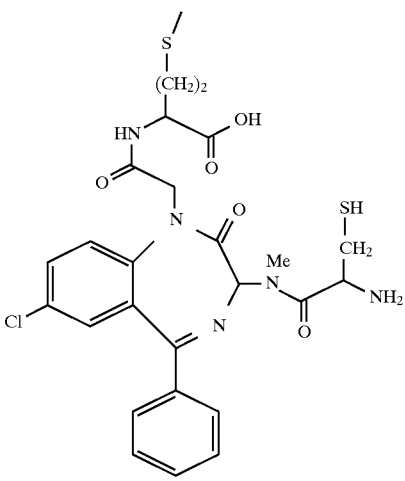

The title compound was prepared using the procedure of Example 9 in which 3-(tert-butoxycarbonyl)methylamino-2,3-dihydro-5-phenyl-7-chloro-1H-1,4-benzodiazepin-2-one-1-acetic acid (prepared in a manner analogous to that shown for the title compound of Example 22; substituting the addition of the 3-amino functionality via reaction at C-3 with trisyl azide to form the 3-azido analog, followed by standard reduction to the amine with triphenylphosphine/ THF/water) was coupled to L-methionine resin. Again, after deprotection and washing steps, Fmoc-L-(S-trityl) cysteine was coupled as above. Purification of 93 mg of the crude material yielded the two diastereomers 67A (23 mg) and 67B (22 mg).
Mass (electrospray, M+H$^+$) calc: 592.3 found: 592 (67A), 592 (67B).

EXAMPLE 68

N-[[3-[(2-amino-3-mercapto-1-oxopropyl)methylaminol-2,3-dihydro-2-oxo-5-phenyl-7-chloro-1H-1,4-benzodiazepin-1-yl]acetyl]-L-phenylalanine (68)

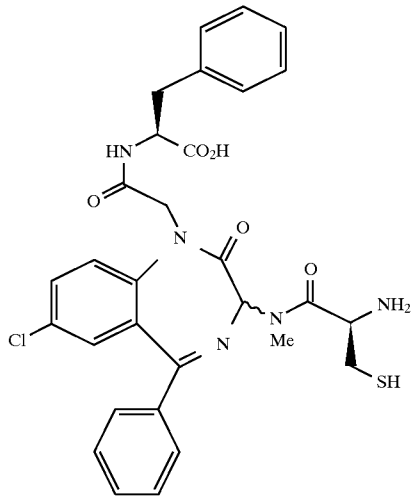

The title compound was prepared using the procedure of Example 9 in which 3-(tert-butoxycarbonyl)methylamino-2,3-dihydro-5-phenyl-7-chloro-1H-1,4-benzodiazepin-2-one-1-acetic acid (see Example 67) was coupled to L-phenylalanine resin. Again, after deprotection and washing steps, Fmoc-L-(S-trityl) cysteine was coupled as above. Purification of 85 mg of the crude material yielded the two diastereomers 68A (18 mg) and 68B (20 mg).

Mass (electrospray, M+H$^+$) calc: 608.9 found: 608.1 (68A), 608.1 (68B).

EXAMPLE 69

N-[[3-[(2-amino-3-mercapto-1-oxopropyl)methylamino]-2,3-dihydro-2-oxo-5phenyl-7-chloro-1H-1,4-benzodiazepin-1-yl]acetyl]-L-phenylalanine amide (69)

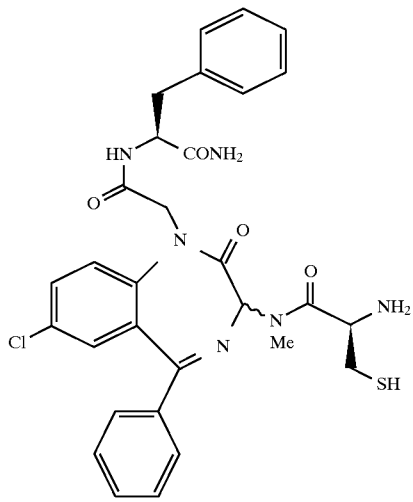

The title compound was prepared using the procedure of Example 9 in which Boc-L-phenylalanine (2.4 mmol) was coupled to MBHA-resin (1.5 gm, 0.53 mmol/gm) using BOP (0.33 gm, 2.4 mmol), HOBt (0.26 gm, 2.4 mmol), and NMM (130 ul, 2.4 mmol). Following suitable deprotection and washing steps, 3-(tert-butoxycarbonyl)methylamino-2,3-dihydro-5-phenyl-7-chloro-1H-1,4-benzodiazepin-2-one-1-acetic acid (see Exampel 67) was coupled as above. Again, after deprotection and washing steps, Fmoc-L-(S-trityl) cysteine was coupled as above. Purification of 63 mg of the crude material yielded the two diastereomers 69A (11 mg) and 69B (11 mg).

Mass (electrospray, M+H$^+$) calc: 607.9 found: 607.2 (69A), 607.2 (69B).

EXAMPLE 70

N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-4-fluoro-phenylalanine (70)

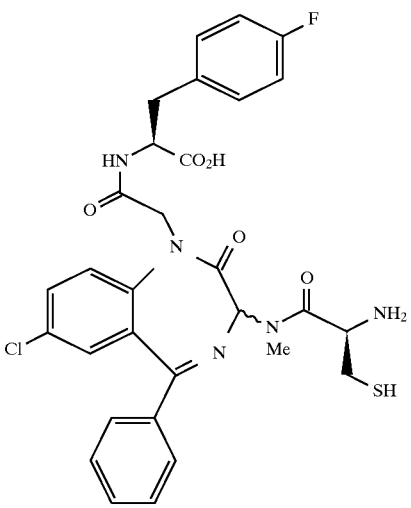

The title compound was prepared using the procedure of Example 9 in which 3-(tert-butoxycarbonyl)methylamino-2,3-dihydro-5-phenyl-7-chloro-1H-1,4-benzodiazepin-2-one-1-acetic acid (see Example 67) was coupled to 4-fluoro-phenylalanine resin. Again, after deprotection and washing steps, Fmoc-L-(S-trityl) cysteine was coupled as above. Purification of 42 mg of the crude material yielded the two diastereomers 70A (3 mg) and 70B (3 mg).

Mass (electrospray, M+H$^+$) calc: 626.9 found: 626.2 (70A), 626.2 (70B).

EXAMPLE 71

N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-(α-cyclohexyl)-glycine (71)

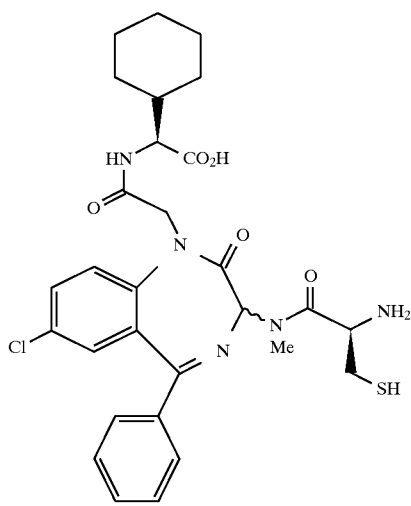

The title compound was prepared using the procedure of Example 9 in which 3-(tert-butoxycarbonyl)methylamino-2,3-dihydro-5-phenyl-7-chloro-1H-1,4benzodiazepin-2-one-1-acetic acid (see Example 67) was coupled to L-(α-cyclohexyl)-glycine resin. Again, after deprotection and washing steps, Fmoc-L-(S-trityl) cysteine was coupled as above. Purification of 27 mg of the crude material yielded the two diastereomers 71A (3 mg) and 71B (2 mg).
Mass (electrospray, M+H⁺) calc: 600.8 found: 600.2 (71A), 600.2 (71B).

EXAMPLE 72

N-[[3-[(2-amino-3-mercapto-1-oxopropyl)methylamino]-2,3-dihydro-2-oxo-5-phenyl-7-chloro-1H-1,4-benzodiazepin-1-yl]acetyl]-L-(α-cyclohexyl)-glycine amide (72)

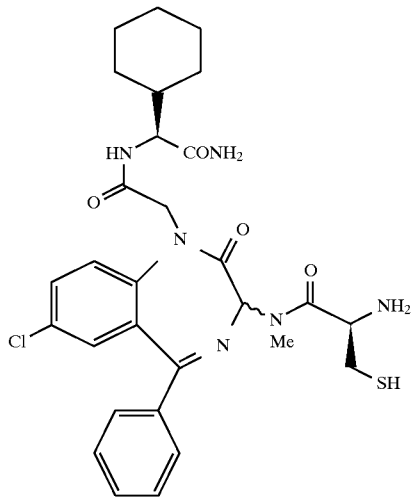

The title compound was prepared using the procedure of Example 9 in which Boc-L-(α-cyclohexyl)-glycine (2.4 mmol) was coupled to MBHA-resin (1.5 gm, 0.53 mmol/gm) using BOP (0.33 gm, 2.4 mmol), HOBt (0.26 gm, 2.4 mmol), and NMM (130 ul, 2.4 mmol). Following suitable deprotection and washing steps, 3-(tert-butoxycarbonyl)methylamino-2,3-dihydro-5-phenyl-7-chloro-1H-1,4-benzodiazepin-2-one-1-acetic acid (see Example 67) was coupled as above. Again, after deprotection and washing steps, Fmoc-L-(S-trityl) cysteine was coupled as above. Purification of 13 mg of the crude material yielded the two diastereomers 72A (2 mg) and 72B (0.5 mg).

Mass (electrospray, M+H⁺) calc: 599.9 found: 599.2 (72A), 599.2 (72B).

In Examples 73 to 79 the parenthetical compounds refer to the numbers in the Scheme below. All other compounds in this series have been prepared by analogous routes.

Scheme 7

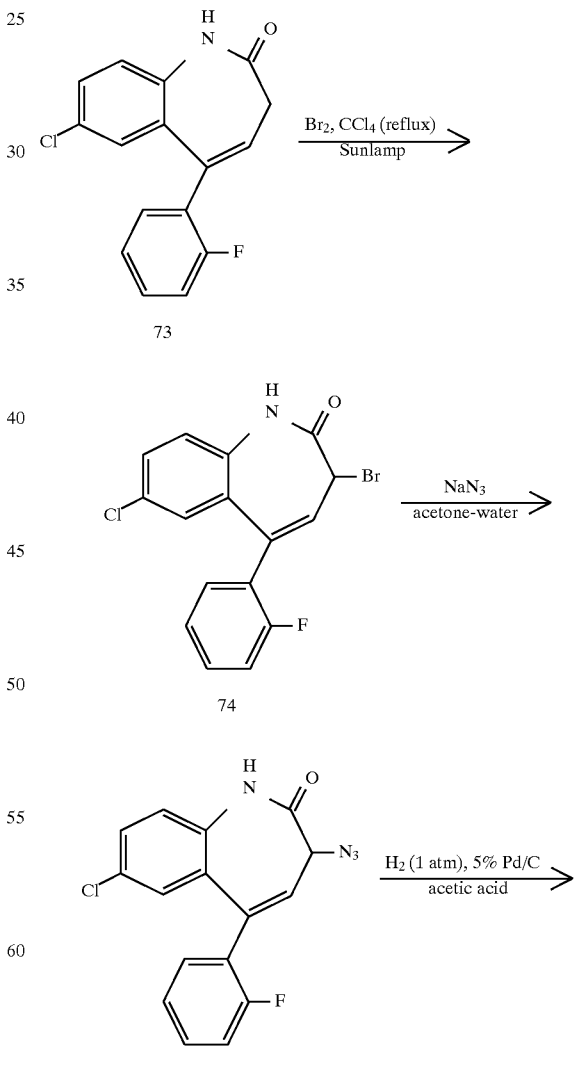

421
-continued
Scheme 7

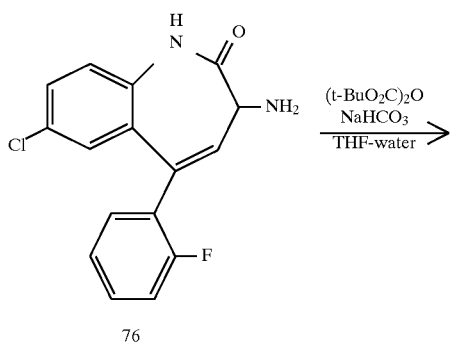

76

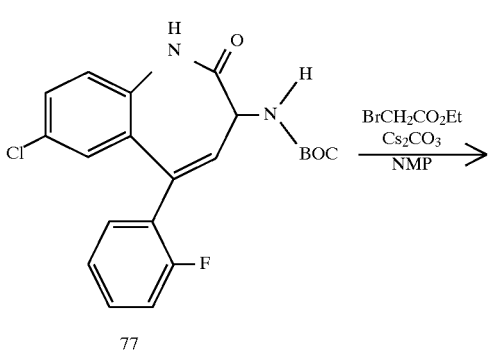

77

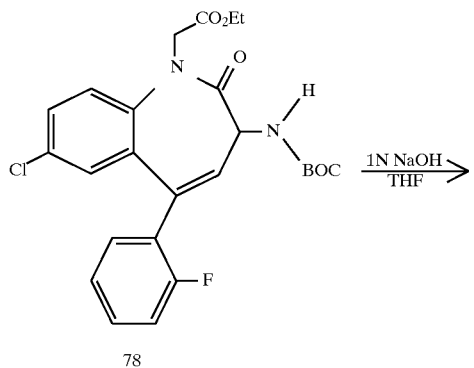

78

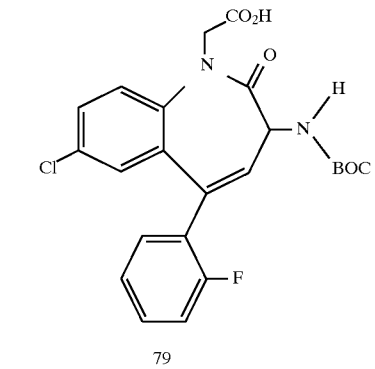

79

EXAMPLE 73

7-Chloro-5-(2-fluorophenyl)-1,3-dihydro-2H-1-benzazepin-2-one (73)

This material was prepared similar to the procedure of B. Loev, et al., published in the Journal of Medicinal Chemistry, Volume 14 (1971), pages 849–852.

EXAMPLE 74 rac-3-Bromo-7-chloro-5-(2-fluorophenyl)-1,3-dihydro-2H-1-benzazepin-2-one (74)

A suspension of 7-chloro-5-(2-fluorophenyl)-1,3-dihydro-2H-1-benzazepin-2-one (0.378 g, 1.31 mmole) in 45 mL of dry carbon tetrachloride was heated to reflux, which generated a clear solution. Bromine (0.15 mL, 2.91 mmole) was added in two portions, 20 minutes apart, and the solution was heated at reflux for a total of 1 hour under a sunlamp. After cooling the reaction solution was washed sequentially with 5% aqueous sodium thiosulfate, dilute aqueous sodium bicarbonate, and 5% aqueous sodium thiosulfate. The organic phase was dried (sodium sulfate) and concentrated. The crude material was purified using a 2 mm chromatotron plate, eluting with 1:1 ethyl acetate-hexane, yielding 0.185 g (72%) of the title compund. IR(KBr): 3386, 1731, 1682 cm$^{-1}$. Mass spec. (EI, m/z 367).

EXAMPLE 75 rac-3-Azido-7-chloro-5-(2-fluorophenyl)-1,3-dihydro-2H-1-benzazepin-2-one (75)

A solution of rac-3-bromo-7-chloro-5-(2-fluorophenyl)-1,3-dihydro-2H-1-benzazepin-2-one (13.2 g, 36.0 mmole) in 180 ml acetone and 24 mL water was treated with a solution of sodium azide (3.51 g, 54.0 mmole) dissolved in 24 mL of water and stirred at ambient temperature. After 30 minutes, 500 mL of water was added. The precipitated product was collected and dried, yielding 10.6 g (89%) of the title compound as a solid.

EXAMPLE 76 rac-3-Amino-7-chloro-5-(2-fluorophenyl)-1,3-dihydro-2H-1-benzazepin-2-one (76)

To a solution of rac-3-azido-7-chloro-5-(2-fluorophenyl)-1,3-dihydro-2H-1-benzazepin-2-one (5 g, 15.2 mmole) in 300 mL of acetic acid was added 5% Pd/C (250 mg). The mixture was hydrogenated at 1 atm pressure for 2 hours. The crude material was purified on activated alumina and crystallized from ether-isopropyl ether yielding 3.4 g (74%) of solid. Melting point: 188°–191° C.

EXAMPLE 77 rac-17-Chloro-5-(2-fluorophenyl)-2,3-dihydro-2-oxo-1H-1-benzazepin-3-yl]carbamic acid 1,1-dimethylethyl ester (77)

The rac-3-amino-7-chloro-5-(2-fluorophenyl)-1,3-dihydro-2H-1-benzazepin-2-one (0.303 g, 1.00 mmole) was dissolved in 10 mL of 1:1 THF-water and treated with sodium bicarbonate (0.125 g, 1.49 mmole) and a solution of di-t-butyl dicarbonate (0.327 g, 1.50 mmole) disssolved in a small volume of THF. This two-phased mixture was stirred at ambient temperature for 1 hour. The mixture was then diluted with EtOAc. The aqueous phase was removed and the organic phase was washed two times with water, dried (sodium sulfate) and concentrated. The crude material was chromatographed on a 4 mm chromatotron plate, eluting with 2:3 ethyl acetate-hexane. Recrystallization from ethyl acetate-hexane gave 0.335 g (83%) of white solid. IR (KBr): 3340, 3235, 1704, 1677 cm$^{-1}$. Mass spec. (EI: m/z 402).

EXAMPLE 78 rac-7-Chloro-3-[[(1,1-dimethylethoxy)carbonyl]amino]-5-(2-fluorophenyl)-2,3-dihydro-2-oxo-1H-1-benzazepine-1-acetic acid ethyl ester (78)

A solution of rac-[7-chloro-5-(2-fluorophenyl)-2,3-dihydro-2-oxo-1H-1-benzazepin-3-yl]carbamic acid 1,1- dimethylethyl ester (0.317 g, 0.787 mmole) in 4 mL of N-methyl-2-pyrolidinone was treated with cesium carbonate (0.365 g, 1.12 mmole) and ethyl bromoacetate (0.125 mL, 1.13 mmole). The mixture was stirred at ambient temperature for 17 hours. After this time, the mixture was diluted with 14 mL of water and extracted three times with ethyl acetate. The three organic phases were combined, washed with water followed by brine, dried (sodium sulfate) and concentrated. The crude material was chromatographed on a 4 mm chromatotron plate, eluting with 2:3 ethyl acetate-hexane, and then crystallized from ether-petroleum ether, yielding 0.326 g (85%) of white solid. Melting point: 174°–178° C. IR (KBr): 1747, 1694, 1669 cm$^{-1}$. Mass spec. (EI: m/z 488).

EXAMPLE 79 rac-7-Chloro-3-[[(1,1-dimethylethoxy)carbonyl] amino]-5-(2-fluorophenyl)-2,3-dihydro-2-oxo-1H-1-benzazepine-1-acetic acid (79)

A solution of rac-7-chloro-3-[[(1,1-dimethylethoxy) carbonyl]amino] -5-(2-fluorophenyl)-2,3-dihydro-2-oxo-1H-1-benzazepine-1-acetic acid ethyl ester (0.601 g, 1.23 mmole) in 6 mL THF was treated with 1.0N aqueous sodium hydroxide(1.9 mL, 1.9 mmole). The two phased mixture was stirred vigorously at ambient temperature for 2.5 hours. After this time, the mixture was diluted with water and concentrated. The residue was dissolved in water and acidified to pH≤3 with 1N HCl. A thick precipitate dropped out of solution which was extracted into ethyl acetate. The organic phase was washed with water and brine, dried (sodium sulfate) and concentrated. The crude material was purified on a 4 mm chromatotron plate and then crystallized form ether-petroleum ether, yielding 0.482 g (85%) of white solid. IR (KBr): 3378, 1672, 1728 cm$^{-1}$. Mass spec. (FAB+: m/z 460).

EXAMPLE 80

N-[[3-[(2-amino-3-mercapto-1-oxopropyl) methylamino]-2,3-dihydro-2-oxo-5-(2'-fluorophenyl) -7-chloro-1H-1,4-benzazepin-1-yl]acetyl]-L-methionine (80)

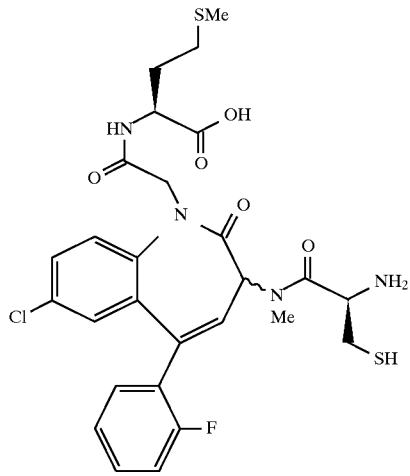

The title compound was prepared using the procedure of Example 9 in which 3-(tert-butoxycarbonyl)amino-2,3-dihydro-5-(2'-fluorophenyl)-7-chloro-1H-1,4-benzazepin-2-one-1-acetic acid was coupled to L-methionine resin. Again, after deprotection and washing steps, the amine was protected via treatment with di(4-methoxyphenyl)methylchloride (0.6 mmol) in CH$_2$Cl$_2$. Alkylation of the secondary amine was accomplished via reductive alkylation with paraformaldehyde (40 mg) and sodium cyanoborohydride (80 mg) in 1% AcOH/dimethylformamide. Removal of the protecting group (10% TFA/CH$_2$Cl$_2$) was followed by coupling of Fmoc-L-(S-trityl) cysteine as above. Purification of 111 mg of the crude material yielded the produce as a mixture of the two diastereomers 80A+B (34 mg).

Mass (electrospray, M+H$^+$) calc: 609.2 found: 609.2 (80A+B).

EXAMPLE 81

N-[[3-[(2-amino-3-mercapto-1-oxopropyl) methylamino]-2,3-dihydro-2-oxo-5-(2'-chlorophenyl)-7-chloro-1H-1,4-benzodiazepin-1-yl] acetyl]-L-methionine (81)

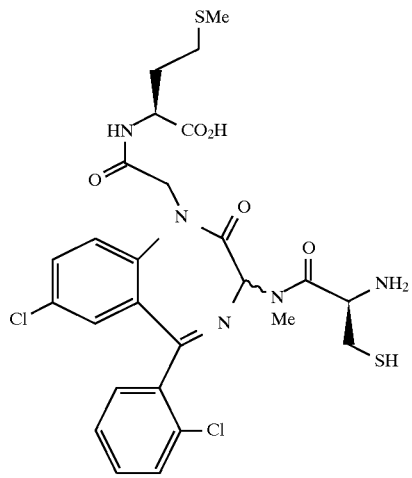

The title compound was prepared using the procedure of Example 9 in which 3-(tert-butoxycarbonyl)methylamino-2,3dihydro-5-(2'-chlorophenyl)-7-chloro-1H-1,4-benzodiazepin-2-one-1-acetic acid was coupled to L-methionine resin. Again, after deprotection and washing steps, Fmoc-L-(S-trityl) cysteine was coupled as above. Purification of 69 mg of the crude material yielded the two diastereomers 81A (13 mg) and 81B (12 mg).

Mass (electrospray, M+H$^+$) calc: 626.4 found: 626.1 (81A), 625.9 (81B).

EXAMPLE 82

N-[[3-[(2-amino-3-mercapto-1-oxopropyl)methylamino]-2,3-dihydro-2-oxo-5-(2'-fluorophenyl)-7-chloro-1H-1,4-benzodiazepin-1-yl]acetyl]-L-methionine (82)

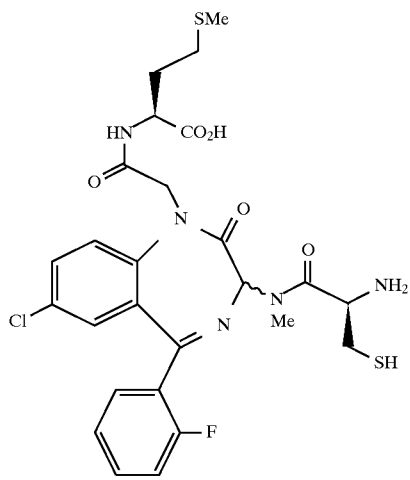

The title compound was prepared using the procedure of Example 9 in which 3-(tert-butoxycarbonyl)methylamino-2,3-dihydro-5-(2fluorophenyl)-7-chloro-1H-1,4-benzodiazepin-2-one-1-acetic acid was coupled to L-methionine resin. Again, after deprotection and washing steps, Fmoc-L-(S-trityl) cysteine was coupled as above. Purification of 93 mg of the crude material yielded the two diastereomers 82A (13 mg) and 82B (12 mg).

Mass (electrospray, M+H$^+$) calc: 610.3 found: 610.1 (82A), 609.9 (82B).

EXAMPLE 83

N-[[3-[(2-amino-3-mercapto-1-oxopropyl)methylamino]-2,3-dihydro-2-oxo-5-phenyl-7-chloro-1H-1,4-benzazepin-1-yl]acetyl]-L-methionine (83)

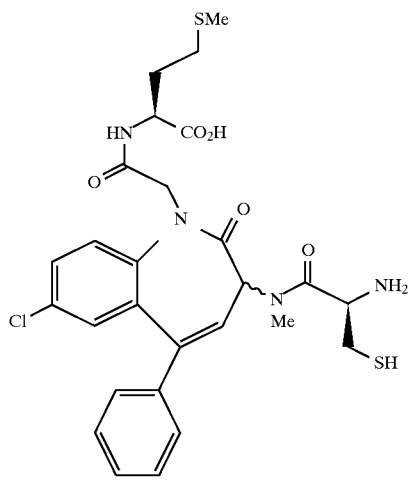

The title compound was prepared using the procedure of Example 9 in which 3-(tert-butoxycarbonyl)methylamino-2,3-dihydro-5-phenyl-7-chloro-1H-1,4-benzazepin-2-one-1-acetic acid (prepared in a manner analogous to that shown for Example 89 below) was coupled to L-methionine resin. Again, after deprotection and washing steps, Fmoc-L-(S-trityl) cysteine was coupled as above. Purification of 106 mg of the crude material yielded the two diastereomers 83A (14 mg) and 83B (17 mg).

Mass (electrospray, M+H$^+$) calc: 590.8 found: 591 (83A), 591.2 (83B).

In Examples 84 to 89 the parenthetical compounds refer to the numbers in the Scheme below. All other compounds in this series have been prepared by analogous routes.

Scheme 8

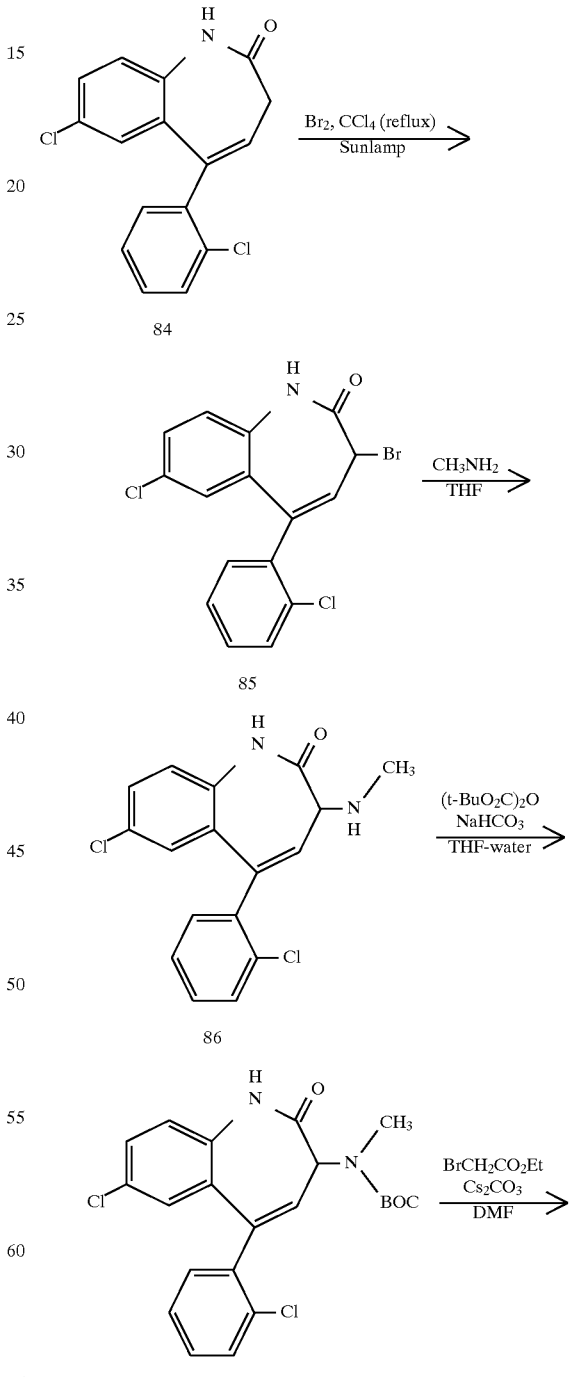

427

-continued
Scheme 8

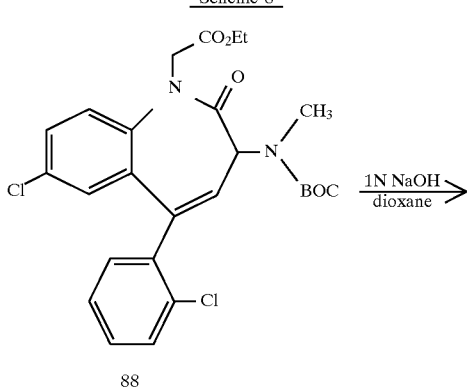

88

89

EXAMPLE 84

7-Chloro-5-(2-chlorophenyl)-1,3-dihydro-2H-1-benzazepin-2-one (84)

This material was prepared similar to the procedure of B. Loev, et al., published in the *Journal of Medicinal Chemistry*, Volume 14 (1971), pages 849–852.

EXAMPLE 85 rac-3-Bromo-7-chloro-5-(2-chlorophenyl)-1,3-dihydro-2H-1-benzazepin-2-one (85)

A suspension of 0.78 g (2.56 mmole) of 7-chloro-5-(2-chlorophenyl)-1,3-dihydro-2H-1-benzazepin-2-one in 100 mL of carbon tetrachloride was heated to reflux, yielding a clear solution. Bromine (0.19 mL, 3.69 mmole) was added in one portion and the solution was, heated at reflux, under a sunlamp, for 15 minutes. Without cooling, the reaction solution was washed with 5% aqueous sodium thiosulfate and water, dried (sodium sulfate), and concentrated. The residue was triturated with ether. The solid was collected on a filter, washed with ether and dried yielding 0.64 g (65%) of the title compound. This crude material (shown by NMR to have a ratio of product to starting material of 85:15) was used as is in the next step.

EXAMPLE 86 rac-7-Chloro-5-(2-chlorophenyl)-1,3-dihydro-3-(methylamino)-2H-1-benzazepin-2-one (86)

A solution of methyl amine (16.0 mL of a 1.1N THF solution, 17.6 mmole) in 50 mL of dry THF was cooled to 0°–5° C. in an ice-water bath. To this solution was added,

428 over a ten minute period, a solution of crude rac-3-bromo-7-chloro-5-(2-chlorophenyl)-1,3-dihydro-2-H1-benzazepin-2-one (3.36 g estimated to be 85% pure, 7.36 mmole), dissolved in 55 mL of THF. After 10 minutes, the reaction solution was diluted with 300 mL of EtOAc, washed with water and brine, and dried (sodium sulfate). Concentration and drying under high vacuum yielded 2.98 g of crude material, which was used as is in the next step.

EXAMPLE 87 rac-[7-Chloro-5-(2-chlorophenyl)-2,3-dihydro-2-oxo-1H-1-benzazepin-3-yl]methyl carbamic acid 1,1-dimethylethyl ester (87)

The crude rac-7-chloro-5-(2-chlorophenyl)-1,3-dihydro-3-(methylamino)-2H-1-benzazepin-2-one (2.98 g) in 55 mL of THF was treated with sodium bicarbonate (0.97 g, 11.5 mmole) in 30 mL of water and di-t-butyldicarbonate (2.53 g,11.6 mmole) in 5 mL of THF. The heterogenous mixture was stirred at ambient temperature for 2 hours. The mixture was then diluted with 300 mL EtOAc. The aqueous phase was removed and the organic phase was washed with water and brine, dried (sodium sulfate), and concentrated. The crude material was chromatographed by flash chromatography, eluting with 40:60 EtOAc-hexane, yielding 2.82 g (55% from 1) of white solid. Mass spec. (EI, m/z 432). (Found: C, 60.73; H, 5.09; N, 6.21; Cl, 16.24. Calc for $C_{22}H_{22}Cl_2N_2O_3$: C, 60.98; H, 5.12; N, 6.46; Cl, 16.36).

EXAMPLE 88 rac-7-Chloro-5-(2-chlorophenyl)-3-[[(1,1-dimethylethoxy)carbonyl]methylamino]-2,3-dihydro-2-oxo-1H-1-benzazepine-1-acetic acid ethyl ester (88)

A solution of rac-[7-chloro-5-(2-chlorophenyl)-2,3-dihydro-2-oxo-1H-1-benzazepin-3-yl]methylcarbamic acid 1,1-dimethylethyl ester (1.346 g, 3.11 mmole) in 17 mL of dimethylformamide was treated with cesium carbonate (1.85 g, 5.68 mmole) and ethyl bromoacetate (0.65 mL, 5.86 mmole). After stirring at ambient temperature for 3 hours, the mixture was diluted with ethyl acetate (150 ml). The organic phase was washed four times with water and once with brine, dried (sodium sulfate) and concentrated. The crude material was chromatographed by flash chromatography, eluting with 40:60 ethyl acetate-hexane, to give 1.506 g (93%) of the title compound. Mass spec. (EI, m/z 518).

EXAMPLE 89 rac-7-Chloro-5-(2-chlorophenyl)-3-[[(1,1-dimethylethoxy)carbonyl]methylamino]-2,3-dihydro-2-oxo-1H-1-benzazepine-1-acetic acid (89)

To a solution of rac-7-chloro-5-(2-chlorophenyl)-3-[[(1, 1-dimethylethoxy)-carbonyl]methylamino]-2,3-dihydro-2-oxo-1H-1-benzazepine-1-acetic acid ethyl ester (1.50 g, 2.89 mmole) in 11 mL of dioxane was added 1.0N aqueous sodium hydroxide solution (4.2 mL, 4.2 mmole). After stirring for 3 hours at ambient temperature, the solution was concentrated under high vacuum. The residue was dissolved in 40 mL of water and acidified to pH 3 with 1N HCl. A thick precipitate formed which was extracted into 100 mL of ethyl acetate. The organic phase was removed, washed with brine, dried (sodium sulfate) and concentrated. The crude product was crystallized from ether-petroleum ether yielding 1.24 g (87%) of white solid. IR (KBr) 1739, 1697 cm$^{-1}$. Mass spec (FAB+, m/z 491). (Found: C, 58.90; H, 5.10; N, 5.40; Cl, 14.13. Calc for $C_4H_{24}N_2O_5Cl_2$: C, 58.67; H, 4.92; N, 5.70; Cl, 14.43).

According to the procedures of examples 84 to 89, the following compounds were also prepared.

EXAMPLE 90 rac-7-Chloro-3-[[(1,1-dimethylethoxy)carbonyl] methylamino]-5-(2-fluorophenyl)-2,3-dihydro-2-oxo-1H-1-benzazepine-1-acetic acid (90).

Mass spec. (FAB+, m/e 475).

EXAMPLE 91 rac-7-Chloro-3-[[(1,1-dimethylethoxy)carbonyl] methylamino]-2,3-dihydro-2-oxo-5-phenyl-1H-1-benzazepine-1-acetic acid (91).

IR (KBr):1685, 1696 cm$^{-1}$. Mass spec. (FAB+, m/z 457).

EXAMPLE 92

N-[[3-[(2-amino-3-mercapto-1-oxopropyl) methylamino]-2,3-dihydro-2-oxo-5-(2'-chlorophenyl)-7-chloro-1H-1,4-benzazepin-1-yl] acetyl]-L-methionine (92)

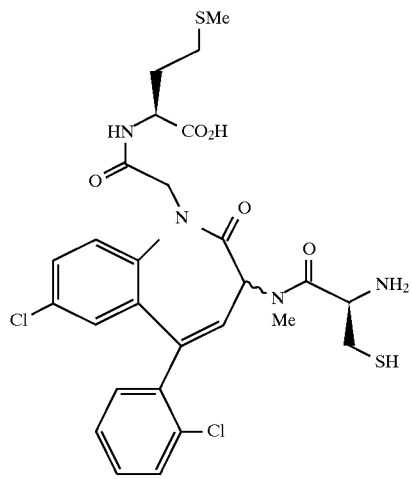

The title compound was prepared using the procedure of Example 9 in which 3-(tert-butoxycarbonyl)methylamino-2,3dihydro-5-(2'-chlorophenyl)-7-chloro-1H-1,4-benzazepin-2-one-1-acetic acid (89) was coupled to L-methionine resin. Again, after deprotection and washing steps, Fmoc-L-(S-trityl) cysteine was coupled as above. Purification of 100 mg of the crude material yielded the product as an unseparable mixture of diastereomers 92A+B (24 mg).

Mass (electrospray, M+H$^+$) calc: 625.7 found: 625 (92A+B).

EXAMPLE 93

N-[[3-[(2-amino-3-mercapto-1-oxopropyl) methylamino]-2,3-dihydro-2-oxo-5-phenyl-1H-1,4-benzodiazepin-1-yl]methyl]-3-benzonitrile (93)

The title compound was prepared as shown in Scheme 9, below.

Scheme 9

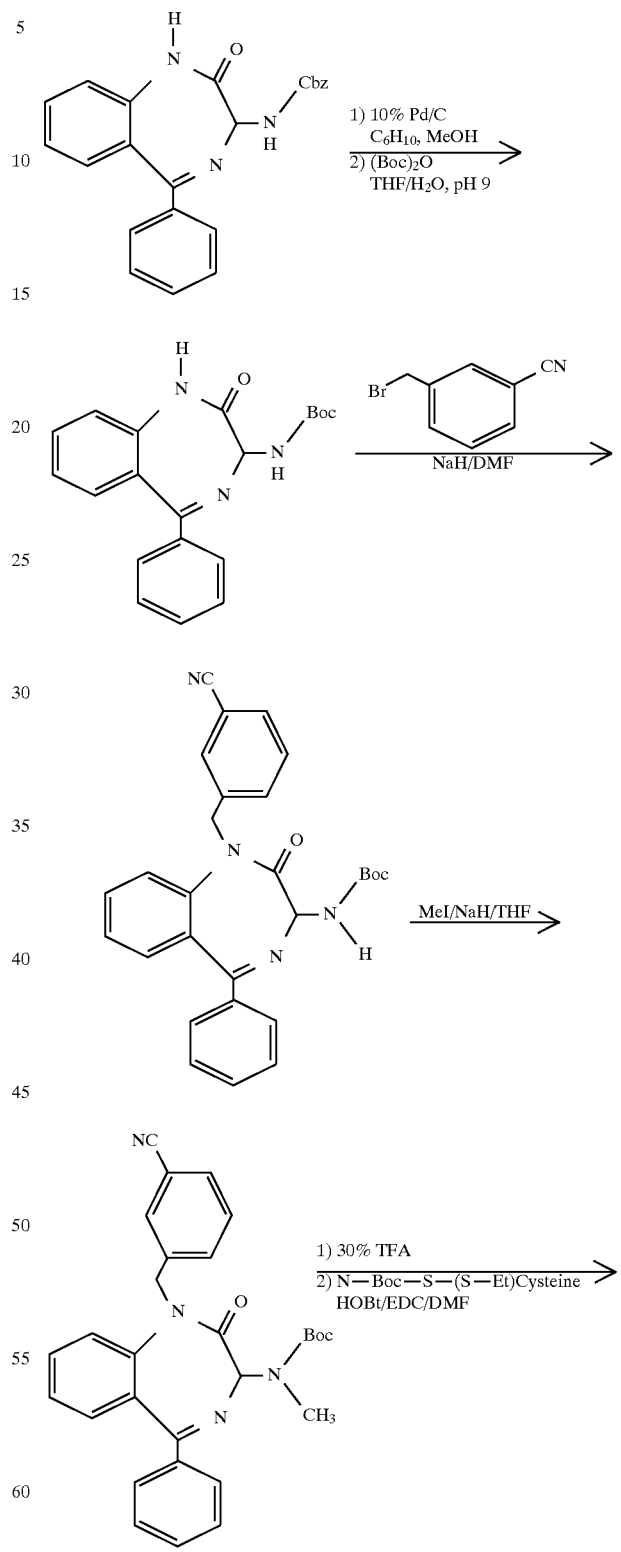

-continued
Scheme 9

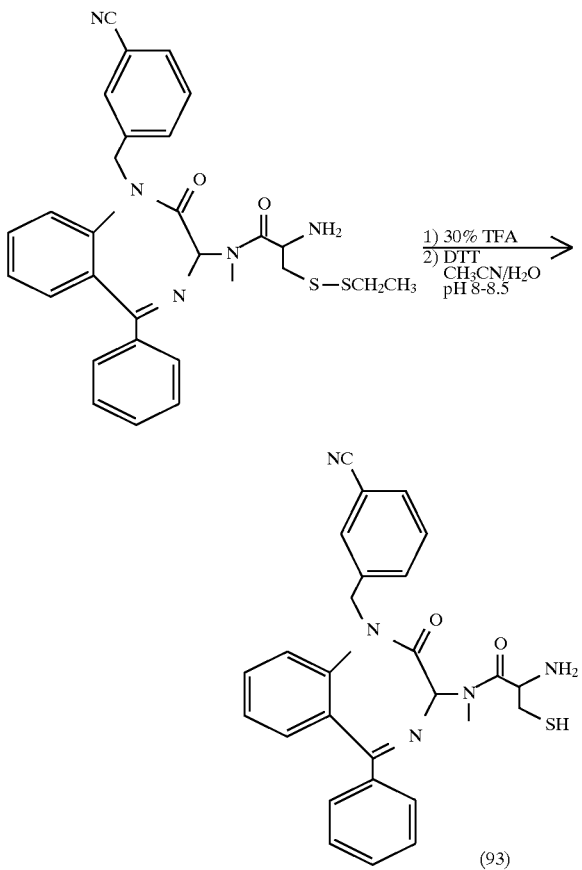

Cbz-protected 3-amino-1,3-dihydro-5-phenyl-1,4-benzodiazapin-2-one (14.37 g, 37.8 mmol) (similar to the synthesis described in Bock, et al., *J. Org. Chem.* 1987, 52, 3232–3239) was suspended in MeOH (280 ml) and deprotected via treatment with cyclohexene (300 ml) and 10% Pd/C (37. g added portionwise) under reflux for 20 min. The solids were removed by filtration through celite, and the solvent removed under reduced pressure yielding the product, 3-amino-1,3-dihydro-5-phenyl-1,4-benzodiazapin-2-one, as a yellow solid (8.99 g, 94.8%).

The crude material was then dissolved in 50% THF/H$_2$O (240 ml), cooled to 0° C., and treated with di-tert-butyl dicarbonate (10.16 g, 46.56 mmol). Solution pH was adjusted to 9 via addition of 1 N NaOH. After stirring overnight, and standard aqueous workup from EtOAc, the product, N-Boc-3-amino-1,3-dihydro-5-phenyl-1,4-benzodiazapin-2-one, was crystallized from EtOAc (5.15 g, 40.9%).

Next, the N-Boc-3-amino-1,3-dihydro-5-phenyl-1,4-benzodiazapin-2-one (1.615 g, 2.9 mmol) was dissolved in DMF (10 ml) and added dropwise to a cooled (0° C.) suspension of NaH (0.15 g, 3.75 mmol) in DMF (10 ml). After stirring for 30 min., the reaction was treated with 3-bromomethyl benzonitrile (0.656 g, 3.35 mmol) and stirred overnight at room temperature. After dilution in ether and standard workup from aqueous NaH$_4$Cl, concentrated, and purified via silica gel chromatography (40% EtOAc/hexane) yielding N-Boc-3-amino-1-(methyl-3-cyanophenyl)-1,3-dihydro-5-phenyl-1,4-benzodiazapin-2-one (1.28 g, 94.9%). Alternatively, CsCO$_3$ can be used in place of NaH.

N-methylation was accomplished via dropwise addition of NaH (0.24 g, 6 mmol, THF) to a solution of the above product, Boc-3-amino-1-(methyl-3-cyanophenyl)-1,3-dihydro-5-phenyl-1,4-benzodiazapin-2-one (1.28 g, 2.74 mmol), in THF (20 ml) containing CH$_3$I (0.65 ml, 10.4 mmol) at 0° C. for 8 hr. After dilution with Et$_2$O and aqueous workup, concentration of the organic phase and flash chromatography (silica gel, 35% EtOAc/hexane) yielded the product, Boc-3-methylamino-1-(methyl-3-cyanophenyl)-1,3-dihydro-5-phenyl-1,4-benzodiazapin-2-one (0.94 g, 71.5 %). 1H NMR, 13C NMR, and mass analysis were consistent with structure.

The title compound was prepared using a procedure similar to that shown in Example 37 in which removal of the Boc protecting group was followed by coupling of Boc-(S-ethylthio)-cysteine. Deprotection and removal of the ethylthio protecting group as abovE yielded N-[[3-[(2-amino-3-mercapto-1-oxopropyl)methylamino]-2,3-dihydro-2-oxo-5-phenyl-1H-1,4-benzodiazepin-1-yl]methyl]-3-benzonitrile (93) as a separable mixture of diasteriomers. Purfication of 132 mg of the crude material yielded the two diasteriomers 93A (16 mg) and 93B (11 mg).

Mass (electrospray, M+H$^+$) calc: 484.4 found: 484.2 (93A), 484.2 (x93B).

EXAMPLE 94

N-[[3-[(2-amino-3-mercapto-1-oxopropyl)methylamino]-2,3-dihydro-2-oxo-5-phenyl-1H-1,4-benzodiazepin-1-yl]methyl]-3-carboxymethylbenzene (94)

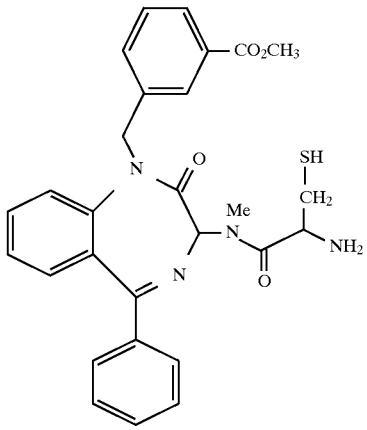

The title compound was prepared using the procedure of Example 93 in which N-Boc-3-amino-1,3-dihydro-5-phenyl-1,4-benzodiazapin-2-one was alkylated at N-1 with 3-bromomethyl carboxymethylbenzene, followed by N-methylation and coupling of Boc-(S-ethylthio)-cysteine and deprotection as above. Purification of 91 mg of the crude material yielded the two diastereomers 94A (22 mg) and 94B (19 mg).

Mass (FAB, M+H$^+$) calc: 517.4 found: 517.2 (94A), 517.2 (94B).

EXAMPLE 95

N-[[3-[(2-amino-3-mercapto-1-oxopropyl)
methylamino]-2,3-dihydro-2-oxo-5-phenyl-1H-1,4-
benzodiazepin-1-yl]methyl]-3-carboxybenzene (95)

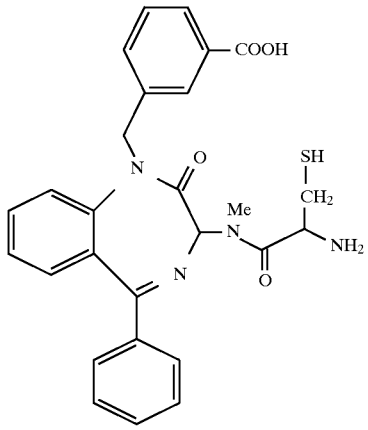

The title compound was prepared from the methyl ester shown above in Example 94 via treatment of N-[[3-[(2-Boc-amino-3-ethylthiomercapto-1-oxopropyl)methylamino]-2,3-dihydro-2-oxo-5-phenyl-1H-1,4-benzodiazepin-1-yl]methyl]-3-carboxymethylbenzene (132 mg, 1.95 mmol) with 5 eq. of LiOH in THF at 0° C. After workup and deprotection, the crude material was purified via HPLC as above yielding the two diastereomers 95A (19 mg) and 95B (4 mg).
Mass (FAB, M+H$^+$) calc: 503.4 found: 503.1 (95A), 503.1 (95B).

EXAMPLE 96

N-[[3-[(2-amino-3-mercapto-1-oxopropyl)
methylanino]-2,3-dihydro-2-oxo-5-phenyl-1H-1,
4benzodiazepin-1-yl]methyl]-3-tetrazolylbenzene
(96)

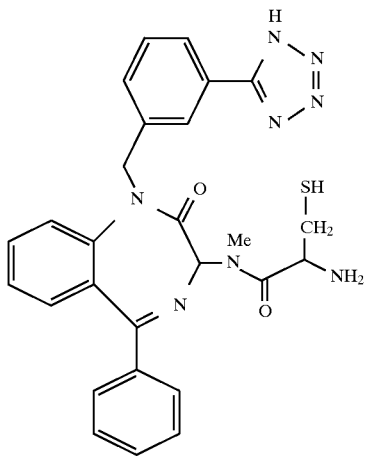

The title compound was prepared using the procedure of Example 93 in which N-Boc-3-amino-1,3-dihydro-5-phenyl-1,4-benzodiazapin-2-one was alkylated at N-1 with 3-bromomethyl benzonitrile, followed by N-methylation as above. Next, conversion of the nitrile (988 mg, 2 mmol) to the tetrazole was accomplished via treatment with NaN$_3$ (1.38 g, 21.2 mmol) and NH$_4$Cl (1.23 g, 23 mmol) in DMF (10 ml) at 105° C. After workup and deprotection, the title compound was prepared by coupling of Boc-(Sethylthio)-cysteine and deprotection as above. Purification of 94 mg of the crude material yielded the two diastereomers 96A (5 mg) and 96B (4 mg).

Mass (FAB, M+H$^+$) calc: 527.5 found: 527.2 (96A), 527.2 (96B).

EXAMPLE 97

N-[[3-[(2-amino-3-mercapto-1-oxopropyl)
methylamino]-2,3-dihydro-2-oxo-5-phenyl-7-chloro-
1H-1,4-benzodiazepin-1-yl]methyl]-3-
carboxymethylbenzene (97)

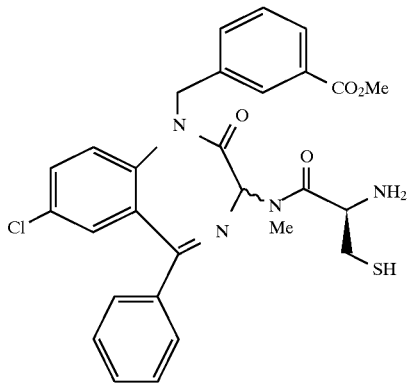

The title compound was prepared using the procedure of Example 93 in which N-Boc-3-amino-1,3-dihydro-5-phenyl-7-chloro-1,4-benzodiazapin-2-one was alkylated at N-1 with 3-bromomethyl carboxymethylbenzene, followed by N-methylation and coupling of Boc-(Sethylthio)-cysteine and deprotection as above. Purification of 1690 mg of the crude material yielded the two diastereomers 97A (71 mg) and 97B (55 mg).

Mass (electrospray, M+H$^+$) calc: 551.3 found: 551.1 (97A), 551.1 (97B).

EXAMPLE 98

N-[[3-[(2-amino-3-mercapto-1-oxopropyl)methylamino]-2,3-dihydro-2-oxo-5-phenyl-1H-1,4-benzodiazepin-1-yl]methyl]-4-(2-tetrazolylphenyl)benzene (98)

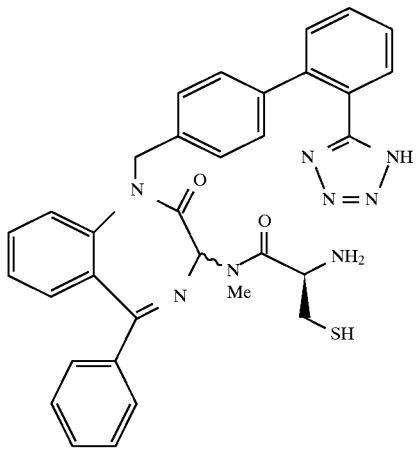

The title compound was prepared using the procedure of Example 93 in which N-Boc-3-amino-1,3-dihydro-5-phenyl-1,4-benzodiazapin-2-one was alkylated at N-1 with 4-bromomethyl-2-tetrazolylphenyl benzene, followed by N-methylation and coupling of Boc-(Sethylthio)-cysteine and deprotection as above. Purification of 41 mg of the crude material yielded the two diastereomers 98A (6 mg) and 98B (11 mg).

Mass (electrospray, M+H$^+$) calc: 603.4 found: 603.2 (98A), 603.2 (98B).

EXAMPLE 99

N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]methyl]-3-carboxymethylbenzene (99)

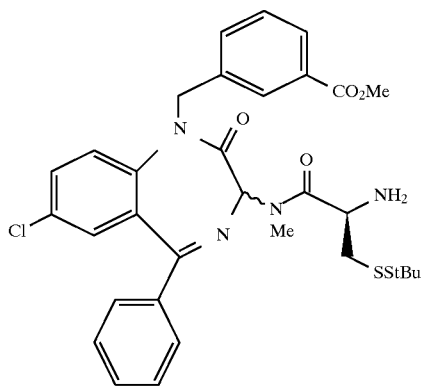

The title compound was prepared using the procedure similar to that described in Example 94 above, followed by coupling of Boc-S(tert-butylthio)-Cysteine, omitting the step for removal of the thiol protecting group. Purification of 950 mg of the crude material yielded the two diastereomers 99A (208 mg) and 99B (315 mg).

Mass (electrospray, M+H$^+$) calc: 639.4 found: 639.2 (99A), 639.2 (99B).

EXAMPLE 100

N-[[3-[(2-methylthiazolidine-4-carboxyl)methylamino]-2,3-dihydro-2-oxo-5-phenyl-7-chloro-1H-1,4-benzodiazepin-1-yl]methyl]-3-carboxymethylbenzene (100)

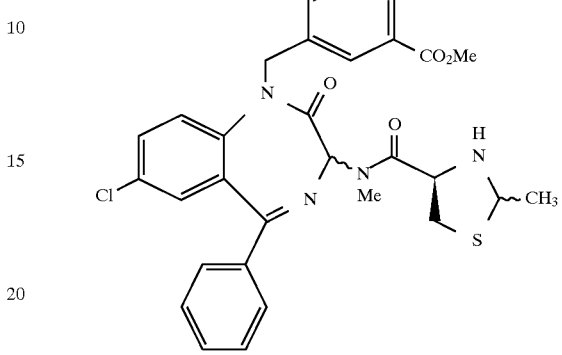

The title compound was prepared using the procedure similar to that described in Example 94 above, followed by coupling of Boc-2-methyl thiazolidine-4-carboxylic acid, omitting the step for removal of the thiol protecting group. Purification of 460 mg of the crude material yielded the two diastereomers 100A (112 mg) and 100B (117 mg).

Mass (electrospray, M+H$^+$) calc: 577.3 found: 577.0 (100A), 577.1 (100B).

EXAMPLE 101

N-[[3-[(2-amino-3-mercapto-1-oxopropyl)methylamino]-2,3-dihydro-2-oxo-5-phenyl-7-chloro-1H-1,4-benzodiazepin-1-yl]methyl]4-benzonitrile (101)

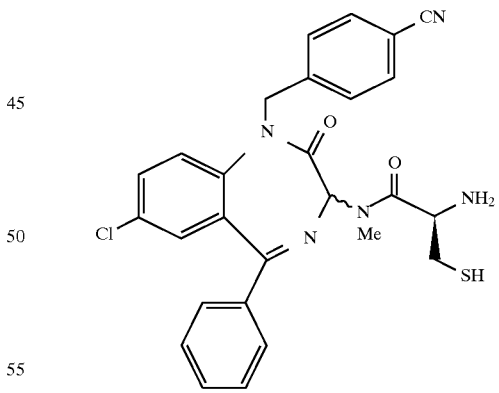

The title compound was prepared similar to the procedure of Example 93 in which N-Boc-3-methylamino-1,3-dihydro-5-phenyl-7-chloro-1,4-benzodiazapin-2-one was alkylated at N-1 with 4-bromomethyl-benzonitrile, followed by coupling of Boc-(Sethylthio)-cysteine and deprotection as above. Purification of 98 mg of the crude material yielded the two diastereomers 101A (5.8 mg) and 101B (4 mg).

Mass (electrospray, M+H$^+$) calc: 518.2 found: 518.0 (101A), 518.2 (101B).

EXAMPLE 102

N-[[3-[(2-amino-3-mercapto-1-oxopropyl)
methylamino]-2,3-dihydro-2-oxo-5-phenyl-7-chloro-
1H-1,4-benzodiazepin-1-yl]methyl]-3-
methylbenzene (102)

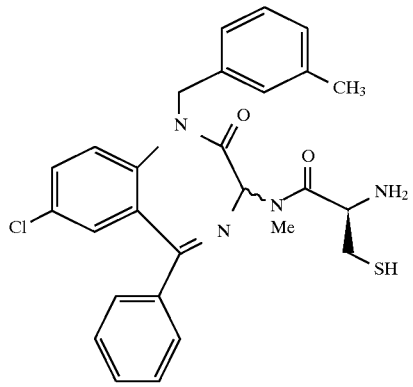

The title compound was prepared similar to the procedure of Example 93 in which N-Boc-3-methylamino-1,3-dihydro-5-phenyl-7-chloro-1,4-benzodiazapin-2-one was alkylated at N-1 with 3-bromomethyl-toluene, followed by coupling of Boc-(Sethylthio)-cysteine and deprotection as above. Purification of 105 mg of the crude material yielded the two diastereomers 102A (1 mg) and 102B (1 mg).
Mass (electrospray, M+H$^+$) calc: 507.2 found: 507.4 (102A), 507.4 (102B).

EXAMPLE 103

N-[[3-[(2-amino-3-mercapto-1-oxopropyl)
methylamino]-2,3-dihydro-2-oxo-5-phenyl-7-chloro-
1H-1,4-benzodiazepin-1-yl]methyl]-3-
trifluoromethylbenzene (103)

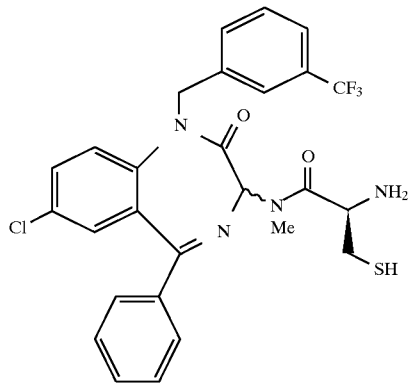

The title compound was prepared similar the procedure of Example 93 in which N-Boc-3-methylamino-1,3-dihydro-5-phenyl-7-chloro-1,4-benzodiazapin-2-one was alkylated at N-1 with 3-bromomethyl-trifluoromethylbenzene, followed by coupling of Boc-(S-ethylthio)-cysteine and deprotection as above. Purification of 108 mg of the crude material yielded the title compound as an unseparable mixture of two diastereomers 103A+B (22 mg).
Mass (electrospray, M+H$^+$) calc: 561.2 found: 561.5 (103A+B).

EXAMPLE 104

N-[[3-[(2-amino-3-mercapto-1-oxopropyl)
methylamino]-2,3-dihydro-2-oxo-5-phenyl-7-chloro-
1H-1,4-benzodiazepin-1-yl]methyl]-4-
methylbenzene (104)

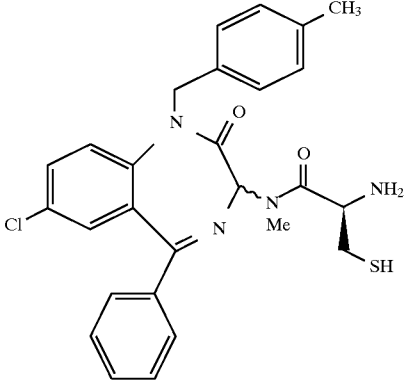

The title compound was prepared similar to the procedure of Example 93 in which N-Boc-3-methylamino-1,3-dihydro-5-phenyl-7-chloro-1,4-benzodiazapin-2-one was alkylated at N-1 with 4-bromomethyl-toluene, followed by coupling of Boc-(S-ethylthio)-cysteine and deprotection as above. Purification of 102 mg of the crude material yielded the title compound as an unseparable mixture of two diastereomers 104A+B (17 mg).
Mass (electrospray, M+H$^+$) calc: 507.2 found: 507.4 (104A+B).

EXAMPLE 105

N-[[3-[(2-amino-3-mercapto-1-oxopropyl)
methylamino]-2,3-dihydro-2-oxo-5-phenyl-7-chloro-
1H-1,4-benzodiazepin-1-yl]methyl]-2,4-
difluorobenzene (105)

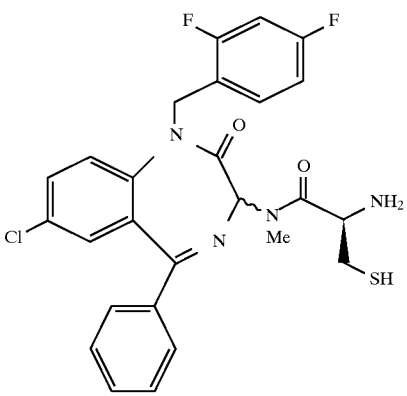

The title compound was prepared similar to the procedure of Example 93 in which N-Boc-3-methylamino-1,3-dihydro-5-phenyl-7-chloro-1,4-benzodiazapin-2-one was alkylated at N-1 with bromomethyl-2,4-difluorobenzene, followed by coupling of Boc-(Sethylthio)-cysteine and deprotection as above. Purification of 100 mg of the crude material yielded the two diastereomers 105A (2 mg) and 105B (4 mg).
Mass (electrospray, M+H$^+$) calc: 529.2 found: 529.0 (105A), 529.0 (105B).

EXAMPLE 106

N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-trifluoromethylbenzene (106)

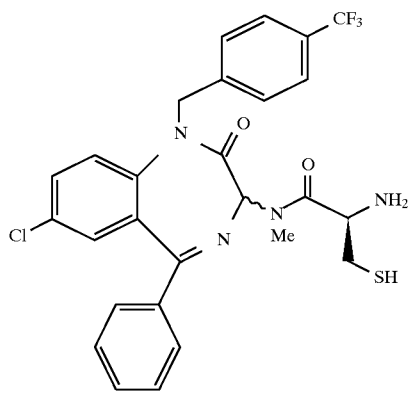

The title compound was prepared similar to the procedure of Example 93 in which N-Boc-3-methylamino-1,3-dihydro-5-phenyl-7-chloro-1,4-benzodiazapin-2-one was alkylated at N-1 with 4-bromomethyl-trifluoromethylbenzene, followed by coupling of Boc-(S-ethylthio)-cysteine and deprotection as above. Purification of 99 mg of the crude material yielded the two diastereomers 106A (5 mg) and 106B (4 mg).
Mass (electrospray, M+H$^+$) calc: 561.2 found: 561.5 (106A), 561.5 (106B).

EXAMPLE 107

N-[[3-[(2-amino-3-mercapto-1-oxopropyl)methylamino]-2,3-dihydro-2-oxo-5-phenyl-7-chloro-1H-1,4-benzodiazepin-1-yl]methyl]-2-chlorobenzene (107)

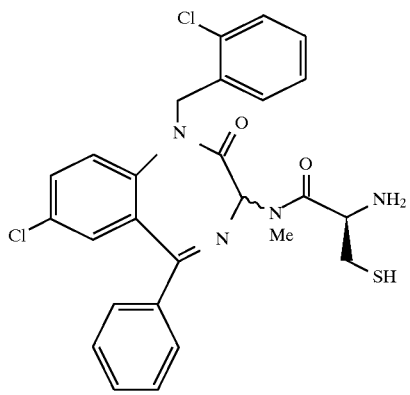

The title compound was prepared similar the procedure of Example 93 in which N-Boc-3-methylamino-1,3-dihydro-5-phenyl-7-chloro-1,4-benzodiazapin-2-one was alkylated at N-1 with 2-bromomethyl-chlorobenzene, followed by coupling of Boc-(Sethylthio)-cysteine and deprotection as above. Purification of 100 mg of the crude material yielded the title compound as an unseparable mixture of two diastereomers 107A+B (11 mg).

Mass (electrospray, M+H$^+$) calc: 527.6 found: 527.2 (107A+B).

EXAMPLE 108

N-[[3-[(2-amino-3-mercapto-1-oxopropyl)methylamino]-2,3-dihydro-2-oxo-5-phenyl-7-chloro-1H-1,4-benzodiazepin-1-yl]methyl]-4-fluorobenzene (108)

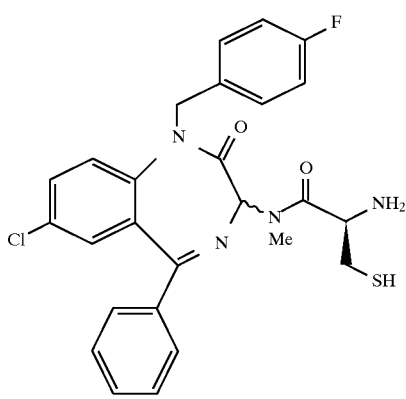

The title compound was prepared similar to the procedure of Example 93 in which N-Boc-3-methylamino-1,3-dihydro-5-phenyl-7-chloro-1,4-benzodiazapin-2-one was alkylated at N-1 with 4-bromomethyl-fluorobenzene, followed by coupling of Boc-(Sethylthio)-cysteine and deprotection as above. Purification of 108 mg of the crude material yielded the title compound as an unseparable mixture of two diastereomers 108A+B (19 mg).

Mass (electrospray, M+H$^+$) calc: 511.2 found: 511.2 (108A+B).

EXAMPLE 109

N-[[3-[(2-methylthiazolidine-4-carboxyl)
methylamino]-2,3-dihydro-2-oxo-5-phenyl-1H-1,4-
benzodiazepin-1-yl]acetyl]-L-methionine ethyl ester
(109)

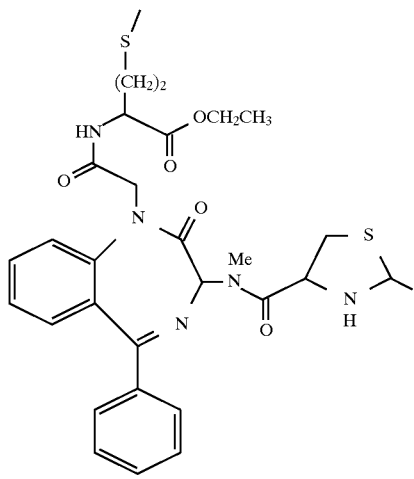

The title compound was prepared using the procedure of Example 37 in which 3-(tert-butoxycarbonyl)methylamino-2,3-dihydro-5-phenyl-1H-1,4-benzodiazepin-2-one-1-acetic acid was coupled to L-methionine ethyl ester as above. After removal of the Boc-protecting group and aqueous workup, coupling of N-Boc-2-methyl thiazolidine-4-carboxylic acid followed by removal of the cysteine Boc-protecting group yielded the title compound in a manner similar to that shown in Example 37, omitting the step for final removal of the thiol protecting group. Purification of 180 mg of the crude material yielded the two diastereomers 109A (18 mg) and 109B (20 mg).

Mass (electrospray, M+H$^+$) calc: 612.4 found: 614.1 (109A), 613.1 (109B).

EXAMPLE 110

N-[[3-[(2-amino-3-tert-butylthiomercapto-1-
oxopropyl)methylamino]-2,3-dihydro-2-oxo-5-
phenyl-1H-1,4-benzodiazepin-1-yl]acetyl]-L-
methionine methyl ester (110)

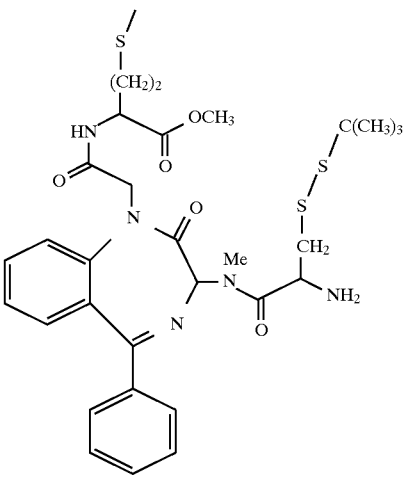

The title compound was prepared using the procedure of Example 37 in which 3-(tert-butoxycarbonyl)methylamino-2,3-dihydro-5-phenyl-1H-1,4-benzodiazepin-2-one-1-acetic acid was coupled to L-methionine methyl ester as above. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 465 mg of the crude material yielded the two diastereomers 110A (75 mg) and 110B (92 mg).

Mass (electrospray, M+H$^+$) calc: 660.4 found: 660 (110A), 659.8 (110B).

EXAMPLE 111

N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-methionine cyclohexyl ester (111)

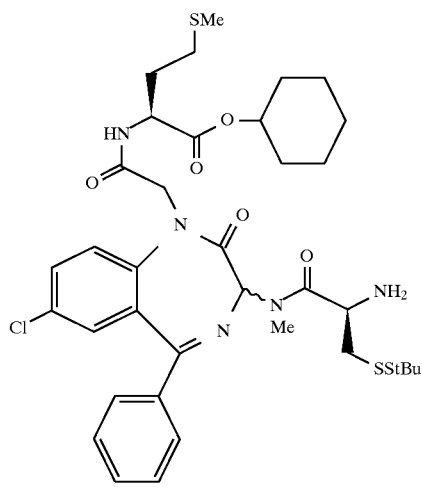

The title compound was prepared using the procedure of Example 37 in which 3-(tert-butoxycarbonyl)methylamino-2,3-dihydro-5-phenyl-7-chloro-1H-1,4-benzodiazepin-2-one-1-acetic acid (see also Example 67) was coupled to L-methionine cyclohexyl ester as above. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 125 mg of the crude material yielded the two diastereomers 111A (10 mg) and 111B (10 mg). Mass (electrospray, M+H$^+$) calc: 762.3 found: 762.3 (111A), 762.3 (111B).

EXAMPLE 112

N-[[3-[(2-amino-3-tert-butylthiomercapto-1-oxopropyl)methylamino]-2,3-dihydro-2-oxo-5-phenyl-1H-1,4-benzodiazepin-1-yl]acetyl]-L-methionine cyclohexyl ester (112)

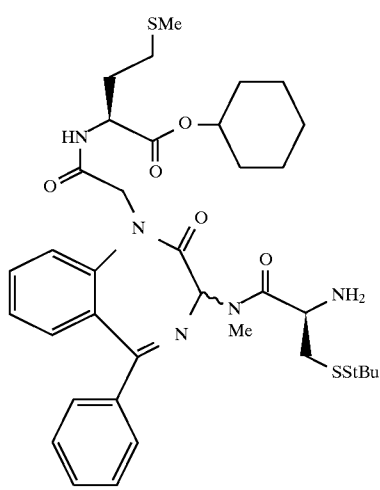

The title compound was prepared using the procedure of Example 37 in which 3-(tert-butoxycarbonyl)methylamino-2,3-dihydro-5-phenyl-1H-1,4-benzodiazepin-2-one-1-acetic acid was coupled to L-methionine cyclohexyl ester as above. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 2500 mg of the crude material yielded the two diastereomers 112A (453 mg) and 112B (383 mg).

Mass (electrospray, M+H$^+$) calc: 728.5 found: 728.4 (112A), 728.4 (112B).

EXAMPLE 113

N-[[3-[(2-amino-3-tert-butylthiomercapto-1-oxopropyl)methylamino]-2,3-dihydro-2-oxo-5-(2'-fluorophenyl)-7-chloro-1H-1,4-benzazepin-1-yl]acetyl]-L-methionine cyclohexyl ester

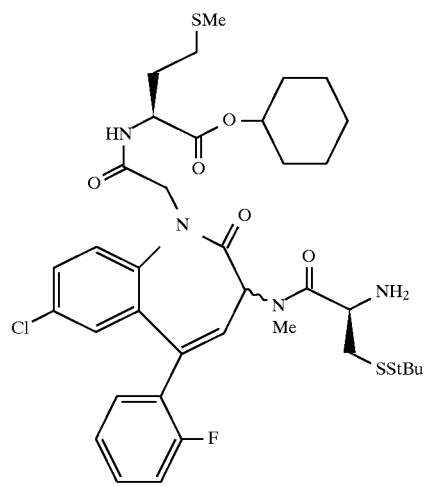

(113)

The title compound was prepared using the procedure of Example 37 in which 3-(tert-butoxycarbonyl)methylamino-2,3-dihydro-5-(2'fluorophenyl)-7-chloro-1H-1,4-benzazepin-2-one-1-acetic acid (90) was coupled to L-methionine cyclohexyl ester as above. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 250 mg of the crude material yielded the two diastereomers 113A (58 mg) and 113B (64 mg).

Mass (electrospray, M+H$^+$) calc: 779.2 found: 779.3 (113A), 779.2 (113B).

EXAMPLE 114

N-[[3-[(2-amino-3-tert-butylthiomercapto-1-oxopropyl)methylamino]-2,3-dihydro-2-oxo-5-phenyl-7-chloro-1H-1,4-benzodiazepin-4-yl]acetyl]-L-leucine tetrazole (114)

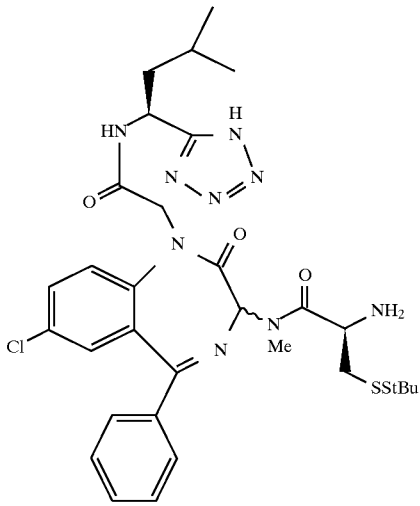

The title compound was prepared using the procedure of Example 37 in which 3-(tert-butoxycarbonyl)methylamino-2,3-dihydro-5-phenyl-7-chloro-1H-1,4-benzazepin-2-one-1-acetic acid (see also Example 67) was coupled to L-leucine tetrazole as above (see also Example 46). After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 750 mg of the crude material yielded the two diastereomers 114A (21 mg) and 114B (16 mg).

Mass (electrospray, M+H$^+$) calc: 686.4 found: 686.3 (114A), 686.3 (114B).

EXAMPLE 115

N-[[3-[(2-amino-3-tert-butylthiomercapto-1-oxopropyl)methylamino]-2,3-dihydro-2-oxo-5-phenyl-7-chloro-1H-1,4-benzazepin-1-yl]acetyl]-L-phenylalanine amide (115)

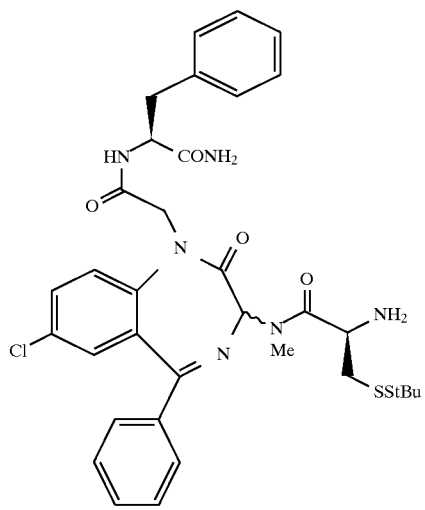

The title compound was prepared using the procedure of Example 37 in which 3-(tert-butoxycarbonyl)methylamino-2,3-dihydro-5-phenyl-7-chloro-1H-1,4-benzazepin-2-one-1-acetic acid (see also Example 67) was coupled to L-phenylalanine amide as shown above for the esters. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 250 mg of the crude material yielded the two diastereomers 115A (12 mg) and 115B (13 mg).

Mass (electrospray, M+H$^+$) calc: 695.3 found: 695.0 (115A), 695.2 (115B).

EXAMPLE 116

N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-methionine tetrazole (116)

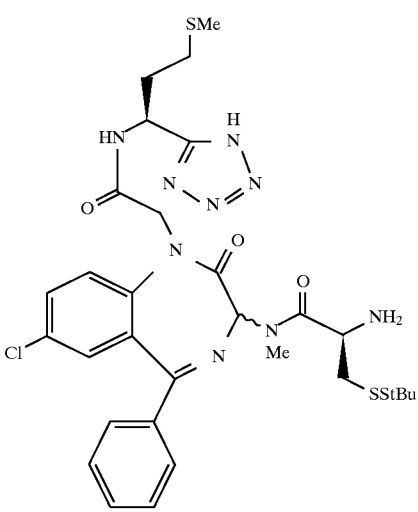

The title compound was prepared using the procedure of Example 37 in which 3-(tert-butoxycarbonyl)methylamino-2,3-dihydro-5-phenyl-7-chloro-1H-1,4-benzazepin-2-one-1-acetic acid (see also Example 67) was coupled to L-methionine tetrazole as above (see also Example 46). After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 1230 mg of the crude material yielded the two diastereomers 116A (60 mg) and 116B (62 mg).

Mass (electrospray, M+H$^+$) calc: 704.3 found: 704.4 (116A), 704.2 (116B).

EXAMPLE 117

N-[[3-[(2-amino-3-tert-butylthiomercapto-1-oxopropyl)methylamino]-2,3-dihydro-2-oxo-5-phenyl-1H-1,4-benzodiazepin-1-yl]acetyl]-L-phenylalanine cyclohexyl ester (117)

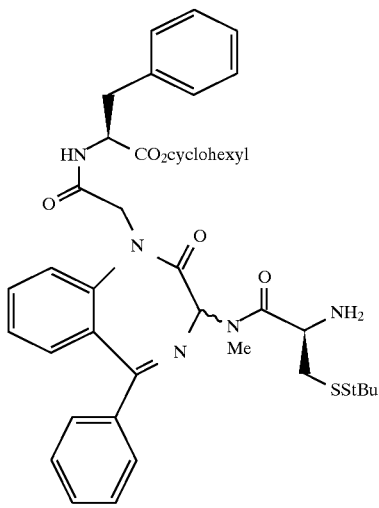

The title compound was prepared using the procedure of Example 37 in which 3-(tert-butoxycarbonyl)methylamino-2,3-dihydro-5-phenyl-1H-1,4-benzodiazepin-2-one-1-acetic acid was coupled to L-phenylalanine cyclohexyl ester as above. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 700 mg of the crude material yielded the two diastereomers 117A (76 mg) and 117B (85 mg).

Mass (electrospray, M+H$^+$) calc: 744.5 found: 744.4 (117A), 744.4 (117B).

EXAMPLE 118

N-[[3-[(2-amino-3-tert-butylthiomercapto-1-oxopropyl)methylamino]-2,3-dihydro-2-oxo-5-phenyl-1H-1,4-benzodiazepin-1-yl]acetyl]-L-methionine tert-butyl ester (118)

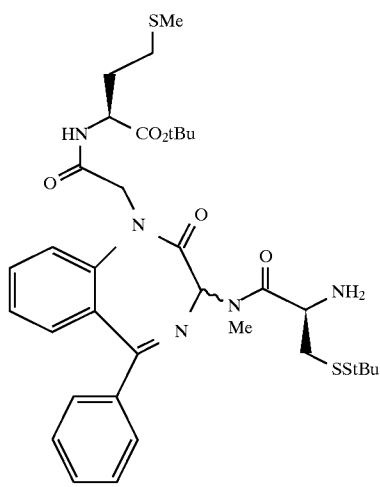

The title compound was prepared using the procedure of Example 37 in which 3-(tert-butoxycarbonyl)methylamino-2,3-dihydro-5-phenyl-1H-1,4-benzodiazepin-2-one-1-acetic acid was coupled to L-phenylalanine tert-butyl ester as above. After removal of the Boc-protecting group with 2%TFA/CH$_2$Cl$_2$ and aqueous workup, coupling of N-Boc-S-tert-butylmercapto cysteine followed by removal of the cysteine Boc-protecting group (again with 2%TFA/CH$_2$Cl$_2$) yielded the title compound in a manner similar to that shown in Example 37, omitting the step for final removal of the thiol protecting group. Purification of 170 mg of the crude material yielded the two diastereomers 118A (27 mg) and 118B (35 mg).

Mass (electrospray, M+H$^+$) calc: 702.6 found: 702.4 (118A), 702A (118B).

EXAMPLE 119

N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-phenylalanine tetrazole (119)

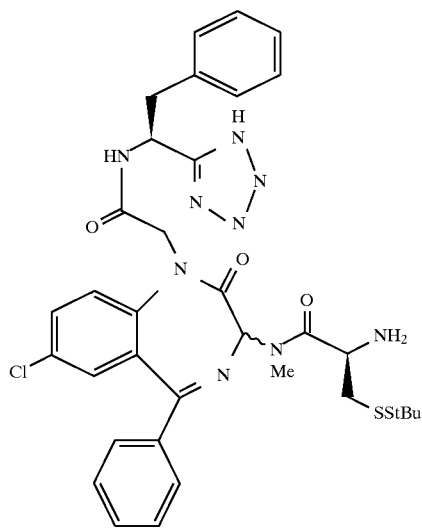

The title compound was prepared using the procedure of Example 37 in which 3-(tert-butoxycarbonyl)methylamino-2,3-dihydro-5-phenyl-7-chloro-1H-1,4-benzazepin-2-one-1-acetic acid (see also Example 67) was coupled to L-phenylalanine tetrazole as above (see also Example 46). After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 1620 mg of the crude material yielded the two diastereomers 119A (50 mg) and 119B (83 mg).

Mass (electrospray, M+H$^+$) calc: 720.2 found: 717.6 (119A), 717.5 (119B).

EXAMPLE 120

N-[[3-[(2-amino-3-tert-butylthiomercapto-1-oxopropyl)methylamino]-2,3-dihydro-2-oxo-5-phenyl-7-chloro-1H-1,4-benzodiazepin-1-yl]acetyl]-L-phenylalanine cyclohexyl ester (120)

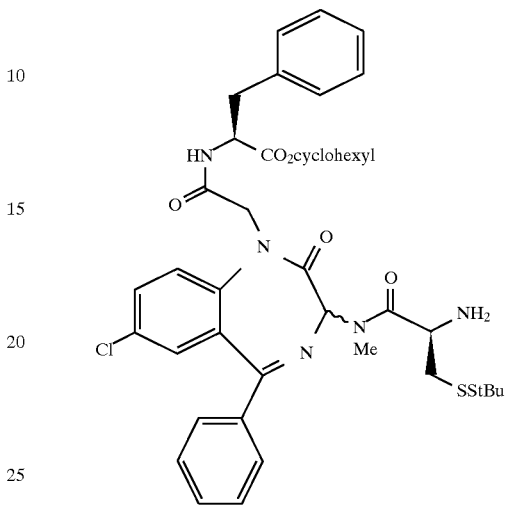

The title compound was prepared using the procedure of Example 37 in which 3-(tert-butoxycarbonyl)methylamino-2,3-dihydro-5-phenyl-7-chloro-1H-1,4-benzodiazepin-2-one-1-acetic acid (see also Example 67) was coupled to L-phenylalanine cyclohexyl ester as above. After removal of the Boc-protecting group and aqueous workup, coupling of N-Boc-S-tert-butylmercapto cysteine followed by removal of the cysteine Boc-protecting group yielded the title compound in a manner similar to that shown in Example 37, omitting the step for final removal of the thiol protecting group. Purification of 86 mg of the crude material yielded the two diastereomers 120A (15 mg) and 120B (24 mg). Mass (electrospray, M+H$^+$) calc: 778.5 found: 778.2 (120A), 778.2 (120B).

EXAMPLE 121

In vitro inhibition of CAAX farnesyltransferase

All compounds were tested for in vitro inhibition of CAAX protein farnesyltransferase. The enzyme was isolated and purified to homogeneity from rat brain homogenates by sequential ammonium sulfate fractionation, Mono Q ion-exchange chromatography, and peptide affinity chromatography as described in Reiss, Y., Seabra, M. C., Goldstein, J. L., and Brown, M. S. *Methods: A Companion to Methods in*

*Enzymology* 1, 241–245 (1990). Alternatively, recombinant CAAX protein farnesyltransferase was also used in this assay. Recombinant enzyme was produced in a baculovirus expression system as in O'Reilly, D. R., Miller, L. K., and Luckow, V. A. Baculovirus Expression Vectors: A Laboratory Manual (W. H. Freeman and Co., New York, 1992). Seventy-two hrs after infection, the cells were harvested and disrupted and the enzyme isolated by chromatography on Q-Sepharose. The recombinant farnesyltransferase was judged to be ~90% pure by Comassie blue staining after SDS gel electrophoresis.

In each experiment, varying concentrations of the inhibitor were mixed with the enzyme, and the amount of [3H] farnesyl transferred from all-trans-[3H]farnesyl pyrophosphate to recombinant p21H-ras was measured in a filter binding assay as described in Reiss, Y., Goldstein, J. L., Seabra, M. C., Casey, P. J., and Brown, M. S. *Cell* 62, 81–88 (1990). Briefly, the assay mixture contained, in a final volume of 50 μl, 50 mM Tris-chloride (pH 7.5), 50 μM ZnCl2, 3 mM MgCl2, 20 mM KCl, 5 mM dithiothreitol (DTT), 0.4% (v/v) octyl-β-glucoside, 1% (v/v) dimethyl sulfoxide (DMSO), 0.6 μM all-trans-[3H]farnesyl pyrophosphate (9730 dpm/pmol; Dupont-New England Nuclear), 40 μM recombinant p21H-ras (see Reiss, Y., Goldstein, J. L., Seabra, M. C., Casey, P. J., and Brown, M. S. *Cell* 62, 81–88 (1990)), 10 ng purified CAAX farnesyltransferase and concentrations of the indicated inhibitor (varying from 0.1 nM to 10 μM). After incubation for 30 min at 37° C., the amount of [3H]farnesyl group transferred to p21H-ras was measured by precipitation with SDS/trichloroacetic acid, filtration onto nitrocellulose, and scintillation counting. Immediately before use, each inhibitor to be tested was diluted into a solution containing 2.5% DMSO, 10 mM DTT, and 0.5% octyl-β-glucoside, and added to the 50 μl reaction mixture in a volume of 20 μl. $EC_{50}$ values were obtained as the estimated concentration of inhibitor yielding 50% of the [3H]-recovered in control samples (no inhibitor).

Structures of the compounds tested are reproduced below. Compound numbers also refer to example numbers above. Table D below shows the results of the CAAX farnesyltransferase assay for each diastereomer (A and B) (except where noted, compound 29).

TABLE A

| cpd. | $R^8$ | $R^{24}$ | $R^{25}$ |
|---|---|---|---|
| 27 | $CH((CH_2)_2SCH_3)COOH$ | $CH_3$ | $CH(CH_2SH)NH_2$ |
| 28 | $CH((CH_2)_2SCH_3)COOH$ | H | $CH(CH_2SH)NH_2$ |
| 29 | $CH((CH_2)_2SCH_3)COOH$ | $CH_3$ | $(CH_2)_2SH$ |
| 30 | $CH(CH_2OH)COOH$ | $CH_3$ | $CH(CH_2SH)NH_2$ |
| 31 | $CH(CH_3CH(CH_3)_2)COOH$ | $CH_3$ | $CH(CH_2SH)NH_2$ |
| 32 | $CH((CH_2)_2SCH_3)COOH$ | $CH_3$ | $CH(CH_2SH)NHCOCH_3$ |
| 33 | $CH((CH_2)_2SCH_3)CONH_2$ | $CH_3$ | $CH(CH_2SH)NH_2$ |
| 34 | $CH(CH_2C_6H_5)COOH$ | $CH_3$ | $CH(CH_2SH)NH_2$ |
| 35 | $CH(CH_3)COOH$ | $CH_3$ | $CH(CH_2SH)NH_2$ |
| 42 | $CH((CH_2)_2SCH_3)COOH$ | $CH_3$ | $CH(CH_2SH)NHC_2H_5$ |
| 43 | $CH((CH_2)_2SCH_3)COOH$ | $CH_3$ | $CH(-CH_2SCH(CH_3)-)NH$ |
| 44 | $CH(CH_2SH)COOH$ | $CH_3$ | $CH(CH_2SH)NH_2$ |
| 45 | $CH((CH_2)_2SCH_3)COOH$ | $CH_3$ | $CH(CH_2OH)NH_2$ |

TABLE B

| cpd. | $R^8$ | $R^{24}$ | $R^{25}$ |
|---|---|---|---|
| 37 | $CH((CH_2)_2SCH_3)CO_2CH_3$ | $CH_3$ | $CH(CH_2SH)NH_2$ |
| 39 | $CH((CH_2)_2SCH_3)CO_2CH_2CH_3$ | $CH_3$ | $CH(CH_2SH)NH_2$ |
| 41 | $CH((CH_2)_2SCH_3)CO_2C_6H_{11}$ | $CH_3$ | $CH(CH_2SH)NH_2$ |
| 46 | $CH(CH_3CH(CH_3)_2)CN_4H$ | $CH_3$ | $CH(CH_2SH)NH_2$ |
| 47 | $CH((CH_2)_2SCH_3)CN_4H$ | $CH_3$ | $CH(CH_2SH)NH_2$ |

TABLE C

[Structure diagram showing a compound with substituents R⁸, R²⁴, R²⁵, R¹, T₁, T₂, Z attached to a benzene ring framework with amide linkages]

| cpd. | R⁸ | R²⁴ | R²⁵ | R¹ | T₁–T₂ | Z |
|---|---|---|---|---|---|---|
| 9 | CH((CH₂)₂SCH₃)COOH | CH₃ | CH(CH₂SH)NH₂ | H | CH—CH₂ | CH₂ |
| 10 | CH((CH₂)₂SCH₃)COOH | H | CH(CH₂SH)NH₂ | H | CH—CH₂ | CH₂ |
| 48 | CH((CH₂)₂5CH₃)COOH | CH₃ | CH(CH₂SH)NH₂ | C₆H₅ | C═N | CH₂CH₂ |

TABLE D

In vitro Inhibition of CAAX Farnesyltransferase

| compound | EC₅₀ (μM) "A" | EC₅₀ (μM) "B" |
|---|---|---|
| 9 | 1.2 | 0.024 |
| 10 | 1.6 | 1.4 |
| 27 | 0.8 | 0.0003 |
| 28 | 0.38 | 0.431 |
| 29 (unseparable) | 1.8 | 1.8 |
| 30 | 10.0 | 0.0084 |
| 31 | 0.084 | 0.0021 |
| 32 | 1.2 | 8.0 |
| 33 | 2.2 | 0.019 |
| 34 | 0.54 | 0.0005 |
| 35 | >10 | 0.022 |
| 36 | >10 | 0.048 |
| 37 | 0.19 | 0.05 |
| 39 | 8.0 | 0.11 |
| 41 | 4.2 | 0.074 |
| 42 | 0.58 | 0.018 |
| 43 | 0.32 | 0.006 |
| 44 | 3.0 | 0.0045 |
| 45 | >10 | >10 |
| 46 | 0.26 | 0.0016 |
| 47 | 0.044 | 0.0046 |
| 48 | 2.5 | 0.004 |
| 49 | 0.74 | 0.006 |
| 50 | >3 | 0.0008 |
| 51 | >3 | 0.0017 |
| 52 | >3 | 0.0018 |
| 53 | >3 | 0.0004 |
| 54 | 1.5 | 0.004 |
| 55 | 0.6 | 0.0006 |
| 56 | 0.5 | 0.0005 |
| 57 | 2 | 0.0015 |
| 58 | 1.1 | 0.0006 |
| 59 | 1.1 | 0.0012 |
| 60 | 0.94 | 0.0005 |
| 61 | 1.7 | 0.0035 |
| 62 | 0.72 | 0.0005 |
| 63 | >10 | 2.0 |
| 64 | 0.26 | 0.002 |
| 65 | >3 | 0.0038 |
| 66 | 2.4 | 0.0006 |
| 67 | 0.31 | 0.0004 |
| 68 | 0.14 | 0.0016 |
| 69 | 1.5 | 0.0036 |
| 70 | 0.13 | 0.0008 |
| 71 | 0.1 | 0.0007 |
| 72 | 0.6 | 0.0017 |
| 80 (unseparable) | 0.0003 | 0.0003 |
| 81 | 0.43 | 0.0002 |
| 82 | 0.25 | 0.001 |
| 83 | ND | 0.0007 |
| 92 (unseparable) | 0.001 | 0.001 |
| 93 | 0.82 | 0.004 |
| 94 | 0.82 | 0.0042 |
| 95 | 0.88 | 0.0066 |
| 96 | 0.23 | 0.0013 |
| 97 | ND | 0.0003 |
| 98 | 0.84 | 0.006 |
| 99 | ND | 0.38 |
| 100 | 0.52 | 0.034 |
| 101 | 3.0 | 0.0009 |
| 102 | 0.11 | 0.038 |
| 103 (unseparable) | 0.0074 | 0.0074 |
| 104 (unseparable) | 0.0048 | 0.0048 |
| 105 | 2.0 | 0.02 |
| 106 | 0.65 | 0.018 |
| 107 (unseparable) | 0.006 | 0.006 |
| 108 (unseparable) | 0.0018 | 0.0018 |
| 109 | 3.1 | 0.1 |
| 110 | >1.5 | >1.5 |
| 111 | >3 | 1.4 |
| 112 | ND | 0.2 |
| 113 | >3 | >3 |
| 114 | ND | 0.12 |
| 115 | >3 | 0.1 |
| 116 | >3 | 0.03 |
| 117 | ND | 1.6 |
| 118 | ND | 0.9 |
| 119 | >3 | 0.017 |
| 120 | >3 | >3 |

EXAMPLE 122

Figure 1B:
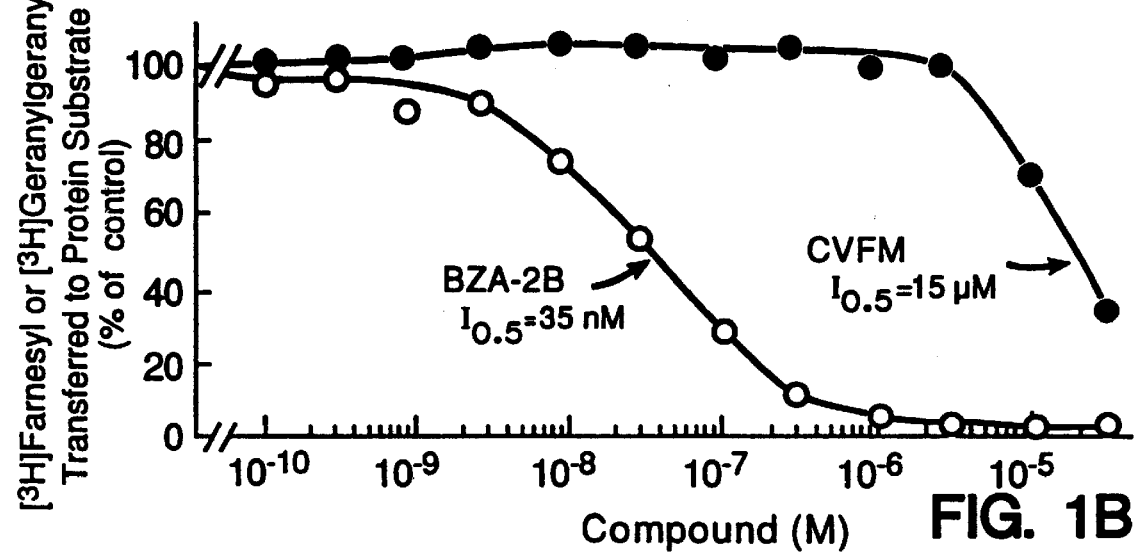
Figure 1C:
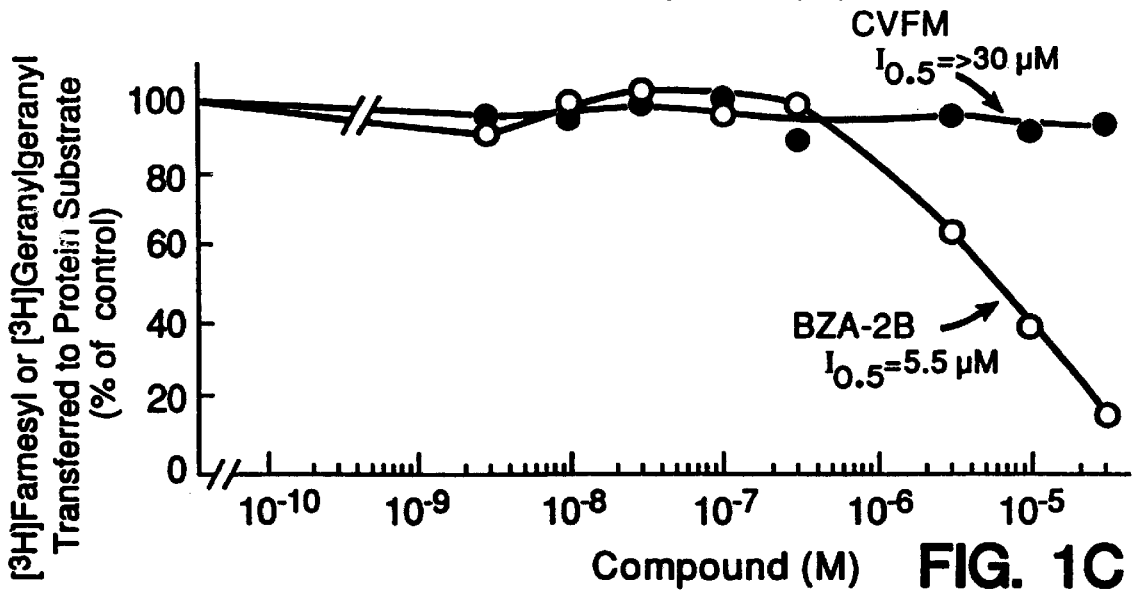

Differential inhibition of CAAX farnesyltransferase, CAAX GG transferase, and Rab GG transferase FIG. 1 compares the inhibitory activity of compound 27B (denoted as BG269B in the figure) on protein prenyltransferases. The compound inhibited recombinant ras CAAX farnesyltransferase by 50% at 0.26 nM, which was nearly 200-fold lower than the inhibitory concentration for the tetrapeptide CVFM. Two other prenyltransferases, both of which transfer 20-carbon geranylgeranyl (GG) groups, have been identified in rat brain. One of thesse, CAAX GG transferase, attaches GG groups to proteins that terminate in CAAX sequences in which X is leucine. The other enzyme, Rab GG transferase, recognizes a different class of substrates that do not terminate in CAAX sequences. Compound 27B (denoted as BG269B in FIG. 1) inhibited the CAAX GG transferase at a concentration more than 100-fold higher than that required to inhibit CAAX farnesyltransferase ($IC_{0.5}$=35 nM; FIG. 1B) and even less active on the third enzyme ($IC_{0.5}$=5.5 μM, FIG. 1C).

The conditions used to assay the inhibition of CAAX farnesyltransferase are identical to those described above for the in vitro, assay described in Example 121. In FIG. 1B the assay mixture contained, in a final volume of 50 μl, 50 mM sodium Hepes (pH 7.2), 5 mM $MgCl_2$, 5 mM DTT, 0.3 mM Nonidet P-40, 0.2% octyl β-glucoside, 1% DMSO, 0.5 μM all trans [3H]geranylgeranyl pyrophosphate (33,000 dpm/pmol; ARC, Inc.), 5 μM recombinant $p21^{H\text{-}rasCVLL}$, 6.3 μg partially purified CAAX GG transferase (see Seabra, M. C., Reiss, Y., Casey, P. J., Brown, M. S., and Goldstein, J. L. *Cell* 268, 4055 (1993)) and varying concentrations of the indicated inhibitor. In FIG. 1C, the assay mixture contained in a final volume of 50 μl, 50 mM sodium Hepes (pH 7.2), 5 mM MgCl2, 5 mM DTT, 0.3 mM Nonidet P-40, 0.2% octyl β-D-glucoside, 1% DMSO, 0.5 μM all trans [3H] geranylgeranyl pyrophosphate (33,000 dpm/pmol; ARC, Inc.), 2 μM recombinant Rab1A, 2 ng each of purified Components A and B of Rab GG transferase (see Seabra, M. C., Goldstein, J. L., Sudhof, T. C., and Brown, M. S. *J. Biol. Chem.* 267, 14497 (1992)) and varying concentrations of the indicated inhibitor.

EXAMPLE 123

Figure 2A:
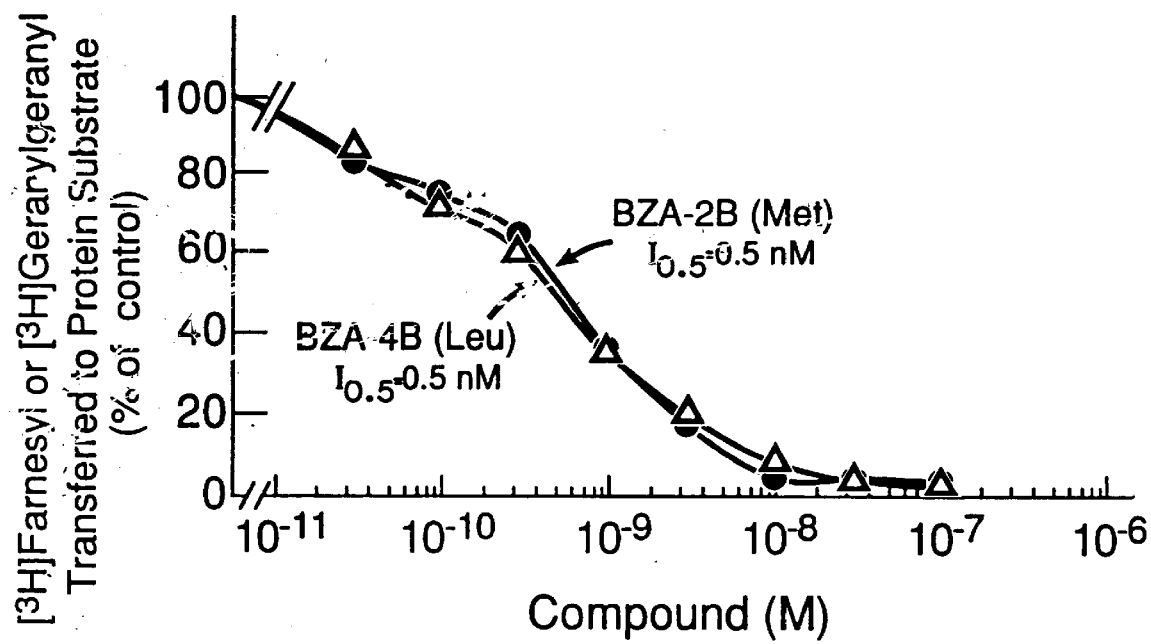
FIG. 2. Differential inhibition of CAAX farnesyltransferase (A) and CAAX GG transferase (B) by compound 27B (denoted as BZA-2B in the figure, closed circles) and compound 31B (denoted as BZA4B in the figure, open triangles).
Figure 2B:
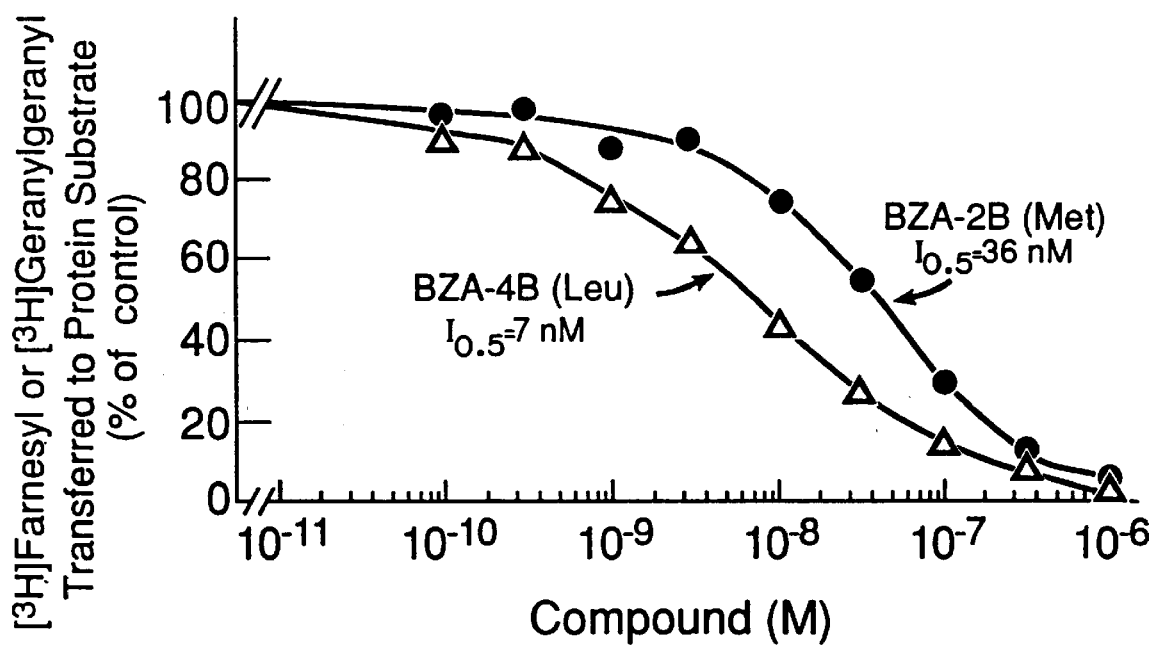

Differential inhibition of CAAX farnesyltransferase and geranylgeranyltransferase FIG. 2 shows that compound 27B (denoted as BG269B in the figure) which contains a C-terminal methionine, and compound 31B (denoted as BG287B in the figure) which contains leucine, were equally potent in inhibiting CAAX farnesyltransferase ($IC_{0.5}$=0.5 nM) (FIG. 2A). This result is surprising because leucine-terminated peptides are much less effective than methionine-terminated peptides in inhibiting farnesylation of p21H-ras. Apparently, important binding determinants are defined by the cysteine and benzodiazepine substituents. The CAAX geranylgeranyltransferase was 5-fold more sensitive to the leucine-terminated inhibitor (FIG. 2B).

Each assay was carried out as described in Examples 121 and 122.

EXAMPLE 124

Quantitation of Farnesyl Group Transfer

As shown for some peptides, several inhibitors tightly bind the enzyme and inhibit its activity, yet are not a substrate for the enzyme. The ability of each compound to act as a substrate for the CAAX farnesyltransferase was examined directly using thin layer chromatography (see Table E) as described in Goldstein, J. L., Brown, M. S., Stradley, S. J., Reiss, Y., and Gierasch, L. M. *J. Biol. Chem.* 266, 15575–15578 (1991) and Brown, M. S., Goldstein, J. L., Paris, K. J., Burnier, J. P., and Marsters, Jr., J. C. *Proc. Natl. Acad. Sci. USA* 89, 8313 (1992). Briefly, each 25 μl reaction mixture contained 50 mM Tris-chloride (pH 7.5), 50 μM ZnCl2, 3 mM MgCl2, 20 mM KCl, 1 mM dithiothreitol (DTT), 0.2 % (v/v) octyl-β-gluoside either 0.6 or 2.4 μM all-trans-[3H]farnesyl pyrophosphate (44,000 dpm/pmol; Dupont-New England Nuclear), ~5 ng purified CAAX farnesyltransferase and 90 pmol of the inhibitor to be tested (3.6 μM). After incubation at 37° C. for 30 min, the reaction was stopped by addition of 2 μl of 250 mM EDTA, and the entire reaction mixture was spotted onto a plastic-backed Silica Gel G thin layer sheet (20×20 cm, Brinkmann Inst.) and placed in a tank containing n-propyl alcohol/ammonium hydroxide/water (6:3:1 v/v/v). The chromatogram was run for 3 hr, after which it was either subjected to autoradiography or quantified by scintillation counting (see Brown, M. S., Goldstein, J. L., Paris, K. J., Burnier, J. P., and Marsters, Jr., J. C. *Proc. Natl. Acad. Sci. USA* 89, 8313 (1992)).

TABLE E

In vitro Farnesylation by CAAX Farnesyltransferase

| compound | % farnesylation [a]"A" | % farnesylation [a]"B" |
|---|---|---|
| 9 | <1 | <1 |
| 10 | 20 | <1 |
| 27 | 5 | <1 |
| 28 | 9 | <1 |
| 29 | <1 | <1 |
| 30 | <1 | <1 |
| 31 | <1 | <1 |
| 32 | 110 | <1 |
| 34 |  | <1 |
| 37 | <1 | 2 |
| 43 | <1 | <1 |
| 46 |  | <1 |

[a] % farnesylation measured as a percentage of [3H]farnesyl transferred to the compound relative to a separate experiment using a good substrate, the tetrapeptide CVIM.

EXAMPLE 125

Assay of Inhibition of CAAX Farnesyltransferase in Cultured Cells.

To study farnesylation in intact cells we used Met18b-2 cells, a line of Chinese hamster ovary (CHO) cells that takes up [3H]mevalonate efficiently (see Faust, J., and Krieger, M. *J. Biol. Chem.* 262, 1966 (1987)) owing to the production of a mevalonate transport protein (see Kim, C. M., Goldstein, J. L., Brown, M. S. J. Biol. Chem. 267, 23113 (1992)). The [3H]mevalonate is converted by the cells into [3H]farnesyl pyrophosphate and [3H]geranylgeranyl pyrophosphate, which are then attached to proteins (Kim, C. M., Goldstein, J. L., Brown, M. S. *J. Biol. Chem.* 267, 23113 (1992)). In the assay, stock cultures of Met18b-2 cells were seeded at a density of 3–105 cells per 60 mm dish in 3 ml of medium A (Dulbecco's modified Eagle medium/Ham's F12 medium (1:1, v/v) containing 100 U/ml penicillin and 100 μg/ml streptomycin) supplemented with 5% (v/v) fetal calf serum (FCS). On day 3, each monolayer was refed with 1 ml medium A supplemented with 1% FCS (dialyzed against 0.15 M NaCl). At this point the cells were treated with 100 μM compactin (see Brown, M. S., Faust, J. R., Goldstein, J. L., Kaneko, I., and Endo, A. *J. Biol. Chem.* 253, 1121 (1978)) which blocks the synthesis of unlabeled mevalonate within the cells. Each compound was dissolved at 25 mM in DMSO/10 mM DTT immediately before use and 10 μl of this solution added directly. After 2 hr incubation at 37° C., each monolayer received 100 μCi [3H]mevalonate (60 Ci/mmol, American Radiolabeled Chemicals, Inc.) added in 100 μl of the medium A, and the incubation continued for 4 hr. The cells were harvested by rinsing three times with 3 ml of 50 mM Tris-HCl/0.15 M NaCl (pH 7.5). 300 μl of lysis buffer (0.5X Dulbecco's phosphate-buffered saline containing 1% Triton X-100, 5 µg/ml leupeptin, 5 µg/ml pepstatin, 0.5 mM phenylmethylsulfonyl fluoride, and 0.05 U/ml aprotinin) was added to each monolayer. After incubation on ice for 5 mon, the lysates were centrifuged 30 sec in a microfuge at 12,000 g. The resulting supernatant was tranferred to a new tube, and each pellet was resuspended in 60 µl of lysis buffer. Protein concentrations were determined using the BCA protein assay reagent (Pierce) according to the manufacturer's instructions. Detergent-soluble (supernatant) and -insoluble (pellet) samples were mixed with 2X SDS sample buffer (see Laemmli, U. K. *Nature* 227, 680 (1970)) and heated at 95° C. for 5 min before electrophoresis. Each lane contained 90 µg protein, and was run on a 12.5% SDS-polyacrylamide gel. The gel was dried, treated with ENTENSIFY (NEN-DuPont), and exposed to Kodak XOMAT-AR film for 9 h at −80° C. to allow visualization of all prenylated proteins. Migration of [14C]methylated molecular weight standards (Amersham) were used as markers.

Figure 3:
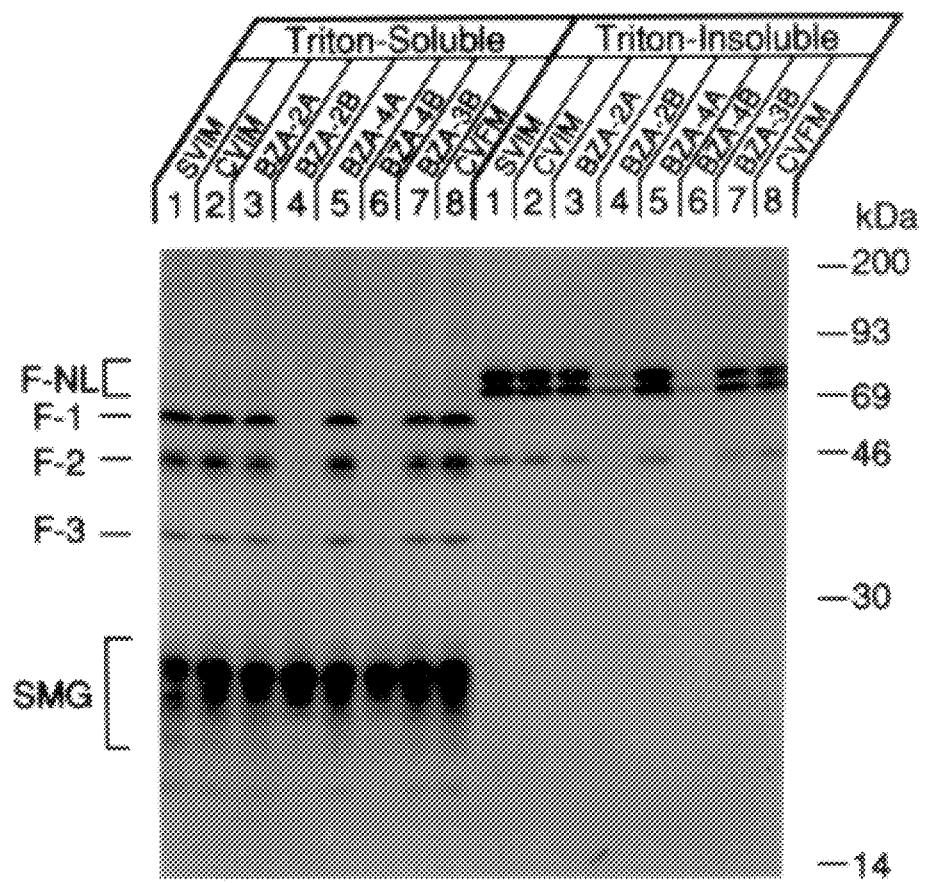
FIG. 3. Inhibition of [3H]mevalonate incorporation into prenylated proteins in monolayers of hamster Met18b-2 cells by compound 31 B (denoted as BZA-4B in the figure). Effects of control peptides SVIM, CVIM and CVFM as well as compound 27 A (BZA-2A in the figure) and 31A (BZA-4A in the figure) are also shown.

The results of this assay are shown in FIG. 3, using a final concentration of 250 µM for each inhibitor. Pilot experiments showed that the tetrapeptide SVIM which does not inhibit prenyltransferases did not alter the pattern of farnesylated proteins in the cells, and this was used as a control for all experiments. The Triton-soluble proteins marked F1 and F2 (unknown functions) have been shown previously to be farnesylated (see Reese, J. H., and Maltese, W. A. Mol. Cell. Biochem. 104, 109 (1991). Protein F3 has been recently purified in the Brown and Goldstein laboratory, and was also demonstrated to be farnesylated. The labeled bands in the 20 to 27-kDa range consist largely of low molecular weight GTP binding proteins, the vast majority of which are geranylgeranylated. The major proteins in the Triton-insoluble pellet are the nuclear lamins A and B, which are farnesylated (see Farnsworth, C. C., Wolda, S. L., Gelb, M. H., and Glomset, J. A. *J. Biol. Chem.* 264, 20422 (1989)). As shown in the figure, none of the control peptides or control benzodiazepine-peptideomimetics altered the prenylation of proteins in intact cells. The high affinity inhibitors 27B and 31B (denoted as BG269B and BG287B in the figure respectively) markedly decreased the labeling of all three Triton-soluble farnesylated proteins (F1 to F3) and reduced moderately the labeling of the farnesylated lamins (F—NL). The inhibitors had little effect on the low molecular weight GTP binding proteins (SMG).

EXAMPLE 126

Dose Dependence of Inhibition of CAAX Farnesyltransferase in Cultured Cells

Figure 4:
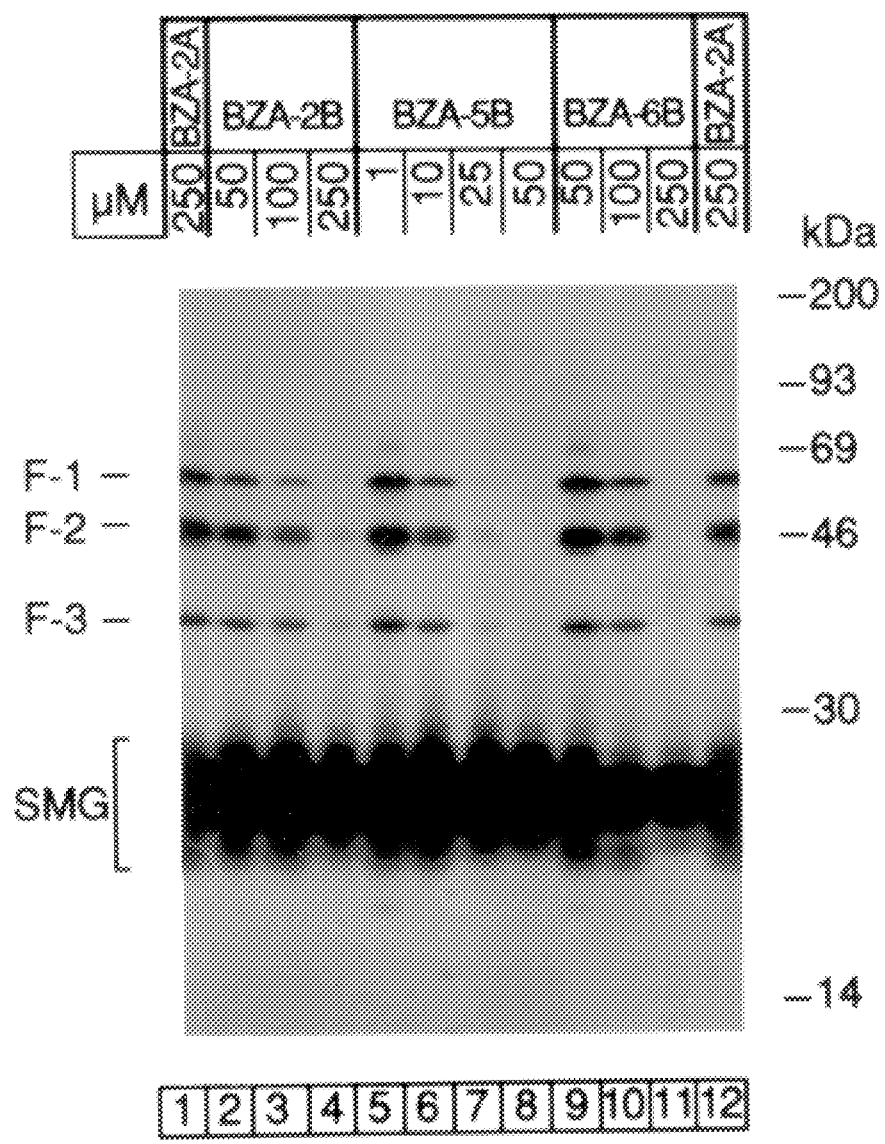
FIG. 4. Dose dependence of inhibition of [3H]mevalonate incorporation into prenylated proteins in monolayers of hamster met18b-2 cells by compound 27B (denoted as BZA-2B in the figure) and compound 37B (denoted as BZA-5B in the figure) and compound 33B (denoted as BZA-6B in the figure).

Using the same cells and procedures followed above for Example 125, we measured the dose dependence upon the inhibition of farnesylation in intact cells. Concentration curves for three of the more potent inhibitors are shown in FIG. 4 for the Triton-soluble proteins. The pro-drug, compound 37B (denoted as BG289B in the figure), was much more potent than the parent, compound 27B (denoted as BG269B in the figure). Compound 37B inhibited the famesylation of F1–3 detectably at 10 µM, and almost completely at 25 µM. Compound 33B, the C-terminal amide, was of intermediate potency.

In this manner, it is possible to obtain data regarding the comparative potency of these inhibitors upon the level of intracellular farnesylation. We have chosen to report the EC90% values for these inhibitors as the concentration required for a reduction in the Triton- soluble labelling (denoted F-1, F-2, and F-3) to 90% of control cells (untreated). This data has been collected for several of the inhibitors described in Table F below.

TABLE F

Inhibition of Intracellular Farnesylation in Intact Met18b-2 Cells

| compound | EC $_{90\%}$ [a] "B isomer" |
|---|---|
| 99 | 30 µM |
| 100 | 30 |
| 101 | 20 |
| 106 | 50 |
| 108 | 50 |
| 109 | 10 |
| 110 | 10 |
| 111 | 2 |
| 112 | 4 |
| 114 | 30 |
| 115 | 50 |
| 116 | 60 |
| 117 | 3 |
| 119 | 30 |
| 120 | 5 |

[a] approximate EC $_{90\%}$ measured as the concentration of inhibitor required to reduce the farnesylation of intracellular proteins F-1, F-2, and F-3 (see Figure 4) by 90% or greater, compared to control untreated cells using the procedure described in Example 125.

EXAMPLE 127

Immunoprecipitation of [3H]-labeled Ras Proteins

To demonstrate the inhibition of farnesylation of Ras proteins directly (see FIG. 5), we incubated the Met18b-2 cells with [3H]mevalonate and then immunoprecipitated the cell lysates with a monoclonal antibody that reacts with all four Ras proteins. In each experiment, aliquots of the Triton X-100 fraction (300 µg protein, prepared as described above) were incubated with 1 µg anti-Ras monoclonal antibody (Oncogene Sciences, Inc.) overnight at 4° C. on a rotating platform. Immune complexes were precipitated by addition of 25 µl Protein A-agarose suspension that had been pre-coated with goat anti-rat IgG (Oncogene Sciences, Inc.) according to the manufacturer's instructions. After a 30 min incubation at 4° C., the agarose beads were pelleted by centrifugation and washed 5 times with 1 ml each of wash solution (50 mM Tris-HCl, 50 mM NaCl, 0.5% (w/v) deoxycholate, 0.5% (v/v) Nonidet P-40, and 0.1% (w/v) SDS at pH 7.5). 75 µl of 1X SDS sample buffer was added and each sample heated for 5 min at 95° C. before electrophoresis as above.

Figure 5:
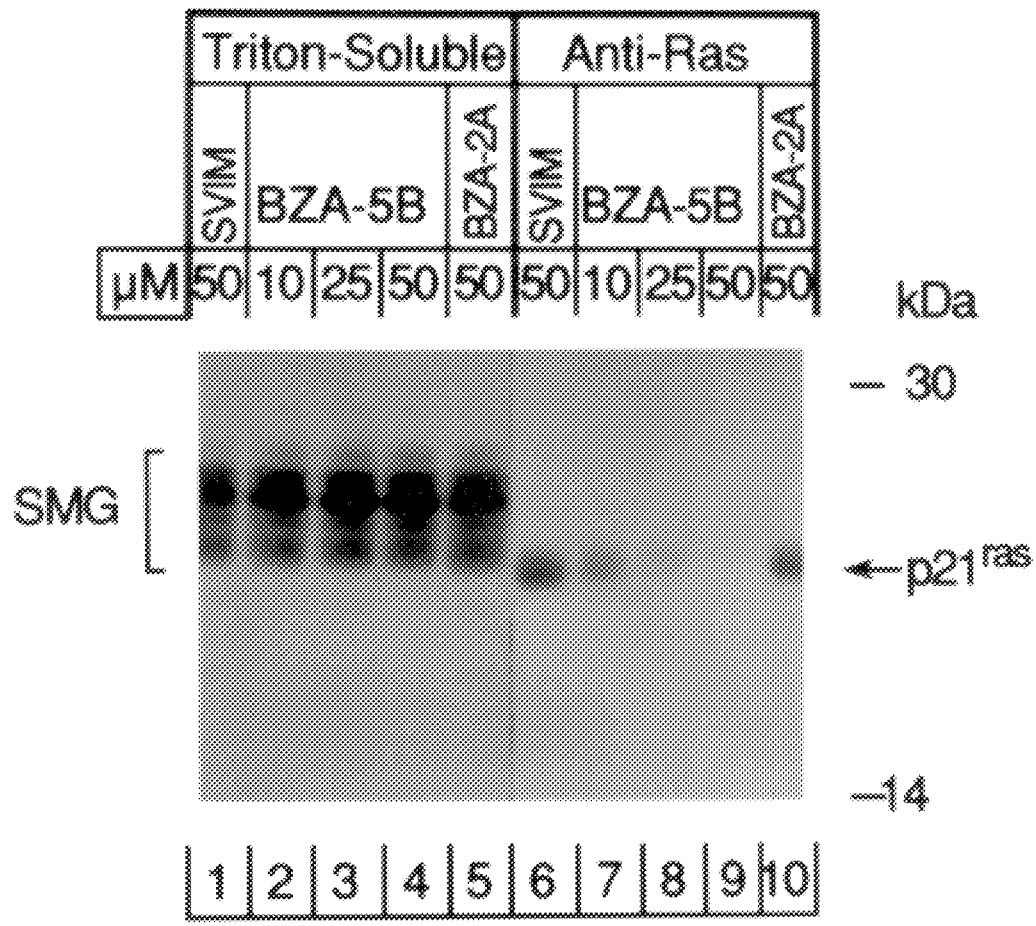
FIG. 5. Inhibition of [3H]mevalonate incorporation into p21H-ras proteins in Met18b-2 cells by compound 37B (denoted as BZA-5B in the figure). Triton soluble fractions (lanes 1–5) and the same fractions following immunopredpitation with an anti-ras monoclonal antibody (lanes 6–10) are also shown.
Figure 6A:
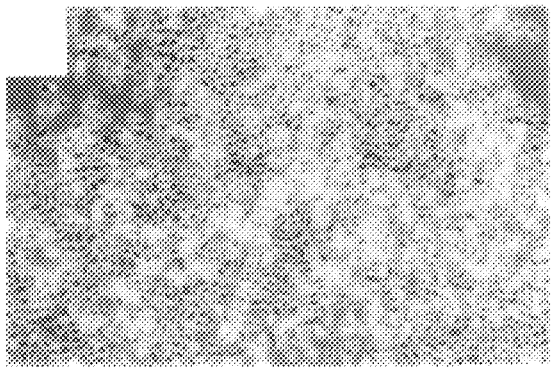
FIG. 6. Morphology of H-ras(Val12)-transformed rat-1 fibroblasts (A,B), src-transformed rat-1 firbroblasts (C,D), and untransformed rat-1 fibroblasts (E,F) incubated in the presence of either compound 27A, N-[[3-(2(S)-amino-3-mercapto-1-oxopropyl)methylamine]-2,3-dihydro-2-oxo-5-phenyl-1H-1,4-benzodiazepin-1-yl]acetyl]-L-methionine (isomer A) denoted BZA-2A in the figure (A,C,E) or compound 27B, N-[[3-(2(S) -amino-3-mercapto-1-oxopropyl) methylamine]-2,3-dihydro-2-oxo-5-phenyl-1H-1,4-benzodiazepin-1-yl]acetyl]-L-methionine (isomer B) (B,D, F).
Figure 6B:
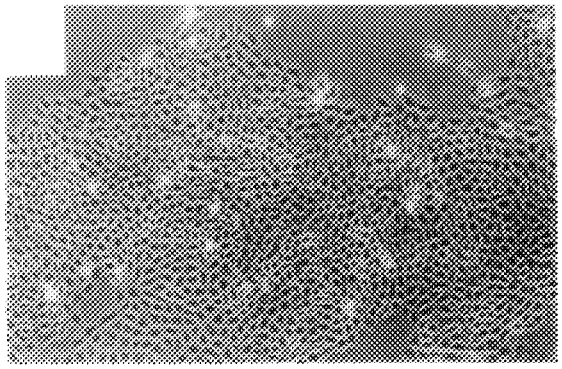
Figure 6C:
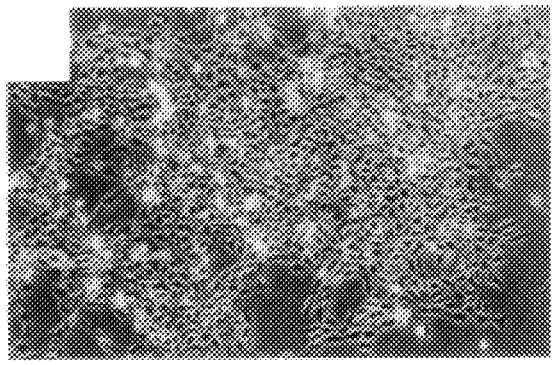
Figure 6D:
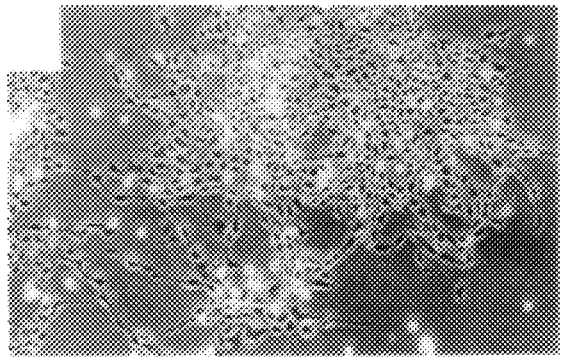
Figure 6E:
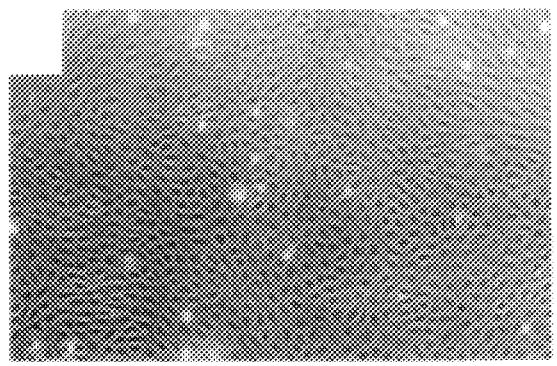
Figure 6F:
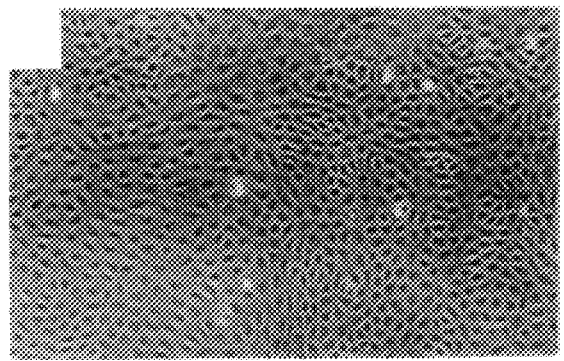
Figure 7A:
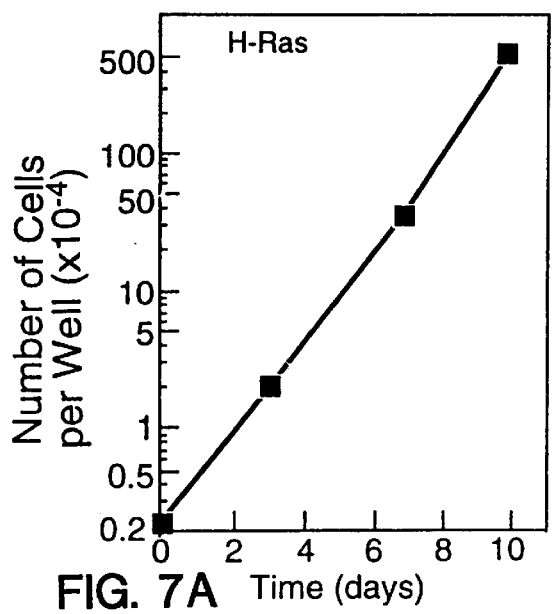
FIG. 7. Effects of farnesyltransferase inhibition on ras-transformed rat-1 fibroblasts (A, B), src-transformed rat-1 fibroblasts (C, D), and untransformed parental rat-1 fibroblasts (E, F). Growth rate of cell lines in the absence (A, C, E) and presence (B, D, F) of the inhibitor BZA-5B is shown.
Figure 7B:
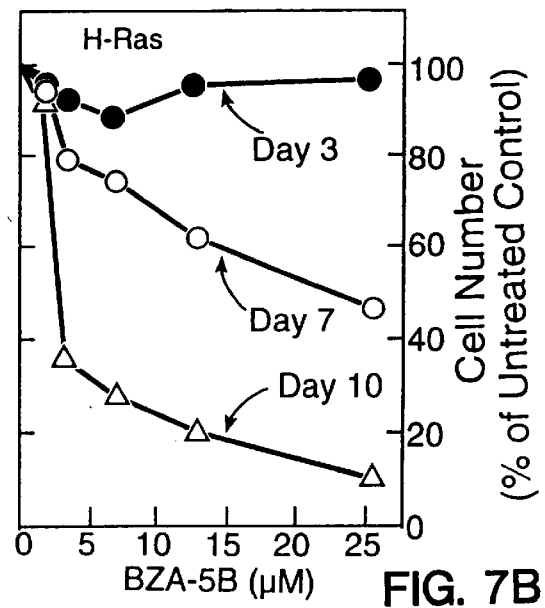
Figure 7C:
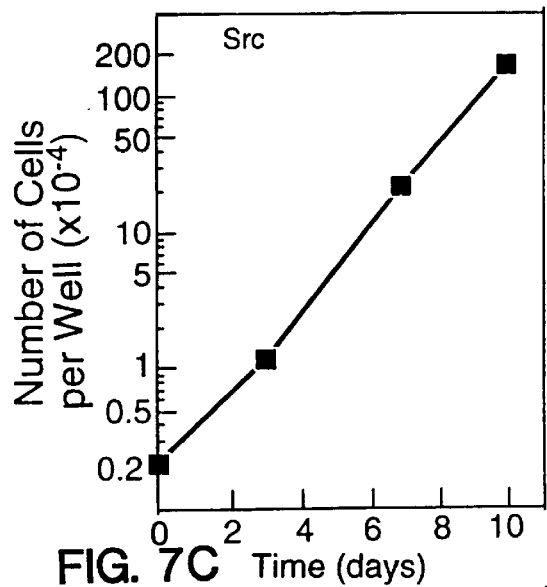
Figure 7D:
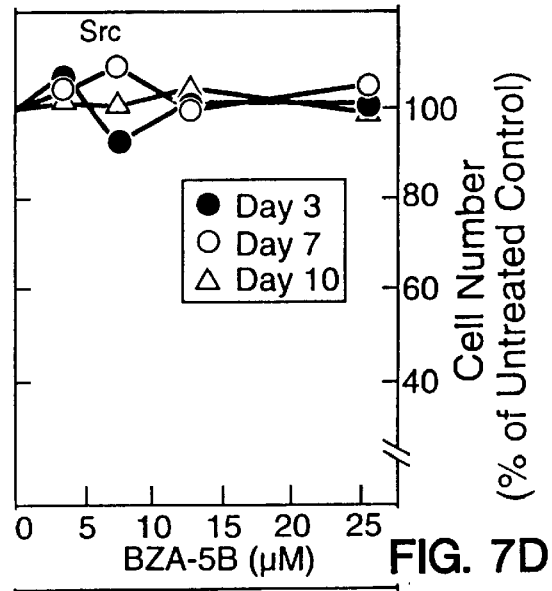
Figure 7E:
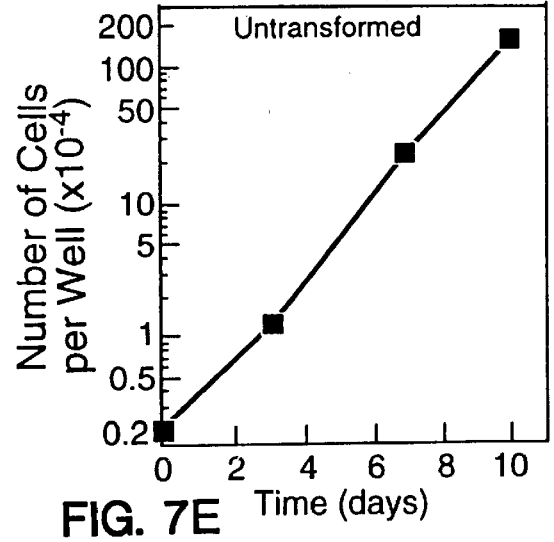
Figure 7F:
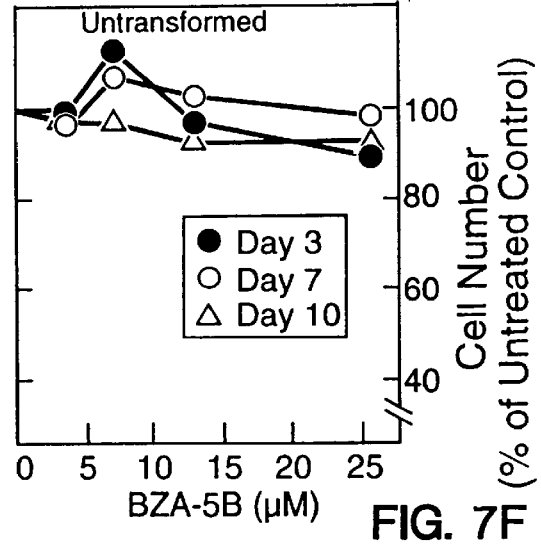

As seen in FIG. 5, increasing concentration of compound 37B (denoted as BZA-5B in the figure) did not detectably inhibit the incorporation of radioactivity into the abundant SMG proteins, most of which are geranylgeranylated (lanes 2–4). However, at 50 µM the compound abolished incorporation of [3H] mevalonate into immunoprecipitated ras proteins (lanes 7–9). Inhibition was readily detectable at 10 µM. The control molecules, the tetrapeptide SVIM and compound 27A (denoted as BZA-2A in the figure), had no effect.

EXAMPLE 128

Assay of Changes in Morphology of Ras-transformed Cells

As shown in FIG. 6, rat-1 fibroblasts transformed with an activated mutant of p21H-ras (Val 12) grow in multilayered clumps, indicative of malignant transformation. Compound 27A (denoted as BG269A in the figure) and compound 27B (denoted as BG269B in the figure) were added at 250 μM to test whether these compounds would induce reversion to a more normal phenotype as had been previously shown with microinjection of anti-Ras antibodies (see Feramisco, J. R. et al *Nature* 314, 639 (1985)). The H-ras transformed cells, denoted as rat 2.2 cells, were generated by transfection of rat-1 fibroblasts as described (see Seeburg, P. H., Colby, W. W., Capon, D. J., Goeddel, D. V., and Levinson, A. D. *Nature* 312,71 (1984)). Cells that overgrew the monolayer were extracted and plated onto agar to obtain a cell line displaying a fully transformed phenotype. Untransformed rat-1 fibroblasts and src-transformed rat-1 fibroblasts were also treated. The src-transformed cells were generated by co-transfection of rat-1 fibroblasts with pSV3.Neo.src, a vector containing the gene for src as well as the gene that confers G418 resistance, both under control of SV40 early promoters. G418-resistant cell clones that diplayed a transformed phenotype were used to generate the cell line. On day 0, cells were plated in monolayer culture at 3×103 cells per well (24-well plates) in 1 ml DMEM supplemented with 10% FCS, 100 U/ml penicillin, 10 μg/ml streptomycin, 2% DMSO, and 0.5 mM DTT with and without 200 μM inhibitor. On day 3, the cells were refed with the same medium. On day 5, the cells were photographed under contrast at a magnification of 100X. Incubation of ras transformed rat 2.2 cells with compound 27B (denoted as BG269B in the figure) for 5 days reversed the transformed phenotype (FIG. 6B) while compound 27A (denoted as BG269A in the figure) had no effect (FIG. 6A). Clearly, after 5 days, the rat 2.2 cells display a more normal, flattened cell morphology and grew to lower cell density. This change in morphology is remarkably similar to that seen following injection of anti-ras antibodies into ras-transformed cells (see Feramisco, J. R. et al *Nature* 314, 639 (1985)). Rat-1 fibroblasts transformed with the src oncogene also grew in a multilayered pattern (FIG. 6C), but this was not affected by compound 27A or compound 27B (FIG. 6D). The compounds also had no apparent effect on the morphology of untransformed rat-1 fibroblasts (FIG. 6E and F).

EXAMPLE 129

Effect of Farnesyltransferase inhibition on cell growth in transformed and untransformed cells To examine the effects of farnesyltransferase inhibition on cell growth, three cell lines (ras-transformed rat-1, src-transformed rat-1, and parental rat-1 cells) were seeded (see FIG. 7) at low density and allowed to grow for 10 days in the absence or presence of increasing concentrations of BZA-5B (compound 37). See Example 128 for description of cells. On day 0, cells were plated in monolayer culture at 2×103 cells per well (24-well plates) in 1 ml DMEM supplemented with 10% fetal calf serum, 100 U/ml penicillin, 100 μg/ml streptomycin, 0.5 mM DTT, 0.025% DMSO, and the indicated concentration of BZA-5B (compound 37). On days 3 and 7, cells were washed and refed with the same medium. At the time indicated in FIG. 7, cells were harvested by trypsinization and counted in a Coulter counter. Panels A, C, E show the growth rate of each cell line in the absence of inhibitor. Panels B, D, F show the inhibition of growth as a function of concentration of BZA-5B at each time point. The "100% values" correspond to the appropriate cell numbers in Panels A, C, E at the indicated time. Each value represents a single incubation. As shown in the panels A, C, and E, all three cell lines grew logarithmically with no added inhibitor. In the presence of BZA-5B, the growth of ras-transformed fibroblasts was inhibited in a time- and dosage-dependent manner, reaching ~90% inhibition after 10 days in the presence of 25 μM BZA-5B (Panel B). The growth of src-transformed (Panel D) and untransformed cells (Panel F) were not affected at concentrations of BZA-5B up to 25 μM. These results show that this inhibitor specifically slows the growth of intact ras-transformed cells with no effect on "normal" non-transformed cells or cells transformed by an alternate oncogenic mutation, suggesting that these inhibitors are potential treatments for tumors in which oncogenic ras may play a role.

These results suggest that the special sensitivity to inhibitor treatment of cells bearing a mutant ras protein is caused by two factors. First, the depletion from the plasma membrane of farnesylated Ras-GTP causes a reduction in stimulation of intracellular kinases, and hence a reversal in transduction of these signals to the cell nucleus. Second, the accumulation of non-farnesylated Ras-GTP in the cytosol of these cells may directly inhibit intracelluar signalling. These two effects may act in synergy to cause a dramatic reduction in cell proliferation.

The tolerance of cells bearing wild-type Ras to inhibitor treatment suggests that normal signalling is unaffected by depletion of Ras-GDP from the plasma membrane. Ras-GDP may be recruited to the membrane by interaction with cytosolic 'linker' proteins such as mSos. Alternatively, cell signalling pathways may be redundant and stimulate cell proliferation through alternate pathways independent of Ras.

EXAMPLE 130

Effect of Farnesyltransferase inhibition on cell growth in transformed and untransformed human tumor cell lines To examine the effects of farnesyltransferase inhibition on the growth of human tumor cell lines, several such lines were treated with 25 μM BZA-5B (compound 37B) using a procedure similar to that described in Example 129 above. Cells were refed with fresh media at days 3 and 6 containing the inhibitor, and were harvested and counted as described above. The effect of 37 on the growth of these cells is reported below in Table G as a percentage of growth (cell count) relative to untreated cell control. These results show that the inhibitor slows the growth of most human tumor lines bearing a mutant ras protein.

TABLE G

Growth Inhibition of Human Tumor Lines Bearing Mutant Ras

| cell line | type | ras xformed? | % growth inhib. |
|---|---|---|---|
| HT-1080 | fibrosarcoma | yes | 64 |
| SW-480 | colon | yes | 45 |
| MCF-231 | breast (human) | yes | 58 |
| CALU-3 | lung | yes | 52 |
| HCT-116 | colon | yes | 0 |
| MDA-7 | breast | no | 0 |
| Hela | cervix | no | 0 |

EXAMPLE 131

Figure 8:
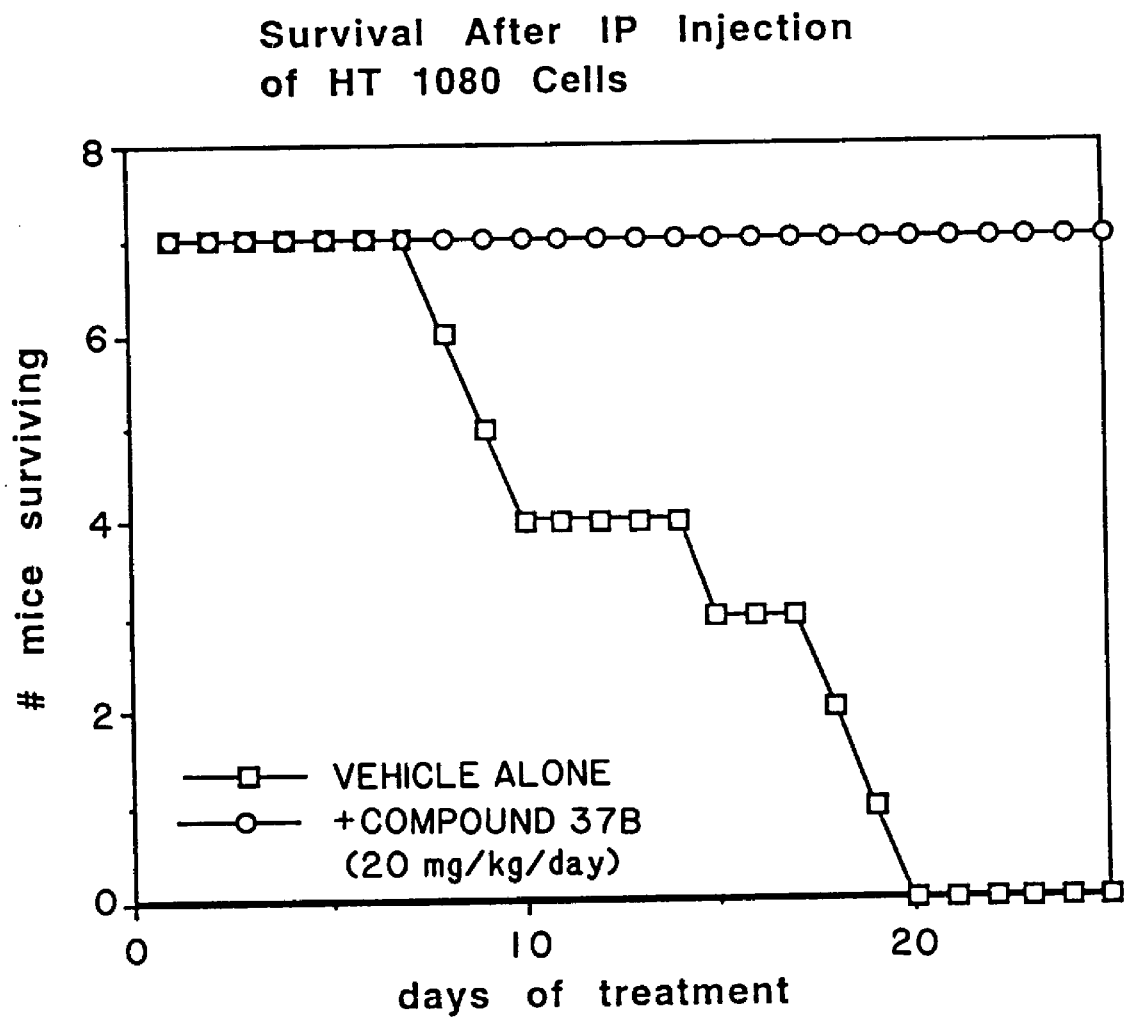
FIG. 8. Survival of nude mice after intraperitoneal implantation of human tumor cells treated with BZA-5B. Treatment with BAZ-5B (—○—) and with vehicle alone (—□—) is shown.

Survival of Nude Mice after intraperitoneal implantation of HT 1080 human tumor cells Implantation of 106 HT 1080 cells in the peritoneal cavity of the nude mouse allows seeding and growth of tumor cell masses within the peritoneum. Treatment with Compound 37B (BZA-5B) caused a reduction in mortality over 25 days (see FIG. 8). In this experiment, fourteen nude mice were injected on day 0 with 106 HT 1080 cells via intraperitoneal injection. Half the animals (seven) immediately began receiving daily treatment with Compound 37B at 20 mg/kg (formulated in approx. 0.25 ml of 1% DMSO, 20% glycerol, 10 mM NaOAc, 130 mM NaCl, pH 4.5). The other seven animals received daily injection of the above vehicle alone. The data in FIG. 8 shows the survival of these mice over the treatment period. Treatment with the inhibitor blocked the rapid mortality associated with IP implantation of tumor cells. However, at the end of the treatment period, sacrafice and dissection of all of the treated animals showed the presence of tumor cell masses in the peritoneum, so the inhibitor did not completely block IP cell growth. These results demonstrate that treatment with the inhibitor slowed the growth of cells in the peritoneum of these mice, allowing increased survival over the duration of study.

What is claimed is:

1. A compound represented by structural formula (II):

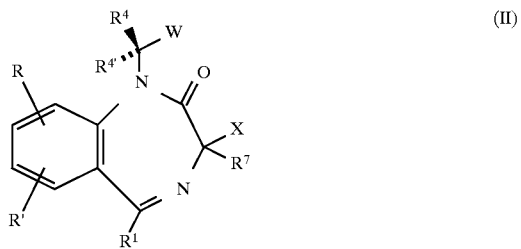

where
$R^1$ is selected from the group

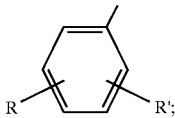

R and R' are independently selected from the group
hydrogen,
halo(F, a, Br, I),
$C_1$–$C_6$ alkyl,
halo(F, Cl, Br, I)$C_1$–$C_6$ alkyl,
$C_1$–$C_6$ alkoxy,
hydroxy,
hydroxy-$C_1$–$C_6$ alkyl,
$C_{16}$–$C_6$ alkylcarbonyl, and
W' is selected from one to three substituents selected from the group
hydrogen,
$SR^9$,
$SSR^9$,
$SC(=O)$—$R^9$,
$OR^9$,
$C(=NH)$—$NH_2$,
$N=CH$—$NH_2$,
$NH$—$CH=NH$,
$R^8$ and
V;
$R^7$ is selected from the group,
hydrogen, benzyl,
$C_1$–$C_4$ alkyl and halo (F, CL, Br, L)$C_1$–$C_4$alkyl, $C_1$–$C_8$alkyl,
$C_2$–$C_8$alkenyl,
$C_2$–$C_8$alkenyl,
$C_3$–$C_2$cycloalkyl-$C_1$–$C_3$aklyl,
$C_3$–$C_{12}$cycloalkyl,
$C_1$–$C_4$alkyl-Z—$C_1$–$C_4$alkyl, where Z is S or O,
$C_2$–$C_4$alkyl-NR—$C_2$–$C_4$alkyl,
$C_2$–$C_4$alkyl-$C_6$–$C_{12}$aryl,
$C_2$–$C_4$alkyl-$C_6$–$C_{12}$cycloalkyl,
$C_2$–$C_8$alkenyl,
$C_6$–$C_{12}$aryl-$C_1$–$C_3$alkyl,
$C_6$–$C_{12}$aryl-$C_2$–$C_4$alkynyl,
indol-3-yl-$C_1$–$C_3$alkyl, and
imidazol-4-yl-$C_1$–$C_3$alkyl,
where any aryl, alkyl, cycloalkyl or alkenyl moiety is optionally substituted with halo(F, Cl, Br, I), or —$OR^9$;
$R^{7'}$ and $R^8$ together with the nitrogen to which they are bonded may form a heterocyclic 5-, 6-, or 7-member ring containing 0, 1, or 2 additional heteroatoms selected from N, S, and O, optionally the heterocyclic ring is substituted with one or two groups selected from
oxo(=O),
$SR^9$,
$SSR^9$,
$SC(=O)$—$R^9$,
$OR^9$,
$C(=O)NHOH$,
$NHR^9$,
$C(=O)NR^{27}R^{28}$, and
V;
$R^8$ is selected from the group unsubstituted and substituted
$C_1$–$C_8$alkyl,
$C_2$–$C_8$alkenyl,
$C_3$–$C_{12}$cycloalkyl-$C_1$–$C_4$alkyl,
$C_3$–$C_{12}$cycloalkyl
$C_1$–$C_4$alkyl-Z—$C_1$–$C_4$aklyl, where Z is S or O,
$C_2$–$C_4$alkyl-NR—$C_2$–$C_4$alkyl,
$C_2$–$C_4$alkyl-$C_6$–$C_{12}$aryl,
$C_2$–$C_4$alkyl-$C_6$–$C_{12}$cycloalkyl,
$C_2$–$C_8$alkenyl,
$C_6$–$C_{12}$aryl-$C_1$–$C_4$alkyl,
$C_6$–$C_{12}$aryl-$C_2$–$C_4$alkynyl,
indol-3-yl-$C_1$–$C_3$alkyl, and
imidazol-4-$C_1$–$C_3$alkyl,
where any aryl moiety is optionally substituted with halo(F, Cl, Br, I), —$OR^9$ and V, and where any alkyl, cycloaLkyl or alkenyl group is optionally substituted with one to three groups selected from the group
$SR^9$,
$SSR^9$,
$SC(=O)$—$R^9$,
$OR^9$,
$C(=NH)$—$NH_2$,
$N=CH$—$NH_2$,
$NH$—$CH=NH$,
$NH$—$C(=NH)$—$NH_2$,
$C(=O)NHOH$,
$C(=O)OR^9$,
$NHR^9$, C(=O)NR$^{27}$R$^{28}$ and
V;

V is selected from the group
  COR$^{10}$,
  SO$_3$R$^{13}$,
  NHSO$_2$CF$_3$,
  PO(OR$^{13}$)$_2$,
  SO$_2$NHR$^{10}$,
  CONHOR$^{13}$,
  C(OH)R$^{10}$PO(OR$^{13}$)$_2$,
  CN,
  SO$_2$NH-heteroaryl where the heteroaryl is a 5- or 6-member aromatic ring containing 1 to 3 heteroatoms selected from O, N, and S, and where the heteroaryl is unsubstituted or substituted with one or two substituents selected from the group
    OH,
    CN,
    C$_1$–C$_4$alky,
    C$_1$–C$_4$alkoxy,
    CF$_3$,
    halo(F, Cl, Br, I),
    NO$_2$,
    COOH,
    COO—(C$_1$–C$_4$alkyl)
    NH$_2$,
    NH(C$_1$–C$_4$alkyl),
    N(C$_1$–C$_4$alkyl)$_2$,
  CONHSO$_2$R$^{15}$,
  SO$_2$NHCOR$^{15}$,
  CONHSO$_2$R$^{13}$,
  CH$_2$CONHSO$_2$R$^{15}$,
  NHCONHSO$_2$R$^{15}$,
  NHSO$_2$NHCOR$^{15}$,
  CONHNHSO$_2$CF$_3$,
  CON(OH)R$^{13}$,
  CONHCOCF$_3$,
  CONHSO$_2$R$^{10}$,
  CONHSO$_2$R$^{11}$,
  CONHSO$_2$R$^{13}$,

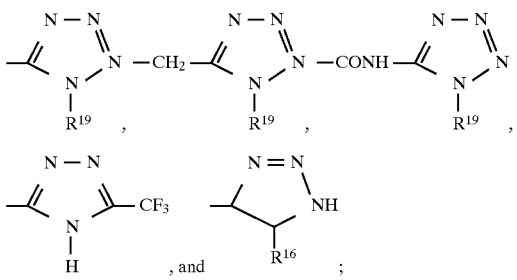

R$^9$ is selected from the group
  hydrogen,
  methyl,
  ethyl,
  isopropyl
  phenyl, and
  benzy
R$^{10}$ is selected from the group
  hydroxy,
  C$_1$–C$_8$-alkoxy,
  C$_3$–C$_{12}$-alkenoxy,
  C$_6$–C$_{12}$-aryloxy,
  C$_1$–C$_6$alkyl-C$_6$–C$_{12}$-aryloxy,
  di-C$_1$–C$_8$-alkylamino-C$_1$–C$_8$-alkoxy,
  alkanoylamino-C$_1$–C$_8$-alkoxy selected from the group
    acetylaminoethoxy,
    nicotinoylaminoethoxy, and
    succinamidoethoxy,
  C$_1$–C$_8$-alkanoyloxy-C$_1$–C$_8$-alkoxy,
  C$_6$–C$_{12}$-aryl-C$_1$–C$_8$-alkoxy where the aryl group is unsubstituted or substituted with one to three of the groups
    nitro,
    halo(F, Cl, Br, I),
    C$_1$–C$_4$-alkoxy, and
    amino,
  hydroxy-C$_2$–C$_8$-alkoxy,
  dihydroxy-C$_3$–C$_8$-alkoxy, and
  NR$^{11}$R$^{12}$;
R$^{11}$ and R$^{12}$ are independently selected from the group
  hydrogen,
  C$_1$–C$_6$ alkyl,
  C$_2$–C$_6$ alkanoyl,
  C$_1$–C$_6$ alkanoyl substituted with from one to three groups selected from
    nitro,
    halo(F, Cl, Br, I),
    C$_1$–C$_4$-alkoxy, and
    amino, and
  C$_6$–C$_{12}$-aryl-C$_1$–C$_8$-alkyl where the aryl group is unsubstituted or substituted with one to three of the groups selected from the group
    nitro,
    halo(F, a, Br, I), and
    C$_1$–C$_4$-alkoxy;
R$^{13}$ is selected from the group
  hydrogen,
  C$_1$–C$_6$alkyl,
  halo(F, Cl, Br, I)-C$_1$–C$_6$ alkyl,
  phenyl,
  benzyl, and
  CH$_2$—O—COCH$_3$;
R$^{15}$ is selected from the group
  C$_6$–C$_{14}$aryl,
  heteroaryl, where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    C$_1$–C$_4$alky,
    C$_1$–C$_4$alkoxy,
    CF$_3$,
    halo(F, Cl, Br, I),
    NO$_2$,
    COOH,
    COO—(C$_1$–C$_4$alkyl),
    NH$_2$,
    NH(C$_1$–C$_4$alkyl), and
    N(C$_1$–C$_4$alkyl)$_2$,
  C$_3$–C$_7$-cycloalkyl,
  C$_1$–C$_4$-alkyl, unsubstituted or substituted with a substituent selected from the group $C_6$–$C_{14}$aryl,
heteroaryl as defined above,
OH,
SH,
$C_1$–$C_4$alkyl,
$C_1$–$C_4$alkoxy,
$C_1$–$C_4$alkylthio,
$CF_3$,
halo(F, Cl, Br, I),
$NO_2$,
$CO_2H$,
$CO_2$-$C_1$–$C_4$-alkyl,
$NH_2$,
$N[(C_1$–$C_4)$-alkyl$]_2$,
$NH[(C_1$–$C_4)$-alkyl],
$PO_3H$,
$PO(OH)(C_1$–$C_4)$-alkoxy, and
$C_1$–$C_4$-perfluoroalkl;

$R^{16}$ is selected from the group
CN,
$NO_2$,
$COOR^{13}$,
$C_1$–$C_6$-perfluoroalkyl, and
$CF_3$;

$R^{19}$ is selected from the group
hydrogen,
$C_1$–$C_6$-alkyl
$C_2$–$C_6$-alkenyl,
$C_1$–$C_6$-alkoxy,
$C_2$–$C_6$-alkoxyalkyl,
$CH_2$—O—$COCH_3$, and
benzyl, where the phenyl moiety is unsubstituted or substituted with a group selected from the group
$NO_2$,
$NH_2$,
OH, and
$OCH_3$;

X is selected from the group
$NR^{24}$—C(=O)—$R^{25}$,
$NR^{24}$—C(=O)—$R^8$,
$NR^{24}$—C(=O)—$NR^{7'}R^8$,
$NR^{24}$—C(=O)O—$R^8$,
$NR^{24}$—C(=O)S—$R^8$,
$(CH_2)_{1-4}$—$NR^{24}$—C(=O)-$R^{25}$,
$NR^{24}$—CH(OH)—$R^{25}$,
$NR^{24}$—$CH_2$—$R^{25}$,
$NR^{24}$—S(O)$_u$—$R^{25}$ where u is 0,1, or 2,
$CHR^{24}$—O—$R^{25}$,
$CHR^{24}$—$CH_2R^{25}$,
$CHR^{24}$—$R^{25}$,
$CR^{24}$=$CHR^{25}$ (E or Z),
$(CH_2)_{1-4}$—C(=O)—$R^{25}$,
$C_6$–$C_{10}$aryl-$R^{25}$,
heterocyle-$R^{25}$,
$C_1$–$C_2$alkyl-$C_6$–$C_{10}$aryl-$R^{25}$, and
$C_1$–$C_2$alkyl-heterocycle-$R^{25}$,
where any heterocycle is a 5- or 6-member saturated or unsaturated ring containing 1 to 3 heteroatoms selected from O, N, and S;

$R^{24}$ is selected from the group
hydrogen,
benzyl,
halo(F, a, Br, I)benzyl,
$C_1$–$C_6$alkyl, and
halo(F, Cl, Br, I)$C_1$–$C_6$alkyl;

$R^{25}$ is selected from $R^{25'}$,

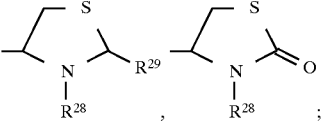

$R^{25'}$ is selected from the group
$SR^{26}$,
$SSR^{26}$,
$OR^{26}$,
$NOR^{26}$,
$C_1$–$C_6$alkyl,
$C_2$–$C_6$alkenyl,
$C_1$–$C_6$alkylamine,
$C_2$–$C_6$alkenylamine, and
halo(F, Cl, Br, I)$C_1$–$C_6$alkyl,
where any alkyl or alkenyl moiety is optionally substituted with one to three
$SR^{26}$,
$SSR^{26}$,
$OR^{26}$,
$NOR^{26}$, and
$NR^{27}R^{28}$,
where any amine moiety is optionally substituted with $R^{27}$or $R^{28}$;

$R^{26}$ is selected from the group
hydrogen,
$C_1$–$C_6$alkyl,
halo(F, Cl, Br, I)$C_1$–$C_6$alkyl, and
$C_1$–$C_6$ alkanoyl;

$R^{27}$ and $R^{28}$ are independently selected from the group
hydrogen,
$C_1$–$C_6$alkyl,
phenyl,
napthyl,
benzyl,
$CH_2$napthyl (α or β)
$C_1$–$C_6$alkanoyl,
$C_1$–$C_6$cycloalkanoyl,
$C_6$–$C_{10}$aroyl,
$C_6$–$C_{10}$aryl$C_1$–$C_6$alkanoyl,
$C_1$–$C_6$alkylsulfonyl,
$C_6$–$C_{10}$arylsulfonyl,
$C_6$–$C_{10}$aryl$C_1$–$C_6$alkylcarbamoyl,
cinnamoyl,
heterocyclecarbonyl,
$C_1$–$C_6$alkoxycarbonyl,
$C_6$–$C_{10}$aryloxycarbonyl,
$C_6$–$C_{10}$aryl$C_1$–$C_6$alkoxycarbonyl, and
pyroglutamyl;

$R^{27}$ and $R^{28}$ together with the nitrogen atom to which they are bonded may form a cyclic amine represented by

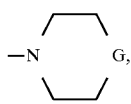

and
a cyclic imide represented by

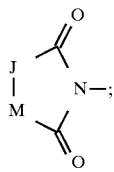

G is selected from —$CH_2$—, O, $S(O)_u$ where u is 0, 1, or 2, and $NR^{28}$;
J–M is selected from $C_2$–$C_4$alkylene and $C_2$–$C_4$alkenylene;
$R^{29}$ is selected from hydrogen and $C_1$–$C_3$alkyl; and
pharmaceutically acceptable salts thereof.

2. The compound of claim 1 represented by structural formula (IIa):

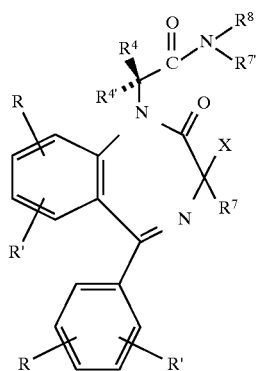

(IIa)

where
R and R' are independently selected from the group
    hydrogen,
    halo(F, Cl, Br, I),
    halo(F, Cl, Br, I)$C_1$–$C_6$ alkyl, and
    $C_1$–$C_6$ alkoxy;
$R^4$ and $R^{4'}$ are independently selected from the group
    hydrogen,
    halo(F, Cl, Br, I),
    $C_1$–$C_6$ alkyl, and
    halo(F, Cl, Br, I)$C_1$–$C_6$ alkyl,
$R^7$ is hydrogen;
$R^{7'}$ is selected from the group
    hydrogen,
    benzyl,
    $C_1$–$C_4$alkyl, and halo (F, Cl, B, I)$C_1$–$C_4$alkyl,
    $C_3$–$C_8$cycloalkyl,
    $C_3$–$C_8$cycloalkyl-$C_1$–$C_4$alkyl,
    $C_1$–$C_6$alkyl, and
    halo(F, Cl, Br, I)$C_1$–$C_6$alkyl;
$R^8$ is selected from the group unsubstituted and substituted
    $C_1$–$C_8$alkyl
    $C_1$–$C_4$alkyl-Z—$C_1$–$C_4$alkyl, where Z is S or O,
    $C_2$–$C_4$alkyl-NR—$C_2$–$C_4$alkyl,
    $C_6$–$C_{12}$aryl-$C_1$–$C_3$alkyl,
    indol-3-yl-$C_1$–$C_3$alkyl, and
    imidazol-4-yl-$C_1$–$C_3$alkyl, and
        where any aryl moiety is optionally substituted with —$OR^9$, and where any alkyl group is optionally substituted with one or two groups selected from the group
        $SR^9$,
        $SSR^9$,
        $SC(=O)$—$R^9$,
        $OR^9$,
        $C(=O)NHOH$,
        $NHR^9$,
        $C(=O)NR^{27}R^{28}$, and
        V;
$R^9$ is selected from the group
    hydrogen,
    methyl,
    ethyl,
    isopropyl,
    t-butyl,
    phenyl, and
    benzyl;
V is selected from the group
    $COR^{10}$, and

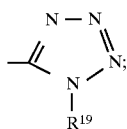

$R^{10}$ is selected from the group
    hydroxy, and
    $C_1$–$C_8$-alkoxy;
$R^{19}$ is selected from the group
    hydrogen,
    $C_1$–$C_6$-alkyl, and
    halo(F, Cl, Br, I)$C_1$–$C_6$-alkyl;
X is selected from the group
    $NR^{24}$—$C(=O)$—$R^{25}$,
    $NR^{24}$—$C(=O)$—$R^8$,
    $NR^{24}$—$C(=O)$—$NR^{7'}R^8$,
    $NR^{24}$—$C(=O)O$—$R^8$,
    $NR^{24}$—$C(=O)S$—$R^8$,
    $NR^{24}$—$CH(OH)$—$R^{25}$,
    $NR^{24}$—$CH_2$—$R^2$,
    $NR^{24}$—$S(O)_u$—$R^{25}$ where u is 0, 1, or 2,
    $CHR^{24}$—$CH_2R^{25}$,
    $CHR^{24}$—$R^{25}$,
    $CR^{24}=CHR^{25}$ (E or Z),
    $C_6$–$C_{10}$aryl-$R^{25}$,
    heterocycle-$R^{25}$,
    $C_1$–$C_2$alkyl-$C_6$–$C_{10}$aryl-$R^{25}$, and
    $C_1$–$C_2$alkyl-heterocycle-$R^{25}$, where any heterocycle is a 5- or 6-member saturated or unsaturated ring containing 1 to 3 heteroatoms selected from O, N, and S;
$R^{24}$ is selected from the group
    hydrogen,
    $C_1$–$C_6$alkyl, and
    halo(F, Cl, Br, I)$C_1$–$C_6$alkyl;

$R^{25}$ is selected from R25',

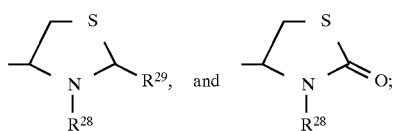

$R^{25'}$ is selected from the group $SR^{26}$,
$SSR^{26}$,
$OR^{26}$,
$NOR^{26}$,
$C_1$-$C_6$alkyl,
$C_2$-$C_6$alkenyl,
$C_1$-$C_6$alkylamine,
$C_2$-$C_6$alkenylamine, and
halo(F, Cl, Br, I)$C_1$-$C_6$alkyl,
  where any alkyl or alkenyl moiety is optionally substituted with
  $SR^{26}$,
  $SSR^{26}$,
  $OR^{26}$,
  $NOR^{26}$, and
  $NR^{27}R^{28}$,
    where any amine moiety is optionally substituted with $R^{27}$ or $R^{28}$;

$R^{26}$ is selected from the group
  hydrogen,
  $C_1$-$C_6$alkyl,
  halo(F, Cl, Br, I)$C_1$-$C_6$alkyl, and
  $C_1$-$C_6$alkanoyl;

$R^{27}$ and $R^{28}$ are independently selected from the group
  hydrogen,
  $C_1$-$C_6$alkyl,
  phenyl,
  napthyl,
  benzyl,
  $CH_2$napthyl (α or β)
  $C_1$-$C_6$alkanoyl,
  $C_1$-$C_6$cycloalkanoyl,
  $C_6$-$C_{10}$aroyl,
  $C_6$-$C_{10}$aryl$C_1$-$C_6$alkanoyl,
  $C_1$-$C_6$alkylsulfonyl,
  $C_6$-$C_{10}$arylsulfonyl,
  $C_6$-$C_{10}$aryl$C_1$-$C_6$alkylcarbamoyl,
  cinnamoyl,
  heterocyclecarbonyl,
  $C_1$-$C_6$alkoxycarbonyl,
  $C_6$-$C_{10}$aryloxycarbonyl,
  $C_6$-$C_{10}$aryl$C_1$-$C_6$alkoxycarbonyl, and
  pyroglutamyl;

$R^{27}$ and $R^{28}$ together with the nitrogen atom to which they are bonded may form a cyclic amine represented by

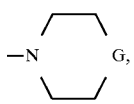

G is selected from —$CH_2$—, O, $S(O)_u$ where u, is 0, 1, or 2, and $NR^{28}$, and pharmaceutically acceptable salts thereof.

3. The compound of claim 2 represented by structural formula (IIb):

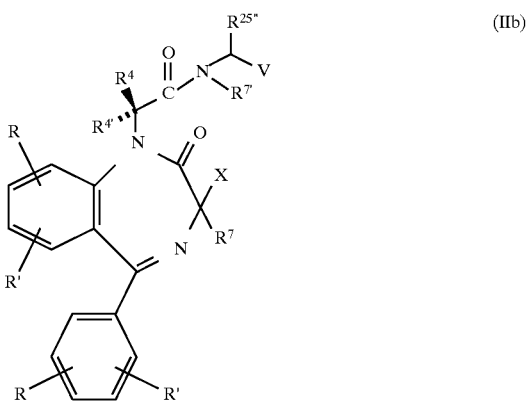

where
R and R' are independently selected from the group
  hydrogen,
  halo(F, Cl, Br, I),
  halo(F, Cl, Br, I)$C_1$-$C_6$ alkyl, and
  $C_1$-$C_6$ alkoxy;

$R^4$ and $R^{4''}$ are independently selected from the group
  hydrogen,
  halo(F, Cl, Br, I),
  $C_1$-$C_6$ alkyl, and
  halo(F, Cl, Br, I)$C_1$-$C_6$ alkyl;

$R^7$ is hydrogen;
$R^{7'}$ is selected from the group
  hydrogen,
  benzyl,
  $C_1$-$C_4$alkyl, and halo (F, Cl, Br, I)$C_1$-$C_4$alkyl,
  $C_1$-$C_4$alkyl, and
  halo(F, Cl, Br, I)$C_1$-$C_4$alkyl;

$R^8$ is selected from the group unsubstituted and substituted
  $C_1$-$C_8$alkyl,
  $C_1$-$C_4$alkyl-Z—$C_1$-$C_4$alklyl, where Z is S or O,
  $C_2$-$C_4$alkyl-NR—$C_2$-$C_4$alkyl,
  $C_2$-$C_8$alkenyl,
  $C_6$-$C_{12}$aryl-$C_1$-$C_3$alkyl,
  indol-3-yl-$C_1$-$C_3$alkyl, and
  imidazol-4-yl-$C_1$-$C_3$alkyl,
    where any aryl moiety is optionally substituted with —$OR^9$ and V, and where any alkyl or alkenyl group is optionally substituted with one to three groups selected from the group
    $SR^9$,
    $SSR^9$,
    $SC(=O)$—$R^9$,
    $OR^9$,
    $C(=NH)$—$NH_2$,
    $N=CH$—$NH_2$,
    $NH$—$CH=NH$, NH—C(=NH)—NH$_2$,
C(=O)NHOH,
NHR$^9$,
C(=O)NR$^{27}$R$^{28}$, and V is selected from the group
COR$^{10}$, and

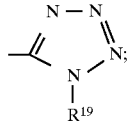

R$^9$ is selected from the group
hydrogen,
methyl,
ethyl,
isopropyl,
t-butyl,
phenyl, and
benzyl;

R$^{10}$ is selected from the group
hydroxy,
C$_3$–C$_8$-cycloalkoxy, and
C$_1$–C$_8$-alkoxy;

R$^{19}$ is selected from the group
hydrogen,
C$_1$–C$_6$-alkyl, and
halo(F, Cl, Br, I)C$_1$–C$_6$-alkyl;

X is selected from the group
NR$^{24}$—C(=O)—R$^{25}$,
NR$^{24}$—C(=O)—NR$^{7'}$R$^8$,
NR$^{24}$—C(=O)O—R$^8$,
NR$^{24}$—CH(OH)—R$^{25}$,
NR$^{24}$—CH$_2$—R$^{25}$,
NR$^{24}$—S(O)$_u$—R$^{25}$ where u is 0, 1, or 2,
CHR$^{24}$—CH$_2$R$^{25}$,
CHR$^{24}$—R$^{25}$,
CR$^{24}$=CHR$^{25}$ (E or Z),
C$_6$–C$_{10}$aryl-R$^{25}$,
heterocycle-R$^{25}$,
C$_1$–C$_2$alkyl-C$_6$–C$_{10}$aryl-R$^{25}$, and
C$_1$–C$_2$alkyl-heterocycle-R$^{25}$, where any heterocycle is a 5- or 6-member saturated or unsaturated ring containing 1 to 3 heteroatoms selected from O, N, and S;

R$^{24}$ is selected from the group
hydrogen,
C$_1$–C$_6$alkyl, and
halo(F, Cl, Br, I)C$_1$–C$_6$aLkyl;

R$^{25}$ is selected from the group R$^{25'}$,

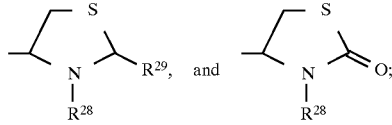

R$^{25'}$ is C$_1$–C$_6$alkyl, substituted with one or two groups selected from the group
SR$^{26}$,
SSR$^{26}$,
OR$^{26}$,
NOR$^{26}$, and
NR$^{27}$R$^{28}$,
where any amine moiety is optionally substituted with R$^{27}$ or R$^{28}$;

R$^{25''}$ is selected from the group
C$_1$–C$_6$alkyl,
halo(F,Cl,Br, I)C$_1$–C$_6$alkyl,
C$_6$–C$_{12}$alkyl,
C$_6$–C$_{12}$arylC$_1$–C$_3$alkyl,
where any alkyl or aryl group is optionally substituted with a group selected SR$^{26}$,
SSR$^{26}$,
COR$^{10}$,
OR$^{26}$, and
NOR$^{26}$;

R$^{26}$ is selected from the group
hydrogen,
C$_1$–C$_6$alkyl,
halo(F, Cl, Br, I)C$_1$–C$_6$alkyl, and
C$_1$–C$_6$alkanoyl;

R$^{27}$ and R$^{28}$ are independently selected from the group
hydrogen,
C$_1$–C$_6$alkyl,
phenyl,
napthyl,
benzyl,
CH$_2$napthyl ($\alpha$ or $\beta$)
C$_1$–C$_6$alkanoyl,
C$_1$–C$_6$cycloalkanoyl,
C$_6$–C$_{10}$aroyl,
C$_6$–C$_{10}$arylC$_1$–C$_6$alkanoyl,
C$_1$–C$_6$alkylsulfonyl,
C$_6$–C$_{10}$arylsulfonyl,
C$_6$–C$_{10}$arylC$_1$–C$_6$alkylcarbamoyl,
cinnamoyl,
heterocyclecarbonyl,
C$_1$–C$_6$alkoxycarbonyl,
C$_6$–C$_{10}$aryloxycarbonyl,
C$_6$–C$_{10}$arylC$_1$–C$_6$alkoxycarbonyl, and
pyroglutamyl;

R$^{27}$ and R$^{28}$ together with the nitrogen atom to which they are bonded may form a cyclic amine represented by

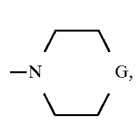

G is selected from —CH$_2$—, O, S(O)$_u$ where u is 0,1, or 2, and NR$^{28}$, and
pharmaceutically acceptable salts thereof.

4. The compound of claim 1 represented by structural formula (IIc):

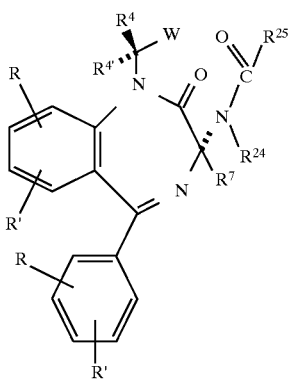

(IIc)

where
R and R' are independently selected from the group
  hydrogen,
  halo(F, Cl, Br, I),
  $C_1$–$C_6$ alkyl,
  halo(F, Cl, Br, I)$C_1$–$C_6$ alkyl,
  $C_1$–$C_6$ alkoxy,
  hydroxy,
  hydroxy-$C_1$–$C_6$ alkyl,
  $C_1$–$C_6$ alkylcarbonyl, and
  $C_1$–$C_6$ alkyloxycarbonyl;
$R^4$ and $R^{4'}$ are independently selected from the group
  hydrogen,
  halo(F, Cl, Br, I),
  $C_1$–$C_6$ alkyl,
  halo(F, Cl, Br, I)$C_1$–$C_6$ alkyl,
  phenyl, and
  benzyl;
$R^7$ is selected from the group
  hydrogen,
  halo(F, Cl, Br, I),
  $C_1$–$C_6$ alkyl, and
  halo(F, Cl, Br, I)$C_1$–$C_6$ alkyl;
W is selected from the group
  C(=O)—$NR^{7'}R^8$,
  $CH_2$—C(=O)—$NR^{7'}R^8$,
  C(=O)—O—$R^8$,
  $CR^{8'}$(OH)—$CHR^7R^8$,
  $CHR^{8'}$—$CHR^7R^8$,
  $CR^{8'}$=$CR^7R^8$ (E or Z),
  C(=O)—$CHR^7R^8$,
  $CHR^{8'}$—$NR^{7'}R^8$,
  $CHR^{8'}$—O—$R^8$,
  $CHR^{8'}$—S(O)$_u$—$R^8$ where u is 0,1, or 2,
  $CR^{8'}$=N—$R^8$,
  $CHR^{8'}$—$R^8$,
  W',
  $C_1$–$C_3$alkyl-W',
  $C_6$–$C_{12}$aryl-W',
  $C_6$–$C_{12}$aryl-$C_1$–$C_3$alkyl-W',
  heterocycle-W',
  heterocycle-$C_1$–$C_3$alkyl-W',
  $C_1$–$C_2$alkyl-$C_6$–$C_{10}$aryl-W', and
  $C_1$–$C_2$alkyl-heterocycle-W', where any heterocycle is a 5- or 6-member saturated or unsaturated ring containing 1 to 3 heteroatoms selected from O, N, and S;
W' is selected from one to three substituents selected from the group
  hydrogen,
  $SR^9$,
  $SSR^9$,
  SC(=O)—$R^9$,
  $OR^9$,
  C(=NH)—$NH_2$,
  N=CH—$NH_2$,
  NH—CH=NH,
  $R^8$ and
  V;
$R^{7'}$ is selected from the group
  hydrogen,
  benzyl,
  $C_1$–$C_4$alkyl, and
  halo(F, Cl, Br, I)$C_1$–$C_4$alkyl,
  $C_1$–$C_4$alkyl, and
  halo(F, Cl, Br, I)$C_1$–$C_4$alkyl;
$R^8$ is selected from the group unsubstituted and substituted
  $C_1$–$C_8$alkyl,
  $C_2$–$C_8$alkenyl,
  phenyl-$C_1$–$C_3$alkyl,
  indol-3-yl-$C_1$–$C_3$alkyl, and
  imidazol-4-yl-$C_1$–$C_3$alkyl,
    where any phenyl moiety is optionally substituted with
    —$OR^9$ and V, and where any alkyl or alkenyl group
    is optionally substituted with one to three groups
    selected from
      $SR^9$,
      $SSR^9$,
      SC(=O)—$R^9$,
      $OR^9$,
      C(=NH)—$NH_2$,
      N=CH—$NH_2$,
      NH—CH=NH,
      NH—C(=NH)—$NH_2$,
      C(=O)NHOH,
      $NHR^9$,
      C(=O)$NR^{27}R^{28}$, and
      V;
V is selected from the group
  $COR^{10}$,
  $SO_3R^{13}$,
  $NHSO_2CF_3$,
  PO($OR^{13}$)$_2$,
  $SO_2NHR^{10}$,
  $CONHOR^{13}$,
  C(OH)$R^{10}$PO($OR^{13}$)$_2$,
  CN,
  $SO_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    $C_1$–$C_4$alkyl
    $C_1$–$C_4$alkoxy, CF$_3$,
COOH,
COO—(C$_1$–C$_4$alkyl),
NH$_2$,
NH(C$_1$–C$_4$alkyl), and
N(C$_1$–C$_4$alkyl)$_2$,
CONHSO$_2$R$^{15}$,
SO$_2$NHCOR$^{15}$,
CONHSO$_2$R$^{13}$,
CH$_2$CONHSO$_2$R$^{15}$,
NHCONHSO$_2$R$^{15}$,
NHSO$_2$NHCOR$^{15}$,
CONHNHSO$_2$CF$^3$,
CON(OH)R$^{13}$,
CONHCOCF$_3$,
CONHSO$_2$R$^{10}$,
CONHSO$_2$R$^{11}$,
CONHSO$_2$R$^{13}$,

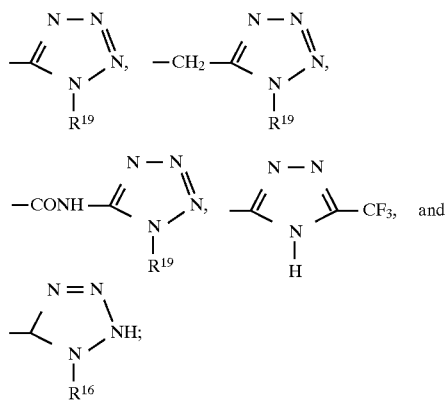

R$^9$ is selected from the group
hydrogen,
methyl,
ethyl,
isopropyl,
t-butyl,
phenyl, and
benzyl;
R$^{10}$ is selected from the group
hydroxy,
C$_1$–C$_8$-alkoxy,
C$_3$–C$_{12}$-alkenoxy,
C$_6$–C$_{12}$-aryloxy,
C$_1$–C$_6$-alkyl-C$_6$–C$_{12}$-aryloxy,
di-C$_1$–C$_8$-alkylamino-C$_1$–C$_8$-alkoxy,
alkanoylamino-C$_1$–C$_8$-alkoxy selected from the group
    acetylaminoethoxy,
    nicotinoylaminoethoxy, and
    succinamidoethoxy,
C$_1$–C$_8$-alkanoyloxy-C$_1$–C$_8$-alkoxy,
C$_6$–C$_{12}$-aryl-C$_1$–C$_8$-alkoxy where the aryl group is unsubstituted or substituted with one to three of the groups
    nitro,
    halo(F, Cl, Br, I),
    C$_1$–C$_4$-alkoxy, and
    amino,
hydroxy-C$_2$–C$_8$-alkoxy,
dihydroxy-C$_3$–C$_8$-alkoxy, and
NR$^{11}$R$^{12}$;
R$^{11}$ and R$^{12}$ are independently selected from the group
hydrogen,
C$_1$–C$_6$ alkyl,
C$_2$–C$_6$ alkanoyl,
C$_1$–C$_6$ alkanoyl substituted with from one to three groups selected from
nitro,
halo(F, Cl, Br, I),
C$_1$–C$_4$-alkoxy, and
amino, and
C$_6$–C$_{12}$-aryl-C$_1$–C$_8$-alkyl where the aryl group is unsubstituted or substituted with one to three of the groups selected from
nitro,
halo(F, Cl, Br, I), and
C$_1$–C4-alkoxy;
R$^{13}$ is selected from the group
hydrogen,
C$_1$–C$_6$ alkyl,
halo(F, Cl, Br, I)-C$_1$–C$_6$alkyl,
phenyl,
benzyl, and
CH$_2$—O—COCH$_3$;
R$^{15}$ is selected from the group
C$_6$–C$_4$aryl,
heteroaryl, where the heteroaryl is a 5- or 6-member aromatic ring containing 1 to 3 heteroatoms selected from O, N, and S and where the heteroaryl is unsubstituted or substituted with one or two substituents selected from the group
OH,
SH,
C$_1$–C$_4$alkyl,
C$_1$–C$_4$alkoxy,
CF$_3$,
halo(F, Cl, Br, I),
NO$_2$,
COOH,
COO—(C$_1$–C$_4$alkyl),
NH$_2$,
NH(C$_1$–C$_4$alkyl), and
N(C$_1$–C$_4$alkyl)$_2$,
C$_3$–C$_7$-cycloalkyl,
C$_1$–C$_4$-alkyl, unsubstituted or substituted with a substituent selected from the group
C$_6$–C$_{14}$aryl,
heteroaryl as defined above,
OH,
SH,
C$_1$–C$_4$-alkyl,
C$_1$–C$_4$-alkoxy,
C$_1$–C$_4$-alkylthio,
CF$_3$,
halo(F, Cl, Br, I),
NO$_2$,
CO$_2$H,
CO$_2$—(C$_1$–C$_4$)-alkyl,
NH$_2$, N[(C₁–C₄)-alkyl]₂,
NH[(C₁–C₄)-alkyl],
PO₃H,
PO(OH)(C₁–C₄)-alkoxy, and
(C₁–C₄)-perfluoroalkyl;

$R^{16}$ is selected from the group
CN,
N₂,
COOR¹³,
C₁–C₆-perfluoroalkyl, and
CF₃;

$R^{19}$ is selected from the group
hydrogen,
C₁–C₆alkyl,
C₂–C₆alkenyl,
C₁–C₆alkoxy,
C₂–C₆alkoxyalkyl,
CH₂—O—COCH₃, and
benzyl, where the phenyl moiety is unsubstituted or substituted with a group selected from the group
NO₂,
NH₂,
OH, and
OCH₃;

$R^{24}$ is selected from the group
hydrogen,
C₁–C₆alkyl, and
halo(F, Cl, Br, I)C₁–C₆alkyl;

$R^{25}$ is selected from $R^{25'}$,

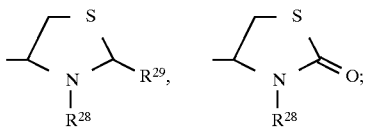

$R^{25'}$ is selected from the group
SR²⁶,
SSR²⁶,
OR²⁶,
NOR²⁶,
C₁–C₆alkyl,
C₂–C₆alkenyl,
C₁–C₆alkylamine,
C₂–C₆alkenylamine, and
halo(F, Cl, Br, I)C₁–C₆alkyl,
  where any alkyl or alkenyl moiety is optionally substituted with one to three
  SR²⁶,
  SSR²⁶,
  OR²⁶,
  NOR²⁶, and
  NR²⁷R²⁸,
    where any amine moiety is optionally substituted with R²⁷ or R²⁸;

$R^{26}$ is selected from the group
hydrogen,
C₁–C₆alkyl,
halo(F, Cl, Br, I)C₁–C₆alkyl, and
C₁–C₆alkanoyl;

$R^{27}$ and $R^{28}$ are independently selected from the group
hydrogen,
C₁–C₆alkyl,
phenyl,
napthyl,
benzyl,
CH₂napthyl (α or β)
C₁–C₆alkanoyl,
C₁–C₆cycloalkanoyl.
C₆–C₁₀aroyl,
C₆–C₁₀aryl-C₁–C₆alkanoyl,
C₁–C₆alkylsulfonyl,
C₆–C₁₀arylsulfonyl,
C₆–C₁₀arylC₁–C₆alkylcarbamoyl,
cinnamoyl,
heterocyclecarbonyl,
C₁–C₆alkoxycarbonyl,
C₆–C₁₀aryloxycarbonyl,
C₆–C₁₀arylC₁₀–C₆alkoxycarbonyl, and
pyroglutamyl;

$R^{27}$ and $R^{28}$ together with the nitrogen atom to which they are bonded may form a cyclic amine represented by

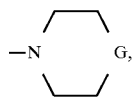

G is selected from —CH₂—, O, S(O)ᵤ where u is 0,1,or 2, and NR²⁸, and
pharmaceutically acceptable salts thereof.

5. The compound of claim 3 represented by structural formula (IId);

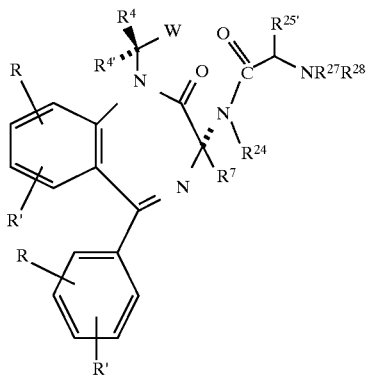

(IId)

where
R and R' are hydrogen or chloro;
R⁴, R⁴', R⁷, and R⁸ are hydrogen;
W is selected from the group
C(=O)—NR⁷'R⁸,
CH₂—C(=O)—NR⁷'R⁸,
C(=O)—O—R⁸,
CR⁸'(OH)—CHR⁷R⁸,
CHR⁸'—CHR⁷R⁸,
CR⁸'=CR⁷R⁸ (E or Z),
C(=O)—CHR⁷R⁸,
CHR⁸'—NR⁷'R⁸,
CHR⁸'—O—R⁸,
CHR⁸'—S(O)ᵤ—R⁸ where u is 0, 1, or 2,
CR⁸'=N—R⁸, CHR$^{8'}$—R$^8$,
W',
C$_1$–C$_3$alkyl-W'
C$_6$–C$_{12}$aryl-W',
heterocycle-W',
C$_1$–C$_2$alkyl-C$_6$–C$_{10}$aryl-W', and
C$_1$–C$_2$alkyl-heterocycle-W', where any heterocycle is a 5- or 6-member saturated or unsaturated ring containing 1 to 3 heteroatoms selected from O, N, and S;
W' is selected from one to three substituents selected from the group
hydrogen,
SR$^9$,
SSR$^9$,
SC(=O)—R$^9$,
OR$^9$,
R$^8$ and
V;
R$^{7'}$ is selected from the group
hydrogen,
benzyl,
C$_1$–C$_4$alkyl, and
halo(F, Cl, Br, I)C$_1$–C$_4$alkyl,
C$_1$–C$_4$alkyl, and
halo(F, Cl, Br, I)C$_1$–C$_4$alkyl;
R$^8$ is selected from the group unsubstituted and substituted
C$_1$–C$_8$alkyl,
C$_2$–C$_8$alkenyl,
phenyl-C$_1$–C$_3$alkyl,
indol-3-yl-C$_1$–C$_3$alkyl, and
imidazol-4-yl-C$_1$–C$_3$alkyl,
where any phenyl moiety is optionally substituted with —OR$^9$ and V, and where any alkyl or alkenyl group is optionally substituted with one to three groups selected from
SR$^9$,
SSR$^9$,
SC(=O)—R$^9$,
OR$^9$,
C(=O)NHOH,
NHR$^9$, and
V;
V is selected from the group
halo(F, Cl, Br, I),
CN,
NO$_2$,
COR$^{10}$,
SO$_3$R$^{13}$,
NHSO$_2$CF$_3$, and

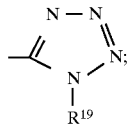

R$^9$ is selected from the group
hydrogen,
methyl,
ethyl,
isopropyl,
t-butyl,
phenyl, and
benzyl;
R$^{10}$ is selected from the group
hydroxy,
C$_1$–C$_8$-alkoxy,
C$_3$–C$_{12}$-alkenoxy,
C$_6$–C$_{12}$-aryloxy,
C$_1$–C$_6$-alkyl-C$_6$–C$_{12}$-aryloxy,
di-C$_1$–C$_8$-alkylamino-C$_1$–C$_8$-alkoxy,
alkanoylamino-C$_1$–C$_8$-alkoxy selected from the group
acetylaminoethoxy,
nicotinoylaminoethoxy, and
succinamidoethoxy,
C$_1$–C$_8$-alkanoyloxy-C$_1$–C$_8$-alkoxy,
C$_6$–C$_{12}$-aryl-C$_1$–C$_8$-alkoxy where the aryl group is unsubstituted or substituted with one to three of the groups
nitro,
halo(F, Cl, Br, I),
C$_1$–C$_4$-alkoxy, and
amino,
hydroxy-C$_2$–C$_8$-alkoxy,
dihydroxy-C$_3$–C$_8$-alkoxy, and
NR$^{11}$R$^{12}$;
R$^{11}$ and R$^{12}$ are independently selected from the group
hydrogen,
C$_1$–C$_6$ alkyl,
C$_2$–C$_6$ alkanoyl,
C$_1$–C$_6$ alkanoyl substituted with from one to three groups selected from
nitro,
halo(F, Cl, Br, I),
C$_1$–C$_4$-alkoxy, and
amino, and
C$_6$–C$_{12}$-aryl-C$_1$–C$_8$-alkyl where the aryl group is unsubstituted or substituted with one to three of the groups selected from
nitro,
halo(F, Cl, Br, I), and
C$_1$–C$_4$-alkoxy;
R$^{13}$ is selected from the group
hydrogen,
C$_1$–C$_6$ alkyl,
halo(F, Cl, Br, I)—C$_1$–C$_6$ alkyl,
phenyl,
benzyl, and
CH$_2$—O—COCH$_3$;
R$^{19}$ is selected from the group
hydrogen, and
(C$_1$–C$_6$)-alkyl;
R$^{24}$ is selected from the group
C$_1$–C$_6$alkyl, and
halo(F, Cl, Br, I)C$_1$–C$_6$alkyl;
R$^{25'}$ is C$_1$–C$_6$alkyl, substituted with a group selected from
SR$^{26}$,
SSR$^{26}$,
OR$^{26}$, and
NOR$^{26}$,
R$^{26}$ is selected from the group
hydrogen, $C_1$–$C_6$ alkyl,
halo(F, Cl, Br, I)$C_1$–$C_6$alkyl, and
$C_1$–$C_6$alkanoyl;
$R^{27}$ and $R^{28}$ are selected from
hydrogen,
$C_1$–$C_6$alkyl,
halo$C_1$–$C_6$alkyl,
or together with the nitrogen to which they are bonded may form morpholino; and
pharmaceutically acceptable salts thereof.

6. The compound of claim 3 represented by structural formula (IIe):

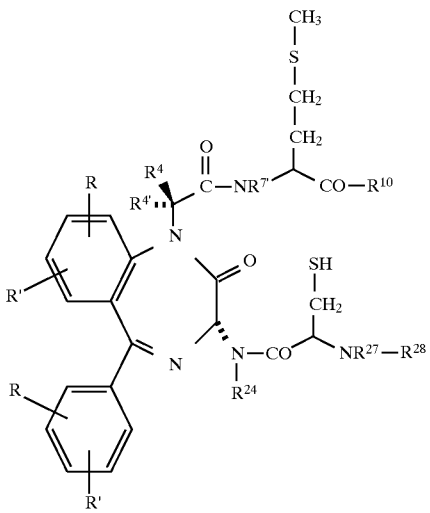 (IIe)

where
R and R' are each independently selected from the group
hydrogen,
halo,
$C_1$–$C_6$ alkyl,
halo-$C_1$–$C_6$-alkyl, and
$C_1$–$C_6$ alkoxy;
$R^4$ and $R^{4'}$ are independently selected from the group
hydrogen,
halo,
$C_1$–$C_6$ alkyl, and
halo $C_1$–$C_6$ alkyl;
$R^{7'}$ and $R^{24}$ are selected from the gro
hydrogen,
benzyl,
$C_1$–$C_4$alkyl, and
halo(F, Cl, Br, I)$C_1$–$C_4$alkyl,
$C_1$–$C_6$alkyl, and
halo $C_1$–$C_6$ alkyl;
$R^{10}$ is selected from the group
hydroxy,
amino,
$C_1$–$C_6$ alkylamino,
di($C_1$–$C_6$) alkylamino,
$C_1$–$C_6$ alkoxy,
$C_3$–$C_8$ cycloalkoxy,
$C_6$–$C_{12}$ aryloxy,
$C_1$–$C_6$ alkyl $C_6$–$C_{12}$ aryloxy,
$C_2$–$C_6$ acylamino $C_1$–$C_6$ alkoxy, $C_1$–$C_6$ alkanoyloxy $C_1$–$C_6$ alkoxy,
hydroxy $C_2$–$C_6$ alkoxy, and
dihydroxy $C_3$–$C_6$ alkoxy;
$R^{27}$ and $R^{28}$ are independently selected from the group
hydrogen, and
$C_1$–$C_6$alkyl;
$R^{27}$ and $R^{28}$ together with the nitrogen atom to which they are bonded may form a cyclic amine represented by

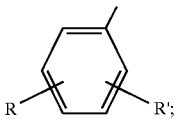

G is selected from —$CH_2$—, O, $S(O)_u$ where u is 0, 1, or 2, and $NR^{28}$; and
pharmaceutically acceptable salts thereof.

7. A compound represented by structural formula (II):

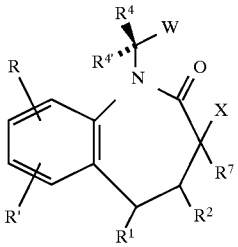 (II)

where
R and R' are independently selected from the group
hydrogen,
halo(F, Cl, Br, I),
$C_1$–$C_6$ alkyl,
halo(F, Cl, Br, I)$C_1$–$C_6$ alkyl,
$C_1$–$C_6$ alkoxy,
hydroxy,
hydroxy-$C_1$–$C_6$ aLkyl,
$C_1$–$C_6$ alkylcarbonyl, and
$C_1$–$C_6$ alkyloxycarbonyl;
$R^1$ and $R^2$ are independently selected from the group
hydrogen,
$C_1$–$C_6$ alkyl,
halo(F, Cl, Br, I)-$C_1$–$C_6$ alkyl, and

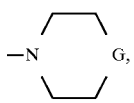

$R^1$ and $R^2$ taken together may form a covalent bond or fused benzene substituted with R and R';
$R^4$ and $R^{4'}$ are independently selected from the group
hydrogen,
halo(F, Cl, Br, I),
$C_1$–$C_6$ alkyl,
halo(F, Cl, Br, I)$C_1$–$C_6$ alkyl,
phenyl, and
benzyl;
$R^7$ is selected from the group
hydrogen,
halo(F, Cl, Br, I), $C_1$–$C_6$ alkyl, and
halo(F, Cl, Br, I)$C_1$–$C_6$ alkyl;
W is selected from the group
  C(=O)—NR$^{7'}$R$^8$,
  CH$_2$—C(=O)—NR$^{7'}$R$^8$,
  C(=O)—R$^8$,
  CR$^{8'}$(OH)—CHR$^7$R$^8$,
  CHR$^{8'}$—CHR$^7$R$^8$,
  CR$^{8'}$=CR$^7$R$^8$ (E or Z),
  C(=O)—CHR$^7$R$^8$,
  CHR$^{8'}$—NR$^{7'}$R$^8$,
  CHR$^{8'}$—O—R$^8$,
  CHR$^{8'}$—S(O)$_u$—R$^8$ where u is 0, 1, or 2,
  CR$^{8'}$=N—R$^8$,
  CHR$^{8'}$—R$^8$,
  W',
  $C_1$–$C_3$alkyl-W',
  $C_6$–$C_{12}$aryl-W',
  $C_6$–$C_{12}$aryl-$C_1$–$C_3$alkyl-W',
  heterocycde-W',
  heterocycl-$C_1$–$C_3$alkyl-W',
  $C_1$–$C_{12}$alkyl-$C_6$–$C_{10}$aryl-W', and
  $C_1$–$C_2$alkyl-heterocyde-W',
    where any heterocycle is a 5- or 6-member saturated or unsaturated ring containing 1 to 3 heteroatoms selected from O, N, and S;
W' is selected from one to three substituents selected from the group
  hydrogen,
  SR$^9$,
  SSR$^9$,
  SC(=O)—R$^9$,
  OR$^9$,
  C(=NH)—NH$_2$,
  N=CH—NH$_2$,
  NH—CH=NH,
  R$^8$, and
  V;
R$^{7'}$ is selected from the group
  hydrogen,
  benzyl,
  $C_1$–$C_6$alkyl, and
  halo(F, Cl, Br, I)$C_1$–$C_6$alkyl;
R$^{7'}$ and R$^8$ together with the nitrogen to which they are bonded may form a pyrrolidinyl or piperidyl ring optionally substituted with one or two groups selected from
  SR$^9$,
  SSR$^9$,
  SC(=O)—R$^9$,
  OR$^9$,
  C(=O)NHOH,
  NHR$^9$,
  C(=O)NR$^{27}$R$^{28}$, and
  V;
R$^8$ is selected from the group unsubstituted and substituted
  $C_1$–$C_8$alkyl,
  $C_1$–$C_4$alkyl-Z—$C_1$–$C_4$alkyl, where Z is S or O,
  $C_2$–$C_4$alkyl-NR—$C_2$–$C_4$alkyl,
  $C_2$–$C_8$alkenyl,
  $C_6$–$C_{12}$aryl$C_1$–$C_3$alkyl,
  indol-3-yl-$C_1$–$C_3$alkyl, and
  imidazol4-yl-$C_1$–$C_3$alkyl,
    where any aryl moiety is optionally substituted with —OR$^9$ and V, and where any alkyl or alkenyl group is optionally substituted with one to three groups selected from
      SR$^9$,
      SSR$^9$,
      SC(=O)—R$^9$,
      OR$^9$,
      C(=NH)—NH$_2$,
      N=CH—NH$_2$,
      NH—CH=NH,
      NH—C(=NH)—NH$_2$,
      C(=O)NHOH,
      NHR$^9$,
      C(=O)NR$^{27}$R$^{28}$, and
      V;
V is selected from the group
  COR$^{10}$,
  SO$_3$R$^{13}$,
  NHSO$_2$CF$_3$,
  PO(OR$^{13}$)$_2$,
  SO$_2$NHR$^{10}$,
  CONHOR$^{13}$,
  C(OH)R$^{10}$PO(OR$^{13}$)$_2$,
  halo(F, Cl, Br, I),
  NO$_2$,
  CN,
  SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    $C_1$–$C_4$alkyl,
    $C_1$–$C_4$alkoxy,
    CF$_3$,
    halo(F, Cl, Br, I),
    NO$_2$,
    COOH,
    COO-($C_1$–$C_4$alkyl),
    NH$_2$,
    NH($C_1$–$C_4$alkyl), and
    N($C_1$–$C_4$alkyl)$_2$,
  CONHSO$_2$R$^{15}$,
  SO$_2$NHCOR$^{15}$,
  CONHSO$_2$R$^{13}$,
  CH$_2$CONHSO$_2$R$^{15}$,
  NHCONHSO$_2$R$^{15}$,
  NHSO$_2$NHCOR$^{15}$,
  CONHNHSO$_2$CF$_3$,
  CON(OH)R$^{13}$,
  CONHCOCF$_3$,
  CONHS$_2$R$^{10}$,

CONHSO$_2$R$^{11}$,
CONHSO$_2$R$^{13}$,

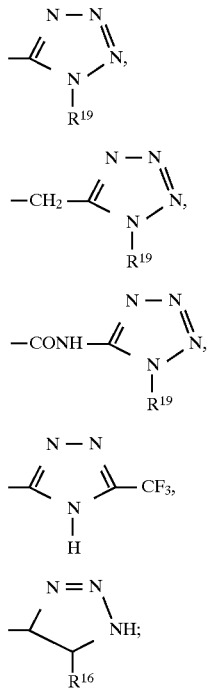

R$^9$ is selected from the group
hydrogen,
methyl,
ethyl,
isopropyl,
t-butyl,
phenyl, and
benzyl;
R$^{10}$ is selected from the group
hydroxy,
C$_1$–C$_8$-alkoxy,
C$_3$–C$_{12}$-alkenoxy,
C$_6$–C$_{12}$-aryloxy,
C$_1$–C$_6$-alkyl-C$_6$–C$_{12}$aryloxy,
di-C$_1$–C$_8$-alkylamino-C$_1$–C$_8$-alkoxy,
alkanoylamino-C$_1$–C$_8$-alkoxy selected from the group
    acetylaminoethoxy,
    nicotinoylaminoethoxy, and
    succinamidoethoxy, and
C$_1$–C$_8$-alkanoyloxy-C$_1$–C$_8$-alkoxy,
C$_6$–C$_{12}$-aryl-C$_1$–C$_8$-alkoxy where the aryl group is unsubstituted or substituted with one to three of the groups
    nitro,
    halo(F, Cl, Br, I),
    C$_1$–C$_4$-alkoxy, and
    amino,
hydroxy-C$_2$–C$_8$-alkoxy,
dihydroxy-C$_3$–C$_8$-alkoxy, and
NR$^{11}$R$^{12}$;
R$^{11}$ and R$^{12}$ are independently selected from the group
hydrogen,
C$_1$–C$_6$ alkyl,
C$_2$–C$_6$ alanoyl,
C$_1$–C$_6$ alkanoyl substituted with from one to three groups selected from
    nitro,
    halo(F, Cl, Br, I),
    C$_1$–C$_4$-alkoxy, and
    amino, and
C$_6$–C$_{12}$-aryl-C$_1$–C$_8$-alkyl where the aryl group is unsubstituted or substituted with one to three of the groups selected from
    nitro,
    halo(F, Cl, Br, I), and
    C$_1$–C$_4$-alkoxy;
R$^{13}$ is selected from the group
hydrogen,
C$_1$–C$_6$ alkyl,
halo(F, Cl, Br, I)—C$_1$–C$_6$ alkyl,
phenyl,
benzyl, and
CH$_2$—O—COCH$_3$;
R$^{15}$ is selected from the group
C$_6$–C$_{14}$aryl,
heteroaryl, where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    C$_1$–C$_4$alkyl,
    C$_1$–C$_4$alkoxy,
    CF$_3$,
    halo(F, Cl, Br, I),
    NO$_2$,
    COOH,
    COO—(C$_1$–C$_4$aLkyl),
    NH$_2$,
    NH(C$_1$–C$_4$alkyl), and
    N(C$_1$–C$_4$alkyl)$_2$,
C$_3$–C$_7$-cycloalkyl,
C$_1$–C$_4$-alkyl, unsubstituted or substituted with a substituent selected from the group
    C$_6$–C$_{14}$aryl,
    heteroaryl as defined above,
    OH,
    SH,
    C$_1$–C$_4$-alkyl,
    C$_1$–C$_4$-alkoxy,
    C$_1$–C$_4$-alkylthio,
    CF$_3$,
    halo(F, Cl, Br, I),
    NO$_2$,
    CO$_2$H,
    CO$_2$-(C$_1$–C$_4$)-alkyl,
    NH$_2$,
    N[(C$_1$–C$_4$)-alkyl]$_2$,
    NH[(C$_1$–C$_4$)-alkyl],
    PO$_3$H,
    PO(OH)(C$_1$–C$_4$)-alkoxy, and
    (C$_1$–C$_4$)-perfluoroalkyl;
R$^{16}$ is selected from the group
CN,
NO$_2$,
COOR$^{13}$, $C_1$–$C_6$-perfluoroalkyl, and
$CF_3$;
$R^{19}$ is selected from the group
  hydrogen,
  $C_1$–$C_6$alkyl,
  $C_2$–$C_6$alkenyl,
  $C_1$–$C_6$alkoxy,
  $C_2$–$C_6$alkoxyalkyl,
  $CH_2$—O—$COCH_3$, or
  benzyl, where the phenyl moiety is unsubstituted or substituted with a group selected from
    $NO_2$,
    $NH_2$,
    OH, or
    $OCH_3$;
X is selected from the group
  $NR^{24}$—C(=O)—$R^{25}$,
  $NR^{24}$—C(=O)—$R^8$,
  $NR^{24}$—C(=O)NH—$R^8$,
  $NR^{24}$—C(=O)O—$R^8$,
  $NR^{24}$—C(=O)S—$R^8$,
  $NR^{24}$—CH(OH)—$R^{25}$,
  $NR^{24}$—$CH_2$—$R^{25}$,
  $NR^{24}$—$S(O)_u$—$R^{25}$ where u is 0, 1, or 2,
  $CHR^{24}$—$CH_2R^{25}$,
  $CHR^{24}$—$R^{25}$,
  $CR^{24}$=$CHR^{25}$ (E or Z),
  $C_6$–$C_{10}$aryl-$R^{25}$,
  heterocycle-$R^{25}$,
  $C_1$–$C_2$alkyl-$C_6$–$C_{10}$aryl-$R^{25}$, and
  $C_1$–$C_2$alkyl-heterocyde-$R^{25}$,
    where any heterocycle is a 5- or 6-member saturated or unsaturated ring containing 1 to 3 heteroatoms selected from O, N, and S;
$R^{24}$ is selected from the group
  hydrogen,
  $C_1$–$C_6$alkyl, and
  halo(F, Cl, Br, I)$C_1$–$C_6$alkyl;
$R^{25}$ is selected from $R^{25'}$,

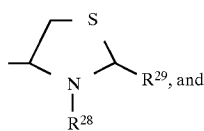

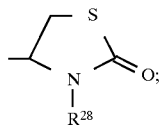

$R^{25'}$ is selected from the group
  $SR^{26}$,
  $SSR^{26}$,
  $OR^{26}$,
  $NOR^{26}$,
  $C_1$–$C_6$alkyl,
  $C_2$–$C_6$alkenyl,
  $C_1$–$C_6$alkylamine,
  $C_2$–$C_6$alkenylamine, and
  halo(F, Cl, Br, I)$C_1$–$C_6$alkyl
    where any alkyl or alkenyl moiety is optionally substituted with
      $SR^{26}$,
      $SSR^{26}$,
      $OR^{26}$,
      $NOR^{26}$, and
      $NR^{27}R^{28}$, and
      where any amine moiety is optionally substituted with $R^{27}$ or $R^{28}$;
$R^{26}$ is selected from
  hydrogen,
  $C_1$–$C_6$alkyl,
  halo(F, Cl, Br, I)$C_1$–$C_6$alkyl, and
  $C_1$–$C_6$alkanoyl;
$R^{27}$ and $R^{28}$ are independently selected from the group
  hydrogen,
  $C_1$–$C_6$alkyl,
  phenyl,
  napthyl,
  benzyl,
  $CH_2$napthyl (α or β)
  $C_1$–$C_6$alkanoyl,
  $C_1$–$C_6$cycloaLkanoyl.
  C6–$C_{10}$aroyl,
  $C_6$–$C_{10}$aryl$C_1$–$C_6$alkanoyl,
  $C_1$–$C_6$alkylsulfonyl,
  $C_6$–$C_{10}$arylsulfonyl,
  $C_6$–$C_{10}$aryl$C_1$–$C_6$alkylcarbamoyl,
  cinnamoyl,
  heterocydecarbonyl,
  $C_1$–$C_6$alkoxycarbonyl,
  $C_6$–$C_{10}$aryloxycarbonyl,
  $C_6$–$C_{10}$aryl$C_1$–$C_6$alkoxycarbonyl, and
  pyroglutamyl;
$R^{27}$ and $R^{28}$ together with the nitrogen atom to which they are bonded may form a cyclic amine represented by

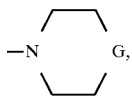

a cyclic imide represented by

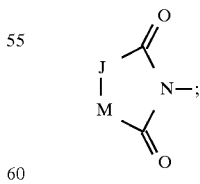

G is selected from —$CH_2$—, O, $S(O)_u$ where u is 0,1,or 2, and $NR^{28}$;
J–M is selected from $C_2$–$C_4$alkylene and $C_2$–$C_4$alkenylene;
$R^{29}$ is selected from hydrogen and $C_1$–$C_3$alkyl; and
pharmaceutically acceptable salts thereof.

8. A compound represented by structural formula (III):

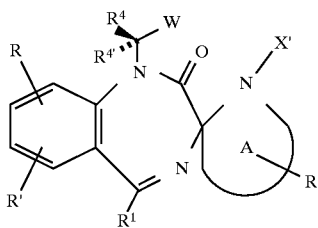

(III)

where
R and R' are independently selected from the group
hydrogen,
halo(F, Cl, Br, I),
$C_1$–$C_6$alkyl,
halo(F, Cl, Br, I)$C_1$–$C_6$alkyl,
$C_1$–$C_6$alkoxy,
hydroxy,
hydroxy-$C_1$–$C_6$alkyl,
$C_1$–$C_6$alkylcarbonyl, and
$C_1$–$C_6$alkyloxycarbonyl;
$R^1$ is selected from the group
hydrogen,
$C_1$–$C_6$alkyl,
halo(F, Cl, Br, I)$C_1$–$C_6$alkyl, and

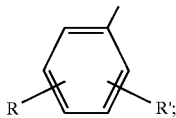

$R^4$ and $R^{4'}$ are independently selected from the group
hydrogen,
halo(F, Cl, Br, I),
$C_1$–$C_6$ alkyl,
halo(F, Cl, Br, I)$C_1$–$C_6$ alkyl,
phenyl, and
benzyl;
W is selected from the group
$C(=O)$—$NR^7R^8$,
$CH_2$—$C(=O)$—$NRR^8$,
$C(=O)$—$O$—$R^8$,
$CR^{8'}(OH)$—$CHR^7R^8$,
$CHR^{8'}$-$CHR^7R^8$,
$CR^{8'}$=$CR^7R^8$ (E or Z),
$C(=O)$—$CHR^7R^8$,
$CHR^{8'}$—$NR^{7'}R^8$,
$CHR^{8'}$—$O$—$R^8$
$CHR^{8'}$—$S(O)_u$—$R^8$ where u is 0, 1, or 2,
$CR^{8'}$=$N$—$R^8$,
$CHR^8$—$R^8$,
W',
$C_1$–$C_3$alkyl-W',
$C_6$–$C_{12}$aryl-W',
$C_6$–$C_{12}$aryl-$C_1$–$C_3$alkyl-W',
heterocyde-W',
heterocycle-$C_1$–$C_3$alkyl-W',
$C_1$–$C_2$alkyl-$C_6$–$C_{10}$aryl-W', and
$C_1$–$C_2$alkyl-heterocycle-W', and
where any heterocycle is a 5- or 6-member saturated or unsaturated ring containing 1 to 3 heteroatoms selected from O, N, and S;
W' is selected from one to three substituents selected from the group
hydrogen,
$SR^9$,
$SSR^9$,
$SC(=O)$—$R^9$,
$OR^9$,
$C(=NH)$—$NH_2$,
$N=CH$—$NH_2$,
$NH$—$CH=NH$,
$R^8$, and
V;
$R^7$, each occurance, is independently selected from the group
hydrogen,
$C_1$–$C_4$alkyl,
halo(F, Cl, Br, I), and
halo(F, Cl, Br, I)$C_1$–$C_4$alkyl;
$R^{7'}$ is selected from the group
hydrogen,
$C_1$–$C_4$alkyl, and
halo(F, Cl, Br, I)$C_1$–$C_4$alkyl;
$R^{7'}$ and $R^8$ together with the nitrogen to which they are bonded may form a pyrrolidinyl or piperidyl ring optionally substituted with one or two groups selected from
$SR^9$,
$SSR^9$,
$SC(=O)$—$R^9$,
$OR^9$,
$C(=O)NHOH$,
$NHR^9$,
$C(=O)NR^{27}R^{28}$, and
V;
$R^8$ is selected from the group unsubstituted and substituted
$C_1$–$C_8$alkyl,
$C_2$–$C_8$alkenyl,
$C_6$–$C_{12}$aryl-$C_1$–$C_3$alkyl,
indol-3-yl-$C_1$–$C_3$alkyl, and
imidazol-4-yl-$C_1$–$C_3$alkyl,
where any aryl moiety is optionally substituted with —$OR^9$ and V, and where any alkyl or alkenyl group is optionally substituted with one to three groups selected from
$SR^9$,
$SSR^9$,
$SC(=O)$—$R^9$,
$OR^9$,
$C(=NH)$—$NH_2$,
$N=CH$—$NH_2$,
$NH$—$CH=NH$,
$NH$—$C(=NH)$—$NH_2$,
$C(=O)NHOH$,
$NHR^9$,
$C(=O)NR^{27}R^{28}$, and
V;
V is selected from the group
$COR^{10}$, SO₃R¹³,
NHSO₂CF₃,
PO(OR¹³)2,
SO₂NHR¹⁰,
CONHOR¹³,
C(OH)R¹⁰PO(OR¹³)2,
halo(F, Cl, Br, I),
NO₂,
CN,
SO₂NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    C₁–C₄alkyl,
    C₁–C₄alkoxyl,
    CF₃,
    halo(F, Cl, Br, I),
    NO₂,
    COOH,
    COO—(C₁–C₄alkyl),
    NH₂,
    NH(C₁–C₄alkyl), and
    N(C₁–C₄alkyl)₂,
CONHSO₂R¹⁵,
SO₂NHCOR¹⁵,
CONHSO₂R¹³,
CH₂CONHSO₂R¹⁵,
NHCONHSO₂R¹⁵,
NHSO₂NHCOR¹⁵,
CONHNHSO₂CF₃,
CON(OH)R¹³,
CONHCOCF₃,
CONHSO₂R¹⁰,
CONHSO₂R¹¹,
CONHSO₂R¹³,

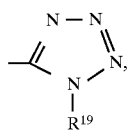

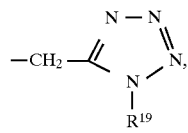

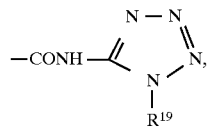

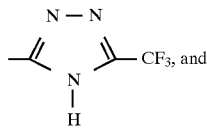

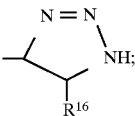

R⁹ is selected from the group
    hydrogen,
    methyl,
    ethyl,
    isopropyl,
    t-butyl,
    phenyl, and
    benzyl;
R¹⁰ is selected from the group
    hydroxy,
    C₁–C₈-alkoxy,
    C₃–C₁₂-alkenoxy,
    C₆–C₁₂-aryloxy,
    C₁–C₆-alkyl-C₆–C₁₂-aryloxy,
    di-C₁–C₈-alkylamino-C₁–C₈-alkoxy,
    alkanoylamino-C₁–C₈-alkoxy selected from the group
        acetylaminoethoxy,
        nicotinoylaminoethoxy, and
        succinamidoethoxy,
    C₁–C₈-alkanoyloxy-C₁–C₈-alkoxy,
    C₆–C₁₂-aryl-C₁–C₈-alkoxy where the aryl group is unsubstituted or substituted with one to three of the groups
        nitro,
        halo(F, Cl, Br, I),
        C₁–C₄-alkoxy, and
        amino,
    hydroxy-C₂–C₈-alkoxy,
    dihydroxy-C₃–C₈-alkoxy, and
    NR¹¹R¹²;
R¹¹ and R¹² are independently selected from the group
    hydrogen,
    C₁–C₆ alkyl,
    C₂–C₆ alkanoyl,
    C₁–C₆ alkanoyl substituted with from one to three groups selected from
        nitro,
        halo(F, Cl, Br, I),
        C₁–C₄-alkoxy, and
        amino, and
    C₆–C₁₂-aryl-C₁–C₈-alkyl where the aryl group is unsubstituted or substituted with one to three of the groups selected from
        nitro,
        halo(F, Cl, Br, I), and
        C₁–C₄-alkoxy;
R¹³ is selected from the group
    hydrogen,
    C₁–C₆ alkyl,
    halo(F, Cl, Br, I)—C₁–C₆ alkyl,
    phenyl,
    benzyl, and
    CH₂COCH₃;
R¹⁵ is selected from the group
    C₆–C₁₄aryl, heteroaryl, where the heteroaryl is a 5- or 6-member aromatic ring containing 1 to 3 heteroatoms selected from O, N, and S and where the heteroaryl is unsubstituted or substituted with one or two substituents selected from the group
OH,
SH,
$C_1$–$C_4$alkyl,
$C_1$–$C_4$alkoxyl,
$CF_3$,
halo(F, Cl, Br, I),
$NO_2$,
COOH,
COO—($C_1$–$C_4$alkyl),
$NH_2$,
NH($C_1$–$C_4$alkyl), and
N($C_1$–$C_4$alkyl)$_2$,
$C_3$–$C_7$-cyloalkyl,
$C_1$–$C_4$-alkyl, unsubstituted or substituted with a substituent selected from the group
$C_6$–$C_{14}$aryl,
heteroaryl as defined above,
OH,
SH,
$C_1$–$C_4$-alkyl,
$C_1$–$C_4$-alkoxy,
$C_1$–$C_4$-alkylthio,
$CF_3$,
halo(F, Cl, Br, I),
$NO_2$,
$CO_2H$,
$CO_2$-($C_1$–$C_4$)-alkyl,
$NH_2$,
N[($C_1$–$C_4$)-alkyl]$_2$,
NH[($C_1$–$C_4$)-alkyl],
$PO_3H$, and
PO(OH)($C_1$–$C_4$)-alkoxy, and
($C_1$–$C_4$)-perfluoroalkyl;
$R^{16}$ is selected from the group
CN,
$NO_2$,
$COOR^{13}$,
$C_1$–$C_6$-perfluoroalkyl, and
$CF_3$;
$R^{19}$ is selected from the group
hydrogen,
$C_1$–$C_6$alkyl,
$C_2$–$C_6$alkenyl,
$C_1$–$C_6$alkoxy,
$C_2$–$C_6$alkoxyalkyl,
$CH_2$—O—$COCH_3$, and
benzyl, where the phenyl moiety is unsubstituted or substituted with a group selected from

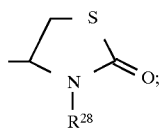

$R^{25}$ is selected from the group
$SR^{26}$,
$SSR^{26}$,
$OR^{26}$,
$NOR^{26}$,
$C_1$–$C_6$alkyl,
$C_2$–$C_6$alkenyl,
$C_1$–$C_6$alkylamine,
$C_2$–C6alkenylamine, and
halo(F, Cl, Br, I)$C_1$–$C_6$alkyl,
where any alkyl or alkenyl moiety is optionally substituted with
$SR^{26}$,
$SSR^{26}$,
$OR^{26}$,
$NOR^{26}$, and
$NR^{27}R^{28}$, and
where any amine moiety is optionally substituted with $R^{27}$or $R^{28}$;
$R^{26}$ is selected from the group
hydrogen,
$C_1$–$C_6$alkyl,
halo(F, Cl, Br, I)$C_1$–$C_6$alkyl, and
$C_1$–$C_6$alkanoyl;
$R^{27}$ and $R^{28}$ are independently selected from the group
hydrogen,
$C_1$–$C_6$alkyl,
phenyl,
napthyl,
benzyl,
$CH_2$napthyl (α or β),
$C_1$–$C_6$alkanoyl,
$C_1$–$C_6$cycloalkanoyl,
$C_6$–$C_{10}$aroyl,
$C_6$–$C_{10}$aryl$C_1$–$C_6$alkanoyl,
$C_1$–$C_6$alkylsulfonyl,
$C_6$–$C_{10}$arylsulfonyl,
$C_6$–$C_{10}$aryl$C_1$–$C_6$alkylcarbamoyl,
cinnamoyl,
heterocyclecarbonyl,
$C_1$–$C_6$–alkoxycarbonyl,
$C_6$–$C_{10}$aryloxycarbonyl,
$C_6$–$C_{10}$aryl$C_1$–$C_6$alkoxycarbonyl, and
pyroglutamyl;
$R^{27}$ and $R^{28}$ together with the nitrogen atom to which they are bonded may form a cyclic amine represented by

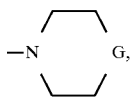

and a cyclic imide represented by

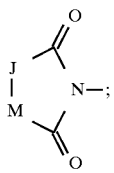

G is selected from —CH$_2$—, O, S(O)$_u$ where u is 0,1,or 2, and NR$^{28}$;
J–M is selected from C$_2$–C$_4$alkylene and C$_2$–C$_4$alkenylene;
R$^{29}$ is selected from hydrogen and C$_1$–C$_3$alkyl; and
pharmaceutically acceptable salts thereof.

9. A compound represented by structural formula (IV):

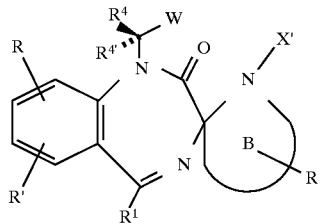

where
R and R' are independently selected from the group
hydrogen,
halo(F, Cl, Br, I),
C$_1$–C$_6$ all,
halo(F, Cl, Br, I)C$_1$–C$_6$ alkyl,
C$_1$–C$_6$ alkoxy,
hydroxy,
hydroxy-CC$_1$–C$_6$ alkyl,
C$_1$–C$_6$ alkylcarbonyl, and
C$_1$–C$_6$ alkyloxycarbonyl;
R$^1$ is selected from the group
hydrogen,
C$_1$–C$_6$ alkyl,
halo(F, Cl, Br, I)-C$_1$–C$_6$ alkyl, and

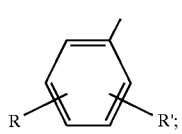

R$^4$ and R$^{4'}$ are independently selected from the group
hydrogen,
halo(F, Cl, Br, I),
C$_1$–C$_6$ alkyl,
halo(F, Cl, Br, I)C$_1$–C$_6$ alkyl,
phenyl, and
benzyl;
W is selected from the group
C(=O)-NR$^{7'}$R$^8$,
CH$_2$—C(=O)-NR$^{7'}$R$^8$,
C(=O)—O—R$^8$,
CR$^{8'}$(OH)—CHR$^7$R$^8$,
CHR$^{8'}$—CHR$^7$R$^8$,
CR$^{8'}$=CR$^7$R$^8$ (E or Z),
C(=O)—CHR$^7$R$^8$, CHR$^{8'}$—NR$^{7'}$R$^8$,
CHR$^{8'}$—O—R$^8$,
CHR$^{8'}$—S(O)$_u$—R$^8$ where u is 0, 1, or 2,
CR$^{8'}$=N—R$^8$,
CHR$^{8'}$—R$^8$,
C$_1$–C$_3$alkyl-W',
C$_6$–C$_{12}$aryl-W',
C$_6$–C$_{12}$aryl-C$_1$–C$_3$alkyl-W',
heterocyde-W',
heterocycle-C$_1$–C$_3$alkyl-W',
C$_1$–C$_2$alkyl-C$_6$–C$_{10}$aryl-W', and
C$_1$–C$_2$alkyl-heterocyle-W', and
where any heterocycle is a 5- or 6-member saturated or unsaturated ring containing 1 to 3 heteroatoms selected from O, N, and S;
W' is selected from one to three substituents selected from the group
hydrogen,
SR$^9$,
SSR$^9$,
SC(=O)—R$^9$,
OR$^9$,
C(=NH)—NH$_2$,
N=CH—NH$_2$,
NH—CH=NH,
R$^8$, and
V;
R$^7$, each occurance, is independently selected from the group
hydrogen,
C$_{1-C4}$alkyl,
halo(F, Cl, Br, I), and
halo(F, Cl, Br, I)C$_1$–C$_4$alkyl;
R$^{7'}$ is selected from the group
hydrogen,
C$_1$–C$_4$alkyl, and
halo(F, Cl, Br, I)C$_1$–C$_4$alkyl;
R$^{7'}$ and R$^8$ together with the nitrogen to which they are bonded may form a pyrrolidinyl or piperidyl ring optionally substituted with one or two groups selected from
SR$^9$,
SSR$^9$,
SC(=O)—R$^9$,
OR$^9$,
C(=O)NHOH,
NHR$^9$,
C(=O)NR$^{27}$R$^{28}$, and
V;
R$^8$ is selected from the group unsubstituted and substituted
C$_1$–C$_8$alkyl,
C$_2$–C$_8$alkenyl,
C$_6$–C$_{12}$arylC$_1$–C$_3$alkyl,
indol-3-yl-C$_1$–C$_3$alkyl, and
imidazol-4-yl-C$_1$–C$_3$alkyl,
where any aryl moiety is optionally substituted with —OR$^9$ and V, and where any alkyl or alkenyl group is optionally substituted with one to three groups selected from
SR$^9$, SSR⁹,
SC(=O)—R⁹,
OR⁹,
C(=NH)—NH₂,
N=CH—NH₂,
NH—CH=NH,
NH—C(=NH)—NH₂,
C(=O)NHOH,
NHR⁹,
C(=O)NR²⁷R²⁸, and
V;

V is selected from the group
COR¹⁰,
SO₃R¹³,
NHSO₂CF₃,
PO(OR¹³)2,
SO₂NHR¹⁰,
CONHOR¹³,
C(OH)R¹⁰PO(OR¹³)2,
CN,
SO₂NH-heteroaryl where the heteroaryl is a 5- or 6-member aromatic ring containing 1 to 3 heteroatoms selected from O, N, and S and where the
NO₂,
NHO₂,
OH, and
OCH₃;

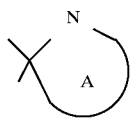

represents a heterocycle bonded to the benzodiazepine moiety through a spiro linkage, where the heterocycle is a 5- or 6-member saturated or unsaturated nitrogen containing ring having from 0 to 2 additional heteroatoms selected from O, N, and S, the ring optionally containing a keto [—C(=O)—] group;

X' is selected from the group
C(=O)—R²⁵,
CH(OH)—R²⁵,
CHR²⁴—R²⁵,
S(O)ᵤ—R²⁵ where u is 0, 1, or 2,
CHR²⁴—R²⁵,
R²⁵,
C₆–C₁₀aryl-R²⁵,
heterocyle-R²⁵,
C₁–C₂alkyl-C₆–C₁₀aryl-R²⁵, and
C₁–C₂alkyl-heterocycle-R²⁵,
where any heterocycle is a 5- or 6-member saturated or unsaturated ring containing 1 to 3 heteroatoms selected from O, N, and S;

R²⁴ is selected from the group
hydrogen,
C₁–C₆alkyl, and
halo(F, Cl, Br, I)C₁–C₆alkyl;

R²⁵ is selected from R²⁵,

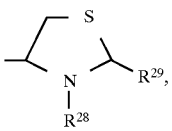

heteroaryl is unsubstituted or substituted with one or two substituents selected from the group
OH,
SH,
C₁–C₄alkyl,
C₁–C₄alkoxy,
CF₃,
halo(F, Cl, Br, I),
NO₂,
COOH,
COO—(C₁–C₄alkyl),
NH₂,
NH(C₁–C4alkyl), and
N(C₁–C₄alkyl)₂,
CONHSO₂R¹⁵,
SO₂NHCOR¹⁵,
CONHSO₂R¹³,
CH₂CONHSO₂R¹⁵,
NHCONHSO₂R¹⁵,
NHSO₂NHCOR¹⁵,
CONHNHSO₂CF₃,
CON(OH)R¹³,
CONHCOCF₃,
CONHSO₂R¹⁰,
CONHSO₂R¹¹,
CONHSO₂R¹³,

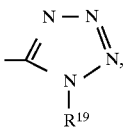

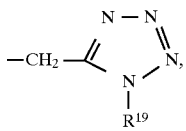

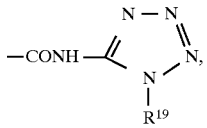

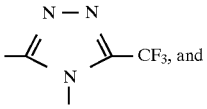

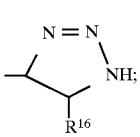

R⁹ is selected from the group
hydrogen,
methyl, ethyl,
isopropyl,
t-bytyl,
phenyl, and
benzyl;
$R^{10}$ is selected from the group
hydroxy,
$C_1–C_8$-alkoxy,
$C_3–C_{12}$-alkenoxy,
$C_6–C_{12}$-aryloxy,
$C_1–C_6$-alkyl-$C_6–C_{12}$-aryloxy,
di-$C_1–C_8$-alkylamino-$C_1–C_8$-alkoxy,
alkanoylamino-$C_1–C_8$-alkoxy selected from the group
  acetylaminoethoxy,
  nicotinoylaminoethoxy, and
  succinamidoethoxy,
$C_1–C_8$-alkanoyloxy-$C_1–C_8$-alkoxy,
$C_6–C_{12}$-aryl-$C_1–C_8$-alkoxy where the aryl group is unsubstituted or substituted with one to three of the groups
  nitro,
  halo(F, Cl, Br, I),
  $C_1–C_4$-alkoxy, and
  amino,
hydroxy-$C_2–C_8$-alkoxy,
dihydroxy-$C_3–C_8$-alkoxy, and
$NR^{11}R^{12}$;
$R^{11}$ and $R^{12}$ are independently selected from the group
hydrogen,
$C_1–C_6$ alkanoyl,
$C_2–C_6$ alkanoyl,
$C_1–C_6$ alkanoyl substituted with from one to three groups selected from
  nitro,
  halo(F, Cl, Br, I),
  $C_1–C_4$-alkoxy, and
  amino, and
$C_6–C_{12}$-aryl-$C_1–C_8$-alkyl where the aryl group is unsubstituted or substituted with one to three of the groups selected from
  nitro,
  halo(F, Cl, Br, I), and
  $C_1–C_4$-alkoxy;
$R^{13}$ is selected from the group
hydrogen,
$C_1–C_6$ alkyl,
halo(F, Cl, Br, I)—$C_1–C_6$ alkyl,
phenyl,
benzyl, and
$CH_2$—O—$COCH_3$;
$R^{15}$ is selected from the group
$C_6–C_{14}$aryl,
heteroaryl, where the heteroaryl is a 5- or 6-member aromatic ring containing 1 to 3 heteroatoms selected from O, N, and S and where the heteroaryl is unsubstituted or substituted with one or two substituents selected from the group
  OH,
  SH,
  $C_1–C_4$alkyl,
  $C_1–C_4$alkoxy,
  $CF_3$,
  halo(F, Cl, Br, I),
  $NO_2$,
  COOH,
  COO—($C_1–C_4$alkyl),
  $NH_2$,
  $NH(C_1–C_4$alkyl), and
  $N(C_1–C_4$alkyl$)_2$,
$C_3–C_7$-cycloalkyl,
$C_1–C_4$-alkyl, unsubstituted or substituted with a substituent selected from the group
  $C_6–C_{14}$aryl,
  heteroaryl as defined above,
  OH,
  SH,
  $C_1–C_4$-alkyl,
  $C_1–C_4$-alkoxy,
  $C_1–C_4$-alkylthio,
  $CF_3$,
  halo(F, Cl, Br, I),
  $NO_2$,
  $CO_2H$,
  $CO_2$—($C_1–C_4$)—alkyl,
  $NH_2$,
  $N[(C_1–C_4)$-alkyl$]_2$,
  $NH[(C_1–C_4)$-alkyl],
  $PO_3H$, and
  $PO(OH)(C_1–C_4)$-alkoxy, and
  ($C_1$–C4)-perfluoroalkyl;
$R^{16}$ is selected from the group
CN,
$NO_2$,
$COOR^{13}$,
$C_1–C_6$-perfluoroalkyl, and
$CF_3$;
$R^{19}$ is selected from the group
hydrogen,
$C_1–C_6$alkyl,
$C_2–C_6$alkeny,
$C_1–C_6$alkoxy,
$C_2–C_6$aloxyalkyl,
$CH_2$—O—$COCH_3$, and
benzyl, where the phenyl moiety is unsubstituted or substituted with a group selected from
  $NO_2$,
  $NH_2$,
  OH, and
  $OCH_3$;

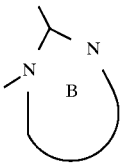

represents a heterocycle fused to the benzodiazepine moiety, where the heterocycle is a 5- or 6-member saturated or unsaturated di-nitrogen containing ring having from 0 to 1 additional heteroatom selected from O, N, and S, the ring optionally containing a keto [—C(=O)—] group;
X' is selected from the group
  C(=O)—$R^{25}$,
  CH(OH)—$R^{25}$, CHR²⁴—R²⁵,
S(O)ᵤ—R²⁵ where u is 0,1, or 2,
CHR²⁴—R²⁵,
R²⁵,
$C_6$–$C_{10}$aryl—R²⁵
heterocyle-R²⁵,
$C_1$–$C_2$alkyl-$C_6$–$C_{10}$aryl—R²⁵, and
$C_1$–$C_2$alkyl-heterocyle-R²⁵,
  where any heterocycle is a 5- or 6-member saturated or unsaturated ring containing 1 to 3 heteroatoms selected from O, N, and S;
R²⁴ is selected from the group
hydrogen,
$C_1$–$C_6$alkyl, and
halo(F, Cl, Br, I)$C_1$–$C_6$alkyl;
R²⁵ is selected from R²⁵',

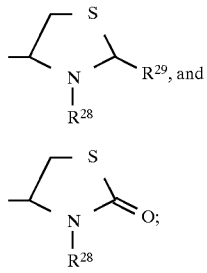

R²⁵' is selected from the group
SR²⁶,
SSR²⁶,
OR²⁶,
NOR²⁶,
$C_1$–$C_6$alkyl,
$C_2$–$C_6$alkenyl,
$C_1$–$C_6$alkylamine,
$C_2$–$C_6$alkenylamine, and
halo(F, Cl, Br, I)$C_1$–$C_6$alkyl,
  where any alkyl or alkenyl moiety is optionally substituted with
SR²⁶,
SSR²⁶,
OR²⁶,
NOR²⁶, and
NR²⁷R²⁸, and
  where any amine moiety is optionally substituted with R²⁷ or R²⁸;
R²⁶ is selected from the group
hydrogen,
$C_1$–$C_6$alkyl,
halo(F, Cl, Br, I)$C_1$–$C_6$alkyl, and
$C_1$–$C_6$akanoyl;
R²⁷ and R²⁸ are independently selected from the group
hydrogen,
$C_1$–$C_6$alkyl,
phenyl,
napthyl,
benzyl,
$CH_2$napthyl (α or β),
$C_1$–$C_6$alkanoyl,
$C_1$–$C_6$cycloalkanoyl,
$C_6$–$C_{10}$aroyl,
$C_6$–$C_{10}$aryl$C_1$–$C_6$alkanoyl,
$C_1$–$C_6$alkylsulfonyl,
$C_6$–$C_{10}$arylsulfonyl,
$C_6$–$C_{10}$aryl$C_1$–$C_6$alkylcarbamoyl,
cinnamoyl,
heterocyclecarbonyl,
$C_1$–$C_6$alkoxycarbonyl,
$C_6$–$C_{10}$aryloxycarbonyl,
$C_6$–$C_{10}$aryl$C_1$–$C_6$alkoxycarbonyl, and
pyroglutamyl;
R²⁷ and R²⁸ together with the nitrogen atom to which they are bonded may form a cyclic amine represented by

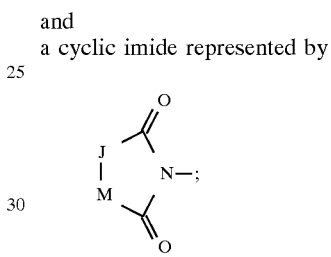

and
a cyclic imide represented by

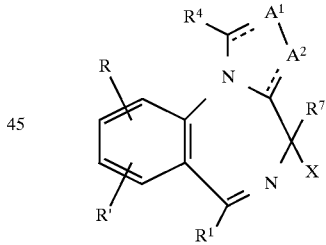

G is selected from —$CH_2$—, O, S(O)ᵤ where u is 0, 1, or 2, and NR²⁸;
J–M is selected from $C_2$–$C_4$alkylene and $C_2$–$C_4$alkenylene;
R²⁹ is selected from hydrogen and $C_1$–$C_3$alkyl; and
pharmaceutically acceptable salt thereof.

10. A compound represented by structural formula (V):

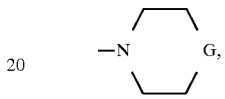

where
R and R' are independently selected from the group
hydrogen,
halo(F, Cl, Br, I),
$C_1$–$C_6$ alkyl,
halo(F, Cl, Br, I)$C_1$–$C_6$ alkyl,
$C_1$–$C_6$ alkoxy,
hydroxy,
hydroxy-$C_1$–$C_6$ alkyl,
$C_1$–$C_6$ alkylcarbonyl, and
$C_1$–$C_6$ alkyloxycarbonyl;
R¹ is selected from the group
hydrogen,
$C_1$–$C_6$ alkyl, halo(F, Cl, Br, I)—$C_1$–$C_6$ alkyl, and

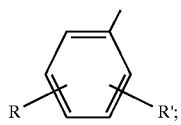

$R^4$ is selected from the group
hydrogen,
halo(F, Cl, Br, I),
$C_1$–$C_6$ alkyl,
halo(F, Cl, Br, I)$C_1$–$C_6$ alkyl,
phenyl, and
benzyl;
$R^7$ is selected from the group
hydrogen,
halo(F, Cl, Br, I),
$C_1$–C6 alkyl, and
halo(F, Cl, Br, I)$C_1$–$C_6$ alkyl;
$A^1$ and $A^2$ are independently selected from the group
CRR',
CR',
$CRR^8$,
$CR^8$,
N,
O, and
S, and
provided one of $A^1$ and $A^2$ is $CRR^8$ or $CR^8$;

---- represents a single or double bond;
$R^8$ is selected from the group unsubstituted and substituted
$C_1$–$C_8$alkyl,
$C_2$–$C_8$alkenyl,
phenyl-$C_1$–$C_3$alkyl,
indol-3-yl-$C_1$–$C_3$alkyl, and
imidazol-4-yl-$C_1$–$C_3$alkyl,
where any phenyl moiety is optionally substituted with $OR^9$ and V, and where any alkyl or alkenyl group is optionally substituted with one to three groups selected from
$SR^9$,
$SSR^9$,
SC(=O)—$R^9$,
$OR^9$,
C(=NH)—$NH_2$,
N=CH—$NH_2$,
NH—CH=NH,
NH—C(=NH)—$NH_2$,
C(=O)NHOH,
$NHR^9$,
C(=O)$NR^{27}R^{28}$, and
V;
V is selected from the group
$COR^{10}$,
$SO_3R^3$,
$NHSO_2CF_3$,
PO($OR^{13}$)$_2$,
$SO_2NHR^{10}$,
$CONHOR^{13}$,
C(OH)$R^{10}$PO($OR^{13}$)$_2$,
CN, $SO_2NH$-heteroaryl where the heteroaryl is a 5- or 6-member aromatic ring containing 1 to 3 heteroatoms selected from O, N, and S and where the heteroaryl is unsubstituted or substituted with one or two substituents selected from the group
OH,
SH,
$C_1$–$C_4$alkyl,
$C_1$–$C_4$alkoxy,
$CF_3$,
halo(F, Cl, Br, I),
$NO_2$,
COOH,
COO—($C_1$–$C_4$alkyl),
$NH_2$,
NH($C_1$–$C_4$alkyl), and
N($C_1$–$C_4$alkyl)$_2$, and
$CONHSO_2R^{15}$,
$SO_2NHCOR^{15}$,
$CONHSO_2R^{13}$,
$CH_2CONHSO_2R_{15}$,
$NHCONHSO_2R^{15}$,
$NHSO_2NHCOR^{15}$,
$CONHNHSO_2CF_3$,
CON(OH)$R^{13}$,
$CONHCOCF_3$,
$CONHSO_2R^{10}$,
$CONHSO_2R^{11}$,
$CONHSO_2R^{13}$,

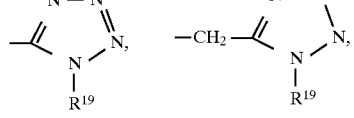

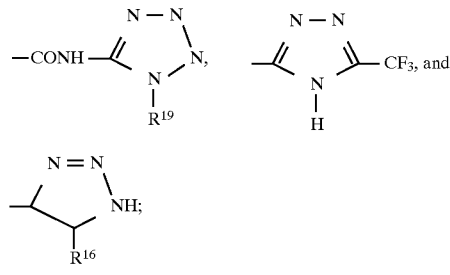

$R^9$ is selected from the group
hydrogen,
methyl,
ethyl,
isopropyl,
t-butyl,
phenyl, and
benzyl;
$R^{10}$ is selected from the group
hydroxy,
$C_1$–$C_8$-alkoxy,
$C_3$–$C_{12}$-alkenoxy,
$C_6$–$C_{12}$-aryloxy,
$C_1$–$C_6$-alkyl-$C_6$–$C_8$-alkoxy,
di-$C_1$–$C_8$-alkylamino-$C_1$–$C_8$-alkoxy,
alkanoylamino-$C_1$–$C_8$-alkoxy selected from the group acetylaminoethoxy,
nicotinoylaminoethoxy, and
succinamidoethoxy, $C_1$–$C_8$-alkanoyloxy-$C_1$–$C_8$-alkoxy, $C_6$–$C_{12}$-aryl-$C_1$–$C_8$-alkoxy where the aryl group is unsubstituted or substituted with one to three of the groups
  nitro,
  halo(F, Cl, Br, I),
  $C_1$–$C_4$-alkoxy, and
  amino, hydroxy-$C_2$–$C_8$-alkoxy,
dihydroxy-$C_3$–$C_8$-alkoxy, and
$NR^{11}R^{12}$;

$R^{11}$ and $R^{12}$ are independently selected from the group
  hydrogen,
  $C_1$–$C_6$ alkyl,
  $C_2$–$C_6$ alkanoyl,
  $C_1$–$C_6$ alkanoyl substituted with from one to three groups selected from
    nitro,
    halo(F, Cl, Br, I),
    $C_1$–$C_4$-alkoxy, and
    amino, and
  $C_6$–$C_{12}$-aryl-$C_1$–$C_8$-alkyl where the aryl group is unsubstituted or substituted with one to three of the groups selected from the group
    nitro,
    halo(F, Cl, Br, I), and
    $C_1$–$C_4$-alkoxy;

$R^{13}$ is selected from the group
  hydrogen,
  $C_1$–$C_6$ alkyl,
  halo(F, Cl, Br, I)—$C_1$–$C_6$ alkyl,
  phenyl,
  benzyl, and
  $CH_2$—O—$COCH_3$;

$R^{15}$ is selected from the group
  $C_6$–$C_{14}$aryl,
  heteroaryl, where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    $C_1$–$C_4$alkyl,
    $C_1$–$C_4$alkoxy,
    $CF_3$,
    halo(F, Cl, Br, I),
    $NO_2$,
    COOH,
    COO—($C_1$–$C_4$alkyl),
    $NH_2$,
    $NH(C_1$–$C_4$alkyl), and
    $N(C_1$–$C_4$alkyl$)_2$,
  $C_3$–$C_7$-cyloalkyl,
  $C_1$–$C_4$-alkyl, unsubstituted or substituted with a substituent selected from the group
    $C_6$–$C_{14}$aryl,
    heteroaryl as defined above,
    OH,
    SH,
    $C_1$–$C_4$-alkyl,
    $C_1$–$C_4$-alkoxy,
    $C_1$–$C_4$-alkylthio,
    $CF_3$,
    halo(F, Cl, Br, I),
    $NO_2$,
    $CO_2H$,
    $CO_2(C_1$–$C_4)$alkyl,
    $NH_2$,
    $N[(C_1$–$C_4)$-alkyl$]_2$,
    $NH[(C_1$–$C_4)$-alkyl],
    $PO_3H$ or
    $PO(OH)(C_1$–$C_4)$-alkoxy, and
    $(C_1$–$C_4)$-perfluoroalkyl;

$R^{16}$ is selected from the group
  CN,
  $NO_2$,
  $COOR^{13}$,
  $C_1$–$C_6$-perfluoroalkyl, and
  $CF_3$;

$R^{19}$ is selected from the group
  hydrogen,
  $C_1$–$C_6$alkyl,
  $C_2$–$C_6$alkenyl,
  $C_1$–$C_6$alkoxy,
  $C_2$–$C_6$alkoxyalkyl,
  $CH_2$—O—$COCH_3$, and
  benzyl, where the phenyl moiety is unsubstituted or substituted with a group selected from
    $NO_2$,
    $NH_2$,
    OH, and
    $OCH_3$;

X is selected from the group
  $NR^{24}$—C(=O)—$R^{25}$,
  $NR^{24}$—CH(OH)—$R^{25}$,
  $NR^{24}$—$CH_2$—$R^{25}$,
  $NR^{24}$—S(O)$_u$—$R^{25}$ where u is 0, 1, or 2,
  $CHR^{24}$—$CH_2R^{25}$,
  $CHR^{24}$—$R^{25}$,
  $CR^{24}$=$CHR^{25}$ (E or Z),
  $C_6$–$C_{10}$aryl- $R^{25}$,
  heterocycle-$R^{25}$,
  $C_1$–$C_2$alkyl-$C_6$–$C_{10}$aryl-$R^{25}$, and
  $C_1$–$C_2$alkyl-heterocycle-$R^{25}$, and
  where any heterocycle is a 5- or 6-member saturated or unsaturated ring containing 1 to 3 heteroatoms selected from O, N, and S;

$R^{24}$ is selected from the group
  hydrogen,
  $C_1$–$C_6$alkyl, and
  halo(F, Cl, Br, I)$C_1$–$C_6$alkyl;

$R^{25}$ is selected from $R^{25'}$,

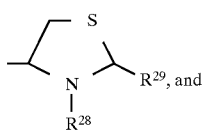

$R^{25'}$ is selected from the group
  $SR^{26}$, $SSR^{26}$,
$OR^{26}$,
$NOR^{26}$,
$C_1-C_6$alkyl,
$C_2-C_6$alkenyl,
$C_1-C_6$alkylamine,
$C_2-C_6$alkenylamine, and
halo(F, Cl, Br, I)$C_1-C_6$alkyl,
  where any alkyl or alkenyl moiety is optionally substituted with
$SR^{26}$,
$SSR^{26}$,
$OR^{26}$,
$NOR^{26}$ and
$NR^{27}R^{28}$, and
  where any amine moiety is optionally substituted with $R^{27}$ or $R^{28}$;

$R^{26}$ is selected from the group
  hydrogen,
  $C_1-C_6$alkyl,
  halo(F, Cl, Br, I)$C_1-C_6$alkyl, and
  $C_1-C_6$alkanoyl;

$R^{27}$ and $R^{28}$ are independently selected from the group
  hydrogen,
  $C_1-C_6$alkyl,
  phenyl,
  napthyl,
  benzyl,
  $CH_2$napthyl (α or β),
  $C_1-C_6$alkanoyl,
  $C_1-C_6$cycloalkanoyl,
  $C_6-C_{10}$aroyl,
  $C_6-C_{10}$aryl$C_1-C_6$alkanoyl,
  $C_1-C_6$alkylsulfonyl,
  $C_6-C_{10}$arylsulfonyl,
  $C_6-C_{10}$aryl$C_1-C_6$alkylcarbamoyl,
  cinnamoyl,
  heterocyclecarbonyl,
  $C_1-C_6$alkoxycarbonyl,
  $C_6-C_{10}$aryloxycarbonyl,
  $C_6-C_{10}$aryl$C_1-C_6$alkoxycarbonyl, and
  pyroglutamyl;

$R^{27}$ and $R^{28}$ together with the nitrogen atom to which they are bonded may form a cyclic amine represented by

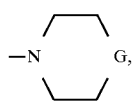

and a cyclic imide represented by

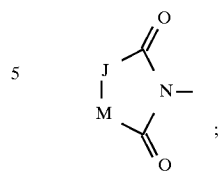

G is selected from $-CH_2-$, O, $S(O)_u$ where u is 0,1,or 2, and $NR^{28}$;
J–M is selected from $C_2-C_4$alkylene and $C_2-C_4$alkenylene;
$R^{29}$ is selected from hydrogen and $C_1-C_3$alkyl; and pharmaceutically acceptable salts thereof.

11. A compound represented by structural formula (VI):

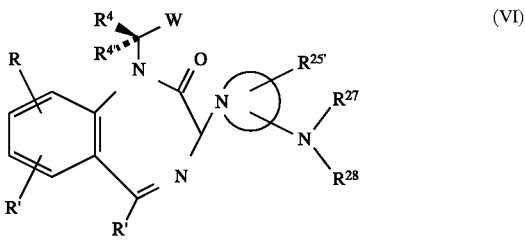

(VI)

where
R and R' are independently selected from the group
  hydrogen,
  halo(F, Cl, Br, I),
  $C_1-C_6$ alkyl,
  halo(F, Cl, Br, I)$C_1-C_6$ alkyl,
  $C_1-C_6$ alkoxy,
  hydroxy,
  hydroxy-$C_1-C_6$ alkyl,
  $C_1-C_6$ alkylcarbonyl, and
  $C_1-C_6$ alkyloxycarbonyl;
$R^1$ is selected from the group
  hydrogen,
  $C_1-C_6$ alkyl,
  halo(F, Cl, Br, I)-$C_1-C_6$ alkyl, and

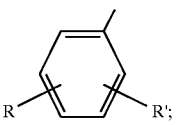

$R^4$ and $R^{4'}$ are independently selected from the group
  hydrogen,
  halo(F, Cl, Br, I),
  $C_1-C_6$ alkyl,
  halo(F, Cl, Br, I)$C_1-C_6$ alkyl,
  phenyl, and
  benzyl;
W is selected from the group
  $C(=O)-NR^{7'8}$,
  $CH_2-C(=O)-NR^{7'}R^8$,
  $C(=O)-O-R^8$,
  $CR^{8'}(OH)-CHR^7R^8$,
  $CHR^{8'}-CHR^7R^8$,
  $CR^{8'}=CR^7R^8$ (E or Z),
  $C(=O)-CHR^7R^8$, CHR$^{8'}$—NR7'R$^8$,
CHR$^{8'}$—O—R$^8$,
CHR$^{8'}$—S(O)$_u$—R$^8$ where u is 0,1, or 2,
CR$^{8'}$=N—R$^8$,
CHR$^{8'}$—R$^8$,
W',
C$_1$–C$_3$alkyl-W',
C$_6$–C$_{12}$aryl-W',
C$_6$–C$_{12}$aryl-C$_1$–C$_3$alkyl-W',
heterocyde-W',
heterocycle-C$_1$–C$_3$alkyl-W',
C$_1$–C$_2$alkyl-C$_6$–C$_{10}$aryl-W', and
C$_1$C$_2$alkyl-heterocyde-W',
  where any heterocycle is a 5- or 6-member saturated or unsaturated ring containing 1 to 3 heteroatoms selected from O, N, and S;
W' is selected from one to three substituents selected from the group
  hydrogen,
  SR$^9$,
  SSR$^9$,
  SC(=O)—R$^9$,
  OR$^9$,
  C(=NH)—NH$_2$,
  N=CH—NH$_2$,
  NH—CH=NH,
  R$^8$, and
  V;
R$^7$, each occurance, is independently selected from the group
  hydrogen,
  C$_1$–C$_4$alkyl, halo(F, Cl, Br, I), and
  halo(F, Cl, Br, I)C$_1$–C$_4$alkyl;
R$^{7'}$ is selected from the group
  hydrogen,
  C$_1$–C$_4$alkyl, and
  halo(F, Cl, Br, I)C$_1$–C$_4$alkyl;
R$^{7'}$ and R$^8$ together with the nitrogen to which they are bonded may form a pyrrolidinyl or piperidyl ring optionally substituted with one or two groups selected from
  SR$^9$,
  SSR$^9$,
  SC(=O)—R$^9$,
  OR$^9$,
  C(=O)NHOH,
  NHR$^9$,
  C(=O)NR$^{27}$R$^{28}$, and
  V;
R$^8$ is selected from the group unsubstituted and substituted
  C$_1$–C$_8$alkyl,
  C$_2$–C$_8$alkenyl,
  phenyl-C$_1$C$_3$alkyl,
  indol-3-yl-C$_1$–C$_3$alkyl, and
  imidazol-4-yl-C$_1$–C$_3$alkyl,
    where any phenyl moiety is optionally substituted with —OR$^9$ and V, and where any alkyl or alkenyl group is optionally substituted with one to three groups selected from
    SR$^9$,
    SSR$^9$,
    SC(=O)—R$^9$,
    OR$^9$,
    C(=NH)—NH$_2$,
    N=CH—NH$_2$,
    NH—CH=NH,
    NH—C(=NH)—NH$_2$,
    C(=O)NHOH,
    NHR$^9$,
    C(=O)NR$^{27}$R$^{28}$, and
    V;
V is selected from the group
  COR$^{10}$,
  SO$_3$R$^{13}$,
  NHSO$_2$CF$_3$,
  PO(OR$^{13}$)$_2$,
  SO$_2$NHR$^{10}$,
  CONHOR$^{13}$,
  C(OH)R$^{10}$PO(OR$^{13}$)$_2$,
  CN,
  SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    C$_1$–C$_4$alkyl,
    C$_1$–C$_4$alkoxy,
    CF$_3$,
    halo(F, Cl, Br, I),
    NO$_2$,
    COOH,
    COO—(C$_1$–C$_4$alkyl),
    NH$_2$,
    NH(C$_1$–C$_4$alkyl), and
    N(C$_1$–C$_4$alkyl)$_2$, and
  CONHSO$_2$R$^{15}$,
  SO$_2$NHCOR$^{15}$,
  CONHSO$_2$R$^{13}$,
  CH$_2$CONHSO$_2$R$^{15}$,
  NHCONHSO$_2$R$^{15}$,
  NHSO$_2$NHCOR$^{15}$,
  CONHNHSO$_2$CF$_3$,
  CON(OH)R$^{13}$,
  CONHCOCF$_3$,
  CONHSO$_2$R$^{10}$,
  CONHSO$_2$R$^{11}$,
  CONHSO$_2$R$^{13}$,

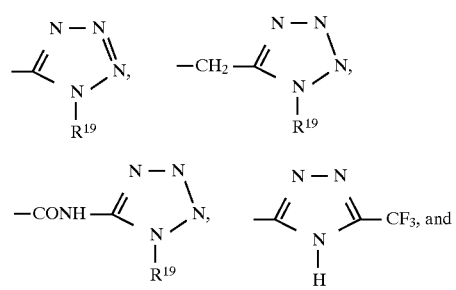

-continued

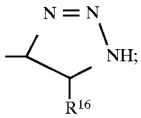

$R^9$ is selected from the group
hydrogen,
methyl,
ethyl,
isopropyl,
t-butyl,
phenyl, and
benzyl;
$R^{10}$ is selected from the group
hydroxy,
$C_1$–$C_8$-alkoxy,
$C_3$–$C_{12}$-alkenoxy,
$C_6$–$C_{12}$-aryloxy,
$C_1$–$C_6$-alkyl-$C_6$–$C_{12}$-aryloxy,
di-$C_1$–$C_8$-alkylamino-$C_1$–$C_8$-alkoxy,
alkanoylamino-$C_1$–$C_8$-alkoxy selected from the group
  acetylaminoethoxy,
  nicotinoylaminoethoxy, and
  succinamidoethoxy, and
$C_1$–$C_8$-alkanoyloxy-$C_1$–$C_8$-alkoxy,
$C_6$–$C_{12}$-aryl-$C_1$–$C_8$-alkoxy where the aryl group is unsubstituted or substituted with one to three of the groups
    nitro,
    halo(F, Cl, Br, I),
    $C_1$–$C_4$-alkoxy, and
    amino, and
hydroxy-$C_2$–$C_8$-alkoxy,
dihydroxy-$C_3$–$C_8$-alkoxy, and
$NR^{11}R^{12}$;
$R^{11}$ and $R^{12}$ are independently selected from the group
hydrogen,
$C_1$–$C_6$ alkyl,
$C_2$–$C_6$ alkanoyl,
$C_1$–$C_6$ alanoyl substituted with from one to three groups selected from
    nitro,
    halo(F, Cl, Br, I),
    $C_1$–$C_4$-alkoxy, and
    amino, and
$C_6$–$C_{12}$-aryl-$C_1$–$C_8$-alkyl where the aryl group is unsubstituted or substituted with one to three of the groups selected from
    nitro,
    halo(F, Cl, Br, I), and
    $C_1$–$C_4$-alkoxy;
$R^{13}$ is selected from the group
hydrogen,
$C_1$–$C_6$ alkyl,
halo(F, Cl, Br, I)-$C_1$–$C_6$ alkyl,
phenyl,
benzyl, and
$CH_2$—O—$COCH_3$;
$R^{15}$ is selected from the group
$C_6$–$C_{14}$aryl, heteroaryl, where the heteroaryl is a 5- or 6-member aromatic ring containing 1 to 3 heteroatoms selected from O, N, and S and where the heteroaryl is unsubstituted or substituted with one or two substituents selected from the group
OH,
SH,
$C_1$–$C_4$alkyl,
$C_1$–$C_4$alkoxy,
$CF_3$,
halo(F, Cl, Br, I),
$NO_2$,
COOH,
COO—($C_1$–$C_4$alkyl),
$NH_2$,
$NH(C_1$–$C_4$alkyl), and
$N(C_1$–$C_4$alkyl)$_2$,
$C_3$–$C_7$-cycloalkyl,
$C_1$–$C_4$-alkyl, unsubstituted or substituted with a substituent selected from
    $C_6$–$C_{14}$aryl,
    heteroaryl as defined above,
    OH,
    SH,
    $C_1$–$C_4$-alkyl,
    $C_1C_4$-alkoxy,
    $C_1$–$C_4$-alkylthio,
    $CF_3$,
    halo(F, Cl, Br, I),
    $NO_2$,
    $CO_2H$,
    $CO_2$–($C_1$–$C_4$)-alkyl,
    $NH_2$,
    $N[(C_1$–$C_4$)-alkyl]$_2$,
    $NH[(C_1$–$C_4$)-alkyl]$,
    $PO_3H$, and
    PO(OH)($C_1$–$C_4$)-alkoxy, and
    ($C_1$–$C_4$)-perfluoroalkyl;
$R^{16}$ is selected from the group
CN,
$NO_2$,
$COOR^{13}$,
$C_1$–$C_6$-perfluoroalkyl, and
$CF_3$;
$R^{19}$ is selected from the group
hydrogen,
$C_1$–$C_6$alkyl,
$C_2$–$C_6$alkenyl,
$C_1$–$C_6$alkoxy,
($C_2$–$C_6$)-alkoxyalkyl,
$CH_2$—O—$COCH_3$, and
benzyl, where the phenyl moiety is unsubstituted or substituted with a group selected from the group
    $NO_2$,
    $NH_2$,
    OH, and
    $OCH_3$;

represents a heterocycle bonded to the benzodiazepine moiety through a ring nitrogen, where the heterocycle is a 5- or 6-member saturated or unsaturated nitrogen containing ring having from 0 to 2 additional heteroatoms selected from O, N, and S, the ring optionally containing a keto [—C(=O)—] group;

$R^{25'}$ is selected from the group $SR^{26}$,
$SSR^{26}$,
$OR^{26}$,
$NOR^{26}$,
$C_1$–$C_6$alkyl,
$C_2$–$C_6$alkenyl,
$C_1$–$C_6$alkylamine,
$C_2$–$C_6$alkenylamine, and
halo(F, Cl, Br, I)$C_1$–$C_6$alkyl,
where any alkyl or alkenyl moiety is optionally substituted with
$SR^{26}$,
$SSR^{26}$,
$OR^{26}$,
$NOR^{26}$ and
$NR^{27}R^{28}$, and
where any amine moiety is optionally substituted with $R^{27}$ or $R^{28}$;

$R^{26}$ is selected from the group hydrogen,
$C_1$–$C_6$alkyl,
halo(F, Cl, Br, I)$C_1$–$C_6$alkyl, and
$C_1$–$C_6$alkanoyl;

$R^{27}$ and $R^{28}$ are independently selected from the group hydrogen,
$C_1$–$C_6$alkyl,
phenyl,
napthyl,
benzyl,
$CH_2$napthyl (α or β)
$C_1$–$C_6$alkanoyl,
$C_1$–$C_6$cycloalkanoyl,
$C_6$–$C_{10}$aroyl,
$C_6$–$C_{10}$aryl$C_1$–$C_6$alkanoyl,
$C_1$–$C_6$alkylsulfonyl,
$C_6$–$C_{10}$arylsulfonyl,
$C_6$–$C_{10}$aryl$C_1$–$C_6$alkycarbamoyl,
cinnamoyl,
heterocyclecarbonyl,
$C_1$–$C_6$alkoxycarbonyl,
$C_6$–$C_{10}$aryloxycarbonyl,
$C_6$–$C_{10}$aryl$C_1$–$C_6$alkoxycarbonyl, and
pyroglutamyl;

$R^{27}$ and $R^{28}$ together with the nitrogen atom to which they are bonded may form a cyclic amine represented by $$-N\diagdown\diagup G,$$

or a cyclic imide represented by $$\begin{array}{c} O \\ J \diagdown \\ | \quad N- \\ M \diagup \\ O \end{array};$$

G is selected from —$CH_2$—, O, $S(O)_u$ where u is 0,1,or 2, and $NR^{28}$;
J–M is selected from $C_2$–$C_4$alkylene and $C_2$–$C_4$alkenylene; and
pharmaceutically acceptable salts thereof.

12. A compound represented by structural formula (VII):

(VII)

where
R and R' are independently selected from the group
hydrogen,
halo(F, Cl, Br, I),
$C_1$–$C_6$ alkyl,
halo(F, Cl, Br, I)$C_1$–$C_6$ alkyl,
$C_1$–$C_6$ alkoxy,
hydroxy,
hydroxy-$C_1$–$C_6$ alkyl,
$C_1$–$C_6$ alkykarbonyl, and
$C_1$–$C_6$alkyloxycarbonyl;

$R^4$ and $R^{4'}$ are independently selected from the group
hydrogen,
halo(F, Cl, Br, I),
$C_1$–$C_6$ alkyl,
halo(F, Cl, Br, I)$C_1$–$C_6$ alkyl,
phenyl, and
benzyl;

$R^7$ is selected from the group
hydrogen,
halo(F, Cl, Br, I),
$C_1$–$C_6$ alkyl, and
halo(F, Cl, Br, I)$C_1$–$C_6$ alkyl;

W is selected from the group the group
$C(=O)$—$NR^{7'}R^8$,
$CH_2$—$C(=O)$—$NR^{7'}R^8$,
$C(=O)$—$O$—$R^8$,
$CR^{8'}(OH)$—$CHR^7R^8$,
$CHR^{8'}$—$CHR^7R^8$,
$CR^{8'}$=$CR^7R^8$ (E or Z),
$C(=O)$—$CHR^7R^8$,
$CHR^{8'}$—$NR^{7'}R^8$,
$CHR^{8'}$—$O$—$R^8$, CHR$^{8'}$—S(O)$_u$—R$^8$ where u is 0, 1, or 2,
CR$^{8'}$=N—R$^8$,
CHR$^{8'}$—R$^8$,
W',
C$_1$-C$_3$alkyl-W',
C$_6$-C$_{12}$aryl-W',
C$_6$-C$_{12}$aryl-C$_1$-C$_3$alkyl-W',
heterocycle-W',
heterocyde-C$_1$-C$_3$alkyl-W',
C$_1$-C$_2$alkyl-C$_6$-C$_{10}$aryl-W', and
C$_1$-C$_2$alkyl-heterocycle-W', and
  where any heterocycle is a 5- or 6-member saturated or unsaturated ring containing 1 to 3 heteroatoms selected from O, N, and S;
W' is selected from one to three substituents selected from the group
hydrogen,
SR$^9$,
SSR$^9$,
SC(=O)—R$^9$,
OR$^9$,
C(=NH)—NH$_2$,
N=CH—NH$_2$,
NH—CH=NH,
R$^8$ and
V;
R$^7$, each occurance, is independently selected from the group
hydrogen,
C$_1$C$_4$alkyl,
halo(F, Cl, Br, I), and
halo(F, Cl, Br, I)C$_1$-C$_4$alkyl;
R$^{7'}$ is selected from the group
hydrogen,
C$_1$-C$_4$alkyl, and
halo(F, Cl, Br, I)C$_1$-C$_4$alkyl;
R$^{7'}$ and R$^8$ together with the nitrogen to which they are bonded may form a pyrrolidinyl or piperidyl ring optionally substituted with one or two groups selected from the group
SR$^9$,
SSR$^9$,
SC(=O)—R$^9$,
OR$^9$,
C(=O)NHOH,
NHR$^9$,
C(=O)NR$^{27}$R$^{28}$, and
V;
R$^8$ is selected from the group unsubstituted and substituted
C$_1$-C$_8$alkyl,
C$_2$-C$_8$alkenyl,
phenyl-C$_1$-C$_3$alkyl,
indol-3-yl-C$_1$-C$_3$alkyl, and
imidazol-4-yl-C$_1$-C$_3$alkyl,
  where any phenyl moiety is optionally substituted with —OR$^9$ and V, and where any alkyl or alkenyl group is optionally substituted with one to three groups selected from
SR$^9$,
SSR$^9$,
SC(=O)R$^9$,
OR$^9$,
C(=NH)—NH$_2$,
N=CH—NH$_2$,
NH—CH=NH,
NH—C(=NH)—NH$_2$,
C(=O)NHOH,
NHR$^9$,
C(=O)NR$^{27}$R$^{28}$, and
V;

V is selected from the group
COR$^{10}$,
SO$_3$R$^{13}$,
NHSO$_2$CF$_3$,
PO(OR$^{13}$)$_2$,
SO$_2$NHR$^{10}$,
CONHOR$^{13}$,
C(OH)R$^{10}$PO(OR$^{13}$)$_2$,
CN,
SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
OH,
SH,
C$_1$-C$_4$alkyl,
C$_1$-C$_4$alkoxy,
CF$_3$,
halo(F, Cl, Br, I),
NO$_2$,
COOH,
COO—(C$_1$-C$_4$alkyl),
NH$_2$,
NH(C$_1$-C$_4$alkyl), and
N(C$_1$-C$_4$alkyl)$_2$,
CONHSO$_2$R$^{15}$,
SO$_2$NHCOR$^{15}$,
CONHSO$_2$R$^{13}$,
CH$_2$CONHSO$_2$R$^{15}$,
NHCONHSO$_2$R$^{15}$,
NHSO$_2$NHCOR$^{15}$,
CONHNSO$_2$CF$_3$,
CON(OH)R$^{13}$,
CONHCOCF$_3$,
CONHSO$_2$R$^{10}$,
CONHSO$_2$R$^{11}$,
CONHSO$_2$R$^{13}$,

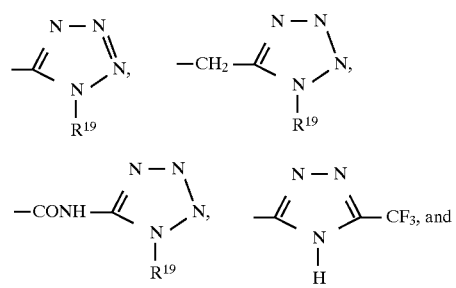

-continued

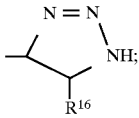

$R^9$ is selected from the group
 hydrogen,
 methyl,
 ethyl,
 isopropyl,
 t-butyl,
 phenyl, and
 benzyl;
$R^{10}$ is selected from the group
 hydroxy,
 $C_1$–$C_8$-alkoxy,
 $C_3$–$C_{12}$-alkenoxy,
 $C_6$–$C_{12}$-aryloxy,
 $C_1$–$C_6$-alkyl-$C_6$–$C_{12}$-aryloxy,
 di-$C_1$–$C_8$-alkylamino-$C_1$–$C_8$-alkoxy,
 alkanoylamino-$C_1$–$C_8$-alkoxy selected from the group
  acetylaminoethoxy,
  nicotinoylaminoethoxy, and
  succiamidoethoxy,
 $C_1$–$C_8$-alkanoyloxy-$C_1$–$C_8$-alkoxy,
 $C_6$–$C_{12}$-aryl-$C_1$–$C_8$-alkoxy where the aryl group is unsubstituted or substituted with one to three of the groups
   nitro,
   halo(F, Cl, Br, I),
   $C_1$–C4-alkoxy, and
   amino,
 hydroxy-$C_2$–$C_8$-alkoxy,
 dihydroxy-$C_3$–$C_8$-alkoxy, and
 $NR^{11}R^{12}$;
$R^{11}$ and $R^{12}$ are independently selected from the group
 hydrogen,
 $C_1$–$C_6$ alkyl,
 $C_2$–$C_6$ alkanoyl,
 $C_1$–$C_6$ alkanoyl substituted with from one to three groups selected from
   nitro,
   halo(F, Cl, Br, I),
   $C_1$–$C_4$-alkoxy, and
   amino, and
 $C_6$–$C_{12}$-aryl-$C_1$–$C_8$-alkyl where the aryl group is unsubstituted or substituted with one to three of the groups selected from
   nitro,
   halo(F, Cl, Br, I), and
   $C_1$–$C_4$-alkoxy;
$R^{13}$ is selected from the group
 hydrogen,
 $C_1$–$C_6$ alkyl,
 halo(F, Cl, Br, I)—$C_1$–$C_6$ alkyl,
 phenyl,
 benzyl, and
 $CH_2$—O—$COCH_3$;
$R^{15}$ is selected from the group
 $C_6$–$C_{14}$aryl,
 heteroaryl, where the heteroaryl is a 5- or 6-member aromatic ring containing 1 to 3 heteroatoms selected from O, N, and S and where the heteroaryl is unsubstituted or substituted with one or two substituents selected from the group
   OH,
   SH,
   $C_1$–$C_4$alkyl,
   $C_1$–$C_4$alkoxy,
   $CF_3$,
   halo(F, Cl, Br, I),
   $NO_2$,
   COOH,
   COO—($C_1$–$C_4$alkyl),
   $NH_2$,
   NH($C_1$–$C_4$alkyl), and
   N($C_1$–$C_4$alkyl)$_2$, and
 $C_3$–$C_7$- cyloalkyl ,
 $C_1$–$C_4$-alkyl, unsubstituted or substituted with a substituent selected from the group
   $C_6$–$C_{14}$aryl,
   heteroaryl as defined above,
   OH,
   SH,
   $C_1$–$C_4$-alkyl,
   $C_1$–$C_4$-alkoxy,
   $C_1$–$C_4$-alkylthio,
   $CF_3$,
   halo(F, Cl, Br, I),
   $NO_2$,
   $CO_2H$,
   $CO_2$—($C_1$–$C_4$)-alkyl,
   $NH_2$,
   $N[(C_1$–$C_4)$-alkyl]$_2$,
   $NH[(C_1$–$C_4)$-alkyl],
   $PO_3H$ or
   PO(OH)($C_1$–$C_4$-alkoxy, and
 ($C_1$–$C_4$)-perfluoroalkyl;
$R^{16}$ is selected from the group
 CN,
 NO,
 $COOR^{13}$,
 $C_1$–$C_6$-perfluoroalkyl, and
 $CF_3$;
$R^{19}$ is selected from the group
 hydrogen,
 $C_1$–$C_6$alkyl,
 $C_2$–$C_6$alkenyl,
 $C_1$–$C_6$alkoxy,
 $C_2$–$C_6$alkoxyalkyl,
 $CH_2$—O—$COCH_3$, and
 benzyl, where the phenyl moiety is unsubstituted or substituted with a group selected from
   $NO_2$,
   $NH_2$,
   OH, and
   $OCH_3$;
X is selected from the group
 $NR^{24}$—C(=O)—$R^{25}$,
 $NR^{24}$—CH(OH)—$R^{25}$,
 $NR^{24}$—$CH_2$—$R^{25}$,
 $NR^{24}$—S(O)$_u$—$R^{25}$ where u is 0, 1, or 2,
 $CHR^{24}$—$CH_2R^{25}$,
 $CHR^{24}$—$R^{25}$, $CR^{24}$=$CHR^{25}$ (E or Z),
$C_6$–$C_{10}$aryl-$R^{25}$,
heterocycle-$R^{25}$,
$C_1$–$C_2$alkyl-$C_6$–$C_{10}$aryl-$R^{25}$, and
$C_1$–$C_2$alkyl-heterocycle-$R^{25}$, and
  where any heterocycle is a 5- or 6-member saturated or unsaturated ring containing 1 to 3 heteroatoms selected from O, N, and S;
$R^{24}$ is selected from the group
  hydrogen,
  $C_1$–$C_6$alkyl, and
  halo(F, Cl, Br, I)$C_1$–$C_6$alkyl;
$R^{25}$ is selected from $R^{25'}$,

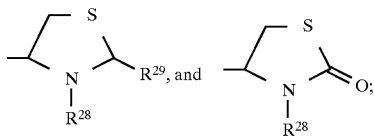

$R^{25'}$ is selected from the group
  $SR^{26}$,
  $SSR^{26}$,
  $OR^{26}$,
  $NOR^{26}$,
  $C_1$–$C_6$alkyl,
  $C_2$–$C_6$alkenyl,
  $C_1$–$C_6$alkylamine,
  $C_2$–$C_6$alkenylamine, and
  halo(F, Cl, Br, I)$C_1$–$C_6$alkyl, and
    where any alkyl or alkenyl moiety is optionally substituted with
      $SR^{26}$,
      $SSR^{26}$,
      $OR^{26}$,
      $NOR^{26}$ and
      $NR^{27}R^{28}$, and
        where any amine moiety is optionally substituted with $R^{27}$ or $R^{28}$;
$R^{26}$ is selected from the group
  hydrogen,
  $C_1$–$C_6$alkyl, halo(F, Cl, Br, I)$C_1$–$C_6$alkyl, and
  $C_1$–$C_6$alkanoyl;
$R^{27}$ and $R^{28}$ are independently selected from the group
  hydrogen,
  $C_1$–$C_6$alkyl,
  phenyl,
  napthyl,
  benzyl,
  $CH_2$napthyl (α or β)
  $C_1$–$C_6$alkanoyl,
  $C_1$–$C_6$cycloalkanoyl,
  $C_6$–$C_{10}$aroyl,
  $C_6$–$C_{10}$aryl$C_1$–$C_6$alanoyl,
  $C_1$–$C_6$alkylsulfonyl,
  $C_6$–$C_{10}$arylsulfonyl,
  $C_6$–$C_{10}$aryl$C_1$–$C_6$alkylcarbamoyl,
  cinnamoyl,
  heterocyclecarbonyl,
  $C_1$–$C_6$alkoxycarbonyl,
  $C_6$–$C_{10}$aryloxycarbonyl,
  $C_6$–$C_{10}$aryl$C_1$–$C_6$alkoxycarbonyl, and
  pyroglutamyl;
$R^{27}$ and $R^{28}$ together with the nitrogen atom to which they are bonded may form a cyclic amine represented by

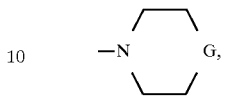

and
a cyclic imide represented by

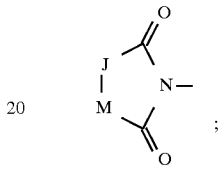

G is selected from —$CH_2$—, O, $S(O)_u$ where u is 0, 1, or 2, and $NR^{28}$;
J–M is selected from $C_2$–$C_4$alkylene and $C_2$–$C_4$alkenylene;
$R^{29}$ is selected from hydrogen and $C_1$–$C_3$alkyl; and
pharmaceutically acceptable salts thereof.
  13. A compound represented by structural formula (VIII):

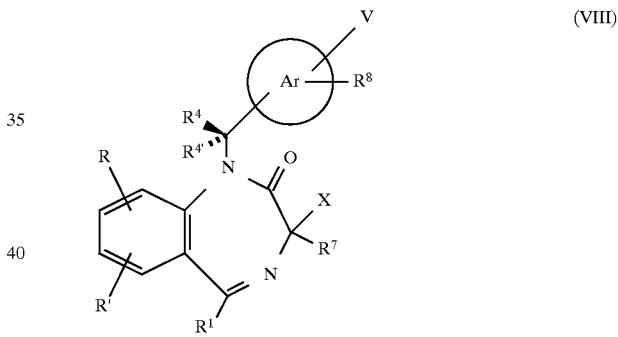

(VIII)

where
$R^1$ is selected from the group
  $CF_3$ and

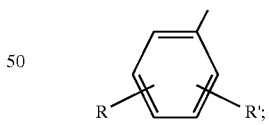

R and R' are independently selected from the group
  hydrogen,
  halo (F, Cl, Br, I),
  $C_1$–$C_6$ alkyl,
  halo(F, Cl, Br, I)$C_1$–$C_6$ alkyl,
  $C_1$–$C_6$ alkoxy,
  hydroxy,
  hydroxy-$C_1$–$C_6$ alkyl,
  $C_1$–$C_6$ alkylcarbonyl, and
  $C_1$–$C_6$ alkyloxycarbonyl;
$R^4$ and $R^{4'}$ are independently selected from the group
  hydrogen, halo(F, Cl, Br, I),
C$_1$–C$_6$ alkyl,
halo(F, Cl, Br, I)C$_1$–C$_6$ alkyl,
phenyl, and
benzyl;
R$^7$ is selected from the group
hydrogen
halo(F, Cl, Br, I),
C$_1$–C$_6$ alkyl, and
halo(F, Cl, Br, I)C$_1$–C$_6$ alkyl;

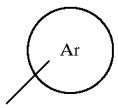

represents C$_6$–C$_{10}$aryl or a heteroaryl where the heteroaryl is a 5- or 6-member aromatic ring containing 1 to 3 heteroatoms selected from O, N, and S, the C$_6$–C$_{10}$aryl or heteroaryl is optionally substituted with V and R$^8$;
R$^8$ is selected from the group unsubstituted and substituted
C$_1$–C$_8$alkyl,
phenyl-C$_1$–C$_3$alkyl,
indol-3-yl-C$_1$–C$_3$alkyl, and
imidazol-4-yl-C$_1$–C$_3$alkyl,
where any phenyl moiety is optionally substituted with —OR$^9$ and V, and where any alkyl or alkenyl group is optionally substituted with one to three groups selected from
SR$^9$,
SSR$^9$,
SC(=O)—R$^9$,
OR$^9$,
C(=NH)—NH$_2$,
N=CH—NH$_2$,
NH—CH=NH,
NH—C(=NH)—NH$_2$,
C(=O)NHOH,
NHR$_9$,
C(=O)NR$^{27}$R$^{28}$, and
V;
V is selected from the group
COR$^{10}$,
SO$_3$R$^{13}$,
NHSO$_2$CF$_3$,
PO(OR$^{13}$)$_2$,
SO$_2$NHR$^{10}$,
CONHOR$^{13}$,
C(OH)R$^{10}$PO(OR$^{13}$)$_2$,
CN,
SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
OH,
SH,
C$_1$–C$_4$alkyl,
C$_1$–C$_4$alkoxy,
CF$_3$,
halo(F, Cl, Br, I),
NO$_2$,
COOH,
COO—(C$_1$–C$_4$alkyl),
NH$_2$,
NH(C$_1$–C$_4$alkyl), and
N(C$_1$–C$_4$alkyl)$_2$,
CONHSO$_2$R$^{15}$,
SO$_2$NHCOR$^{15}$,
CONHSO$_2$R$^{13}$,
CH$_2$CONHSO$_2$R$^{15}$,
NHCONHSO$_2$R$^{15}$,
NHSO$_2$NHCOR$^{15}$,
CONHNHSO$_2$CF$_3$,
CON(OH)R$^{13}$,
CONHCOCF$_3$,
CONHSO$_2$R$^{10}$,
CONHSO$_2$R$^{11}$,
CONHSO$_2$R$^{13}$,

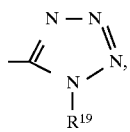

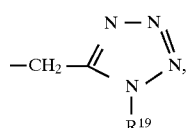

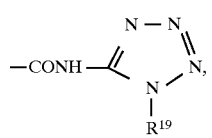

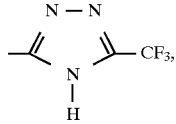

and

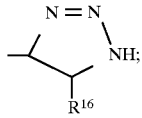

R$^9$ is selected from the group
hydrogen,
methyl,
ethyl,
isopropyl,
phenyl, and
benzyl;
R$^{10}$ is selected from the group
hydroxy,
C$_1$–C$_8$-alkoxy,
C$_3$–C$_{12}$-alkenoxy,
C$_6$–C$_{12}$-aryloxy,
C$_1$–C$_6$-alkyl-C$_6$–C$_2$-aryloxy,
di-C$_1$–C$_8$-alkylamino-C$_1$–C$_8$-alkoxy, alkanoylamino-$C_1$–$C_8$-alkoxy selected from the group
  acetylaminoethoxy,
  nicotinoylaminoethoxy, and
  succinamidoethoxy,
$C_1$–$C_8$-alkanoyloxy-$C_1$–$C_8$-alkoxy,
$C_6$–$C_{12}$-aryl-$C_1$–$C_8$-alkoxy where the aryl group is unsubstituted or substituted with one to three of the groups
  nitro,
    halo(F, Cl, Br, I),
    $C_1$–$C_4$-alkoxy, and
    amino,
hydroxy-$C_2$–$C_8$-alkoxy,
dihydroxy-$C_3$–$C_8$-alkoxy, and
$NR^{11}R^{12}$;
$R^{11}$ and $R^{12}$ are independently selected from the group
  hydrogen,
  $C_1$–$C_6$ alkyl,
  $C_2$–$C_6$ alkanoyl,
  $C_1$–$C_6$ alkanoyl substituted with from one to three groups selected from
    nitro,
    halo(F, Cl, Br, I),
    $C_1$–$C_4$-alkoxy, and
    amino, and
  $C_6$–$C_{12}$-aryl-$C_1$–$C_8$-alkyl where the aryl group is unsubstituted or substituted with one to three of the groups selected from
    nitro,
    halo(F, Cl, Br, I), and
    $C_1$–$C_4$-alkoxy;
$R^{13}$ is selected from the group
  hydrogen,
  $C_1$–$C_6$ alkyl,
  halo(F, Cl, Br, I)—$C_1$–$C_6$ alkyl,
  phenyl,
  benzyl, and
  $CH_2$—O—$COCH_3$;
$R^{15}$ is selected from the group
  $C_6$–$C_{14}$aryl,
  heteroaryl, where the heteroaryl is a 5- or 6-member aromatic ring containing 1 to 3 heteroatoms selected from O, N, and S and where the heteroaryl is unsubstituted or substituted with one or two substituents selected from the group
    OH,
    SH,
    $C_1$–$C_4$alkyl,
    $C_1$–$C_4$alkoxy,
    $CF_3$,
    halo(F, Cl, Br, I),
    $NO_2$,
    COOH,
    COO—($C_1$–$C_4$alkyl),
    $NH_2$,
    NH($C_1$–$C_4$alkyl), and
    N($C_1$–$C_4$alkyl)$_2$,
  $C_3$–$C_7$-cydoalkyl,
  $C_1$–$C_4$-alkyl, unsubstituted or substituted with a substituent selected from the group
    $C_6$–$C_{14}$aryl,
    heteroaryl as defined above,
    OH,
    SH,
    $C_1$–$C_4$-alkyl,
    $C_1$–$C_4$-alkoxy,
    $C_1$–$C_4$-alkylthio,
    $CF_3$,
    halo(F, Cl, Br, I),
    $NO_2$,
    $CO_2H$,
    $CO_2$—($C_1$–$C_4$)-alkyl,
    $NH_2$,
    $N[(C_1$–$C_4)$-alkyl]$_2$,
    $NH[(C_1$–$C_4)$-alkyl],
    $PO_3H$, and
    $PO(OH)(C_1$–$C_4)$-alkoxy, and
  ($C_1$–$C_4$)-perfluoroalkyl;
$R^{16}$ is selected from the group
  CN,
  $NO_2$,
  $COOR^{13}$,
  $C_1$–$C_6$-perfluoroalkyl, and
  $CF_3$;
$R^{19}$ is selected from the group
  hydrogen,
  ($C_1$–$C_6$)-alkyl,
  ($C_2$–$C_6$)-alkenyl,
  ($C_1$–$C_6$)-alkoxy,
  ($C_2$–$C_6$)-alkoxyalkyl,
  $CH_2$—O—$COCH_3$, or
  benzyl, where the phenyl moiety is unsubstituted or substituted with a group selected from
    $NO_2$,
    $NH_2$,
    OH, or
    $OCH_3$;
X is selected from the group
  $NR^{24}$—C(=O)—$R^{25}$,
  $NR^{24}$—CH(OH)—$R^{25}$,
  $NR^{24}$—$CH_2$—$R^{25}$,
  $NR^{24}$—S(O)$_u$—$R^{25}$ where u is 0, 1, or 2,
  $CHR^{24}$—$CH_2R^{25}$,
  $CHR^{24}$—$R^{25}$,
  $CR^{24}$=$CHR^{25}$ (E or Z),
  $C_6$–$C_{10}$aryl-$R^{25}$,
  heterocycle-$R^{25}$,
  $C_1$–$C_2$alkyl-$C_6$–$C_{10}$aryl-$R^{25}$,
  $C_1$–$C_2$alkyl-heterocycle-$R^{25}$, and
    where any heterocycle is a 5- or 6-member saturated or unsaturated ring containing 1 to 3 heteroatoms selected from O, N, and S;
$R^{24}$ is selected from the group
  hydrogen,
  $C_1$–$C_6$aLkyl, and
  halo(F, Cl, Br, I)$C_1$–$C_6$alkyl;

$R^{25}$ is selected from $R^{25}$,

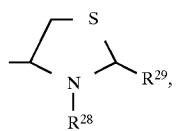

and

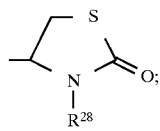

$R^{25'}$ is selected from the group
- $SR^{26}$,
- $SSR^{26}$,
- $OR^{26}$,
- $NOR^{26}$,
- $C_1-C_6$alkyl,
- $C_2-C_6$alkenyl,
- $C_1-C_6$alkylamine,
- $C_2-C_6$alkenylamine, and
- halo(F, Cl, Br, I)$C_1-C_6$alkyl,
  where any alkyl or alkenyl moiety is optionally substituted with
- $SR^{26}$,
- $SSR^{26}$,
- $OR^{26}$,
- $NOR^{26}$ and
- $NR^{27}R^{28}$, and
  where any amine moiety is optionally substituted with $R^{27}$ or $R^{28}$;

$R^{26}$ is selected from
- hydrogen,
- $C_1-C_6$alkyl,
- halo(F, Cl, Br, I)$C_1-C_6$alkyl, and
- $C_1-C_6$alkanoyl;

$R^{27}$ and $R^{28}$ are independently selected from the group
- hydrogen,
- $C_1-C_6$alkyl,
- phenyl,
- napthyl,
- benzyl,
- $CH_2$napthyl ($\alpha$ or $\beta$)
- $C_1-C_6$ alkanoyl,
- $C_1-C_6$cycloalkanoyl,
- $C_6-C_{10}$aroyl,
- $C_6-C_{10}$aryl$C_1-C_6$alkanoyl,
- $C_1-C_6$alkylsulfonyl,
- $C_6-C_{10}$arylsulfonyl,
- $C_6-C_{10}$aryl$C_1-C_6$alkylcarbamoyl,
- cinnamoyl,
- heterocyclecarbonyl,
- $C_1-C_6$alkoxycarbonyl,
- $C_6-C_{10}$aryloxycarbonyl,
- $C_6-C_{10}$aryl$C_1-C_6$alkoxycarbonyl, and
- pyroglutamyl;

$R^{27}$ and $R^{28}$ together with the nitrogen atom to which they are bonded may form a cyclic amime represented by

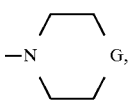

and
a cyclic imide represented by

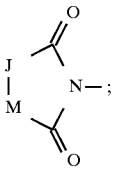

G is selected from —$CH_2$—, O, $S(O)_u$ where u is 0,1,or 2, and $NR^{28}$
J—M is selected from $C_2-C_4$alkylene and $C_2-C_4$alkenylene;
$R^{29}$ is selected from hydrogen and $C_1-C_3$alkyl; and
pharmaceutically acceptable salts thereof.

14. A compound represented by structural formula (IXa)-(IXd):

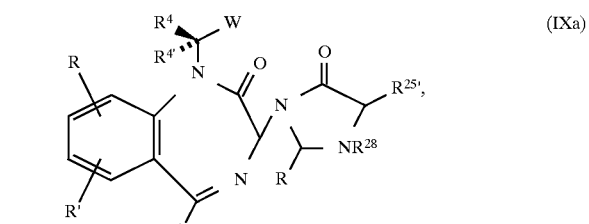

(IXa)

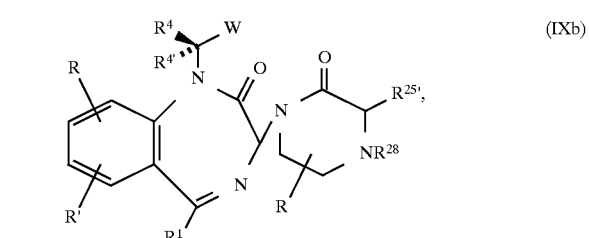

(IXb)

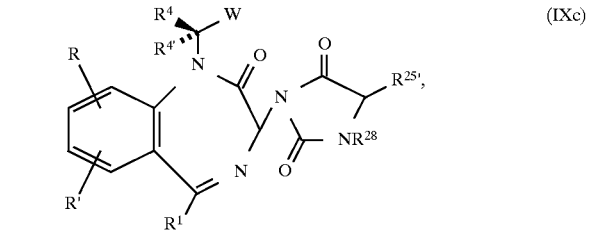

(IXc)

and

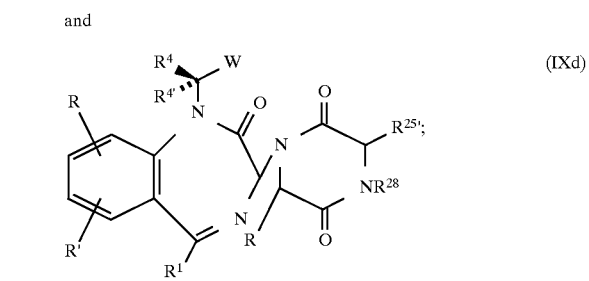

(IXd)

where
R and R' are independently selected from the group
- hydrogen,
- halo(F, Cl, Br, I), $C_1$–$C_6$ alkyl,
halo(F, Cl, Br, I)$C_1$–$C_6$ alkyl,
$C_1$–$C_6$ alkoxy,
hydroxy,
hydroxy-$C_1$–$C_6$ alkyl,
$C_1$–$C_6$ alkylcarbonyl, and
$C_1$–$C_6$ alkyloxycarbonyl;
$R^1$ is selected from the group
hydrogen,
$C_1$–$C_6$ alkyl,
halo(F, Cl, Br, I)—$C_1$–$C_6$ alkyl, and

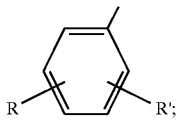

$R^4$ and $R^{4'}$ are independently selected from the group
hydrogen,
halo(F, Cl, Br, I),
$C_1$–$C_6$ alkyl,
halo(F, Cl, Br, I)$C_1$–$C_6$ alkyl,
phenyl, and
benzyl;
W is selected from the group
C(=O)—NR$^{7'}$R$^8$,
CH$_2$—C(=O)NR$^{7'}$R$^8$,
C(=O)—O—R$^8$,
CR$^{8'}$(OH)—CHR$^7$R$^8$,
CHR$^{8'}$—CHR$^7$R$^8$,
CR$^{8'}$=CR$^7$R$^8$ (E or Z),
C(=O)—CHR$^7$R$^8$,
CHR$^{8'}$—NR$^{7'}$R$^8$,
CHR$^{8'}$—O—R$^8$,
CHR$^{8'}$—S(O)$_u$—R$^8$ where u is 0,1, or 2,
CR$^{8'}$=N—R$^8$,
CHR$^{8'}$—R$^8$,
W',
$C_1$–$C_3$alkyl-W',
$C_6$–$C_{12}$aryl-W',
$C_6$–$C_{12}$aryl-$C_1$–$C_3$alkyl-W',
heterocycle-W',
heterocyde-$C_1$–$C_3$alkyl-W',
$C_1C_2$alkyl-$C_6$–$C_{10}$aryl-W', and
$C_1$–$C_2$alkyl-heterocycle-W',
where any heterocycle is a 5- or 6-member saturated or unsaturated ring containing 1 to 3 heteroatoms selected from O, N, and S;
W' is selected from one to three substituents selected from the group
hydrogen,
SR$^9$,
SSR$^9$,
SC(=O)—R$^9$,
OR$^9$,
C(=NH)—NH$_2$,
N=CH—NH$_2$,
NH—CH=NH,
R$^8$, and
V;
R$^7$, each occurance, is independently selected from the group
hydrogen,
$C_1$–$C_4$alkyl,
halo(F, Cl, Br, I), and
halo(F, Cl, Br, I)$C_1$–$C_4$alkyl;
R$^{7'}$ is selected from the group
hydrogen,
$C_1$–$C_4$alkyl, and
halo(F, CL Br, I)$C_1$–$C_4$alkyl;
R$^{7'}$ and R$^8$ together with the nitrogen to which they are bonded may form a pyrrolidinyl or piperidyl ring optionally substituted with one or two groups selected from
SR$^9$,
SSR$^9$,
SC(=O)—R$^9$,
OR$^9$,
C(=O)NHOH,
NHR$^9$,
C(=O)NR$^{27}$R$^{28}$, and
V;
R$^8$ is selected from the group unsubstituted and substituted
$C_1$–$C_8$alkyl,
$C_2$–$C_8$alkenyl,
phenyl-$C_1$–$C_3$alkyl,
indol-3-yl-$C_1$–$C_3$alkyl, and
imidazol-4-yl-$C_1$–$C_3$alkyl,
where any phenyl moiety is optionally substituted with —OR$^9$ and V, and where any alkyl or alkenyl group is optionally substituted with one to three groups selected from
SR$^9$,
SSR$^9$,
SC(=P)—R$^9$,
OR$^9$,
C(=NH)—NH$_2$,
N=CH—NH$_2$,
NH—CH=NH,
NH—C(=NH)—NH$_2$,
C(=O)NHOH,
NHR$^9$,
C(=O)NR$^{27}$R$^{28}$, and
V;
V is selected from the group
COR$^{10}$,
SO$_3$R$^{13}$,
NHSO$_2$CF$_3$,
PO(OR$^{13}$)$_2$,
SO$_2$NHR$^{10}$,
CONHOR$^{13}$,
C(OH)R$^{10}$PO(OR$^{13}$)$_2$,
CN,
SO$_2$NH-heteroaryl where the heteroaryl is a 5- or 6-member aromatic ring containing 1 to 3 heteroatoms selected from O, N, and S and where the heteroaryl is unsubstituted or substituted with one or two substituents selected from the group
OH,
SH,
$C_1$–$C_4$alkyl, $C_1$–$C_4$alkoxy,
$CF_3$,
halo(F, Cl, Br, I),
$NO_2$,
COOH,
COO—($C_1$–$C_4$alkyl),
$NH_2$,
NH($C_1$–$C_4$alkyl), and
N($C_1$–$C_4$alkyl)$_2$,
CONHSO$_2$R$^{15}$,
SO$_2$NHCOR$^{15}$,
CONHSO$_2$R$^{13}$,
CH$_2$CONHSO$_2$R$^{15}$,
NHCONHSO$_2$R$^{15}$,
NHSO$_2$NHCOR$^{15}$,
CONHNSO$_2$CF$_3$,
CON(OH)R$^{13}$,
CONHCOCF$_3$,
CONHSO$_2$R$^{10}$,
CONHSO$_2$R$^{11}$,
CONHSO$_2$R$^{13}$,

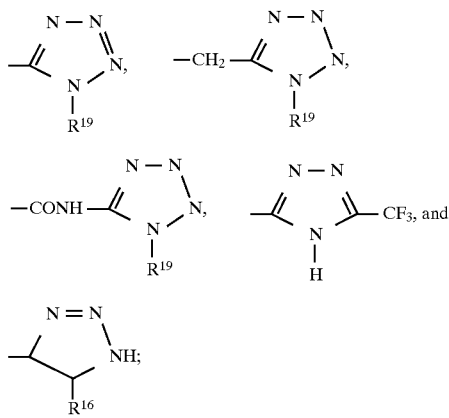

$R^9$ is selected from the group
hydrogen,
methyl,
ethyl,
isopropyl,
t-butyl,
phenyl, and
benzyl;
$R^{10}$ is selected from the group
hydroxy,
$C_1$–$C_8$-alkoxy,
$C_3$–$C_{12}$-alkenoxy,
$C_6$–$C_{12}$-aryloxy,
$C_1$–$C_6$-alkyl-$C_6$–$C_{12}$-ayloxy,
di-$C_1$–$C_8$-alkylamino-$C_1$–$C_8$-alkoxy,
alkanoylamino-$C_1$–$C_8$-alkoxy selected from the group
acetylaninoethoxy,
nicotinoylaminoethoxy, and
succinamidoethoxy, and
$C_1$–$C_8$-alkanoyloxy-$C_1$–$C_8$-alkoxy,
$C_6$–$C_{12}$-aryl-$C_1$–$C_8$-alkoxy where the aryl group is unsubstituted or substituted with one to three of the groups nitro,
halo(F, Cl, Br, I),
$C_1$–$C_4$-alkoxy, and amino, and
hydroxy-$C_2$–$C_8$-alkoxy,
dihydroxy-$C_3$–C8-alkoxy, and
NR$^{11}$R$^{12}$;
$R^{11}$ and $R^{12}$ are independently selected from the group
hydrogen,
$C_1$–$C_6$ alkyl,
$C_2$–$C_6$ alkanoyl,
$C_1$–$C_6$ alkanoyl substituted with from one to three groups selected from
nitro,
halo(F, Cl, Br, I),
$C_1$–$C_4$-alkoxy, and
amino, and
$C_6$–$C_{12}$-aryl-$C_1$–$C_8$-alkyl where the aryl group is unsubstituted or substituted with one to three of the groups selected from
nitro,
halo(F, Cl, Br, I),and
$C_1$–$C_4$-alkoxy;
$R^{13}$ is selected from the group
hydrogen,
$C_1$–$C_6$ alkyl,
halo(F, Cl, Br, I)—$C_1$–$C_6$ alkyl,
phenyl,
benzyl, and
CH$_2$—O—COCH$_3$;
$R^{15}$ is selected from the group
$C_6$–$C_{14}$aryl,
heteroaryl, where the heteroaryl is a 5- or 6-member aromatic ring containing 1 to 3 heteroatoms selected from O, N, and S and where the heteroaryl is unsubstituted or substituted with one or two substituents selected from the group
OH,
SH,
$C_1$–$C_4$alkyl,
$C_1$–$C_4$alkoxy,
CF$_3$,
halo(F, Cl, Br, I),
NO$_2$,
COOH,
COO—($C_1$–$C_4$alkyl),
NH$_2$,
NH($C_1$–$C_4$alkyl), and
N($C_1$–$C_4$alkyl)$_2$, and
$C_3$–$C_7$-cycloalkyl,
$C_1$–$C_4$-alkyl, unsubstituted or substituted with a substituent selected from
$C_6$–$C_{14}$aryl,
heteroaryl as defined above,
OH,
SH,
$C_1$–$C_4$-alkyl,
$C_1$–$C_4$-alkoxy,
$C_1$–$C_4$-alkylthio,
CF$_3$,
halo(F, Cl, Br, I),
NO$_2$,
CO$_2$H,
CO$_2$—($C_1$–$C_4$)-alkyl,
NH$_2$, N[($C_1$–$C_4$)-alkyl]$_2$,
NH[($C_1$–$C_4$)-alkyl],
PO$_3$H, and
PO(OH)($C_1$–$C_4$)-alkoxy, and
($C_1$–$C_4$)-perfluoroalkyl;

$R^{16}$ is selected from the group
CN,
NO$_2$,
COOR$^{13}$,
$C_1$–$C_6$-perfluoroalkyl, and
CF$_3$;

$R^{19}$ is selected from the group
hydrogen,
$C_1$–$C_6$alkyl,
$C_2$–$C_6$alkenyl,
$C_1$–$C_6$alkoxy,
($C_2$–$C_6$)-alkoxyalkyl,
CH$_2$—O—COCH$_3$, and
benzyl, where the phenyl moiety is unsubstituted or substituted with a group selected from the group
NO$_2$,
NH$_2$,
OH, and
OCH$_3$;

R25' is selected from the group
SR$^{26}$,
SSR$^{26}$,
OR$^{26}$,
NOR$^{26}$,
$C_1$–$C_6$alkyl,
$C_2$–$C_6$alkenyl,
$C_1$–C6alkylamine,
$C_2$–$C_6$alkenylamine, and
halo(F, Cl, Br, I)$C_1$–$C_6$alkyl,
    where any alkyl or alkenyl moiety is optionally substituted with
SR$^{26}$,
SSR$^{26}$,
OR$^{26}$,
NOR$^{26}$ and
NR$^{27}$R$^{28}$, and where any amine moiety is optionally substituted with R$^{27}$or R$^{28}$;

$R^{26}$ is selected from the group
hydrogen,
$C_1$–$C_6$alkyl
halo(F, Cl, Br, I)$C_1$–$C_6$alkyl, and
$C_1$–$C_6$alkanoyl;

$R^{28}$ is selected from the group
hydrogen,
$C_1$–$C_6$alkyl,
phenyl,
napthyl,
benzyl,
CH$_2$napthyl (α or β)
$C_1$–$C_6$alkanoyl,
$C_1$–$C_6$cycloalkanoyl,
$C_6$–$C_{10}$aroyl,
$C_6$–$C_{10}$aryl$C_1$–$C_6$alanoyl,
$C_1$–$C_6$alkylsulfonyl,
$C_6$–$C_{10}$arylsulfonyl,
$C_6$–$C_{10}$aryl$C_1$–$C_6$alkylcarbamoyl,
cinnamoyl,
heterocyclecarbonyl,
$C_1$–$C_6$alkoxycarbonyl,
$C_6$–$C_{10}$aryloxycarbonyl,
$C_6$–$C_{10}$aryl$C_1$–$C_6$alkoxycarbonyl, and
pyroglutamyl; and
pharmaceutically acceptable salts thereof.

15. A pharmaceutical composition comprising a pharmaceutically acceptable excipient and the compound of claim 1.

16. A method of inhibiting farnesyl:protein transferse comprising administering to a subject in need of such treatment a therapeutically effective amount of the composition of claim 15.

17. A method of inhibiting farnesylation of the oncogene protein ras comprising administering to a mammal in need of such treatment a therapeutically effective amount of the composition of claim 15.

* * * * *